United States Patent
Bissantz et al.

(10) Patent No.: US 9,321,727 B2
(45) Date of Patent: Apr. 26, 2016

(54) PYRIDINE DERIVATIVES AS AGONISTS OF THE CB2 RECEPTOR

(75) Inventors: Caterina Bissantz, Village-Neuf (FR); Uwe Grether, Efringen-Kirchen (DE); Paul Hebeisen, Basel (CH); Atsushi Kimbara, Tokyo (JP); Qingping Liu, Beijing (CN); Matthias Nettekoven, Grenzach-Wyhlen (DE); Marco Prunotto, Delémont (CH); Stephan Roever, Inzlingen (DE); Mark Rogers-Evans, Bottmingen (CH); Tanja Schulz-Gasch, Ziefen (CH); Christoph Ullmer, Fischingen (DE); Zhiwei Wang, Beijing (CN); Wulun Yang, Beijing (CN)

(73) Assignee: Hoffmann-La Roche Inc., Nutley, NJ (US)

(*) Notice: Subject to any disclaimer, the term of this patent is extended or adjusted under 35 U.S.C. 154(b) by 68 days.

(21) Appl. No.: 13/486,057

(22) Filed: Jun. 1, 2012

(65) Prior Publication Data
US 2012/0316147 A1      Dec. 13, 2012

(30) Foreign Application Priority Data

Jun. 10, 2011 (WO) ................ PCT/CN2011/075606

(51) Int. Cl.

| | | |
|---|---|---|
| C07D 211/68 | (2006.01) | |
| C07D 211/80 | (2006.01) | |
| C07D 213/02 | (2006.01) | |
| C07D 401/00 | (2006.01) | |
| C07D 419/00 | (2006.01) | |
| C07D 417/00 | (2006.01) | |
| C07D 405/00 | (2006.01) | |
| C07D 213/62 | (2006.01) | |
| C07D 213/78 | (2006.01) | |
| C07D 211/78 | (2006.01) | |
| C07D 211/90 | (2006.01) | |
| C07D 213/81 | (2006.01) | |
| C07D 401/04 | (2006.01) | |
| C07D 401/14 | (2006.01) | |
| C07D 405/04 | (2006.01) | |
| C07D 405/12 | (2006.01) | |
| C07D 405/14 | (2006.01) | |
| C07D 409/12 | (2006.01) | |
| C07D 409/14 | (2006.01) | |
| C07D 413/12 | (2006.01) | |
| C07D 413/14 | (2006.01) | |
| C07D 417/06 | (2006.01) | |
| C07D 417/12 | (2006.01) | |
| C07D 491/107 | (2006.01) | |

(52) U.S. Cl.
CPC ............ *C07D 213/81* (2013.01); *C07D 401/04* (2013.01); *C07D 401/14* (2013.01); *C07D 405/04* (2013.01); *C07D 405/12* (2013.01); *C07D 405/14* (2013.01); *C07D 409/12* (2013.01); *C07D 409/14* (2013.01); *C07D 413/12* (2013.01); *C07D 413/14* (2013.01); *C07D 417/06* (2013.01); *C07D 417/12* (2013.01); *C07D 491/107* (2013.01)

(58) Field of Classification Search
CPC ..... A61K 31/397; A61K 31/00; C07D 213/00
See application file for complete search history.

(56) References Cited

U.S. PATENT DOCUMENTS

| | | | | |
|---|---|---|---|---|
| 5,294,597 A | * | 3/1994 | Foster et al. ................... | 504/255 |
| 5,384,305 A | * | 1/1995 | Foster et al. ................... | 504/130 |
| 7,122,580 B2 | * | 10/2006 | Mjalli et al. ................... | 514/576 |
| 2004/0110832 A1 | | 6/2004 | Mjalli et al. | |
| 2006/0235028 A1 | | 10/2006 | Li et al. | |
| 2007/0244153 A1 | * | 10/2007 | Kakimoto et al. ............ | 514/311 |

FOREIGN PATENT DOCUMENTS

| | | |
|---|---|---|
| EP | 0447004 | 9/1991 |
| GB | 2277930 | 11/1994 |
| WO | WO 9310096 A1 * | 5/1993 |

(Continued)

OTHER PUBLICATIONS

Carey, FA. Organic Chemistry 6th Ed. McGraw Hill. 2006, chapter 1, p. 9.*
Hoornaert, Gj. et al. Generation of Polysubstituted 2-Pyridinecarboxylic Acid Derivatives from the Reaction of (Functionalized) 2-Oxa-5-azabicyclo[2.2.2]oct-5-en-3-ones with Various Nucleophiles. Tetrahedron. 1996, vol. 52, p. 12532.*
Defer et al., The FASEB Journal 23:2120-2130 ( 2009).
Julien et al., Gastroenterology 128:742-755 ( 2005).
Mallat et al., Expert Opin. Ther. Targets 11(3):403-409 ( 2007).
Wright et al., British Journal of Pharmacology 153:263-270 ( 2008).
Beltramo et al., Mini-Reviews in Medicinal Chemistry 9:11-25 ( 2009).
International Search Report for PCT/EP2012/060785 dated Jul. 19, 2012.

(Continued)

*Primary Examiner* — Rita Desai
*Assistant Examiner* — Ben S Michelson

(57) ABSTRACT

The invention relates to a compound of formula (I)

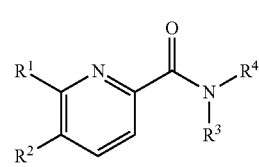

Wherein $R^1$, $R^2$, $R^3$ and $R^4$ are defined as in the description and in the claims. The said compounds of the invention are preferential agoniste of the Carsonabinocid Receptor 2 and thus useful as medicaments and may be used in treatment of chronic pain, atherosclerosis, ischemic/reperfusion injury and other related diseases.
A representative compound of this invention is 6-cyclopropylmethoxy-5-(tetrahydro-pyradine-2-carboxglic acid [1-methyl-1-(5-methyl-(1,2,4]oxadiazol-3-yl)-ethyl)-amide.

4 Claims, No Drawings

(56) References Cited

FOREIGN PATENT DOCUMENTS

| WO | 03/084930 | | 10/2003 |
|---|---|---|---|
| WO | 2004/029026 | | 8/2004 |
| WO | 2005/079802 | | 9/2005 |
| WO | WO 2005/079802 A1 | * | 9/2005 |
| WO | 2006106054 | | 10/2006 |
| WO | WO 2007/011760 A2 | * | 1/2007 |
| WO | 2008/000729 | | 1/2008 |
| WO | 2008/040649 | | 4/2008 |
| WO | 2008106692 | | 9/2008 |
| WO | 2012/032018 | | 3/2012 |

OTHER PUBLICATIONS

Miller et al., British Journal of Pharmacology 153:299-308 ( 2008).
Lotersztajn et al., Gastroenterol Clin Biol 31:255-258 ( 2007).
Kiselyov, Tetrahedron Letters 46:4487-4490 ( 2005).
Garcia-Gonzalez et al., Rheumatology 48:1050-1056 ( 2009).
Lotersztajn et al., British Journal of Pharmacology 153:286-289 ( 2008).
Akhmetshina et al., Arthritis & Rheumatism 60(4):1129-1136 (2009).
Ashton et al., Current Neuropharmacology 5:73-80 ( 2007).
Cabral et al., Journal of Leukocyte Biology 78:1192-1197 ( 2005).
Munoz-Luque et al., The Journal of Pharmacology and Experimental Therapeutics 324(2):475-483 ( 2008).
Zhang et al., Journal of Cerebral Blood Flow & Metabolism 27:1387-1396 ( 2007).
Pacher et al., British Journal of Pharmacology 153:252-262 ( 2008).
Batkai et al., FASEB Journal 21:1788-1800 ( 2007).
Mach et al., Journal of Neuroendocrinology 20( SUPPL 1):53-57 ( 2008).
Centonze et al., Current Pharmaceutical Design 14:2370-2382 ( 2008).
Haring et al., Helvetica Chimica Acta 37:147-154 (Jan. 1, 1954).
Feizi et al., Experimental and Toxicologic Pathology 60:405-410 ( 2008).
Yang et al., Liver International 29(5):678-685 ( 2009).
Bab et al., British Journal of Pharmacology 153:182-188 ( 2008).
Cabral et al., British Journal of Pharmacology 153:240-251 ( 2008).
The English translation of the Colombian Office Action, issued on Feb. 3, 2015, in the corresponding Colombian Application No. 13-281.333.
Kiselyov et al., "Reaction of N-fluropyridinium fluoride with isonitriles and TMSN3: a convenient one-pot synthesis of tetrazol-5-yl pyridines," Tetrahedron Letters, vol. 46, No. 29, 4851-4854 (2005).
The Chinese Office Action, issued on Oct. 27, 2014, in the corresponding Chinese Application No. 201280028511.3.
Compound Summary for CID 11208110, retrieved from the Internet: http://pubchem.ncbi.nlm.nig.gov/compound/11208110#section=Top.
Kim et al, "Discovery of PyrrolopyridineÿPyridone Based Inhibitors of Met Kinase: Synthesis, X-ray Crystallographic Analysis, and Biological Activities," Journal of Medicinal Chemistry, vol. 51, No. 17, 5330-5341, (2008).
The English translation of the Chinese Office Action, issued on Jan. 6, 2016, in the corresponding Chinese Application No. 201280028511.3.
Sarri et al., "Microwave-assisted synthesis of quinoline, isoquinoline, quinoxaline and quinazoline derivatives as CB2 receptor agonists," Bioorganic & Medicinal Chemistry, 19, 939-950 (2001).
Vedantham et al., "Studies Towards the Synthesis of Methionine Aminopeptidase Inhibitors: Diversification Utilizing a ROMP-Derived Coupling Reagent," J.Comb. Chem. 10(2), 195-203 (2008).
The English translation of the Japanese Office Action, issued on Jan. 26, 2016, in the corresponding Japanese Application No. 2014-514063.
The English translation of the Eurasian Search Report, completed on Dec. 24, 2015, in the corresponding Eurasian Patent Application No. 201591527.
The New Experimental Chemistry No. 14, 1136-1141 (1977).

* cited by examiner

PYRIDINE DERIVATIVES AS AGONISTS OF THE CB2 RECEPTOR

PRIORITY TO RELATED APPLICATION(S)

This application claims the benefit of International Application No. PCT/CN2011/075606, filed Jun. 10, 2011, which is hereby incorporated by reference in its entirety.

FIELD OF THE INVENTION

The present invention relates to organic compounds useful for therapy and/or prophylaxis in a mammal, and in particular to compounds that are preferential agonists of the Cannabinoid Receptor 2.

BACKGROUND OF THE INVENTION

The cannabinoid receptors are a class of cell membrane receptors belonging to the G protein-coupled receptor superfamily. There are currently two known subtypes, termed Cannabinoid Receptor 1 (CB1) and Cannabinoid Receptor 2 (CB2). The CB1 receptor is mainly expressed in the central nervous (i.e. amygdala cerebellum, hippocampus) system and to a lesser amount in the periphery. CB2, which is encoded by the CNR2 gene, is mostly expressed peripherally, on cells of the immune system, such as macrophages and T-cells (Ashton, J. C. et al. Curr Neuropharmacol 2007, 5(2), 73-80; Miller, A. M. et al. Br J Pharmacol 2008, 153(2), 299-308; Centonze, D., et al. Curr Pharm Des 2008, 14(23), 2370-42), and in the gastrointestinal system (Wright, K. L. et al. Br J Pharmacol 2008, 153(2), 263-70). The CB2 receptor is also widely distributed in the brain where it is found primarily on microglia and not neurons (Cabral, G. A. et al. Br J Pharmacol 2008, 153(2): 240-51).

The interest in CB2 receptor agonists has been steadily on the rise during the last decade (currently 30-40 patent applications/year) due to the fact that several of the early compounds have been shown to have beneficial effects in preclinical models for a number of human diseases including chronic pain (Beltramo, M. Mini Rev Med Chem 2009, 9(1), 11-25), atherosclerosis (Mach, F. et al. J Neuroendocrinol 2008, 20 Suppl 1, 53-7), regulation of bone mass (Bab, I. et al. Br J Pharmacol 2008, 153(2), 182-8), neuroinflammation (Cabral, G. A. et al. J Leukoc Biol 2005, 78(6), 1192-7), ischemia/reperfusion injury (Pacher, P. et al. Br J Pharmacol 2008, 153(2), 252-62), systemic fibrosis (Akhmetshina, A. et al. Arthritis Rheum 2009, 60(4), 1129-36; Garcia-Gonzalez, E. et al. Rheumatology (Oxford) 2009, 48(9), 1050-6), liver fibrosis (Julien, B. et al. Gastroenterology 2005, 128(3), 742-55; Munoz-Luque, J. et al. J Pharmacol Exp Ther 2008, 324(2), 475-83).

Ischemia/reperfusion (I/R) injury is the principal cause of tissue damage occurring in conditions such as stroke, myocardial infarction, cardiopulmonary bypass and other vascular surgeries, and organ transplantation, as well as a major mechanism of end-organ damage complicating the course of circulatory shock of various etiologies. All these conditions are characterized by a disruption of normal blood supply resulting in an insufficient tissue oxygenation. Re-oxygenation e.g., reperfusion is the ultimate treatment to restore normal tissue oxygenation. However the absence of oxygen and nutrients from blood creates a condition in which the restoration of circulation results in further tissue damage. The damage of reperfusion injury is due in part to the inflammatory response of damaged tissues. White blood cells, carried to the area by the newly returning blood, release a host of inflammatory factors such as interleukins as well as free radicals in response to tissue damage. The restored blood flow reintroduces oxygen within cells that damages cellular proteins, DNA, and the plasma membrane.

Remote ischemic preconditioning (RIPC) represents a strategy for harnessing the body's endogenous protective capabilities against the injury incurred by ischemia and reperfusion. It describes the intriguing phenomenon in which transient non-lethal ischemia and reperfusion of one organ or tissue confers resistance to a subsequent episode of "lethal" ischemia reperfusion injury in a remote organ or tissue. The actual mechanism through which transient ischemia and reperfusion of an organ or tissue confers protection is currently unknown although several hypotheses have been proposed.

The humoral hypothesis proposes that the endogenous substance (such as adenosine, bradykinin, opioids, CGRP, endocannabinoids, Angiotensin I or some other as yet unidentified humoral factor) generated in the remote organ or tissue enters the blood stream and activates its respective receptor in the target tissue and thereby recruiting the various intracellular pathways of cardioprotection implicated in ischemic preconditioning.

Recent data indicates that endocannabinnoids and their receptors, in particular CB2 might be involved in pre-conditioning and contribute to prevent reperfusion injury by downregulation of the inflammatory response (Pacher, P. et al. Br J Pharmacol 2008, 153(2), 252-62). Specifically, recent studies using CB2 tool agonists demonstrated the efficacy of this concept for reducing the I/R injury in the heart (Defer, N. et al. Faseb J 2009, 23(7), 2120-30), the brain (Zhang, M. et al. J Cereb Blood Flow Metab 2007, 27(7), 1387-96), the liver (Batkai, S. et al. Faseb J 2007, 21(8), 1788-800) and the kidney (Feizi, A. et al. Exp Toxicol Pathol 2008, 60(4-5), 405-10).

Moreover, over the last few years, a growing body of literature indicates that CB2 can also be of interest in sub-chronic and chronic setting. Specific upregulation of CB 1 and CB2 has been shown to be associated in animal models of chronic diseases associated with fibrosis (Garcia-Gonzalez, E. et al. Rheumatology (Oxford) 2009, 48(9), 1050-6; Yang, Y. Y. et al. Liver Int 2009, 29(5), 678-85) with a relevant expression of CB2 in myofibroblasts, the cells responsible for fibrosis progression.

Activation of CB2 receptor by selective CB2 agonist has in fact been shown to exert anti-fibrotic effect in diffuse systemic sclerosis (Garcia-Gonzalez, E. et al. Rheumatology (Oxford) 2009, 48(9), 1050-6) and CB2 receptor has emerged as a critical target in experimental dermal fibrosis (Akhmetshina, A. et al. Arthritis Rheum 2009, 60(4), 1129-36) and in liver pathophysiology, including fibrogenesis associated with chronic liver diseases (Lotersztajn, S. et al. Gastroenterol Clin Biol 2007, 31(3), 255-8; Mallat, A. et al. Expert Opin Ther Targets 2007, 11(3), 403-9; Lotersztajn, S. et al. Br J Pharmacol 2008, 153(2), 286-9).

SUMMARY OF THE INVENTION

The present invention relates in part to a compound of formula (I)

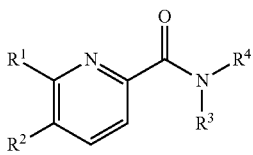

wherein
R¹ is selected from the group consisting of: cycloalkyl, cycloalkylalkoxy, haloalkoxy, alkoxyalkoxy, phenyl, halophenyl, haloalkylphenyl, phenylalkyl, halophenylalkyl, phenylhydroxyalkyl, phenyloxyalkyl, phenylalkoxy, alkoxyphenyl, halophenyloxy, piperidinylsulfonyl, tetrahydropyranyl, 3-alkoxy-azetidinyl, tetrahydropyranylalkyl, tetrahydropyranylalkoxy, tetrahydrothiopyranyl 1,1-dioxide, 1,1-dioxo-[1,2]thiazinan-4-yl, piperidin-2-onyl, tetrahydrofuranylalkoxy, pyridinylalkoxy, alkyloxetanylalkoxy, hydroxyhaloalkyloxy, halophenylhydroxyalkyl, alkylsulfonyl, alkylsulfanyl and (halo)(haloalkyl)phenyl;

R² is selected from the group consisting of: hydrogen, halogen, alkyl, haloalkyl, hydroxyalkyl, cycloalkyl, hydroxycycloalkyl, alkoxy, haloalkoxy, alkylamino, haloalkylamino, tetrahydropyranyl, 1H-pyrazolyl, pyrrolidinyl, alkylpyrrolidinyl, halopyrrolidinyl, oxopyrrolidinyl, haloazetidinyl, hydroxyazetidinyl, 1,1-dioxido-2-isothioazolidinyl, tetrahydrofuranyl, cycloalkylamino, hydroxyoxetanyl, alkylsulfonyl, oxetanyl, 6-oxa-1-aza-spiro[3.3]heptyl, 3,3-difluoro-2-oxo-azetidinyl, oxo-azetidinyl and oxo-pyrrolidinyl;

or R¹ and R² together with the ring to which they are attached form tetrahydroquinolinyl or alkyltetrahydroquinolinyl;

one of R³ and R⁴ is hydrogen and the other one is —(CR⁵R⁶)$_m$(CR⁷R⁸)$_n$—R⁹;

or R³ and R⁴ together with the nitrogen atom to which they are attached form piperidinyl, 1,1-dioxidotetrahydro-2H-thiopyranyl, thiomorpholinyl, 2-oxa-6-aza-spiro[3.3]heptyl or 1-hydroxyalkylpyrrolidinyl;

R⁵ and R⁶ are each independently selected from the group consisting of: hydrogen, alkyl, haloalkyl, cycloalkyl, cycloalkylalkyl, phenyl, pyridazinyl, halophenyl, pyrimidinyl, alkylsulfanylalkyl and alkylsulfonylalkyl;

or R⁵ and R⁶ together with the carbon atom to which they are attached form cycloalkyl, tetrahydropyranyl or oxetanyl;

R⁷ and R⁸ are each independently selected from the group consisting of: hydrogen, alkyl and cycloalkyl;

R⁹ is selected from the group consisting of: alkyl, hydroxyl, cyano, carboxyl, alkoxycarbonyl, alkyl[1,2,4]oxadiazolyl, oxazolyl, thiazolyl, [1,3,4]oxadiazolyl, cycloalkyl, phenyl, pyridinyl, tetrahydropyranyl, alkyl[1,2,4]thiadiazolyl, [1,2,4]thiadiazolyl, alkylaminocarbonyl, alkyltetrahydropyranyl, alkylisoxazolyl, aminocarbonyl, morpholinyl, dihydro-oxazolyl, [1,2,4]oxadiazolyl, hydroxycycloalkyl, alkoxycarbonylcycloalkyl, alkoxyalkoxy, hydroxyalkylcycloalkyl, alkoxypyridinyl, piperidinyl, hydroxypiperidinyl, hydroxyalkylpiperidinyl, isoxazolyl, azetidine-carbonyl, alkoxyalkylaminocarbonyl, cycloalkylalkylaminocarbonyl, haloazetidinylcarbonyl, alkoxypyrrolidinyl, 1,1-dioxo-tetrahydro-1λ6-thiophenyl, 1,1-dioxo-tetrahydro-1λ6-thiophenylamino, amino[1,2,4]oxadiazolyl, 4-alkyl-5-oxo-4,5-dihydro-[1,2,4]oxadiazolyl, nitro-benzo[1,2,5]oxadiazolyl, alkylsulfonyl, alkyl[1,2,4]thiazolyl, hydroxyalkylaminocarbonyl, oxotetrahydrofuranyl, (cycloalkylalkyl)(alkoxycarbonyl)amino, 2-oxo-[1,3]oxazinanyl, haloalkyl and hydroxypyrrolidinylaminocarbonyl;

m is 0 or 1; and n is 0, 1 or 2;

or a pharmaceutically acceptable salt or ester thereof.

The compounds of the invention bind to and modulate the CB2 receptor and have lower CB1 receptor activity.

The present invention relates also to a pharmaceutical composition comprising a compound according as described above and a therapeutically inert carrier.

DETAILED DESCRIPTION OF THE INVENTION

The present invention relates in part to a compound of formula (I)

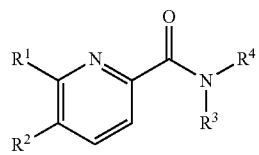

wherein
R¹ is selected from the group consisting of: cycloalkyl, cycloalkylalkoxy, haloalkoxy, alkoxyalkoxy, phenyl, halophenyl, haloalkylphenyl, phenylalkyl, halophenylalkyl, phenylhydroxyalkyl, phenyloxyalkyl, phenylalkoxy, alkoxyphenyl, halophenyloxy, piperidinylsulfonyl, tetrahydropyranyl, 3-alkoxy-azetidinyl, tetrahydropyranylalkyl, tetrahydropyranylalkoxy, tetrahydrothiopyranyl 1,1-dioxide, 1,1-dioxo-[1,2]thiazinan-4-yl, piperidin-2-onyl, tetrahydrofuranylalkoxy, pyridinylalkoxy, alkyloxetanylalkoxy, hydroxyhaloalkyloxy, halophenylhydroxyalkyl, alkylsulfonyl, alkylsulfanyl and (halo)(haloalkyl)phenyl;

R² is selected from the group consisting of: hydrogen, halogen, alkyl, haloalkyl, hydroxyalkyl, cycloalkyl, hydroxycycloalkyl, alkoxy, haloalkoxy, alkylamino, haloalkylamino, tetrahydropyranyl, 1H-pyrazolyl, pyrrolidinyl, alkylpyrrolidinyl, halopyrrolidinyl, oxopyrrolidinyl, haloazetidinyl, hydroxyazetidinyl, 1,1-dioxido-2-isothioazolidinyl, tetrahydrofuranyl, cycloalkylamino, hydroxyoxetanyl, alkylsulfonyl, oxetanyl, 6-oxa-1-aza-spiro[3.3]heptyl, 3,3-difluoro-2-oxo-azetidinyl, oxo-azetidinyl and oxo-pyrrolidinyl;

or R¹ and R² together with the ring to which they are attached form tetrahydroquinolinyl or alkyltetrahydroquinolinyl;

one of R³ and R⁴ is hydrogen and the other one is —(CR⁵R⁶)$_m$(CR⁷R⁸)$_n$—R⁹;

or R³ and R⁴ together with the nitrogen atom to which they are attached form piperidinyl, 1,1-dioxidotetrahydro-2H-thiopyranyl, thiomorpholinyl, 2-oxa-6-aza-spiro[3.3]heptyl or 1-hydroxyalkylpyrrolidinyl;

R⁵ and R⁶ are each independently selected from the group consisting of: hydrogen, alkyl, haloalkyl, cycloalkyl, cycloalkylalkyl, phenyl, pyridazinyl, halophenyl, pyrimidinyl, alkylsulfanylalkyl and alkylsulfonylalkyl;

or R⁵ and R⁶ together with the carbon atom to which they are attached form cycloalkyl, tetrahydropyranyl or oxetanyl;

$R^7$ and $R^8$ are each independently selected from the group consisting of: hydrogen, alkyl and cycloalkyl;

$R^9$ is selected from the group consisting of: alkyl, hydroxyl, cyano, carboxyl, alkoxycarbonyl, alkyl[1,2,4]oxadiazolyl, oxazolyl, thiazolyl, [1,3,4]oxadiazolyl, cycloalkyl, phenyl, pyridinyl, tetrahydropyranyl, alkyl[1,2,4]thiadiazolyl, [1,2,4]thiadiazolyl, alkylaminocarbonyl, alkyltetrahydropyranyl, alkylisoxazolyl, aminocarbonyl, morpholinyl, dihydro-oxazolyl, [1,2,4]oxadiazolyl, hydroxycycloalkyl, alkoxycarbonylcycloalkyl, alkoxyalkoxy, hydroxyalkylcycloalkyl, alkoxypyridinyl, piperidinyl, hydroxypiperidinyl, hydroxyalkylpiperidinyl, isoxazolyl, azetidine-carbonyl, alkoxyalkylaminocarbonyl, cycloalkylalkylaminocarbonyl, haloazetidinylcarbonyl, alkyloxopyrrolidinyl, 1,1-dioxo-tetrahydro-1λ6-thiophenyl, 1,1-dioxo-tetrahydro-1λ6-thiophenylamino, amino[1,2,4]oxadiazolyl, 4-alkyl-5-oxo-4,5-dihydro-[1,2,4]oxadiazolyl, nitro-benzo[1,2,5]oxadiazolyl, alkylsulfonyl, alkyl[1,2,4]thiazolyl, hydroxyalkylaminocarbonyl, oxotetrahydrofuranyl, (cycloalkylalkyl)(alkoxycarbonyl)amino, 2-oxo-[1,3]oxazinanyl, haloalkyl and hydroxypyrrolidinylaminocarbonyl;

m is 0 or 1; and n is 0, 1 or 2;

or a pharmaceutically acceptable salt or ester thereof.

The compound of formula (I) is particularly useful in the treatment or prophylaxis of e.g. pain, in particular chronic pain, atherosclerosis, regulation of bone mass, inflammation, ischemia, reperfusion injury, systemic fibrosis, liver fibrosis, lung fibrosis, kidney fibrosis, chronic allograft nephropathy, congestive heart failure, myocardial infarction, systemic sclerosis, glomerulonephropathy, thermal injury, burning, hypertrophic scars, keloids, gingivitis pyrexia, liver cirrhosis or tumors.

In the present description the term "alkyl", alone or in combination with other groups, signifies a straight-chain or branched-chain alkyl group with 1 to 8 carbon atoms, particularly a straight or branched-chain alkyl group with 1 to 6 carbon atoms and more particularly a straight or branched-chain alkyl group with 1 to 4 carbon atoms. Examples of straight-chain and branched-chain $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, particularly methyl, ethyl, propyl, butyl and pentyl more particularly methyl, ethyl, propyl, isopropyl, isobutyl, tert.-butyl and isopentyl.

The term "cycloalkyl", alone or in combination with other groups, signifies a cycloalkyl ring with 3 to 8 carbon atoms and particularly a cycloalkyl ring with 3 to 6 carbon atoms. Examples of cycloalkyl are cyclopropyl, cyclobutyl, cyclopentyl and cyclohexyl, cycloheptyl and cyclooctyl. Particular cycloalkyl are cyclopropyl, cyclobutyl, cyclopentyl and cyclohexyl. Cyclopropyl, cyclobutyl and cyclopentyl are particular examples.

The term "alkoxy", alone or in combination with other groups, signifies a group of the formula alkyl-O— in which the term "alkyl" has the previously given significance, such as methoxy, ethoxy, n-propoxy, isopropoxy, n-butoxy, isobutoxy, sec-butoxy and tert-butoxy, particularly methoxy and ethoxy.

The terms "cycloalkyloxy" or "cycloalkoxy", alone or in combination with other groups, signify a group of the formula cycloalkyl-O— in which the term "cycloalkyl" has the previously given significance, such as cyclobutyloxy, cyclopentyloxy or cyclohexyloxy.

The term "phenyloxy", alone or in combination with other groups, signifies a phenyl-O—group.

The term "oxy", alone or in combination with other groups, signifies the —O— group.

The terms "halogen" or "halo", alone or in combination with other groups, signifies fluorine, chlorine, bromine or iodine and particularly fluorine, chlorine or bromine, more particularly fluorine and chlorine. The term "halo", in combination with another group, denotes the substitution of said group with at least one halogen, particularly substituted with one to five halogens, particularly one to three halogens.

The terms "haloalkyl", "halocycloalkyl" and "haloalkoxy", alone or in combination with other groups, denote an alkyl group, a cycloalkyl group and an alkoxy group respectively, substituted with at least one halogen, particularly substituted with one to five halogens, particularly one to three halogens. Particular "haloalkyl" are trifluoromethyl, trifluoroethyl and trifluoropropyl. Particular "haloalkoxy" is trifluoroethoxy.

The terms "halophenyl", "halopyrrolidinyl", "halopyridinyl" and "haloazetidinyl", alone or in combination with other groups, denote a phenyl group, a pyrrolidinyl group, a pyridinyl group and an azetidinyl group respectively, substituted with at least one halogen, particularly substituted with one to three halogens. Particular "halophenyl" are chlorophenyl, fluorophenyl, dichlorophenyl and chlorofluorophenyl. Particular "halopyrrolidinyl" is difluoropyrrolidinyl. Particular "haloazetidinyl" is difluoroazetidinyl.

The terms "hydroxyl" or "hydroxy", alone or in combination with other groups, signify the —OH group.

The term "carbonyl", alone or in combination with other groups, signifies the —C(O)— group.

The term "carboxy" or "carboxyl", alone or in combination with other groups, signifies the —COOH group.

The term "amino", alone or in combination with other groups, signifies the primary amino group (—NH$_2$), the secondary amino group (—NH—) or the tertiary amino group (—N—).

The term "sulfonyl", alone or in combination, signifies the —SO$_2$— group.

The term "sulfanyl", alone or in combination, signifies the —SO— group.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid, particularly hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein. In addition these salts may be prepared form addition of an inorganic base or an organic base to the free acid. Salts derived from an inorganic base include, but are not limited to, the sodium, potassium, lithium, ammonium, calcium, magnesium salts. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins. The compound of formula (I) can also be present in the form of zwitterions. Particularly preferred pharmaceutically acceptable salts of compounds of formula (I) are the salts of hydrochloric acid, hydrobromic acid, sulfuric acid, phosphoric acid and methanesulfonic acid.

If one of the starting materials or compounds of formula (I) contain one or more functional groups which are not stable or are reactive under the reaction conditions of one or more reaction steps, appropriate protecting groups (as described e.g. in "Protective Groups in Organic Chemistry" by T. W. Greene and P. G. M. Wutts, $3^{rd}$ Ed., 1999, Wiley, New York) can be introduced before the critical step applying methods well known in the art. Such protecting groups can be removed at a later stage of the synthesis using standard methods described in the literature. Examples of protecting groups are tert-butoxycarbonyl (Boc), 9-fluorenylmethyl carbamate (Fmoc), 2-trimethylsilylethyl carbamate (Teoc), carbobenzyloxy (Cbz) and p-methoxybenzyloxycarbonyl (Moz).

The compound of formula (I) can contain several asymmetric centers and can be present in the form of optically pure enantiomers, mixtures of enantiomers such as, for example, racemates, mixtures of diastereoisomers, diastereoisomeric racemates or mixtures of diastereoisomeric racemates.

The term "asymmetric carbon atom" means a carbon atom with four different substituents. According to the Cahn-Ingold-Prelog Convention an asymmetric carbon atom can be of the "R" or "S" configuration.

The invention relates in particular to a compound of formula (I) wherein:

$R^1$ is selected from the group consisting of: cycloalkyl, cycloalkylalkoxy, haloalkoxy, alkoxyalkoxy, phenyl, halophenyl, haloalkylphenyl, phenylalkyl, halophenylalkyl, phenylhydroxyalkyl, phenyloxyalkyl, phenylalkoxy, alkoxyphenyl, halophenyloxy, piperidinylsulfonyl, tetrahydropyranyl, 3-alkoxy-azetidinyl, tetrahydropyranylalkyl, tetrahydropyranylalkoxy, tetrahydrothiopyranyl 1,1-dioxide, 1,1-dioxo-[1,2]thiazinan-4-yl, piperidin-2-onyl, tetrahydrofuranylalkoxy and pyridinylalkoxy;

$R^2$ is selected from the group consisting of: hydrogen, halogen, alkyl, haloalkyl, hydroxyalkyl, cycloalkyl, hydroxycycloalkyl, alkoxy, haloalkoxy, alkylamino, haloalkylamino, tetrahydropyranyl, 1H-pyrazolyl, pyrrolidinyl, alkylpyrrolidinyl, halopyrrolidinyl, oxopyrrolidinyl, haloazetidinyl, hydroxyazetidinyl, 1,1-dioxido-2-isothioazolidinyl, tetrahydrofuranyl, cycloalkylamino, hydroxyoxetanyl, alkylsulfonyl and oxetanyl;

or $R^1$ and $R^2$ together with the ring to which they are attached form a tetrahydroquinolinyl or alkyltetrahydroquinolinyl;

one of $R^3$ and $R^4$ is hydrogen and the other one is $-(CR^5R^6)_m(CR^7R^8)_n-R^9$;

or $R^3$ and $R^4$ together with the nitrogen atom to which they are attached form piperidinyl, 1,1-dioxidotetrahydro-2H-thiopyranyl, thiomorpholinyl, 2-oxa-6-aza-spiro[3.3]heptyl or 1-hydroxyalkylpyrrolidinyl;

$R^5$ and $R^6$ are each independently selected from the group consisting of: hydrogen, alkyl, haloalkyl, cycloalkyl, cycloalkylalkyl and phenyl;

or $R^5$ and $R^6$ together with the carbon atom to which they are attached form cycloalkyl or tetrahydropyranyl;

$R^7$ and $R^8$ are each independently selected from the group consisting of: hydrogen, alkyl and cycloalkyl;

$R^9$ is selected from the group consisting of: alkyl, hydroxyl, cyano, carboxyl, alkoxycarbonyl, alkyl[1,2,4]oxadiazolyl, oxazolyl, thiazolyl, [1,3,4]oxadiazolyl, cycloalkyl, phenyl, pyridinyl, tetrahydropyranyl, alkyl[1,2,4]thiadiazolyl, [1,2,4]thiadiazolyl, alkylaminocarbonyl, alkyltetrahydropyranyl, alkylisoxazolyl, aminocarbonyl, morpholinyl, alkylaminocarbonyl, dihydro-oxazolyl, [1,2,4]oxadiazolyl, hydroxycycloalkyl, alkoxycarbonylcycloalkyl, alkoxyalkoxy, hydroxyalkylcycloalkyl, alkoxypyridinyl, piperidinyl, hydroxypiperidinyl, hydroxyalkylpiperidinyl, isoxazolyl and piperidinyl;

m is 0 or 1; and n is 0, 1 or 2;

or a pharmaceutically acceptable salt or ester thereof.

A particular embodiment of the invention is a compound of formula (I) wherein $R^1$ is selected from the group consisting of: cycloalkyl, cycloalkylalkoxy, haloalkoxy, alkoxyalkoxy, phenyl, halophenyl, haloalkylphenyl, halophenylalkyl, halophenyloxy, piperidinylsulfonyl, tetrahydropyranyl, tetrahydropyranylalkoxy, tetrahydrofuranylalkoxy and pyridinylalkoxy.

A further particular embodiment of the invention is a compound of formula (I) wherein $R^1$ is selected from the group consisting of: cycloalkyl, cycloalkylalkoxy, haloalkoxy, alkoxyalkoxy, halophenyl, halophenylalkyl, alkoxyphenyl, halophenyloxy, piperidinylsulfonyl, tetrahydropyranyl, tetrahydropyranylalkoxy and tetrahydrofuranylalkoxy.

A still further particular embodiment of the invention is a compound of formula (I) wherein $R^1$ is selected from the group consisting of: cycloalkylalkoxy, halophenyl, halophenylalkyl, tetrahydropyranylmethoxy and tetrahydrofuranylalkoxy.

Another particular embodiment of the invention is a compound of formula (I) wherein $R^1$ is selected from the group consisting of: cyclopropylmethoxy, chlorophenyl, fluorophenylmethyl, fluorochlorophenyl and tetrahydrofuranylalkoxy.

A compound of formula (I) wherein $R^2$ is selected from the group consisting of: hydrogen, halogen, alkyl, haloalkyl, cycloalkyl, hydroxycycloalkyl, alkoxy, haloalkylamino, tetrahydropyranyl, 1H-pyrazolyl, pyrrolidinyl, alkylpyrrolidinyl, halopyrrolidinyl, oxopyrrolidinyl, haloazetidinyl, hydroxyazetidinyl, 1,1-dioxido-2-isothioazolidinyl, tetrahydrofuranyl, cycloalkylamino and hydroxyoxetanyl is a particular embodiment of the invention.

A compound of formula (I) wherein $R^2$ is selected from the group consisting of: hydrogen, alkyl, haloalkyl, cycloalkyl, haloalkylamino, tetrahydropyranyl, pyrrolidinyl, alkylpyrrolidinyl, halopyrrolidinyl, haloazetidinyl, tetrahydrofuranyl and cycloalkylamino is a particular embodiment of the invention.

A compound of formula (I) wherein $R^2$ is selected from the group consisting of:

hydrogen, methyl, trifluoromethyl, cyclopropyl, cyclopentyl, bis(trifluoroethyl)amino, tetrahydropyranyl, pyrrolidinyl, methylpyrrolidinyl, difluoropyrrolidinyl, difluoroazetidinyl, tetrahydrofuranyl and cyclopropylamino is a particular embodiment of the invention.

A compound of formula (I) wherein $R^1$ and $R^2$ together with the ring to which they are attached form dimethyltetrahydroquinolinyl is a further particular embodiment of the invention.

An embodiment of the present invention is a compound of formula (I) wherein $R^5$ and $R^6$ are each independently selected from the group consisting of: hydrogen, methyl, ethyl, propyl, butyl, pentyl, trifluoromethyl, cyclopropyl, cyclopropylmethyl and phenyl or $R^5$ and $R^6$ together with the carbon atom to which they are attached form cyclobutyl or tetrahydropyranyl.

The invention also relates in particular to a compound of formula (I) wherein $R^7$ and $R^8$ are each independently selected from hydrogen and methyl.

An embodiment of the present invention is a compound of formula (I) wherein $R^9$ is selected from the group consisting of: hydroxyl, cyano, carboxyl, alkoxycarbonyl, alkyl[1,2,4] oxadiazolyl, oxazolyl, thiazolyl, [1,3,4]oxadiazolyl, cycloalkyl, phenyl, pyridinyl, tetrahydropyranyl, alkyl[1,2,4] thiadiazolyl, alkylaminocarbonyl, alkyltetrahydropyranyl, alkylisoxazolyl, aminocarbonyl, morpholinyl, alkylaminocarbonyl, dihydro-oxazolyl, [1,2,4]oxadiazolyl, hydroxycycloalkyl, alkoxycarbonylcycloalkyl, alkoxyalkoxy, hydroxyalkylcycloalkyl or piperidinyl.

A compound of formula (I) wherein $R^9$ is selected from the group consisting of: hydroxyl, carboxyl, alkyl[1,2,4]oxadiazolyl, thiazolyl, alkylaminocarbonyl, aminocarbonyl, morpholinyl, alkoxyalkoxy and piperidinyl is a particular embodiment of the invention.

A compound of formula (I) wherein $R^9$ is selected from the group consisting of: hydroxyl, methyl[1,2,4]oxadiazolyl, thiazolyl, methylaminocarbonyl, aminocarbonyl, morpholinyl, methoxymethoxy and piperidinyl is another particular embodiment of the invention.

Particular compounds of the invention are selected from the group consisting of:

Methyl 2-(6-(3-chlorophenyl)picolinamido)-2-methylpropanoate;
Methyl 2-(6-(2-chlorophenyl)picolinamido)-2-methylpropanoate;
6-(4-Chloro-phenyl)-pyridine-2-carboxylic acid [1-methyl-1-(5-methyl-[1,2,4]oxadiazol-3-yl)-ethyl]-amide;
Methyl 2-methyl-2-(5-methyl-6-(2,2,2-trifluoroethoxy)picolinamido)propanoate;
Methyl 2-(5-cyclopropyl-6-(2,4-dichlorophenylamino)picolinamido)-2-methylpropanoate;
Methyl 2-(6-(2,4-dichlorophenylamino)-5-methylpicolinamido)-2-methylpropanoate;
2-[(6-Cyclohexyl-pyridine-2-carbonyl)-amino]-2-methyl-propionic acid methyl ester;
6-(3-Chloro-phenyl)-pyridine-2-carboxylic acid (1-methyl-1-oxazol-2-yl-ethyl)-amide;
2-{[6-Cyclopropylmethoxy-5-(tetrahydro-pyran-4-yl)-pyridine-2-carbonyl]-amino}-2-methyl-propionic acid methyl ester;
6-Cyclopropylmethoxy-5-(tetrahydro-pyran-4-yl)-pyridine-2-carboxylic acid [1-methyl-1-(5-methyl-[1,2,4]oxadiazol-3-yl)-ethyl]-amide;
6-(3-Chloro-phenyl)-pyridine-2-carboxylic acid piperidin-1-ylamide;
6-(3-Chloro-phenyl)-pyridine-2-carboxylic acid (1-methyl-1-thiazol-2-yl-ethyl)-amide;
2-{[6-Cyclopropylmethoxy-5-(1H-pyrazol-3-yl)-pyridine-2-carbonyl]-amino}-2-methyl-propionic acid methyl ester;
6-Cyclopropylmethoxy-5-pyrrolidin-1-yl-pyridine-2-carboxylic acid ((S)-1-hydroxymethyl-3-methyl-butyl)-amid;
(6-Cyclopropylmethoxy-5-pyrrolidin-1-yl-pyridin-2-yl)-(1,1-dioxidotetrahydro-2H-thiopyran-4-yl)-methanone;
(6-Cyclopropylmethoxy-5-pyrrolidin-1-yl-pyridin-2-yl)-thiomorpholin-4-yl-methanone;
6-(3-Chloro-phenyl)-pyridine-2-carboxylic acid (1-methyl-1-[1,3,4]oxadiazol-2-yl-ethyl)-amide;
6-(3-Chloro-phenyl)-pyridine-2-carboxylic acid cyclohexylamide;
6-(3-Chloro-phenyl)-pyridine-2-carboxylic acid phenylamide;
6-(3-Chloro-phenyl)-pyridine-2-carboxylic acid pyridin-2-ylamide;
6-(3-Chloro-phenyl)-pyridine-2-carboxylic acid (tetrahydro-pyran-4-yl)-amide;
6-(3-Chloro-phenyl)-pyridine-2-carboxylic acid [1-methyl-1-(3-methyl-[1,2,4]thiadiazol-5-yl)-ethyl]-amide;
6-(3-Chloro-phenyl)-pyridine-2-carboxylic acid (1-dimethylcarbamoyl-1-ethyl-propyl)-amide;
6-Cyclohexyl-pyridine-2-carboxylic acid piperidin-1-ylamide;
[5-Methyl-6-(piperidine-1-sulfonyl)-pyridin-2-yl]-piperidin-1-yl-methanone;
6-(3-Chloro-phenyl)-pyridine-2-carboxylic acid (2-methyl-tetrahydro-pyran-4-yl)-amide;
2-[(6-Cyclopropylmethoxy-5-pyrrolidin-1-yl-pyridine-2-carbonyl)-amino]-2-methyl-propionic acid methyl ester;
6-(3-Chloro-phenyl)-pyridine-2-carboxylic acid [1-methyl-1-(3-methyl-isoxazol-5-yl)-ethyl]-amide;
6-(3-Chloro-phenyl)-pyridine-2-carboxylic acid (1-ethyl-1-hydroxymethyl-propyl)-amide;
6-(3-Chloro-phenyl)-pyridine-2-carboxylic acid (tetrahydro-pyran-3-yl)-amide
(6-Cyclopropylmethoxy-5-pyrrolidin-1-yl-pyridin-2-yl)-(2-oxa-6-aza-spiro[3.3]hept-6-yl)-methanone;
6-Cyclopropylmethoxy-5-(2-methyl-pyrrolidin-1-yl)-pyridine-2-carboxylic acid ((S)-1-carbamoyl-3-methyl-butyl)-amide;
6-Cyclopropylmethoxy-5-pyrrolidin-1-yl-pyridine-2-carboxylic acid [1-methyl-1-(5-methyl-[1,2,4]oxadiazol-3-yl)-ethyl]-amide;
6-Cyclopropylmethoxy-5-(tetrahydro-pyran-4-yl)-pyridine-2-carboxylic acid (1-methyl-1-thiazol-2-yl-ethyl)-amide;
6-Cyclopropylmethoxy-5-pyrrolidin-1-yl-pyridine-2-carboxylic acid (1,1-dimethyl-3-morpholin-4-yl-propyl)-amide;
6-Cyclopropylmethoxy-5-methyl-pyridine-2-carboxylic acid (1-methyl-1-methylcarbamoyl-ethyl)-amide;
6-(Tetrahydro-pyran-4-yl)-pyridine-2-carboxylic acid piperidin-1-ylamide;
6-(3-Chloro-phenyl)-pyridine-2-carboxylic acid [(S)-2-cyclopropyl-1-(5-methyl-[1,2,4]oxadiazol-3-yl)-ethyl]-amide;
(5-Cyclopentyl-6-cyclopropylmethoxy-pyridin-2-yl)-(1,1-dioxidotetrahydro-2H-thiopyran-4-yl)-methanone;
5-Cyclopentyl-6-cyclopropylmethoxy-pyridine-2-carboxylic acid (1-methyl-1-methylcarbamoyl-ethyl)-amide;
6-(3-Chloro-phenyl)-pyridine-2-carboxylic acid [1-methyl-1-(5-methyl-[1,2,4]oxadiazol-3-yl)-ethyl]-amide;
5-Cyclopropyl-6-cyclopropylmethoxy-pyridine-2-carboxylic acid piperidin-1-ylamide;
5-Cyclopropyl-6-cyclopropylmethoxy-pyridine-2-carboxylic acid (1-methyl-1-methylcarbamoyl-ethyl)-amide;
5-Cyclopropyl-6-cyclopropylmethoxy-pyridine-2-carboxylic acid (1-methyl-1-thiazol-2-yl-ethyl)-amide;
5-Cyclopropyl-6-cyclopropylmethoxy-pyridine-2-carboxylic acid [1-methyl-1-(5-methyl-[1,2,4]oxadiazol-3-yl)-ethyl]-amide;
6-(4-Chloro-phenyl)-pyridine-2-carboxylic acid piperidin-1-ylamide;
6-Cyclopropylmethoxy-5-methyl-pyridine-2-carboxylic acid piperidin-1-ylamide;
[6-(3-Chloro-phenyl)-5-cyclopropyl-pyridin-2-yl]-(1,1-dioxidotetrahydro-2H-thiopyran-4-yl)-methanone;
6-(3-Chloro-phenyl)-5-methyl-pyridine-2-carboxylic acid (1-methyl-1-oxazol-2-yl-ethyl)-amide;
6-(3-Chloro-phenyl)-5-methyl-pyridine-2-carboxylic acid (1-methyl-1-thiazol-2-yl-ethyl)-amide;

6-(3-Chloro-phenyl)-5-methyl-pyridine-2-carboxylic acid [1-methyl-1-(5-methyl-[1,2,4]oxadiazol-3-yl)-ethyl]-amide;
6-(3-Chloro-phenyl)-5-methyl-pyridine-2-carboxylic acid piperidin-1-ylamide;
5-Cyclopentyl-6-cyclopropylmethoxy-pyridine-2-carboxylic acid [(S)-2-cyclopropyl-1-(5-methyl-[1,2,4]oxadiazol-3-yl)-ethyl]-amide;
5-Cyclopentyl-6-cyclopropylmethoxy-pyridine-2-carboxylic acid [1-methyl-1-(5-methyl-[1,2,4]oxadiazol-3-yl)-ethyl]-amide;
5-Cyclopentyl-6-cyclopropylmethoxy-pyridine-2-carboxylic acid (1-methyl-1-thiazol-2-yl-ethyl)-amide;
6-(3-Chloro-phenyl)-pyridine-2-carboxylic acid ((S)-3-methyl-1-thiazol-2-yl-butyl)-amide;
6-Cyclopropylmethoxy-5-methyl-pyridine-2-carboxylic acid [(S)-2-cyclopropyl-1-(5-methyl-[1,2,4]oxadiazol-3-yl)-ethyl]-amide;
5-Chloro-6-(3-chloro-phenyl)-pyridine-2-carboxylic acid (1-methyl-1-thiazol-2-yl-ethyl)-amide;
6-Cyclopropylmethoxy-5-(tetrahydro-pyran-4-yl)-pyridine-2-carboxylic acid ((S)-2-cyclopropyl-1-thiazol-2-yl-ethyl)-amide;
6-(3-Chloro-phenyl)-pyridine-2-carboxylic acid ((S)-2-cyclopropyl-1-thiazol-2-yl-ethyl)-amide;
6-Cyclopropylmethoxy-5-(2-oxo-pyrrolidin-1-yl)-pyridine-2-carboxylic acid (1-methyl-1-oxazol-2-yl-ethyl)-amide;
6-Cyclopropylmethoxy-5-methyl-pyridine-2-carboxylic acid (1-methyl-1-thiazol-2-yl-ethyl)-amide;
6-Cyclopropylmethoxy-5-pyrrolidin-1-yl-pyridine-2-carboxylic acid [1-(4,5-dihydro-oxazol-2-yl)-1-methyl-ethyl]-amide;
6-Cyclopropylmethoxy-5-methyl-pyridine-2-carboxylic acid ((S)-3-methyl-1-thiazol-2-yl-butyl)-amide;
6-Cyclopropylmethoxy-5-methyl-pyridine-2-carboxylic acid ((S)-2-cyclopropyl-1-thiazol-2-yl-ethyl)-amide;
5-Chloro-6-(3-chloro-phenyl)-pyridine-2-carboxylic acid piperidin-1-ylamide;
6-(3-Chloro-phenyl)-5-cyclopropyl-pyridine-2-carboxylic acid (1-methyl-1-methylcarbamoyl-ethyl)-amide;
6-Cyclopropylmethoxy-pyridine-2-carboxylic acid piperidin-1-ylamide;
6-Cyclopropylmethoxy-5-(3,3-difluoro-azetidin-1-yl)-pyridine-2-carboxylic acid (1-methyl-1-thiazol-2-yl-ethyl)-amide;
6-(3-Chloro-phenyl)-5-methyl-pyridine-2-carboxylic acid (1-ethyl-1-methylcarbamoyl-propyl)-amide;
6-(3-Chloro-phenyl)-5-cyclopropyl-pyridine-2-carboxylic acid (1-ethyl-1-methylcarbamoyl-propyl)-amide;
6-(3-Chloro-phenyl)-pyridine-2-carboxylic acid (1-methyl-1-[1,2,4]oxadiazol-3-yl-ethyl)-amide;
5-Cyclopropyl-6-cyclopropylmethoxy-pyridine-2-carboxylic acid (1-methyl-1-[1,2,4]oxadiazol-3-yl-ethyl)-amide;
5-Cyclopropyl-6-cyclopropylmethoxy-pyridine-2-carboxylic acid (1-ethyl-1-methylcarbamoyl-propyl)-amide;
6-Cyclopropylmethoxy-5-(3-hydroxy-azetidin-1-yl)-pyridine-2-carboxylic acid (1-methyl-1-thiazol-2-yl-ethyl)-amide;
6-(4-Chloro-phenyl)-pyridine-2-carboxylic acid (1-ethyl-1-methylcarbamoyl-propyl)-amide;
6-(Cyclopropylmethoxy)-5-(1,1-dioxido-1,2-isothiazolidin-2-yl)-N-[2-(1,3-thiazol-2-yl)propan-2-yl]pyridine-2-carboxamide;
6-Cyclopropylmethoxy-5-(3,3-difluoro-pyrrolidin-1-yl)-pyridine-2-carboxylic acid (1-ethyl-1-methylcarbamoyl-propyl)-amide;
[6-Cyclopropylmethoxy-5-(3,3-difluoro-pyrrolidin-1-yl)-pyridin-2-yl]-(1,1-dioxidotetrahydro-2H-thiopyran-4-yl)-methanone;
6-Cyclopropylmethoxy-5-(3,3-difluoro-pyrrolidin-1-yl)-pyridine-2-carboxylic acid (1-methyl-1-methylcarbamoyl-ethyl)-amide;
6-(3-Chloro-phenyl)-5-methoxy-pyridine-2-carboxylic acid (1-ethyl-1-methylcarbamoyl-propyl)-amide;
6-(3-Chloro-phenyl)-5-methoxy-pyridine-2-carboxylic acid (1-methyl-1-thiazol-2-yl-ethyl)-amide;
5-Chloro-6-cyclopropylmethoxy-pyridine-2-carboxylic acid (1-methyl-1-[1,2,4]oxadiazol-3-yl-ethyl)-amide;
6-Cyclohexyl-pyridine-2-carboxylic acid (2-hydroxy-cyclohexyl)-amide;
6-Cyclopropylmethoxy-5-(tetrahydro-pyran-4-yl)-pyridine-2-carboxylic acid (1-ethyl-1-methylcarbamoyl-propyl)-amide;
6-Cyclopropylmethoxy-5-(3,3-difluoro-azetidin-1-yl)-pyridine-2-carboxylic acid (1-ethyl-1-methylcarbamoyl-propyl)-amide;
6-Cyclopropylmethoxy-5-(3,3-difluoro-azetidin-1-yl)-pyridine-2-carboxylic acid (1-methyl-1-methylcarbamoyl-ethyl)-amide;
5-Chloro-6-(3-chloro-phenyl)-pyridine-2-carboxylic acid (1-methyl-1-[1,2,4]oxadiazol-3-yl-ethyl)-amide;
6-(3-Chloro-phenyl)-5-methoxy-pyridine-2-carboxylic acid [1-methyl-1-(5-methyl-[1,2,4]oxadiazol-3-yl)-ethyl]-amide;
6-(3-Chloro-phenyl)-5-methoxy-pyridine-2-carboxylic acid (1-methyl-1-oxazol-2-yl-ethyl)-amide;
5-Chloro-6-(3-chloro-phenyl)-pyridine-2-carboxylic acid (1-ethyl-1-methylcarbamoyl-propyl)-amide;
2-[(6-Cyclohexyl-pyridine-2-carbonyl)-amino]-cyclohexanecarboxylic acid methyl ester;
6-Cyclopropylmethoxy-5-(tetrahydro-pyran-4-yl)-pyridine-2-carboxylic acid (1-methyl-1-oxazol-2-yl-ethyl)-amide;
6-Cyclopentyl-pyridine-2-carboxylic acid piperidin-1-ylamide;
6-(3-Chloro-phenyl)-5-cyclopropyl-pyridine-2-carboxylic acid (1-methyl-1-oxazol-2-yl-ethyl)-amide;
6-(3-Chloro-phenyl)-5-cyclopropyl-pyridine-2-carboxylic acid [1-methyl-1-(5-methyl-[1,2,4]oxadiazol-3-yl)-ethyl]-amide;
6-(3-Chloro-phenyl)-5-cyclopropyl-pyridine-2-carboxylic acid ((S)-1-carbamoyl-2-cyclopropyl-ethyl)-amide;
5-Cyclopropyl-6-cyclopropylmethoxy-pyridine-2-carboxylic acid ((S)-1-carbamoyl-2-cyclopropyl-ethyl)-amide;
5-Cyclopropyl-6-cyclopropylmethoxy-pyridine-2-carboxylic acid ((S)-2-cyclopropyl-1-thiazol-2-yl-ethyl)-amide;
5-Cyclopropyl-6-cyclopropylmethoxy-pyridine-2-carboxylic acid ((S)-1-carbamoyl-3-methyl-butyl)-amide;
6-(3-Chloro-phenyl)-5-(tetrahydro-furan-3-yl)-pyridine-2-carboxylic acid (1-methyl-1-thiazol-2-yl-ethyl)-amide;
6-Cyclopropylmethoxy-5-(3,3-difluoro-azetidin-1-yl)-pyridine-2-carboxylic acid [1-methyl-1-(5-methyl-[1,2,4]oxadiazol-3-yl)-ethyl]-amide;
6-Cyclopropylmethoxy-5-(3,3-difluoro-azetidin-1-yl)-pyridine-2-carboxylic acid ((S)-1-carbamoyl-2-cyclopropyl-ethyl)-amide;
5-Chloro-6-(3-chloro-phenyl)-pyridine-2-carboxylic acid (1-methyl-1-oxazol-2-yl-ethyl)-amide;
5-Chloro-6-(3-chloro-phenyl)-pyridine-2-carboxylic acid ((S)-1-carbamoyl-3-methyl-butyl)-amide;
6-(3-Chloro-phenyl)-5-cyclopentyl-pyridine-2-carboxylic acid [1-methyl-1-(5-methyl-[1,2,4]oxadiazol-3-yl)-ethyl]-amide;

5-Cyclopentyl-6-cyclopropylmethoxy-pyridine-2-carboxylic acid ((S)-1-carbamoyl-2-cyclopropyl-ethyl)-amide;
5-Chloro-6-cyclopropylmethoxy-pyridine-2-carboxylic acid [1-methyl-1-(5-methyl-[1,2,4]oxadiazol-3-yl)-ethyl]-amide;
5-Chloro-6-cyclopropylmethoxy-pyridine-2-carboxylic acid (1-ethyl-1-methylcarbamoyl-propyl)-amide;
5-Bromo-6-cyclopropylmethoxy-pyridine-2-carboxylic acid ((S)-1-carbamoyl-2-cyclopropyl-ethyl)-amide;
5-Cyclopentyl-6-cyclopropylmethoxy-pyridine-2-carboxylic acid (1-ethyl-1-methylcarbamoyl-propyl)-amide;
6-Cyclopropylmethoxy-5-(3,3-difluoro-pyrrolidin-1-yl)-pyridine-2-carboxylic acid ((S)-1-carbamoyl-2-cyclopropyl-ethyl)-amide;
6-Cyclopropylmethoxy-5-trifluoromethyl-pyridine-2-carboxylic acid ((S)-1-carbamoyl-2-cyclopropyl-ethyl)-amide;
6-Cyclopropylmethoxy-5-(tetrahydro-furan-3-yl)-pyridine-2-carboxylic acid ((S)-1-carbamoyl-3-methyl-butyl)-amide;
6-Cyclopropylmethoxy-5-(tetrahydro-furan-2-yl)-pyridine-2-carboxylic acid ((S)-1-carbamoyl-3-methyl-butyl)-amide;
6-(3-Chloro-phenyl)-5-cyclopropyl-pyridine-2-carboxylic acid (1-methyl-1-thiazol-2-yl-ethyl)-amide;
5-Cyclopropyl-6-cyclopropylmethoxy-pyridine-2-carboxylic acid [2-(2-methoxy-ethoxy)-1,1-dimethyl-ethyl]-amide;
6-Cyclopropylmethoxy-5-trifluoromethyl-pyridine-2-carboxylic acid ((S)-1-carbamoyl-3-methyl-butyl)-amide;
6-Cyclopropylmethoxy-5-trifluoromethyl-pyridine-2-carboxylic acid (1-methyl-1-[1,2,4]oxadiazol-3-yl-ethyl)-amide;
6-Cyclopropylmethoxy-5-trifluoromethyl-pyridine-2-carboxylic acid [1-methyl-1-(5-methyl-[1,2,4]oxadiazol-3-yl)-ethyl]-amide;
6-Cyclopropylmethoxy-5-trifluoromethyl-pyridine-2-carboxylic acid (1-methyl-1-thiazol-2-yl-ethyl)-amide;
6-Cyclohexyl-pyridine-2-carboxylic acid (2-hydroxymethyl-cyclohexyl)-amide;
6-Cyclopropylmethoxy-5-(tetrahydro-furan-2-yl)-pyridine-2-carboxylic acid [1-methyl-1-(5-methyl-[1,2,4]oxadiazol-3-yl)-ethyl]-amide;
6-Cyclopropylmethoxy-5-(tetrahydro-furan-3-yl)-pyridine-2-carboxylic acid [1-methyl-1-(5-methyl-[1,2,4]oxadiazol-3-yl)-ethyl]-amide;
6-(3-Chloro-phenyl)-5-(tetrahydro-furan-2-yl)-pyridine-2-carboxylic acid [1-methyl-1-(5-methyl-[1,2,4]oxadiazol-3-yl)-ethyl]-amide;
6-(3-Chloro-phenyl)-5-(tetrahydro-furan-2-yl)-pyridine-2-carboxylic acid (1-methyl-1-oxazol-2-yl-ethyl)-amide;
6-(3-Chloro-phenyl)-5-(tetrahydro-furan-2-yl)-pyridine-2-carboxylic acid (1-methyl-1-thiazol-2-yl-ethyl)-amide;
6-(3-Chloro-phenyl)-5-cyclopentyl-pyridine-2-carboxylic acid (1-methyl-1-thiazol-2-yl-ethyl)-amide;
6-Cyclopropylmethoxy-5-trifluoromethyl-pyridine-2-carboxylic acid (1-methyl-1-oxazol-2-yl-ethyl)-amide;
6-Cyclopropylmethoxy-5-methyl-pyridine-2-carboxylic acid ((S)-1-carbamoyl-2-cyclopropyl-ethyl)-amide;
6-Cyclopropylmethoxy-5-(3-hydroxy-azetidin-1-yl)-pyridine-2-carboxylic acid ((S)-1-carbamoyl-3-methyl-butyl)-amide;
6-Cyclopropylmethoxy-5-(3,3-difluoro-azetidin-1-yl)-pyridine-2-carboxylic acid ((S)-1-carbamoyl-3-methyl-butyl)-amide;
5-Cyclopropylamino-6-cyclopropylmethoxy-pyridine-2-carboxylic acid ((S)-1-carbamoyl-2-cyclopropyl-ethyl)-amide;
5-Cyclopropylamino-6-cyclopropylmethoxy-pyridine-2-carboxylic acid ((S)-1-carbamoyl-3-methyl-butyl)-amide;
6-Cyclopropylmethoxy-5-(3,3-difluoro-azetidin-1-yl)-pyridine-2-carboxylic acid ((S)-1-cyclopropylmethyl-2-hydroxy-2-methyl-propyl)-amide;
6-Cyclopropylmethoxy-5-(tetrahydro-furan-3-yl)-pyridine-2-carboxylic acid ((S)-1-carbamoyl-2-cyclopropyl-ethyl)-amide;
6-Cyclopropylmethoxy-5-(3,3-difluoro-azetidin-1-yl)-pyridine-2-carboxylic acid (2-hydroxy-cyclohexyl)-amide;
6-Cyclopropylmethoxy-5-(3,3-difluoro-azetidin-1-yl)-pyridine-2-carboxylic acid [(S)-2-cyclopropyl-1-(5-methyl-[1,2,4]oxadiazol-3-yl)-ethyl]-amide;
5-Cyclopropyl-6-cyclopropylmethoxy-pyridine-2-carboxylic acid ((S)-1-cyclopropylmethyl-2-hydroxy-2-methyl-propyl)-amide;
6-(3-Chloro-phenyl)-5-(3,3-difluoro-azetidin-1-yl)-pyridine-2-carboxylic acid ((S)-1-carbamoyl-3-methyl-butyl)-amide;
6-Cyclopropylmethoxy-5-(tetrahydro-furan-3-yl)-pyridine-2-carboxylic acid (2-hydroxy-1,1-dimethyl-ethyl)-amide;
5-Cyclopropyl-6-(2-methoxy-ethoxy)-pyridine-2-carboxylic acid ((S)-1-carbamoyl-3-methyl-butyl)-amide;
7,7-Dimethyl-5,6,7,8-tetrahydro-quinoline-2-carboxylic acid ((R)-2-cyclopropyl-2-hydroxy-propyl)-amide;
7,7-Dimethyl-N-(2-(5-methyl-1,2,4-oxadiazol-3-yl)propan-2-yl)-5,6,7,8-tetrahydroquinoline-2-carboxamide;
N-(1-Hydroxy-2-methylpropan-2-yl)-7,7-dimethyl-5,6,7,8-tetrahydroquinoline-2-carboxamide;
6-Cyclopropylmethoxy-5-(3,3-difluoro-azetidin-1-yl)-pyridine-2-carboxylic acid ((S)-2-cyclopropyl-1-thiazol-2-yl-ethyl)-amide;
6-Cyclopropylmethoxy-5-(3,3-difluoro-azetidin-1-yl)-pyridine-2-carboxylic acid (pyridin-2-ylmethyl)-amide;
6-Cyclopropylmethoxy-5-(3,3-difluoro-azetidin-1-yl)-pyridine-2-carboxylic acid (2-hydroxy-1,1-dimethyl-ethyl)-amide;
[6-Cyclopropylmethoxy-5-(3,3-difluoro-azetidin-1-yl)-pyridin-2-yl]-((S)-2-hydroxymethyl-pyrrolidin-1-yl)-methanone;
6-Cyclopropylmethoxy-5-(3-hydroxy-oxetan-3-yl)-pyridine-2-carboxylic acid ((S)-1-carbamoyl-3-methyl-butyl)-amide;
6-(3-Chloro-phenyl)-5-(tetrahydro-furan-3-yl)-pyridine-2-carboxylic acid [1-methyl-1-(5-methyl-[1,2,4]oxadiazol-3-yl)-ethyl]-amide;
6-(3-Chloro-phenyl)-5-(3,3-difluoro-azetidin-1-yl)-pyridine-2-carboxylic acid [2-(2-methoxy-ethoxy)-1,1-dimethyl-ethyl]-amide;
5-Cyclopropyl-6-(2-methoxy-ethoxy)-pyridine-2-carboxylic acid [1-methyl-1-(5-methyl-[1,2,4]oxadiazol-3-yl)-ethyl]-amide;
5-Cyclopropyl-6-cyclopropylmethoxy-pyridine-2-carboxylic acid (1,1-dimethyl-3-morpholin-4-yl-propyl)-amide;
5-Cyclopropyl-6-(4-fluoro-benzyl)-pyridine-2-carboxylic acid ((S)-1-carbamoyl-3-methyl-butyl)-amide;
6-(3-Chloro-phenyl)-5-(3,3-difluoro-azetidin-1-yl)-pyridine-2-carboxylic acid (1-methyl-1-thiazol-2-yl-ethyl)-amide;
6-Cyclopropylmethoxy-5-(3,3-difluoro-azetidin-1-yl)-pyridine-2-carboxylic acid [(S)-2-cyclopropyl-1-(2-methoxy-ethoxymethyl)-ethyl]-amide;

5-(3,3-Difluoro-azetidin-1-yl)-6-(2-methoxy-ethoxy)-pyridine-2-carboxylic acid ((S)-1-carbamoyl-3-methyl-butyl)-amide;

5-Cyclopropylamino-6-cyclopropylmethoxy-pyridine-2-carboxylic acid (2-hydroxy-1,1-dimethyl-ethyl)-amide;

6-Cyclopropylmethoxy-5-(1-hydroxy-cyclobutyl)-pyridine-2-carboxylic acid [1-methyl-1-(5-methyl-[1,2,4]oxadiazol-3-yl)-ethyl]-amide;

5-Cyclopropyl-6-(2-methoxy-ethoxy)-pyridine-2-carboxylic acid ((S)-1-carbamoyl-2-cyclopropyl-ethyl)-amide;

5-[Bis-(2,2,2-trifluoro-ethyl)-amino]-6-cyclopropylmethoxy-pyridine-2-carboxylic acid ((S)-1-carbamoyl-2-cyclopropyl-ethyl)-amide;

5-Cyclopropyl-6-cyclopropylmethoxy-pyridine-2-carboxylic acid [(S)-2-cyclopropyl-1-(5-methyl-[1,2,4]oxadiazol-3-yl)-ethyl]-amide;

6-(3-Chloro-phenyl)-5-(3,3-difluoro-azetidin-1-yl)-pyridine-2-carboxylic acid [(S)-2-cyclopropyl-1-(5-methyl-[1,2,4]oxadiazol-3-yl)-ethyl]-amide;

5-[Bis-(2,2,2-trifluoro-ethyl)-amino]-6-cyclopropylmethoxy-pyridine-2-carboxylic acid (1-ethyl-1-methylcarbamoyl-propyl)-amide;

5-Cyclopropyl-6-(tetrahydro-furan-2-ylmethoxy)-pyridine-2-carboxylic acid [1-methyl-1-(5-methyl-[1,2,4]oxadiazol-3-yl)-ethyl]-amide; *

N-(2-Cyanopropan-2-yl)-5-cyclopropyl-6-(cyclopropylmethoxy)picolinamide;

(S)-5-Cyclopropyl-6-(cyclopropylmethoxy)-N-(3,3-dimethyl-1-(methylamino)-1-oxobutan-2-yl)picolinamide;

N-(1-Amino-2,3-dimethyl-1-oxobutan-2-yl)-5-cyclopropyl-6-(cyclopropylmethoxy)picolinamide;

N-(1-Amino-2-methyl-1-oxobutan-2-yl)-5-cyclopropyl-6-(cyclopropylmethoxy) picolinamide;

5-Cyclopropyl-6-(cyclopropylmethoxy)-N-(1-(5-methyl-1,2,4-oxadiazol-3-yl)cyclobutyl)picolinamide;

(S)-N-(2-Amino-2-oxo-1-phenylethyl)-5-cyclopropyl-6-(cyclopropylmethoxy) picolinamide;

(R)-N-(2-Amino-2-oxo-1-phenylethyl)-5-cyclopropyl-6-(cyclopropylmethoxy)picolinamide;

(R)-5-Cyclopropyl-6-(cyclopropylmethoxy)-N-(1-hydroxy-4-methylpentan-2-yl)picolinamide;

5-Cyclopropyl-6-(cyclopropylmethoxy)-N-(1-(hydroxymethyl)cyclopentyl)picolinamide;

5-Cyclopropyl-6-(cyclopropylmethoxy)-N-(2-(3-methyl-1,2,4-oxadiazol-5-yl)propan-2-yl)picolinamide;

5-Bromo-6-(4-fluoro-phenoxy)-pyridine-2-carboxylic acid ((S)-1-carbamoyl-3-methyl-butyl)-amide;

N-(1-Amino-2,4-dimethyl-1-oxopentan-2-yl)-5-cyclopropyl-6-(cyclopropylmethoxy)picolinamide;

N-(1-Amino-3,3-dimethyl-1-oxobutan-2-yl)-5-cyclopropyl-6-(cyclopropylmethoxy)picolinamide;

5-Cyclopropyl-6-cyclopropylmethoxy-pyridine-2-carboxylic acid (4-carbamoyl-tetrahydro-pyran-4-yl)-amide;

(S)-5-Cyclopropyl-6-(cyclopropylmethoxy)-N-(4-methyl-1-(methylamino)-1-oxopentan-2-yl)picolinamide;

(S)-5-Cyclopropyl-6-(cyclopropylmethoxy)-N-(4,4-dimethyl-1-(methylamino)-1-oxopentan-2-yl)picolinamide;

5-Cyclopropyl-N-((S)-3,3-dimethyl-1-(methylamino)-1-oxobutan-2-yl)-6-((tetrahydrofuran-2-yl)methoxy)picolinamide;

5-Cyclopropyl-N-((S)-4-methyl-1-(methylamino)-1-oxopentan-2-yl)-6-((tetrahydrofuran-2-yl)methoxy)picolinamide;

5-Cyclopropyl-N-((S)-4,4-dimethyl-1-(methylamino)-1-oxopentan-2-yl)-6-((tetrahydrofuran-2-yl)methoxy)picolinamide;

N-((S)-1-Amino-4-methyl-1-oxopentan-2-yl)-5-cyclopropyl-6-((tetrahydrofuran-2-yl)methoxy)picolinamide;

5-Cyclopropyl-6-(4-fluoro-phenoxy)-pyridine-2-carboxylic acid ((S)-1-carbamoyl-3-methyl-butyl)-amide;

5-Bromo-6-(tetrahydro-furan-2-ylmethoxy)-pyridine-2-carboxylic acid ((S)-2,2-dimethyl-1-methylcarbamoyl-propyl)-amide;

5-Cyclopropyl-N-(1-(5-methyl-1,2,4-oxadiazol-3-yl)cyclobutyl)-6-(pyridin-2-ylmethoxy)picolinamide;

5-Cyclopropyl-N-(cyclopropyl(5-methyl-1,2,4-oxadiazol-3-yl)methyl)-6-(cyclopropylmethoxy)picolinamide;

5-Cyclopropyl-6-cyclopropylmethoxy-pyridine-2-carboxylic acid ((R)-1-hydroxymethyl-1,2-dimethyl-propyl)-amide;

(S)-6-(3-Chlorophenyl)-N-(3,3-dimethyl-1-(methylamino)-1-oxobutan-2-yl)picolinamide;

(S)-6-(3-Chlorophenyl)-N-(4,4-dimethyl-1-(methylamino)-1-oxopentan-2-yl)picolinamide;

5-Cyclopropyl-6-(cyclopropylmethoxy)-N-(4-hydroxy-2-methylbutan-2-yl)picolinamide;

(S)-5-Cyclopropyl-N-(3,3-dimethyl-1-(methylamino)-1-oxobutan-2-yl)-6-((tetrahydro-2H-pyran-4-yl)methoxy)picolinamide;

(S)-5-Cyclopropyl-N-(4,4-dimethyl-1-(methylamino)-1-oxopentan-2-yl)-6-((tetrahydro-2H-pyran-4-yl)methoxy)picolinamide;

(−)-5-Cyclopropyl-6-cyclopropylmethoxy-pyridine-2-carboxylic acid [cyclopropyl-(5-methyl-[1,2,4]oxadiazol-3-yl)-methyl]-amide;

(+)-5-Cyclopropyl-6-cyclopropylmethoxy-pyridine-2-carboxylic acid [cyclopropyl-(5-methyl-[1,2,4]oxadiazol-3-yl)-methyl]-amide;

5-Cyclopropyl-N-(2-(5-methyl-1,2,4-oxadiazol-3-yl)propan-2-yl)-6-(pyridin-2-ylmethoxy)picolinamide;

(S)-N-(1-Amino-4-methyl-1-oxopentan-2-yl)-5-cyclopropyl-6-(pyridin-2-ylmethoxy)picolinamide;

(S)-5-Cyclopropyl-N-(3,3-dimethyl-1-(methylamino)-1-oxobutan-2-yl)-6-(pyridin-2-ylmethoxy)picolinamide;

5-Cyclopropyl-N-(2-(5-methyl-1,2,4-oxadiazol-3-yl)propan-2-yl)-6-((tetrahydro-2H-pyran-4-yl)methoxy)picolinamide;

(S)-5-Cyclopropyl-N-(4-methyl-1-(methylamino)-1-oxopentan-2-yl)-6-((tetrahydro-2H-pyran-4-yl)methoxy)picolinamide;

(S)-N-(3,3-Dimethyl-1-(methylamino)-1-oxobutan-2-yl)-6-phenylpicolinamide;

(S)-N-(4-Methyl-1-(methylamino)-1-oxopentan-2-yl)-6-phenylpicolinamide;

5-(3,3-Difluoroazetidin-1-yl)-N-((S)-3,3-dimethyl-1-(methylamino)-1-oxobutan-2-yl)-6-((tetrahydrofuran-2-yl)methoxy)picolinamide;

2-(6-(Cyclopropylmethoxy)-5-(3,3-difluoroazetidin-1-yl)picolinamido)-2-ethylbutanoic acid;

(S)-6-(Cyclopropylmethoxy)-5-(3,3-difluoroazetidin-1-yl)-N-(3,3-dimethyl-1-(methylamino)-1-oxobutan-2-yl)picolinamide;

(S)-6-(Cyclopropylmethoxy)-5-(3,3-difluoroazetidin-1-yl)-N-(4,4-dimethyl-1-(methylamino)-1-oxopentan-2-yl)picolinamide;

(S)-6-(3-Fluorophenyl)-N-(4-methyl-1-(methylamino)-1-oxopentan-2-yl) picolinamide;

(S)-N-(4-Methyl-1-(methylamino)-1-oxopentan-2-yl)-6-(3-(trifluoromethyl)phenyl)picolinamide;

(S)-6-(3-Chloro-4-fluorophenyl)-N-(4-methyl-1-(methylamino)-1-oxopentan-2-yl)picolinamide;

(S)-N-(3,3-Dimethyl-1-(methylamino)-1-oxobutan-2-yl)-6-(3-fluorophenyl) picolinamide;

(S)-N-(3,3-Dimethyl-1-(methylamino)-1-oxobutan-2-yl)-6-(3-(trifluoromethyl)phenyl)picolinamide;

(S)-N-(3,3-Dimethyl-1-(methylamino)-1-oxobutan-2-yl)-6-(3-methoxyphenyl) picolinamide;

(S)-6-(3-Chloro-4-fluorophenyl)-N-(3,3-dimethyl-1-(methylamino)-1-oxobutan-2-yl)picolinamide;

(S)-5-Cyclopropyl-6-(cyclopropylmethoxy)-N-(2,2,2-trifluoro-1-(pyridin-3-yl)ethyl)picolinamide; and (R)-5-Cyclopropyl-6-(cyclopropylmethoxy)-N-(2,2,2-trifluoro-1-(pyridin-3-yl)ethyl)picolinamide;

Further particular compounds of formula (I) are selected from the group consisting of:

6-Cyclopropylmethoxy-5-(tetrahydro-pyran-4-yl)-pyridine-2-carboxylic acid [1-methyl-1-(5-methyl-[1,2,4]oxadiazol-3-yl)-ethyl]-amide;

6-(3-Chloro-phenyl)-pyridine-2-carboxylic acid piperidin-1-ylamide;

6-Cyclopropylmethoxy-5-pyrrolidin-1-yl-pyridine-2-carboxylic acid ((S)-1-hydroxymethyl-3-methyl-butyl)-amide;

6-Cyclopropylmethoxy-5-(2-methyl-pyrrolidin-1-yl)-pyridine-2-carboxylic acid ((S)-1-carbamoyl-3-methyl-butyl)-amide;

6-Cyclopropylmethoxy-5-pyrrolidin-1-yl-pyridine-2-carboxylic acid (1,1-dimethyl-3-morpholin-4-yl-propyl)-amide;

5-Cyclopentyl-6-cyclopropylmethoxy-pyridine-2-carboxylic acid (1-methyl-1-methylcarbamoyl-ethyl)-amide;

5-Cyclopropyl-6-cyclopropylmethoxy-pyridine-2-carboxylic acid (1-methyl-1-thiazol-2-yl-ethyl)-amide;

5-Cyclopentyl-6-cyclopropylmethoxy-pyridine-2-carboxylic acid [(S)-2-cyclopropyl-1-(5-methyl-[1,2,4]oxadiazol-3-yl)-ethyl]-amide;

6-Cyclopropylmethoxy-5-methyl-pyridine-2-carboxylic acid ((S)-3-methyl-1-thiazol-2-yl-butyl)-amide;

6-Cyclopropylmethoxy-5-(3,3-difluoro-azetidin-1-yl)-pyridine-2-carboxylic acid (1-methyl-1-thiazol-2-yl-ethyl)-amide;

6-Cyclopropylmethoxy-5-(3,3-difluoro-pyrrolidin-1-yl)-pyridine-2-carboxylic acid (1-ethyl-1-methylcarbamoyl-propyl)-amide;

6-Cyclopropylmethoxy-5-(3,3-difluoro-azetidin-1-yl)-pyridine-2-carboxylic acid (1-ethyl-1-methylcarbamoyl-propyl)-amide;

5-Cyclopropyl-6-cyclopropylmethoxy-pyridine-2-carboxylic acid ((S)-1-carbamoyl-2-cyclopropyl-ethyl)-amide;

5-Cyclopropyl-6-cyclopropylmethoxy-pyridine-2-carboxylic acid ((S)-1-carbamoyl-3-methyl-butyl)-amide;

6-Cyclopropylmethoxy-5-(3,3-difluoro-azetidin-1-yl)-pyridine-2-carboxylic acid ((S)-1-carbamoyl-2-cyclopropyl-ethyl)-amide;

6-Cyclopropylmethoxy-5-(3,3-difluoro-pyrrolidin-1-yl)-pyridine-2-carboxylic acid ((S)-1-carbamoyl-2-cyclopropyl-ethyl)-amide;

6-Cyclopropylmethoxy-5-(tetrahydro-furan-3-yl)-pyridine-2-carboxylic acid ((S)-1-carbamoyl-3-methyl-butyl)-amide;

6-Cyclopropylmethoxy-5-(tetrahydro-furan-2-yl)-pyridine-2-carboxylic acid ((S)-1-carbamoyl-3-methyl-butyl)-amide;

6-Cyclopropylmethoxy-5-trifluoromethyl-pyridine-2-carboxylic acid ((S)-1-carbamoyl-3-methyl-butyl)-amide;

6-Cyclopropylmethoxy-5-(tetrahydro-furan-2-yl)-pyridine-2-carboxylic acid [1-methyl-1-(5-methyl-[1,2,4]oxadiazol-3-yl)-ethyl]-amide;

6-Cyclopropylmethoxy-5-(3,3-difluoro-azetidin-1-yl)-pyridine-2-carboxylic acid ((S)-1-carbamoyl-3-methyl-butyl)-amide;

5-Cyclopropylamino-6-cyclopropylmethoxy-pyridine-2-carboxylic acid ((S)-1-carbamoyl-3-methyl-butyl)-amide;

6-Cyclopropylmethoxy-5-(3,3-difluoro-azetidin-1-yl)-pyridine-2-carboxylic acid ((S)-1-cyclopropylmethyl-2-hydroxy-2-methyl-propyl)-amide;

6-Cyclopropylmethoxy-5-(3,3-difluoro-azetidin-1-yl)-pyridine-2-carboxylic acid ((S)-2-cyclopropyl-1-thiazol-2-yl-ethyl)-amide;

5-Cyclopropyl-6-(4-fluoro-benzyl)-pyridine-2-carboxylic acid ((S)-1-carbamoyl-3-methyl-butyl)-amide;

6-Cyclopropylmethoxy-5-(3,3-difluoro-azetidin-1-yl)-pyridine-2-carboxylic acid [(S)-2-cyclopropyl-1-(2-methoxy-ethoxymethyl)-ethyl]-amide;

5-Cyclopropyl-6-cyclopropylmethoxy-pyridine-2-carboxylic acid [(S)-2-cyclopropyl-1-(5-methyl-[1,2,4]oxadiazol-3-yl)-ethyl]-amide;

5-[Bis-(2,2,2-trifluoro-ethyl)-amino]-6-cyclopropylmethoxy-pyridine-2-carboxylic acid (1-ethyl-1-methylcarbamoyl-propyl)-amide;

(S)-5-Cyclopropyl-6-(cyclopropylmethoxy)-N-(3,3-dimethyl-1-(methylamino)-1-oxobutan-2-yl)picolinamide;

(S)-N-(2-amino-2-oxo-1-phenylethyl)-5-cyclopropyl-6-(cyclopropylmethoxy)picolinamide;

N-((S)-1-amino-4-methyl-1-oxopentan-2-yl)-5-cyclopropyl-6-((tetrahydrofuran-2-yl)methoxy)picolinamide;

5-Cyclopropyl-6-cyclopropylmethoxy-pyridine-2-carboxylic acid ((R)-1-hydroxymethyl-1,2-dimethyl-propyl)-amide;

(S)-5-Cyclopropyl-N-(4,4-dimethyl-1-(methylamino)-1-oxopentan-2-yl)-6-((tetrahydro-2H-pyran-4-yl)methoxy)picolinamide;

(+)-5-Cyclopropyl-6-cyclopropylmethoxy-pyridine-2-carboxylic acid [(SR)-cyclopropyl-(5-methyl-[1,2,4]oxadiazol-3-yl)-methyl]-amide;

2-(6-(Cyclopropylmethoxy)-5-(3,3-difluoroazetidin-1-yl)picolinamido)-2-ethylbutanoic acid;

and (S)-6-(3-Chloro-4-fluorophenyl)-N-(3,3-dimethyl-1-(methylamino)-1-oxobutan-2-yl)picolinamide.

Further particular embodiments of the present invention include:

A compound of formula (I) wherein $R^1$ is selected from the group consisting of: cycloalkyl, cycloalkylalkoxy, haloalkoxy, alkoxyalkoxy, phenyl, halophenyl, haloalkylphenyl, halophenylalkyl, halophenyloxy, piperidinylsulfonyl, tetrahydropyranyl, tetrahydropyranylalkoxy, tetrahydrofuranylalkoxy, pyridinylalkoxy, hydroxyhaloalkyloxy, halophenylhydroxyalkyl, alkylsulfanyl and alkylsulfonyl;

A compound of formula (I) wherein $R^1$ is selected from the group consisting of: cycloalkyl, cycloalkylalkoxy, haloalkoxy, alkoxyalkoxy, halophenyl, halophenylalkyl, alkoxyphenyl, halophenyloxy, piperidinylsulfonyl, tetrahydropyranyl, tetrahydropyranylalkoxy, tetrahydrofuranylalkoxy, hydroxyhaloalkyloxy, halophenylhydroxyalkyl, alkylsulfanyl and alkylsulfonyl;

A compound of formula (I) wherein $R^1$ is selected from the group consisting of: cycloalkylalkoxy, halophenyl, halophenylalkyl, tetrahydropyranylalkoxy, tetrahydrofuranylalkoxy, haloalkoxy, hydroxylhaloalkyloxy, halophenylhydroxyalkyl, alkylsulfanyl or alkylsulfonyl;

A compound of formula (I) wherein $R^1$ is selected from the group consisting of: cyclopropylmethoxy, chlorophenyl, fluorophenylmethyl, fluorochlorophenyl, tetrahydropyranylmethoxy, tetrahydrofuranylmethoxy, pentafluoropopyloxy, trifluorohydroxybutyloxy, fluorophenylhydroxymethyl, butylsulfanyl and butylsulfonyl;

A compound of formula (I) wherein $R^2$ is selected from the group consisting of: hydrogen, halogen, alkyl, haloalkyl, cycloalkyl, hydroxycycloalkyl, alkoxy, haloalkylamino, tetrahydropyranyl, 1H-pyrazolyl, pyrrolidinyl, alkylpyrrolidinyl, halopyrrolidinyl, oxopyrrolidinyl, haloazetidinyl, hydroxyazetidinyl, 1,1-dioxido-2-isothioazolidinyl, tetrahydrofuranyl, cycloalkylamino, hydroxyoxetanyl and 6-oxa-1-aza-spiro[3.3]heptyl;

A compound of formula (I) wherein $R^2$ is selected from the group consisting of: hydrogen, alkyl, haloalkyl, cycloalkyl, haloalkylamino, tetrahydropyranyl, pyrrolidinyl, alkylpyrrolidinyl, halopyrrolidinyl, haloazetidinyl, tetrahydrofuranyl, cycloalkylamino and 6-oxa-1-aza-spiro[3.3]heptyl;

A compound of formula (I) wherein $R^2$ is selected from the group consisting of: hydrogen, methyl, trifluoromethyl, cyclopropyl, cyclopentyl, bis(trifluoroethyl)amino, tetrahydropyranyl, pyrrolidinyl, methylpyrrolidinyl, difluoropyrrolidinyl, difluoroazetidinyl, tetrahydrofuranyl, cyclopropylamino and 6-oxa-1-aza-spiro[3.3]heptyl;

A compound of formula (I) wherein $R^5$ and $R^6$ are each independently selected from the group consisting of: hydrogen, methyl, ethyl, propyl, butyl, pentyl, trifluoromethyl, cyclopropyl, cyclopropylmethyl, phenyl, fluorophenyl and pyridazinyl, or $R^5$ and $R^6$ together with the carbon atom to which they are attached form cyclobutyl, tetrahydropyranyl or cyclopropyl;

A compound of formula (I) wherein $R^9$ is selected from the group consisting of: hydroxyl, cyano, carboxyl, alkoxycarbonyl, alkyl[1,2,4]oxadiazolyl, oxazolyl, thiazolyl, [1,3,4]oxadiazolyl, cycloalkyl, phenyl, pyridinyl, tetrahydropyranyl, alkyl[1,2,4]thiadiazolyl, alkylaminocarbonyl, alkyltetrahydropyranyl, alkylisoxazolyl, aminocarbonyl, morpholinyl, dihydro-oxazolyl, [1,2,4]oxadiazolyl, hydroxycycloalkyl, alkoxycarbonylcycloalkyl, alkoxyalkoxy, hydroxyalkylcycloalkyl, piperidinyl, haloazetidinylcarbonyl, nitro-benzo[1,2,5]oxadiazolyl and alkyl;

A compound of formula (I) wherein $R^9$ is selected from the group consisting of: hydroxyl, carboxyl, alkyl[1,2,4]oxadiazolyl, thiazolyl, alkylaminocarbonyl, aminocarbonyl, morpholinyl, alkoxyalkoxy, piperidinyl, cyano, pyridinyl, haloazetidinylcarbonyl, nitro-benzo[1,2,5]oxadiazolyl, alkoxycarbonyl and alkyl;

A compound of formula (I) wherein $R^9$ is selected from the group consisting of:
hydroxyl, methyl[1,2,4]oxadiazolyl, thiazolyl, methylaminocarbonyl, aminocarbonyl, morpholinyl, methoxymethoxy piperidinyl, cyano, pyridinyl, nitro-benzo[1,2,5]oxadiazolyl, dimethylaminocarbonyl, methoxycarbonyl, N-methyl-N-ethylaminocarbonyl, difluoroazetidinylcarbonyl and methyl;

A compound of formula (I) wherein m is 1; and

A compound of formula (I) wherein n is 0.

The invention further relates to a compound of formula (I) selected from the group consisting of:

5-Cyclopropyl-6-(tetrahydro-pyran-4-ylmethoxy)-pyridine-2-carboxylic acid [cyclopropyl-(5-methyl-[1,2,4]oxadiazol-3-yl)-methyl]-amide;

2-({5-[Bis-(2,2,2-trifluoro-ethyl)-amino]-6-cyclopropylmethoxy-pyridine-2-carbonyl}-amino)-2-ethyl-butyric acid methyl ester;

6-Cyclopropylmethoxy-5-(3,3-difluoro-azetidin-1-yl)-pyridine-2-carboxylic acid [cyclopropyl-(5-methyl-[1,2,4]oxadiazol-3-yl)-methyl]-amide;

5-Cyclopropyl-6-cyclopropylmethoxy-pyridine-2-carboxylic acid ((S)-2-cyclopropyl-1-dimethylcarbamoyl-ethyl)-amide;

5-Cyclopropyl-6-(tetrahydro-pyran-4-ylmethoxy)-pyridine-2-carboxylic acid (2,2,2-trifluoro-1-pyridin-2-yl-ethyl)-amide;

6-Cyclopropylmethoxy-5-(3,3-difluoro-azetidin-1-yl)-pyridine-2-carboxylic acid (2,2,2-trifluoro-1-pyridin-2-yl-ethyl)-amide;

5-Cyclopropyl-6-cyclopropylmethoxy-pyridine-2-carboxylic acid ((−)-methylcarbamoyl-phenyl-methyl)-amide;

5-Cyclopropyl-6-cyclopropylmethoxy-pyridine-2-carboxylic acid ((+)-dimethylcarbamoyl-phenyl-methyl)-amide;

5-Cyclopropyl-6-cyclopropylmethoxy-pyridine-2-carboxylic acid ((−)-dimethylcarbamoyl-phenyl-methyl)-amide;

6-Cyclopropylmethoxy-5-trifluoromethyl-pyridine-2-carboxylic acid ((S)-3,3-dimethyl-1-methylcarbamoyl-butyl)-amide;

6-Cyclopropylmethoxy-5-trifluoromethyl-pyridine-2-carboxylic acid [cyclopropyl-(5-methyl-[1,2,4]oxadiazol-3-yl)-methyl]-amide;

6-(Tetrahydro-pyran-4-ylmethoxy)-5-trifluoromethyl-pyridine-2-carboxylic acid ((S)-3,3-dimethyl-1-methylcarbamoyl-butyl)-amide;

5-Cyclopropyl-6-cyclopropylmethoxy-pyridine-2-carboxylic acid ((S)-1-dimethylcarbamoyl-3-methyl-butyl)-amide;

6-(3-Chloro-4-fluoro-phenyl)-pyridine-2-carboxylic acid [cyclopropyl-(5-methyl-[1,2,4]oxadiazol-3-yl)-methyl]-amide;

2-{[5-Cyclopropyl-6-(tetrahydro-furan-2-ylmethoxy)-pyridine-2-carbonyl]-amino}-2-ethyl-butyric acid methyl ester;

6-Cyclopropylmethoxy-5-(6-oxa-1-aza-spiro[3.3]hept-1-yl)-pyridine-2-carboxylic acid ((S)-3,3-dimethyl-1-methylcarbamoyl-butyl)-amide;

6-Cyclopropylmethoxy-5-(6-oxa-1-aza-spiro[3.3]hept-1-yl)-pyridine-2-carboxylic acid [1-methyl-1-(5-methyl-[1,2,4]oxadiazol-3-yl)-ethyl]-amide;

6-Cyclopropylmethoxy-5-(6-oxa-1-aza-spiro[3.3]hept-1-yl)-pyridine-2-carboxylic acid [cyclopropyl-(5-methyl-[1,2,4]oxadiazol-3-yl)-methyl]-amide;

6-Cyclopropylmethoxy-5-(3,3-difluoro-azetidin-1-yl)-pyridine-2-carboxylic acid ((R)-2,2,2-trifluoro-1-pyridin-3-yl-ethyl)-amide;

2-Ethyl-2-{[6-(tetrahydro-pyran-4-ylmethoxy)-5-trifluoromethyl-pyridine-2-carbonyl]-amino}-butyric acid methyl ester;

(S)-2-[(5-Cyclopropyl-6-cyclopropylmethoxy-pyridine-2-carbonyl)-amino]-3,3-dimethyl-butyric acid methyl ester;

5-Cyclopropyl-6-cyclopropylmethoxy-pyridine-2-carboxylic acid ((S)-2,2,2-trifluoro-1-pyridin-2-yl-ethyl)-amide;

5-Cyclopropyl-6-cyclopropylmethoxy-pyridine-2-carboxylic acid [(−)-1-(5-methyl-[1,2,4]oxadiazol-3-yl)-ethyl]-amide;

5-Cyclopropyl-6-cyclopropylmethoxy-pyridine-2-carboxylic acid [(+)-3-methyl-1-(5-methyl-[1,2,4]oxadiazol-3-yl)-butyl]-amide;

5-Cyclopropyl-6-cyclopropylmethoxy-pyridine-2-carboxylic acid [(−)-3-methyl-1-(5-methyl-[1,2,4]oxadiazol-3-yl)-butyl]-amide;

5-Cyclopropyl-6-cyclopropylmethoxy-pyridine-2-carboxylic acid [(+)-1-(5-methyl-[1,2,4]oxadiazol-3-yl)-propyl]-amide;

5-Cyclopropyl-6-cyclopropylmethoxy-pyridine-2-carboxylic acid [(−)-1-(5-methyl-[1,2,4]oxadiazol-3-yl)-propyl]-amide;

5-Cyclopropyl-6-cyclopropylmethoxy-pyridine-2-carboxylic acid ((−)-cyano-methyl-methyl)-amide;
5-Cyclopropyl-6-cyclopropylmethoxy-pyridine-2-carboxylic acid ((−)-1-cyano-3-methyl-butyl)-amide;
5-Cyclopropyl-6-cyclopropylmethoxy-pyridine-2-carboxylic acid ((+)-cyano-cyclopropyl-methyl)-amide;
2-[(6-Cyclopropylmethoxy-5-trifluoromethyl-pyridine-2-carbonyl)-amino]-2-ethyl-butyric acid methyl ester;
5-Cyclopropyl-6-(tetrahydro-furan-2-ylmethoxy)-pyridine-2-carboxylic acid (1-ethyl-1-methylcarbamoyl-propyl)-amide;
2-[(5-Cyclopropyl-6-cyclopropylmethoxy-pyridine-2-carbonyl)-amino]-2-ethyl-butyric acid methyl ester;
2-[(6-Cyclopropylmethoxy-5-trifluoromethyl-pyridine-2-carbonyl)-amino]-2-ethyl-butyric acid;
6-(Tetrahydro-pyran-4-ylmethoxy)-5-trifluoromethyl-pyridine-2-carboxylic acid (1-ethyl-1-methylcarbamoyl-propyl)-amide;
2-Ethyl-2-{[6-(tetrahydro-furan-2-ylmethoxy)-5-trifluoromethyl-pyridine-2-carbonyl]-amino}-butyric acid ethyl ester;
6-Cyclopropylmethoxy-5-(3,3-difluoro-azetidin-1-yl)-pyridine-2-carboxylic acid (dimethylcarbamoyl-phenyl-methyl)-amide;
6-Cyclopropylmethoxy-5-(3,3-difluoro-azetidin-1-yl)-pyridine-2-carboxylic acid ((S)-2-cyclopropyl-1-dimethylcarbamoyl-ethyl)-amide;
2-[(5-Cyclopropyl-6-cyclopropylmethoxy-pyridine-2-carbonyl)-amino]-2-ethyl-butyric acid ethyl ester;
(S)-3-Cyclopropyl-2-[(5-cyclopropyl-6-cyclopropylmethoxy-pyridine-2-carbonyl)-amino]-propionic acid methyl ester;
6-Cyclopropylmethoxy-5-trifluoromethyl-pyridine-2-carboxylic acid (1-ethyl-1-methylcarbamoyl-propyl)-amide;
6-(3-Chloro-4-fluoro-phenyl)-pyridine-2-carboxylic acid [(−)-cyclopropyl-(5-methyl-[1,2,4]oxadiazol-3-yl)-methyl]-amide;
6-(3-Chloro-4-fluoro-phenyl)-pyridine-2-carboxylic acid [(+)-cyclopropyl-(5-methyl-[1,2,4]oxadiazol-3-yl)-methyl]-amide;
6-(Tetrahydro-pyran-4-ylmethoxy)-5-trifluoromethyl-pyridine-2-carboxylic acid (1-dimethylcarbamoyl-1-ethyl-propyl)-amide;
2-{[6-Cyclopropylmethoxy-5-(6-oxa-1-aza-spiro[3.3]hept-1-yl)-pyridine-2-carbonyl]-amino}-2-ethyl-butyric acid ethyl ester;
6-(Tetrahydro-furan-2-ylmethoxy)-5-trifluoromethyl-pyridine-2-carboxylic acid (1-dimethylcarbamoyl-1-ethyl-propyl)-amide;
2-[(5-Bromo-6-cyclopropylmethoxy-pyridine-2-carbonyl)-amino]-2-ethyl-butyric acid ethyl ester;
2-{[6-Cyclopropylmethoxy-5-(3,3-difluoro-azetidin-1-yl)-pyridine-2-carbonyl]-amino}-2-ethyl-butyric acid ethyl ester;
6-(4-Chloro-3-fluoro-phenyl)-pyridine-2-carboxylic acid [1-methyl-1-(5-methyl-[1,2,4]oxadiazol-3-yl)-ethyl]-amide;
6-(3-Chloro-4-fluoro-phenyl)-pyridine-2-carboxylic acid [1-methyl-1-(5-methyl-[1,2,4]oxadiazol-3-yl)-ethyl]-amide;
2-{[6-Cyclopropylmethoxy-5-(3,3-difluoro-2-oxo-azetidin-1-yl)-pyridine-2-carbonyl]-amino}-2-ethyl-butyric acid methyl ester;
(S)-2-[(5-Cyclopropyl-6-cyclopropylmethoxy-pyridine-2-carbonyl)-amino]-4-methyl-pentanoic acid methyl ester;
6-Cyclopropylmethoxy-5-(3,3-difluoro-azetidin-1-yl)-pyridine-2-carboxylic acid (1-cyano-3-methyl-butyl)-amide;
6-Cyclopropylmethoxy-5-(3,3-difluoro-azetidin-1-yl)-pyridine-2-carboxylic acid [3-methyl-1-(5-methyl-[1,2,4]oxadiazol-3-yl)-butyl]-amide;
6-Cyclopropylmethoxy-5-(3,3-difluoro-azetidin-1-yl)-pyridine-2-carboxylic acid (1-hydroxymethyl-1,3-dimethyl-butyl)-amide;
5-Cyclopropyl-6-cyclopropylmethoxy-pyridine-2-carboxylic acid [1-(azetidine-1-carbonyl)-1-ethyl-propyl]-amide;
5-Cyclopropyl-6-cyclopropylmethoxy-pyridine-2-carboxylic acid [1-ethyl-1-(2-methoxy-ethylcarbamoyl)-propyl]-amide;
5-Cyclopropyl-6-cyclopropylmethoxy-pyridine-2-carboxylic acid [1-ethyl-1-(ethyl-methyl-carbamoyl)-propyl]-amide;
6-(4-Fluoro-benzyl)-pyridine-2-carboxylic acid ((S)-1-carbamoyl-3-methyl-butyl)-amide;
6-(4-Fluoro-benzyl)-pyridine-2-carboxylic acid ((R)-2,2,2-trifluoro-1-pyridin-2-yl-ethyl)-amide;
5-Cyclopropyl-6-cyclopropylmethoxy-pyridine-2-carboxylic acid ((S)-1-hydroxymethyl-1,2-dimethyl-propyl)-amide;
5-Bromo-6-(3-methyl-oxetan-3-ylmethoxy)-pyridine-2-carboxylic acid (1-methyl-1-thiazol-2-yl-ethyl)-amide;
5-Bromo-6-(3-methyl-oxetan-3-ylmethoxy)-pyridine-2-carboxylic acid (3-thiazol-2-yl-oxetan-3-yl)-amide;
5-Bromo-6-(2,2,2-trifluoro-ethoxy)-pyridine-2-carboxylic acid (3-thiazol-2-yl-oxetan-3-yl)-amide;
5-Bromo-6-(3-methyl-oxetan-3-ylmethoxy)-pyridine-2-carboxylic acid (2,2,2-trifluoro-1-pyridin-2-yl-ethyl)-amide;
5-Cyclopropyl-6-cyclopropylmethoxy-pyridine-2-carboxylic acid [1-(cyclopropylmethyl-carbamoyl)-1-ethyl-propyl]-amide;
5-Cyclopropyl-6-cyclopropylmethoxy-pyridine-2-carboxylic acid (1-methyl-1-pyridin-2-yl-ethyl)-amide;
6-(4-Fluoro-benzyl)-pyridine-2-carboxylic acid ((S)-3,3-dimethyl-1-methylcarbamoyl-butyl)-amide;
5-Cyclopropyl-6-cyclopropylmethoxy-pyridine-2-carboxylic acid [1-(3,3-difluoro-azetidine-1-carbonyl)-1-ethyl-propyl]-amide;
5-(3,3-Difluoro-azetidin-1-yl)-6-(2,2,2-trifluoro-ethoxy)-pyridine-2-carboxylic acid (1-methyl-1-thiazol-2-yl-ethyl)-amide;
2-[(6-Cyclopropylmethoxy-5-pyrrolidin-1-yl-pyridine-2-carbonyl)-amino]-2-ethyl-butyric acid ethyl ester;
6-Cyclopropylmethoxy-5-(3,3-difluoro-azetidin-1-yl)-pyridine-2-carboxylic acid (1-methyl-5-oxo-pyrrolidin-3-yl)-amide;
2-[(6-Cyclopropylmethoxy-5-pyrrolidin-1-yl-pyridine-2-carbonyl)-amino]-2-ethyl-butyric acid;
6-Cyclopropylmethoxy-5-(3,3-difluoro-azetidin-1-yl)-pyridine-2-carboxylic acid (1,1-dioxo-tetrahydro-1$\lambda^6$-thiophen-3-yl)-amide;
6-Cyclopropylmethoxy-5-(3,3-difluoro-azetidin-1-yl)-pyridine-2-carboxylic acid N'-(1,1-dioxo-tetrahydro-1$\lambda^6$-thiophen-3-yl)-hydrazide;
5-Cyclopropyl-6-cyclopropylmethoxy-pyridine-2-carboxylic acid [1-methyl-1-(4-methyl-thiazol-2-yl)-ethyl]-amide;
5-(3,3-Difluoro-azetidin-1-yl)-6-(3-methyl-oxetan-3-ylmethoxy)-pyridine-2-carboxylic acid (1-methyl-1-thiazol-2-yl-ethyl)-amide;
5-Cyclopropyl-6-cyclopropylmethoxy-pyridine-2-carboxylic acid [1-(5-amino-[1,2,4]oxadiazol-3-yl)-1-methyl-ethyl]-amide;
6-(2,2,3,3,3-Pentafluoro-propoxy)-pyridine-2-carboxylic acid (1-ethyl-1-methylcarbamoyl-propyl)-amide;

5-Cyclopropyl-6-(2,2,3,3,3-pentafluoro-propoxy)-pyridine-2-carboxylic acid (1-ethyl-1-methylcarbamoyl-propyl)-amide;
5-Cyclopropyl-6-(2,2,3,3,3-pentafluoro-propoxy)-pyridine-2-carboxylic acid ((S)-3,3-dimethyl-1-methylcarbamoyl-butyl)-amide;
5-Cyclopropyl-6-(2,2,3,3,3-pentafluoro-propoxy)-pyridine-2-carboxylic acid [(S)-2-cyclopropyl-1-(5-methyl-[1,2,4]oxadiazol-3-yl)-ethyl]-amide;
5-Cyclopropyl-6-(2,2,2-trifluoro-ethoxy)-pyridine-2-carboxylic acid ((S)-carbamoyl-phenyl-methyl)-amide;
5-Cyclopropyl-6-(2,2,2-trifluoro-ethoxy)-pyridine-2-carboxylic acid (2,2,2-trifluoro-1-pyridin-2-yl-ethyl)-amide;
5-Cyclopropyl-6-(2,2,2-trifluoro-ethoxy)-pyridine-2-carboxylic acid ((S)-1-hydroxymethyl-3-methyl-butyl)-amide;
5-Cyclopropyl-6-(2,2,2-trifluoro-ethoxy)-pyridine-2-carboxylic acid (3-thiazol-2-yl-oxetan-3-yl)-amide;
5-Cyclopropyl-6-(2,2,2-trifluoro-ethoxy)-pyridine-2-carboxylic acid (1-methyl-1-thiazol-2-yl-ethyl)-amide;
5-Cyclopropyl-6-(2,2,2-trifluoro-ethoxy)-pyridine-2-carboxylic acid (2,2-dimethyl-1-thiazol-2-yl-propyl)-amide;
6-Cyclopropylmethoxy-5-(3,3-difluoro-azetidin-1-yl)-pyridine-2-carboxylic acid [1-(3,3-difluoro-azetidine-1-carbonyl)-1-ethyl-propyl]-amide;
6-(4-Fluoro-benzyl)-pyridine-2-carboxylic acid N'-(1,1-dioxo-tetrahydro-1λ⁶-thiophen-3-yl)-hydrazide;
5-Cyclopropyl-6-cyclopropylmethoxy-pyridine-2-carboxylic acid [1-(3-amino-[1,2,4]oxadiazol-5-yl)-1-methyl-ethyl]-amide;
6-Cyclopropylmethoxy-5-(3,3-difluoro-azetidin-1-yl)-pyridine-2-carboxylic acid [(S)-1-(3,3-difluoro-azetidine-1-carbonyl)-2,2-dimethyl-propyl]-amide;
6-Cyclopropylmethoxy-5-(3,3-difluoro-azetidin-1-yl)-pyridine-2-carboxylic acid [(S)-1-(3,3-difluoro-azetidine-1-carbonyl)-3-methyl-butyl]-amide;
2-[(6-Cyclopropylmethoxy-5-trifluoromethyl-pyridine-2-carbonyl)-amino]-2-ethyl-butyric acid ethyl ester;
5-Cyclopropyl-6-((R)-3-hydroxy-1-trifluoromethyl-propoxy)-pyridine-2-carboxylic acid (1-ethyl-1-methylcarbamoyl-propyl)-amide;
5-Cyclopropyl-6-((R)-4,4,4-trifluoro-3-hydroxy-butoxy)-pyridine-2-carboxylic acid (1-ethyl-1-methylcarbamoyl-propyl)-amide;
6-Cyclopropylmethoxy-5-(3,3-difluoro-azetidin-1-yl)-pyridine-2-carboxylic acid (3-methyl-1-pyridin-2-yl-butyl)-amide;
6-Cyclopropylmethoxy-5-trifluoromethyl-pyridine-2-carboxylic acid [1-(3,3-difluoro-azetidine-1-carbonyl)-1-ethyl-propyl]-amide;
6-[(4-Fluoro-phenyl)-hydroxy-methyl]-pyridine-2-carboxylic acid ((S)-1-carbamoyl-3-methyl-butyl)-amide;
6-[(4-Fluoro-phenyl)-hydroxy-methyl]-pyridine-2-carboxylic acid [(S)-3-methyl-1-(5-methyl-[1,2,4]oxadiazol-3-yl)-butyl]-amide;
5-Cyclopropyl-6-((S)-3-hydroxy-1-trifluoromethyl-propoxy)-pyridine-2-carboxylic acid (1-ethyl-1-methylcarbamoyl-propyl)-amide;
5-Cyclopropyl-6-((S)-4,4,4-trifluoro-3-hydroxy-butoxy)-pyridine-2-carboxylic acid (1-ethyl-1-methylcarbamoyl-propyl)-amide;
6-Cyclopropylmethoxy-5-(3,3-difluoro-azetidin-1-yl)-pyridine-2-carboxylic acid (3-methyl-1-pyridazin-3-yl-butyl)-amide;
6-Cyclopropylmethoxy-5-(3-oxo-azetidin-1-yl)-pyridine-2-carboxylic acid [1-methyl-1-(5-methyl-[1,2,4]oxadiazol-3-yl)-ethyl]-amide;
5-Cyclopropyl-6-cyclopropylmethoxy-pyridine-2-carboxylic acid [(+)-1-cyclopropyl-1-(5-methyl-[1,2,4]oxadiazol-3-yl)-ethyl]-amide;
5-Cyclopropyl-6-cyclopropylmethoxy-pyridine-2-carboxylic acid [(−)-1-cyclopropyl-1-(5-methyl-[1,2,4]oxadiazol-3-yl)-ethyl]-amide;
6-Cyclopropylmethoxy-5-(3,3-difluoro-azetidin-1-yl)-pyridine-2-carboxylic acid (3-methyl-1-pyridin-3-yl-butyl)-amide;
5-Cyclopropyl-6-(4-fluoro-benzyl)-pyridine-2-carboxylic acid ((S)-1-carbamoyl-2-cyclopropyl-ethyl)-amide;
5-Cyclopropyl-6-(4-fluoro-benzyl)-pyridine-2-carboxylic acid [(S)-2-cyclopropyl-1-(5-methyl-[1,2,4]oxadiazol-3-yl)-ethyl]-amide;
5-Cyclopropyl-6-cyclopropylmethoxy-pyridine-2-carboxylic acid [(S)-carbamoyl-(4-fluoro-phenyl)-methyl]-amide;
5-Cyclopropyl-6-cyclopropylmethoxy-pyridine-2-carboxylic acid [(S)-carbamoyl-(4-chloro-phenyl)-methyl]-amide;
6-(2-Methyl-propane-1-sulfonyl)-pyridine-2-carboxylic acid ((S)-1-carbamoyl-3-methyl-butyl)-amide;
6-Isobutylsulfanyl-pyridine-2-carboxylic acid ((S)-1-carbamoyl-3-methyl-butyl)-amide;
5-Cyclopropyl-6-(4-fluoro-benzyl)-pyridine-2-carboxylic acid ((S)-2,2,2-trifluoro-1-pyridin-2-yl-ethyl)-amide;
2-{[5-Cyclopropyl-6-(4-fluoro-benzyl)-pyridine-2-carbonyl]-amino}-2-ethyl-butyric acid;
6-Cyclopropylmethoxy-5-(3-oxo-pyrrolidin-1-yl)-pyridine-2-carboxylic acid [1-methyl-1-(5-methyl-[1,2,4]oxadiazol-3-yl)-ethyl]-amide;
6-(2-Methyl-propane-1-sulfonyl)-pyridine-2-carboxylic acid [(S)-3-methyl-1-(5-methyl-[1,2,4]oxadiazol-3-yl)-butyl]-amide;
(S)-2-{[5-Cyclopropyl-6-(4-fluoro-benzyl)-pyridine-2-carbonyl]-amino}-4-methyl-pentano ic acid;
2-{[5-Cyclopropyl-6-(tetrahydro-pyran-4-ylmethoxy)-pyridine-2-carbonyl]-amino}-2-ethyl-butyric acid;
5-Cyclopropyl-6-cyclopropylmethoxy-pyridine-2-carboxylic acid [1-methyl-1-(4-methyl-5-oxo-4,5-dihydro-[1,2,4]oxadiazol-3-yl)-ethyl]-amide;
6-Cyclopropylmethoxy-5-(3,3-difluoro-azetidin-1-yl)-pyridine-2-carboxylic acid (3-methyl-1-pyrimidin-2-yl-butyl)-amide;
6-Cyclopropylmethoxy-5-(3,3-difluoro-azetidin-1-yl)-pyridine-2-carboxylic acid [1-cyclopropyl-1-(5-methyl-[1,2,4]oxadiazol-3-yl)-ethyl]-amide;
6-Cyclopropylmethoxy-5-(3,3-difluoro-azetidin-1-yl)-pyridine-2-carboxylic acid [2-cyclopropyl-1-methyl-1-(5-methyl-[1,2,4]oxadiazol-3-yl)-ethyl]-amide;
6-Cyclopropylmethoxy-5-(3,3-difluoro-azetidin-1-yl)-pyridine-2-carboxylic acid ((S)-1-carbamoyl-3-methylsulfanyl-propyl)-amide;
6-(3-Chloro-4-fluoro-phenyl)-pyridine-2-carboxylic acid [(S)-2-cyclopropyl-1-(5-methyl-[1,2,4]oxadiazol-3-yl)-ethyl]-amide;
6-Cyclopropylmethoxy-5-pyrrolidin-1-yl-pyridine-2-carboxylic acid {(S)-3-methyl-1-[(7-nitro-benzo[1,2,5]oxadiazol-4-ylamino)-methyl]-butyl}-amide;
6-Cyclopropylmethoxy-5-(3,3-difluoro-azetidin-1-yl)-pyridine-2-carboxylic acid ((S)-1-carbamoyl-3-methanesulfonyl-propyl)-amide;
5-Cyclopropyl-6-isobutylsulfanyl-pyridine-2-carboxylic acid ((S)-1-carbamoyl-3-methyl-butyl)-amide;
6-(3-Fluoro-phenyl)-pyridine-2-carboxylic acid [(S)-2-cyclopropyl-1-(5-methyl-[1,2,4]oxadiazol-3-yl)-ethyl]-amide;

6-(4-Fluoro-3-trifluoromethyl-phenyl)-pyridine-2-carboxylic acid [(S)-2-cyclopropyl-1-(5-methyl-[1,2,4]oxadiazol-3-yl)-ethyl]-amide;
5-Cyclopropyl-6-cyclopropylmethoxy-pyridine-2-carboxylic acid (3-methanesulfonyl-1,1-dimethyl-propyl)-amide;
5-Cyclopropyl-6-cyclopropylmethoxy-pyridine-2-carboxylic acid [1-methyl-1-(5-methyl-thiazol-2-yl)-ethyl]-amide;
5-Cyclopropyl-6-(2-methyl-propane-1-sulfonyl)-pyridine-2-carboxylic acid ((S)-1-carbamoyl-3-methyl-butyl)-amide;
5-Cyclopropyl-6-(2-methyl-propane-1-sulfonyl)-pyridine-2-carboxylic acid [(S)-2-cyclopropyl-1-(5-methyl-[1,2,4]oxadiazol-3-yl)-ethyl]-amide;
6-Cyclopropylmethoxy-5-(3,3-difluoro-azetidin-1-yl)-pyridine-2-carboxylic acid [1-methyl-1-(5-methyl-thiazol-2-yl)-ethyl]-amide;
6-Cyclopropylmethoxy-5-(3,3-difluoro-azetidin-1-yl)-pyridine-2-carboxylic acid ((R)-3-methyl-1-pyridazin-3-yl-butyl)-amide;
6-Cyclopropylmethoxy-5-(3,3-difluoro-azetidin-1-yl)-pyridine-2-carboxylic acid ((S)-3-methyl-1-pyridazin-3-yl-butyl)-amide;
5-Cyclopropyl-6-cyclopropylmethoxy-pyridine-2-carboxylic acid [1-ethyl-1-(2-hydroxy-ethylcarbamoyl)-propyl]-amide;
5-Cyclopropyl-6-cyclopropylmethoxy-pyridine-2-carboxylic acid [(+)-2-cyclopropyl-1-methyl-1-(5-methyl-[1,2,4]oxadiazol-3-yl)-ethyl]-amide;
5-Cyclopropyl-6-cyclopropylmethoxy-pyridine-2-carboxylic acid [(−)-2-cyclopropyl-1-methyl-1-(5-methyl-[1,2,4]oxadiazol-3-yl)-ethyl]-amide;
6-Cyclopropylmethoxy-5-(3,3-difluoro-azetidin-1-yl)-pyridine-2-carboxylic acid tert-butylamide;
2-{[5-Cyclopropyl-6-(2-methyl-propane-1-sulfonyl)-pyridine-2-carbonyl]-amino}-2-ethyl-butyric acid ethyl ester;
5-Cyclopropyl-6-(2-methyl-propane-1-sulfonyl)-pyridine-2-carboxylic acid ((S)-3,3-dimethyl-1-methylcarbamoyl-butyl)-amide;
5-Cyclopropyl-6-cyclopropylmethoxy-pyridine-2-carboxylic acid ((S)-2-oxo-tetrahydro-furan-3-yl)-amide;
N'-(5-Cyclopropyl-6-cyclopropylmethoxy-pyridine-2-carbonyl)-N-cyclopropylmethyl-hydrazinecarboxylic acid tert-butyl ester;
5-Cyclopropyl-6-(2-methyl-propane-1-sulfonyl)-pyridine-2-carboxylic acid ((S)-2,2-dimethyl-1-methylcarbamoyl-propyl)-amide;
5-Cyclopropyl-6-(2-methyl-propane-1-sulfonyl)-pyridine-2-carboxylic acid ((S)-2,2,2-trifluoro-1-pyridin-3-yl-ethyl)-amide;
(S)-2-[(5-Cyclopropyl-6-cyclopropylmethoxy-pyridine-2-carbonyl)-amino]-4-methyl-pentanoic acid tert-butyl ester;
5-Cyclopropyl-6-(2-methyl-propane-1-sulfonyl)-pyridine-2-carboxylic acid (1-ethyl-1-methylcarbamoyl-propyl)-amide;
5-Cyclopropyl-6-cyclopropylmethoxy-pyridine-2-carboxylic acid tert-butylamide;
5-Cyclopropyl-6-(tetrahydro-furan-2-ylmethoxy)-pyridine-2-carboxylic acid tert-butylamide;
6-Cyclopropylmethoxy-5-(3,3-difluoro-azetidin-1-yl)-pyridine-2-carboxylic acid (3-methyl-oxetan-3-yl)-amide;
5-Cyclopropyl-6-cyclopropylmethoxy-pyridine-2-carboxylic acid (2-oxo-[1,3]oxazinan-3-yl)-amide;
5-Cyclopropyl-6-(2,2,2-trifluoro-1-methyl-ethoxy)-pyridine-2-carboxylic acid ((S)-1-carbamoyl-3-methyl-butyl)-amide;
5-Cyclopropyl-6-(2,2,2-trifluoro-1-methyl-ethoxy)-pyridine-2-carboxylic acid [1-methyl-1-(5-methyl-[1,2,4]oxadiazol-3-yl)-ethyl]-amide;
5-Cyclopropyl-6-cyclopropylmethoxy-pyridine-2-carboxylic acid ((+)-carbamoyl-cyclopropyl-methyl)-amide;
5-Cyclopropyl-6-cyclopropylmethoxy-pyridine-2-carboxylic acid ((−)-carbamoyl-cyclopropyl-methyl)-amide;
6-Cyclopropylmethoxy-5-(3,3-difluoro-azetidin-1-yl)-pyridine-2-carboxylic acid ((+)-carbamoyl-cyclopropyl-methyl)-amide;
6-Cyclopropylmethoxy-5-(3,3-difluoro-azetidin-1-yl)-pyridine-2-carboxylic acid ((−)-carbamoyl-cyclopropyl-methyl)-amide;
6-Cyclopropylmethoxy-5-(3,3-difluoro-azetidin-1-yl)-pyridine-2-carboxylic acid (1-trifluoromethyl-cyclopropyl)-amide;
(+)-5-Cyclopropyl-6-cyclopropylmethoxy-pyridine-2-carboxylic acid [(S)-2-cyclopropyl-1-(3-hydroxy-pyrrolidin-1-ylcarbamoyl)-ethyl]-amide;
(−)-5-Cyclopropyl-6-cyclopropylmethoxy-pyridine-2-carboxylic acid [(S)-2-cyclopropyl-1-(3-hydroxy-pyrrolidin-1-ylcarbamoyl)-ethyl]-amide;
(+)-5-Cyclopropyl-6-(2-methyl-propane-1-sulfonyl)-pyridine-2-carboxylic acid [1-cyclopropyl-1-(5-methyl-[1,2,4]oxadiazol-3-yl)-ethyl]-amide; and
(+5-Cyclopropyl-6-(2-methyl-propane-1-sulfonyl)-pyridine-2-carboxylic acid [1-cyclopropyl-1-(5-methyl-[1,2,4]oxadiazol-3-yl)-ethyl]-amide.

The invention also relates in particular to a compound of formula (I) selected from the group consisting of:
5-Cyclopropyl-6-(tetrahydro-pyran-4-ylmethoxy)-pyridine-2-carboxylic acid [cyclopropyl-(5-methyl-[1,2,4]oxadiazol-3-yl)-methyl]-amide;
5-Cyclopropyl-6-cyclopropylmethoxy-pyridine-2-carboxylic acid ((S)-2-cyclopropyl-1-dimethylcarbamoyl-ethyl)-amide;
5-Cyclopropyl-6-cyclopropylmethoxy-pyridine-2-carboxylic acid ((+)-dimethylcarbamoyl-phenyl-methyl)-amide;
6-Cyclopropylmethoxy-5-trifluoromethyl-pyridine-2-carboxylic acid ((S)-3,3-dimethyl-1-methylcarbamoyl-butyl)-amide;
6-(3-Chloro-4-fluoro-phenyl)-pyridine-2-carboxylic acid [cyclopropyl-(5-methyl-[1,2,4]oxadiazol-3-yl)-methyl]-amide;
2-{[5-Cyclopropyl-6-(tetrahydro-furan-2-ylmethoxy)-pyridine-2-carbonyl]-amino}-2-ethyl-butyric acid methyl ester;
6-Cyclopropylmethoxy-5-(6-oxa-1-aza-spiro[3.3]hept-1-yl)-pyridine-2-carboxylic acid ((S)-3,3-dimethyl-1-methylcarbamoyl-butyl)-amide;
2-Ethyl-2-{[6-(tetrahydro-pyran-4-ylmethoxy)-5-trifluoromethyl-pyridine-2-carbonyl]-amino}-butyric acid methyl ester;
(S)-2-[(5-Cyclopropyl-6-cyclopropylmethoxy-pyridine-2-carbonyl)-amino]-3,3-dimethyl-butyric acid methyl ester;
5-Cyclopropyl-6-cyclopropylmethoxy-pyridine-2-carboxylic acid [(+)-1-(5-methyl-[1,2,4]oxadiazol-3-yl)-butyl]-amide;
5-Cyclopropyl-6-cyclopropylmethoxy-pyridine-2-carboxylic acid ((−)-1-cyano-3-methyl-butyl)-amide;
(S)-3-Cyclopropyl-2-[(5-cyclopropyl-6-cyclopropylmethoxy-pyridine-2-carbonyl)-amino]-propionic acid methyl ester;
6-Cyclopropylmethoxy-5-trifluoromethyl-pyridine-2-carboxylic acid (1-ethyl-1-methylcarbamoyl-propyl)-amide;

6-(3-Chloro-4-fluoro-phenyl)-pyridine-2-carboxylic acid [1-methyl-1-(5-methyl-[1,2,4]oxadiazol-3-yl)-ethyl]-amide;

6-Cyclopropylmethoxy-5-(3,3-difluoro-azetidin-1-yl)-pyridine-2-carboxylic acid (1-hydroxymethyl-1,3-dimethyl-butyl)-amide;

5-Cyclopropyl-6-cyclopropylmethoxy-pyridine-2-carboxylic acid [1-ethyl-1-(ethyl-methyl-carbamoyl)-propyl]-amide;

6-(4-Fluoro-benzyl)-pyridine-2-carboxylic acid ((R)-2,2,2-trifluoro-1-pyridin-2-yl-ethyl)-amide;

5-Cyclopropyl-6-cyclopropylmethoxy-pyridine-2-carboxylic acid ((S)-1-hydroxymethyl-1,2-dimethyl-propyl)-amide;

5-Cyclopropyl-6-cyclopropylmethoxy-pyridine-2-carboxylic acid [1-(3,3-difluoro-azetidine-1-carbonyl)-1-ethyl-propyl]-amide;

5-Cyclopropyl-6-(2,2,3,3,3-pentafluoro-propoxy)-pyridine-2-carboxylic acid (1-ethyl-1-methylcarbamoyl-propyl)-amide;

5-Cyclopropyl-6-(2,2,3,3,3-pentafluoro-propoxy)-pyridine-2-carboxylic acid ((S)-3,3-dimethyl-1-methylcarbamoyl-butyl)-amide;

6-Cyclopropylmethoxy-5-(3,3-difluoro-azetidin-1-yl)-pyridine-2-carboxylic acid [1-(3,3-difluoro-azetidine-1-carbonyl)-1-ethyl-propyl]-amide;

5-Cyclopropyl-6-((R)-4,4,4-trifluoro-3-hydroxy-butoxy)-pyridine-2-carboxylic acid (1-ethyl-1-methylcarbamoyl-propyl)-amide;

6-Cyclopropylmethoxy-5-trifluoromethyl-pyridine-2-carboxylic acid [1-(3,3-difluoro-azetidine-1-carbonyl)-1-ethyl-propyl]-amide;

6-[(4-Fluoro-phenyl)-hydroxy-methyl]-pyridine-2-carboxylic acid ((S)-1-carbamoyl-3-methyl-butyl)-amide;

5-Cyclopropyl-6-((S)-4,4,4-trifluoro-3-hydroxy-butoxy)-pyridine-2-carboxylic acid (1-ethyl-1-methylcarbamoyl-propyl)-amide;

5-Cyclopropyl-6-cyclopropylmethoxy-pyridine-2-carboxylic acid [(+)-1-cyclopropyl-1-(5-methyl-[1,2,4]oxadiazol-3-yl)-ethyl]-amide;

6-Cyclopropylmethoxy-5-(3,3-difluoro-azetidin-1-yl)-pyridine-2-carboxylic acid (3-methyl-1-pyridin-3-yl-butyl)-amide;

5-Cyclopropyl-6-(4-fluoro-benzyl)-pyridine-2-carboxylic acid ((S)-1-carbamoyl-2-cyclopropyl-ethyl)-amide;

5-Cyclopropyl-6-cyclopropylmethoxy-pyridine-2-carboxylic acid [(S)-carbamoyl-(4-fluoro-phenyl)-methyl]-amide;

5-Cyclopropyl-6-(4-fluoro-benzyl)-pyridine-2-carboxylic acid ((S)-2,2,2-trifluoro-1-pyridin-2-yl-ethyl)-amide;

6-Cyclopropylmethoxy-5-(3,3-difluoro-azetidin-1-yl)-pyridine-2-carboxylic acid [1-cyclopropyl-1-(5-methyl-[1,2,4]oxadiazol-3-yl)-ethyl]-amide;

6-Cyclopropylmethoxy-5-(3,3-difluoro-azetidin-1-yl)-pyridine-2-carboxylic acid [2-cyclopropyl-1-methyl-1-(5-methyl-[1,2,4]oxadiazol-3-yl)-ethyl]-amide;

6-(3-Chloro-4-fluoro-phenyl)-pyridine-2-carboxylic acid [(S)-2-cyclopropyl-1-(5-methyl-[1,2,4]oxadiazol-3-yl)-ethyl]-amide;

6-Cyclopropylmethoxy-5-pyrrolidin-1-yl-pyridine-2-carboxylic acid {(S)-3-methyl-1-[(7-nitro-benzo[1,2,5]oxadiazol-4-ylamino)-methyl]-butyl}-amide;

5-Cyclopropyl-6-isobutylsulfanyl-pyridine-2-carboxylic acid ((S)-1-carbamoyl-3-methyl-butyl)-amide;

5-Cyclopropyl-6-(2-methyl-propane-1-sulfonyl)-pyridine-2-carboxylic acid ((S)-1-carbamoyl-3-methyl-butyl)-amide;

6-Cyclopropylmethoxy-5-(3,3-difluoro-azetidin-1-yl)-pyridine-2-carboxylic acid [1-methyl-1-(5-methyl-thiazol-2-yl)-ethyl]-amide;

6-Cyclopropylmethoxy-5-(3,3-difluoro-azetidin-1-yl)-pyridine-2-carboxylic acid ((R)-3-methyl-1-pyridazin-3-yl-butyl)-amide;

5-Cyclopropyl-6-cyclopropylmethoxy-pyridine-2-carboxylic acid [(+)-2-cyclopropyl-1-methyl-1-(5-methyl-[1,2,4]oxadiazol-3-yl)-ethyl]-amide;

5-Cyclopropyl-6-cyclopropylmethoxy-pyridine-2-carboxylic acid [(−)-2-cyclopropyl-1-methyl-1-(5-methyl-[1,2,4]oxadiazol-3-yl)-ethyl]-amide;

6-Cyclopropylmethoxy-5-(3,3-difluoro-azetidin-1-yl)-pyridine-2-carboxylic acid tert-butylamide;

5-Cyclopropyl-6-(2-methyl-propane-1-sulfonyl)-pyridine-2-carboxylic acid ((S)-2,2,2-trifluoro-1-pyridin-3-yl-ethyl)-amide;

5-Cyclopropyl-6-cyclopropylmethoxy-pyridine-2-carboxylic acid ((+)-carbamoyl-cyclopropyl-methyl)-amide;

6-Cyclopropylmethoxy-5-(3,3-difluoro-azetidin-1-yl)-pyridine-2-carboxylic acid (1-trifluoromethyl-cyclopropyl)-amide; and (+)-5-Cyclopropyl-6-(2-methyl-propane-1-sulfonyl)-pyridine-2-carboxylic acid [1-cyclopropyl-1-(5-methyl-[1,2,4]oxadiazol-3-yl)-ethyl]-amide.

The compounds of the present invention can be prepared, for example, by the general synthetic procedures described below.

In the following schemes and description, $R^1$ to $R^4$ have, unless otherwise indicated, the meaning of $R^1$ to $R^4$ as defined above.

Coupling agents for the reaction of compounds of formula II with acids of formula III are for example N,N'-carbonyldiimidazole (CDI), N,N'-dicyclohexylcarbodiimide (DCC), 1-(3-dimethylaminopropyl)-3-ethylcarbodiimide hydrochloride (EDCI), 1-[bis(dimethylamino)-methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU) or O-benzotriazole-N,N,N',N'-tetramethyl-uronium-hexafluoro-phosphate (HBTU). Particular coupling agent is HBTU. Suitable bases include triethylamine, diisopropylethylamine and, particularly, N-methylmorpholine.

The synthesis of the compounds with the general structure I can, for example, be accomplished according to the following schemes.

Following the procedure according to scheme 1, compound AA (X=Cl, Br, I, trifluoromethanesulfonate; R'=H, methyl, ethyl, isopropyl, tert.butyl or another suitable protecting group described for example in T. W. Greene et al., Protective Groups in Organic Chemistry, John Wiley and Sons Inc. New York 1999, 3$^{rd}$ edition) can be used as starting material. AA is either commercially available, described in the literature, can be synthesized by a person skilled in the art, can be synthesized as described in schemes 3 and 6 or as described in the experimental part.

Scheme 1

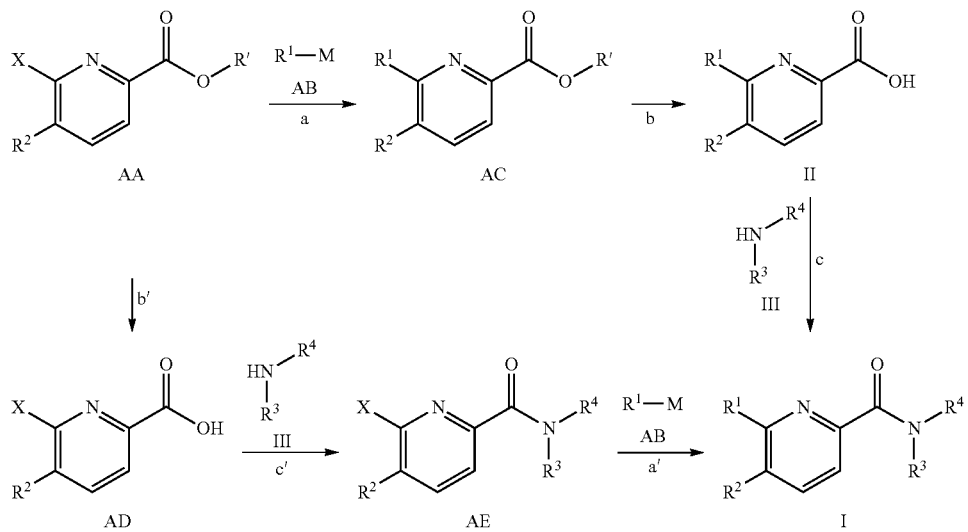

Compound AC can be prepared from AA by coupling a suitably substituted aryl, heteroaryl or alkenyl metal species of formula AB (step a), particularly an arylboronic acid or arylboronic acid ester in the presence of a suitable catalyst, in particular a palladium catalyst and more particularly palladium(II)acetate/triphenylphosphine mixtures or palladium (II)chloride-dppf (1,1'-bis(diphenylphosphino)ferrocene) complexes and a base such as triethylamine, sodium carbonate or potassium phosphate in an inert solvent such as dimethylformamide, toluene, tetrahydrofuran, acetonitrile and dimethoxyethane. Optionally, alkenyl containing $R^1$ residues can be transformed to the corresponding alkyl congeners AC using conditions described in the literature such as e.g. via a hydrogenation reaction using hydrogen gas in the presence of a catalyst such as palladium on carbon in a solvent such as ethanol or ethyl acetate particularly at ambient temperature.

The saponification of the ester of general formula AC(R'≠H) by methods well known to the ones skilled in the art—using e.g. aqueous LiOH, NaOH or KOH in tetrahydrofuran/ethanol or another suitable solvent at temperatures between 0° C. and the reflux temperature of the solvent employed—leads to an acid of general formula II (step b).

Compound I can be prepared from II and the corresponding amine or hydrazine of formula III by suitable amide bond forming reactions (step c). These reactions are known in the art. For example coupling reagents like N,N'-carbonyl-diimidazole (CDI), N,N'-dicyclohexylcarbodiimide (DCC), 1-(3-dimethylaminopropyl)-3-ethylcarbodiimide hydrochloride (EDCI), 1-[bis(dimethylamino)-methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU), and O-benzotriazole-N,N,N',N'-tetramethyl-uronium-hexafluoro-phosphate (HBTU) can be employed to affect such transformation. A convenient method is to use for example HBTU and a base, for example N-methylmorpholine in an inert solvent such as for example dimethylformamide at room temperature.

Alternatively esters of general formula AA (R'≠H) can be saponified by methods well known to the ones skilled in the art—using e.g. aqueous LiOH, NaOH or KOH in tetrahydrofuran/ethanol or another suitable solvent at temperatures between 0° C. and the reflux temperature of the solvent employed—to give acids of general formula AD (step b').

Compounds AE can be prepared from AD and the corresponding amine or hydrazine of formula III by suitable amide bond forming reactions (step c'). These reactions are known in the art. For example coupling reagents like N,N'-carbonyl-diimidazole (CDI), N,N'-dicyclohexylcarbodiimide (DCC), 1-(3-dimethylaminopropyl)-3-ethylcarbodiimide hydrochloride (EDCI), 1-[bis(dimethylamino)-methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU), and O-benzotriazole-N,N,N',N'-tetramethyl-uronium-hexafluoro-phosphate (HBTU) can be employed to affect such transformation. A convenient method is to use for example HBTU and a base, for example N-methylmorpholine in an inert solvent such as for example dimethylformamide at room temperature.

Compound I can be prepared from AE by coupling a suitably substituted aryl, heteroaryl or alkenyl metal species of formula AB (step a'), particularly an arylboronic acid or arylboronic acid ester in the presence of a suitable catalyst, in particular a palladium catalyst and more particularly palladium(II)acetate/triphenylphosphine mixtures or palladium (II)chloride-dppf (1,1'-bis(diphenylphosphino)ferrocene) complexes and a base such as triethylamine, sodium carbonate or potassium phosphate in an inert solvent such as dimethylformamide, toluene, tetrahydrofuran, acetonitrile and dimethoxyethane. Optionally, alkenyl containing $R^1$ residues can be transformed to the corresponding alkyl congeners AE using conditions described in the literature such as e.g. via a hydrogenation reaction using hydrogen gas in the presence of a catalyst such as palladium on carbon in a solvent such as ethanol or ethyl acetate particularly at ambient temperature.

Amines or hydrazines III are either commercially available, described in the literature, can be synthesized by a person skilled in the art or as described in the experimental part.

If one of the starting materials, compounds of formulae AA, AB or III, contains one or more functional groups which are not stable or are reactive under the reaction conditions of one or more reaction steps, appropriate protecting groups (P)

(as described e.g. in T. W. Greene et al., Protective Groups in Organic Chemistry, John Wiley and Sons Inc. New York 1999, 3$^{rd}$ edition) can be introduced before the critical step applying methods well known in the art. Such protecting groups can be removed at a later stage of the synthesis using standard methods known in the art.

If one or more compounds of formulae AA to AE, II or III contain chiral centers, picolines of formula I can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbent or a chiral eluent.

Following the procedure according to scheme 2, compound BA (R'=H, methyl, ethyl, isopropyl, tert.butyl or another suitable protecting group described for example in T. W. Greene et al., Protective Groups in Organic Chemistry, John Wiley and Sons Inc. New York 1999, 3$^{rd}$ edition) can be used as starting material. BA is either commercially available, described in the literature or can be synthesized by a person skilled in the art.

well known in the art (step c), for example using a palladium promoted amination reaction with palladium(II)acetate/2-(dicyclohexylphosphino)biphenyl as the catalyst system in the presence of a base such as potassium carbonate in dioxane under reflux conditions.

Compound BD can be further elaborated to compound I by: i) saponification (for compounds BD with R'≠H) as described in step b of scheme 1 (step d); ii) amide bond formation as described in step c of scheme 1 (step e).

Alternatively, compound AA' (R'=methyl, ethyl, isopropyl, tert. butyl or another suitable protecting group described for example in T. W. Greene et al., Protective Groups in Organic Chemistry, John Wiley and Sons Inc. New York 1999, 3$^{rd}$ edition) can be: i) converted into its acid congener AA' (R'=H) as described in step b of scheme 1; ii) transformed into the corresponding amide or hydrazide by treatment with amine or hydrazine III as described in step c of scheme 1; and iii) reacted with alcohol BC as described in step c to arrive at compound I.

If one of the starting materials, compounds of formulae BA, BC or III, contains one or more functional groups which are not stable or are reactive under the reaction conditions of one or more reaction steps, appropriate protecting groups (P)

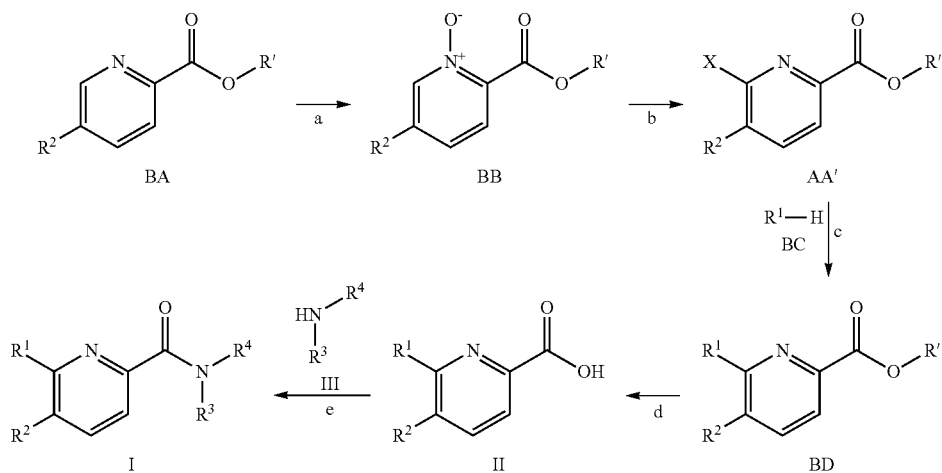

Scheme 2

Compound BB can be prepared from BA by oxidation with a suitable oxidizing reagent under conditions known to a person skilled in the art (step a), e.g. by treatment with 3-chloro perbenzoic acid in dichloromethane at ambient temperature.

Conversion of compound BB to 6-chloro or 6-bromo-picoline AA' (X=Cl, Br) can be achieved e.g. by treatment with phosphoryl trichloride or tribromide either without an additional solvent or in a suitable solvent such as chloroform at temperatures between 20° C. and the boiling point of the solvent, or by using other conditions known in the literature (step b).

6-Chloro- or bromo-picoline AA' (X=Cl, Br) can be transformed to compound BD by reaction with a suitably substituted primary or secondary alcohol BC in the presence of a base, for example sodium hydride, with or without an inert solvent, for example dimethylformamide, at temperatures ranging from room temperature to the reflux temperature of the solvent, particularly at room temperature (step c). Alternatively, compound AA' can be converted to amino derivatives BD by treatment with an amine BC applying methods (as described e.g. in T. W. Greene et al., Protective Groups in Organic Chemistry, John Wiley and Sons Inc. New York 1999, 3$^{rd}$ edition) can be introduced before the critical step applying methods well known in the art. Such protecting groups can be removed at a later stage of the synthesis using standard methods known in the art.

If one or more compounds of formulae BA to BD, AA', II or III contain chiral centers, picolines of formula I can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbent or a chiral eluent.

Following the procedure according to scheme 3, compound CA (R'=H, methyl, ethyl, isopropyl, tert.butyl or another suitable protecting group described for example in T. W. Greene et al., Protective Groups in Organic Chemistry, John Wiley and Sons Inc. New York 1999, 3$^{rd}$ edition) can be used as starting material. CA is either commercially available (e.g. for R'=methyl: 5-bromo-6-chloro-pyridine-2-carboxylic acid methyl ester CAN 1214353-79-3), described in the literature or can be synthesized by a person skilled in the art.

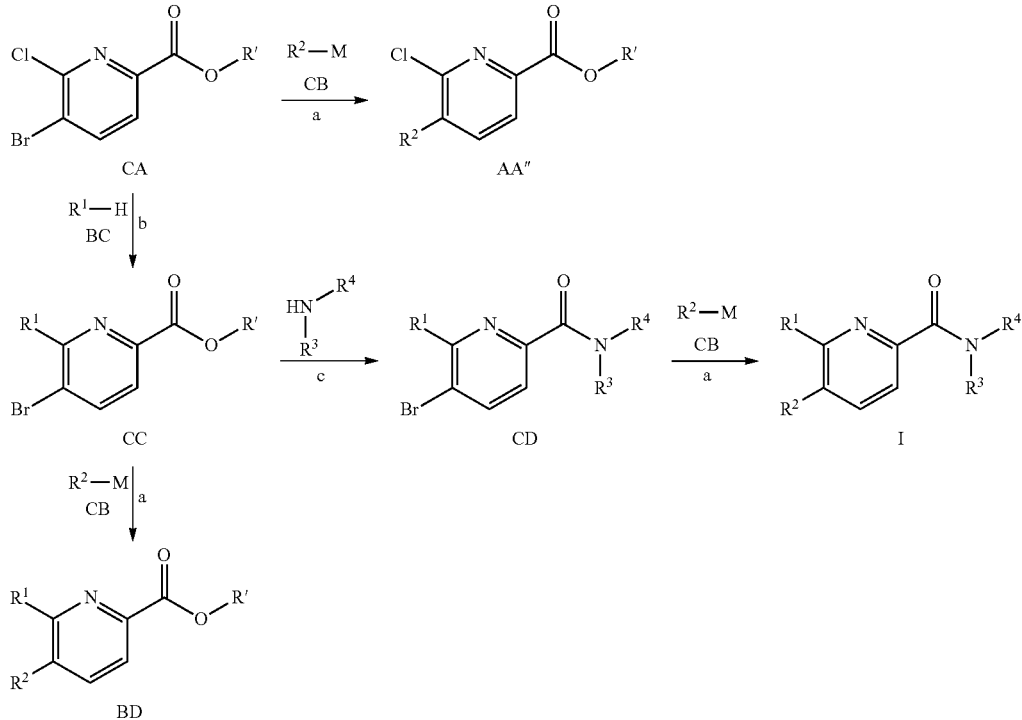

Scheme 3

Compound AA" can be prepared from CA by coupling a suitably substituted aryl, heteroaryl or alkenyl metal species of formula CB (step a), e.g. an organotrifluoroborate potassium salt in the presence of a palladium catalyst such as palladium(II)acetate/butyl-1-adamantylphosphine and a base such as cesium carbonate in an inert solvent such as toluene at temperatures between 50° C. and the boiling temperature of the solvent, or an arylboronic acid or arylboronic acid ester in the presence of a suitable catalyst, in particular a palladium catalyst and more particularly palladium(II)acetate/triphenylphosphine mixtures or palladium(II)chloride-dppf (1,1'-bis(diphenylphosphino) ferrocene) complexes and a base such as triethylamine, sodium carbonate or potassium phosphate in an inert solvent such as dimethylformamide, toluene, tetrahydrofuran, acetonitrile or dimethoxyethane. Optionally, compound CB can also be an amine or amide which is coupled to CA by methods well known to a person skilled in the art, e.g. using a palladium catalyst such as tris(dibenzylideneacetone)dipalladium/dimethylbisdiphenyl-phosphinoxanthene and a base such as cesium carbonate in a solvent such as 1,4-dioxane, preferentially at the boiling point of the solvent. Alternatively, compound CB can also be a sulfonamide which undergoes a copper(I) mediated reaction with CA to form AA" following procedures described in the literature, e.g. using copper(I) iodide and 1,3-di(pyridin-2-yl)propane-1,3-dione in the presence of a base such as potassium carbonate in a solvent such as dimethylformamide at elevated temperatures preferentially at the boiling point of the solvent. Optionally, alkenyl containing $R^2$ residues can be transformed to the corresponding alkyl congeners AA" using conditions described in the literature such as e.g. a hydrogenation reaction using hydrogen gas in the presence of a catalyst such as palladium on carbon in a solvent such as ethanol or ethyl acetate particularly at ambient temperature.

Compound AA' can be further elaborated to compound I by: i) reaction with compound BC to form compound BD as described in step c of scheme 2; ii) saponification as described in step b of scheme 1; and iii) amide bond formation as described in step c of scheme 1.

Furthermore, compound CA can be converted into compound CC by treatment with compound BC as described in step c of scheme 2 (step b).

Subsequent transformation of compound CC into compound BD can be achieved as discussed for the conversion of CA into AA" (step a).

Compound BD can be further elaborated to compound I by: i) saponification as described in step b of scheme 1; ii) amide bond formation as described in step c of scheme 1.

Alternatively, compound CC(R'=methyl, ethyl, isopropyl, tert.butyl or another suitable protecting group described for example in T. W. Greene et al., Protective Groups in Organic Chemistry, John Wiley and Sons Inc. New York 1999, 3$^{rd}$ edition) can be: i) converted into its acid congener CC(R'=H) as described in step b of scheme 1; ii) transformed into the corresponding amide or hydrazide CD by treatment with amine or hydrazine III as described in step c of scheme 1; and iii) reacted with CB as described in step a to arrive at compound I.

Furthermore, compound I can also be synthesized applying the following reaction sequence: i) saponification of compound CA (R'=methyl, ethyl, isopropyl, tert.butyl or another suitable protecting group described for example in T. W. Greene et al., Protective Groups in Organic Chemistry, John Wiley and Sons Inc. New York 1999, 3rd edition) to its acid congener CC(R'=H) as described in step b of scheme 1; ii) conversion to the corresponding amide or hydrazide by treatment with amine or hydrazine III as described in step c of scheme 1; iii) reaction with compound CB as described in step a; and iv) reaction with compound BC as described in step c. Optionally step iii) and step iv) can be interchanged.

If one of the starting materials, compounds of formulae CA, CB or BC contains one or more functional groups which are not stable or are reactive under the reaction conditions of one or more reaction steps, appropriate protecting groups (P) (as described e.g. in T. W. Greene et al., Protective Groups in Organic Chemistry, John Wiley and Sons Inc. New York 1999, 3rd edition) can be introduced before the critical step applying methods well known in the art. Such protecting groups can be removed at a later stage of the synthesis using standard methods known in the art.

If one or more compounds of formulae CA, CB or BC contain chiral centers, picolines of formula AA" and BD can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbent or a chiral eluent.

Following the procedure according to scheme 4, compound CC(R'=H, methyl, ethyl, isopropyl, tert.butyl or another suitable protecting group described for example in T. W. Greene et al., Protective Groups in Organic Chemistry, John Wiley and Sons Inc. New York 1999, 3rd edition) can be used as starting material. CC is either commercially available, described in the literature, can be synthesized by methods described in scheme 3 or by other methods known to a person skilled in the art.

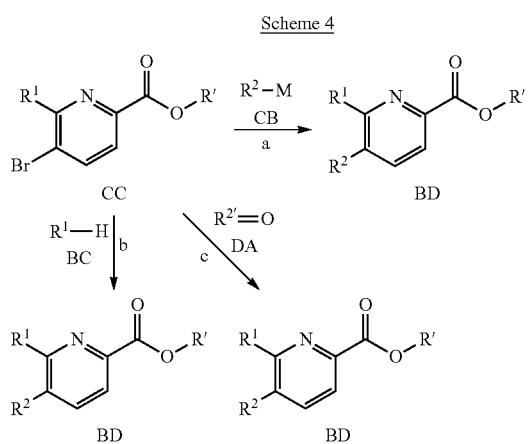

Scheme 4

Compound BD can be prepared from CC by coupling a suitably substituted aryl, heteroaryl or alkenyl metal species of formula CB (step a), e.g. an organotrifluoroborate potassium salt in the presence of a palladium catalyst such as palladium(II)acetate/butyl-1-adamantylphosphine and a base such as cesium carbonate in an inert solvent such as toluene at temperatures between 50° C. and the boiling temperature of the solvent, or an arylboronic acid or arylboronic acid ester in the presence of a suitable catalyst, in particular a palladium catalyst and more particularly palladium(II)acetate/triphenylphosphine mixtures or palladium(II)chloride-dppf (1,1'-bis(diphenylphosphino) ferrocene) complexes and a base such as triethylamine, sodium carbonate or potassium phosphate in an inert solvent such as dimethylformamide, toluene, tetrahydrofuran, acetonitrile and dimethoxyethane. Optionally, alkenyl containing $R^2$ residues can be transformed to the corresponding alkyl congeners BD using conditions described in the literature such as e.g. a hydrogenation reaction using hydrogen gas in the presence of a catalyst such as palladium on carbon in a solvent such as ethanol or ethyl acetate particularly at ambient temperature.

Alternatively, compound CC can be converted to amino derivatives BD by treatment with an amine BC applying methods well known in the art (step b), for example using a palladium promoted amination with palladium(II)acetate/2-(dicyclohexylphosphino) biphenyl in the presence of a base such as potassium carbonate in dioxane under reflux conditions or by using tris(dibenzylideneacetone)dipalladium/rac-BINAP (2,2'-bis(diphenylphosphino)-1,1'-binaphthyl) in the presence of a base such as cesium carbonate in toluene at 100° C. Optionally, compound BC can also be an amide which is coupled to CC by methods well known to a person skilled in the art, e.g. using a palladium catalyst such as tris(dibenzylideneacetone)dipalladium/dimethylbisdiphenyl-phosphinoxanthene and a base such as cesium carbonate in a solvent such as 1,4-dioxane preferentially at the boiling point of the solvent.

Compound CC can furthermore be reacted with ketone DA ($R^{2'}$=alkyl, cycloalkyl, or oxyoxetanyl) to obtain compound BD following procedures known to a person skilled in the art, e.g.: i) treatment with n-butyl lithium in a solvent such as tetrahydrofuran at a temperature of −78° C.; ii) addition of a ketone DA or optionally another suitable electrophile at temperatures between −78° C. and ambient temperature (step c).

Compound BD can be further elaborated to compound I by: i) saponification as described in step b of scheme 1; ii) amide bond formation as described in step c of scheme 1.

If one of the starting materials, compounds of formulae CC, CB, BC or DA, contains one or more functional groups which are not stable or are reactive under the reaction conditions of one or more reaction steps, appropriate protecting groups (P) (as described e.g. in T. W. Greene et al., Protective Groups in Organic Chemistry, John Wiley and Sons Inc. New York 1999, 3rd edition) can be introduced before the critical step applying methods well known in the art. Such protecting groups can be removed at a later stage of the synthesis using standard methods known in the art.

If one or more compounds of formulae CC, CB, BC or DA, contain chiral centers, picolines of formula BD can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbens or a chiral eluent.

Following the procedure according to scheme 5, compound AA" (R'=H) can be used as starting material. AA" is either commercially available, described in the literature, can be synthesized as described in scheme 2 or by other methods known to a person skilled in the art.

Scheme 5

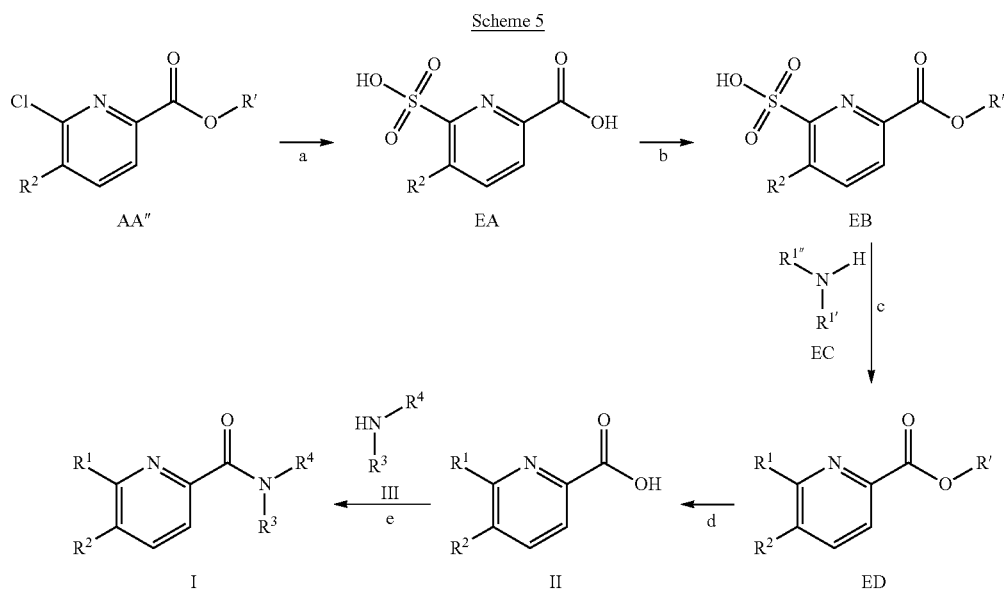

Compound EA can be prepared from AA" e.g. by treatment with sodium sulfite in a mixture of ethanol and water at a temperature of 180° C. in a sealed tube or by using alternative conditions known to a person skilled in the art (step a).

Subsequent esterification of EA to compound EB (R'=methyl, ethyl, isopropyl, tert.butyl or another suitable protecting group (P) as described e.g. in T. W. Greene et al., Protective Groups in Organic Chemistry, John Wiley and Sons Inc. New York 1999, 3$^{rd}$ edition) can e.g. be performed using a solution of hydrogen chloride in methanol at ambient temperature or by alternative methods described for example in T. W. Greene et al., Protective Groups in Organic Chemistry, John Wiley and Sons Inc. New York 1999, 3$^{rd}$ edition (step b).

Sulfonic acid EB can be converted to sulfonamide ED, after prior activation e.g. by using thionyl chloride and DMF in an inert solvent such as dichloromethane at temperatures between 0° C. and the boiling point of the solvent, particularly at 40° C. to form the corresponding sulfonic acid chloride, by reaction with a suitable amine EC (R$^{1'}$=alkyl, R$_{1''}$=alkyl or R$^{1'}$ and R$^{1'''}$ together with the nitrogen atom to which they are attached form a cyclic amine) particularly at ambient temperature or by using any other method known to a person skilled in the art (step c).

Compound ED can be further elaborated to compound I by: i) saponification as described in step b of scheme 1 (step d); ii) amide bond formation as described in step c of scheme 1 (step e).

If one of the starting materials, compounds of formulae AA", EC or III, contains one or more functional groups which are not stable or are reactive under the reaction conditions of one or more reaction steps, appropriate protecting groups (P) (as described e.g. in T. W. Greene et al., Protective Groups in Organic Chemistry, John Wiley and Sons Inc. New York 1999, 3$^{rd}$ edition) can be introduced before the critical step applying methods well known in the art. Such protecting groups can be removed at a later stage of the synthesis using standard methods known in the art.

If one or more compounds of formulae AA", EA to ED, II or III contain chiral centers, picolines of formula I can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbent or a chiral eluent.

Following the procedure according to scheme 6, compound FA (X=Cl, Br, I, trifluoromethanesulfonate; R'=H, methyl, ethyl, isopropyl, tert.butyl or another suitable protecting group described for example in T. W. Greene et al., Protective Groups in Organic Chemistry, John Wiley and Sons Inc. New York 1999, 3$^{rd}$ edition) can be used as starting material. FA is either commercially available, described in the literature or can be synthesized by a person skilled in the art.

Scheme 6

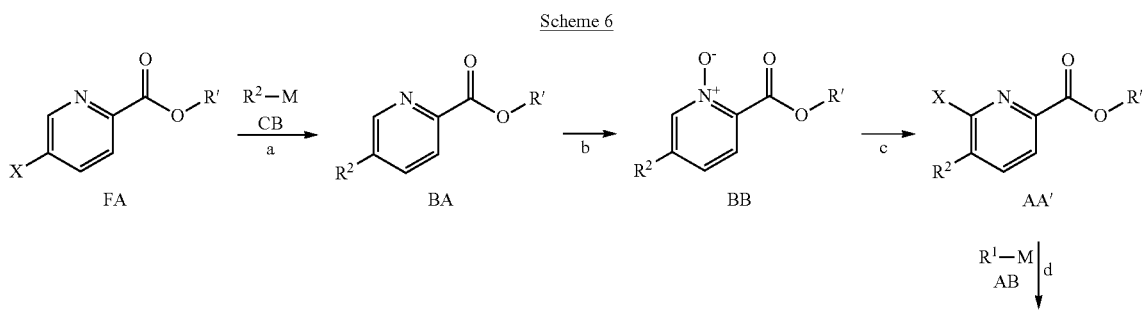

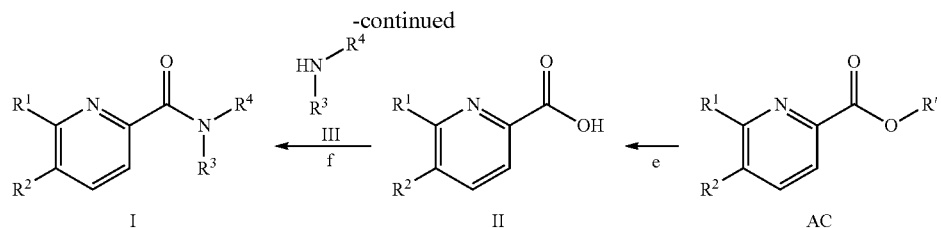

Compound BA can be prepared from FA by coupling a suitably substituted aryl, heteroaryl or alkenyl metal species of formula CB (step a), e.g. an organotrifluoroborate potassium salt in the presence of a palladium catalyst such as palladium(II)acetate/butyl-1-adamantylphosphine and a base such as cesium carbonate in an inert solvent such as toluene at temperatures between 50° C. and the boiling temperature of the solvent, or an arylboronic acid or arylboronic acid ester in the presence of a suitable catalyst, in particular a palladium catalyst and more particularly palladium(II)acetate/triphenylphosphine mixtures or palladium(II)chloride-dppf (1,1'-bis(diphenylphosphino) ferrocene) complexes and a base such as triethylamine, sodium carbonate or potassium phosphate in an inert solvent such as dimethylformamide, toluene, tetrahydrofuran, acetonitrile and dimethoxyethane. Optionally, compound CB can also be an amine or amide which is coupled to FA by methods well known to a person skilled in the art, e.g. using a palladium catalyst such as tris(dibenzylideneacetone)dipalladium/dimethylbisdiphenyl-phosphinoxanthene and a base such as cesium carbonate in a solvent such as 1,4-dioxane preferentially at the boiling point of the solvent. Optionally, alkenyl containing $R^2$ residues can be transformed to the corresponding alkyl congeners BA using conditions described in the literature such as e.g. a hydrogenation reaction using hydrogen gas in the presence of a catalyst such as palladium on carbon in a solvent such as ethanol or ethyl acetate particularly at ambient temperature.

Compound BB can be prepared from BA by oxidation with a suitable oxidizing reagent as described in step a of scheme 2 (step b).

Conversion of compound BB to 6-chloro- or 6-bromo-picoline AA' (X=Cl, Br) can be achieved as described in step b of scheme 2 (step c).

Compound AC can be prepared from AA' by coupling a suitably substituted aryl, heteroaryl or alkenyl metal species of formula AB (step d), particularly an arylboronic acid or arylboronic acid ester in the presence of a suitable catalyst, in particular a palladium catalyst and more particularly palladium(II)acetate/triphenylphosphine mixtures or palladium(II)chloride-dppf (1,1'-bis(diphenylphosphino)ferrocene) complexes and a base such as triethylamine, sodium carbonate or potassium phosphate in an inert solvent such as dimethylformamide, toluene, tetrahydrofuran, acetonitrile and dimethoxyethane. Optionally, alkenyl containing $R^1$ residues can be transformed to the corresponding alkyl congeners AC using conditions described in the literature such as e.g. a hydrogenation reaction using hydrogen gas in the presence of a catalyst such as palladium on carbon in a solvent such as ethanol or ethyl acetate particularly at ambient temperature.

Compound AC can be further elaborated to compound I by: i) saponification as described in step b of scheme 1 (step e); ii) amide bond formation as described in step c of scheme 1 (step f).

If one of the starting materials, compounds of formulae FA, CB, AB or III, contains one or more functional groups which are not stable or are reactive under the reaction conditions of one or more reaction steps, appropriate protecting groups (P) (as described e.g. in T. W. Greene et al., Protective Groups in Organic Chemistry, John Wiley and Sons Inc. New York 1999, $3^{rd}$ edition) can be introduced before the critical step applying methods well known in the art. Such protecting groups can be removed at a later stage of the synthesis using standard methods known in the art.

If one or more compounds of formulae FA, CB, BA, BB, AA', AB, AC, II or III contain chiral centers, picolines of formula I can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbent or a chiral eluent.

Following the procedure according to scheme 7, compound GA can be used as starting material. GA is either commercially available, described in the literature or can be synthesized by a person skilled in the art.

Scheme 7

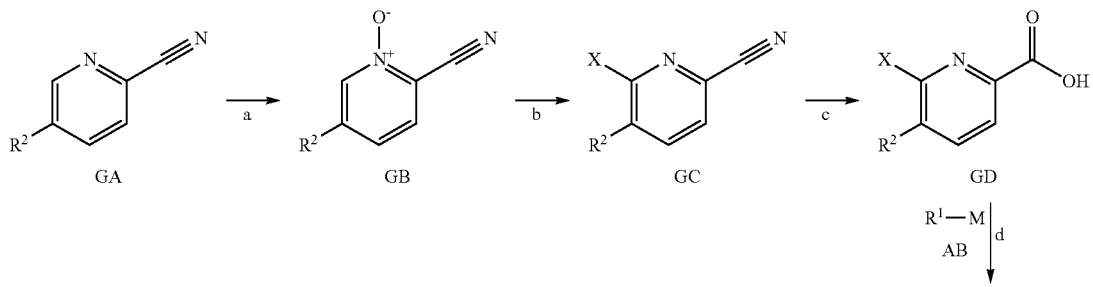

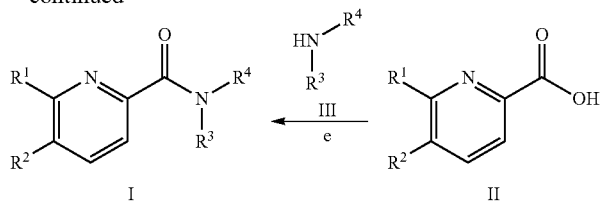

Compound GB can be prepared from GA by oxidation with a suitable oxidizing reagent under conditions known to a person skilled in the art (step a), e.g. by treatment with 3-chloro perbenzoic acid in dichloromethane at ambient temperature.

Conversion of compound GB to 6-chloro or 6-bromo compound GC(X=Cl, Br) can be achieved e.g. by treatment with phosphoryl trichloride or tribromide either without an additional solvent or in a suitable solvent such as chloroform at temperatures between 20° C. and the boiling point of the solvent or by using other conditions known in the literature (step b).

Hydrolysis of compound GC leads to picoline GD and can be performed under acidic or basic conditions known to a person skilled in the art, e.g. by treatment with an aqueous solution of sodium hydroxide at 100° C. (step c).

Compound II can be prepared from GD by coupling a suitably substituted aryl, heteroaryl or alkenyl metal species of formula AB (step d) as described in step d of scheme 6. Optionally, alkenyl containing $R^1$ residues can be transformed to the corresponding alkyl congeners II using conditions described in the literature such as e.g. a hydrogenation reaction using hydrogen gas in the presence of a catalyst such as palladium on carbon in a solvent such as ethanol or ethyl acetate particularly at ambient temperature. In cases where the acid group of compound GD is not compatible with the conditions applied to introduce the $R^1$ residue, suitable protecting groups such as ester protecting groups e.g. a methyl ester can be introduced prior to step d and removed at a later point of the synthesis. Protecting group introduction and removal can be carried out by suitable methods known in the art (for more details see T. W. Greene et al., Protective Groups in Organic Chemistry, John Wiley and Sons Inc. New York 1999, $3^{rd}$ edition).

Further conversion of compound II to compound I can be done by applying amide bond formation conditions as depicted in step c of scheme 1 (step e).

If one of the starting materials, compounds of formulae GA, AB or III, contains one or more functional groups which are not stable or are reactive under the reaction conditions of one or more reaction steps, appropriate protecting groups (P) (as described e.g. in T. W. Greene et al., Protective Groups in Organic Chemistry, John Wiley and Sons Inc. New York 1999, $3^{rd}$ edition) can be introduced before the critical step applying methods well known in the art. Such protecting groups can be removed at a later stage of the synthesis using standard methods known in the art.

If one or more compounds of formulae GA, to GD, AB, II or III contain chiral centers, picolines of formula I can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbent or a chiral eluent.

Following the procedure according to scheme 8, compound HA can be used as starting material ($R^{10}$=hydrogen or alkyl; $R^{11}$=hydrogen or alkyl). HA is either commercially available, described in the literature or can be synthesized by a person skilled in the art.

Scheme 8

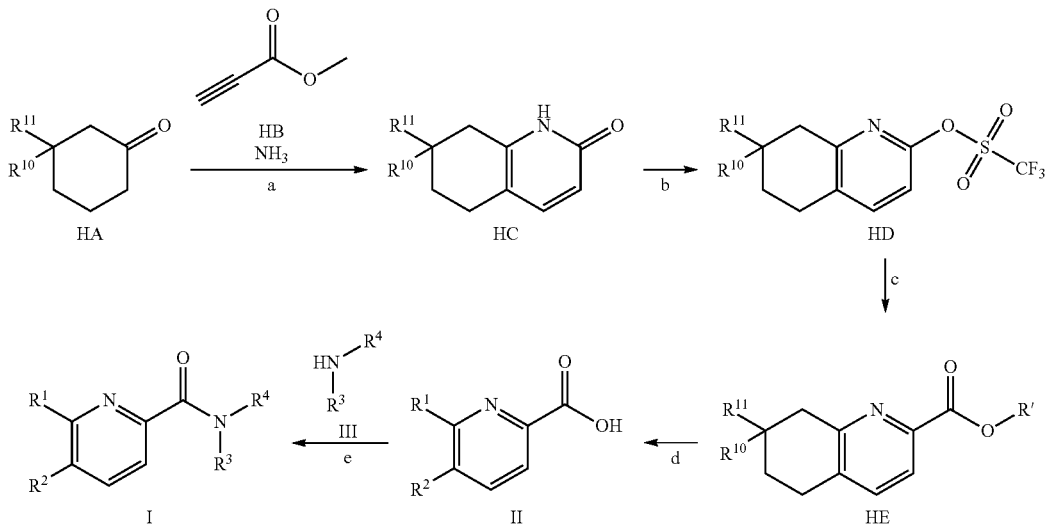

Compound HC can be prepared from HA applying methods described in the literature, e.g. by treatment with methyl propiolate in ammonia at elevated temperatures in an autoclave (step a).

Conversion of compound HC to HD can be performed e.g. using trifluoromethanesulfonic acid anhydride in the presence of a base such as triethylamine in a solvent such as dichloromethane at temperatures preferentially between −50° C. and ambient temperature or applying any other suitable method known to the ones skilled in the art (step b). Alternatively, other groups than trifluoromethane sulfonate suitable for the transformation of HD to HE can be introduced following procedures described in the literature.

Compound HE (R'=methyl, ethyl, isopropyl, tert.butyl or another suitable protecting group) can be synthesized from HD via palladium catalyzed carbonylation using a palladium catalyst such as palladium(II)chloride-dppf (1,1'-bis(diphenylphosphino)ferrocene) complexes under a carbon monoxide atmosphere preferentially under pressures of 70 bar in the presence of an amine such as triethylamine in a solvent system consisting e.g. of methanol and ethyl acetate at elevated temperatures (step c).

Compound HE can be further elaborated to compound I by:
i) saponification as described in step b of scheme 1 (step d); ii) amide bond formation as described in step c of scheme 1 (step e).

If one of the starting materials, compounds of formulae HA or III, contains one or more functional groups which are not stable or are reactive under the reaction conditions of one or more reaction steps, appropriate protecting groups (P) (as described e.g. in T. W. Greene et al., Protective Groups in Organic Chemistry, John Wiley and Sons Inc. New York 1999, 3$^{rd}$ edition) can be introduced before the critical step applying methods well known in the art. Such protecting groups can be removed at a later stage of the synthesis using standard methods known in the art.

If one or more compounds of formulae HA, HC to HE, II or III contain chiral centers, picolines of formula I can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbent or a chiral eluent.

Following the procedure according to scheme 9, commercially available 5-bromo-6-methyl-pyridine-2-carbonitrile IA (CAN 1173897-86-3) can be used as starting material. In scheme 9, $R^1$ is benzyl or halobenzyl; $R^{1'}$ is phenyl or halohenyl.

Scheme 9

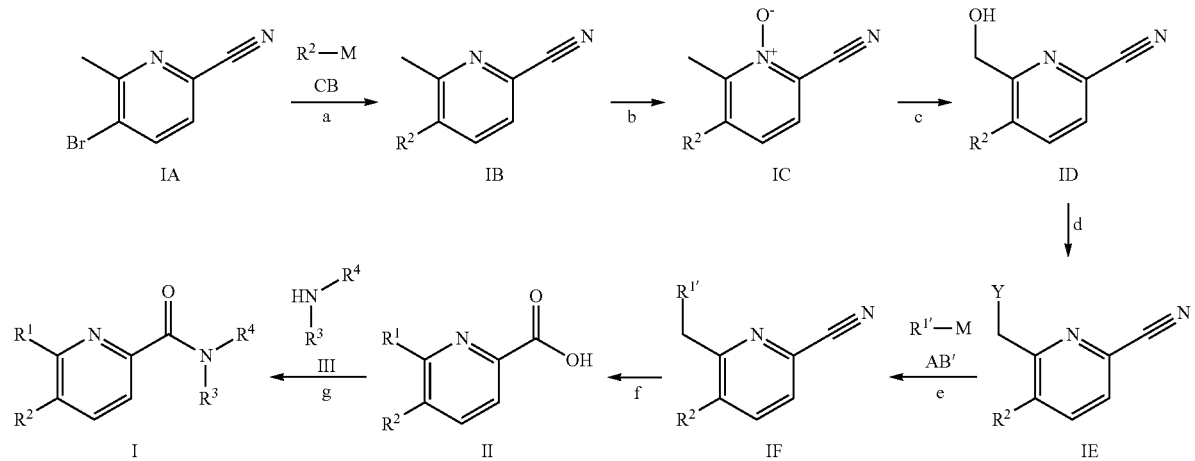

Compound IB can be prepared from IA by treatment with compound CB as described in step a of scheme 6 (step a).

Further transformation of IB to IC can be achieved by oxidation with a suitable oxidizing reagent as described in step a of scheme 7 (step b).

Conversion of N-oxide IC to alcohol ID can be performed under conditions well known to a person skilled in the art, e.g. by reaction with trifluoroacetic acid anhydride in a solvent such as dichloromethane preferentially at ambient temperature and subsequent treatment with a base such as sodium hydroxide (step c).

Reactions how to convert alcohol ID into compound IE containing a leaving group (Y=Cl, Br or another suitable leaving group) are well described in the literature and known to those skilled in the art (step d). For example alcohol ID can be transformed to compound IE with Y=Br by reaction with carbon tetrabromide and triphenylphosphine in a solvent such as tetrahydrofuran at temperatures between 0° C. and the boiling point of the solvent, preferentially at 40° C.

Conversion of compound IE to compound IF can e.g. be accomplished by coupling a suitably substituted aryl metal species of formula AB', particularly an arylboronic acid or arylboronic acid ester in the presence of a suitable catalyst, in particular a palladium catalyst and more particularly palladium(II)acetate/triphenylphosphine mixtures or palladium (II)chloride-dppf (1,1'-bis(diphenylphosphino)ferrocene) complexes and a base such as triethylamine, cesium carbonate or potassium phosphate in an inert solvent such as dimethylformamide, toluene, tetrahydrofuran and 1,4-dioxane (step e).

Nitrile IF can be hydrolyzed to acid II applying the method described in step c of scheme 7 (step f).

Further conversion of compound II to compound I can be done by applying amide bond formation conditions as depicted in step c of scheme 1 (step e).

If one of the starting materials, compounds of formulae IA, CB, AB' or III, contains one or more functional groups which are not stable or are reactive under the reaction conditions of one or more reaction steps, appropriate protecting groups (P) (as described e.g. in T. W. Greene et al., Protective Groups in Organic Chemistry, John Wiley and Sons Inc. New York 1999, $3^{rd}$ edition) can be introduced before the critical step applying methods well known in the art. Such protecting groups can be removed at a later stage of the synthesis using standard methods known in the art.

If one or more compounds of formulae IA to IF, CB, AB', II or III contain chiral centers, picolines of formula I can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbent or a chiral eluent.

Compounds I may be further processed to give additional compounds of the general structure I by methods known in the art. Some examples are shown in scheme 10. In scheme 10, $R^{12}$ is isobutyl, n is 0, 1 or 2.

Compounds of the general structure KB (a subgroup of I) can be prepared from compounds of general structure KA (another subgroup of I) by oxidative methods well known in the art, e.g. by Swern-oxidation using DMSO and a suitable activating agent as for example oxalyl chloride in an inert solvent as for example dichloromethane in the presence of a suitable base at temperatures ranging from −70° C. to room temperature.

Compounds of the general structure KD (a subgroup of I) can be prepared from compounds of general structure KC (another subgroup of I) by converting an alcohol functionality to an azide functionality by methods known in the art. This transformation can for example be affected by treating a solution of the alcohol in an inert solvent like DMF with sodium azide, triphenylphosphine and carbon tetrachloride at elevated temperatures as for example 90° C. Further elaboration to the corresponding amine KE is done by reduction methods well known in the art as for example by reduction with sodium borohydride in 2-propanol in the presence of 1,3-propanedithiol and triethylamine at ambient temperatures. The amines KD can be further transformed into compounds of general structure KF, by reaction with 7-nitro-2,1,3-benzooxadiazol-4-amine in an inert solvent like THF at temperatures ranging from room temperature to the boiling point of the solvent.

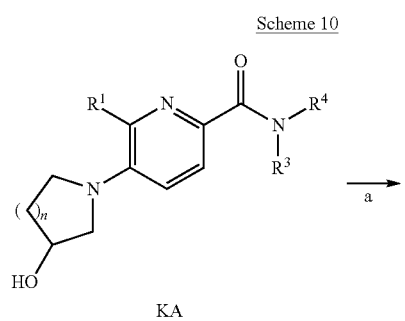

Scheme 10

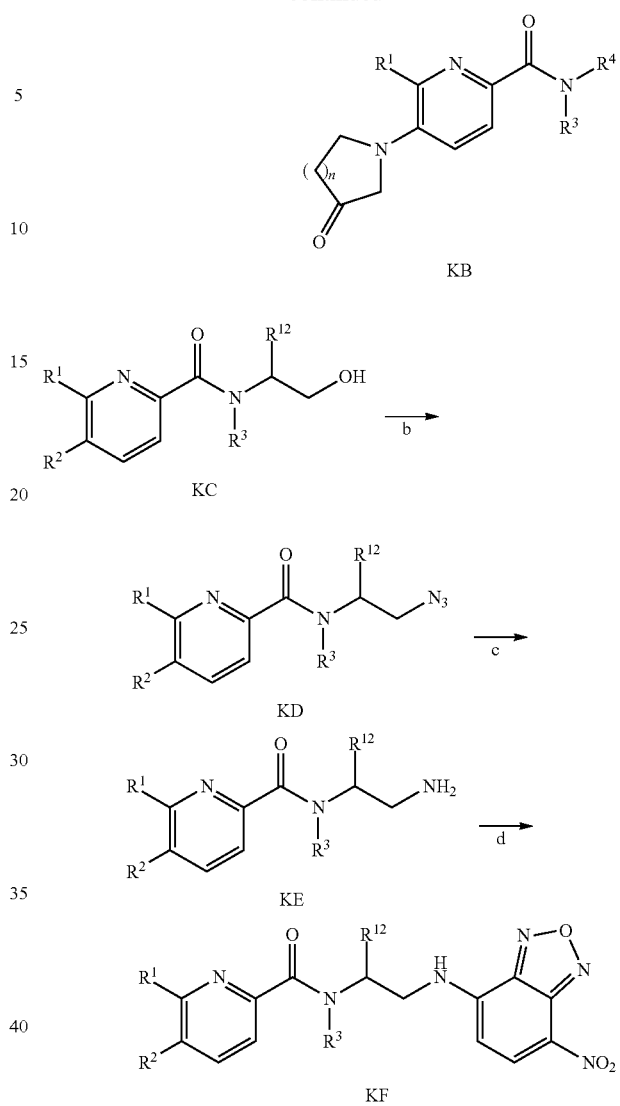

If one of the starting materials, compounds of formulae KA or KC contains one or more functional groups which are not stable or are reactive under the reaction conditions of one or more reaction steps, appropriate protecting groups (P) (as described e.g. in T. W. Greene et al., Protective Groups in Organic Chemistry, John Wiley and Sons Inc. New York 1999, $3^{rd}$ edition) can be introduced before the critical step applying methods well known in the art. Such protecting groups can be removed at a later stage of the synthesis using standard methods known in the art.

If one or more compounds of formulae KA or KC contain chiral centers, picolines of formula I can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbent or a chiral eluent.

The invention also relates to a process for the preparation of a compound of formula (I) comprising the reaction of a compound of formula (A)

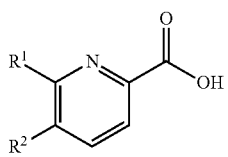

(A)

in the presence of $NHR^3R^4$, an amide bond forming coupling agent and a base, wherein $R^1$ to $R^4$ are defined above.

Examples of amide bond forming coupling agents are N,N'-carbonyl-diimidazole (CDI), N,N'-dicyclohexylcarbodiimide (DCC), 1-(3-dimethylaminopropyl)-3-ethylcarbodiimide hydrochloride (EDCI), 1-[bis(dimethylamino)-methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU) and O-benzotriazole-N,N,N',N'-tetramethyl-uronium-hexafluoro-phosphate (HBTU).

Examples of suitable bases are tertiary amine bases like triethylamine, N-methylmorpholine, N,N-diisopropylethylamin or 4-(dimethylamino)-pyridine.

The reaction temperature is for example room temperature.

A convenient method is to use for example HBTU and a base, for example N-methylmorpholine in an inert solvent such as for example dimethylformamide at room temperature.

The invention further relates to a compound of formula (I) for use as therapeutically active substance.

The invention further relates to a pharmaceutical composition comprising a compound of formula (I) and a therapeutically inert carrier.

The use of a compound of formula (I) for the treatment or prophylaxis of pain, in particular chronic pain, atherosclerosis, regulation of bone mass, inflammation, ischemia, reperfusion injury, systemic fibrosis, liver fibrosis, lung fibrosis, kidney fibrosis, chronic allograft nephropathy, congestive heart failure, myocardial infarction, systemic sclerosis, glomerulonephropathy, thermal injury, burning, hypertrophic scars, keloids, gingivitis pyrexia, liver cirrhosis or tumors is another object of the invention.

The use of a compound of formula (I) for the preparation of a medicament for the treatment or prophylaxis of chronic pain, in particular chronic pain, atherosclerosis, regulation of bone mass, inflammation, ischemia, reperfusion injury, systemic fibrosis, liver fibrosis, lung fibrosis, kidney fibrosis, chronic allograft nephropathy, congestive heart failure, myocardial infarction, systemic sclerosis, glomerulonephropathy, thermal injury, burning, hypertrophic scars, keloids, gingivitis pyrexia, liver cirrhosis or tumors is a further object of the invention.

The invention also relates to a compound of formula (I) for the treatment or prophylaxis of pain, in particular chronic pain, atherosclerosis, regulation of bone mass, inflammation, ischemia, reperfusion injury, systemic fibrosis, liver fibrosis, lung fibrosis, kidney fibrosis, chronic allograft nephropathy, congestive heart failure, myocardial infarction, systemic sclerosis, glomerulonephropathy, thermal injury, burning, hypertrophic scars, keloids, gingivitis pyrexia, liver cirrhosis or tumors.

The invention particularly relates to a compound of formula (I) for the treatment or prophylaxis of ischemia, reperfusion injury, liver fibrosis or kidney fibrosis, in particular ischemia or reperfusion injury.

The invention is further directed to a compound of formula (I), when manufactured according to a process according to the invention.

A method for the treatment or prophylaxis of pain, in particular chronic pain, atherosclerosis, regulation of bone mass, inflammation, ischemia, reperfusion injury, systemic fibrosis, liver fibrosis, lung fibrosis, kidney fibrosis, chronic allograft nephropathy, congestive heart failure, myocardial infarction, systemic sclerosis, glomerulonephropathy, thermal injury, burning, hypertrophic scars, keloids, gingivitis pyrexia, liver cirrhosis or tumors, which method comprises administering an effective amount of a compound of formula (I) is also an object of the invention.

Another embodiment of the invention provides pharmaceutical compositions or medicaments containing the compounds of the invention and a therapeutically inert carrier, diluent or excipient, as well as methods of using the compounds of the invention to prepare such compositions and medicaments. In one example, compounds of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compounds of formula (I) are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

The invention will now be illustrated by the following examples which have no limiting character.

EXAMPLES

Abbreviations

MS=mass spectrometry; EI=electron impact; ISP=ion spray, corresponds to ESI (electrospray); NMR data are reported in parts per million (δ) relative to internal tetramethylsilane and are referenced to the deuterium lock signal from the sample solvent (d$_6$-DMSO unless otherwise stated); coupling constants (J) are in Hertz, mp=melting point; bp=boiling point; DIEA=N-ethyl-N-isopropylpropan-2-amine; DMF=dimethylformamide; DMSO=dimethyl-sulfoxide; dppf=1,1'-bis(diphenylphosphino)ferrocene; HATU=2-(3H-[1,2,3]triazolo[4,5-b]pyridin-3-yl)-1,1,3,3-tetramethylisouronium hexafluorophosphate(V); HBTU=O-benzotriazole-N,N,N',N'-tetramethyl-uronium-hexafluoro-phosphate; HPLC=LC=high performance liquid chromatography; m-CPBA=meta-chloroperoxybenzoic acid; Rt=retention time; TBTU=O-(benzotriazol-1-yl)-N,N,N',N'-tetramethyl-uronium-tetrafluoroborate; TEMPO=2,2,6,6-tetra-methylpiperidine 1-oxyl radical; THF=tetrahydrofuran; tlc=thin layer chromatography.

Example 1

Methyl 2-(6-(3-chlorophenyl)picolinamido)-2-methylpropanoate

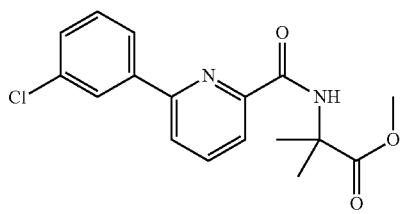 [SMILES: COC(=O)C(C)(C)NC(=O)c1cccc(-c2cccc(Cl)c2)n1]

A solution of 6-(3-chlorophenyl)-2-pyridinecarboxylic acid (CAN 863704-38-5, 0.2 mmol), 2-methyl-alanine methyl ester (0.2 mmol) and HBTU (CAN 94790-37-1, 114 mg, 0.3 mmol) in DMF (0.5 mL) was stirred for 20 h at room temperature. The crude reaction mixture was concentrated in vacuo by centrifugation and purified by flash chromatography (silica gel, 20 g, 0% to 100% ethyl acetate in heptane) to give the desired product together with some impurities (73 mg, 116%) as light yellow oil; MS (LC/MS): 333.1 (M+H).

Example 2

Methyl 2-(6-(2-chlorophenyl)picolinamido)-2-methylpropanoate

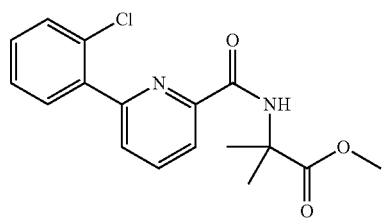 [SMILES: COC(=O)C(C)(C)NC(=O)c1cccc(-c2ccccc2Cl)n1]

The title compound was synthesized in analogy to Example 1, using 6-(2-chlorophenyl)-2-pyridinecarboxylic acid (CAN 887982-21-0) and 2-methyl-alanine methyl ester as starting materials, MS (LC/MS): 333.1 (M+H).

Example 3

6-(4-Chloro-phenyl)-pyridine-2-carboxylic acid [1-methyl-1-(5-methyl-[1,2,4]oxadiazol-3-yl)-ethyl]-amide

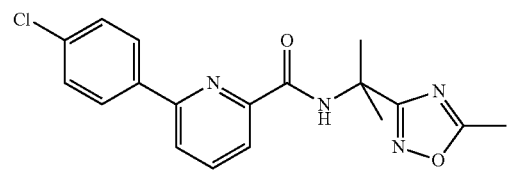 [SMILES: Cc1nc(C(C)(C)NC(=O)c2cccc(-c3ccc(Cl)cc3)n2)no1]

The title compound was synthesized in analogy to Example 1, using 6-(4-chlorophenyl)-2-pyridinecarboxylic acid (CAN 135432-77-8) and α,α,5-trimethyl-1,2,4-oxadiazole-3-methanamine (CAN 1153831-97-0) as starting materials, MS (LC/MS): 357.1 (M+H).

Example 4

Methyl 2-methyl-2-(5-methyl-6-(2,2,2-trifluoroethoxy)picolinamido)propanoate a) 5-Methyl-6-(2,2,2-trifluoro-ethoxy)-pyridine-2-carboxylic acid

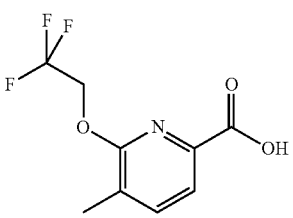 [SMILES: Cc1ccc(C(=O)O)nc1OCC(F)(F)F]

A mixture of 6-chloro-5-methyl-pyridine-2-carboxylic acid (CAN 1166828-13-2, 200 mg, 1.17 mmol), 2,2,2-trifluoroethanol (466 mg, 336 µl, 4.66 mmol) and 1,8-diazabicyclo(5.4.0)undec-7-ene (CAN 83329-50-4, 887 mg, 870 µl, 5.83 mmol) was shaken in a sealed tube for 2 days at 140° C.

and subsequently for additional 5 days at 150° C. The brown solution was poured into 25 mL ice/0.1 N HCl and extracted with i-PrOAc (2×25 mL). The organic layers were washed with ice/brine (2×25 mL). The organic layers were dried over sodium sulfate and concentrated in vacuo to give the title compound (198 mg, 58%) as off-white solid containing traces of starting material, MS (EI): m/e=233.9 [M−H]⁻.

b) Methyl 2-methyl-2-(5-methyl-6-(2,2,2-trifluoroethoxy)picolinamido)propanoate

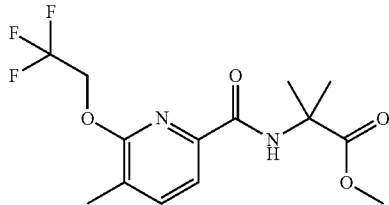 [SMILES: COC(=O)C(C)(C)NC(=O)c1ccc(C)c(OCC(F)(F)F)n1]

A solution of 5-methyl-6-(2,2,2-trifluoro-ethoxy)-pyridine-2-carboxylic acid (30 mg, 128 μmol), 2-methyl-alanine methyl ester hydrochloride (23.5 mg, 153 μmol), HATU (CAN 148893-10-1, 97.0 mg, 255 μmol) and DIEA (82.4 mg, 109 μl, 638 μmol) in DMF was stirred at ambient temperature for 72 h. The crude reaction mixture was concentrated in vacuo to give 53 mg of a yellow solid. This solid was purified by preparative TLC (silica gel, 2.0 mm, 1:1 heptane/i-PrOAc) and eluted from the silica gel with i-PrOAc. Filtration over speedex and evaporation under reduced pressure provided the title compound (10 mg, 23%) as colorless liquid, MS (EI): m/e=335.2 [M+H]⁺.

Example 5

Methyl 2-(5-cyclopropyl-6-(2,4-dichlorophenylamino)picolinamido)-2-methylpropanoate a) 6-Chloro-5-cyclopropyl-pyridine-2-carboxylic acid methyl ester

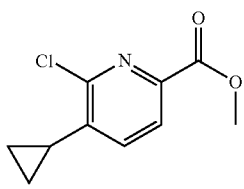

To a mixture of palladium(II)acetate (17.9 mg, 79.8 μmol), butyl-1-adamantylphosphine (42.9 mg, 120 μmol), potassium cyclopropyltrifluoroborate (597 mg, 4.03 mmol) and cesium carbonate (3.9 g, 12.0 mmol) under an argon atmosphere was added a solution of 5-bromo-6-chloro-pyridine-2-carboxylic acid methyl ester (CAN 1214353-79-3, 1 g, 3.99 mmol) in toluene (25.2 ml) and water (2.8 mL) under an argon atmosphere. The reaction mixture was heated to 100° C. for 20 h, diluted with water (17.5 ml), poured onto 100 ml ice/brine and extracted with i-PrOAc (2×100 mL). The combined extracts were dried over sodium sulfate and concentrated in vacuo to give a yellow liquid. This crude material was purified by column chromatography (70 g SiO₂, n-heptane/i-PrOAc 0-10% over 120 min) to give the title compound (497 mg, 59%) as yellow solid, MS (EI): m/e=212.0 [M+H]⁺.

b) 5-Cyclopropyl-6-(2,4-dichloro-phenylamino)-pyridine-2-carboxylic acid methyl ester

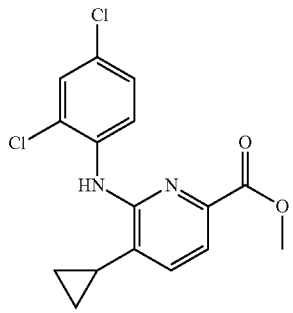 [SMILES: COC(=O)c1ccc(C2CC2)c(Nc2ccc(Cl)cc2Cl)n1]

A solution of palladium(II)acetate (4.24 mg, 18.9 μmol) and 2-(dicyclohexylphosphino) biphenyl (13.2 mg, 37.8 μmol) in dioxane (1.9 ml) under an argon atmosphere was stirred for 10 min at ambient temperature and subsequently added to a suspension of 6-chloro-5-cyclopropyl-pyridine-2-carboxylic acid methyl ester (100 mg, 472 μmol), 2,4-dichloroaniline (76.6 mg, 472 μmol) and potassium carbonate (1.31 g, 9.45 mmol) in dioxane (3.24 ml) under an argon atmosphere. The yellow suspension was heated to reflux and stirred for 20 h. The reaction mixture was poured into 20 mL ice/brine and extracted with i-PrOAc (2×50 mL). The combined organic layers were washed with ice/brine (1×50 mL), dried over sodium sulfate and concentrated in vacuo to give a brown oil. The crude product was purified by flash chromatography (silica gel, 4 g, 0% to 10% heptane/iPrOAc) to give the title compound (62 mg, 39%) as light brown liquid, MS (EI): m/e=337.2 [M+H]⁺.

c) 5-Cyclopropyl-6-(2,4-dichloro-phenylamino)-pyridine-2-carboxylic acid

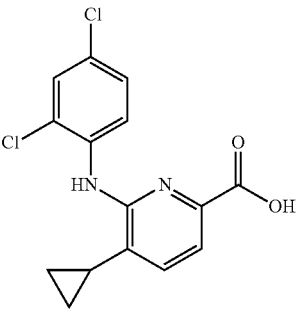 [SMILES: O=C(O)c1ccc(C2CC2)c(Nc2ccc(Cl)cc2Cl)n1]

A solution of 5-cyclopropyl-6-(2,4-dichloro-phenylamino)-pyridine-2-carboxylic acid methyl ester (62 mg, 184 μmol) and lithium hydroxide hydrate (9.3 mg, 221 μmol) in THF (100 μl) and water (50 μl) was stirred at ambient temperature for 20 h. The reaction mixture was poured onto 1 M HCl/ice water (1×20 mL) and extracted with i-PrOAc (2×25 mL). The combined organic layers were dried over sodium sulfate. The solvent was removed under reduced pressure to obtain the title compound (6 mg, 10%) as colorless liquid, which was sufficiently pure to be used in the next reaction step, MS (EI): m/e=323.3 [M+H]⁺.

d) Methyl 2-(5-cyclopropyl-6-(2,4-dichlorophenylamino)picolinamido)-2-methylpropanoate

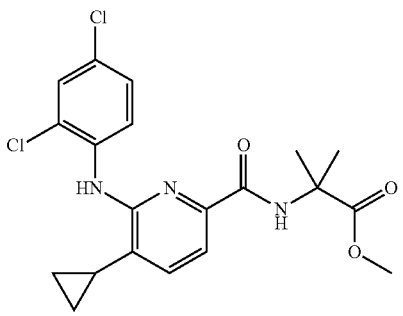 [SMILES: COC(=O)C(C)(C)NC(=O)c1ccc(C2CC2)c(Nc2ccc(Cl)cc2Cl)n1]

The title compound was synthesized in analogy to Example 4 b, using 5-cyclopropyl-6-(2,4-dichloro-phenylamino)-pyridine-2-carboxylic acid and 2-methyl-alanine methyl ester as starting materials, MS (EI): m/e 422.1 [M+H]$^+$.

Example 6

Methyl 2-(6-(2,4-dichlorophenylamino)-5-methylpicolinamido)-2-methylpropanoate a) 6-(2,4-Dichloro-phenylamino)-5-methyl-pyridine-2-carboxylic acid methyl ester

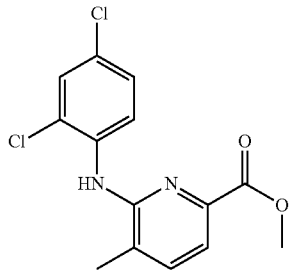 [SMILES: COC(=O)c1ccc(C)c(Nc2ccc(Cl)cc2Cl)n1]

6-(2,4-Dichloro-phenylamino)-5-methyl-pyridine-2-carboxylic acid methyl ester was synthesized in analogy to Example 5 b, using 6-chloro-5-methyl-pyridine-2-carboxylic acid methyl ester (CAN 178421-22-2) and 2,4-dichloroaniline as starting materials, MS (EI): m/e 311.3 [M+H]$^+$.

b) 6-(2,4-Dichloro-phenylamino)-5-methyl-pyridine-2-carboxylic acid

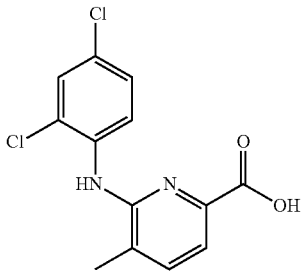 [SMILES: Cc1ccc(C(=O)O)nc1Nc1ccc(Cl)cc1Cl]

6-(2,4-Dichloro-phenylamino)-5-methyl-pyridine-2-carboxylic acid was synthesized in analogy to Example 5 c, using 6-(2,4-dichloro-phenylamino)-5-methyl-pyridine-2-carboxylic acid methyl ester as starting material, MS (EI): m/e 297.2 [M+H]$^+$.

c) Methyl 2-(6-(2,4-dichlorophenylamino)-5-methylpicolinamido)-2-methylpropanoate

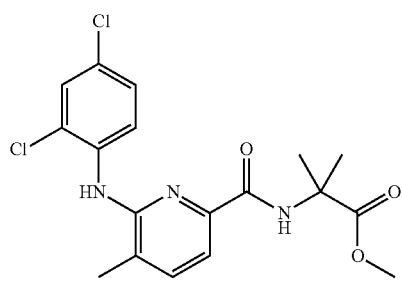 [SMILES: COC(=O)C(C)(C)NC(=O)c1ccc(C)c(Nc2ccc(Cl)cc2Cl)n1]

The title compound was synthesized in analogy to Example 4 b, using 6-(2,4-dichloro-phenylamino)-5-methyl-pyridine-2-carboxylic acid and 2-methyl-alanine methyl ester as starting materials, MS (EI): m/e 396.0 [M+H]$^+$.

Example 7

2-[(6-Cyclohexyl-pyridine-2-carbonyl)-amino]-2-methyl-propionic acid methyl ester a) 6-Cyclohexenyl-pyridine-2-carboxylic acid

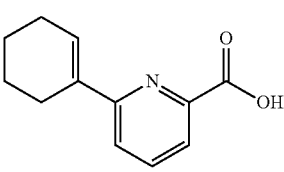 [SMILES: O=C(O)c1cccc(C2=CCCCC2)n1]

Under an atmosphere of nitrogen, a solution of 6-bromo-pyridine-2-carboxylic acid (CAN 1190-87-4, 3 g, 6.4 mol), cyclohexenylboronic acid (CAN 21190-87-4, 0.89 g, 7.1 mmol), 1,1'-bis(diphenyl-phosphino)ferrocene-palladium (II)dichloride methylene chloride complex (CAN 95464-05-4, 8 mg, 0.13 mmol), potassium carbonate (1.78 g, 12.9 mmol) in H$_2$O (30 mL) was heated to 100° C. overnight. The reaction mixture was extracted with ethyl acetate (50 mL). The pH of the aqueous layer was adjusted to 5 by addition of 1 N hydrochloric acid and the resulting mixture was extracted with ethyl acetate (3×50 mL). The combined organic extracts were washed with water and brine, dried over anhydrous sodium sulfate and evaporated. The residue was purified by prep-HPLC to yield the title compound (0.8 g, 3.94 mmol, 61.2%) as yellow oil; MS (EI): m/e=204.2 [M+H]$^+$.

b) 6-Cyclohexyl-pyridine-2-carboxylic acid

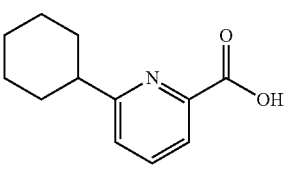 [SMILES: O=C(O)c1cccc(C2CCCCC2)n1]

To a solution of 6-cyclohexenyl-pyridine-2-carboxylic acid (0.8 g, 3.94 mmol) in ethanol (50 mL) was added 10% palladium on carbon (20%, 0.16 g) under an atmosphere of nitrogen. The suspension was degassed under vacuum and exchanged with hydrogen several times. The mixture was stirred under hydrogen balloon at ambient temperature overnight. The reaction mixture was filtered through a pad of celite, the pad was washed with ethanol and the combined filtrates were concentrated to dryness. The crude title compound (0.62 g, green oil) was used for the next reaction step without further purification; MS (EI): m/e 206.2 [M+H]$^+$ c) 2-[(6-Cyclohexyl-pyridine-2-carbonyl)-amino]-2-methyl-propionic acid methyl ester

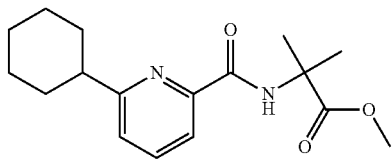 [SMILES: COC(=O)C(C)(C)NC(=O)c1cccc(C2CCCCC2)n1]

The title compound was synthesized in analogy to Example 1, using 6-cyclohexyl-pyridine-2-carboxylic acid and 2-methyl-alanine methyl ester as starting materials, MS (LC/MS): 305.1 (M+H).

Example 8

6-(3-Chloro-phenyl)-pyridine-2-carboxylic acid (1-methyl-1-oxazol-2-yl-ethyl)-amide a) 2-(Benzyloxycarbonylamino)-2-methylpropanoic acid

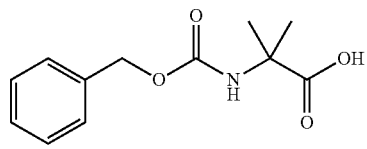 [SMILES: CC(C)(NC(=O)OCc1ccccc1)C(=O)O]

To a solution of 2-methylalanine (CAN 62-57-7, 30.9 g, 0.3 mol) and sodium hydroxide (20 g, 0.5 mol) in water (500 mL) was added benzyl chloroformate (61.4 g, 0.36 mol) at ice-water bath temperature. The reaction mixture was allowed to warm to room temperature and stirred overnight. The resulting solution was washed with ethyl acetate (2×80 mL), then the aqueous layer was adjusted to pH=2 with conc. hydrochloric acid and the solution was extracted with ethyl acetate (3×150 mL). The combined organic layers were dried over anhydrous sodium sulfate and concentrated under reduced pressure to give the crude target compound (26 g, 36%) which was used directly for the next step without further purification; MS: m/e 238.0 [M+H]$^+$.

b) Benzyl 1-(2,2-dimethoxyethylamino)-2-methyl-1-oxopropan-2-ylcarbamate

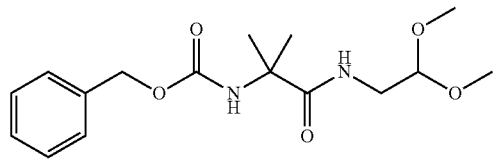 [SMILES: COC(CNC(=O)C(C)(C)NC(=O)OCc1ccccc1)OC]

A mixture of 2-(benzyloxycarbonylamino)-2-methylpropanoic acid (20 g, 0.084 mol), HATU (CAN 148893-10-1, 41.56 g, 0.11 mol) and N-methylmorpholine (CAN 109-02-4, 25.54 g, 0.253 mol) in DMF (400 mL) was stirred at room temperature for 10 min. 2,2-Dimethoxyethanamine (CAN 22483-09-6, 9.75 g, 0.093 mol) was added and the mixture was stirred overnight. After evaporation of solvents, the residue was diluted with methylene chloride (500 mL) and saturated sodium bicarbonate solution (500 mL). After being separated, the organic layer was washed with 5 N citric acid solution (500 mL), brine (500 mL) and dried over anhydrous sodium sulfate. Removal of the solvent under reduced pressure left a yellow oil (27 g, 99%) which was used in the next reaction step without further purification. $^1$H NMR (300 MHz, CDCl$_3$): δ 7.36-7.33 (m, 5H), 6.44-6.38 (b, 1H), 5.31 (s, 1H), 5.09 (s, 2H), 4.34-4.33 (m, 1H), 3.40-3.37 (m, 8H), 2.06-2.03 (m, 6H).

c) Benzyl 2-methyl-1-oxo-1-(2-oxoethylamino)propan-2-ylcarbamate

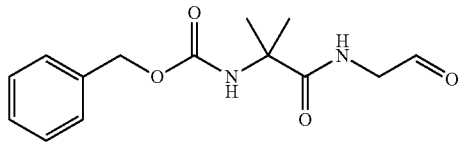 [SMILES: CC(C)(NC(=O)OCc1ccccc1)C(=O)NCC=O]

To a solution of benzyl 1-(2,2-dimethoxyethylamino)-2-methyl-1-oxopropan-2-ylcarbamate (0.52 g, 1.6 mmol) in THF (20 mL) was added 5 M hydrochloric acid (10 mL) and the mixture was stirred at room temperature until TLC showed the reaction was completed. Ethyl acetate (50 mL) was added and the phases were separated. The organic layer was washed with brine (4×30 mL) to pH=6-7, dried over anhydrous sodium sulfate and concentrated to yield product (0.445 g, 100%) as yellow oil, which was used directly in the next step without purification; MS: m/e 279.1 [M+H]$^+$.

d) Benzyl 2-(oxazol-2-yl)propan-2-ylcarbamate

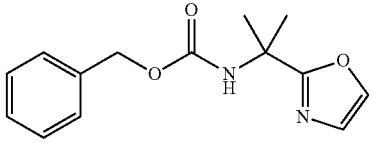 [SMILES: CC(C)(NC(=O)OCc1ccccc1)c1ncco1]

A solution of benzyl 2-methyl-1-oxo-1-(2-oxoethylamino) propan-2-ylcarbamate (2.23 g, 8 mmol) in methylene chloride (50 mL) was added to a freshly prepared solution of PPh$_3$ (3.15 g, 12 mmol), I$_2$ (3.05 g, 12 mmol) and Et$_3$N (2.43 g, 24 mmol) in methylene chloride (100 mL). The resulting mixture was stirred at room temperature until TLC showed the reaction was completed. Then water (150 mL) was added. The organic layer was washed with 5% sodium bisulfite (150 mL×2), brine (150 mL) and dried over anhydrous sodium sulfate. Removal of the solvent under reduced pressure left a yellow oil which was purified by column chromatography (silica gel, 50 g, eluting with 25% ethyl acetate in petroleum ether) to yield the title compound (0.63 g, 30%) as colorless oil; MS: m/e 261.2 [M+H]$^+$. $^1$H NMR (300 MHz, CDCl$_3$): δ 7.57 (s, 1H), 7.37-7.33 (m, 5H), 7.05 (s, 1H), 5.06 (s, 2H), 1.74 (s, 6H).

e) α,α-Dimethyl-2-oxazolemethanamine

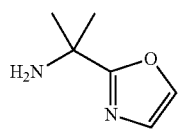

A mixture of benzyl 2-(oxazol-2-yl)propan-2-ylcarbamate (0.63 g, 24 mmol) and palladium 10% on carbon (0.06 g) in ethanol (20 mL) was charged with hydrogen balloon and stirred at room temperature for 2 h. TLC showed the reaction was completed; it was filtered and concentrated to give a yellow oil (0.1 g, 33%); MS: m/e 127.1 [M+H]$^+$. $^1$H NMR (300 MHz, CDCl$_3$): δ 7.58 (d, 1H, J=0.6 Hz), 7.02 (s, 1H), 2.56 (bs, 4H), 1.59 (s, 6H).

f) 6-(3-Chloro-phenyl)-pyridine-2-carboxylic acid (1-methyl-1-oxazol-2-yl-ethyl)-amide

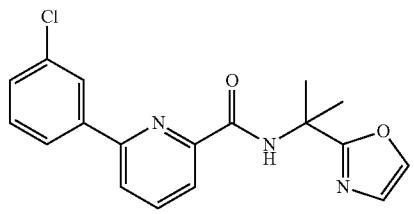

The title compound was synthesized in analogy to Example 1, using 6-(3-chlorophenyl)-2-pyridinecarboxylic acid (CAN 863704-38-5) and α,α-dimethyl-2-oxazolemethanamine (CAN 1211519-76-4) as starting materials, MS (LC/MS): 341.9 [M+H]$^+$.

Example 9

2-{[6-Cyclopropylmethoxy-5-(tetrahydro-pyran-4-yl)-pyridine-2-carbonyl]-amino}-2-methyl-propionic acid methyl ester a) 3,6-Dihydro-2H-pyran-4-yl trifluoromethanesulfonate

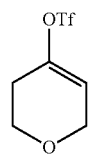

Under an atmosphere of nitrogen, to a solution of diisopropylamine (CAN 180-18-9, 2.42 g, 0.024 mol) in THF (40 mL) was added n-butyl lithium (10.4 mL, 2.5 M solution in hexane, 26 mmol) at −78° C. The reaction mixture was reacted for 30 min at −50° C. Then tetrahydropyran-4-one (CAN 29943-42-8, 2 g, 0.020 mol) in THF (10 mL) was added dropwise to the above solution at −78° C. The reaction mixture was reacted for 30 min at −78° C. Then trifluoro-N-phenyl-N-(trifluoromethylsulfonyl)methanesulfonamide (CAN 37595-74-7, 7.85 g, 0.022 mol) in THF (50 mL) was added dropwise to the above solution at −78° C. The reaction mixture was stirred for 10 min at room temperature. The reaction mixture was quenched with a saturated solution of sodium bicarbonate (10 mL) and extracted with ethyl acetate (3×30 mL). The combined organic extracts were washed with citric acid (50 mL) and sodium hydroxide solution (1 N, 50 mL), dried over anhydrous sodium sulfate and evaporated. The residue was purified by column chromatography (silica gel, 10 g, 1% ethyl acetate in petroleum ether) to yield the title compound (0.7 g, 3 mmol, 15.1%) as yellow oil. $^1$H NMR (300 MHz, d$^6$-DMSO): 6.05-6.03 (m, 1H), 4.17 (d, J=3 Hz, 2H), 3.78 (t, J=4.5 Hz, 2H), 2.38 (t, J=3 Hz, 2H).

b) 2-(3,6-Dihydro-2H-pyran-4-yl)-4,4,5,5-tetramethyl-1,3,2-dioxaborolane

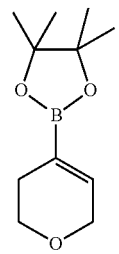

Under an atmosphere of nitrogen, a solution of 3,6-dihydro-2H-pyran-4-yl trifluoromethanesulfonate (0.7 g, 3.0 mmol), 4,4,4',4',5,5,5',5'-octamethyl-2,2'-bi(1,3,2-dioxaborolane) (CAN 3183-34-3, 0.84 g, 3.3 mmol), 1,1'-bis (diphenylphosphino) ferrocene-palladium(II)dichloride methylene chloride complex (CAN 95464-05-4, 0.05 g, 0.06 mmol) and potassium acetate (0.89 g, 9.0 mmol) in DMSO (10 mL) was heated to 80° C. overnight. Water (50 mL) was added to the reaction mixture which then was extracted with ethyl acetate (3×30 mL). The combined organic extracts were washed with brine, dried over anhydrous sodium sulfate and evaporated. The residue was purified by column chromatography (silica gel, 9 g, 1% ethyl acetate in petroleum ether) to yield the title compound (0.32 g, 2 mmol, 50.5%) as colorless oil. $^1$H NMR (300 MHz, CDCl$_3$): δ 6.53 (s, 1H), 4.20 (t, J=3 Hz, 2H), 3.76 (t, J=6 Hz, 2H), 2.24 (dd, J$_1$=6 Hz, J$_2$=6 Hz, 2H), 1.28 (s, 12H).

c) 5-Bromo-6-chloro-pyridine-2-carboxylic acid methyl ester

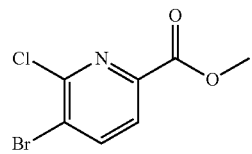

A mixture of 5-bromo-pyridine-2-carboxylic acid methyl ester (CAN 29682-15-3, 50 g, 0.23 mol) and m-CPBA (CAN 937-14-4, 80 g, 0.46 mol) in 400 mL dry methylene chloride was heated to 60° C. for 20 h. After that, the mixture was quenched with saturated sodium sulfite solution and extracted with ethyl acetate (2×200 mL). The organic layer was washed with brine (2×200 mL) and evaporated to dryness. The residue was purified by column chromatography (silica gel, 300 g, eluting with 15% ethyl acetate in petroleum ether) to obtain a brown oil. The brown oil, 5-bromo-2-(methoxycarbonyl) pyridine 1-oxide (30 g, 0.13 mol) was added into phosphoryl trichloride (CAN 10025-87-3, 80 mL) at 0° C. over 1 h, then the mixture was heated to 95° C. for 1 h. After that the mixture was evaporated to dryness, the residue was dissolved in water (50 mL), extracted with ethyl acetate (3×50 mL) and the organic layer was evaporated to dryness to obtain the product as a white solid (19 g, 59%); MS (EI): m/e=249.9 [M+H]$^+$.

d) 5-Bromo-6-cyclopropylmethoxy-pyridine-2-carboxylic acid

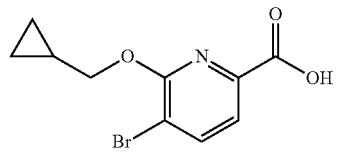 [SMILES: O=C(O)c1ccc(Br)c(OCC2CC2)n1]

Sodium hydride (4.83 g, 0.12 mol) was added into cyclopropanemethanol (CAN 2516-33-8, 30 g) at 0° C. and the mixture was stirred at 0° C. for 1 h. Then to the mixture was added methyl 5-bromo-6-chloro-pyridine-2-carboxylic acid methyl ester (3 g, 12.75 mmol). The obtained solution was heated to 90° C. for 2 h. Then the mixture was evaporated to dryness, the residue was dissolved in 40 mL of water, and adjusted to pH=4 with hydrochloric acid (3 N), and extracted with ethyl acetate (3×30 mL). The combined organic layer was washed with water (2×30 mL) and brine (2×50 mL) then evaporated to dryness to obtain the product as a white solid (2.5 g, 76.7%); MS (EI): m/e=272.0 [M+H]$^+$.

e) 6-(Cyclopropylmethoxy)-5-(tetrahydro-2H-pyran-4-yl)-pyridine-2-carboxylic acid

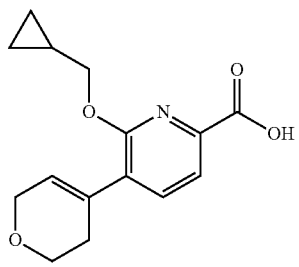 [SMILES: O=C(O)c1ccc(C2=CCOCC2)c(OCC2CC2)n1]

Under an atmosphere of nitrogen, a solution of 5-bromo-6-(cyclopropylmethoxy)-pyridine-2-carboxylic acid (300 mg, 1.1 mmol), 2-(3,6-dihydro-2H-pyran-4-yl)-4,4,5,5-tetramethyl-1,3,2-dioxaborolane (278 mg, 1.3 mmol), 1,1'-bis(diphenylphosphino) ferrocene-palladium(II)dichloride methylene chloride complex (CAN 95464-05-4, 45 mg, 0.06 mmol) and sodium carbonate (964 mg, 9.1 mmol) in DMF (10 mL) was heated to 100° C. overnight. The reaction mixture was poured into water, extracted with ethyl acetate (30 mL), the pH of the aqueous layer was adjusted to 2 by addition of 1 N hydrochloric acid and the resulting mixture was extracted with ethyl acetate (3×30 mL). The combined organic extracts were washed six times with brine, dried over anhydrous sodium sulfate and evaporated. The residue was purified by column chromatography (silica gel, 8 g, 30% ethyl acetate in petroleum ether) to yield the title compound (0.15 g, 1 mmol, 49.4%) as white solid; MS (EI): m/e 276.0 [M+H]$^+$.

f) 6-Cyclopropylmethoxy-5-(tetrahydro-pyran-4-yl)-pyridine-2-carboxylic acid

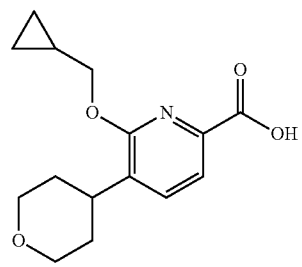 [SMILES: O=C(O)c1ccc(C2CCOCC2)c(OCC2CC2)n1]

In analogy to the procedure described in example 7b, the title compound was obtained (0.15 g, 1 mmol, 99%) as a yellow solid starting from 6-(cyclopropylmethoxy)-5-(3,6-dihydro 2H-pyran-4-yl)-pyridine-2-carboxylic acid; MS (EI): m/e 270.8 [M+H]$^+$ g) 2-{[6-Cyclopropylmethoxy-5-(tetrahydro-pyran-4-yl)-pyridine-2-carbonyl]-amino}-2-methyl-propionic acid methyl ester

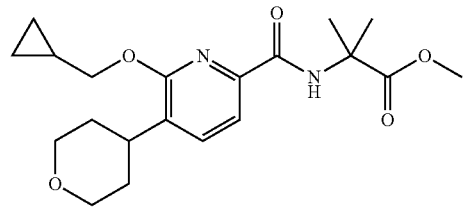 [SMILES: COC(=O)C(C)(C)NC(=O)c1ccc(C2CCOCC2)c(OCC2CC2)n1]

The title compound was synthesized in analogy to Example 1, using 6-cyclopropylmethoxy-5-(tetrahydro-pyran-4-yl)-pyridine-2-carboxylic acid and 2-methyl-alanine methyl ester as starting materials, MS (EI): m/e 377.2 [M+H]$^+$.

Example 10

6-Cyclopropylmethoxy-5-(tetrahydro-pyran-4-yl)-pyridine-2-carboxylic acid [1-methyl-1-(5-methyl-[1,2,4]oxadiazol-3-yl)-ethyl]-amide

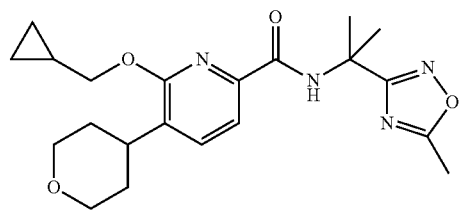 [SMILES: Cc1nc(C(C)(C)NC(=O)c2ccc(C3CCOCC3)c(OCC3CC3)n2)no1]

The title compound was synthesized in analogy to Example 1, using 6-cyclopropylmethoxy-5-(tetrahydro-pyran-4-yl)-pyridine-2-carboxylic acid (Example 9 f) and α,α,5-trimethyl-1,2,4-oxadiazole-3-methanamine (CAN 1153831-97-0) as starting materials, MS (EI): m/e 401.1 [M+H]+.

Example 11

6-(3-Chloro-phenyl)-pyridine-2-carboxylic acid piperidin-1-ylamide

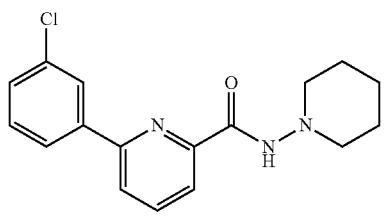 [SMILES: O=C(NN1CCCCC1)c1cccc(-c2cccc(Cl)c2)n1]

The title compound was synthesized in analogy to Example 1, using 6-(3-chlorophenyl)-2-pyridinecarboxylic acid (CAN 863704-38-5) and 1-piperidinamine (CAN 2213-43-6) as starting materials, MS (EI): m/e 316.0 [M+H]+.

Example 12

6-(3-Chloro-phenyl)-pyridine-2-carboxylic acid (1-methyl-1-thiazol-2-yl-ethyl)-amide a) tert-Butyl 1-amino-2-methyl-1-oxopropan-2-ylcarbamate

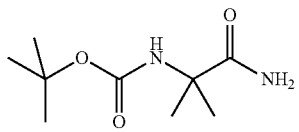

A mixture of 2-(tert-butoxycarbonylamino)-2-methylpropanoic acid (CAN: 30992-29-1, 20 g, 98 mmol), di-tert-butyl dicarbonate (CAN 24424-99-5, 27.67 g, 147 mmol) and pyridine (4.6 mL) in acetonitrile (500 mL) was stirred at room temperature for 20 min. Ammonia (10 mL) was added dropwise for 20 min. The resulting reaction mixture was stirred for 4 h. After removal of most of the solvent under reduced pressure, the solid was filtered off and washed with acetonitrile. The solid was brought to dryness under reduced pressure to give the title compound (17.5 g, 88%) as white solid; MS (EI): m/e 225.1 [M+Na]+.

b) tert-Butyl 1-amino-2-methyl-1-thioxopropan-2-ylcarbamate

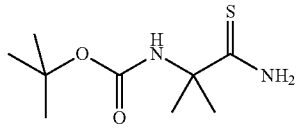

To a mixture of tert-butyl 1-amino-2-methyl-1-oxopropan-2-ylcarbamate (10 g, 49 mmol) in toluene (200 mL) was added Lawesson's reagent (CAN 19172-47-5, 10 g, 25 mmol). The suspension was heated to 90° C. and stirred for 6 h. After evaporation of solvents, the residue was purified by column chromatography (silica gel, 120 g) eluting with 30% ethyl acetate in petroleum ether to yield the title compound (6 g, 56%); MS: m/e 241.2 [M+Na]+.

c) α,α-Dimethyl-2-thiazolemethanamine

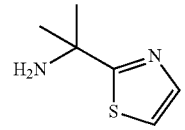

A mixture of tert-butyl 1-amino-2-methyl-1-thioxopropan-2-ylcarbamate (5.31 g, 24 mmol), 2-bromo-1,1-dimethoxyethane (CAN:7252-83-7, 5.11 g, 30 mmol) and TsOH (0.49 g, 3 mmol) in acetic acid (50 mL) was stirred at 120° C. for 4 h. After evaporation of solvents, the residue was diluted with ethyl acetate (50 mL) and water (50 mL). The water phase was washed with ethyl acetate (3×50 mL). Then water phase was lyophilized to give the title compound as brown solid (2.1 g, 65%); MS (LC/MS): 143.1 [M+H]+.

d) 6-(3-Chloro-phenyl)-pyridine-2-carboxylic acid (1-methyl-1-thiazol-2-yl-ethyl)-amide

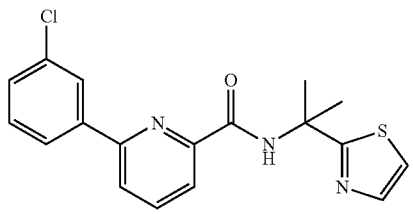 [SMILES: CC(C)(NC(=O)c1cccc(-c2cccc(Cl)c2)n1)c1nccs1]

The title compound was synthesized in analogy to Example 1, using 6-(3-chlorophenyl)-2-pyridinecarboxylic acid (CAN 863704-38-5) and α,α-dimethyl-2-thiazolemethanamine (CAN 1082393-38-1) as starting materials, MS (LC/MS): 358.0 [M+H]+.

Example 13

2-{[6-Cyclopropylmethoxy-5-(1H-pyrazol-3-yl)-pyridine-2-carbonyl]-amino}-2-methyl-propionic acid methyl ester a) 6-Cyclopropylmethoxy-5-(1H-pyrazol-3-yl)-pyridine-2-carboxylic acid

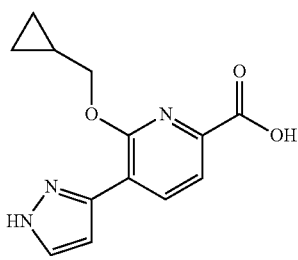 [SMILES: O=C(O)c1ccc(-c2cc[nH]n2)c(OCC2CC2)n1]

Under an atmosphere of nitrogen, a solution of 5-bromo-6-(cyclopropylmethoxy)-pyridine-2-carboxylic acid (Example 9 d, 0.4 g, 1.5 mmol), 1H-pyrazol-3-ylboronic acid (CAN 376584-63-3, 0.2 g, 1.8 mmol), 1,1'-bis(diphenylphosphino)ferrocene-palladium(II)dichloride methylene chloride complex (CAN 95464-05-4, 60 mg, 0.07 mmol) and sodium carbonate (1.3 g, 12 mmol) in DMF (10 mL) was heated to 100° C. for 5 h. The reaction mixture was poured into water and extracted with ethyl acetate (30 mL). The aqueous layer was adjusted to pH=2 by addition of 1 N hydrochloric acid and the resulting mixture was extracted with ethyl acetate (3×30 mL). The combined organic extracts were washed with water and brine, dried over anhydrous sodium sulfate and evaporated. The residue was purified by column chromatography (silica gel, 15 g, eluting with 30% ethyl acetate in petroleum ether) to yield the title compound (0.23 g, 1 mmol, 60.3%) as white solid; MS (EI): m/e 260.1 [M+H]$^+$.

b) 2-{[6-Cyclopropylmethoxy-5-(1H-pyrazol-3-yl)-pyridine-2-carbonyl]-amino}-2-methyl-propionic acid methyl ester

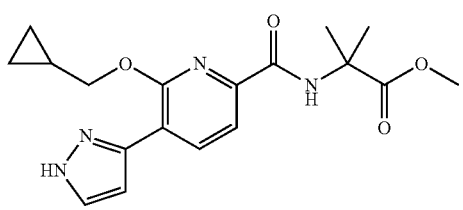 [SMILES: COC(=O)C(C)(C)NC(=O)c1ccc(-c2cc[nH]n2)c(OCC2CC2)n1]

The title compound was synthesized in analogy to Example 1, using 6-cyclopropylmethoxy-5-(1H-pyrazol-3-yl)-pyridine-2-carboxylic acid and 2-methyl-alanine methyl ester as starting materials, MS (LC/MS): 359.1 [M+H]$^+$.

Example 14

6-Cyclopropylmethoxy-5-pyrrolidin-1-yl-pyridine-2-carboxylic acid ((S)-1-hydroxymethyl-3-methyl-butyl)-amide a) 6-Cyclopropylmethoxy-5-pyrrolidin-1-yl-pyridine-2-carboxylic acid

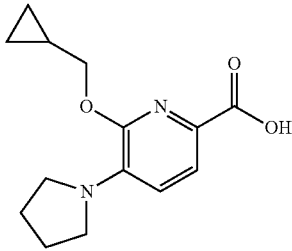

A mixture of 5-bromo-6-(cyclopropylmethoxy)-pyridine-2-carboxylic acid (Example 9 d, 600 mg, 2 mmol), pyrrolidine (CAN 123-75-1, 1.57 g 22 mmol), tris(dibenzylideneacetone)dipalladium (CAN 52409-22-0, 202 mg 0.2 mmol), rac-BINAP (CAN 76189-55-4, 275 mg, 0.4 mmol) and Cs$_2$CO$_3$ (2.88 mg 9 mmol) in toluene (50 mL) was heated to 95° C. for 20 h in a nitrogen atmosphere. Then the mixture was diluted with methanol (30 mL), filtered and the filtrate was evaporated to dryness. The residue was purified by column chromatography (silica gel, 5 g, eluting with 10% ethyl acetate in petroleum ether) to obtain the product as a white solid (0.26 g 45%), MS (LC/MS): 263.1 [M+H]$^+$.

b) 6-Cyclopropylmethoxy-5-pyrrolidin-1-yl-pyridine-2-carboxylic acid ((S)-1-hydroxymethyl-3-methyl-butyl)-amide

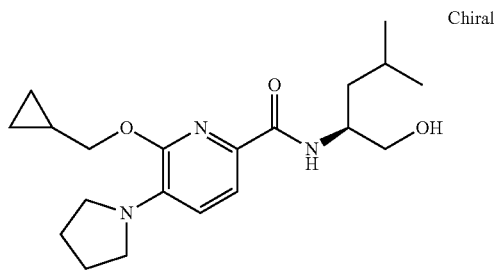 [SMILES: CC(C)C[C@@H](CO)NC(=O)c1ccc(N2CCCC2)c(OCC2CC2)n1]

The title compound was synthesized in analogy to Example 1, using 6-cyclopropylmethoxy-5-pyrrolidin-1-yl-pyridine-2-carboxylic acid and (2S)-2-amino-4-methyl-1-pentanol (CAN 7533-40-6) as starting materials, MS (LC/MS): 362.2 [M+H]$^+$.

Example 15

(6-Cyclopropylmethoxy-5-pyrrolidin-1-yl-pyridin-2-yl)-(1,1-dioxidotetrahydro-2H-thiopyran-4-yl)-methanone

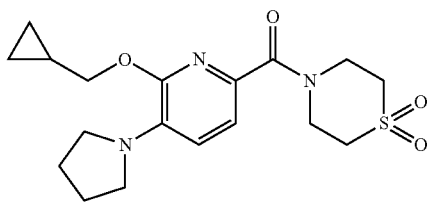 [SMILES: O=C(c1ccc(N2CCCC2)c(OCC2CC2)n1)N1CCS(=O)(=O)CC1]

The title compound was synthesized in analogy to Example 1, using 6-cyclopropylmethoxy-5-pyrrolidin-1-yl-pyridine-2-carboxylic acid (Example 14 a) and 1,1-dioxide-thiomorpholine (CAN 39093-93-1) as starting materials, MS (LC/MS): 380.1 [M+H]$^+$.

Example 16

(6-Cyclopropylmethoxy-5-pyrrolidin-1-yl-pyridin-2-yl)-thiomorpholin-4-yl-methanone

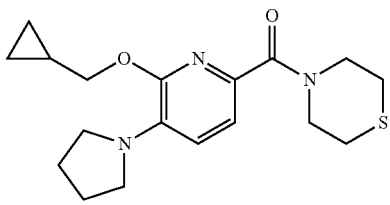 [SMILES: O=C(c1ccc(N2CCCC2)c(OCC2CC2)n1)N1CCSCC1]

The title compound was synthesized in analogy to Example 1, using 6-cyclopropylmethoxy-5-pyrrolidin-1-yl-pyridine-2-carboxylic acid (Example 14 a) and thiomorpholine (CAN 123-90-0) as starting materials, MS (LC/MS): 348.1 [M+H]$^+$.

Example 17

6-(3-Chloro-phenyl)-pyridine-2-carboxylic acid (1-methyl-1-[1,3,4]oxadiazol-2-yl-ethyl)-amide a) Benzyl 1-(2-formylhydrazinyl)-2-methyl-1-oxo-propan-2-ylcarbamate

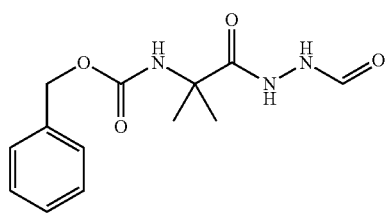 [SMILES: CC(C)(NC(=O)OCc1ccccc1)C(=O)NNC=O]

A mixture of 2-(benzyloxycarbonylamino)-2-methylpropanoic acid (Example 8 a, 1.9 g, 8 mmol), HATU (CAN 148893-10-1, 3.97 g, 10 mmol) and N-methylmorpholine (CAN 109-02-4, 2.43 g, 24 mmol) in DMF (20 mL) was stirred at room temperature for 15 min. Then hydrazinecarboxaldehyde (CAN 624-84-0, 0.53 g, 9 mmol) was added and the reaction mixture was stirred at room temperature overnight. After evaporation of solvents, the residue was diluted with ethyl acetate (30 mL) and water (30 mL). The organic layer was washed with saturated sodium bicarbonate solution (30 mL), hydrochloric acid (30 mL, 1 M), brine (30 mL) and dried over anhydrous sodium sulfate. Removal of the solvent under reduced pressure left the title compounds as yellow oil (2.1 g, 94%); MS: m/e 280.1 [M+H]$^+$.

b) Benzyl 2-(1,3,4-oxadiazol-2-yl)propan-2-ylcarbamate

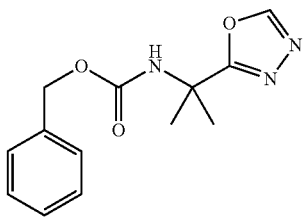 [SMILES: CC(C)(NC(=O)OCc1ccccc1)c1nnco1]

To a suspension of benzyl 1-(2-formylhydrazinyl)-2-methyl-1-oxopropan-2-ylcarbamate (0.9 g, 3 mmol) and PPh$_3$ (CAN 603-35-0, 1.268 g, 5 mmol) in acetonitrile (20 mL) was added DIPEA (CAN 7087-68-5, 1.249 g, 10 mmol) and hexachloroethane (CAN 67-72-1, 0.991 g, 4 mmol). The reaction mixture was stirred at room temperature under nitrogen atmosphere for 4 h. After evaporation of solvents, the residue was diluted with ethyl acetate (30 mL) and water (30 mL). The organic layer was washed with brine (30 mL), dried over anhydrous sodium sulfate and evaporated. The remaining residue was then purified by column chromatography (silica gel, 30 g, eluting with 10% ethyl acetate in petroleum ether) to give the title compound (1 g, 30% purity, 36%) as colorless oil containing OPPh$_3$ and PPh$_3$; MS: m/e 262.2 [M+H]$^+$.

c) 1-Methyl-1-[1,3,4]oxadiazol-2-yl-ethylamine

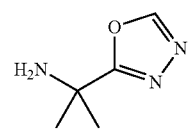

A solution of benzyl 2-(1,3,4-oxadiazol-2-yl)propan-2-ylcarbamate (1 g, 30% purity) and 10% Pd/C (0.06 g) in ethanol (30 mL) was charged with hydrogen balloon and stirred at room temperature overnight. After filtration, it was concentrated to give crude product which was directly used in the next reaction step without further purification but still contained OPPh$_3$ and PPh$_3$; MS: m/e 128.1 [M+H]$^+$.

d) 6-(3-Chloro-phenyl)-pyridine-2-carboxylic acid (1-methyl-1-[1,3,4]oxadiazol-2-yl-ethyl)-amide

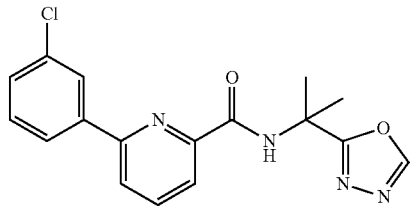 [SMILES: CC(C)(NC(=O)c1cccc(-c2cccc(Cl)c2)n1)c1nnco1]

The title compound was synthesized in analogy to Example 1, using 6-(3-chlorophenyl)-2-pyridinecarboxylic acid (CAN 863704-38-5) and 1-methyl-1-[1,3,4]oxadiazol-2-yl-ethylamine as starting materials, MS (LC/MS): 343.0 [M+H]$^+$.

Example 18

6-(3-Chloro-phenyl)-pyridine-2-carboxylic acid cyclohexylamide

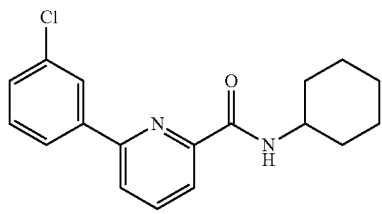 [SMILES: O=C(NC1CCCCC1)c1cccc(-c2cccc(Cl)c2)n1]

The title compound was synthesized in analogy to Example 1, using 6-(3-chlorophenyl)-2-pyridinecarboxylic acid (CAN 863704-38-5) and cyclohexanamine (CAN 108-91-8) as starting materials, MS (EI) m/e: 315.1 [M+H]$^+$.

Example 19

6-(3-Chloro-phenyl)-pyridine-2-carboxylic acid phenylamide

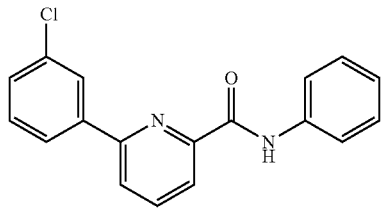 [SMILES: O=C(Nc1ccccc1)c1cccc(-c2cccc(Cl)c2)n1]

The title compound was synthesized in analogy to Example 1, using 6-(3-chlorophenyl)-2-pyridinecarboxylic acid (CAN 863704-38-5) and aniline (CAN 62-53-3) as starting materials, MS (EI) m/e: 309.1 [M+H]$^+$.

Example 20

6-(3-Chloro-phenyl)-pyridine-2-carboxylic acid pyridin-2-ylamide

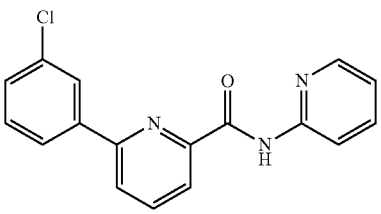 [SMILES: O=C(Nc1ccccn1)c1cccc(-c2cccc(Cl)c2)n1]

The title compound was synthesized in analogy to Example 1, using 6-(3-chlorophenyl)-2-pyridinecarboxylic acid (CAN 863704-38-5) and 2-pyridinamine (CAN 504-29-0) as starting materials, MS (D) m/e: 310.0 [M+H]$^+$.

Example 21

6-(3-Chloro-phenyl)-pyridine-2-carboxylic acid (tetrahydro-pyran-4-yl)-amide

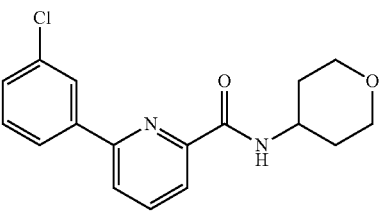 [SMILES: O=C(NC1CCOCC1)c1cccc(-c2cccc(Cl)c2)n1]

The title compound was synthesized in analogy to Example 1, using 6-(3-chlorophenyl)-2-pyridinecarboxylic acid (CAN 863704-38-5) and tetrahydro-2H-pyran-4-amine (CAN 38041-19-9) as starting materials, MS (LC/MS): 317.1 [M+H]$^+$.

Example 22

6-(3-Chloro-phenyl)-pyridine-2-carboxylic acid [1-methyl-1-(3-methyl-[1,2,4]thiadiazol-5-yl)-ethyl]-amide a) tert-Butyl-1-(1-(dimethylamino)ethylideneamino)-2-methyl-1-thioxopropan-2-ylcarbamate

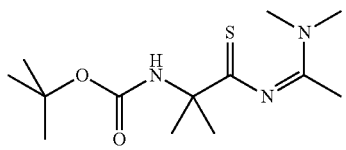 [SMILES: C/C(=N/C(=S)C(C)(C)NC(=O)OC(C)(C)C)N(C)C]

A mixture of tert-butyl 1-amino-2-methyl-1-thioxopropan-2-ylcarbamate (Example 12 b, 0.218 g, 1 mmol) and 1,1-dimethoxy-N,N-dimethylethanamine (CAN 18871-66-4, 0.16 g, 1.2 mmol) in methylene chloride (10 mL) was stirred at room temperature for 24 h. Then it was concentrated to give crude product, which was used directly in the next step without further purification (0.28 g, 98%) as yellow oil; MS (EI): m/e 288.2 [M+H]$^+$.

b) tert-Butyl 2-(3-methyl-1,2,4-thiadiazol-5-yl)propan-2-ylcarbamate

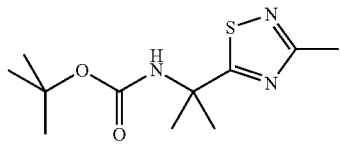 [SMILES: Cc1nsc(C(C)(C)NC(=O)OC(C)(C)C)n1]

A mixture of tert-butyl 1-(1-(dimethylamino)ethylideneamino)-2-methyl-1-thioxopropan-2-ylcarbamate (2.9 g, 10 mmol), hydroxylamine-O-sulfonic acid (CAN 2950-43-8, 1.37 g, 12 mmol), pyridine (1.6 g, 20.2 mmol) and methanol (4 mL) in ethanol (20 mL) was stirred at room temperature for 2 h. After evaporation of solvents, the residue was diluted with ethyl acetate (40 mL) and water (40 mL). The organic layer was washed with brine (40 mL), dried over anhydrous sodium sulfate and concentrated to give crude product (2.5 g, 96%) as yellow oil. The product was used directly in the next step without further purification; MS (EI): m/e 258.2 [M+H]$^+$.

c) 1-Methyl-1-(3-methyl-[1,2,4]thiadiazol-5-yl)-ethylamine

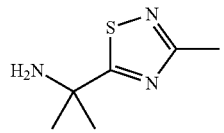

A solution of tert-butyl 2-(3-methyl-1,2,4-thiadiazol-5-yl)propan-2-ylcarbamate (0.15 g, 0.58 mmol) in saturated hydrochloride in ethyl acetate (10 mL) was stirred at room temperature for 1 h. Then water (20 mL) was added. The water phase was washed with ethyl acetate (2×20 mL). Then the water phase was adjusted with sodium hydroxide solution (2 M) to pH=9~10 and extracted with ethyl acetate (3×20 mL). The combined organic layer was washed with brine (20 mL), dried over anhydrous sodium sulfate and concentrated to give product (0.08 g, 87%) as yellow oil; MS (EI): m/e 231.1 [M+H]$^+$.

d) 6-(3-Chloro-phenyl)-pyridine-2-carboxylic acid [1-methyl-1-(3-methyl-[1,2,4]thiadiazol-5-yl)-ethyl]-amide

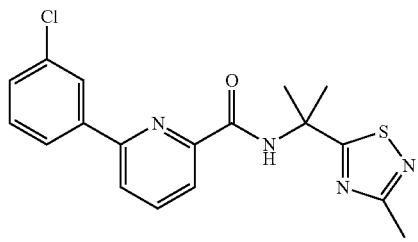 [SMILES: Cc1nsc(C(C)(C)NC(=O)c2cccc(-c3cccc(Cl)c3)n2)n1]

The title compound was synthesized in analogy to Example 1, using 6-(3-chlorophenyl)-2-pyridinecarboxylic acid (CAN 863704-38-5) and 1-methyl-1-(3-methyl-[1,2,4]thiadiazol-5-yl)-ethylamine as starting materials, MS (LC/MS): 373.0 (M+H).

Example 23

6-(3-Chloro-phenyl)-pyridine-2-carboxylic acid (1-dimethylcarbamoyl-1-ethyl-propyl)-amide a) 2-(tert-Butoxycarbonylamino)-2-ethylbutanoic acid

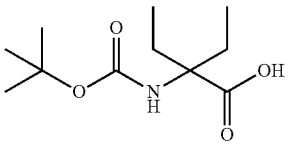 [SMILES: CCC(CC)(NC(=O)OC(C)(C)C)C(=O)O]

3-aminopentane-3-carboxylic acid (CAN 2566-29-2, 2.0 g, 15.3 mmol) was combined with dioxane (100 mL) to give a colorless suspension. Sodium hydroxide (22.7 ml, 22.7 mmol, 1N) was added dropwise at 0° C. within 10 min to give a colorless solution. Di-tert-butyl dicarbonate (CAN 24424-99-5, 6.7 g, 30.9 mmol) was added in three portions. The reaction was stirred for 30 min to give a colorless suspension. Then dioxane (30 mL) was added (using less solvent resulted in a thick suspension) and the mixture was stirred for 17 h at ambient temperature. The reaction mixture was concentrated in vacuo to a volume of 50 mL and poured into 200 mL water. Then the mixture was washed with ethyl acetate (3×80 ml). The aqueous layers were combined, 2N hydrochloric acid was added to adjust the pH to 2, and the mixture was extracted with ethyl acetate (3×60 mL). The organic layers were combined, dried over anhydrous sodium sulfate and concentrated in vacuo to give product (1.0 g, 28%).

b) tert-Butyl 3-(dimethylcarbamoyl)pentan-3-ylcarbamate

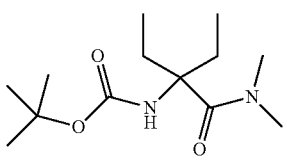 [SMILES: CCC(CC)(NC(=O)OC(C)(C)C)C(=O)N(C)C]

2-(tert-butoxycarbonylamino)-2-ethylbutanoic acid ((200 mg, 0.87 mmol), HATU (CAN 148893-10-1, 660 mg, 1.74 mmol) and triethylamine (CAN 121-44-8, 260 mg, 2.61 mmol) was added to a solution of dimethylamine hydrochloride (CAN 506-59-2, 117 mg, 1.74 mmol) in DMF (10 mL). The mixture was stirred overnight at room temperature. The mixture was added to water (20 mL) and extracted with ethyl acetate (30 mL). The organic extracts were washed with brine, dried over anhydrous sodium sulfate, concentrated, and purified by prep-HPLC (eluting with 30% ethyl acetate in petroleum ether) to give the product (120 mg, 53.7%); MS (EI): m/e=259.2 [M+H]+ c) 2-Amino-2-ethyl-N,N-dimethylbutanamide hydrogen chloride

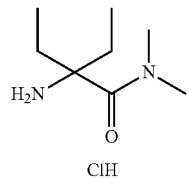

tert-Butyl 3-(dimethylcarbamoyl)pentan-3-ylcarbamate (0.12 g, 0.47 mmol) was added to a saturated solution of hydrochloride in ethyl acetate (5 mL) and the mixture was stirred overnight. The solvent was removed by reduced pressure to give the crude product (0.1 g); MS (EI): m/e=159.2 [M+H]+.

d) 6-(3-Chloro-phenyl)-pyridine-2-carboxylic acid (1-dimethylcarbamoyl-1-ethyl-propyl)-amide

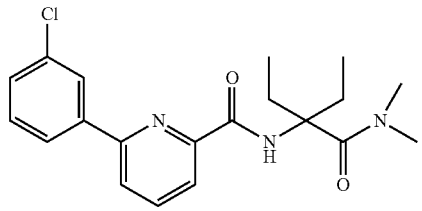 [SMILES: CCC(CC)(NC(=O)c1cccc(-c2cccc(Cl)c2)n1)C(=O)N(C)C]

The title compound was synthesized in analogy to Example 1, using 6-(3-chlorophenyl)-2-pyridinecarboxylic acid (CAN 863704-38-5) and 2-amino-2-ethyl-N,N-dimethyl-butyramide as starting materials, MS (EI): 374.2 [M+H]+.

Example 24

6-Cyclohexyl-pyridine-2-carboxylic acid piperidin-1-ylamide

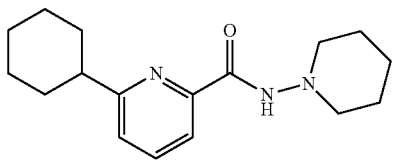 [SMILES: O=C(NN1CCCCC1)c1cccc(C2CCCCC2)n1]

The title compound was synthesized in analogy to Example 1, using 6-cyclohexyl-pyridine-2-carboxylic acid (Example 7 b) and 1-piperidinamine (CAN 2213-43-6) as starting materials, MS (EI): 288.3 [M+H]+.

Example 25

[5-Methyl-6-(piperidine-1-sulfonyl)-pyridin-2-yl]-piperidin-1-yl-methanone a) 5-Methyl-2-pyridinecarboxylic acid 1-oxide

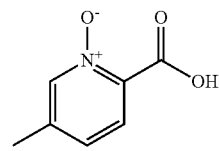

m-CPBA (CAN 937-14-4, 5.0 g, 29.2 mmol) was added to a solution of 5-methyl-pyridine-2-carboxylic acid (CAN 4434-13-3, 2.0 g, 14.6 mmol) in methylene chloride (50 mL) and the mixture was stirred overnight at room temperature. The solid was filtered off, quenched with a saturated solution of sodium thiosulfate (50 mL), and the mixture was extracted with methylene chloride (3×60 mL). The organic layers were combined, dried over anhydrous sodium sulfate and concentrated in vacuo to give yellow solid which was washed with ether (5×20 mL) to give the product (0.9 g, 40.3%); MS (EI): m/e=154.1 [M+H]+.

b) 6-Chloro-5-methyl-pyridine-2-carboxylic acid

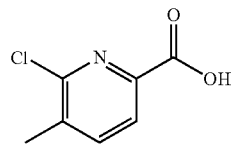

5-Methyl-2-pyridinecarboxylic acid 1-oxide (0.9 g, 5.88 mmol) was added to phosphoryl trichloride (30 mL). The mixture was stirred at 105° C. for 3 h. After that the mixture was cooled to room temperature, added to ice water slowly and extracted with methylene chloride (4×30 mL). The organic layer was washed with brine (50 mL), dried over anhydrous sodium sulfate, and concentrated to give the crude product (0.85 g, 84.3%); MS (EI): m/e=172.0 [M+H]+.

c) 5-Methyl-6-sulfo-pyridine-2-carboxylic acid

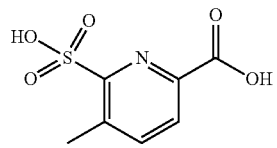

6-chloro-5-methyl-pyridine-2-carboxylic acid (0.85 g, 4.97 mmol) and sodium sulfite (CAN 7757-83-7, 1.5 g, 11.9 mmol) were added to water (3 mL) and ethanol (3 mL). The mixture was heated to 180° C. for 4 h in a sealed tube. After that the mixture was cooled to room temperature and a solid precipitated that was removed by filtration. The filtrate was concentrated and added to water (20 mL). The aqueous phase was washed with ethyl acetate (2×20 mL). Subsequently the aqueous phase was adjusted to pH=2 with 2 N hydrochloric acid. Water was removed in vacuo to give the product as solid (1.2 g); MS (EI): m/e=218.0 [M+H]⁺.

d) 5-Methyl-6-sulfo-pyridine-2-carboxylic acid methyl ester

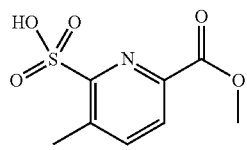

To a mixture of 5-methyl-6-sulfo-pyridine-2-carboxylic acid (0.8 g, 3.69 mmol) in methanol (20 mL) was added 4 N hydrogen chloride in dioxane (8 mL). The mixture was stirred overnight at room temperature. Undissolved solid was filtered off, and the filtrate was concentrated to give the product as yellow solid 0.5 g; MS (EI): m/e=232.0 [M+H]⁺.

e) 5-Methyl-6-(piperidine-1-sulfonyl)-pyridine-2-carboxylic acid methyl ester

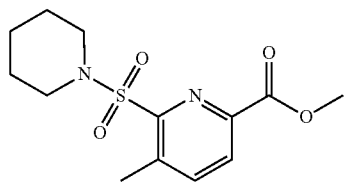 [SMILES: COC(=O)c1ccc(C)c(S(=O)(=O)N2CCCCC2)n1]

5-Methyl-6-sulfo-pyridine-2-carboxylic acid methyl ester (340 mg, 1.47 mmol), thionyl chloride (CAN 7719-09-7, 1 mL) and 1 drop of DMF were added to methylene chloride (10 mL), and the mixture was stirred for 2 h at 40° C. The mixture was cooled to room temperature, and piperidine (CAN 110-89-4, 1.0 g, 12 mmol) in methylene chloride (10 mL) was added to the above mixture. The solvent was removed in vacuo, and the crude product was purified by prep-HPLC (eluting with 50% ethyl acetate in petroleum ether) to give the product (53 mg, 12%); MS (EI): m/e=299.1 [M+H]⁺.

f) 5-Methyl-6-(piperidine-1-sulfonyl)-pyridine-2-carboxylic acid

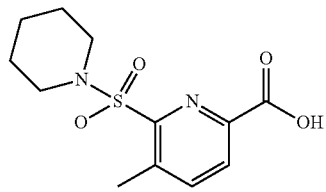

5-Methyl-6-(piperidine-1-sulfonyl)-pyridine-2-carboxylic acid methyl ester (53 mg, 0.178 mmol) in dioxane (2 mL) was added to a solution of lithium hydroxide monohydrate (CAN 1310-66-3, 0.1 g, 2.38 mmol) in water (2 mL) and the mixture was stirred for 2 h at room temperature. The solvent was removed in vacuo, water (10 mL) was added, and the pH was adjusted to 3 with 1 N hydrochloric acid. The mixture was extracted by ethyl acetate (2×10 mL). The organic layer was washed with brine (20 mL), dried over anhydrous sodium sulfate, and concentrated to give the product (36 mg, 71%); MS (EI): m/e=285.2 [M+H]⁺.

g) [5-Methyl-6-(piperidine-1-sulfonyl)-pyridin-2-yl]-piperidin-1-yl-methanone

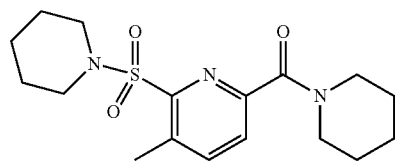 [SMILES: Cc1ccc(C(=O)N2CCCCC2)nc1S(=O)(=O)N1CCCCC1]

The title compound was synthesized in analogy to Example 1, using 5-methyl-6-(piperidine-1-sulfonyl)-pyridine-2-carboxylic acid and piperidine (CAN 110-89-4) as starting materials, MS (EI): 352.2 [M+H]⁺.

Example 26

6-(3-Chloro-phenyl)-pyridine-2-carboxylic acid (2-methyl-tetrahydro-pyran-4-yl)-amide

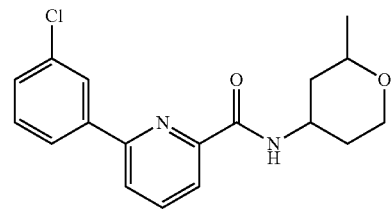

The title compound was synthesized in analogy to Example 1, using 6-(3-chlorophenyl)-2-pyridinecarboxylic acid (CAN 863704-38-5) and tetrahydro-2-methyl-2H-pyran-4-amine (CAN 89584-06-5) as starting materials, MS (EI): m/e=331.1 [M+H]⁺.

Example 27

2-[(6-Cyclopropylmethoxy-5-pyrrolidin-1-yl-pyridine-2-carbonyl)-amino]-2-methyl-propionic acid methyl ester

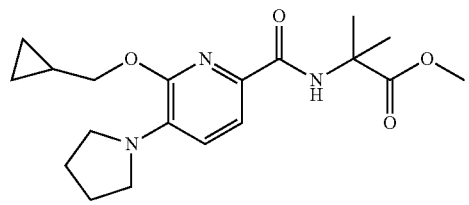 [SMILES: COC(=O)C(C)(C)NC(=O)c1ccc(N2CCCC2)c(OCC2CC2)n1]

The title compound was synthesized in analogy to Example 1, using 6-cyclopropylmethoxy-5-pyrrolidin-1-yl-pyridine-2-carboxylic acid (Example 14 a) and 2-methyl-alanine methyl ester as starting materials, MS (LC/MS): 362.2 [M+H]⁺.

Example 28

6-(3-Chloro-phenyl)-pyridine-2-carboxylic acid [1-methyl-1-(3-methyl-isoxazol-5-yl)-ethyl]-amide a) 1-Methyl-1-(3-methyl-isoxazol-5-yl)-ethylamine

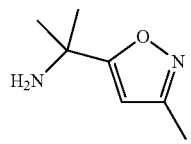

To a solution of (E)-acetaldehyde oxime (CAN 107-29-9, 1.0 g, 16.9 mmol), 2-methylbut-3-yn-2-amine (CAN 2978-58-7, 1.4 g, 16.9 mmol) and triethylamine (CAN 121-44-8, 0.17 g, 1.69 mmol) in methylene chloride (25 mL) at 0° C. was added a 5% aqueous solution of sodium hypochlorite (5%, 42.6 g) over 3 h. The reaction was allowed to warm to 4° C. and stirring continued for 5 h. The organic layer was separated, and the aqueous layer was extracted with methylene chloride (50 mL). The combined methylene chloride extracts were washed with saturated aqueous sodium chloride (60 mL) and dried over anhydrous magnesium sulfate. The solvent was removed to give a yellow oil. The crude product was purified by column chromatography (silica gel 30 g, eluting with 30% ethyl acetate in petroleum ether) to yield the product as yellow solid (0.1 g, 4.2%); MS (EI): m/e=141.2 [M+H]⁺.

b) 6-(3-Chloro-phenyl)-pyridine-2-carboxylic acid [1-methyl-1-(3-methyl-isoxazol-5-yl)-ethyl]-amide

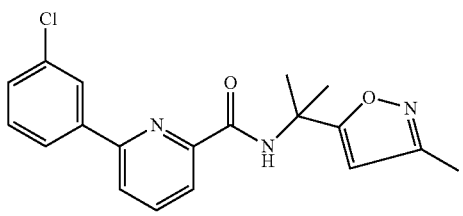 [SMILES: Cc1cc(C(C)(C)NC(=O)c2cccc(-c3cccc(Cl)c3)n2)on1]

The title compound was synthesized in analogy to Example 1, using 6-(3-chlorophenyl)-2-pyridinecarboxylic acid (CAN 863704-38-5) and 1-methyl-1-(3-methyl-isoxazol-5-yl)-ethylamine as starting materials, MS (EI): 356.0 (M+H)⁺.

Example 29

6-(3-Chloro-phenyl)-pyridine-2-carboxylic acid (1-ethyl-1-hydroxymethyl-propyl)-amide

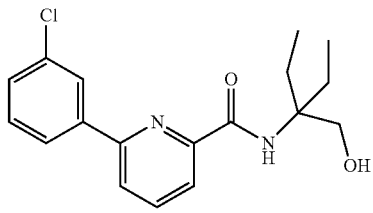 [SMILES: CCC(CC)(CO)NC(=O)c1cccc(-c2cccc(Cl)c2)n1]

The title compound was synthesized in analogy to Example 1, using 6-(3-chlorophenyl)-2-pyridinecarboxylic acid (CAN 863704-38-5) and 2-amino-2-ethyl-1-butanol (CAN 19792-52-0) as starting materials, MS (LC/MS): 333.1 (M+H).

Example 30

6-(3-Chloro-phenyl)-pyridine-2-carboxylic acid (tetrahydro-pyran-3-yl)-amide

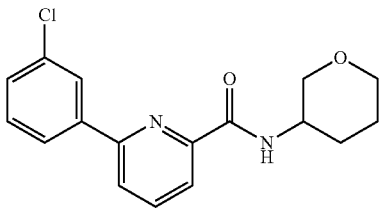 [SMILES: O=C(NC1CCCOC1)c1cccc(-c2cccc(Cl)c2)n1]

The title compound was synthesized in analogy to Example 1, using 6-(3-chlorophenyl)-2-pyridinecarboxylic acid (CAN 863704-38-5) and tetrahydro-2H-pyran-3-amine (CAN 120811-32-7) as starting materials, MS (LC/MS): 317.1 (M+H).

Example 31

(6-Cyclopropylmethoxy-5-pyrrolidin-1-yl-pyridin-2-yl)-(2-oxa-6-aza-spiro[3.3]hept-6-yl)-methanone

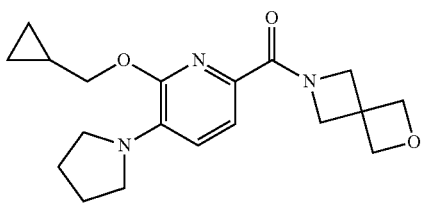 [SMILES: O=C(c1ccc(N2CCCC2)c(OCC2CC2)n1)N1CC2(COC2)C1]

The title compound was synthesized in analogy to Example 1, using 6-cyclopropylmethoxy-5-pyrrolidin-1-ylpyridine-2-carboxylic acid (Example 14 a) and 2-oxa-6-aza-spiro[3.3]heptane (CAN 174-78-7) as starting materials, MS (EI): m/e=344.3 [M+H]$^+$.

Example 32

6-Cyclopropylmethoxy-5-(2-methyl-pyrrolidin-1-yl)-pyridine-2-carboxylic acid ((S)-1-carbamoyl-3-methyl-butyl)-amide a) 6-Cyclopropylmethoxy-5-(2-methyl-pyrrolidin-1-yl)-pyridine-2-carboxylic acid

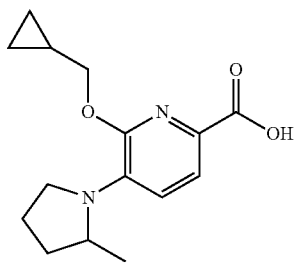 [SMILES: CC1CCCN1c1ccc(C(=O)O)nc1OCC1CC1]

Under an atmosphere of nitrogen, a solution of 5-bromo-6-(cyclopropylmethoxy)-pyridine-2-carboxylic acid (Example 9 d, 0.4 g, 1.5 mmol), 2-methylpyrrolidine (CAN 765-38-8, 188 mg, 2.2 mmol), R)-(+)-2,2'-bis(diphenylphosphino)-1,1'-binaphthyl (CAN 76189-55-4, 183 mg, 0.3 mmol), tris-(dibenzylidene-acetone)dipalladium (CAN 51364-51-3, 135 mg, 0.15 mmol) and cesium carbonate (1.9 g, 6 mmol) in toluene (50 mL) was heated to 90° C. overnight. The reaction mixture was concentrated under reduced pressure. The residue was dissolved in water (10 mL) and extracted with ethyl acetate (30 mL), the pH of the aqueous layer was adjusted to 2 by addition of 1 N hydrochloric acid and the resulting mixture was extracted with ethyl acetate (3×30 mL). The combined organic extracts were washed with water and brine, dried over sodium sulfate and evaporated. The residue was purified by column chromatography (silica gel, 10 g, 50% ethyl acetate in petroleum ether) to yield the title compound (0.15 g, 36.9%) as yellow solid; MS (EI): m/e=277.2 [M+H]$^+$.

b) 6-Cyclopropylmethoxy-5-(2-methyl-pyrrolidin-1-yl)-pyridine-2-carboxylic acid ((S)-1-carbamoyl-3-methyl-butyl)-amide

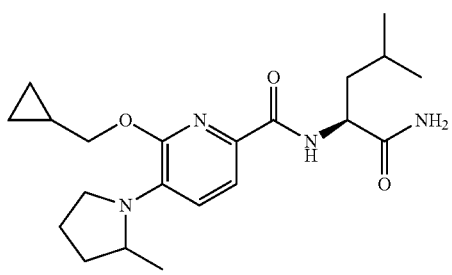 [SMILES: CC(C)C[C@H](NC(=O)c1ccc(N2CCCC2C)c(OCC2CC2)n1)C(N)=O]

The title compound was synthesized in analogy to Example 1, using 6-cyclopropylmethoxy-5-(2-methyl-pyrrolidin-1-yl)-pyridine-2-carboxylic acid and (2S)-2-amino-4-methyl-pentanamide (CAN 687-51-4) as starting materials, MS (LC/MS): 389.2 [M+H]$^+$.

Example 33

6-Cyclopropylmethoxy-5-pyrrolidin-1-yl-pyridine-2-carboxylic acid [1-methyl-1-(5-methyl-[1,2,4]oxadiazol-3-yl)-ethyl]-amide a) tert-Butyl 2-cyanopropan-2-ylcarbamate

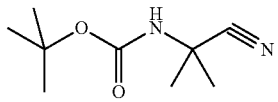

To a solution of tert-butyl 1-amino-2-methyl-1-oxopropan-2-ylcarbamate (Example 12 a, 12.5 g) and triethylamine (CAN 121-44-8, 29 g) in methylene chloride (150 mL) was added trifluoroacetic acid anhydride (CAN 407-25-0, 27.2 g) dropwise at 0° C. The resulting mixture was allowed to warm to room temperature and stirred for 4 h. After that the mixture was washed with water, 5 N citric acid and brine, the organic phase was dried over anhydrous sodium sulfate and concentrated to give the title compound (11 g, 97%) as a yellow solid; MS: m/e=207.1 [M+Na]$^+$.

b) (Z)-tert-Butyl 1-amino-1-(hydroxyimino)-2-methylpropan-2-ylcarbamate

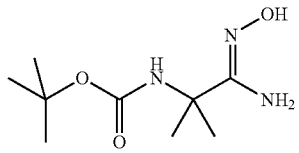

Potassium carbonate (3.64 g) was dissolved in water (12 mL) and hydroxylammonium chloride (CAN: 5470-11-1, 1.7 g, mmol) was added. A solution of tert-butyl 2-cyanopropan-2-ylcarbamate (4.84 g, 26 mmol) in ethanol (42 mL) was added and the resulting reaction mixture was stirred for 18 h at ambient temperature. The solvent was removed under reduced pressure and the residue was diluted with ethyl acetate (20 mL). The mixture was filtered and the filtrate was concentrated to yield the crude product (5 g, 87.6%) as yellow solid. MS: m/e=218.2 [M+H]$^+$.

c) tert-Butyl 2-(5-methyl-1,2,4-oxadiazol-3-yl)propan-2-ylcarbamate

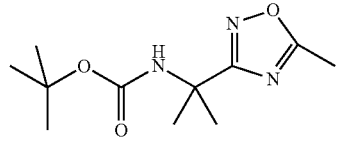 [SMILES: Cc1nc(C(C)(C)NC(=O)OC(C)(C)C)no1]

To a solution of acetic acid (1.8 g) in DMF (50 mL) was added N,N'-carbonyldiimidazole (CAN 530-62-1, 4.865 g, mmol). The solution was stirred at ambient temperature for 0.5 h. (Z)-tert-butyl 1-amino-1-(hydroxyimino)-2-methylpropan-2-ylcarbamate (6.07 g) was added and the reaction mixture was stirred at 120° C. for 10 h. Removal of the solvent under reduced pressure left a yellow oil which was purified by column chromatography (silica gel 120 g, eluting with 30% ethyl acetate in petroleum ether) to give the title compound (5.38 g, 80%) as colorless oil; MS: m/e=264.1 [M+Na]⁺.

d) α,α,5-Trimethyl-1,2,4-oxadiazole-3-methanamine

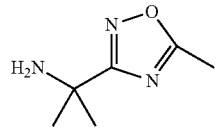

tert-Butyl-2-(5-methyl-1,2,4-oxadiazol-3-yl)propan-2-yl-carbamate (5.38 g) was dissolved in in ethyl acetate (30 mL) saturated with hydrochloride and stirred at room temperature for 1 h. Then water (50 mL) was added. The aqueous phase was washed with ethyl acetate (2×30 mL) and the pH adjusted with 1 M sodium hydroxide solution to 9~10. The solution was extracted with ethyl acetate (2×30 mL). The combined extracts were washed with brine and dried over anhydrous sodium sulfate. Removal of the solvent under reduced pressure left the title compound (1.7 g, 54%) as colorless oil; MS: m/e 142.2 [M+H]⁺.

e) 6-Cyclopropylmethoxy-5-pyrrolidin-1-yl-pyridine-2-carboxylic acid [1-methyl-1-(5-methyl-[1,2,4]oxadiazol-3-yl)-ethyl]-amide

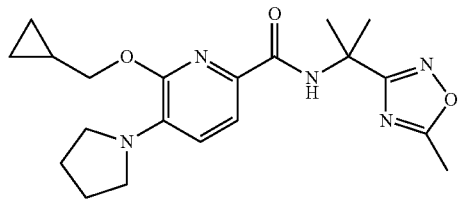 [SMILES: Cc1nc(C(C)(C)NC(=O)c2ccc(N3CCCC3)c(OCC3CC3)n2)no1]

The title compound was synthesized in analogy to Example 1, using 6-cyclopropylmethoxy-5-pyrrolidin-1-yl-pyridine-2-carboxylic acid (Example 14 a) and α,α,5-trimethyl-1,2,4-oxadiazole-3-methanamine (CAN 1153831-97-0) as starting materials, MS (LC/MS): 386.2 [M+H]⁺.

Example 34

6-Cyclopropylmethoxy-5-(tetrahydro-pyran-4-yl)-pyridine-2-carboxylic acid (1-methyl-1-thiazol-2-yl-ethyl)-amide

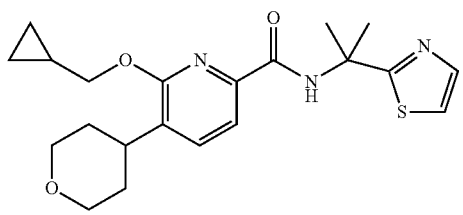 [SMILES: CC(C)(NC(=O)c1ccc(C2CCOCC2)c(OCC2CC2)n1)c1nccs1]

The title compound was synthesized in analogy to Example 1, using 6-cyclopropylmethoxy-5-(tetrahydro-pyran-4-yl)-pyridine-2-carboxylic acid (Example 9 f) and α,α-dimethyl-2-thiazolemethanamine (CAN 1082393-38-1) as starting materials, MS (LC/MS): 402.1 [M+H]⁺.

Example 35

6-Cyclopropylmethoxy-5-pyrrolidin-1-yl-pyridine-2-carboxylic acid (1,1-dimethyl-3-morpholin-4-yl-propyl)-amide a) 3-(tert-Butoxycarbonylamino)-3-methylbutanoic acid

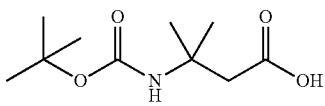

3-Amino-3-methylbutanoic acid (CAN 625-05-8, 2.0 g, 17 mmol) was combined with dioxane (60 mL) to give a colorless suspension. 1 N sodium hydroxide solution (17.0 mL, 17.0 mmol) was added dropwise at 0° C. within 10 min Di-tert-butyldicarbonate (4.8 g, 22.2 mmol) was added in three portions. The reaction was stirred for 30 min to give a colorless suspension. Then dioxane (30 mL) was added (using less solvent resulted in a thick suspension) and the mixture was stirred for 17 hours at ambient temperature. The reaction mixture was concentrated in vacuo to a volume of 50 mL and poured into 200 mL water. Then the mixture was washed with ethyl acetate (3×80 ml). The aqueous layers were combined, 2 N HCl was added and after adjusting the pH to 2 the mixture was extracted with ethyl acetate (3×60 mL). The organic layers were combined, dried over sodium sulfate and concentrated in vacuo to give product (2.7 g, 72.9%).

b) tert-Butyl 2-methyl-4-morpholino-4-oxobutan-2-ylcarbamate

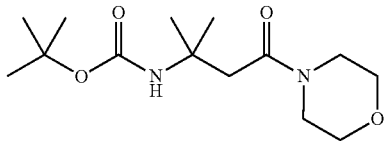 [SMILES: CC(C)(CC(=O)N1CCOCC1)NC(=O)OC(C)(C)C]

3-(tert-Butoxycarbonylamino)-3-methylbutanoic acid (2.7 g, 12.4 mmol), HBTU (CAN 94790-37-1, 6.1 g, 16.1 mmol) and triethylamine (CAN 121-44-8, 2.5 g, 24.8 mmol) was added to a solution of morpholine (CAN 110-91-8, 2.2 g, 24.8 mmol) in methylene chloride (50 mL). The mixture was stirred overnight at room temperature. Aqueous hydrochloride (1 N, 50 mL) was added, and the mixture extracted with methylene chloride. The organic extracts were washed with saturated aqueous sodium bicarbonate and brine, dried over anhydrous sodium sulfate, concentrated, and purified by column chromatography (silica gel, 50 g, eluting with 30% ethyl acetate in petroleum ether) to give the product (2.1 g, 59%); MS (EI): m/e 287.1 [M+H]⁺.

c) 3-Amino-3-methyl-1-morpholinobutan-1-one hydrochloride

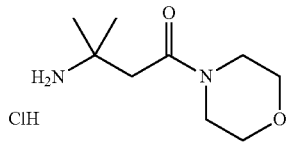

tert-Butyl 2-methyl-4-morpholino-4-oxobutan-2-ylcarbamate (0.5 g, 1.7 mmol) was dissolved in a saturated solution of hydrogen chloride in ethyl acetate (20 mL). The mixture was stirred for 3 h. The solvent was removed by reduced pressure to give crude product (0.55 g).

d) 1,1-Dimethyl-3-morpholin-4-yl-propylamine

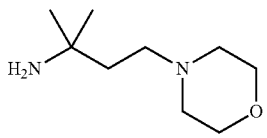

3-Amino-3-methyl-1-morpholinobutan-1-one (0.55 g, 2.96 mmol) and borane in THF (1 M, 6 mL, 6 mmol) were mixed together. The mixture was stirred at room temperature overnight, another portion borane in THF (6 mL) was added and the mixture stirred for another day. Methanol (5 mL) was added and the solvent was removed in vacuo. Water (20 mL) was added and the mixture was extracted with ethyl acetate (3×20 mL). The LC-MS showed still product in the water phase which was now extracted with methylene chloride (2×20 mL). The organic phases were combined, dried over anhydrous sodium sulfate and the solvent was removed in vacuo to give the crude product (0.09 g); MS (EI): m/e=173.2 [M+H]$^+$.

e) 6-Cyclopropylmethoxy-5-pyrrolidin-1-yl-pyridine-2-carboxylic acid (1,1-dimethyl-3-morpholin-4-yl-propyl)-amide

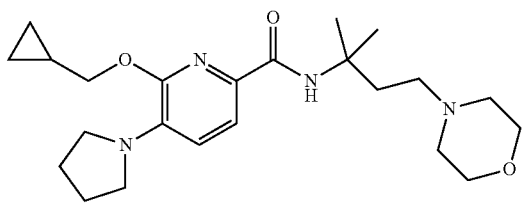 [SMILES: CC(C)(CCN1CCOCC1)NC(=O)c1ccc(N2CCCC2)c(OCC2CC2)n1]

The title compound was synthesized in analogy to Example 1, using 6-cyclopropylmethoxy-5-pyrrolidin-1-yl-pyridine-2-carboxylic acid (Example 14 a) and 1,1-dimethyl-3-morpholin-4-yl-propylamine as starting materials, MS (EI): 417.2 [M+H]$^+$.

Example 36

6-Cyclopropylmethoxy-5-methyl-pyridine-2-carboxylic acid (1-methyl-1-methylcarbamoyl-ethyl)-amide a) 5-Methyl-2-pyridinecarbonitrile

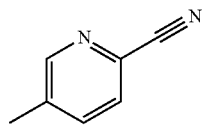

A solution of 2-fluoro-5-methylpyridine (CAN: 2369-19-9, 10 g, 90 mmol) and sodium cyanide (8.8 g, 180 mmol) in DMSO (15 mL) was heated to 150° C. for 48 h. Then water was added, the resulting mixture was extracted with ethyl acetate (3×50 mL) and the combined extracts were washed with sodium hypochlorite solution and brine, dried over anhydrous sodium sulfate and evaporated. The residue was purified by column chromatography (silica gel, 40 g, 10% ethyl acetate in petroleum ether) to yield the title compound (3.2 g, 27 mmol, 30.1%) as yellow solid; MS (EI): m/e=119.1 [M+H]$^+$.

b) 5-Methyl-1-oxy-pyridine-2-carbonitrile

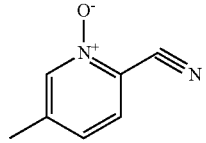

m-CPBA (CAN 937-14-4, 0.58 g, 3.4 mmol) was added in batches to a solution of 5-methyl-2-pyridinecarbonitrile (3 g, 25 mmol) in methylene chloride (60 mL) at room temperature and the reaction mixture was heated to 60° C. overnight. Then the reaction mixture was washed with sodium thiosulphate solution (3×50 mL) and brine (3×50 mL), dried over anhydrous sodium sulfate and evaporated. The residue was purified by column chromatography (silica gel, 35 g, 50% ethyl acetate in petroleum ether) to yield the title compound (2.6 g, 19 mmol, 77.6%) as yellow solid; MS (EI): m/e=135.1 [M+H]$^+$.

c) 6-Chloro-5-methylpicolinonitrile

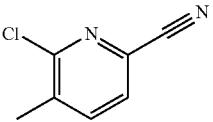

5-Methyl-1-oxy-pyridine-2-carbonitrile (2.6 g, 19 mmol) was added in batches to phosphorus oxychloride (CAN 10025-87-3, 20 mL) at 0° C. The reaction mixture was heated to 90° C. for 2 h. The volatiles were then removed and the remaining residue was neutralized with a saturated solution of sodium bicarbonate. This mixture was extracted with ethyl acetate (3×30 mL) and the combined extracts were dried over anhydrous sodium sulfate and evaporated. The residue was purified by column chromatography (silica gel, 30 g, 10% ethyl acetate in petroleum ether) to yield the title compound (1.6 g, 10 mmol, 54.1%) as yellow solid; MS (EI): m/e=153.1 [M+H]$^+$.

d) 6-Cyclopropylmethoxy-5-methyl-pyridine-2-carboxylic acid

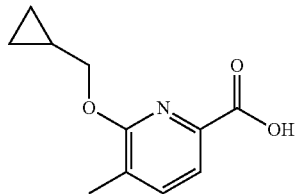

Sodium hydride (CAN 7646-69-7, 1.24 g, 37 mmol) was added in batches to a solution of cyclopropanemethanol (CAN 2516-33-8, 20 mL) and the reaction mixture was reacted for 30 min at ambient temperature. Then 6-chloro-5-methylpicolinonitrile (1.1 g, 7.2 mmol) was added to the above reaction mixture. The reaction mixture was heated to 100° C. overnight, quenched with water and evaporated. The residue was dissolved in water, extracted with ethyl acetate (50 mL). The pH of the aqueous layer was adjusted to 2 by addition of 1 N hydrochloric acid and the resulting mixture was extracted with ethyl acetate (3×50 mL). The combined organic extracts were washed with water and brine, dried over anhydrous sodium sulfate and evaporated. The residue was purified by column chromatography (silica gel, 25 g, 50% ethyl acetate in Petroleum ether) to yield the title compound (1 g, 5 mmol, 67%) as yellow solid; MS (EI): m/e=208.1 [M+H]$^+$.

e) 6-Cyclopropylmethoxy-5-methyl-pyridine-2-carboxylic acid (1-methyl-1-methylcarbamoyl-ethyl)-amide

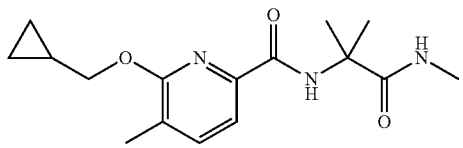 [SMILES: CNC(=O)C(C)(C)NC(=O)c1ccc(C)c(OCC2CC2)n1]

The title compound was synthesized in analogy to Example 1, using 6-cyclopropylmethoxy-5-methyl-pyridine-2-carboxylic acid and 2-amino-N,2-dimethyl-propanamide (CAN 106914-07-2) as starting materials, MS (EI): m/e=318.1 [M+H]$^+$.

Example 37

6-(Tetrahydro-pyran-4-yl)-pyridine-2-carboxylic acid piperidin-1-ylamide a) 6-(3,6-Dihydro-2H-pyran-4-yl)-pyridine-2-carboxylic acid

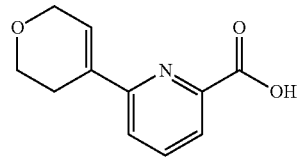 [SMILES: O=C(O)c1cccc(C2=CCOCC2)n1]

Under an atmosphere of nitrogen, a solution of 6-bromo-pyridine-2-carboxylic acid (CAN: 21190-87-4, 1 g, 4.9 mmol), 2-(3,6-dihydro-2H-pyran-4-yl)-4,4,5,5-tetramethyl-1,3,2-dioxaborolane (Example 9-d, 1.1 g, 5.4 mmol), 1,1'-bis(diphenylphosphino) ferrocene-palladium(II)dichloride methylene chloride complex (CAN 95464-05-4, 0.08 g, 0.1 mmol) and potassium carbonate (1.37 g, 10 mmol) in water (50 mL) was stirred for 24 h at 100° C. The reaction mixture was extracted with ethyl acetate (50 mL), the pH of the aqueous layer was adjusted to 2 by addition of 1 N hydrochloric acid and the resulting mixture was extracted with ethyl acetate (3×50 mL). The combined organic extracts were washed with brine (6×50 mL), dried over anhydrous sodium sulfate and evaporated. The residue was purified by prep-HPLC to yield the title compound (0.3 g, 1.5 mmol, 29.5%) as white solid; MS (EI): m/e=206.1 [M+H]$^+$.

b) 6-(Tetrahydro-pyran-4-yl)-pyridine-2-carboxylic acid

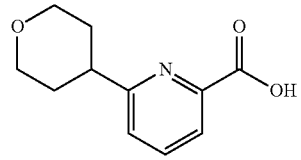 [SMILES: O=C(O)c1cccc(C2CCOCC2)n1]

The title compound was synthesized in analogy to Example 7 b, using 6-(3,6-dihydro-2H-pyran-4-yl)-pyridine-2-carboxylic acid and 10% Pd/C as starting materials, MS (EI): m/e 208.1 [M+H]$^+$.

c) 6-(Tetrahydro-pyran-4-yl)-pyridine-2-carboxylic acid piperidin-1-ylamide

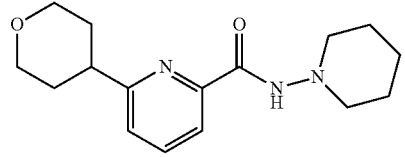 [SMILES: O=C(NN1CCCCC1)c1cccc(C2CCOCC2)n1]

The title compound was synthesized in analogy to Example 1, using 6-(tetrahydro-pyran-4-yl)-pyridine-2-carboxylic acid and 1-piperidinamine (CAN 2213-43-6) as starting materials, MS (LC/MS): 290.2 [M+H]$^+$.

Example 38

6-(3-Chloro-phenyl)-pyridine-2-carboxylic acid [(S)-2-cyclopropyl-1-(5-methyl-1,2,4]oxadiazol-3-yl)-ethyl]-amide a) (S)-tert-Butyl 1-amino-3-cyclopropyl-1-oxopropan-2-ylcarbamate

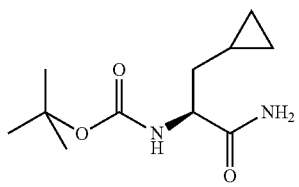 [SMILES: CC(C)(C)OC(=O)N[C@@H](CC1CC1)C(N)=O]

A mixture of (S)-2-(tert-butoxycarbonylamino)-3-cyclopropylpropanoic acid (CAN 89483-06-7, 10 g, 44 mmol), di-tert-butyl dicarbonate (CAN:24424-99-5, 14.28 g, 66 mmol) and pyridine (2.4 mL) in acetonitrile (200 mL) was stirred at room temperature for 20 min. Ammonia (10 mL) was added dropwise for 20 min. The resulting reaction mixture was stirred for 4 h. During removal of most of the solvent under reduced pressure the product precipitated and the solid was filtered off and washed with acetonitrile (20 mL). The solid was dried under reduced pressure to give the title compound (7.73 g, 78%) as white solid; MS (EI): m/e 251.2 [M+Na]+.

b) (S)-tert-Butyl 1-cyano-2-cyclopropylethylcarbamate

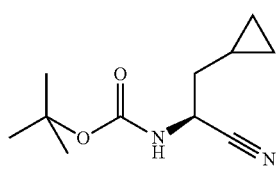

To a solution of (S)-tert-butyl 1-amino-3-cyclopropyl-1-oxopropan-2-ylcarbamate (3.7 g, 16 mmol) and triethylamine (6.55 g, 65 mmol) in methylene chloride (50 mL) was added trifluoroacetic acid anhydride (6.81 g, 32 mmol) dropwise at 0° C. The resulting mixture was allowed to warm to room temperature and stirred for 4 h. The mixture was washed with water (150 mL), citric acid (150 mL, 5 M) and brine (150 mL). The organic phase was dried over anhydrous sodium sulfate and concentrated to give product (3.31 g, 97%) as a yellow solid; MS (EI): m/e 233.1 [M+Na]+.

c) (S,Z)-tert-Butyl 1-amino-3-cyclopropyl-1-(hydroxyimino)propan-2-ylcarbamate

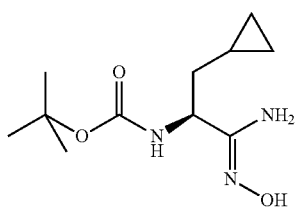 [SMILES: CC(C)(C)OC(=O)N[C@@H](CC1CC1)/C(N)=N/O]

Potassium carbonate (2.18 g, 16 mmol) was dissolved in water (8 mL) and hydroxylamine hydrochloride (1.1 g, 16 mmol) was added. A solution of (S)-tert-butyl 1-cyano-2-cyclopropylethylcarbamate (3.31 g, 16 mmol) in ethanol (24 mL) was added thereto and the resulting reaction mixture was stirred for 72 h. After evaporation of solvents, the residue was dissolved with ethyl acetate (20 mL) and then filtered. The filtrate was concentrated to yield crude product as yellow solid (3.61 g, 94%); MS (EI): m/e 244.2 [M+H]+.

d) (S)-tert-Butyl 2-cyclopropyl-1-(5-methyl-1,2,4-oxadiazol-3-yl)ethylcarbamate

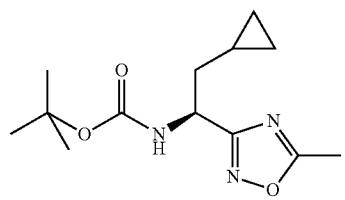 [SMILES: Cc1nc([C@H](CC2CC2)NC(=O)OC(C)(C)C)no1]

To a solution of acetic acid (0.224 g, 4 mmol) in DMF (5 mL) was added N,N'-carbonyldiimidazole (0.6 g, 4 mmol) and the mixture was stirred for 0.5 h at room temperature. (S,Z)-tert-butyl 1-amino-3-cyclopropyl-1-(hydroxyimino)propan-2-ylcarbamate (0.84 g, 3 mmol) was added and the mixture was heated to 120° C. and stirred for 4 h. After evaporation of solvents, the residue was purified by column chromatography (silica gel, 20 g, eluting with 10% ethyl acetate in petroleum ether) to give the title compound (0.5 g; 54%) as yellow solid; MS (EI): m/e 290.1 [M+Na]+.

e) (S)-2-Cyclopropyl-1-(5-methyl-[1,2,4]oxadiazol-3-yl)-ethylamine

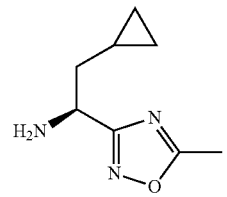

A solution of (S)-tert-butyl 2-cyclopropyl-1-(5-methyl-1,2,4-oxadiazol-3-yl)ethylcarbamate (0.5 g, 2 mmol) in sat. hydrochloric acid (10 mL) was stirred at room temperature for 1 h. Then water (20 mL) was added. The water phase was washed with ethyl acetate (2×20 mL) and adjusted with 2 M sodium hydroxide solution to pH=9~10. It was then extracted with ethyl acetate (2×20 mL). The organic layer was washed with brine (20 mL), dried over anhydrous sodium sulfate and concentrated to give crude product as a white solid (0.25 g, 80%); MS (EI): m/e 168.2 [M+H]+.

f) 6-(3-Chloro-phenyl)-pyridine-2-carboxylic acid [(S)-2-cyclopropyl-1-(5-methyl-1,2,4]oxadiazol-3-yl)-ethyl]-amide Chiral

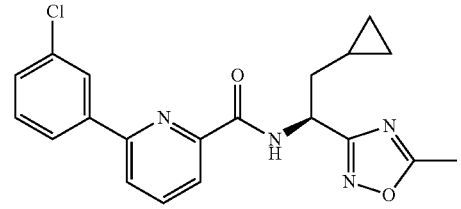

The title compound was synthesized in analogy to Example 1, using 6-(3-chlorophenyl)-2-pyridinecarboxylic acid (CAN 863704-38-5) and (S)-2-cyclopropyl-1-(5-methyl-[1,2,4]oxadiazol-3-yl)-ethylamine as starting materials, MS (EI): m/e 383.1 [M+H]⁺.

Example 39

(5-Cyclopentyl-6-cyclopropylmethoxy-pyridin-2-yl)-(1,1-dioxidotetrahydro-2H-thiopyran-4-yl)-methanone a) 5-Cyclopentenyl-6-(cyclopropylmethoxy)-pyridine-2-carboxylic acid

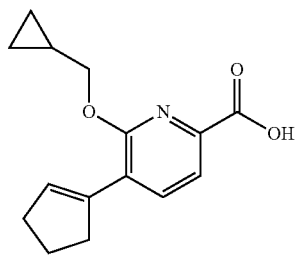 [SMILES: O=C(O)c1ccc(C2=CCCC2)c(OCC2CC2)n1]

The mixture of 5-bromo-6-(cyclopropylmethoxy)-pyridine-2-carboxylic acid (Example 9 d, 1.0 g, 4 mmol), 2-cyclopentenyl-4,4,5,5-tetramethyl-1,3,2-dioxaborolane (CAN 287944-10-9, 0.86 g, 4 mmol), 1,1'-bis(diphenylphosphino)ferrocene-palladium(II)dichloride methylene chloride complex (CAN 95464-05-4, 150 mg 0.18 mmol) and aqueous sodium carbonate solution (2N, 16 mL) was added to DMF (10 ml). The mixture was heated to 100° C. overnight; then the solution was diluted with water (15 mL), extracted with ethyl acetate (30 mL), the water layer was adjusted to pH=3.0 by hydrochloric acid (3N) and extracted with ethyl acetate (2×50 mL). The combined organic layers were washed with water (2×100 mL) and brine (80 mL) and evaporated to dryness. The residue was purified by column chromatography (silica gel, 8 g, eluting with 15% ethyl acetate in petroleum ether) to obtain the product (0.85 g, 89%) as a white solid; MS (LC/MS): 260.1 [M+H]⁺.

b) 5-Cyclopentyl-6-cyclopropylmethoxy-pyridine-2-carboxylic acid

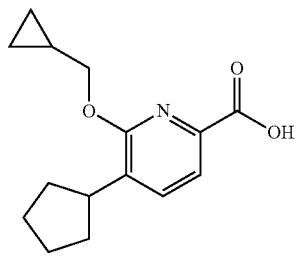 [SMILES: O=C(O)c1ccc(C2CCCC2)c(OCC2CC2)n1]

The mixture of 5-cyclopentenyl-6-(cyclopropylmethoxy)-pyridine-2-carboxylic acid (0.95 g, 4 mmol), Pd/C (10% w/w, 0.2 g) in 30 mL of ethanol in a hydrogen atmosphere was stirred for 4 h at room temperature. The mixture was filtered and the filtrate was evaporated to dryness to obtain the product (0.76 g, 79%) as white solid. The product was directly used for the next step; MS (LC/MS): 262.1 [M+H]⁺.

c) (5-Cyclopentyl-6-cyclopropylmethoxy-pyridin-2-yl)-(1,1-dioxidotetrahydro-2H-thiopyran-4-yl)-methanone

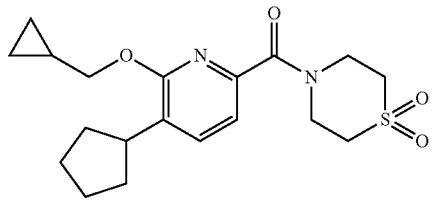 [SMILES: O=C(c1ccc(C2CCCC2)c(OCC2CC2)n1)N1CCS(=O)(=O)CC1]

The title compound was synthesized in analogy to Example 1, using 5-cyclopentyl-6-cyclopropylmethoxy-pyridine-2-carboxylic acid and 1,1-dioxide-thiomorpholine (CAN 39093-93-1) as starting materials, MS (LC/MS): 379.2 [M+H]⁺.

Example 40

5-Cyclopentyl-6-cyclopropylmethoxy-pyridine-2-carboxylic acid (1-methyl-1-methylcarbamoyl-ethyl)-amide

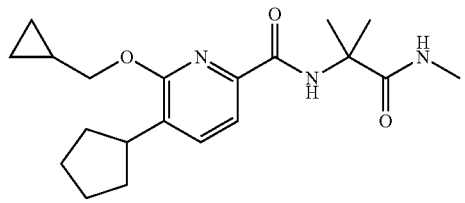 [SMILES: CNC(=O)C(C)(C)NC(=O)c1ccc(C2CCCC2)c(OCC2CC2)n1]

The title compound was synthesized in analogy to Example 1, using 5-cyclopentyl-6-cyclopropylmethoxy-pyridine-2-carboxylic acid (Example 39 b) and 2-amino-N,2-dimethyl-propanamide (CAN 106914-07-2) as starting materials, MS (LC/MS): 360.2 [M+H]⁺.

Example 41

6-(3-Chloro-phenyl)-pyridine-2-carboxylic acid [1-methyl-1-(5-methyl-[1,2,4]oxadiazol-3-yl)-ethyl]-amide

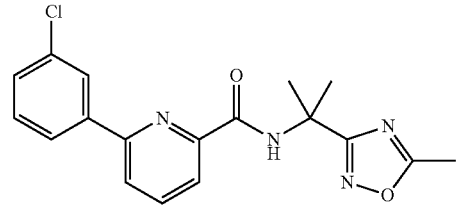 [SMILES: Cc1nc(C(C)(C)NC(=O)c2cccc(-c3cccc(Cl)c3)n2)no1]

The title compound was synthesized in analogy to Example 1, using 6-(3-chlorophenyl)-2-pyridinecarboxylic acid (CAN 863704-38-5) and α,α,5-trimethyl-1,2,4-oxadiazole-3-methanamine (Example 33 d, CAN 1153831-97-0) as starting materials, MS (LC/MS): 357.1 [M+H]⁺.

Example 42

5-Cyclopropyl-6-cyclopropylmethoxy-pyridine-2-carboxylic acid piperidin-1-ylamide a) 5-Cyclopropyl-6-cyclopropylmethoxy-pyridine-2-carboxylic acid

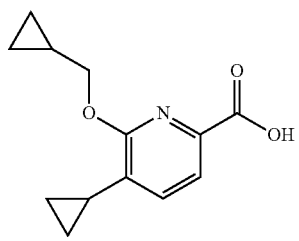 [SMILES: O=C(O)c1ccc(C2CC2)c(OCC2CC2)n1]

A mixture of 5-bromo-6-(cyclopropylmethoxy)-pyridine-2-carboxylic acid (Example 9 d, 1.5 g, 5.5 mmol), cyclopropylboronic acid (CAN 411235-57-9, 0.57 g, 7 mmol), palladium diacetate (CAN 3375-31-3, 62 mg, 0.28 mmol), tricyclohexylphosphine (CAN 2622-14-2, 154 mg, 0.1 mmol) and potassium phosphate (4.1 g, 19 mmol) in toluene/water (20/1v/v, 30 mL) was heated to 100° C. overnight. After that the mixture was evaporated to dryness, dissolved in 30 mL of water, extracted with ethyl acetate (30 mL) and the organic layer was dropped. The water layer was adjusted to pH=3 and extracted with ethyl acetate (2×30 mL), this organic layer was washed with water (30 mL) and brine (30 mL), dried over anhydrous sodium sulfate then evaporated to dryness. The residue was purified by column chromatography (silica gel, 10 g, eluting with 15% ethyl acetate in petroleum ether) to obtain the title compound (0.96 g, 75%) as white solid; MS (LC/MS): 234.1 [M+H]⁺.

b) 5-Cyclopropyl-6-cyclopropylmethoxy-pyridine-2-carboxylic acid piperidin-1-ylamide

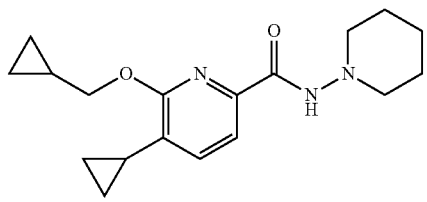 [SMILES: O=C(NN1CCCCC1)c1ccc(C2CC2)c(OCC2CC2)n1]

The title compound was synthesized in analogy to Example 1, using 5-cyclopropyl-6-cyclopropylmethoxy-pyridine-2-carboxylic acid and 1-piperidinamine (CAN 2213-43-6) as starting materials, MS (LC/MS): 316.2 [M+H]⁺.

Example 43

5-Cyclopropyl-6-cyclopropylmethoxy-pyridine-2-carboxylic acid (1-methyl-1-methylcarbamoyl-ethyl)-amide

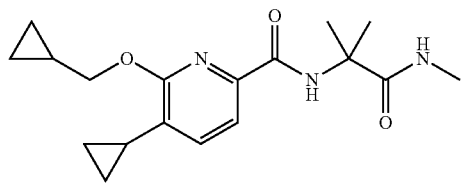 [SMILES: CNC(=O)C(C)(C)NC(=O)c1ccc(C2CC2)c(OCC2CC2)n1]

The title compound was synthesized in analogy to Example 1, using 5-cyclopropyl-6-cyclopropylmethoxy-pyridine-2-carboxylic acid (Example 42 a) and 2-amino-N,2-dimethyl-propanamide (CAN 106914-07-2) as starting materials, MS (LC/MS): 332.2 [M+H]⁺.

Example 44

5-Cyclopropyl-6-cyclopropylmethoxy-pyridine-2-carboxylic acid (1-methyl-1-thiazol-2-yl-ethyl)-amide

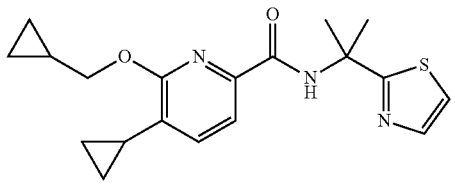 [SMILES: CC(C)(NC(=O)c1ccc(C2CC2)c(OCC2CC2)n1)c1nccs1]

The title compound was synthesized in analogy to Example 1, using 5-cyclopropyl-6-cyclopropylmethoxy-pyridine-2-carboxylic acid (Example 42 a) and α,α-dimethyl-2-thiazolemethanamine (CAN 1082393-38-1) as starting materials, MS (LC/MS): 358.1 [M+H]⁺.

Example 45

5-Cyclopropyl-6-cyclopropylmethoxy-pyridine-2-carboxylic acid [1-methyl-1-(5-methyl-[1,2,4]oxadiazol-3-yl)-ethyl]-amide

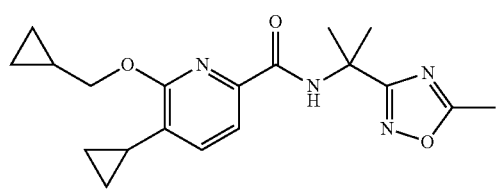 [SMILES: Cc1nc(C(C)(C)NC(=O)c2ccc(C3CC3)c(OCC3CC3)n2)no1]

The title compound was synthesized in analogy to Example 1, using 5-cyclopropyl-6-cyclopropylmethoxy-pyridine-2-carboxylic acid (Example 42 a) and α,α,5-trimethyl- 1,2,4-oxadiazole-3-methanamine (CAN 1153831-97-0) as starting materials, MS (LC/MS): 357.1 [M+H]⁺.

Example 46

6-(4-Chloro-phenyl)-pyridine-2-carboxylic acid piperidin-1-ylamide

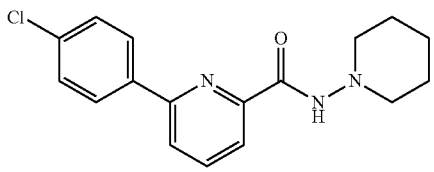 [SMILES: O=C(NN1CCCCC1)c1cccc(-c2ccc(Cl)cc2)n1]

The title compound was synthesized in analogy to Example 1, using 6-(4-chlorophenyl)-2-pyridinecarboxylic acid (CAN 135432-77-8) and 1-piperidinamine (CAN 2213-43-6) as starting materials, MS (EI): m/e=316.1 [M+H]⁺.

Example 47

6-Cyclopropylmethoxy-5-methyl-pyridine-2-carboxylic acid piperidin-1-ylamide

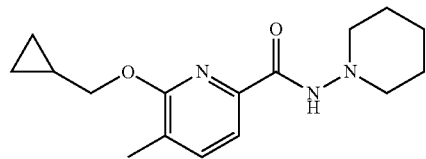 [SMILES: Cc1ccc(C(=O)NN2CCCCC2)nc1OCC1CC1]

The title compound was synthesized in analogy to Example 1, using 6-cyclopropylmethoxy-5-methyl-pyridine-2-carboxylic acid (Example 36 d) and 1-piperidinamine (CAN 2213-43-6) as starting materials, MS (EI): m/e 290.2 [M+H]⁺.

Example 48

[6-(3-Chloro-phenyl)-5-cyclopropyl-pyridin-2-yl]-(1,1-dioxidotetrahydro-2H-thiopyran-4-yl)-methasone a) 5-Cyclopropyl-pyridine-2-carboxylic acid methyl ester

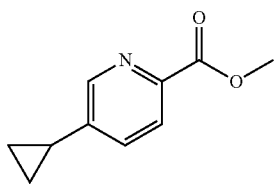

5-Bromo-pyridine-2-carboxylic acid methyl ester (CAN 29682-15-3, 2.16 g, 0.01 mol), cyclopropylboronic acid (CAN 411235-57-9, 0.9 g, 0.01 mol), tris(dibenzylideneacetone)dipalladium (CAN 52409-22-0, 0.2 g), 9,9-dimethyl-4,5-bis(diphenylphosphino)xanthene (CAN 161265-03-8, 0.3 g) and cesium carbonate (CAN 534-17-8, 3.3 g, 0.01 mol) was added into 1,4-dioxane (40 mL). The mixture was stirred for 12 h at 110° C. under nitrogen atmosphere. Subsequently, the mixture was filtered and concentrated. The residue was poured into water (20 mL) and extracted with ethyl acetate (3×20 mL). The combined organic layers were dried over anhydrous sodium sulfate and concentrated to give crude product. The crude product was purified by a flash column chromatography (silica gel, 50 g, eluting with 20% ethyl acetate in petroleum ether) to give product (0.8 g, 45%); MS (EI): m/e 178.1 [M+H]⁺.

b) 5-Cyclopropyl-1-oxy-pyridine-2-carboxylic acid methyl ester

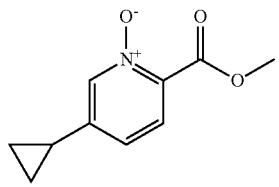

5-Cyclopropyl-pyridine-2-carboxylic acid methyl ester (0.8 g, 5 mmol) and m-CPBA (CAN 937-14-4, 1.2 g, 7 mmol) was added into methylene chloride (15 mL). The mixture was stirred for 6 hours at 60° C. Subsequently the mixture was concentrated to the crude product. The crude product was purified by a flash column chromatography (silica gel, 20 g, eluting with ethyl acetate) to give product (0.3 g, 34%); MS (EI): m/e 194.1 [M+H]⁺.

c) 6-Bromo-5-cyclopropyl-pyridine-2-carboxylic acid methyl ester

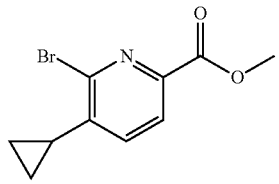

5-Cyclopropyl-1-oxy-pyridine-2-carboxylic acid methyl ester (0.3 g, 2 mmol) was added into phosphorus oxybromide (CAN 7789-59-5, 5 g, 17 mmol). The mixture was stirred for 2 h at 80° C. Subsequently, the reaction solution was poured into water (30 mL) and extracted with ethyl acetate (3×10 mL). The combined organic layer was dried over anhydrous sodium sulfate and concentrated to give crude product. The crude product was purified by a flash column chromatography (silica gel, 10 g, 20%, ethyl acetate in petroleum ether) to give product (0.1 g, 25%); MS: (EI) m/e 256.0 [M+H]⁺.

d) 6-(3-Chloro-phenyl)-5-cyclopropyl-pyridine-2-carboxylic acid methyl ester

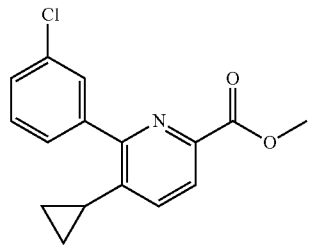 [SMILES: COC(=O)c1ccc(C2CC2)c(-c2cccc(Cl)c2)n1]

6-Bromo-5-cyclopropyl-pyridine-2-carboxylic acid methyl ester (0.1 g, 0.4 mmol), 3-chlorophenylboronic acid (CAN 63503-60-6, 0.08 g, 0.5 mmol), 1,1'-bis(diphenylphosphino)-ferrocene-palladium(II)dichloride methylene chloride adduct (CAN 95464-05-4, 50 mg) and cesium carbonate (CAN 534-17-8, 0.2 g, 0.6 mmol) was added into 1,4-dioxane (10 mL) under nitrogen atmosphere. The mixture was stirred for 12 h at 110° C. Subsequently, the mixture was concentrated to give crude product. The crude product was purified by a flash column chromatography (silica gel, 5 g, 20% ethyl acetate in petroleum ether) to give product (80 mg, 71%); MS: (EI) m/e 288.1 [M+H]+.

e) 6-(3-Chloro-phenyl)-5-cyclopropyl-pyridine-2-carboxylic acid

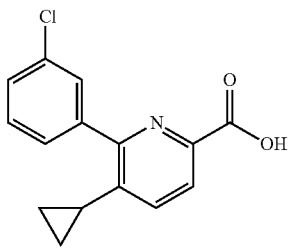 [SMILES: O=C(O)c1ccc(C2CC2)c(-c2cccc(Cl)c2)n1]

6-(3-Chloro-phenyl)-5-cyclopropyl-pyridine-2-carboxylic acid methyl ester (80 mg, 0.28 mmol) and sodium hydroxide (CAN 1310-73-2, 30 mg,) was added into water (10 mL). The mixture was stirred for 2 h at ambient temperature. Subsequently the pH was adjusted to 3 with 1M hydrochloric acid, the mixture extracted with ethyl acetate (3×10 mL), the organic phases were combined, dried over anhydrous sodium sulfate and concentrated to give product (60 mg, 78%); MS (EI): m/e 274.1 [M+H]+.

f) [6-(3-Chloro-phenyl)-5-cyclopropyl-pyridin-2-yl]-(1,1-dioxidotetrahydro-2H-thiopyran-4-yl)-methanone

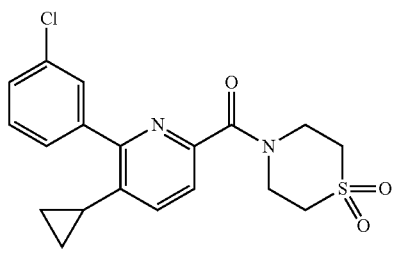 [SMILES: O=C(c1ccc(C2CC2)c(-c2cccc(Cl)c2)n1)N1CCS(=O)(=O)CC1]

The title compound was synthesized in analogy to Example 1, using 6-(3-chloro-phenyl)-5-cyclopropyl-pyridine-2-carboxylic acid and 1,1-dioxide-thiomorpholine (CAN 39093-93-1) as starting materials, MS (LC/MS): m/e 391.0 [M+H]+.

Example 49

6-(3-Chloro-phenyl)-5-methyl-pyridine-2-carboxylic acid (1-methyl-t-oxazol-2-yl-ethyl)-amide a) 5-Methyl-pyridine-2-carbonitrile

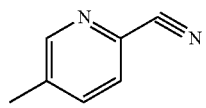

2-Fluoro-5-methylpyridine (CAN 2369-19-9, 50 g, 90 mmol) and sodium cyanide (CAN 143-33-9, 70 g, 1.43 mol) were dissolved in DMSO (200 mL), the mixture was stirred for 3 days at 150° C. The mixture was cooled to room temperature, ice water (200 mL) was added and the product was obtained as red solid (26.5 g, 50%) by filtration and drying; MS (EI): m/e 119.1 [M+H]+.

b) 5-Methyl-1-oxy-pyridine-2-carbonitrile

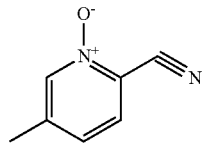

Hydrogen peroxide (CAN 7722-84-1, 30%, 30 mL) was added to a solution of 5-methyl-pyridine-2-carbonitrile (3.0 g, 25 mmol) in acetic acid (30 mL) and the mixture was stirred at 60° C. overnight. The solvent was removed by reduced pressure to give the crude product (3.0 g, 88%); MS (EI): m/e 135.1[M+H]+.

c) 6-Bromo-5-methyl-pyridine-2-carbonitrile

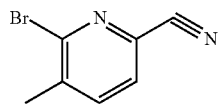

5-Methyl-1-oxy-pyridine-2-carbonitrile (example 36b, 1.5 g, 11 mmol) and phosphorus oxide tribromide (CAN 7789-59-5, 10 g) were mixed together. The mixture was stirred for 1 h at 100° C. Ice water was added, and the mixture extracted with ethyl acetate (10 mL). The organic phase was dried over d) 6-Bromo-5-methyl-pyridine-2-carboxylic acid

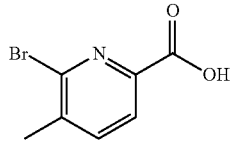

6-Bromo-5-methyl-pyridine-2-carbonitrile (1.0 g, 5.0 mmol) was added to a solution of sodium hydroxide (0.3 g, 7 mmol) in water (20 mL), the mixture was stirred at 120° C. overnight. Subsequently, the mixture was adjusted to pH=3 and extracted with ethyl acetate (2×15 mL). The organic extracts were washed with brine, dried over anhydrous sodium sulfate and concentrated to give the product (0.7 g, 63.8%); MS (EI): m/e 216.0 [M+H]+.

e) 6-(3-Chloro-phenyl)-5-methyl-pyridine-2-carboxylic acid

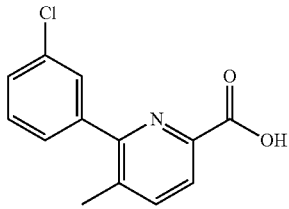 [SMILES: Cc1ccc(C(=O)O)nc1-c1cccc(Cl)c1]

3-Chlorophenylboronic acid (CAN 63503-60-6, 0.61 g, 3.9 mmol), 1,1'-bis(diphenyl-phosphino)ferrocene-palladium(II)dichloride methylene chloride complex (CAN 95464-05-4, 53 mg, 0.065 mmol) and potassium carbonate (CAN 584-08-7, 0.54 g, 3.9 mmol) was added to a solution of 6-bromo-5-methyl-pyridine-2-carboxylic acid (0.7 g, 3.2 mmol) in water (30 mL). The mixture was stirred at 100° C. overnight. The reaction mixture was adjusted to pH=3 and the mixture was extracted with ethyl acetate (3×20 mL). The organic layers were combined, dried over anhydrous sodium sulfate and concentrated in vacuo to give product (0.55 g, 56.9%); MS (EI): m/e 248.1 [M+H]+.

f) 6-(3-Chloro-phenyl)-5-methyl-pyridine-2-carboxylic acid (1-methyl-1-oxazol-2-yl-ethyl)-amide

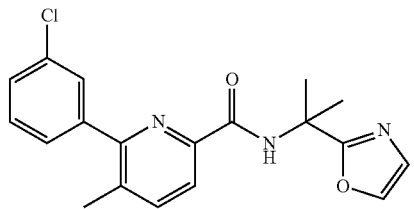 [SMILES: Cc1ccc(C(=O)NC(C)(C)c2ncco2)nc1-c1cccc(Cl)c1]

The title compound was synthesized in analogy to Example 1, using 6-(3-chloro-phenyl)-5-methyl-pyridine-2-carboxylic acid and α,α-dimethyl-2-oxazolemethanamine (CAN 1211519-76-4) as starting materials, MS (EI): 356.1 (M+H)+.

Example 50

6-(3-Chloro-phenyl)-5-methyl-pyridine-2-carboxylic acid (1-methyl-1-thiazol-2-yl-ethyl)-amide

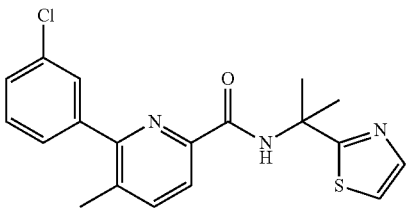 [SMILES: Cc1ccc(C(=O)NC(C)(C)c2nccs2)nc1-c1cccc(Cl)c1]

The title compound was synthesized in analogy to Example 1, using 6-(3-chloro-phenyl)-5-methyl-pyridine-2-carboxylic acid (Example 49 e) and α,α-dimethyl-2-thiazolemethanamine (CAN 1082393-38-1) as starting materials, MS (EI): 372.0 [M+H]+.

Example 51

6-(3-Chloro-phenyl)-5-methyl-pyridine-2-carboxylic acid [1-methyl-1-(5-methyl-[1,2,4]oxadiazol-3-yl)-ethyl]-amide

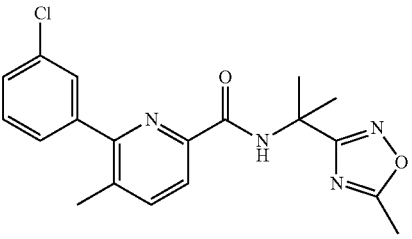 [SMILES: Cc1nc(C(C)(C)NC(=O)c2ccc(C)c(-c3cccc(Cl)c3)n2)no1]

The title compound was synthesized in analogy to Example 1, using 6-(3-chloro-phenyl)-5-methyl-pyridine-2-carboxylic acid (Example 49 e) and α,α,5-trimethyl-1,2,4-oxadiazole-3-methanamine (CAN 1153831-97-0) as starting materials, MS (D): 371.1 [M+H]+.

Example 52

6-(3-Chloro-phenyl)-5-methyl-pyridine-2-carboxylic acid piperidin-1-yl-amide

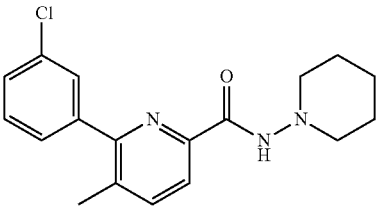 [SMILES: Cc1ccc(C(=O)NN2CCCCC2)nc1-c1cccc(Cl)c1]

The title compound was synthesized in analogy to Example 1, using 6-(3-chloro-phenyl)-5-methyl-pyridine-2-carboxylic acid (Example 49 e) and 1-piperidinamine (CAN 2213-43-6) as starting materials, MS (D): 330.1 [M+H]+.

Example 53

5-Cyclopentyl-6-cyclopropylmethoxy-pyridine-2-carboxylic acid [(S)-2-cyclopropyl-1-(5-methyl-[1,2,4]oxadiazol-3-yl)-ethyl]-amide

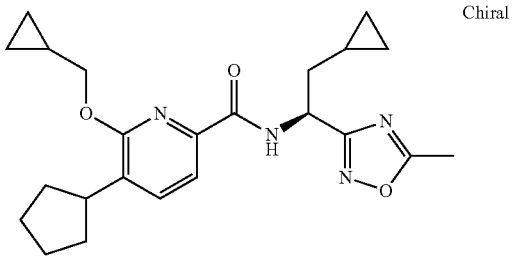 [SMILES: Cc1nc([C@H](CC2CC2)NC(=O)c2ccc(C3CCCC3)c(OCC3CC3)n2)no1]

The title compound was synthesized in analogy to Example 1, using 5-cyclopentyl-6-cyclopropylmethoxy-pyridine-2-carboxylic acid (Example 39 b) and (S)-2-cyclopropyl-1-(5-methyl-[1,2,4]oxadiazol-3-yl)-ethylamine (Example 38 e) as starting materials, MS (LC/MS): 411.2 [M+H]$^+$.

Example 54

5-Cyclopentyl-6-cyclopropylmethoxy-pyridine-2-carboxylic acid [1-methyl-1-(5-methyl-[1,2,4]oxadiazol-3-yl)-ethyl]-amide

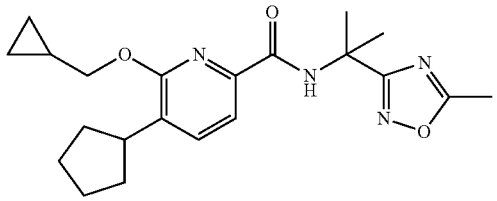 [SMILES: Cc1nc(C(C)(C)NC(=O)c2ccc(C3CCCC3)c(OCC3CC3)n2)no1]

The title compound was synthesized in analogy to Example 1, using 5-cyclopentyl-6-cyclopropylmethoxy-pyridine-2-carboxylic acid (Example 39 b) and α,α,5-trimethyl-1,2,4-oxadiazole-3-methanamine (CAN 1153831-97-0, Example 33 d) as starting materials, MS (LC/MS): 385.2 [M+H]$^+$.

Example 55

5-Cyclopentyl-6-cyclopropylmethoxy-pyridine-2-carboxylic acid (1-methyl-1-thiazol-2-yl-ethyl)-amide

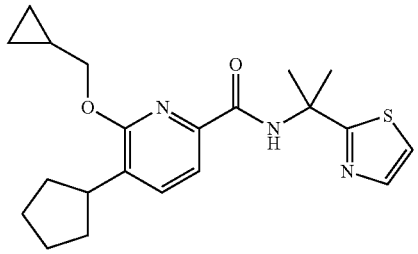 [SMILES: CC(C)(NC(=O)c1ccc(C2CCCC2)c(OCC2CC2)n1)c1nccs1]

The title compound was synthesized in analogy to Example 1, using 5-cyclopentyl-6-cyclopropylmethoxy-pyridine-2-carboxylic acid (Example 39 b) and α,α-dimethyl-2-thiazolemethanamine (CAN 1082393-38-1) as starting materials, MS (LC/MS): 386.1 [M+H]$^+$.

Example 56

6-(3-Chloro-phenyl)-pyridine-2-carboxylic acid ((S)-3-methyl-1-thiazol-2-yl-butyl)-amide a) (S)-2-(tert-Butoxycarbonylamino)-4-methylpentanoic acid

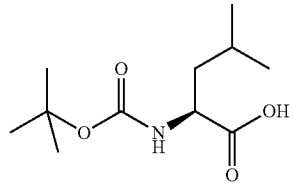 [SMILES: CC(C)C[C@H](NC(=O)OC(C)(C)C)C(=O)O]

To a mixture of L-leucine (CAN: 61-90-5, 8 g, 0.061 mmol) in 1,4-dioxane (200 mL) was added aqueous sodium hydroxide solution (1N, 8.5 mL) and di-tert-butyl dicarbonate (17.5 g, 80 mmol), and the mixture was stirred overnight. After evaporation of solvents, the residue was diluted with water (50 mL) and washed with ethyl acetate (2×50 mL). The aqueous phase was adjusted to pH=2~3 and then extracted with ethyl acetate (3×50 mL). The combined organic layer was washed with brine (2×50 mL), dried over anhydrous sodium sulfate and concentrated to give product (6.75 g, 48%) as a white solid; MS (EI): m/e=232.2 [M+H]$^+$.

b) (S)-tert-Butyl 1-amino-4-methyl-1-oxopentan-2-ylcarbamate

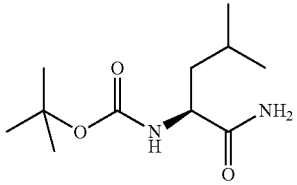 [SMILES: CC(C)C[C@H](NC(=O)OC(C)(C)C)C(N)=O]

A mixture of (S)-2-(tert-butoxycarbonylamino)-4-methylpentanoic acid (1.8 g), di-tert-butyl dicarbonate (CAN: 24424-99-5, 12 mmol) and pyridine (3 mL) in CH$_3$CN (50 mL) was stirred at room temperature for 20 min. Ammonium hydroxide solution (25%-28% NH$_3$, 15 mL) was added dropwise during 30 min. The resulting reaction mixture was stirred overnight. During the removal of solvents, the product precipitated, was collected by filtration and dried to give the target compound as a white solid (1.55 g, 86%). MS (D): m/e=253.2 [M+Na]$^+$.

c) ((S)-3-Methyl-1-thiocarbamoyl-butyl)-carbamic acid tert-butyl ester

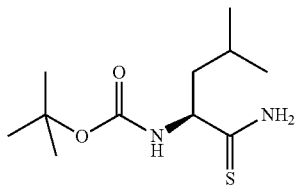 [SMILES: CC(C)C[C@H](NC(=O)OC(C)(C)C)C(N)=S]

A mixture of (S)-tert-butyl 1-amino-4-methyl-1-oxopentan-2-ylcarbamate (1.8 g, 8 mmol) and Lawesson's reagent (1.58 g, 4 mmol) in toluene (20 mL) was stirred at 90° C. for 2.5 h. After removal of the solvent under reduced pressure, the residue was purified by column chromatography (silica gel, 30 g, ethyl acetate/MeOH, 20/1) to yield the title compound (1.38 g, 72%) as yellow solid; MS: m/e 269.2 [M+H]$^+$.

d) (S)-α-(2-Methylpropyl)-2-thiazolemethanamine acetate

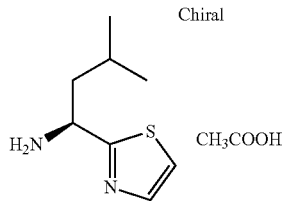

A mixture of ((S)-3-methyl-1-thiocarbamoyl-butyl)-carbamic acid tert-butyl ester (1.38 g, 6 mmol), 2-bromo-1,1-dimethoxyethane (CAN:7252-83-7, 1.14 g, 7 mmol) and p-toluene sulfonic acid (50 mg) in acetic acid (20 mL) was stirred at 120° C. for 4. After evaporation of solvents, the residue was diluted with ethyl acetate (20 mL) and water (20 mL). The aqueous phase was washed with ethyl acetate (3×20 mL) and lyophilized to give a brown solid (0.6 g, 63%); MS: m/e 171.1 [M+H$^+$].

e) 6-(3-Chloro-phenyl)-pyridine-2-carboxylic acid ((S)-3-methyl-1-thiazol-2-yl-butyl)-amide

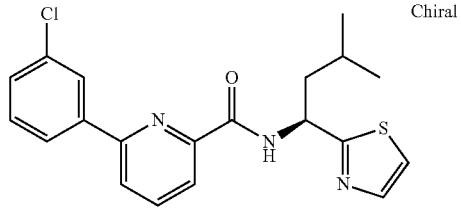 [SMILES: CC(C)C[C@H](NC(=O)c1cccc(-c2cccc(Cl)c2)n1)c1nccs1]

The title compound was synthesized in analogy to Example 1, using 6-(3-chlorophenyl)-2-pyridinecarboxylic acid (CAN 863704-38-5) and (S)-α-(2-methylpropyl)-2-thiazolemethanamine as starting materials, MS (LC/MS): 386.1 [M+H]$^+$.

Example 57

6-Cyclopropylmethoxy-5-methyl-pyridine-2-carboxylic acid [(S)-2-cyclopropyl-1-(5-methyl-[1,2,4]oxadiazol-3-yl)-ethyl]-amide

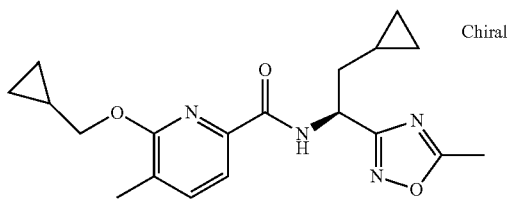 [SMILES: Cc1nc([C@H](CC2CC2)NC(=O)c2ccc(C)c(OCC3CC3)n2)no1]

The title compound was synthesized in analogy to Example 1, using 6-cyclopropylmethoxy-5-methyl-pyridine-2-carboxylic acid (Example 36 d) and (S)-2-cyclopropyl-1-(5-methyl-[1,2,4]oxadiazol-3-yl)-ethylamine (Example 38 e) as starting materials, MS (EI): m/e 357.2 [M+H]$^+$.

Example 58

5-Chloro-6-(3-chloro-phenyl)-pyridine-2-carboxylic acid (1-methyl-1-thiazol-2-yl-ethyl)-amide a) 5-Chloro-1-oxy-pyridine-2-carboxylic acid

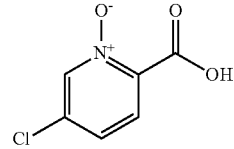 [SMILES: O=C(O)c1ccc(Cl)c[n+]1[O-]]

A mixture of 5-chloro-pyridine-2-carboxylic acid (CAN 86873-60-1, 6.3 g, 0.04 mol) and m-CPBA (CAN 937-14-4, 20.7 g, 0.12 mol) in methylene chloride (200 ml) was stirred overnight at 40° C. After evaporation of solvents, the crude product was purified by column chromatography (silica gel, 200 g, petroleum ether/ethyl acetate 4/1 firstly, then methanol/ethyl acetate 1/1) to give the title compound (6.5 g, 94%) as yellow solid; MS (EI): m/e=174.0 [M+H]$^+$.

b) 6-Bromo-5-chloro-pyridine-2-carboxylic acid

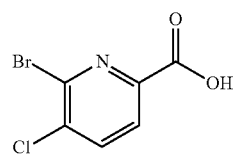

5-Chloro-1-oxy-pyridine-2-carboxylic acid (3.5 g, 20 mmol) was added into phosphorus oxide tribromide (CAN 7789-59-5, 30 g) at 80° C., stirred for 2 h. The mixture was poured into water (100 mL), extracted with ethyl acetate (3×50 mL), dried over anhydrous sodium sulfate, and solvent removed in vacuo. The crude product was purified by column chromatography (silica gel, 100 g, eluting with 50% ethyl acetate in petroleum ether) to give the title compound (1.12 g, 23%) as grey solid; MS (EI): m/e: 236.0 [M+H]$^+$.

c) 5-Chloro-6-(3-chloro-phenyl)-pyridine-2-carboxylic acid

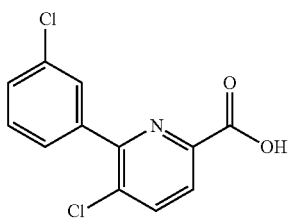 [SMILES: O=C(O)c1ccc(Cl)c(-c2cccc(Cl)c2)n1]

Under nitrogen atmosphere, 6-bromo-5-chloro-pyridine-2-carboxylic acid (0.38 g, 1.6 mmol), 3-chlorophenylboronic acid (CAN 63503-60-6, 0.33 g, 2.1 mmol), 1,1'-bis(diphenylphosphino)-ferrocene-palladium(II) dichloride methylene chloride complex (CAN 95464-05-4, 30 mg) and cesium carbonate (CAN 534-17-8, 1.6 g, 4.8 mmol) was added into DMF (30 mL). The mixture was stirred at 80° C. overnight. After evaporation of solvents, the crude product was purified by column chromatography (silica gel, 12 g, petroleum ether/ethyl acetate 4/1 firstly, then methanol/methylene chloride 1/10) to give the title compound (0.14 g, 32%) as brown solid; MS (EI): m/e=268.0 [M+H]$^+$.

d) 5-Chloro-6-(3-chloro-phenyl)-pyridine-2-carboxylic acid (1-methyl-1-thiazol-2-yl-ethyl)-amide

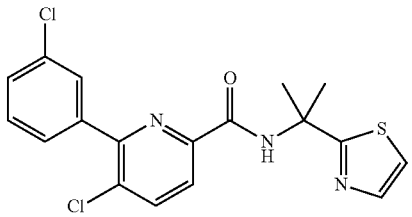

The title compound was synthesized in analogy to Example 1, using 5-chloro-6-(3-chloro-phenyl)-pyridine-2-carboxylic acid and α,α-dimethyl-2-thiazolemethanamine (CAN 1082393-38-1) as starting materials, MS (LC/MS): 392.0 [M+H]$^+$.

Example 59

6-Cyclopropylmethoxy-5-(tetrahydro-pyran-4-yl)-pyridine-2-carboxylic acid ((S)-2-cyclopropyl-1-thiazol-2-yl-ethyl)-amide a) (S)-tert-Butyl 1-amino-3-cyclopropyl-1-thioxopropan-2-ylcarbamate

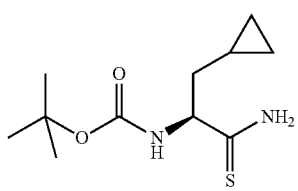 [SMILES: CC(C)(C)OC(=O)N[C@@H](CC1CC1)C(N)=S]

A mixture of (S)-tert-butyl 1-amino-3-cyclopropyl-1-oxopropan-2-ylcarbamate (Example 38 a, 6.7 g, 29 mmol) and Lawesson's reagent (CAN 19172-47-5, 6.06 g, 15 mmol) in toluene (60 mL) was stirred at 90° C. for 2.5 h. After removal of the solvent in vacuo, the residue was purified by column chromatography (silica gel, 100 g, eluting with 5% methanol in ethyl acetate) to yield the title compound (5.1 g, 71%) as yellow solid; MS: m/e=267.1 [M+Na]$^+$ b) (S)-2-Cyclopropyl-1-thiazol-2-yl-ethylamine acetate

CH$_3$COOH

In analogy to the procedure described in Example 56 d, the title compound was obtained as yellow oil starting from (S)-tert-butyl 1-amino-3-cyclopropyl-1-thioxopropan-2-ylcarbamate (0.75 g, 31%); MS: m/e=169.1 [M+H]$^+$.

c) 6-Cyclopropylmethoxy-5-(tetrahydro-pyran-4-yl)-pyridine-2-carboxylic acid ((S)-2-cyclopropyl-1-thiazol-2-yl-ethyl)-amide

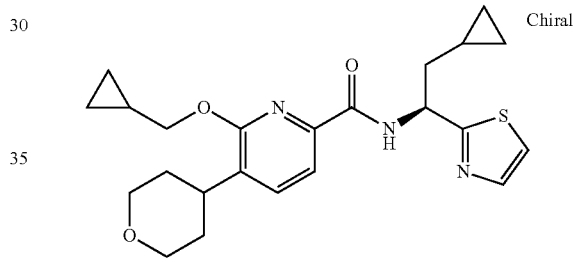

The title compound was synthesized in analogy to Example 1, using 6-cyclopropylmethoxy-5-(tetrahydro-pyran-4-yl)-pyridine-2-carboxylic acid (Example 9 f) and (S)-2-cyclopropyl-1-thiazol-2-yl-ethylamine as starting materials, MS (LC/MS): 428.2 [M+H]$^+$.

Example 60

6-(3-Chloro-phenyl)-pyridine-2-carboxylic acid ((S)-2-cyclopropyl-1-thiazol-2-yl-ethyl)-amide

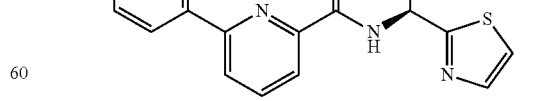

The title compound was synthesized in analogy to Example 1, using 6-(3-chlorophenyl)-2-pyridinecarboxylic acid (CAN 863704-38-5) and (S)-2-cyclopropyl-1-thiazol-2-yl-ethylamine (Example 59 b) as starting materials, MS (LC/MS): 384.1 [M+H]$^+$.

Example 61

6-Cyclopropylmethoxy-5-(2-oxo-pyrrolidin-1-yl)-pyridine-2-carboxylic acid (1-methyl-1-oxazol-2-yl-ethyl)-amide a) 4-Chlorobutanamide

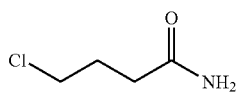

A solution of 4-chlorobutanoyl chloride (CAN 4635-59-0, 20 g, 140 mmol) in THF (100 mL) was added dropwise to ammonium hydroxide (100 mL) at 0° C. and the reaction mixture was stirred at room temperature overnight. The reaction mixture was poured into water, extracted with ethyl acetate (3×30 mL), the organic layers were combined, washed with brine (6×30 mL), dried over anhydrous sodium sulfate, and concentrated in vacuo to give the crude product. The crude product was used directly for the next step without purification. $^1$H-NMR (d$^6$-DMSO): δ 7.32 (s, 1H), 6.78 (s, 1H), 3.66-3.62 (m, 2H), 2.38 (t, J=7 Hz, 1H), 2.20 (t, J=7 Hz, 1H), 1.96-1.93 (m, 2H).

b) Pyrrolidin-2-one

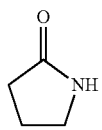

A solution of 4-chlorobutanamide (4.4 g, 36 mmol) and potassium tert-butoxide (CAS 865-47-4, 8.1 g, 72 mmol) in THF (50 mL) was stirred for 36 h at room temperature. The reaction mixture was filtered and the filter cake was washed with ethyl acetate. The combined filtrates were concentrated to dryness to give the crude product. The crude product was purified by flash chromatography (silica gel, 100 g, 0% to 50% ethyl acetate in petroleum ether) to give the desired product (2.7 g) as a colorless oil. $^1$H-NMR (d$^6$-DMSO): δ 6.64 (s, 1H) 3.38 (t, J=6 Hz, 2H), 2.28-2.25 (m, 2H), 2.17-2.14 (m, 2H).

c) 6-Cyclopropylmethoxy-5-(2-oxo-pyrrolidin-1-yl)-pyridine-2-carboxylic acid

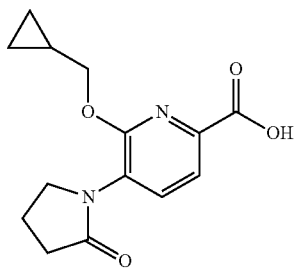 [SMILES: O=C(O)c1ccc(N2CCCC2=O)c(OCC2CC2)n1]

Under nitrogen atmosphere, pyrrolidin-2-one (375 mg, 4.4 mmol), dimethylbisdiphenyl-phosphinoxanthene (CAS 161265-03-8, 127 mg, 2.4 mmol), tris(dibenzylideneacetone)dipalladium (CAS 51364-51-3, 67 mg, 0.1 mmol) and cesium carbonate (CAS 534-17-8, 1.8 g, 6 mmol) in 1,4-dioxane (100 mL) were added to a solution of 5-bromo-6-cyclopropylmethoxy-pyridine-2-carboxylic acid (Example 9 d, 1 g, 4 mmol) and the reaction mixture was stirred overnight at 110° C. The reaction mixture was concentrated in vacuo, dissolved in water and extracted with ethyl acetate (3×30 mL). The aqueous layer was adjusted to pH=2 with aqueous solution of hydrochloride (1N), the resulting precipitate was collected by filtration and dried. The crude product was purified by column chromatography (silica gel, 20 g, eluting with 30% ethyl acetate in petroleum ether) to give the desired product (600 mg) as a yellow solid; MS (EI): m/e=277.1 [M+H]$^+$.

c) 6-Cyclopropylmethoxy-5-(2-oxo-pyrrolidin-1-yl)-pyridine-2-carboxylic acid (1-methyl-1-oxazol-2-yl-ethyl)-amide

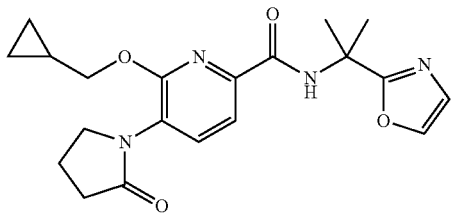 [SMILES: CC(C)(NC(=O)c1ccc(N2CCCC2=O)c(OCC2CC2)n1)c1ncco1]

The title compound was synthesized in analogy to Example 1, using 6-cyclopropylmethoxy-5-(2-oxo-pyrrolidin-1-yl)-pyridine-2-carboxylic acid and α,α-dimethyl-2-oxazolemethanamine (CAN 1211519-76-4) as starting materials, MS (EI): m/e=358.2 [M+H]$^+$.

Example 62

6-Cyclopropylmethoxy-5-methyl-pyridine-2-carboxylic acid (1-methyl-1-thiazol-2-yl-ethyl)-amide

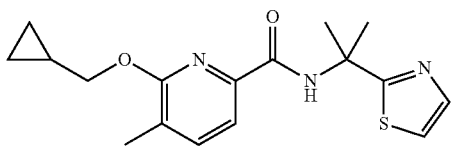 [SMILES: Cc1ccc(C(=O)NC(C)(C)c2nccs2)nc1OCC1CC1]

The title compound was synthesized in analogy to Example 1, using 6-cyclopropylmethoxy-5-methyl-pyridine-2-carboxylic acid (Example 36 d) and α,α-dimethyl-2-thiazolemethanamine (CAN 1082393-38-1) as starting materials, MS (EI): m/e=332.2 [M+H]$^+$.

Example 63

6-Cyclopropylmethoxy-5-pyrrolidin-1-yl-pyridine-2-carboxylic acid [1-(4,5-dihydro-oxazol-2-yl)-1-methyl-ethyl]-amide a) 1-(4,5-Dihydro-oxazol-2-yl)-1-methyl-ethylamine

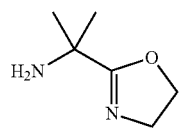

A mixture of benzyl 2-(oxazol-2-yl)propan-2-ylcarbamate (Example 8 d, 0.63 g) and palladium on carbon (10% w/w, 0.06 g) in ethanol (20 mL) was charged with hydrogen balloon and stirred at room temperature for 2 h. TLC showed the reaction was complete; it was filtered and concentrated to give the product as yellow oil (0.1 g, 33%); MS (EI): m/e=129.1 [M+H]+.

b) 6-Cyclopropylmethoxy-5-pyrrolidin-1-yl-pyridine-2-carboxylic acid [1-(4,5-dihydro-oxazol-2-yl)-1-methyl-ethyl]-amide

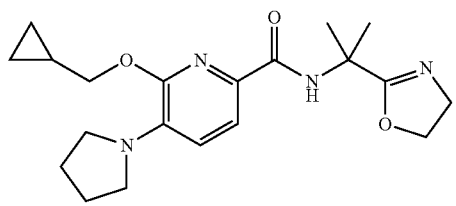 [SMILES: CC(C)(NC(=O)c1ccc(N2CCCC2)c(OCC2CC2)n1)C1=NCCO1]

The title compound was synthesized in analogy to Example 1, using 6-cyclopropylmethoxy-5-pyrrolidin-1-yl-pyridine-2-carboxylic acid (Example 14 a) and 1-(4,5-dihydro-oxazol-2-yl)-1-methyl-ethylamine as starting materials, MS (EI): m/e=373.2 [M+H]+.

Example 64

6-Cyclopropylmethoxy-5-methyl-pyridine-2-carboxylic acid ((S)-3-methyl-1-thiazol-2-yl-butyl)-amide

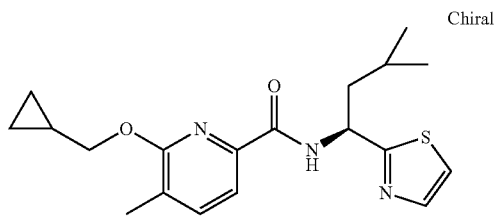 [SMILES: Cc1ccc(C(=O)N[C@@H](CC(C)C)c2nccs2)nc1OCC1CC1]

The title compound was synthesized in analogy to Example 1, using 6-cyclopropylmethoxy-5-methyl-pyridine-2-carboxylic acid (Example 36 d) and (S)-α-(2-methylpropyl)-2-thiazolemethanamine (Example 56 d) as starting materials, MS (EI): m/e=360.2 [M+H]+.

Example 65

6-Cyclopropylmethoxy-5-methyl-pyridine-2-carboxylic acid ((S)-2-cyclopropyl-1-thiazol-2-yl-ethyl)-amide

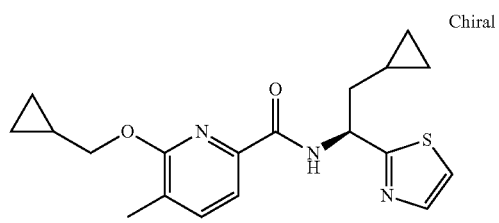 [SMILES: Cc1ccc(C(=O)N[C@@H](CC2CC2)c2nccs2)nc1OCC1CC1]

The title compound was synthesized in analogy to Example 1, using 6-cyclopropylmethoxy-5-methyl-pyridine-2-carboxylic acid (Example 36 d) and (S)-2-cyclopropyl-1-thiazol-2-yl-ethylamine (Example 59 b) as starting materials, MS (LC/MS): 358.2 [M+H]+.

Example 66

5-Chloro-6-(3-chloro-phenyl)-pyridine-2-carboxylic acid piperidin-1-ylamide

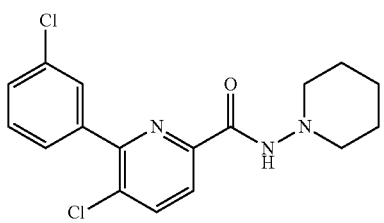 [SMILES: O=C(NN1CCCCC1)c1ccc(Cl)c(-c2cccc(Cl)c2)n1]

The title compound was synthesized in analogy to Example 1, using 5-chloro-6-(3-chloro-phenyl)-pyridine-2-carboxylic acid (Example 58 c) and 1-piperidinamine (CAN 2213-43-6) as starting materials, MS (LC/MS): 350.1 [M+H]+.

Example 67

6-(3-Chloro-phenyl)-5-cyclopropyl-pyridine-2-carboxylic acid (1-methyl-1-methylcarbamoyl-ethyl)-amide

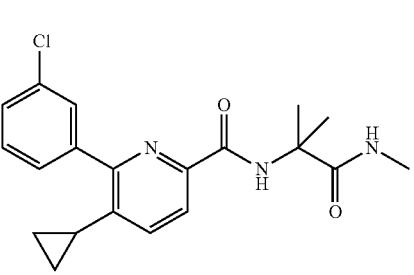 [SMILES: CNC(=O)C(C)(C)NC(=O)c1ccc(C2CC2)c(-c2cccc(Cl)c2)n1]

The title compound was synthesized in analogy to Example 1, using 6-(3-chloro-phenyl)-5-cyclopropyl-pyridine-2-carboxylic acid (Example 48 e) and 2-amino-N,2-dimethyl-propanamide (CAN 106914-07-2) as starting materials, MS (EI) m/e: 372.1 [M+H]$^+$.

Example 68

6-Cyclopropylmethoxy-pyridine-2-carboxylic acid piperidin-1-ylamide

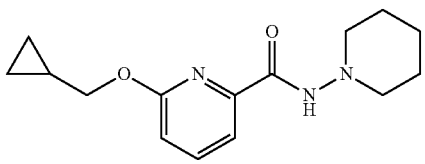 [SMILES: O=C(NN1CCCCC1)c1cccc(OCC2CC2)n1]

The title compound was synthesized in analogy to Example 1, using 6-cyclopropylmethoxy-pyridine-2-carboxylic acid (CAN 1248077-05-5) and 1-piperidinamine (CAN 2213-43-6) as starting materials, MS (LC/MS): 276.1 (M+H).

Example 69

6-Cyclopropylmethoxy-5-(3,3-difluoro-azetidin-1-yl)-pyridine-2-carboxylic acid (1-methyl-1-thiazol-2-yl-ethyl)-amide a) 6-Chloro-5-(3,3-difluoro-azetidin-1-yl)-pyridine-2-carboxylic acid methyl ester

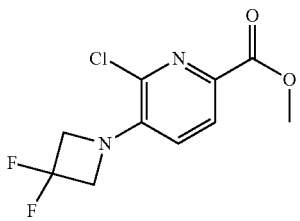 [SMILES: COC(=O)c1ccc(N2CC(F)(F)C2)c(Cl)n1]

Under a nitrogen atmosphere a mixture of methyl 5-bromo-6-chloro-pyridine-2-carboxylic acid methyl ester (Example 9 c, 2 g, 8 mmol), 3,3-difluoroazetidine hydrochloride (CAN 288315-03-7, 1 g, 8 mmol), tris(dibenzylideneacetone)dipalladium (CAN 51364-51-3, 0.16 g, 0.16 mmol), (R)-(+)-2,2'-bis(diphenylphosphino)-1,1'-binaphthyl (CAN 76189-55-4, 0.19 g, 0.32 mmol) and cesium carbonate (3.9 g, 12 mmol) in toluene (50 mL) was stirred at 110° C. overnight. After concentration, the residue was partitioned between water (50 mL) and ethyl acetate (40 mL), the aqueous phase was extracted with ethyl acetate (2×40 mL). The combined organic phase was washed with brine (40 mL), dried over anhydrous sodium sulfate, filtered and concentrated to give a residue. The residue was purified by column chromatography (silica gel, 20 g, 10% ethyl acetate in petroleum ether) to give the target compound (0.44 g, 21%) as light-yellow solid; MS (EI): m/e=263.0 [M+H]$^+$.

b) 6-Cyclopropylmethoxy-5-(3,3-difluoro-azetidin-1-yl)-pyridine-2-carboxylic acid

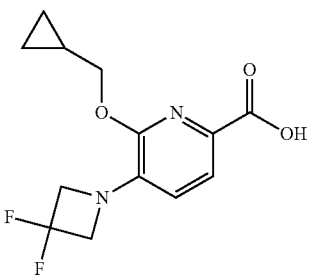 [SMILES: O=C(O)c1ccc(N2CC(F)(F)C2)c(OCC2CC2)n1]

Sodium hydride (0.29 g, 8.4 mmol) was added in portion to a solution of cyclopropylmethanol (CAN 2516-33-8, 0.36 g, 5 mmol) in DMF (3 mL) and the mixture was stirred at room temperature for 2 h. 6-Chloro-5-(3,3-difluoro-azetidin-1-yl)-pyridine-2-carboxylic acid methyl ester (0.44 g, 1.68 mmol) was added to the mixture and the resulting solution was stirred at 110° C. overnight. After concentration, water (20 mL) was added to the residue and the solution was acidified with an aqueous solution of hydrochloride (6 N), then extracted with ethyl acetate (2×20 mL). The combined organic phase was washed with brine (20 mL), dried over anhydrous sodium sulfate, filtered and concentrated to give a residue. The residue was purified by prep-TLC (eluting with 50% ethyl acetate in petroleum ether) to give the target compound (0.07 g, 14%); MS (EI): m/e=285.1 [M+H]$^+$.

c) 6-Cyclopropylmethoxy-5-(3,3-difluoro-azetidin-1-yl)-pyridine-2-carboxylic acid (1-methyl-1-thiazol-2-yl-ethyl)-amide

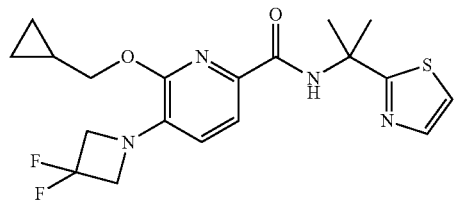 [SMILES: CC(C)(NC(=O)c1ccc(N2CC(F)(F)C2)c(OCC2CC2)n1)c1nccs1]

The title compound was synthesized in analogy to Example 1, using 6-cyclopropylmethoxy-5-(3,3-difluoro-azetidin-1-yl)-pyridine-2-carboxylic acid and α,α-dimethyl-2-thiazolemethanamine (CAN 1082393-38-1) as starting materials, MS (EI): m/e=409.1 [M+H]$^+$.

Example 70

6-(3-Chloro-phenyl)-5-methyl-pyridine-2-carboxylic acid (1-ethyl-1-methylcarbamoyl-propyl)-amide a) tert-Butyl 3-(methylcarbamoyl)pentan-3-ylcarbamate

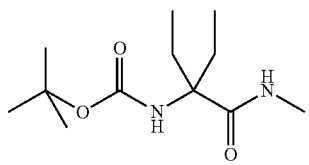 [SMILES: CCC(CC)(NC(=O)OC(C)(C)C)C(=O)NC]

A mixture of 2-(tert-butoxycarbonylamino)-2-ethylbutanoic acid (Example 23 a, 400 mg 2 mmol), HBTU (CAN 94790-37-1, 1.3 g, 3 mmol), Et₃N (0.7 g, 7 mmol) in DMF (10 mL) was stirred for 30 min, then methanamine hydrochloride (CAN 593-51-1, 260 mg, 6 mmol) was added into the mixture and the solution was stirred overnight. After that, the solution was diluted with water (20 mL) and extracted with ethyl acetate (3×30 mL), the combined organic layer was washed with water (3×50 mL) and brine (60 mL), then evaporated to dryness. The crude product (0.18 g, 45%) obtained as a light yellow solid was used for the next step directly.

b) 2-Amino-2-ethyl-N-methyl-butyramide

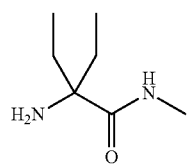

A mixture of tert-butyl 3-(methylcarbamoyl)pentan-3-ylcarbamate (0.18 g, 0.74 mmol) in 10 ml saturated hydrochloride in ethyl acetate was stirred for 60 min at room temperature. Then the solution was evaporated to dryness to obtain the product (80 mg, 75%) as a light yellow solid; MS (LC/MS): 145.2 [M+H]⁺.

c) 6-(3-Chloro-phenyl)-5-methyl-pyridine-2-carboxylic acid (1-ethyl-1-methylcarbamoyl-propyl)-amide

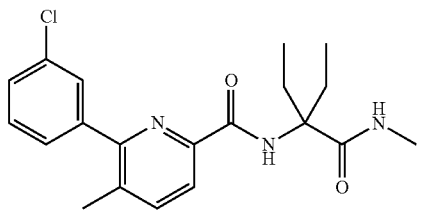 [SMILES: CCC(CC)(NC(=O)c1ccc(C)c(-c2cccc(Cl)c2)n1)C(=O)NC]

The title compound was synthesized in analogy to Example 1, using 6-(3-chloro-phenyl)-5-methyl-pyridine-2-carboxylic acid (Example 49 e) and 2-amino-2-ethyl-N-methyl-butyramide as starting materials, MS (LC/MS): 374.2 [M+H]⁺.

Example 71

6-(3-Chloro-phenyl)-5-cyclopropyl-pyridine-2-carboxylic acid (1-ethyl-1-methylcarbamoyl-propyl)-amide

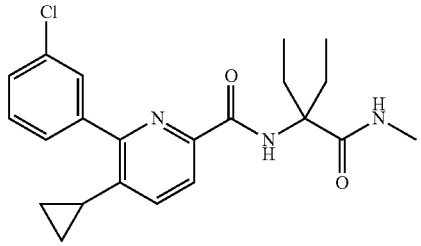 [SMILES: CCC(CC)(NC(=O)c1ccc(C2CC2)c(-c2cccc(Cl)c2)n1)C(=O)NC]

The title compound was synthesized in analogy to Example 1, using 6-(3-chloro-phenyl)-5-cyclopropyl-pyridine-2-carboxylic acid (Example 48 e) and 2-amino-2-ethyl-N-methyl-butyramide (Example 70 b) as starting materials, MS (EI): m/e=400.2 [M+H]⁺.

Example 72

6-(3-Chloro-phenyl)-pyridine-2-carboxylic acid (1-methyl-1-[1,2,4]oxadiazol-3-yl-ethyl)-amide a) tert-Butyl 2-(1,2,4-oxadiazol-3-yl)propan-2-ylcarbamate

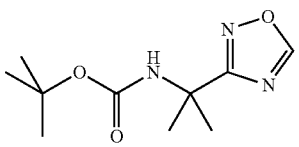 [SMILES: CC(C)(C)OC(=O)NC(C)(C)c1ncon1]

To a solution of (Z)-tert-butyl 1-amino-1-(hydroxyimino)-2-methylpropan-2-ylcarbamate (Example 33 b, 2 g, 9.2 mmol) in acetonitrile (10 mL) was added triethoxymethane (CAN 122-51-0, 4.8 mL) and trifluoroacetic acid (CAN 76-05-1, 0.1 mL). The mixture was heated to 50° C. and stirred overnight. The reaction mixture was added to methanol (10 mL) and water (10 mL). After evaporation of solvents, the residue was purified by column chromatography (silica gel, 60 g, eluting with 30% to 50% ethyl acetate in petroleum ether) to give the target product (0.668 g, 32%) MS (EI): m/e=250.1 [M+H]⁺.

b) 1-Methyl-1-[1,2,4]oxadiazol-3-yl-ethylamine hydrochloride

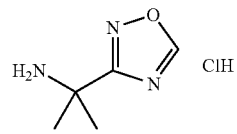

tert-Butyl 2-(1,2,4-oxadiazol-3-yl)propan-2-ylcarbamate (0.668 g, 2.9 mmol) was dissolved in in ethyl acetate saturated with hydrochloride (10 mL) and stirred at room temperature for 0.5 h. Then it was concentrated to give product (0.45 g, 94%); MS (EI): m/e=128.2 [M+H]⁺.

c) 6-(3-Chloro-phenyl)-pyridine-2-carboxylic acid (1-methyl-1-[1,2,4]oxadiazol-3-yl-ethyl)-amide

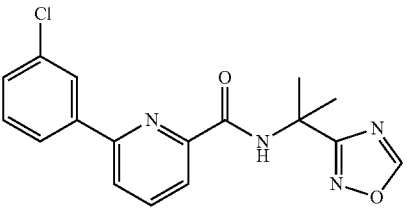 [SMILES: CC(C)(NC(=O)c1cccc(-c2cccc(Cl)c2)n1)c1ncon1]

The title compound was synthesized in analogy to Example 1, using 6-(3-chlorophenyl)-2-pyridinecarboxylic acid (CAN 863704-38-5) and 1-methyl-1-[1,2,4]oxadiazol-3-yl-ethylamine (CAN 1153757-41-5) as starting materials, MS (EI): m/e=343.1 [M+H]⁺.

Example 73

5-Cyclopropyl-6-cyclopropylmethoxy-pyridine-2-carboxylic acid (1-methyl-1-[1,2,4]oxadiazol-3-yl-ethyl)-amide

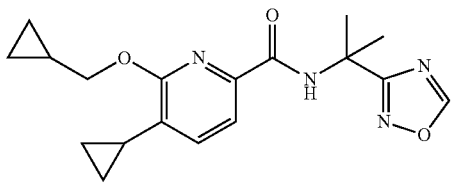 [SMILES: CC(C)(NC(=O)c1ccc(C2CC2)c(OCC2CC2)n1)c1ncon1]

The title compound was synthesized in analogy to Example 1, using 5-cyclopropyl-6-cyclopropylmethoxy-pyridine-2-carboxylic acid (Example 42 a) and 1-methyl-1-[1,2,4]oxadiazol-3-yl-ethylamine (CAN 1153757-41-5) as starting materials, MS (LC/MS): 343.1 (M+H).

Example 74

5-Cyclopropyl-6-cyclopropylmethoxy-pyridine-2-carboxylic acid (1-ethyl-1-methylcarbamoyl-propyl)-amide

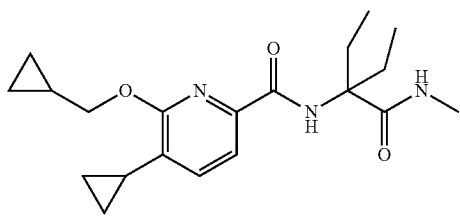 [SMILES: CCC(CC)(NC(=O)c1ccc(C2CC2)c(OCC2CC2)n1)C(=O)NC]

The title compound was synthesized in analogy to Example 1, using 5-cyclopropyl-6-cyclopropylmethoxy-pyridine-2-carboxylic acid (Example 42 a) and 2-amino-2-ethyl-N-methyl-butyramide (Example 70 b) as starting materials, MS (LC/MS): 360.2 (M+H).

Example 75

6-Cyclopropylmethoxy-5-(3-hydroxy-azetidin-1-yl)-pyridine-2-carboxylic acid (1-methyl-1-thiazol-2-yl-ethyl)-amide a) 6-Cyclopropylmethoxy-5-(3-hydroxy-azetidin-1-yl)-pyridine-2-carboxylic acid

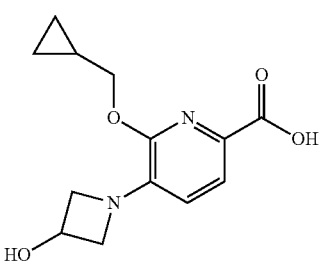 [SMILES: O=C(O)c1ccc(N2CC(O)C2)c(OCC2CC2)n1]

To a mixture of azetidin-3-ol (CAN 45347-82-8, 200 mg, 3 mmol), (±)-2,2'-bis(diphenylphosphino)-1,1'-binaphthalene (CAS 98327-87-8, 114 mg, 0.185 mmol), tris(dibenzylideneacetone)dipalladium (CAS 51364-51-3, 85 mg, 0.1 mmol) and cesium carbonate (CAS 534-17-8, 1.8 mg, 5.55 mmol) in toluene (8 mL) under nitrogen atmosphere, was added a solution of 5-bromo-6-cyclopropylmethoxy-pyridine-2-carboxylic acid (Example 9 d, 500 mg, 1.85 mmol). The reaction mixture was stirred overnight at 110° C. The reaction mixture was concentrated in vacuo and the residue dissolved in water and extracted with ethyl acetate (1×30 mL). The aqueous layer was adjusted to pH=2 by addition of 1 N hydrochloric acid, the resulting precipitate was collected by filtration, the solid was lyophilized. The crude product was purified by flash chromatography (silica gel, 50 g, 0% to 100% ethyl acetate in petroleum ether) to give the desired product (180 mg) as a yellow solid; MS (EI): m/e=265.2 [M+H]$^+$.

b) 6-Cyclopropylmethoxy-5-(3-hydroxy-azetidin-1-yl)-pyridine-2-carboxylic acid (1-methyl-1-thiazol-2-yl-ethyl)-amide

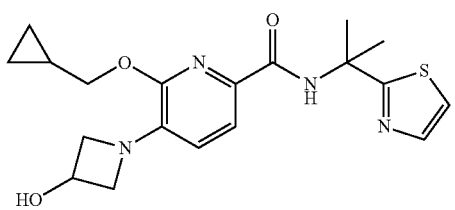 [SMILES: CC(C)(NC(=O)c1ccc(N2CC(O)C2)c(OCC2CC2)n1)c1nccs1]

The title compound was synthesized in analogy to Example 1, using 6-cyclopropylmethoxy-5-(3-hydroxy-azetidin-1-yl)-pyridine-2-carboxylic acid and α,α-dimethyl-2-thiazolemethanamine (CAN 1082393-38-1) as starting materials, MS (EI): m/e=389.1 [M+H]$^+$.

Example 76

6-(4-Chloro-phenyl)-pyridine-2-carboxylic acid (1-ethyl-1-methylcarbamoyl-propyl)-amide

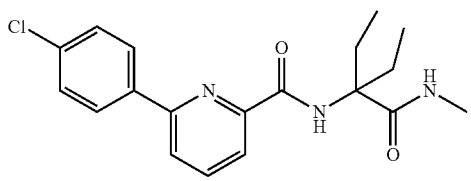 [SMILES: CCC(CC)(NC(=O)c1cccc(-c2ccc(Cl)cc2)n1)C(=O)NC]

The title compound was synthesized in analogy to Example 1, using 6-(4-chlorophenyl)-2-pyridinecarboxylic acid (CAN 135432-77-8) and 2-amino-2-ethyl-N-methyl-butyramide (Example 70 b) as starting materials, MS (EI): m/e=360.1 [M+H]$^+$.

Example 77

6-(Cyclopropylmethoxy)-5-(1,1-dioxido-isothiazolidin-2-yl)-N-[2-(1,3-thiazol-2-yl)propan-2-yl]pyridine-2-carboxamide a) 3-Chloropropane-1-sulfonamide

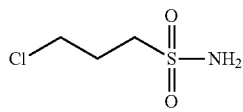

Ammonia gas was bubbled through a stirred solution of 3-chloropropane-1-sulfonyl chloride (CAN 1633-82-5, 10 g, 56 mmol) in methylene chloride (100 mL) for 30 min at 0° C. The reaction mixture was stirred for 1 h at room temperature. The ammonium chloride precipitate was removed by filtration. The solvent was removed under reduced pressure, the solid was purified by re-crystallization from methylene chloride to give the title compound (7.9 g, 0.05 mol, 88.7%) as white solid. $^1$H NMR (300 MHz, d$^6$-DMSO): δ 6.88 (s, 2H), 3.75 (t, J=6.5 Hz, 2H), 3.11-3.06 (m, 2H), 2.16-2.07 (m, 2H).

b) Isothiazolidine 1,1-dioxide

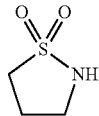

Sodium (1.6 g, 70 mmol) was added in portions to ethanol (50 mL) at room temperature. After complete dissolution of sodium, 3-chloropropane-1-sulfonamide (7.9 g, 50 mmol) was added to the above solution. The reaction mixture was reacted for 2 h at 90° C. After that the reaction mixture was cooled, the precipitate was removed by filtration, the solvent was removed under reduced pressure, the product was dissolved in ethyl acetate, the precipitate was removed by filtration and the solvent was removed under reduced pressure. The crude title compound (3.2 g, yellow oil) was used for the next reaction step without further purification. $^1$H NMR (300 MHz, d$^6$-DMSO): δ 6.70 (s, 1H), 3.13 (t, J=6.9 Hz, 2H), 2.99-2.94 (m, 2H), 2.28-2.19 (m, 2H).

c) 6-Chloro-5-(1,1-dioxido-isothiazolidin-2-yl)-pyridine-2-carboxylic acid methyl ester

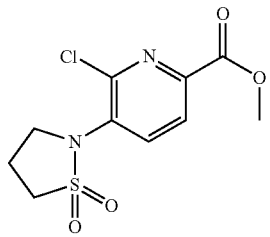 [SMILES: COC(=O)c1ccc(N2CCCS2(=O)=O)c(Cl)n1]

Under a nitrogen atmosphere, a solution of 5-bromo-6-chloro-pyridine-2-carboxylic acid methyl ester (Example 9 c, 1 g, 4 mmol), isothiazolidine 1,1-dioxide (730 mg, 06 mmol), copper(I) iodide (150 mg, 0.8 mmol), 1,3-di(pyridin-2-yl)propane-1,3-dione (CAN 10198-89-7, 180 mg, 0.8 mmol) and potassium carbonate (1.1 g, 8 mmol) in DMF (20 mL) was reacted for 24 h at 110° C. The reaction mixture was poured into water, and extracted with ethyl acetate (3×50 mL). The combined organic extracts were washed with water and brine, dried over anhydrous sodium sulfate and evaporated. The residue was purified by column chromatography (silica gel, 4 g, 10% ethyl acetate in petroleum ether) to yield the title compound (0.048 g, 1.6 mmol, 41.4%) as yellow solid; MS (EI): m/e=291.0 [M+H]$^+$.

d) 6-Cyclopropylmethoxy-5-(1,1-dioxido-isothiazolidin-2-yl)-pyridine-2-carboxylic acid

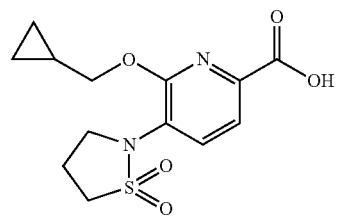 [SMILES: O=C(O)c1ccc(N2CCCS2(=O)=O)c(OCC2CC2)n1]

Sodium hydride (0.029 g, 0.86 mmol) was added in portions to a solution of cyclopropanemethanol (CAN 2516-33-8, 20 mL) and the reaction mixture was stirred for 30 min at room temperature. 6-Chloro-5-(1,1-dioxido-isothiazolidin-2-yl)-pyridine-2-carboxylic acid methyl ester (0.050 g, 0.17 mmol) was added and the mixture was heated to 100° C. overnight, quenched with water and concentrated under reduced pressure. The residue was dissolved in water, extracted with ethyl acetate (50 mL). The pH of the aqueous layer was adjusted to 2 by addition of 1 N hydrochloric acid and subsequently extracted with ethyl acetate (3×20 mL). The combined extracts were washed with water and brine, dried over anhydrous sodium sulfate and concentrated under reduced pressure to give the crude product. The crude product was purified by column chromatography (silica gel, 4 g, 33% ethyl acetate in petroleum ether) to yield the title compound (25 mg, 0.08 mmol, 46%) as yellow solid; MS (EI): m/e=313.1 [M+H]$^+$.

e) 6-(Cyclopropylmethoxy)-5-(1,1-dioxido-isothiazolidin-2-yl)-N-[2-(1,3-thiazol-2-yl)propan-2-yl]pyridine-2-carboxamide

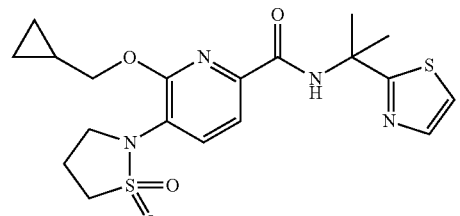

The title compound was synthesized in analogy to Example 1, using 6-cyclopropylmethoxy-5-(1,1-dioxido-isothiazolidin-2-yl)-pyridine-2-carboxylic acid and α,α-dimethyl-2-thiazolemethanamine (CAN 1082393-38-1) as starting materials, MS (EI): m/e=437.0 [M+H]$^+$.

Example 78

6-Cyclopropylmethoxy-5-(3,3-difluoro-pyrrolidin-1-yl)-pyridine-2-carboxylic acid (1-ethyl-1-methylcarbamoyl-propyl)-amide a) 6-Chloro-5-(3,3-difluoro-pyrrolidin-1-yl)-pyridine-2-carboxylic acid methyl ester

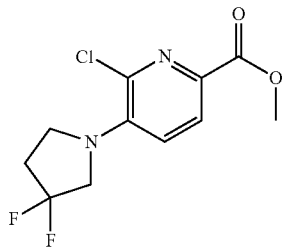 [SMILES: COC(=O)c1ccc(N2CCC(F)(F)C2)c(Cl)n1]

Under nitrogen atmosphere, a suspension of 5-bromo-6-chloro-pyridine-2-carboxylic acid methyl ester (Example 9 c, 1.5 g, 6 mmol), 3,3-difluoropyrrolidine hydrochloride (CAN 163457-23-6, 0.64 g, 6 mmol), tris(dibenzylideneacetone) dipalladium (CAN 51364-51-3, 120 mg, 0.12 mmol), (R)-(+)-2,2'-bis(diphenylphosphino)-1,1'-binaphthyl (CAN 76189-55-4, 150 mg, 0.24 mmol) and cesium carbonate (3.9 g, 12 mmol) in toluene (30 mL) was stirred at 110° C. overnight. After concentration, the residue was partitioned between water (30 mL) and ethyl acetate (30 mL). The aqueous phase was extracted with ethyl acetate (2×30 mL). The combined organic phase was washed with brine (30 mL), dried over anhydrous sodium sulfate, filtered and concentrated to give the crude product. The crude product was purified by column chromatography (silica gel, 15 g, 10% ethyl acetate in petroleum ether) to give the target compound (0.5 g, 30%) as light-yellow solid; MS (EI): m/e=277.0 [M+H]$^+$.

b) 6-Cyclopropylmethoxy-5-(3,3-difluoro-pyrrolidin-1-yl)-pyridine-2-carboxylic acid

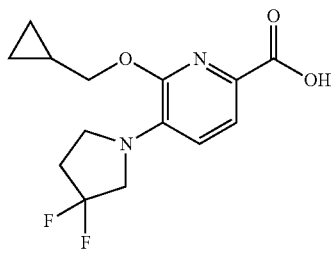 [SMILES: O=C(O)c1ccc(N2CCC(F)(F)C2)c(OCC2CC2)n1]

Sodium hydride (0.27 g, 8 mmol) was added in portions to cyclopropylmethanol (CAN 2516-33-8, 6 mL) and the mixture was stirred at room temperature for 2 hours. 6-Chloro-5-(3,3-difluoro-pyrrolidin-1-yl)-pyridine-2-carboxylic acid methyl ester (0.45 g, 1.6 mmol) was added to the mixture and the resulting solution was stirred in a sealed tube at 110° C. overnight. After concentration under reduced pressure, water (15 mL) was added to the residue and the solution was acidified with hydrochloric acid (6 N). The aqueous solution was extracted with ethyl acetate (3×20 mL) and the combined organic phase was washed with brine (20 mL), dried over anhydrous sodium sulfate, filtered and concentrated to give the target compound which was used directly in the next step without further purification; MS (EI): m/e=299.1 [M+H]$^+$.

c) 6-Cyclopropylmethoxy-5-(3,3-difluoro-pyrrolidin-1-yl)-pyridine-2-carboxylic acid (1-ethyl-1-methyl-carbamoyl-propyl)-amide

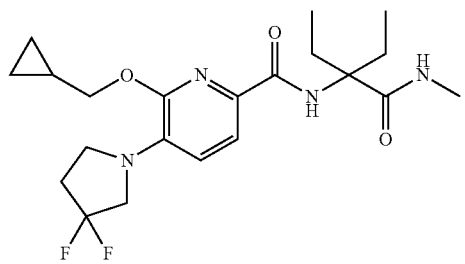 [SMILES: CCC(CC)(NC(=O)c1ccc(N2CCC(F)(F)C2)c(OCC2CC2)n1)C(=O)NC]

The title compound was synthesized in analogy to Example 1, using 6-cyclopropylmethoxy-5-(3,3-difluoro-pyrrolidin-1-yl)-pyridine-2-carboxylic acid and 2-amino-2-ethyl-N-methyl-butyramide (Example 70 b) as starting materials, MS (EI): m/e=425.3 [M+H]$^+$.

Example 79

[6-Cyclopropylmethoxy-5-(3,3-difluoro-pyrrolidin-1-yl)-pyridin-2-yl]-(1,1-dioxidotetrahydro-2H-thiopyran-4-yl)-methanone

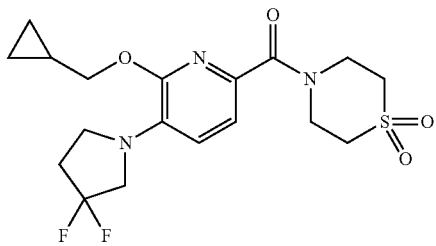 [SMILES: O=C(c1ccc(N2CCC(F)(F)C2)c(OCC2CC2)n1)N1CCS(=O)(=O)CC1]

The title compound was synthesized in analogy to Example 1, using 6-cyclopropylmethoxy-5-(3,3-difluoro-pyrrolidin-1-yl)-pyridine-2-carboxylic acid (Example 78 b) and 1,1-dioxide-thiomorpholine (CAN 39093-93-1) as starting materials, MS (EI): m/e=416.1 [M+H]$^+$.

Example 80

6-Cyclopropylmethoxy-5-(3,3-difluoro-pyrrolidin-1-yl)-pyridine-2-carboxylic acid (1-methyl-1-methylcarbamoyl-ethyl)-amide

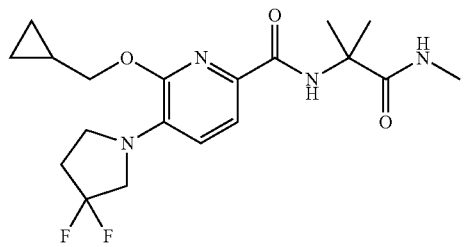 [SMILES: CNC(=O)C(C)(C)NC(=O)c1ccc(N2CCC(F)(F)C2)c(OCC2CC2)n1]

The title compound was synthesized in analogy to Example 1, using 6-cyclopropylmethoxy-5-(3,3-difluoro-pyrrolidin-1-yl)-pyridine-2-carboxylic acid (Example 78 b) and 2-amino-N,2-dimethyl-propanamide (CAN 106914-07-2) as starting materials, MS (EI): m/e=397.1 [M+H]$^+$.

Example 81

6-(3-Chloro-phenyl)-5-methoxy-pyridine-2-carboxylic acid (1-ethyl-1-methylcarbamoyl-propyl)-amide a) 5-Methoxy-1-oxy-pyridine-2-carboxylic acid

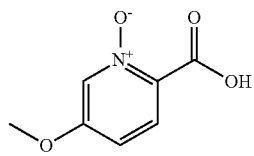

A mixture of 5-methoxy-pyridine-2-carboxylic acid (CAN 29082-92-6, 3 g, 20 mmol) and m-CPBA (CAN 937-14-4, 8 g, 47 mmol) in methylene chloride (100 mL) was stirred for 12 hours at 60° C. The reaction mixture was cooled to ambient temperature, filtered, concentrated and purified by column chromatography (silica gel, 100 g, eluting with 10% methanol in methylene chloride) to give the title compound (1.2 g, 36%); MS (EI): m/e=170.2 [M+H]$^+$.

b) 6-Bromo-5-methoxy-pyridine-2-carboxylic acid

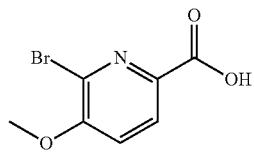

5-Methoxy-1-oxy-pyridine-2-carboxylic acid (1.2 g, 7 mmol) was added to phosphorus oxybromide (CAN 7789-59-5, 10 g) at 80° C. and stirred for 3 h. The mixture was poured into water (100 mL), extracted with ethyl acetate (3×50 mL), dried over anhydrous sodium sulfate, concentrated and purified by column chromatography (silica gel, 60 g, eluting with 10% methanol in methylene chloride) to give the title compound (1 g, 61%); MS (EI): m/e=232.0 [M+H]$^+$.

c) 6-(3-Chlorophenyl)-5-methoxy-pyridine-2-carboxylic acid

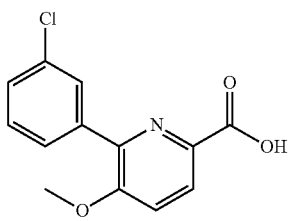 [SMILES: COc1ccc(C(=O)O)nc1-c1cccc(Cl)c1]

A mixture of 6-bromo-5-methoxy-pyridine-2-carboxylic acid (0.3 g, 1 mmol), 3-chlorophenylboronic acid (CAN 63503-60-6, 0.23 g, 1 mmol), tris(dibenzylidene-acetone)-dipalladium(0) (CAN 52409-22-0, 0.12 g), 9,9-dimethyl-4,5-bis(diphenylphosphino)xanthene (CAN 161265-03-8, 0.15 g) and potassium carbonate (0.21 g, 2 mmol) in 1,4-dioxane (10 mL) was stirred for 12 h at 110° C. under a nitrogen atmosphere. The reaction mixture was filtered, concentrated under reduced pressure and purified by column chromatography (silica gel, 10 g, eluting with 10% methanol in methylene chloride) to give the title compound (0.1 g, 29%); MS (EI): m/e=264.0 [M+H]$^+$.

d) 6-(3-Chloro-phenyl)-5-methoxy-pyridine-2-carboxylic acid (1-ethyl-1-methylcarbamoyl-propyl)-amide

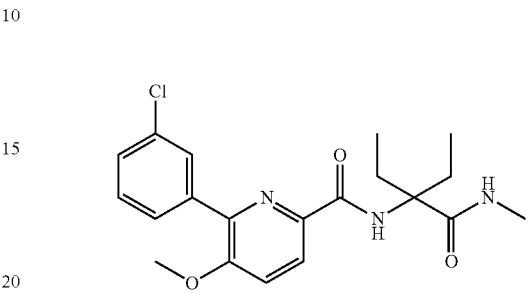

The title compound was synthesized in analogy to Example 1, using 6-(3-chloro-phenyl)-5-methoxy-pyridine-2-carboxylic acid and 2-amino-2-ethyl-N-methyl-butyramide (Example 70 b) as starting materials, MS (EI): m/e=390.2 [M+H]$^+$.

Example 82

6-(3-Chloro-phenyl)-5-methoxy-pyridine-2-carboxylic acid (1-methyl-1-thiazol-2-yl-ethyl)-amide

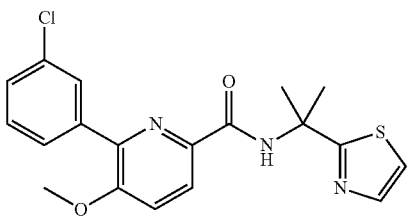

The title compound was synthesized in analogy to Example 1, using 6-(3-chloro-phenyl)-5-methoxy-pyridine-2-carboxylic acid and (Example 81 c) and α,α-dimethyl-2-thiazolemethanamine (CAN 1082393-38-1) as starting materials, MS (EI): m/e=388.0 [M+H]$^+$.

Example 83

5-Chloro-6-cyclopropylmethoxy-pyridine-2-carboxylic acid (1-methyl-1-[1,2,4]oxadiazol-3-yl-ethyl)-amide a) 5,6-Dichloro-pyridine-2-carboxylic acid

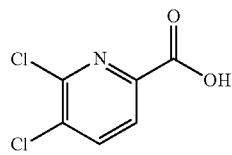 [SMILES: O=C(O)c1ccc(Cl)c(Cl)n1]

A mixture of 5-chloro-pyridine-2-carboxylic acid (CAN 86873-60-1, 9.8 g, 62 mmol) and m-CPBA (CAN 937-14-4, 21.5 g, 0.124 mol) in methylene chloride (100 mL) was heated to reflux for 48 h. The reaction mixture was quenched with saturated sodium sulfite solution (70 mL), filtered and extracted with methylene chloride (50 mL). The organic layer was washed with water (2×100 ml) and brine (100 mL) and evaporated to dryness. The residue was purified by column chromatography (silica gel, 80 g, eluting with 15% ethyl acetate in petroleum ether) to obtain a colorless oil (3.3 g, 30%). The colorless oil, 5-chloro-1-oxy-pyridine-2-carboxylic acid (1.2 g, 7 mmol) was added into POCl₃ (10 g) at 0° C. and the mixture was heated to 95° C. for 1 h. The reaction mixture was evaporated to dryness. The residue was dissolved in 15 mL water and extracted with ethyl acetate (2×15 mL), the combined organic layer was washed with water (2×30 mL) and brine (30 mL), then evaporated to dryness to obtain the title compound (1 g, 75%) as a yellow solid, MS (EI): m/e=191.9 [M+H]⁺.

b) 5-Chloro-6-(cyclopropylmethoxy)-pyridine-2-carboxylic acid

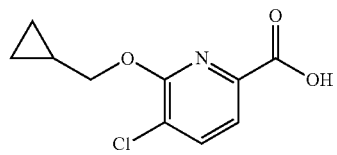 [SMILES: O=C(O)c1ccc(Cl)c(OCC2CC2)n1]

Sodium hydride (CAN 7646-69-7, 60% w/w, 1.05 g, 26 mmol) was added to cyclopropylmethanol (CAN 2516-33-8, 7.5 g) at 0° C. and the mixture was stirred for 1 h. 5,6-Dichloro-pyridine-2-carboxylic acid (1 g, 5 mmol) was added and the mixture was heated to 95° C. for 3 h. The solvent was removed under reduced pressure. The residue was diluted with water (10 mL) and adjusted to pH=3.0 by hydrochloric acid (3 N). The solution was extracted with ethyl acetate (3×15 mL). The combined organic layers were washed with water (3×30 mL) and brine (2×40 mL) and evaporated to dryness to give the crude product (0.35 g, 25%), which was used in the next step without further purification, MS (EI): m/e=228.1 [M+H]⁺.

c) 5-Chloro-6-cyclopropylmethoxy-pyridine-2-carboxylic acid (1-methyl-1-[1,2,4]oxadiazol-3-yl-ethyl)-amide

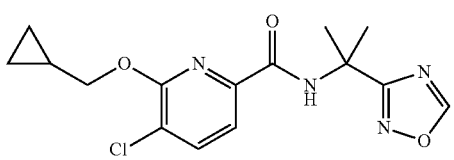 [SMILES: CC(C)(NC(=O)c1ccc(Cl)c(OCC2CC2)n1)c1ncon1]

The title compound was synthesized in analogy to Example 1, using 5-chloro-6-cyclopropylmethoxy-pyridine-2-carboxylic acid and 1-methyl-1-[1,2,4]oxadiazol-3-yl ethylamine (CAN 1153757-41-5) as starting materials, MS (LC/MS): m/e=337.1 [M+H]⁺.

Example 84

6-Cyclohexyl-pyridine-2-carboxylic acid (2-hydroxy-cyclohexyl)-amide

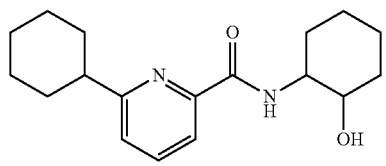 [SMILES: O=C(NC1CCCCC1O)c1cccc(C2CCCCC2)n1]

The title compound was synthesized in analogy to Example 1, using 6-cyclohexyl-pyridine-2-carboxylic acid (Example 7 b) and 2-aminocyclohexanol (CAN 6850-38-0) as starting materials, MS (EI): m/e=303.2 [M+H]⁺.

Example 85

6-Cyclopropylmethoxy-5-(tetrahydro-pyran-4-yl)-pyridine-2-carboxylic acid (1-ethyl-1-methylcarbamoyl-propyl)-amide

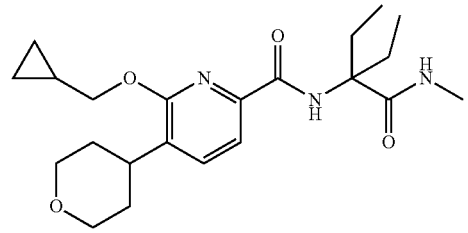 [SMILES: CCC(CC)(NC(=O)c1ccc(C2CCOCC2)c(OCC2CC2)n1)C(=O)NC]

The title compound was synthesized in analogy to Example 1, using 6-cyclopropylmethoxy-5-(tetrahydro-pyran-4-yl)-pyridine-2-carboxylic acid (Example 9 f) and 2-amino-2-ethyl-N-methyl-butyramide (Example 70 b) as starting materials, MS (EI): m/e=404.2 [M+H]⁺.

Example 86

6-Cyclopropylmethoxy-5-(3,3-difluoro-azetidin-1-yl)-pyridine-2-carboxylic acid (1-ethyl-1-methylcarbamoyl-propyl)-amide

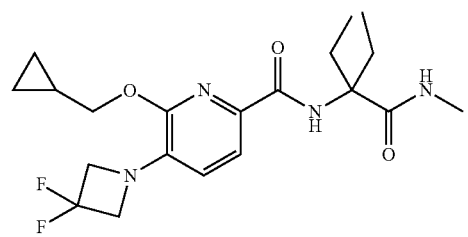 [SMILES: CCC(CC)(NC(=O)c1ccc(N2CC(F)(F)C2)c(OCC2CC2)n1)C(=O)NC]

The title compound was synthesized in analogy to Example 1, using 6-cyclopropylmethoxy-5-(3,3-difluoro-azetidin-1-yl)-pyridine-2-carboxylic acid (Example 69 b) and 2-amino-2-ethyl-N-methyl-butyramide (Example 70 b) as starting materials, MS (EI): m/e=411.1 [M+H]⁺.

Example 87

6-Cyclopropylmethoxy-5-(3,3-difluoro-azetidin-1-yl)-pyridine-2-carboxylic acid (1-methyl-1-methyl-carbamoyl-ethyl)-amide

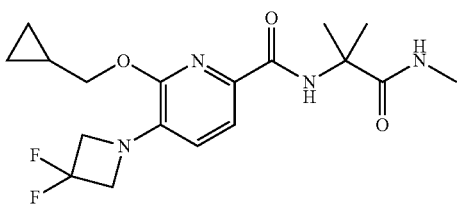 [SMILES: CNC(=O)C(C)(C)NC(=O)c1ccc(N2CC(F)(F)C2)c(OCC2CC2)n1]

The title compound was synthesized in analogy to Example 1, using 6-cyclopropylmethoxy-5-(3,3-difluoro-azetidin-1-yl)-pyridine-2-carboxylic acid (Example 69 b) and 2-amino-N,2-dimethyl-propanamide (CAN 106914-07-2) as starting materials, MS (EI): m/e=383.1 [M+H]$^+$.

Example 88

5-Chloro-6-(3-chloro-phenyl)-pyridine-2-carboxylic acid (1-methyl-1-[1,2,4]oxadiazol-3-yl-ethyl)-amide

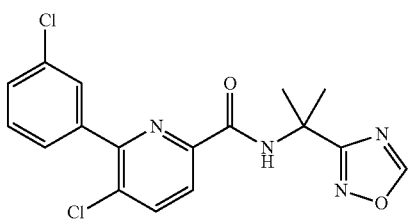 [SMILES: CC(C)(NC(=O)c1ccc(Cl)c(-c2cccc(Cl)c2)n1)c1ncon1]

The title compound was synthesized in analogy to Example 1, using 5-chloro-6-(3-chloro-phenyl)-pyridine-2-carboxylic acid (Example 58 c) and 1-methyl-1-[1,2,4]oxadiazol-3-yl ethylamine (CAN 1153757-41-5) as starting materials, MS (EI): m/e=377.0 [M+H]$^+$.

Example 89

6-(3-Chloro-phenyl)-5-methoxy-pyridine-2-carboxylic acid [1-methyl-1-(5-methyl-[1,2,4]oxadiazol-3-yl)-ethyl]-amide

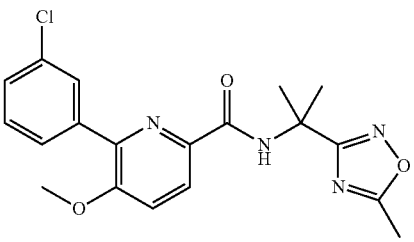 [SMILES: COc1ccc(C(=O)NC(C)(C)c2noc(C)n2)nc1-c1cccc(Cl)c1]

The title compound was synthesized in analogy to Example 1, using 6-(3-chloro-phenyl)-5-methoxy-pyridine-2-carboxylic acid (Example 81 c) and α,α,5-trimethyl-1,2,4-oxadiazole-3-methanamine (CAN 1153831-97-0) as starting materials, MS (EI): m/e=387.0 [M+H]$^+$.

Example 90

6-(3-Chloro-phenyl)-5-methoxy-pyridine-2-carboxylic acid (1-methyl-1-oxazol-2-yl-ethyl)-amide

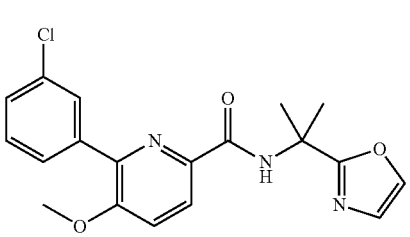

The title compound was synthesized in analogy to Example 1, using 6-(3-chloro-phenyl)-5-methoxy-pyridine-2-carboxylic acid (Example 81 c) and α,α-dimethyl-2-oxazolemethanamine (CAN 1211519-76-4) as starting materials, MS (EI): m/e=372.1 [M+H]$^+$.

Example 91

5-Chloro-6-(3-chloro-phenyl)-pyridine-2-carboxylic acid (1-ethyl-1-methylcarbamoyl-propyl)-amide

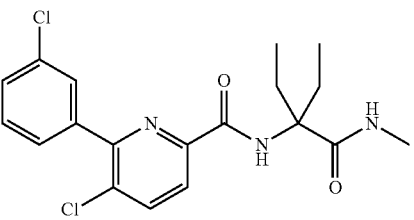 [SMILES: CCC(CC)(NC(=O)c1ccc(Cl)c(-c2cccc(Cl)c2)n1)C(=O)NC]

The title compound was synthesized in analogy to Example 1, using 5-chloro-6-(3-chloro-phenyl)-pyridine-2-carboxylic acid (Example 58 c) and 2-amino-2-ethyl-N-methyl-butyramide (Example 70 b) as starting materials, MS (EI): m/e=394.1 [M+H]$^+$.

Example 92

2-[(6-Cyclohexyl-pyridine-2-carbonyl)-amino]-cyclohexanecarboxylic acid methyl ester

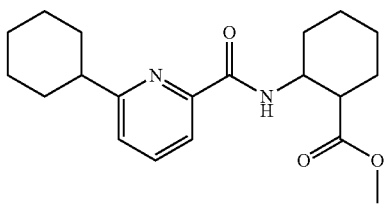 [SMILES: COC(=O)C1CCCCC1NC(=O)c1cccc(C2CCCCC2)n1]

The title compound was synthesized in analogy to Example 1, using 6-cyclohexyl-pyridine-2-carboxylic acid (Example 7 b) and methyl 2-aminocyclohexane-1-carboxylate (CAN 40015-88-1) as starting materials, MS (EI): m/e=345.2 [M+H]$^+$.

Example 93

6-Cyclopropylmethoxy-5-(tetrahydro-pyran-4-yl)-pyridine-2-carboxylic acid (1-methyl-1-oxazol-2-yl-ethyl)-amide

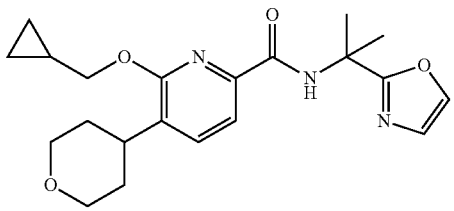 [SMILES: CC(C)(NC(=O)c1ccc(C2CCOCC2)c(OCC2CC2)n1)c1ncco1]

The title compound was synthesized in analogy to Example 1, using 6-cyclopropylmethoxy-5-(tetrahydro-pyran-4-yl)-pyridine-2-carboxylic acid (Example 9 f) and α,α-dimethyl-2-oxazolemethanamine (CAN 1211519-76-4) as starting materials, MS (EI): m/e=386.2 [M+H]$^+$.

Example 94

6-Cyclopentyl-pyridine-2-carboxylic acid piperidin-1-ylamide a) 6-Cyclopentenyl-pyridine-2-carboxylic acid

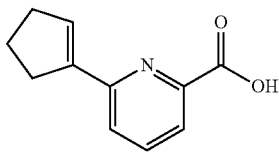 [SMILES: O=C(O)c1cccc(C2=CCCC2)n1]

A mixture of 6-bromo-pyridine-2-carboxylic acid (CAN 21190-87-4, 0.375 g, 1.86 mmol), 2-cyclopentenyl-4,4,5,5-tetramethyl-1,3,2-dioxaborolane (CAN 287944-10-9, 0.3 g, 1.6 mmol), Pd(dppf)Cl$_2$ (CAN 95464-05-4, 0.06 g, 0.08 mmol) and K$_2$CO$_3$ (0.642 g, 4.7 mmol) in DMF (10 mL) and water (1 mL) was heated to 100° C. overnight. After filtration, the filtrate was concentrated and the residue was purified by column chromatography (silica gel, 15 g, eluting with 10% ethyl acetate in petroleum ether) to give the title compound (0.08 g, 23%) as white solid; MS (EI): m/e=190.1 [M+H]$^+$.

b) 6-Cyclopentyl-pyridine-2-carboxylic acid

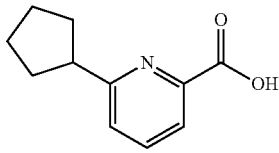 [SMILES: O=C(O)c1cccc(C2CCCC2)n1]

A mixture of 6-cyclopentenyl-pyridine-2-carboxylic acid (0.08 g, 0.42 mmol) and palladium on carbon (10% w/w, 0.04 g, 0.3 mmol) in ethanol (10 mL) was charged with a hydrogen balloon and stirred at room temperature overnight. The reaction mixture was filtered and the filtrate was concentrated to obtain the crude product as white solid (0.08 g, 99%) which was used directly in the next step without further purification; MS (EI): m/e=192.2 [M+H]$^+$.

c) 6-Cyclopentyl-pyridine-2-carboxylic acid piperidin-1-ylamide

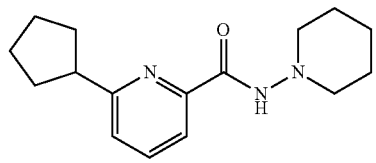 [SMILES: O=C(NN1CCCCC1)c1cccc(C2CCCC2)n1]

The title compound was synthesized in analogy to Example 1, using 6-cyclopentyl-pyridine-2-carboxylic acid and 1-piperidinamine (CAN 2213-43-6) as starting materials, MS (EI): m/e=274.1 [M+H]$^+$.

Example 95

6-(3-Chloro-phenyl)-5-cyclopropyl-pyridine-2-carboxylic acid (1-methyl-1-oxazol-2-yl-ethyl)-amide

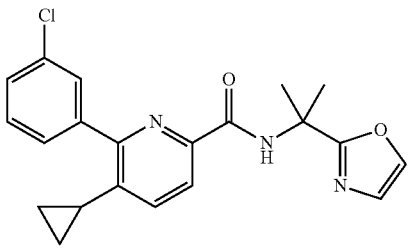 [SMILES: CC(C)(NC(=O)c1ccc(C2CC2)c(-c2cccc(Cl)c2)n1)c1ncco1]

The title compound was synthesized in analogy to Example 1, using 6-(3-chloro-phenyl)-5-cyclopropyl-pyridine-2-carboxylic acid (Example 48 e) and α,α-dimethyl-2-oxazolemethanamine (CAN 1211519-76-4) as starting materials, MS (EI): m/e=382.1 [M+H]$^+$.

Example 96

6-(3-Chloro-phenyl)-5-cyclopropyl-pyridine-2-carboxylic acid [1-methyl-1-(5-methyl-[1,2,4]oxadiazol-3-yl)-ethyl]-amide

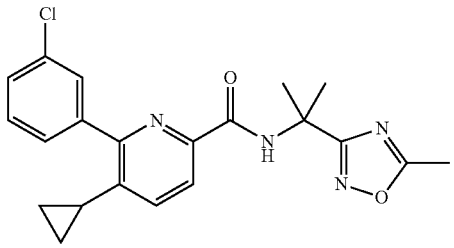 [SMILES: Cc1nc(C(C)(C)NC(=O)c2ccc(C3CC3)c(-c3cccc(Cl)c3)n2)no1]

The title compound was synthesized in analogy to Example 1, using 6-(3-chloro-phenyl)-5-cyclopropyl-pyridine-2-carboxylic acid (Example 48 e) and α,α,5-trimethyl-1,2,4-oxadiazole-3-methanamine (CAN 1153831-97-0) as starting materials, MS (EI): m/e=397.1 [M+H]$^+$.

Example 97

6-(3-Chloro-phenyl)-5-cyclopropyl-pyridine-2-carboxylic acid ((S)-1-carbamoyl-2-cyclopropyl-ethyl)-amide a) (S)-2-Amino-3-cyclopropylpropanamide hydrochloride

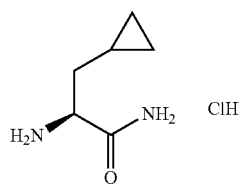

(S)-2-(tert-butoxycarbonylamino)-3-cyclopropylpropanoic acid (CAN 89483-06-7, 1.2 g, 5 mmol) was dissolved in ethyl acetate saturated with hydrochloride (30 mL) and stirred for 30 min. The solvent was removed under reduced pressure to give the title compound; MS (EI): m/e=129.1 [M+H]$^+$.

b) 6-(3-Chloro-phenyl)-5-cyclopropyl-pyridine-2-carboxylic acid ((S)-1-carbamoyl-2-cyclopropyl-ethyl)-amide

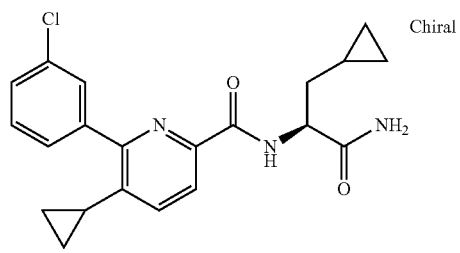

The title compound was synthesized in analogy to Example 1, using 6-(3-chloro-phenyl)-5-cyclopropyl-pyridine-2-carboxylic acid (Example 48 e) and (S)-2-amino-3-cyclopropyl-propanamide hydrochloride as starting materials, MS (EI): m/e=384.2 [M+H]$^+$.

Example 98

5-Cyclopropyl-6-cyclopropylmethoxy-pyridine-2-carboxylic acid ((S)-1-carbamoyl-2-cyclopropyl-ethyl)-amide

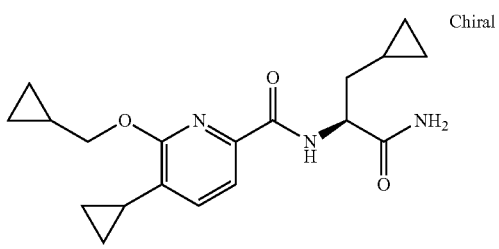

The title compound was synthesized in analogy to Example 1, using 5-cyclopropyl-6-cyclopropylmethoxy-pyridine-2-carboxylic acid (Example 42 a) and (S)-2-amino-3-cyclopropyl-propanamide (CAN 156077-93-9) as starting materials, MS (LC/MS): m/e=344.3 [M+H]$^+$.

Example 99

5-Cyclopropyl-6-cyclopropylmethoxy-pyridine-2-carboxylic acid ((S)-2-cyclopropyl-1-thiazol-2-yl-ethyl)-amide

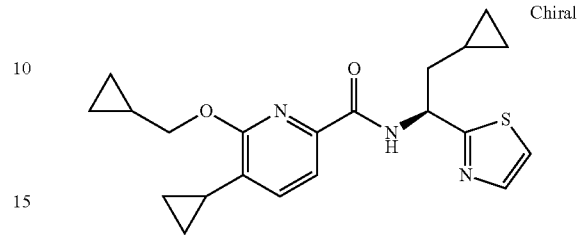

The title compound was synthesized in analogy to Example 1, using 5-cyclopropyl-6-cyclopropylmethoxy-pyridine-2-carboxylic acid (Example 42 a) and (S)-2-cyclopropyl-1-thiazol-2-yl-ethylamine (Example 59 b) as starting materials, MS (LC/MS): m/e=384.3 [M+H]$^+$.

Example 100

5-Cyclopropyl-6-cyclopropylmethoxy-pyridine-2-carboxylic acid ((S)-1-carbamoyl-3-methyl-butyl)-amide

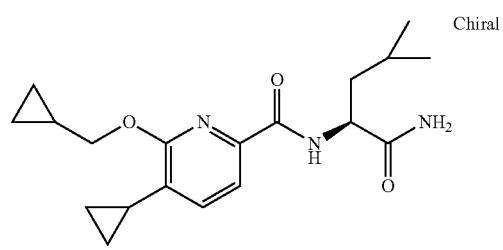

The title compound was synthesized in analogy to Example 1, using 5-cyclopropyl-6-cyclopropylmethoxy-pyridine-2-carboxylic acid (Example 42 a) and (2S)-2-amino-4-methyl-pentanamide (CAN 687-51-4) as starting materials, MS (LC/MS): m/e=346.2 [M+H]$^+$.

Example 101

6-(3-Chloro-phenyl)-5-(tetrahydro-furan-3-yl)-pyridine-2-carboxylic acid (1-methyl-1-thiazol-2-yl-ethyl)-amide a) 5-(2,5-Dihydrofuran-3-yl)-pyridine-2-carboxylic acid methyl ester (a1) and 5-(4,5-dihydrofuran-2-yl)-pyridine-2-carboxylic acid methyl ester (a2)

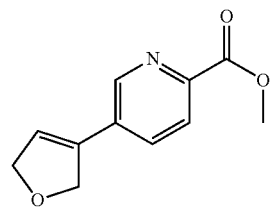

-continued

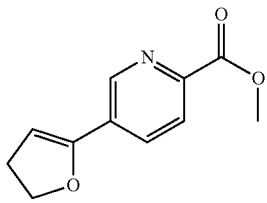
a2

A mixture of 5-bromo-pyridine-2-carboxylic acid methyl ester (CAN 29682-15-3, 15 g, 69 mmol), 2,5-dihydrofuran (CAN 36620-92-5, 48 g, 0.69 mol), palladium diacetate (CAN 3375-31-3, 0.8 g, 3.6 mmol), sodium acetate (6.9 g, 84 mmol) and tri-tert-butylphosphine (CAN 13716-12-6, 10%, 14 g, 7 mmol) in DMF (50 ml) was stirred at 120° C. in a sealed tube for 2.5 h. After cooling to room temperature, the reaction mixture was concentrated. The crude product was purified by column chromatography (silica gel, 200 g, eluting with 30% ethyl acetate in petroleum ether) to give 5-(2,5-dihydrofuran-3-yl)-pyridine-2-carboxylic acid methyl ester (a1) and 5-(4,5-dihydrofuran-2-yl)-pyridine-2-carboxylic acid methyl ester (a2) (mixture, a1/a2=1/0.94 at UV 254 nm, 10.8 g, 76%) as colorless oil; MS (EI): m/e=206.1 [M+H]$^+$.

b) 5-(Tetrahydrofuran-3-yl)-pyridine-2-carboxylic acid methyl ester (b1) and 5-(tetrahydrofuran-2-yl)-pyridine-2-carboxylic acid methyl ester (b2)

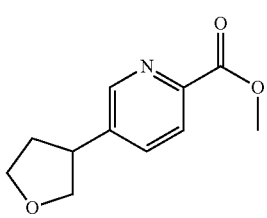
b1

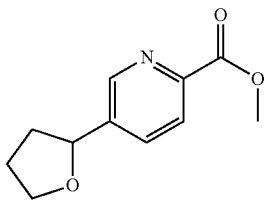
b2

To a solution of 5-(2,5-dihydrofuran-3-yl)-pyridine-2-carboxylic acid methyl ester (a1) and 5-(4,5-dihydrofuran-2-yl)-pyridine-2-carboxylic acid methyl ester (a2) (mixture from Example 101 a, 8 g, 39 mmol) in methanol (200 ml) was added palladium on carbon (10% w/w, 0.8 g). The mixture was stirred under hydrogen balloon overnight at room temperature. After concentration, the crude product was purified by column chromatography (silica gel, 100 g, eluting with 30% ethyl acetate in petroleum ether) to give 5-(tetrahydrofuran-3-yl)-pyridine-2-carboxylic acid methyl ester (b1) and 5-(tetrahydrofuran-2-yl)-pyridine-2-carboxylic acid methyl ester (b2) (mixture, b1/b2=1/0.85 at UV 254 nm, 7.8 g, 97%) as colorless oil; MS (EI): m/e=208.1 [M+H]$^+$.

c) 1-Oxy-5-(tetrahydro-furan-3-yl)-pyridine-2-carboxylic acid methyl ester (c1) and 1-Oxy-5-(tetrahydro-furan-2-yl)-pyridine-2-carboxylic acid methyl ester (c2)

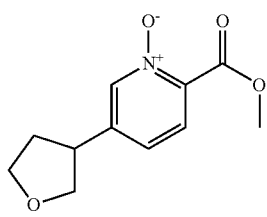
c1

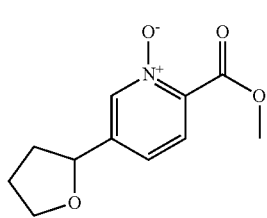
c2

A mixture of 5-(tetrahydrofuran-3-yl)-pyridine-2-carboxylic acid methyl ester (b1) and 5-(tetrahydrofuran-2-yl)-pyridine-2-carboxylic acid methyl ester (b2) (mixture from Example 101 b, 8 g, 39 mmol) and m-CPBA (CAN 937-14-4, 13.3 g, 77 mmol) in methylene chloride (100 ml) was stirred at 40° C. overnight. After concentration, the crude product was purified by column chromatography (silica gel, 100 g, eluting with 25% ethyl acetate in petroleum ether firstly, then 50% methanol in ethyl acetate) to give 1-oxy-5-(tetrahydrofuran-3-yl)-pyridine-2-carboxylic acid methyl ester (c1) and 1-oxy-5-(tetrahydro-furan-2-yl)-pyridine-2-carboxylic acid methyl ester (c2) (mixture, c1/c2=1/0.67 at UV 254 nm, 8 g, 93%) as yellow oil; MS (EI): m/e=224.1 [M+H]$^+$.

d) 6-Bromo-5-(tetrahydrofuran-3-yl)-pyridine-2-carboxylic acid methyl ester (d1) and 6-bromo-5-(tetrahydrofuran-2-yl)-pyridine-2-carboxylic acid methyl ester (d2)

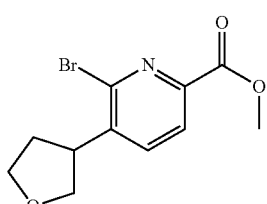
d1

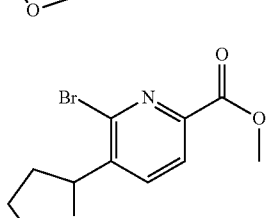
d2

Phosphorus oxide bromide (CAN 7789-59-5, 11 g, 38 mmol) was added to a solution of 1-oxy-5-(tetrahydro-furan- 3-yl)-pyridine-2-carboxylic acid methyl ester (c1) and 1-oxy-5-(tetrahydro-furan-2-yl)-pyridine-2-carboxylic acid methyl ester (c2) (mixture from Example 101 c, 2.86 g, 13 mmol) in methylene chloride. The reaction mixture was stirred at room temperature overnight and poured into 100 ml methanol. After removal of the solvents by evaporation, the mixture was diluted with ethyl acetate, and washed with $H_2O$ (2×100 mL). The organic layer was evaporated to dryness. The crude product was purified by column chromatography (silica gel, 40 g, petroleum ether/ethyl acetate 3/1) to give 6-bromo-5-(tetrahydrofuran-3-yl)-pyridine-2-carboxylic acid methyl ester (d1) (185 g, 5%) as yellow solid, MS (EI): m/e=286.0 and also 6-bromo-5-(tetrahydrofuran-2-yl)-pyridine-2-carboxylic acid methyl ester (d2) (0.138 g, 4%) as yellow solid; MS (EI): m/e=286.0 [M+H]$^+$.

e) 6-(3-Chlorophenyl)-5-(tetrahydrofuran-3-yl)-pyridine-2-carboxylic acid methyl ester

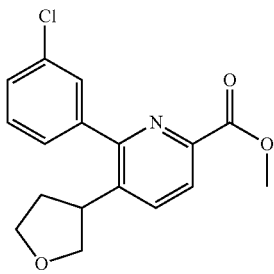 [SMILES: COC(=O)c1ccc(C2CCOC2)c(-c2cccc(Cl)c2)n1]

A solution of methyl 6-bromo-5-(tetrahydrofuran-3-yl)-pyridine-2-carboxylic acid methyl ester (0.185 g, 0.65 mmol), 3-chlorophenylboronic acid (CAN 63503-60-6, 0.15 g, 0.96 mmol), 1,1'-bis(diphenylphosphino)-ferrocene-palladium(II) dichloride methylene chloride complex (CAN 95464-05-4, 20 mg) and cesium carbonate (CAN 534-17-8, 0.63 g, 2 mmol) in DMF (10 mL) was stirred overnight at 80° C. under a nitrogen atmosphere. After filtration, the reaction mixture was poured into water (20 mL) and washed with ethyl acetate (2×20 mL). The organic layer was concentrated in vacuo to provide the title compound (0.75 g, 73%) as black oil which was used in the next step without further purification; MS (EI): m/e=318.1 [M+H]$^+$.

f) 6-(3-Chloro-phenyl)-5-(tetrahydro-furan-3-yl)-pyridine-2-carboxylic acid

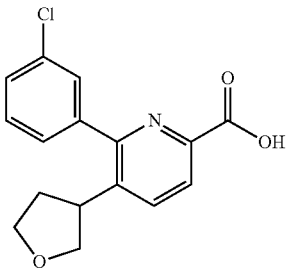 [SMILES: O=C(O)c1ccc(C2CCOC2)c(-c2cccc(Cl)c2)n1]

A mixture of 6-(3-chlorophenyl)-5-(tetrahydrofuran-3-yl)-pyridine-2-carboxylic acid methyl ester (0.15 g, 0.5 mmol) and lithium hydroxide monohydrate (CAN 1310-66-3, 88 mg, 2.1 mmol) in THF/$H_2O$ 1/1 (20 mL)) was stirred at room temperature for 1 h. After removal of the organic solvent under reduced pressure, the aqueous phase was washed with ethyl acetate (10 mL) and acidified with 1 N HCl to pH=3. The resulting solution was extracted with ethyl acetate (2×20 mL). The combined organic layer was concentrated under reduced pressure to provide the title compound (0.12 g, 81%) as black oil which was used in the next step without further purification; MS (EI): m/e=304.1 [M+H]$^+$.

g) 6-(3-Chloro-phenyl)-5-(tetrahydro-furan-3-yl)-pyridine-2-carboxylic acid (1-methyl-1-thiazol-2-yl-ethyl)-amide

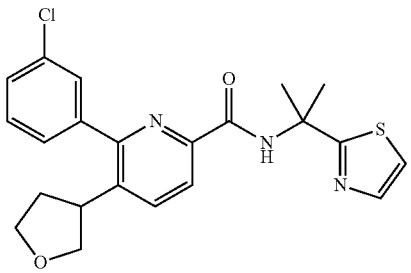 [SMILES: CC(C)(NC(=O)c1ccc(C2CCOC2)c(-c2cccc(Cl)c2)n1)c1nccs1]

The title compound was synthesized in analogy to Example 1, using 6-(3-chloro-phenyl)-5-(tetrahydro-furan-3-yl)-pyridine-2-carboxylic acid and α,α-dimethyl-2-thiazolemethanamine (CAN 1082393-38-1) as starting materials, MS (EI): m/e=428.1 [M+H]$^+$.

Example 102

6-Cyclopropylmethoxy-5-(3,3-difluoro-azetidin-1-yl)-pyridine-2-carboxylic acid [1-methyl-1-(5-methyl-[1,2,4]oxadiazol-3-yl)-ethyl]-amide

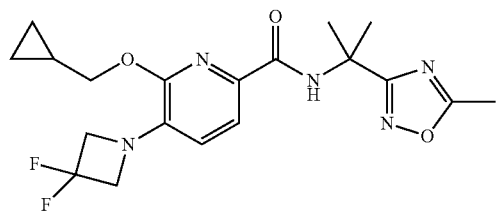 [SMILES: Cc1nc(C(C)(C)NC(=O)c2ccc(N3CC(F)(F)C3)c(OCC3CC3)n2)no1]

The title compound was synthesized in analogy to Example 1, using 6-cyclopropylmethoxy-5-(3,3-difluoro-azetidin-1-yl)-pyridine-2-carboxylic acid (Example 69 b) and α,α,5-trimethyl-1,2,4-oxadiazole-3-methanamine (CAN 1153831-97-0) as starting materials, MS (EI): m/e=408.1 [M+H]$^+$.

Example 103

6-Cyclopropylmethoxy-5-(3,3-difluoro-azetidin-1-yl)-pyridine-2-carboxylic acid ((S)-1-carbamoyl-2-cyclopropyl-ethyl)-amide

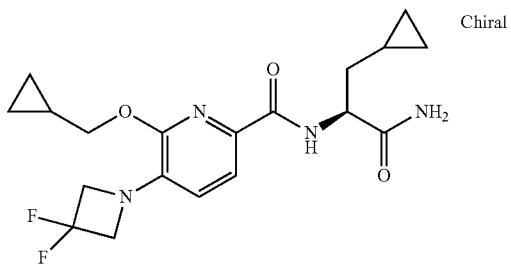 [SMILES: NC(=O)[C@H](CC1CC1)NC(=O)c1ccc(N2CC(F)(F)C2)c(OCC2CC2)n1]

The title compound was synthesized in analogy to Example 1, using 6-cyclopropylmethoxy-5-(3,3-difluoro-azetidin-1-yl)-pyridine-2-carboxylic acid (Example 69 b) and (S)-2-amino-3-cyclopropyl-propionamide (CAN 156077-93-9) as starting materials, MS (EI): m/e=395.2 [M+H]$^+$.

Example 104

5-Chloro-6-(3-chloro-phenyl)-pyridine-2-carboxylic acid (1-methyl-1-oxazol-2-yl-ethyl)-amide

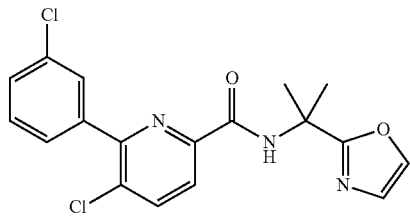 [SMILES: CC(C)(NC(=O)c1ccc(Cl)c(-c2cccc(Cl)c2)n1)c1ncco1]

The title compound was synthesized in analogy to Example 1, using 5-chloro-6-(3-chloro-phenyl)-pyridine-2-carboxylic acid (Example 58 c) and α,α-dimethyl-2-oxazolemethanamine (CAN 1211519-76-4) as starting materials, MS (EI): m/e=376.0 [M+H]$^+$.

Example 105

5-Chloro-6-(3-chloro-phenyl)-pyridine-2-carboxylic acid ((S)-1-carbamoyl-3-methyl-butyl)-amide

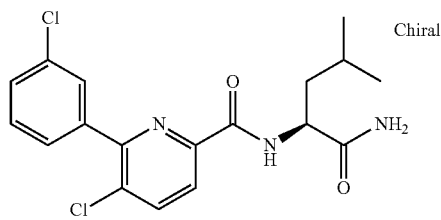

The title compound was synthesized in analogy to Example 1, using 5-chloro-6-(3-chloro-phenyl)-pyridine-2-carboxylic acid (Example 58 c) and (2S)-2-amino-4-methyl-pentanamide (CAN 687-51-4) as starting materials, MS (EI): m/e=380.0 [M+H]$^+$.

Example 106

6-(3-Chloro-phenyl)-5-cyclopentyl-pyridine-2-carboxylic acid [1-methyl-1-(5-methyl-[1,2,4]oxadiazol-3-yl)-ethyl]-amide a) 5-Cyclopentenyl-pyridine-2-carboxylic acid

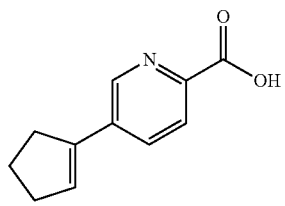 [SMILES: O=C(O)c1ccc(C2=CCCC2)cn1]

5-Bromo-pyridine-2-carboxylic acid (CAN 30766-11-1, 3.4 g, 17 mmol), 1,1'-bis(diphenylphosphino)ferrocene-palladium(II)dichloride methylene chloride complex (CAN 95464-05-4, 530 mg, 0.65 mmol) and Cs$_2$CO$_3$ (6.3 g, 19 mmol) were added to a solution of 2-cyclopentenyl-4,4,5,5-tetramethyl-1,3,2-dioxaborolane (CAN 287944-10-9, 2.5 g, 13 mmol) in DMF (50 mL) and water (10 mL). The mixture was stirred at 150° C. overnight and concentrated in vacuo. Water (50 mL) was added and the mixture was extracted with ethyl acetate (3×40 mL). The organic layers were combined, dried over anhydrous sodium sulfate and concentrated to give the title compound (1.0 g, 31%); MS (EI): m/e=190.1 [M+H]$^+$.

b) 5-Cyclopentyl-pyridine-2-carboxylic acid

A suspension of 5-cyclopentenyl-pyridine-2-carboxylic acid (2.0 g, 11 mmol) and palladium on carbon (10% w/w, 0.5 g) in methanol (20 mL) under a hydrogen atmosphere was stirred at ambient temperature overnight. The mixture was filtered and the filtrate concentrated in vacuo to give the title compound which was used in the next step without further purification (1.4 g, 72%); MS (EI): m/e=192.1 [M+H]$^+$.

c) 5-Cyclopentyl-1-oxy-pyridine-2-carboxylic acid

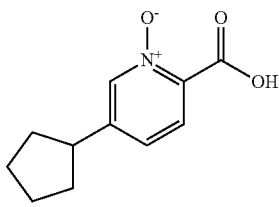 [SMILES: O=C(O)c1ccc(C2CCCC2)c[n+]1[O-]]

m-CPBA (CAN 937-14-4, 4.5 g, 22 mmol) was added to a solution of 5-cyclopentyl-pyridine-2-carboxylic acid (1.4 g, 7.3 mmol) in methylene chloride (20 mL). The mixture was stirred overnight at room temperature. The solid was filtered off, a saturated solution of sodium thiosulfate (50 mL) was added, and the mixture was extracted with methylene chloride (3×60 mL). The organic layers were combined, dried over anhydrous sodium sulfate and concentrated in vacuo to obtain the crude product. The crude product was purified by column chromatography (silica gel, 200 g, eluting with 10% ethyl acetate in petroleum ether) to give the title compound (0.3 g, 66%); MS (EI): m/e=208.1 [M+H]$^+$.

d) 6-Bromo-5-cyclopentyl-pyridine-2-carboxylic acid methyl ester

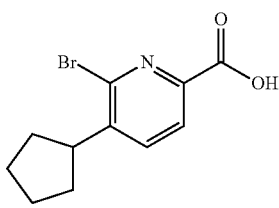 [SMILES: O=C(O)c1ccc(C2CCCC2)c(Br)n1]

5-Cyclopentyl-1-oxy-pyridine-2-carboxylic acid (1.0 g, 4.8 mmol) was added to POBr$_3$ (15 g) and the mixture was stirred for 2 h at 80° C. Ice water was added and the mixture was extracted with methylene chloride (3×50 mL). The combined organic layer was dried over sodium sulfate and concentrated to give the crude product. The crude product was purified by column chromatography (silica gel, 30 g, eluting with 50% ethyl acetate in petroleum ether) to give the title compound (0.6 g, 46%); MS (EI): m/e=270.1 [M+H]$^+$.

e) 6-(3-Chloro-phenyl)-5-cyclopentyl-pyridine-2-carboxylic acid

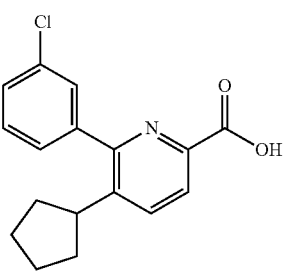 [SMILES: O=C(O)c1ccc(C2CCCC2)c(-c2cccc(Cl)c2)n1]

6-Bromo-5-cyclopentyl-pyridine-2-carboxylic acid methyl ester (0.6 g, 2.1 mmol), bis(diphenylphosphino)ferrocene-palladium(II)dichloride methylene chloride complex (CAN 95464-05-4, 90 mg, 0.11 mmol) and potassium carbonate (0.37 g, 2.68 mmol) were added to a solution of 3-chlorophenylboronic acid (CAN 63503-60-6, 0.42 g, 2.69 mmol) in water (20 mL) and DMF (2 mL). The mixture was stirred for 48 h at 100° C. Its pH was adjusted to pH=3 with diluted hydrochloric acid. The mixture was extracted with methylene chloride (3×20 mL). The organic layers were combined, dried over sodium sulfate and concentrated under reduced pressure to give the title compound (130 mg, 20%) which was used in the next step without further purification; MS (EI): m/e=302.0 [M+H]$^+$.

f) 6-(3-Chloro-phenyl)-5-cyclopentyl-pyridine-2-carboxylic acid [1-methyl-1-(5-methyl-[1,2,4]oxadiazol-3-yl)-ethyl]-amide

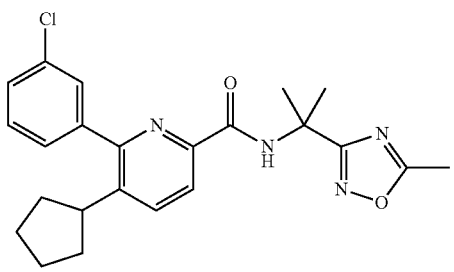 [SMILES: Cc1nc(C(C)(C)NC(=O)c2ccc(C3CCCC3)c(-c3cccc(Cl)c3)n2)no1]

The title compound was synthesized in analogy to Example 1, using 6-(3-chloro-phenyl)-5-cyclopentyl-pyridine-2-carboxylic acid and α,α,5-trimethyl-1,2,4-oxadiazole-3-methanamine (CAN 1153831-97-0) as starting materials, MS (EI): m/e=425.2 [M+H]$^+$.

Example 107

5-Cyclopentyl-6-cyclopropylmethoxy-pyridine-2-carboxylic acid ((S)-1-carbamoyl-2-cyclopropyl-ethyl)-amide

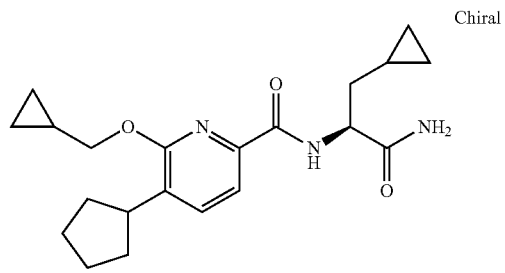

The title compound was synthesized in analogy to Example 1, using 5-cyclopentyl-6-cyclopropylmethoxy-pyridine-2-carboxylic acid (Example 39 b) and (S)-2-amino-3-cyclopropyl-propionamide (CAN 156077-93-9) as starting materials, MS (EI): m/e=372.3 [M+H]$^+$.

Example 108

5-Chloro-6-cyclopropylmethoxy-pyridine-2-carboxylic acid [1-methyl-1-(5-methyl-[1,2,4]oxadiazol-3-yl)-ethyl]-amide

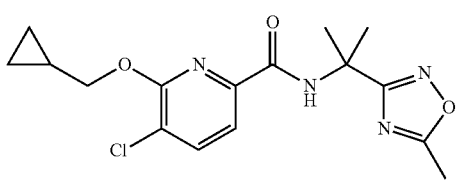 [SMILES: Cc1nc(C(C)(C)NC(=O)c2ccc(Cl)c(OCC3CC3)n2)no1]

The title compound was synthesized in analogy to Example 1, using 5-chloro-6-cyclopropylmethoxy-pyridine-2-carboxylic acid (Example 83 b) and α,α,5-trimethyl-1,2,4-oxadiazole-3-methanamine (CAN 1153831-97-0) as starting materials, MS (EI): m/e=351.1 [M+H]$^+$.

Example 109

5-Chloro-6-cyclopropylmethoxy-pyridine-2-carboxylic acid (1-ethyl-1-methylcarbamoyl-propyl)-amide

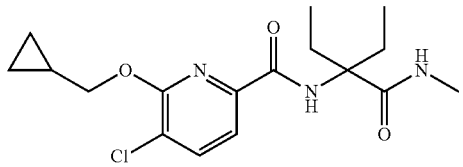 [SMILES: CCC(CC)(NC(=O)c1ccc(Cl)c(OCC2CC2)n1)C(=O)NC]

The title compound was synthesized in analogy to Example 1, using 5-chloro-6-cyclopropylmethoxy-pyridine-2-carboxylic acid (Example 83 b) and 2-amino-2-ethyl-N-methyl-butyramide (Example 70 b) as starting materials, MS (EI): m/e=354.2 [M+H]$^+$.

Example 110

5-Bromo-6-cyclopropylmethoxy-pyridine-2-carboxylic acid ((S)-1-carbamoyl-2-cyclopropyl-ethyl)-amide

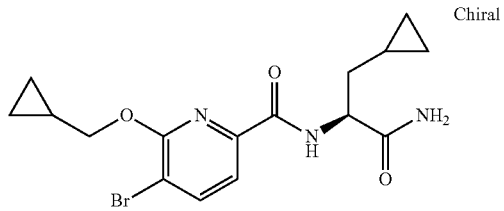

The title compound was synthesized in analogy to Example 1, using 5-bromo-6-cyclopropylmethoxy-pyridine-2-carboxylic acid (Example 9 d) and (S)-2-amino-3-cyclopropyl-propionamide (CAN 156077-93-9) as starting materials, MS (EI): m/e=382.0 [M+H]$^+$.

Example 111

5-Cyclopentyl-6-cyclopropylmethoxy-pyridine-2-carboxylic acid (1-ethyl-1-methylcarbamoyl-propyl)-amide

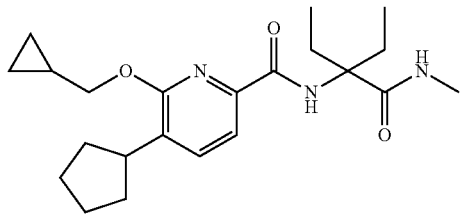 [SMILES: CCC(CC)(NC(=O)c1ccc(C2CCCC2)c(OCC2CC2)n1)C(=O)NC]

The title compound was synthesized in analogy to Example 1, using 5-cyclopentyl-6-cyclopropylmethoxy-pyridine-2-carboxylic acid (Example 39 b) and 2-amino-2-ethyl-N-methyl-butyramide (Example 70 b) as starting materials, MS (EI): m/e=388.2 [M+H]$^+$.

Example 112

6-Cyclopropylmethoxy-5-(3,3-difluoro-pyrrolidin-1-yl)-pyridine-2-carboxylic acid ((S)-1-carbamoyl-2-cyclopropyl-ethyl)-amide

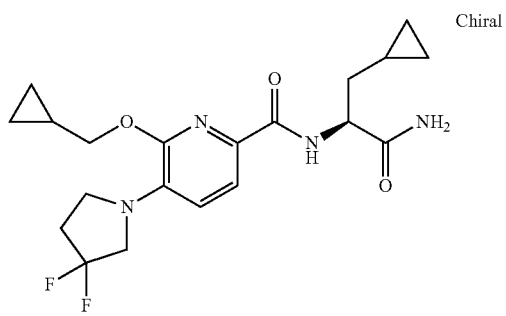

The title compound was synthesized in analogy to Example 1, using 6-cyclopropylmethoxy-5-(3,3-difluoro-pyrrolidin-1-yl)-pyridine-2-carboxylic acid (Example 78 b) and (S)-2-amino-3-cyclopropyl-propionamide (CAN 156077-93-9) as starting materials, MS (EI): m/e=409.3 [M+H]$^+$.

Example 113

6-Cyclopropylmethoxy-5-trifluoromethyl-pyridine-2-carboxylic acid ((S)-1-carbamoyl-2-cyclopropyl-ethyl)-amide a) 5-(Trifluoromethyl)-pyridine-2-carboxylic acid methyl ester

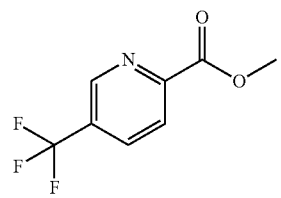

A solution of 5-(trifluoromethyl)-pyridine-2-carboxylic acid (CAN 80194-69-0, 3 g, 15.7 mmol) and sulfurous dichloride (0.1 mL) in methanol (30 mL) was stirred under reflux conditions overnight. Removal of the solvent provided the crude title compound which was purified by column chromatography (silica gel, 20 g, 10% ethyl acetate in petroleum ether) to obtain the title compound (2.7 g, 84%) as white solid; MS (EI): m/e=206.1 [M+H]$^+$.

b) 1-Oxy-5-trifluoromethyl-pyridine-2-carboxylic acid methyl ester

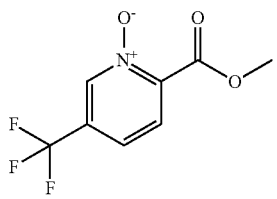

A mixture of 5-(trifluoromethyl)-pyridine-2-carboxylic acid methyl ester (2.7 g, 13 mmol) and m-CPBA (CAN 937-14-4, 6.7 g, 39 mmol) in dry methylene chloride (30 mL) was stirred under reflux conditions overnight. Removal of the solvent in vacuo and purification of the obtained residue by column chromatography (silica gel, 15 g, 20% ethyl acetate in petroleum ether) provided the title compound (2.2 g, 76%) as light-yellow solid; MS (EI): m/e=222.1 [M+H]$^+$.

c) 6-Chloro-5-(trifluoromethyl)-pyridine-2-carboxylic acid methyl ester

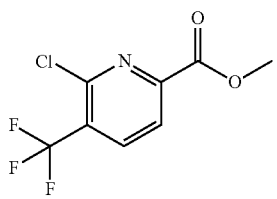

Oxy-5-trifluoromethyl-pyridine-2-carboxylic acid methyl ester (2.2 g, 10 mmol) was added in portions to phosphoryl trichloride (CAN 10025-87-3, 10 mL) at 0° C. and the resulting mixture was stirred at 50° C. overnight. Removal of the solvent in vacuo gave a brown oil which was dissolved in ethyl acetate (30 mL) and carefully neutralized with a aqueous solution of sodium carbonate. The mixture was extracted with ethyl acetate (2×30 mL) and the combined organic phase was washed with brine (30 mL), dried over anhydrous sodium sulfate, filtered and concentrated to give a light-brown solid. The solid was purified by column chromatography (silica gel, 15 g, 3% ethyl acetate in petroleum ether) to give the target compound (1.5 g, 63%) as white solid; MS (EI): m/e=240.0 [M+H]$^+$.

d) 6-Cyclopropylmethoxy-5-trifluoromethyl-pyridine-2-carboxylic acid

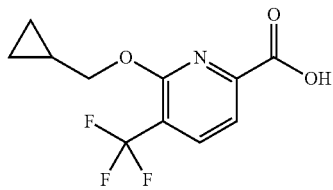 [SMILES: O=C(O)c1ccc(C(F)(F)F)c(OCC2CC2)n1]

Sodium hydride (1.1 g, 31.4 mmol) was added in portions to cyclopropylmethanol (20 mL) and the mixture was stirred at room temperature for 0.5 hours. 6-Chloro-5-(trifluoromethyl)-pyridine-2-carboxylic acid methyl ester (1.5 g, 6.3 mmol) was added and the resulting solution was stirred at 80° C. for 1 h. Water (20 mL) was added; the solution was acidified with 6 N hydrochloric acid and then concentrated to give a residue which was partitioned between water (30 mL) and ethyl acetate (20 mL). The aqueous solution was extracted with ethyl acetate (2×20 mL) and the combined organic phase was washed with brine (20 mL), dried over anhydrous sodium sulfate, filtered and concentrated to give the crude target compound. The crude target compound was purified by column chromatography (silica gel, 10 g, 15% ethyl acetate in petroleum ether) to give the title compound (1.4 g, 85%) as white solid; MS (EI): m/e=262.0 [M+H]$^+$.

e) 6-Cyclopropylmethoxy-5-trifluoromethyl-pyridine-2-carboxylic acid ((S)-1-carbamoyl-2-cyclopropyl-ethyl)-amide

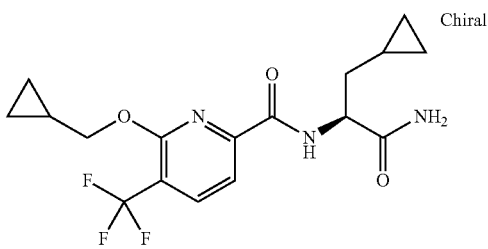 [SMILES: NC(=O)[C@H](CC1CC1)NC(=O)c1ccc(C(F)(F)F)c(OCC2CC2)n1]

The title compound was synthesized in analogy to Example 1, using 6-cyclopropylmethoxy-5-trifluoromethyl-pyridine-2-carboxylic acid and (S)-2-amino-3-cyclopropyl-propionamide (CAN 156077-93-9) as starting materials, MS (EI): m/e=372.1 [M+H]$^+$.

Example 114

6-Cyclopropylmethoxy-5-(tetrahydro-furan-3-yl)-pyridine-2-carboxylic acid ((S)-1-carbamoyl-3-methyl-butyl)-amide a) 5-Bromo-6-(cyclopropylmethoxy)-pyridine-2-carboxylic acid methyl ester

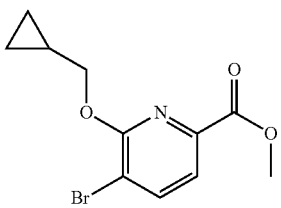 [SMILES: COC(=O)c1ccc(Br)c(OCC2CC2)n1]

A solution of 5-bromo-6-(cyclopropylmethoxy)-pyridine-2-carboxylic acid (Example 9 d, 0.4 g, 1.5 mmol), iodomethane (CAN 16519-98-5, 0.42 g, 3 mmol), sodium carbonate (0.16 g, 1.5 mmol) in DMF (10 mL) was stirred overnight at room temperature. Water was poured into the reaction solution and the resulting mixture was extracted with ethyl acetate (3×30 mL). The combined organic extracts were washed with water and brine, dried over anhydrous sodium sulfate and evaporated. The residue was purified by column chromatography (silica gel, 20 g, 5% ethyl acetate in petroleum ether) to yield the title compound (0.2 g, 0.7 mmol, 48%) as white solid; MS (EI): m/e=286.0 [M+H]$^+$.

b) 6-(Cyclopropylmethoxy)-5-(2,5-dihydrofuran-3-yl)-pyridine-2-carboxylic acid methyl ester (b1) and 6-(cyclopropylmethoxy)-5-(4,5-dihydrofuran-2-yl)-pyridine-2-carboxylic acid methyl ester (b2)

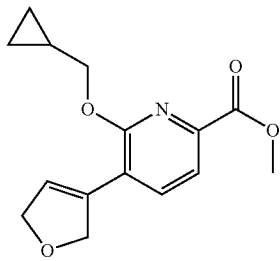

b1

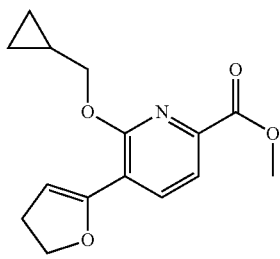

b2

A mixture of 5-bromo-6-(cyclopropylmethoxy)-pyridine-2-carboxylic acid methyl ester (0.5 g, 1.7 mmol), 2,5-dihydrofuran (CAN 1708-29-8, 1.2 g, 17 mmol), palladium(II) acetate (CAN 3375-31-3, 0.02 g, 0.09 mmol), sodium acetate (0.17 g, 2 mmol) and tri-tert-butylphosphine (CAN 13716-12-6, 0.037 g, 0.2 mmol) in DMF (10 mL) was stirred at 120° C. for 2.5 h under a nitrogen atmosphere. Water was poured into the reaction mixture and the resulting mixture was extracted with ethyl acetate (3×30 mL). The combined organic extracts were washed with water and brine, dried over anhydrous sodium sulfate and evaporated. The residue was purified by column chromatography (silica gel, 10 g, eluting with 5% ethyl acetate in petroleum ether) to yield 6-(cyclopropylmethoxy)-5-(2,5-dihydrofuran-3-yl)-pyridine-2-carboxylic acid methyl ester (b1) and 6-(cyclopropylmethoxy)-5-(4,5-dihydrofuran-2-yl)-pyridine-2-carboxylic acid methyl ester (b2) (mixture b1:b2=3:2, 0.38 g, 1.4 mmol, 79%) as yellow oil; MS (EI): m/e=376.1 [M+H]$^+$.

c) 6-(Cyclopropylmethoxy)-5-(tetrahydrofuran-3-yl)-pyridine-2-carboxylic acid methyl ester (c1) and 6-(cyclopropylmethoxy)-5-(tetrahydrofuran-2-yl)-pyridine-2-carboxylic acid methyl ester (c2)

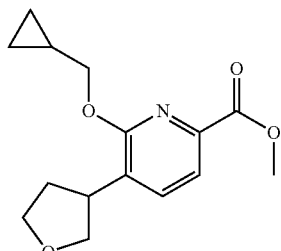

c1

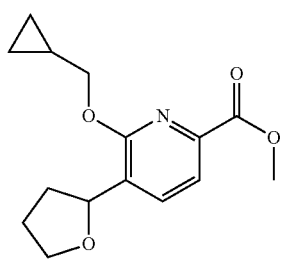

c2

To a solution of 6-(cyclopropylmethoxy)-5-(2,5-dihydrofuran-3-yl)-pyridine-2-carboxylic acid methyl ester (b1) and 6-(cyclopropylmethoxy)-5-(4,5-dihydrofuran-2-yl)-pyridine-2-carboxylic acid methyl ester (b2) (mixture from Example 114 b, 0.38 g, 1.38 mmol) in EtOH (50 mL) was added Pd/C (20%, 0.08 g) under N$_2$. The suspension was degassed under vacuum and purged with H$_2$ several times. The mixture was stirred under H$_2$ balloon at room temperature overnight. The reaction mixture was filtered through a pad of celite, the pad was washed with EtOH and the combined filtrates were concentrated to dryness. The crude product 6-(cyclopropylmethoxy)-5-(tetrahydrofuran-3-yl)-pyridine-2-carboxylic acid methyl ester (c1) and 6-(cyclopropylmethoxy)-5-(tetrahydrofuran-2-yl)-pyridine-2-carboxylic acid methyl ester (c2) (mixture, c1:c2=3:2, 0.36 g) was used for next step without further purification; MS (EI): m/e=278.1 [M+H]$^+$, Rt=1.71 min.

d) 6-(Cyclopropylmethoxy)-5-(tetrahydrofuran-3-yl)-pyridine-2-carboxylic acid (d1) and 6-(Cyclopropylmethoxy)-5-(tetrahydrofuran-2-yl)-pyridine-2-carboxylic acid (d2)

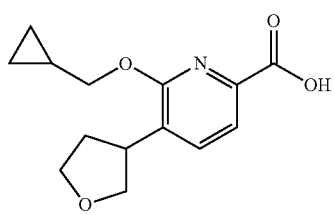

d1

-continued

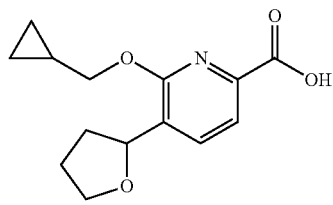

A solution of 6-(cyclopropylmethoxy)-5-(tetrahydrofuran-3-yl)-pyridine-2-carboxylic acid methyl ester (c1) and 6-(cyclopropylmethoxy)-5-(tetrahydrofuran-2-yl)-pyridine-2-carboxylic acid methyl ester (c2) (mixture from Example 114 c, 0.35 g, 1.3 mmol) and sodium hydroxide (55 mg, 1.4 mmol) in ethanol (50 mL) was heated to 90° C. for 2 h. The reaction mixture was evaporated, dissolved in water and extracted with ethyl acetate (30 mL). The pH of the aqueous layer was adjusted to 2 by addition of 1 N hydrochloric acid and the resulting precipitate was collected by filtration and dried in vacuo to give 6-(cyclopropylmethoxy)-5-(tetrahydrofuran-3-yl)-pyridine-2-carboxylic acid (d1) and 6-(cyclopropylmethoxy)-5-(tetrahydrofuran-2-yl)-pyridine-2-carboxylic acid (d2) (mixture, d1:d2=3:2, 0.33 g, 1.3 mmol, 100%) as yellow solid; MS (EI): m/e=264.2 [M+H]$^+$.

e) 6-Cyclopropylmethoxy-5-(tetrahydro-furan-3-yl)-pyridine-2-carboxylic acid ((S)-1-carbamoyl-3-methyl-butyl)-amide

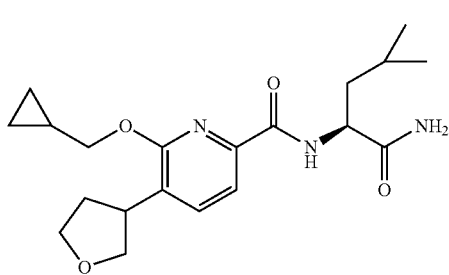 [SMILES: CC(C)C[C@H](NC(=O)c1ccc(C2CCOC2)c(OCC2CC2)n1)C(N)=O]

The title compound was synthesized in analogy to Example 1, using the mixture of 6-(cyclopropylmethoxy)-5-(tetrahydrofuran-3-yl)-pyridine-2-carboxylic acid and 6-(cyclopropylmethoxy)-5-(tetrahydrofuran-2-yl)-pyridine-2-carboxylic acid (mixture from Example 114 d), and (2S)-2-amino-4-methyl-pentanamide (CAN 687-51-4) as starting materials, MS (EI): m/e=376.2 [M+H]$^+$.

Example 115

6-Cyclopropylmethoxy-5-(tetrahydro-furan-2-yl)-pyridine-2-carboxylic acid ((S)-1-carbamoyl-3-methyl-butyl)-amide

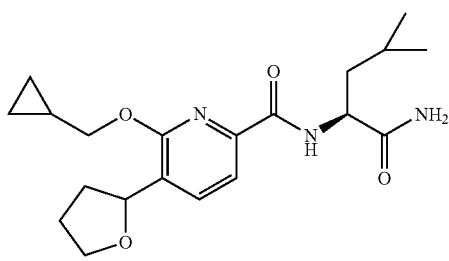 [SMILES: CC(C)C[C@H](NC(=O)c1ccc(C2CCCO2)c(OCC2CC2)n1)C(N)=O]

The title compound was synthesized in analogy to Example 1, using the mixture of 6-(cyclopropylmethoxy)-5-(tetrahydrofuran-3-yl)-pyridine-2-carboxylic acid and 6-(cyclopropylmethoxy)-5-(tetrahydrofuran-2-yl)-pyridine-2-carboxylic acid (mixture from Example 114 d), and (2S)-2-amino-4-methyl-pentanamide (CAN 687-51-4) as starting materials, MS (EI): m/e=376.2 [M+H]$^+$.

Example 116

6-(3-Chloro-phenyl)-5-cyclopropyl-pyridine-2-carboxylic acid (1-methyl-1-thiazol-2-yl-ethyl)-amide

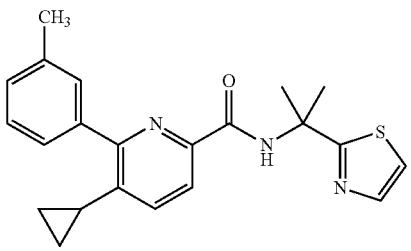

The title compound was synthesized in analogy to Example 1, using 6-(3-chloro-phenyl)-5-cyclopropyl-pyridine-2-carboxylic acid (Example 48 e) and α,α-dimethyl-2-thiazolemethanamine (CAN 1082393-38-1) as starting materials, MS (EI): m/e=398.1 [M+H]$^+$.

Example 117

5-Cyclopropyl-6-cyclopropylmethoxy-pyridine-2-carboxylic acid [2-(2-methoxy-ethoxy)-1,1-dimethyl-ethyl]-amide

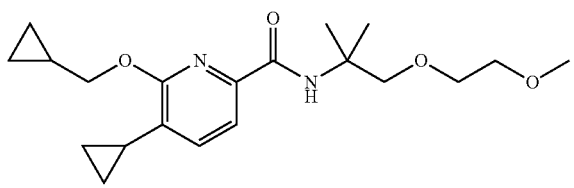 [SMILES: COCCOCC(C)(C)NC(=O)c1ccc(C2CC2)c(OCC2CC2)n1]

The title compound was synthesized in analogy to Example 1, using 5-cyclopropyl-6-cyclopropylmethoxy-pyridine-2-carboxylic acid (Example 42 a) and 2-(2-methoxy-ethoxy)-1,1-dimethyl-ethylamine (CAN 947723-29-7) as starting materials, MS (EI): m/e=363.2 [M+H]$^+$.

Example 118

6-Cyclopropylmethoxy-5-trifluoromethyl-pyridine-2-carboxylic acid ((S)-1-carbamoyl-3-methyl-butyl)-amide

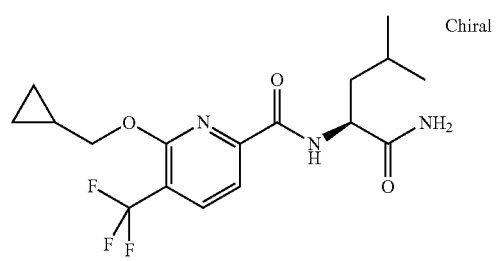 [SMILES: CC(C)C[C@H](NC(=O)c1ccc(C(F)(F)F)c(OCC2CC2)n1)C(N)=O]

The title compound was synthesized in analogy to Example 1, using 6-cyclopropylmethoxy-5-trifluoromethyl-pyridine-2-carboxylic acid (Example 113 d) and (2S)-2-amino-4-methyl-pentanamide (CAN 687-51-4) as starting materials, MS (EI): m/e=374.1 [M+H]⁺.

Example 119

6-Cyclopropylmethoxy-5-trifluoromethyl-pyridine-2-carboxylic acid (1-methyl-1-[1,2,4]oxadiazol-3-yl-ethyl)-amide

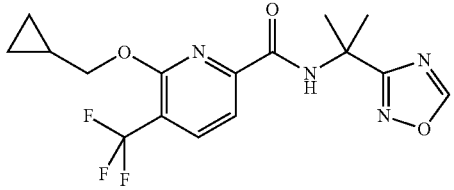 [SMILES: CC(C)(NC(=O)c1ccc(C(F)(F)F)c(OCC2CC2)n1)c1ncon1]

The title compound was synthesized in analogy to Example 1, using 6-cyclopropylmethoxy-5-trifluoromethyl-pyridine-2-carboxylic acid (Example 113 d) and 1-methyl-1-[1,2,4]oxadiazol-3-yl ethylamine (CAN 1153757-41-5) as starting materials, MS (EI): m/e=371.2 [M+H]⁺.

Example 120

6-Cyclopropylmethoxy-5-trifluoromethyl-pyridine-2-carboxylic acid [1-methyl-1-(5-methyl-[1,2,4]oxadiazol-3-yl)-ethyl]-amide

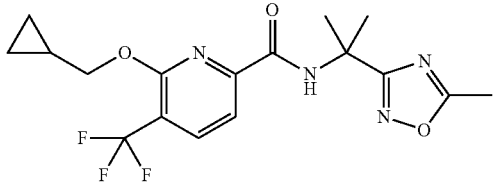 [SMILES: Cc1nc(C(C)(C)NC(=O)c2ccc(C(F)(F)F)c(OCC3CC3)n2)no1]

The title compound was synthesized in analogy to Example 1, using 6-cyclopropylmethoxy-5-trifluoromethyl-pyridine-2-carboxylic acid (Example 113 d) and α,α,5-trimethyl-1,2,4-oxadiazole-3-methanamine (CAN 1153831-97-0) as starting materials, MS (EI): m/e=385.1 [M+H]⁺.

Example 121

6-Cyclopropylmethoxy-5-trifluoromethyl-pyridine-2-carboxylic acid (1-methyl-1-thiazol-2-yl-ethyl)-amide

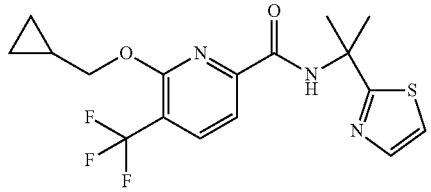 [SMILES: CC(C)(NC(=O)c1ccc(C(F)(F)F)c(OCC2CC2)n1)c1nccs1]

The title compound was synthesized in analogy to Example 1, using 6-cyclopropylmethoxy-5-trifluoromethyl-pyridine-2-carboxylic acid (Example 113 d) and α,α-dimethyl-2-thiazolemethanamine (CAN 1082393-38-1) as starting materials, MS (EI): m/e=386.0 [M+H]⁺.

Example 122

6-Cyclohexyl-pyridine-2-carboxylic acid (2-hydroxymethyl-cyclohexyl)-amide

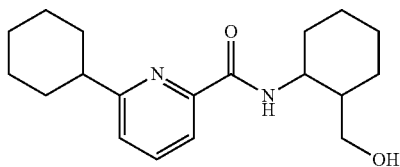 [SMILES: O=C(NC1CCCCC1CO)c1cccc(C2CCCCC2)n1]

The title compound was synthesized in analogy to Example 1, using 6-cyclohexyl-pyridine-2-carboxylic acid (Example 7 b) and 2-amino-cyclohexanemethanol (CAN 89854-92-2) as starting materials, MS (EI): m/e=317.2 [M+H]⁺.

Example 123

6-Cyclopropylmethoxy-5-(tetrahydro-furan-2-yl)-pyridine-2-carboxylic acid [1-methyl-1-(5-methyl-[1,2,4]oxadiazol-3-yl)-ethyl]-amide

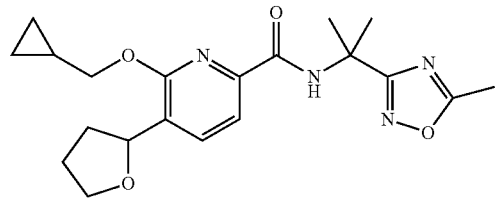 [SMILES: Cc1nc(C(C)(C)NC(=O)c2ccc(C3CCCO3)c(OCC3CC3)n2)no1]

The title compound was synthesized in analogy to Example 1, using the mixture of 6-(cyclopropylmethoxy)-5-(tetrahydrofuran-3-yl)-pyridine-2-carboxylic acid and 6-(cyclopropylmethoxy)-5-(tetrahydrofuran-2-yl)-pyridine-2-carboxylic acid (mixture from Example 114 d) and α,α,5-trimethyl-1,2,4-oxadiazole-3-methanamine (CAN 1153831-97-0) as starting materials, MS (EI): m/e=387.2 [M+H]⁺.

Example 124

6-Cyclopropylmethoxy-5-(tetrahydro-furan-3-yl)-pyridine-2-carboxylic acid [1-methyl-1-(5-methyl-[1,2,4]oxadiazol-3-yl)-ethyl]-amide

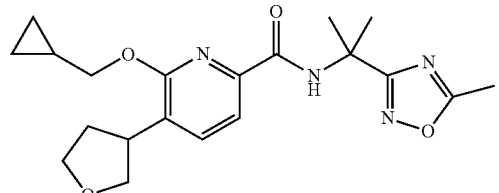

The title compound was synthesized in analogy to Example 1, using the mixture of 6-(cyclopropylmethoxy)-5-(tetrahydrofuran-3-yl)-pyridine-2-carboxylic acid and 6-(cyclopropylmethoxy)-5-(tetrahydrofuran-2-yl)-pyridine-2-carboxylic acid (mixture from Example 114 d), and α,α,5-trimethyl-1,2,4-oxadiazole-3-methanamine (CAN 1153831-97-0) as starting materials, MS (EI): m/e=387.2 [M+H]⁺.

Example 125

6-(3-Chloro-phenyl)-5-(tetrahydro-furan-2-yl)-pyridine-2-carboxylic acid [1-methyl-1-(5-methyl-[1,2,4]oxadiazol-3-yl)-ethyl]-amide a) 6-(3-Chlorophenyl)-5-(tetrahydrofuran-2-yl)-pyridine-2-carboxylic acid methyl ester

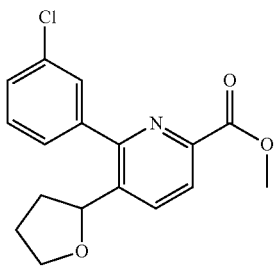 [SMILES: COC(=O)c1ccc(C2CCCO2)c(-c2cccc(Cl)c2)n1]

A solution of 6-bromo-5-(tetrahydrofuran-2-yl)-pyridine-2-carboxylic acid methyl ester (mixture of example 101d, 0.296 g, 1 mmol), 3-chlorophenylboronic acid (CAN 63503-60-6, 0.24 g, 1.5 mmol), 1,1'-bis(diphenylphosphino)ferrocene-palladium(II) dichloride methylene chloride complex (CAN 95464-05-4, 34 mg) and cesium carbonate (CAN 534-17-8, 1 g, 3 mmol) in DMF (10 mL) was stirred overnight at 80° C. under a nitrogen atmosphere. After filtration, the reaction mixture was poured into 20 mL H₂O and washed with ethyl acetate (2×20 mL). The organic layer was concentrated under reduced pressure to provide the title compound (0.3 g, 91%) as black oil which was used in the next step without further purification; MS (EI): m/e=318.1 [M+H]⁺.

b) 6-(3-Chloro-phenyl)-5-(tetrahydro-furan-2-yl)-pyridine-2-carboxylic acid

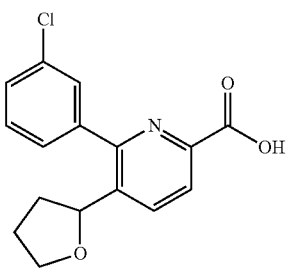 [SMILES: O=C(O)c1ccc(C2CCCO2)c(-c2cccc(Cl)c2)n1]

A mixture of 6-(3-chlorophenyl)-5-(tetrahydrofuran-2-yl)-pyridine-2-carboxylic acid methyl ester (0.3 g, 1 mmol) and lithium hydroxide monohydrate (CAN 1310-66-3, 130 mg, 3 mmol) in THF/H₂O 1/1 (20 mL) was stirred at room temperature for 1 h. After removal of the organic solvent under reduced pressure the aqueous phase was washed with ethyl acetate (10 mL) and acidified with 1 N HCl to pH=3. The resulting solution was extracted with ethyl acetate (2×20 mL). The organic layer was concentrated under reduced pressure to give the title compound (0.28 g, 98%) as black oil which was used in the next step without further purification; MS (EI): m/e=304.0 [M+H]⁺.

c) 6-(3-Chloro-phenyl)-5-(tetrahydro-furan-2-yl)-pyridine-2-carboxylic acid [1-methyl-1-(5-methyl-[1,2,4]oxadiazol-3-yl)-ethyl]-amide

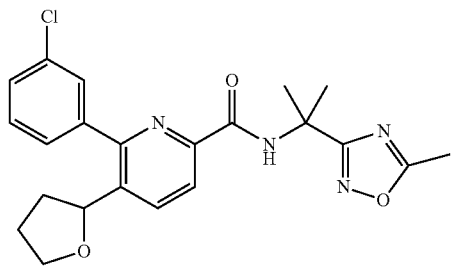 [SMILES: Cc1nc(C(C)(C)NC(=O)c2ccc(C3CCCO3)c(-c3cccc(Cl)c3)n2)no1]

The title compound was synthesized in analogy to Example 1, using 6-(3-chloro-phenyl)-5-(tetrahydro-furan-2-yl)-pyridine-2-carboxylic acid and α,α,5-trimethyl-1,2,4-oxadiazole-3-methanamine (CAN 1153831-97-0) as starting materials, MS (EI): m/e=427.1 [M+H]⁺.

Example 126

6-(3-Chloro-phenyl)-5-(tetrahydro-furan-2-yl)-pyridine-2-carboxylic acid (1-methyl-1-oxazol-2-yl-ethyl)-amide

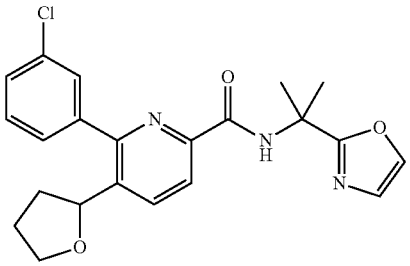 [SMILES: CC(C)(NC(=O)c1ccc(C2CCCO2)c(-c2cccc(Cl)c2)n1)c1ncco1]

The title compound was synthesized in analogy to Example 1, using 6-(3-chloro-phenyl)-5-(tetrahydro-furan-2-yl)-pyridine-2-carboxylic acid (Example 125 b) and α,α-dimethyl-2-oxazolemethanamine (CAN 1211519-76-4) as starting materials, MS (EI): m/e=412.1 [M+H]⁺.

Example 127

6-(3-Chloro-phenyl)-5-(tetrahydro-furan-2-yl)-pyridine-2-carboxylic acid (1-methyl-1-thiazol-2-yl-ethyl)-amide

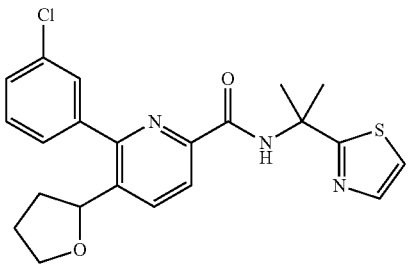 [SMILES: CC(C)(NC(=O)c1ccc(C2CCCO2)c(-c2cccc(Cl)c2)n1)c1nccs1]

The title compound was synthesized in analogy to Example 1, using 6-(3-chloro-phenyl)-5-(tetrahydro-furan-2-yl)-pyridine-2-carboxylic acid (Example 125 b) and α,α-dimethyl-2-thiazolemethanamine (CAN 1082393-38-1) as starting materials, MS (EI): m/e=428.1 [M+H]⁺.

Example 128

6-(3-Chloro-phenyl)-5-cyclopentyl-pyridine-2-carboxylic acid (1-methyl-1-thiazol-2-yl-ethyl)-amide

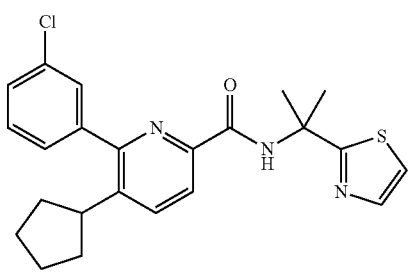 [SMILES: CC(C)(NC(=O)c1ccc(C2CCCC2)c(-c2cccc(Cl)c2)n1)c1nccs1]

The title compound was synthesized in analogy to Example 1, using 6-(3-chloro-phenyl)-5-cyclopentyl-pyridine-2-carboxylic acid (Example 106 e) and α,α-dimethyl-2-thiazolemethanamine (CAN 1082393-38-1) as starting materials, MS (EI): m/e=426.1 [M+H]$^+$.

Example 129

6-Cyclopropylmethoxy-5-trifluoromethyl-pyridine-2-carboxylic acid (1-methyl-1-oxazol-2-yl-ethyl)-amide

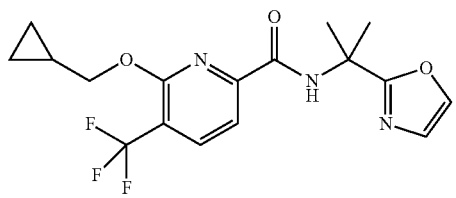 [SMILES: CC(C)(NC(=O)c1ccc(C(F)(F)F)c(OCC2CC2)n1)c1ncco1]

The title compound was synthesized in analogy to Example 1, using 6-cyclopropylmethoxy-5-trifluoromethyl-pyridine-2-carboxylic acid (Example 113 d) and α,α-dimethyl-2-oxazolemethanamine (CAN 1211519-76-4) as starting materials, MS (EI): m/e=370.1 [M+H]$^+$.

Example 130

6-Cyclopropylmethoxy-5-methyl-pyridine-2-carboxylic acid ((S)-1-carbamoyl-2-cyclopropyl-ethyl)-amide

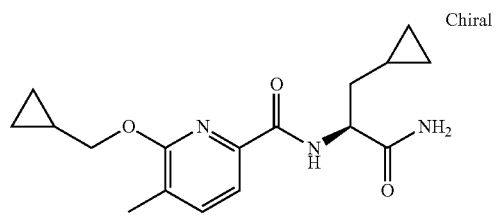 [SMILES: Cc1ccc(C(=O)N[C@@H](CC2CC2)C(N)=O)nc1OCC1CC1]

The title compound was synthesized in analogy to Example 1, using 6-cyclopropylmethoxy-5-methyl-pyridine-2-carboxylic acid (Example 36 d) and (S)-2-amino-3-cyclopropyl-propionamide (CAN 156077-93-9) as starting materials, MS (EI): m/e=318.2 [M+H]$^+$.

Example 131

6-Cyclopropylmethoxy-5-(3-hydroxy-azetidin-1-yl)-pyridine-2-carboxylic acid ((S)-1-carbamoyl-3-methyl-butyl)-amide

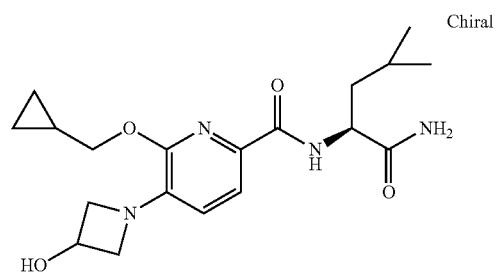 [SMILES: CC(C)C[C@H](NC(=O)c1ccc(N2CC(O)C2)c(OCC2CC2)n1)C(N)=O]

The title compound was synthesized in analogy to Example 1, using 6-cyclopropylmethoxy-5-(3-hydroxy-azetidin-1-yl)-pyridine-2-carboxylic acid (Example 75 a) and (2S)-2-amino-4-methyl-pentanamide (CAN 687-51-4) as starting materials, MS (EI): m/e=377.2 [M+H]$^+$.

Example 132

6-Cyclopropylmethoxy-5-(3,3-difluoro-azetidin-1-yl)-pyridine-2-carboxylic acid ((S)-1-carbamoyl-3-methyl-butyl)-amide

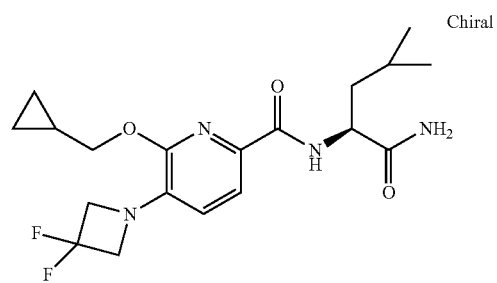 [SMILES: CC(C)C[C@H](NC(=O)c1ccc(N2CC(F)(F)C2)c(OCC2CC2)n1)C(N)=O]

The title compound was synthesized in analogy to Example 1, using 6-cyclopropylmethoxy-5-(3,3-difluoro-azetidin-1-yl)-pyridine-2-carboxylic acid (Example 69 b) and (2S)-2-amino-4-methyl-pentanamide (CAN 687-51-4) as starting materials, MS (EI): m/e=397.2 [M+H]$^+$.

Example 133

5-Cyclopropylamino-6-cyclopropylmethoxy-pyridine-2-carboxylic acid ((S)-1-carbamoyl-2-cyclopropyl-ethyl)-amide a) 5-(Cyclopropylamino)-6-(cyclopropylmethoxy)-pyridine-2-carboxylic acid methyl ester

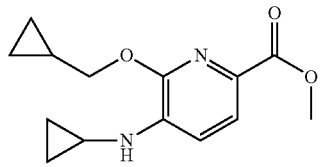 [SMILES: COC(=O)c1ccc(NC2CC2)c(OCC2CC2)n1]

Cyclopropanamine (CAS 765-30-0, 158 mg, 2.8 mmol), bis(diphenylphosphino)-1,1'-binaphthalene (CAS 98327-87-8, 115 mg, 0.19 mmol), tris(dibenzylideneacetone)dipalladium (CAS 51364-51-3, 84 mg, 0.093 mmol) and cesium carbonate (CAS 534-17-8, 1.8 g, 6.6 mmol) were added to solution of 5-bromo-6-(cyclopropylmethoxy)-pyridine-2-carboxylic acid methyl ester (Example 114 a, 530 mg, 1.85 mmol) in toluene (20 mL) under a nitrogen atmosphere. The reaction mixture was stirred overnight at 110° C. and concentrated in vacuo. The residue was dissolved in water and extracted with ethyl acetate (30 mL). The pH of the aqueous layer was adjusted to 2 by addition of 1 N HCl, the resulting precipitate was collected by filtration, dried in vacuo and purified by column chromatography (silica gel, 50 g, 50% ethyl acetate in petroleum ether) to yield the title compound (400 mg, 82%) as a yellow solid; MS (EI): m/e=263.1 [M+H]$^+$.

b) 5-Cyclopropylamino-6-cyclopropylmethoxy-pyridine-2-carboxylic acid

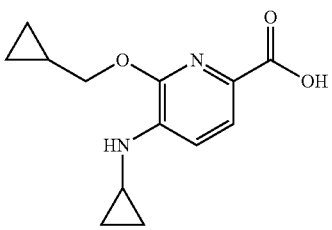 [SMILES: O=C(O)c1ccc(NC2CC2)c(OCC2CC2)n1]

A solution of 5-(cyclopropylamino)-6-(cyclopropylmethoxy)-pyridine-2-carboxylic acid methyl ester (400 mg, 1.53 mmol), sodium hydroxide (244 mg, 6.1 mmol) in THF/H$_2$O 1/1 (10 mL) was stirred for 1 h at room temperature. The reaction mixture was concentrated under reduced pressure. Water was added and the pH was adjusted to 2 by addition of 1 N HCl. Extraction with ethyl acetate (30 mL) was followed by washing with brine (6×30 mL). The organic layer was dried over sodium sulfate and concentrated in vacuo. The residue was purified by column chromatography (silica gel, 50 g, 50% ethyl acetate in petroleum ether) to yield the title compound (350 mg, 92%) as yellow solid; MS (EI): m/e=249.3 [M+H]$^+$.

c) 5-Cyclopropylamino-6-cyclopropylmethoxy-pyridine-2-carboxylic acid ((S)-1-carbamoyl-2-cyclopropyl-ethyl)-amide

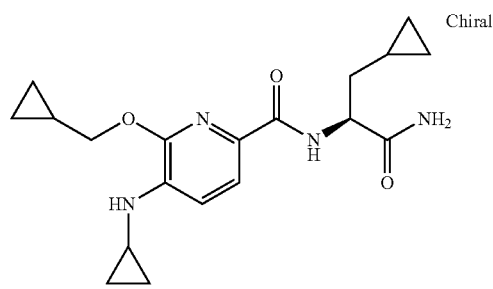 [SMILES: NC(=O)[C@H](CC1CC1)NC(=O)c1ccc(NC2CC2)c(OCC2CC2)n1]

The title compound was synthesized in analogy to Example 1, using 5-cyclopropylamino-6-cyclopropylmethoxy-pyridine-2-carboxylic acid and (S)-2-amino-3-cyclopropyl-propionamide (CAN 156077-93-9) as starting materials, MS (EI): m/e=359.2 [M+H]$^+$.

Example 134

5-Cyclopropylamino-6-cyclopropylmethoxy-pyridine-2-carboxylic acid ((S)-1-carbamoyl-3-methyl-butyl)-amide

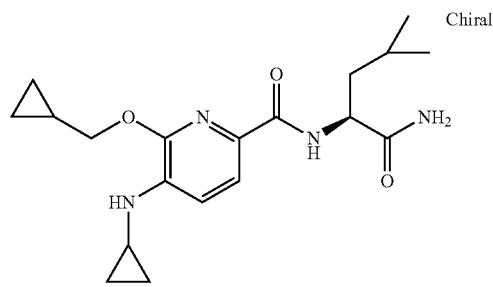 [SMILES: CC(C)C[C@H](NC(=O)c1ccc(NC2CC2)c(OCC2CC2)n1)C(N)=O]

The title compound was synthesized in analogy to Example 1, using 5-cyclopropylamino-6-cyclopropylmethoxy-pyridine-2-carboxylic acid (Example 133 b) and (2S)-2-amino-4-methyl-pentanamide (CAN 687-51-4) as starting materials, MS (EI): m/e=361.3 [M+H]$^+$.

Example 135

6-Cyclopropylmethoxy-5-(3,3-difluoro-azetidin-1-yl)-pyridine-2-carboxylic acid ((S)-1-cyclopropylmethyl-2-hydroxy-2-methyl-propyl)-amide a) (S)-Methyl 2-(tert-butoxycarbonylamino)-3-cyclopropylpropanoate

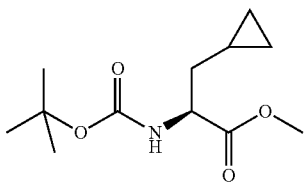 [SMILES: COC(=O)[C@H](CC1CC1)NC(=O)OC(C)(C)C]

To a mixture of (S)-2-(tert-butoxycarbonylamino)-3-cyclopropylpropanoic acid (CAN 89483-06-7, 6.792 g, 30 mmol) and K$_2$CO$_3$ (8.173 g, 59 mmol) in DMF (100 mL) was added MeI (10.37 g, 73 mmol). The reaction mixture was stirred overnight at room temperature. After filtration, the filtrate was concentrated to give the title compound as yellow oil (6.44 g, 89%); MS (EI): m/e=266.2 [M+Na]$^+$.

b) (S)-tert-Butyl 1-cyclopropyl-3-hydroxy-3-methylbutan-2-ylcarbamate

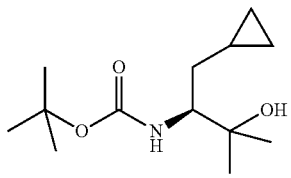 [SMILES: CC(C)(C)OC(=O)N[C@@H](CC1CC1)C(C)(C)O]

To a solution of (S)-methyl 2-(tert-butoxycarbonylamino)-3-cyclopropylpropanoate (0.972 g, 4 mmol) in THF (20 mL) was added a solution of MeMgBr in diethyl ether (3 M, 3.34 mL, 10 mmol) at 0° C. The resulting mixture was stirred at 0° C. for 3 h. Then it was quenched with water. The mixture was diluted with ethyl acetate (20 mL) and brine (20 mL). The organic layer was washed with brine (20 mL) again, dried over anhydrous sodium sulfate and concentrated to give the title compound as white solid (0.8 g, 82%); MS (EI): m/e=266.2 [M+Na]$^+$.

c) (S)-3-Amino-4-cyclopropyl-2-methyl-butan-2-ol

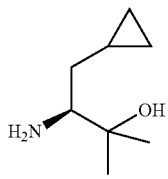

A solution of (S)-tert-butyl 1-cyclopropyl-3-hydroxy-3-methylbutan-2-ylcarbamate (0.8 g, 3 mmol) in ethyl acetate was saturated with hydrochloride (10 mL) and stirred for 1 h at room temperature. After diluting with water (20 mL), the layers were separated and the water phase was washed with ethyl acetate (20 mL). Then it was adjusted with 1 N NaOH to pH=8~9 and extracted with methylene chloride (3×20 mL). The combined organic layer was dried over anhydrous sodium sulfate and concentrated to give the title compound as yellow oil (0.3 g, 64%); MS (EI): m/e=144.2 [M+Na]$^+$.

d) 6-Cyclopropylmethoxy-5-(3,3-difluoro-azetidin-1-yl)-pyridine-2-carboxylic acid ((S)-1-cyclopropylmethyl-2-hydroxy-2-methyl-propyl)-amide

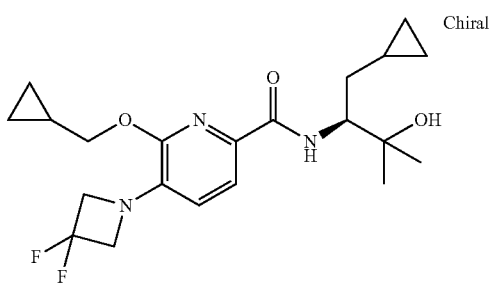 [SMILES: CC(C)(O)[C@H](CC1CC1)NC(=O)c1ccc(N2CC(F)(F)C2)c(OCC2CC2)n1]

The title compound was synthesized in analogy to Example 1, using 6-cyclopropylmethoxy-5-(3,3-difluoro-azetidin-1-yl)-pyridine-2-carboxylic acid (Example 69 b) and (S)-3-amino-4-cyclopropyl-2-methyl-butan-2-ol as starting materials, MS (EI): m/e=410.2 [M+H]$^+$.

Example 136

6-Cyclopropylmethoxy-5-(tetrahydro-furan-3-yl)-pyridine-2-carboxylic acid ((S)-1-carbamoyl-2-cyclopropyl-ethyl)-amide

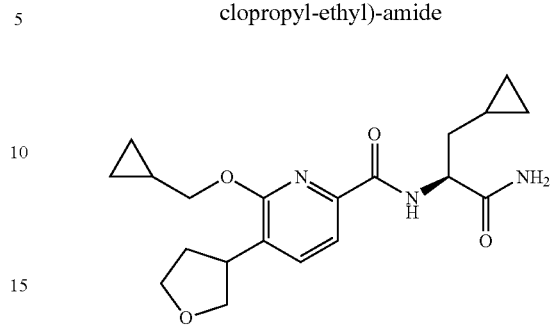

The title compound was synthesized in analogy to Example 1, using the mixture of 6-(cyclopropylmethoxy)-5-(tetrahydrofuran-3-yl)-pyridine-2-carboxylic acid and 6-(cyclopropylmethoxy)-5-(tetrahydrofuran-2-yl)-pyridine-2-carboxylic acid (mixture from Example 114 d), and (S)-2-amino-3-cyclopropyl-propionamide (CAN 156077-93-9) as starting materials, MS (EI): m/e=374.2 [M+H]$^+$.

Example 137

6-Cyclopropylmethoxy-5-(3,3-difluoro-azetidin-1-yl)-pyridine-2-carboxylic acid (2-hydroxy-cyclohexyl)-amide

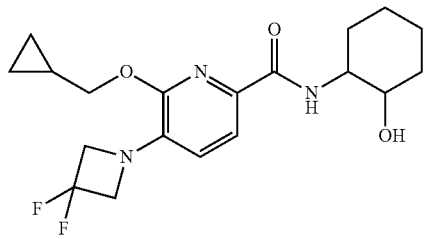 [SMILES: O=C(NC1CCCCC1O)c1ccc(N2CC(F)(F)C2)c(OCC2CC2)n1]

The title compound was synthesized in analogy to Example 1, using 6-cyclopropylmethoxy-5-(3,3-difluoro-azetidin-1-yl)-pyridine-2-carboxylic acid (Example 69 b) and 2-amino-cyclohexanol (CAN 6850-38-0) as starting materials, MS (EI): m/e=382.2 [M+H]$^+$.

Example 138

6-Cyclopropylmethoxy-5-(3,3-difluoro-azetidin-1-yl)-pyridine-2-carboxylic acid [(S)-2-cyclopropyl-1-(5-methyl-[1,2,4]oxadiazol-3-yl)-ethyl]-amide

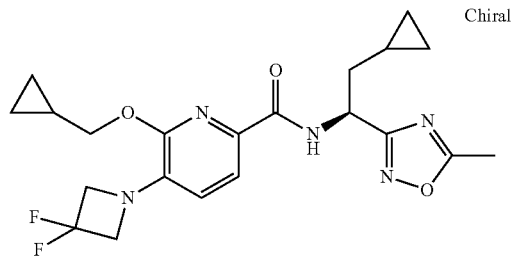 [SMILES: Cc1nc([C@H](CC2CC2)NC(=O)c2ccc(N3CC(F)(F)C3)c(OCC3CC3)n2)no1]

The title compound was synthesized in analogy to Example 1, using 6-cyclopropylmethoxy-5-(3,3-difluoro-azetidin-1-yl)-pyridine-2-carboxylic acid (Example 69 b) and (S)-2-cyclopropyl-1-(5-methyl-[1,2,4]oxadiazol-3-yl)-ethylamine (Example 38 e) as starting materials, MS (EI): m/e=434.2 [M+H]⁺.

Example 139

5-Cyclopropyl-6-cyclopropylmethoxy-pyridine-2-carboxylic acid ((S)-1-cyclopropylmethyl-2-hydroxy-2-methyl-propyl)-amide

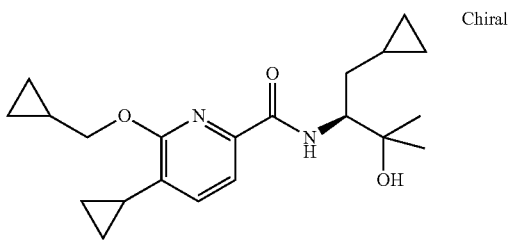 [SMILES: CC(C)(O)[C@H](CC1CC1)NC(=O)c1ccc(C2CC2)c(OCC2CC2)n1]

The title compound was synthesized in analogy to Example 1, using 5-cyclopropyl-6-cyclopropylmethoxy-pyridine-2-carboxylic acid (Example 42 a) and (S)-3-amino-4-cyclopropyl-2-methyl-butan-2-ol (Example 135 c) as starting materials, MS (EI): m/e=359.2 [M+H]⁺.

Example 140

6-(3-Chloro-phenyl)-5-(3,3-difluoro-azetidin-1-yl)-pyridine-2-carboxylic acid ((S)-1-carbamoyl-3-methyl-butyl)-amide a) 6-(3-Chloro-phenyl)-5-(3,3-difluoro-azetidin-1-yl)-pyridine-2-carboxylic acid

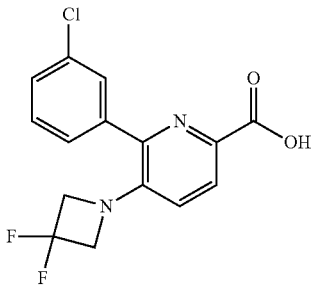 [SMILES: O=C(O)c1ccc(N2CC(F)(F)C2)c(-c2cccc(Cl)c2)n1]

6-Chloro-5-(3,3-difluoroazetidin-1-yl)-pyridine-2-carboxylic acid methyl ester (Example 69 a, 0.3 g, 1.15 mmol), 1,1'-bis(diphenylphosphino)ferrocene-palladium(II)dichloride methylene chloride complex (CAN 72287-26-4, 47 mg, 0.058 mmol) and cesium carbonate (CAN 534-17-8, 0.56 g, 1.72 mmol) were added to a solution of 3-chlorophenylboronic acid (CAN 63503-60-6, 0.27 g, 1.72 mmol) in water (20 mL) and DMF (10 mL). The mixture was stirred for 48 h at 100° C. The reaction mixture was adjusted to pH=3 and extracted with methylene chloride (3×20 mL). The organic layers were combined, dried over sodium sulfate and concentrated to give the crude product (110 mg, 30%); MS (EI): 325.0 [M+H]⁺.

b) 6-(3-Chloro-phenyl)-5-(3,3-difluoro-azetidin-1-yl)-pyridine-2-carboxylic acid ((S)-1-carbamoyl-3-methyl-butyl)-amide

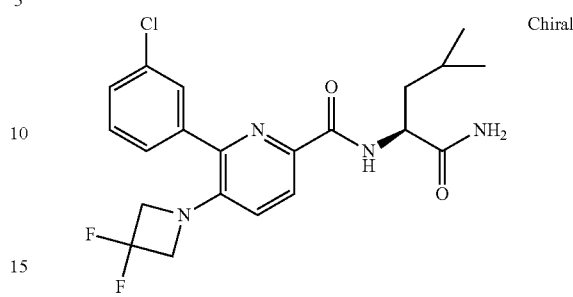

The title compound was synthesized in analogy to Example 1, using 6-(3-chloro-phenyl)-5-(3,3-difluoro-azetidin-1-yl)-pyridine-2-carboxylic acid and (2S)-2-amino-4-methyl-pentanamide (CAN 687-51-4) as starting materials, MS (EI): m/e=437.2 [M+H]⁺.

Example 141

6-Cyclopropylmethoxy-5-(tetrahydro-furan-3-yl)-pyridine-2-carboxylic acid (2-hydroxy-1,1-dimethyl-ethyl)-amide

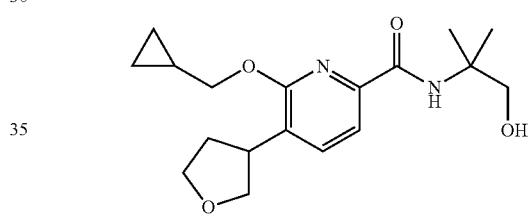

The title compound was synthesized in analogy to Example 1, using the mixture of 6-(cyclopropylmethoxy)-5-(tetrahydrofuran-3-yl)-pyridine-2-carboxylic acid and 6-(cyclopropylmethoxy)-5-(tetrahydrofuran-2-yl)-pyridine-2-carboxylic acid (mixture from Example 114 d), and 2-amino-2-methyl-1-propanol (CAN 124-68-5) as starting materials, MS (EI): m/e=335.1 [M+H]⁺.

Example 142

5-Cyclopropyl-6-(2-methoxy-ethoxy)-pyridine-2-carboxylic acid ((S)-1-carbamoyl-3-methyl-butyl)-amide a) 5-Bromo-6-(2-methoxyethoxy)-pyridine-2-carboxylic acid

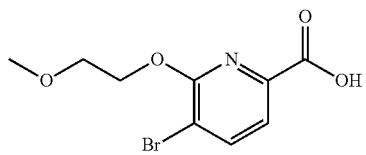

NaH (2.26 g, 66 mmol) was added in portions to a solution of 2-methoxyethanol (30 mL). The mixture was stirred for 30 min at room temperature. Then 5-bromo-6-chloro-pyridine- 2-carboxylic acid methyl ester (Example 9 c, 3 g, 12 mmol) was added and the reaction mixture was heated to 100° C. overnight. The mixture was poured into water and extracted with ethyl acetate (30 mL). The pH of the aqueous layer was adjusted to 2 by addition of 1 N hydrochloric acid and the resulting mixture was extracted with ethyl acetate (3×50 mL). The combined organic extracts were washed three times with brine, dried (sodium sulfate) and evaporated. The crude title compound (2.48 g, yellow solid) was used for the next reaction step without further purification; MS (EI): m/e 276.0 [M+H]⁺.

b) 5-Bromo-6-(2-methoxyethoxy)-pyridine-2-carboxylic acid methyl ester

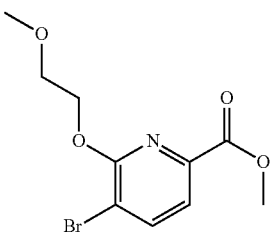

A solution of 5-bromo-6-(2-methoxyethoxy)-pyridine-2-carboxylic acid (2.48 g, 9 mmol), iodomethane (2.55 g, 18 mmol) and sodium carbonate (0.106 g, 9 mmol) in DMF (30 mL) was stirred overnight at room temperature. The reaction mixture was poured into water and extracted with ethyl acetate (3×50 mL). The combined organic extracts were washed three times with brine, dried (sodium sulfate) and evaporated. The residue was purified by column chromatography (silica gel, 50 g, 30% ethyl acetate in petroleum ether) to yield the title compound (1.7 g, 6 mmol, 65%) as yellow solid; MS (EI): m/e 290.0 [M+H]⁺.

c) 5-Cyclopropyl-6-(2-methoxyethoxy)-pyridine-2-carboxylic acid methyl ester

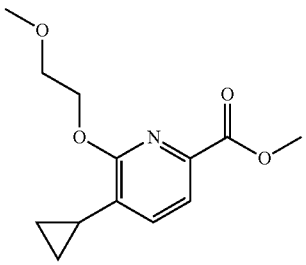

Under an atmosphere of nitrogen, a solution of 5-bromo-6-(2-methoxyethoxy)-pyridine-2-carboxylic acid methyl ester (0.2 g, 0.7 mmol), cyclopropylboronic acid (CAN 411235-57-9, 81 mg, 0.9 mmol), palladium acetate (CAN 3375-31-3, 8 mg, 0.037 mmol), tricyclohexylphosphine (CAN 2622-14-2, 0.021 g, 0.07 mmol) and potassium phosphate (0.54 g, 0.20 mmol) in toluene (20 mL) and water (1 mL) was heated to 110° C. for 48 h. The reaction mixture was concentrated under reduced pressure, dissolved in water, extracted with ethyl acetate (3×30 mL), washed with brine, dried (sodium sulfate) and evaporated to dryness. The residue was purified by column chromatography (silica gel, 10 g, 5% ethyl acetate in petroleum ether) to yield the title compound (0.16 g, 1 mmol, 93%) as yellow oil; MS (EI): m/e 252.2 [M+H]⁺.

d) 5-Cyclopropyl-6-(2-methoxyethoxy)-pyridine-2-carboxylic acid

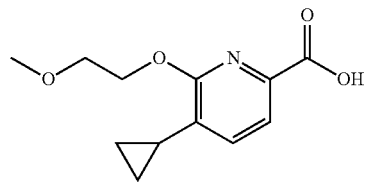 [SMILES: COCCOc1nc(C(=O)O)ccc1C1CC1]

A solution of 5-cyclopropyl-6-(2-methoxyethoxy)-pyridine-2-carboxylic acid methyl ester (0.16 g, 0.6 mmol) and sodium hydroxide (31 mg, 0.7 mmol) in ethanol (40 mL) was heated to 90° C. for 2 h. The reaction mixture was evaporated, dissolved in water and extracted with ethyl acetate (30 mL). The pH of the aqueous layer was adjusted to 2 by addition of 1 N hydrochloric acid, the resulting precipitate was collected by filtration and dried in vacuo to give the title compound (0.11 g, 0.5 mmol; 73%) as yellow oil; MS: m/e=238.1 [M+H]⁺.

e) 5-Cyclopropyl-6-(2-methoxy-ethoxy)-pyridine-2-carboxylic acid ((S)-1-carbamoyl-3-methyl-butyl)-amide

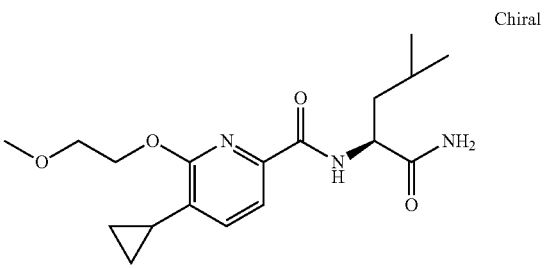 [SMILES: COCCOc1nc(C(=O)N[C@@H](CC(C)C)C(N)=O)ccc1C1CC1]

The title compound was synthesized in analogy to Example 1, using 5-cyclopropyl-6-(2-methoxy-ethoxy)-pyridine-2-carboxylic acid and (2S)-2-amino-4-methyl-pentanamide (CAN 687-51-4) as starting materials, MS (EI): m/e=350.2 [M+H]⁺.

Example 143

7,7-Dimethyl-5,6,7,8-tetrahydro-quinoline-2-carboxylic acid ((R)-2-cyclopropyl-2-hydroxy-propyl)-amide a) 7,7-Dimethyl-5,6,7,8-tetrahydro-1H-quinolin-2-one

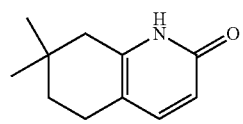

A solution of 3,3-dimethylcyclohexanone (10 g, 71.3 mmol) and methyl propiolate (11.5 g, 136 mmol) in ammonia (390 ml, 2.73 mol) was heated and stirred in an autoclave at 140° C. for 16 h. The autoclave was cooled to ambient temperature, and the reaction mixture was transferred into a 1 L round-bottomed flask and was evaporated in vacuo to give a solid residue which was purified by gradient chromatography on silica with ethyl acetate in heptane to give 7.0 g (55%) of the title compound as colorless oil; LC-MS (UV peak area/EIC) 85%, 178.1228 (M+H)⁺.

b) Trifluoro-methanesulfonic acid 7,7-dimethyl-5,6,7,8-tetrahydro-quinolin-2-yl ester

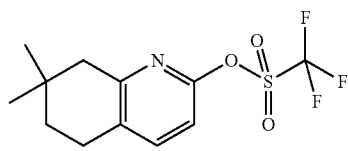 [SMILES: CC1(C)CCc2ccc(OS(=O)(=O)C(F)(F)F)nc2C1]

7,7-Dimethyl-5,6,7,8-tetrahydro-1H-quinolin-2-one (2.0 g, 11.3 mmol) was dissolved in CH₂Cl₂ (50 ml). After addition of triethylamine (1.37 g, 1.89 mL, 13.5 mmol) the mixture was cooled to −45° C. with stirring. Trifluoromethanesulfonic anhydride (4.78 g, 2.86 mL, 16.9 mmol) was added slowly over a period of 10 min at −50 to −45° C. The mixture was stirred for 15 min at this temperature. The cooling-bath was removed and the reaction mixture was stirred for 1 h at room temperature; poured onto ice (50 mL) and stirred for 5 min after adding 20 mL 15% NaOH solution. Phases were separated and the aqueous phase was extracted with CH₂Cl₂ (2×30 mL). The org. layers were combined, washed with 15%-NaOH (2×20 mL), dried with Na₂SO₄, and concentrated in vacuo. The resulting light brown oil was purified by gradient chromatography on silica with ethyl acetate in heptane to give 3.3 g (94%) of the title compound as colorless oil; LC-MS (UV peak area/EIC) 100%, 310.0722 (M+H)⁺.

c) 7,7-Dimethyl-5,6,7,8-tetrahydro-quinoline-2-carboxylic acid methyl ester

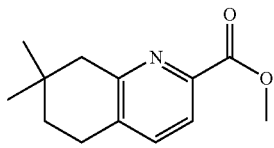

Trifluoro-methanesulfonic acid 7,7-dimethyl-5,6,7,8-tetrahydro-quinolin-2-yl ester (3.1 g, 10.0 mmol) was dissolved in methanol (45 mL) and ethyl acetate (45 mL). PdCl₂(dppf)-CH₂Cl₂ adduct (311 mg, 381 μmol) and triethylamine (1.52 g, 2.1 mL, 15.0 mmol) were added and the mixture was stirred in an autoclave at 110° C. with a CO pressure of 70 bar for 24 h. The solvents were evaporated to give a red-brown oily residue that was purified by gradient chromatography on silica with ethyl acetate in heptane. The chromatography yielded 1.9 g (86%) of the title compound as white solid; LC-MS (UV peak area/EIC) 100%, 220.1335 (M+H)⁺.

d) 7,7-Dimethyl-5,6,7,8-tetrahydro-quinoline-2-carboxylic acid

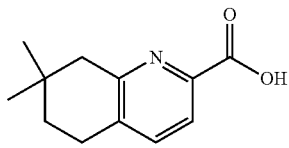

7,7-Dimethyl-5,6,7,8-tetrahydro-quinoline-2-carboxylic acid methyl ester (1.88 g, 8.57 mmol) was dissolved in THF (30 mL) and water (10 mL). Lithium hydroxide monohydrate (616 mg, 25.7 mmol) was added with stirring at room temperature and the reaction mixture was stirred at reflux temperature for 1 h. The mixture was cooled, acidified with 2 N HCl to pH=5 and extracted with ethyl acetate. The organic phases were combined, dried with Na₂SO₄, and concentrated in vacuo. The residue was stirred with ethyl acetate (5 mL) at 40° C.; n-heptane (10 mL) was added and stirring at room temperature continued for 30 min. The precipitate was filtered and dried to give 1.7 g (96%) of the title compound as white solid; MS (ISP): m/e 206.1 [M+H]⁺.

e) 7,7-Dimethyl-5,6,7,8-tetrahydro-quinoline-2-carboxylic acid ((R)-2-cyclopropyl-2-hydroxy-propyl)-amide

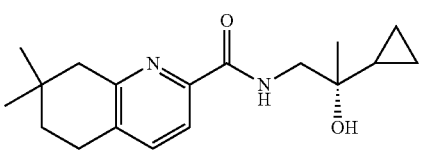 [SMILES: CC1(C)CCc2ccc(C(=O)NC[C@](C)(O)C3CC3)nc2C1]

The title compound was synthesized in analogy to Example 1, using 7,7-dimethyl-5,6,7,8-tetrahydro-quinoline-2-carboxylic acid and (αR)-α-(aminomethyl)-α-methyl-cyclo-propanemethanol (CAN 912454-48-9) as starting materials, LC-MS (UV peak area/EIC) 99.3%, 303.2078 (M+H)⁺.

Example 144

7,7-dimethyl-N-(2-(5-methyl-1,2,4-oxadiazol-3-yl)propan-2-yl)-5,6,7,8-tetrahydroquinoline-2-carboxamide

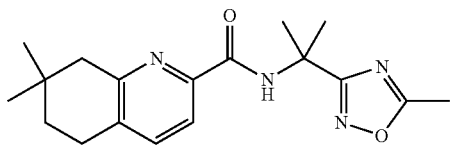

The title compound was synthesized in analogy to Example 1, using 7,7-dimethyl-5,6,7,8-tetrahydro-quinoline-2-carboxylic acid (Example 143 d) and α,α,5-trimethyl-1,2,4-oxadiazole-3-methanamine (CAN 1153831-97-0) as starting materials, LC-MS (UV peak area/EIC) 100%, 329.1977 (M+H)⁺.

Example 145

N-(1-hydroxy-2-methylpropan-2-yl)-7,7-dimethyl-5,6,7,8-tetrahydroquinoline-2-carboxamide

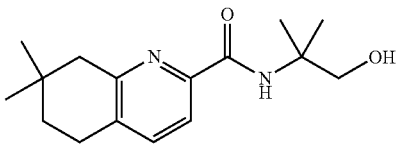 [SMILES: CC1(C)CCc2ccc(C(=O)NC(C)(C)CO)nc2C1]

The title compound was synthesized in analogy to Example 1, using 7,7-dimethyl-5,6,7,8-tetrahydro-quinoline-2-carboxylic acid (Example 143 d) and 2-amino-2-me-

Example 146

6-Cyclopropylmethoxy-5-(3,3-difluoro-azetidin-1-yl)-pyridine-2-carboxylic acid ((S)-2-cyclopropyl-1-thiazol-2-yl-ethyl)-amide

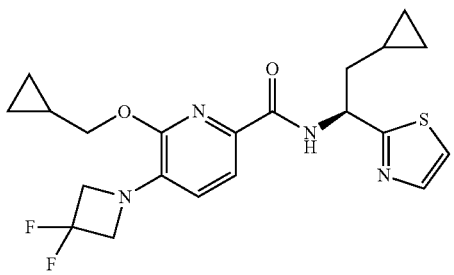 [SMILES: O=C(N[C@@H](CC1CC1)c1nccs1)c1ccc(N2CC(F)(F)C2)c(OCC2CC2)n1]

The title compound was synthesized in analogy to Example 1, using 6-cyclopropylmethoxy-5-(3,3-difluoro-azetidin-1-yl)-pyridine-2-carboxylic acid (Example 69 b) and (S)-2-cyclopropyl-1-thiazol-2-yl-ethylamine (Example 59 b) as starting materials, MS (EI): m/e=435.1 [M+H]⁺.

Example 147

6-Cyclopropylmethoxy-5-(3,3-difluoro-azetidin-1-yl)-pyridine-2-carboxylic acid (pyridin-2-ylmethyl)-amide

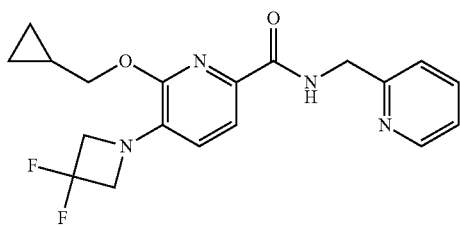 [SMILES: O=C(NCc1ccccn1)c1ccc(N2CC(F)(F)C2)c(OCC2CC2)n1]

The title compound was synthesized in analogy to Example 1, using 6-cyclopropylmethoxy-5-(3,3-difluoro-azetidin-1-yl)-pyridine-2-carboxylic acid (Example 69 b) and pyridin-2-yl-methylamine (CAN 3731-51-9) as starting materials, MS (EI): m/e=375.2 [M+H]⁺.

Example 148

6-Cyclopropylmethoxy-5-(3,3-difluoro-azetidin-1-yl)-pyridine-2-carboxylic acid (2-hydroxy-1,1-dimethyl-ethyl)-amide

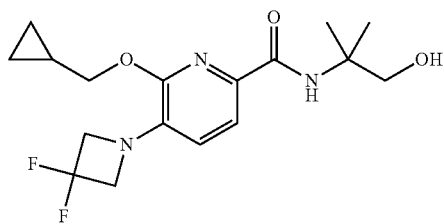 [SMILES: CC(C)(CO)NC(=O)c1ccc(N2CC(F)(F)C2)c(OCC2CC2)n1]

The title compound was synthesized in analogy to Example 1, using 6-cyclopropylmethoxy-5-(3,3-difluoro-azetidin-1-yl)-pyridine-2-carboxylic acid (Example 69 b) and 2-amino-2-methyl-1-propanol (CAN 124-68-5) as starting materials, MS (EI): m/e=356.2 [M+H]⁺.

Example 149

[6-Cyclopropylmethoxy-5-(3,3-difluoro-azetidin-1-yl)-pyridin-2-yl]-((S)-2-hydroxymethyl-pyrrolidin-1-yl)-methanone

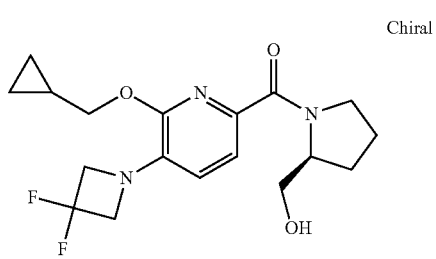 [SMILES: O=C(c1ccc(N2CC(F)(F)C2)c(OCC2CC2)n1)N1CCC[C@H]1CO]

The title compound was synthesized in analogy to Example 1, using 6-cyclopropylmethoxy-5-(3,3-difluoro-azetidin-1-yl)-pyridine-2-carboxylic acid (Example 69 b) and (S)-1-pyrrolidin-2-yl-methanol (CAN 23356-96-9) as starting materials, MS (EI): m/e=368.2 [M+H]⁺.

Example 150

6-Cyclopropylmethoxy-5-(3-hydroxy-oxetan-3-yl)-pyridine-2-carboxylic acid ((S)-1-carbamoyl-3-methyl-butyl)-amide a) 6-Cyclopropylmethoxy-5-(3-hydroxy-oxetan-3-yl)-pyridine-2-carboxylic acid

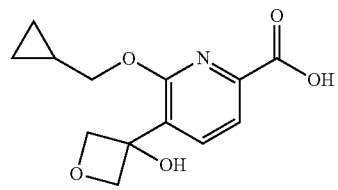 [SMILES: O=C(O)c1ccc(C2(O)COC2)c(OCC2CC2)n1]

Under a nitrogen atmosphere, n-BuLi (3.23 mL, 5.6 mmol) was added dropwise to a solution of 5-bromo-6-cyclopropylmethoxy-pyridine-2-carboxylic acid (Example 9 d, 1.1 g, 4.0 mmol) in THF (50 mL) at −78° C. and stirred for 1 h at this temperature. Then a solution of oxetan-3-one (CAN 6704-31-0, 0.73 g, 10 mmol) in THF (5 mL) was added at −78° C. The reaction mixture was stirred for 1 h at room temperature and quenched with aq. NH₄Cl solution. The pH was adjusted to 2 with conc. HCl. The mixture was extracted with ethyl acetate (3×50 mL), the organic layers were combined, washed with brine (2×50 mL) and dried over Na₂SO₄. The solvent was removed under reduced pressure and the crude product was purified by chromatography over silica gel using petroleum ether/ethyl acetate=1/1 to give the title compound (0.13 g, 30.8%) as a yellow solid; MS (EI): m/e=266.1 [M+H]⁺.

b) 6-Cyclopropylmethoxy-5-(3-hydroxy-oxetan-3-yl)-pyridine-2-carboxylic acid ((S)-1-carbamoyl-3-methyl-butyl)-amide

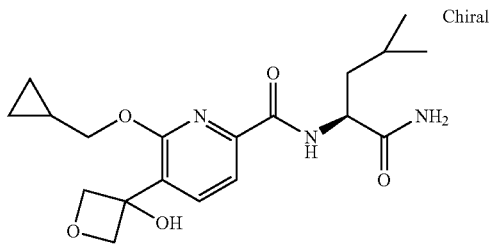 [SMILES: CC(C)C[C@H](NC(=O)c1ccc(C2(O)COC2)c(OCC2CC2)n1)C(N)=O]

The title compound was synthesized in analogy to Example 1, using 6-cyclopropylmethoxy-5-(3-hydroxy-oxetan-3-yl)-pyridine-2-carboxylic acid and (2S)-2-amino-4-methyl-pentanamide (CAN 687-51-4) as starting materials, MS (EI): m/e=378.2 [M+H]⁺.

Example 151

6-(3-Chloro-phenyl)-5-(tetrahydro-furan-3-yl)-pyridine-2-carboxylic acid [1-methyl-1-(5-methyl-[1,2,4]oxadiazol-3-yl)-ethyl]-amide

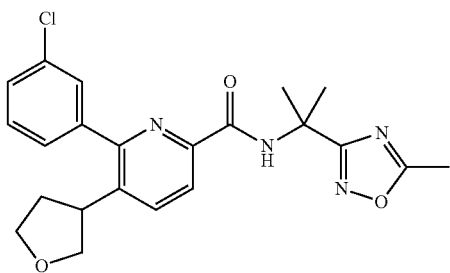 [SMILES: Cc1nc(C(C)(C)NC(=O)c2ccc(C3CCOC3)c(-c3cccc(Cl)c3)n2)no1]

The title compound was synthesized in analogy to Example 1, using 6-(3-chloro-phenyl)-5-(tetrahydro-furan-3-yl)-pyridine-2-carboxylic acid (Example 101.0 and α,α,5-trimethyl-1,2,4-oxadiazole-3-methanamine (CAN 1153831-97-0) as starting materials, MS (EI): m/e=427.1 [M+H]⁺.

Example 152

6-(3-Chloro-phenyl)-5-(3,3-difluoro-azetidin-1-yl)-pyridine-2-carboxylic acid [2-(2-methoxy-ethoxy)-1,1-dimethyl-ethyl]-amide

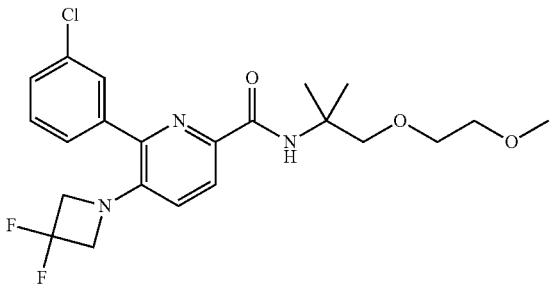 [SMILES: COCCOCC(C)(C)NC(=O)c1ccc(N2CC(F)(F)C2)c(-c2cccc(Cl)c2)n1]

The title compound was synthesized in analogy to Example 1, using 6-(3-chloro-phenyl)-5-(3,3-difluoro-azetidin-1-yl)-pyridine-2-carboxylic acid (Example 140 a) and 2-(2-methoxy-ethoxy)-1,1-dimethyl-ethylamine (CAN 947723-29-7) as starting materials, MS (EI): m/e=454.1 [M+H]⁺.

Example 153

5-Cyclopropyl-6-(2-methoxy-ethoxy)-pyridine-2-carboxylic acid [1-methyl-1-(5-methyl-[1,2,4]oxadiazol-3-yl)-ethyl]-amide

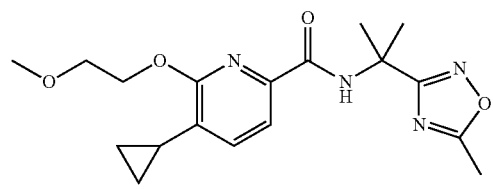 [SMILES: COCCOc1nc(C(=O)NC(C)(C)c2noc(C)n2)ccc1C1CC1]

The title compound was synthesized in analogy to Example 1, using 5-cyclopropyl-6-(2-methoxyethoxy)-pyridine-2-carboxylic acid (Example 142 d) and α,α,5-trimethyl-1,2,4-oxadiazole-3-methanamine (CAN 1153831-97-0) as starting materials, MS (EI): m/e=361.1 [M+H]⁺.

Example 154

5-Cyclopropyl-6-cyclopropylmethoxy-pyridine-2-carboxylic acid (1,1-dimethyl-3-morpholin-4-yl-propyl)-amide

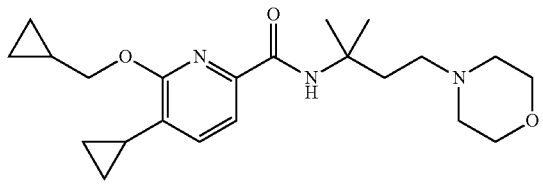 [SMILES: CC(C)(CCN1CCOCC1)NC(=O)c1ccc(C2CC2)c(OCC2CC2)n1]

The title compound was synthesized in analogy to Example 1, using 5-cyclopropyl-6-cyclopropylmethoxy-pyridine-2-carboxylic acid (Example 42 a) and 1,1-dimethyl-3-morpholin-4-yl-propylamine (Example 35 d) as starting materials, MS (EI): m/e=388.3 [M+H]⁺.

Example 155

5-Cyclopropyl-6-(4-fluoro-benzyl)-pyridine-2-carboxylic acid ((S)-1-carbamoyl-3-methyl-butyl)-amide a) 5-Bromo-6-methyl-pyridine-2-carbonitrile

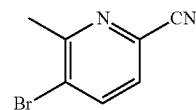

NaCN (4 g, 82 mmol) was added to a solution of 3-bromo-6-fluoro-2-methyl-pyridine (4 g, 21 mmol) in DMSO (100 mL) The mixture was stirred for 2 h at 100° C., poured into H₂O (100 mL) and extracted with ethyl acetate (2×100 mL). The organic layers were dried over Na₂SO₄, concentrated and purified by flash column chromatography (silica gel, 10 g, eluting with 10% ethyl acetate in petroleum ether) to give the title compound (0.6 g, 15%) as white solid; MS (D): m/e=197.0 [M+H]⁺.

b) 5-Cyclopropyl-6-methyl-pyridine-2-carbonitrile

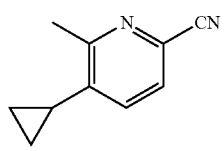

5-Bromo-6-methyl-pyridine-2-carbonitrile (0.5 g, 2.5 mmol), cyclopropylboronic acid (CAN:411235-57-9, 0.36 g, 4 mmol), Pd₂(dba)₃ (CAN:411235-57-9, 0.1 g, 0.2 mmol), xantphos (CAN:161265-03-8, 0.15 g, 0.26 mmol) and Cs₂CO₃ (1.1 g, 3 mmol) were suspended in 1,4-dioxane (30 mL) under a nitrogen atmosphere. The mixture was stirred for 12 h at 110° C., filtered, concentrated under reduced pressure and purified by column chromatography (silica gel, 5 g, eluting with 10% ethyl acetate in petroleum ether) to give the title compound (0.3 g, 75%) as yellow solid; MS (D): m/e=159.2 [M+H]⁺.

c) 5-Cyclopropyl-6-methyl-1-oxy-pyridine-2-carbonitrile

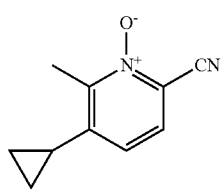

A mixture of 5-cyclopropyl-6-methyl-pyridine-2-carbonitrile (0.2 g, 1.3 mmol) and m-CPBA (0.5 g, 3 mmol) in CH₂Cl₂ (10 mL) was stirred for 12 hours at 60° C. After cooling to ambient temperature, the mixture was filtered, concentrated under reduced pressure and purified by column chromatography (silica gel, 3 g, eluting with 50% ethyl acetate in petroleum ether) to give the title compound (0.2 g, 91%) as yellow solid; MS (D): m/e=175.0 [M+H]⁺.

d) 5-Cyclopropyl-6-hydroxymethyl-pyridine-2-carbonitrile

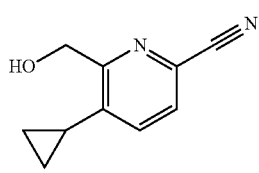 [SMILES: N#Cc1ccc(C2CC2)c(CO)n1]

Trifluoroacetic acid anhydride (CAN 457-25-0, 1 mL) was added to a solution of 5-cyclopropyl-6-methyl-1-oxy-pyridine-2-carbonitrile (0.2 g, 1.1 mmol) in CH₂Cl₂ (10 mL). The reaction mixture was stirred for 12 h at ambient temperature and then partitioned between 6 N NaOH aq. (10 mL) and CH₂Cl₂ (10 mL). The aqueous phase was washed several times with CH₂Cl₂ and the combined organic fractions were dried over Na₂SO₄ and concentrated under reduced pressure. The residue was purified by column chromatography (silica gel, 3 g, eluting with 1% methanol in methylene chloride) to give the title compound (0.1 g, 50%) as yellow oil; MS (EI): m/e=175.2 [M+H]⁺.

e) 6-Bromomethyl-5-cyclopropyl-pyridine-2-carbonitrile

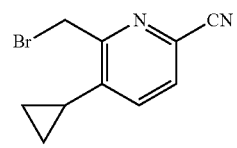

A solution of 5-cyclopropyl-6-hydroxymethyl-pyridine-2-carbonitrile (0.1 g, 0.6 mmol), CBr₄ (0.8 g, 1.2 mmol), PPh₃ (0.3 g, 1.2 mmol) in THF (10 mL) was stirred for 12 h at 40° C. The solvent was removed under reduced pressure and the crude product purified by flash column chromatography (silica gel, 3 g, eluting with 25% ethyl acetate in petroleum ether) to give the title compound (0.1 g, 74%) as yellow solid; MS (EI): m/e=236.9 [M+H]⁺.

f) 5-Cyclopropyl-6-(4-fluoro-benzyl)-pyridine-2-carbonitrile

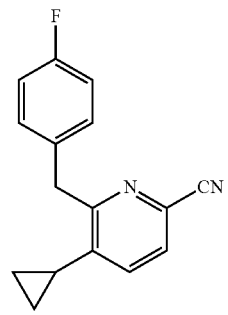 [SMILES: N#Cc1ccc(C2CC2)c(Cc2ccc(F)cc2)n1]

A mixture of 6-bromomethyl-5-cyclopropyl-pyridine-2-carbonitrile (0.1 g, 0.4 mmol), 4-fluoro-benzylboronic acid (CAN 1765-93-1, 0.1 g, 0.7 mmol), Pd(dppf)Cl₂ (CAN 95464-05-4, 50 mg, 0.068 mmol), Cs₂CO₃ (0.2 g, 0.6 mmol) in 1.4-dioxane (10 mL) was stirred for 12 h at 110° C. under a nitrogen atmosphere. The mixture was filtered, concentrated and purified by flash column chromatography (silica gel, 3 g, eluting with 25% ethyl acetate in petroleum ether) to give the title compound (80 mg, 75%) as yellow solid; MS (EI): m/e=253.2 [M+H]⁺.

g) 5-Cyclopropyl-6-(4-fluoro-benzyl)-pyridine-2-carboxylic acid

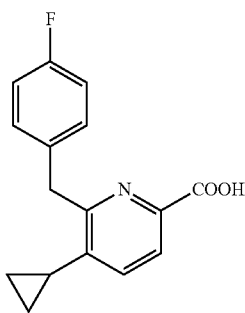 [SMILES: O=C(O)c1ccc(C2CC2)c(Cc2ccc(F)cc2)n1]

A solution of 5-cyclopropyl-6-(4-fluoro-benzyl)-pyridine-2-carbonitrile (0.08 g, 0.3 mmol) and NaOH (0.05 g, 1.2 mmol) in H$_2$O (10 mL) was stirred for 2 hours at 90° C. The pH was adjusted to 3 with 1 M HCl. The mixture was extracted with ethyl acetate (3×10 mL), dried over Na$_2$SO$_4$, concentrated under reduced pressure and purified by column chromatography to give the title compound (0.06 g, 70%) as yellow solid; MS (EI): m/e=272.1 [M+H]$^+$.

h) 5-Cyclopropyl-6-(4-fluoro-benzyl)-pyridine-2-carboxylic acid ((S)-1-carbamoyl-3-methyl-butyl)-amide

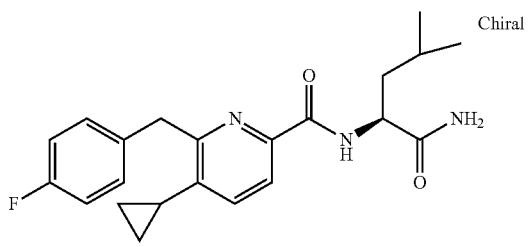 [SMILES: CC(C)C[C@H](NC(=O)c1ccc(C2CC2)c(Cc2ccc(F)cc2)n1)C(N)=O]

The title compound was synthesized in analogy to Example 1, using 5-cyclopropyl-6-(4-fluoro-benzyl)-pyridine-2-carboxylic acid and (2S)-2-amino-4-methyl-pentanamide (CAN 687-51-4) as starting materials, MS (EI): m/e=384.2 [M+H]$^+$.

Example 156

6-(3-Chloro-phenyl)-5-(3,3-difluoro-azetidin-1-yl)-pyridine-2-carboxylic acid (1-methyl-1-thiazol-2-yl-ethyl)-amide

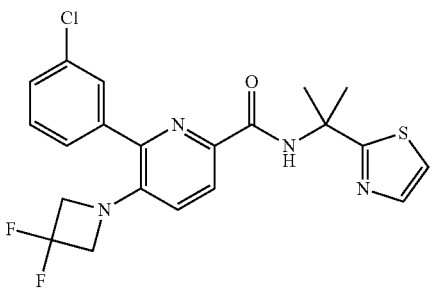 [SMILES: CC(C)(NC(=O)c1ccc(N2CC(F)(F)C2)c(-c2cccc(Cl)c2)n1)c1nccs1]

The title compound was synthesized in analogy to Example 1, using 6-(3-chloro-phenyl)-5-(3,3-difluoro-azetidin-1-yl)-pyridine-2-carboxylic acid (Example 140 a) and α,α-dimethyl-2-thiazolemethanamine (CAN 1082393-38-1) as starting materials, MS (EI): m/e=449.1 [M+H]$^+$.

Example 157

6-Cyclopropylmethoxy-5-(3,3-difluoro-azetidin-1-yl)-pyridine-2-carboxylic acid [(S)-2-cyclopropyl-1-(2-methoxy-ethoxymethyl)-ethyl]-amide a) (S)-tert-Butyl 1-cyclopropyl-3-hydroxypropan-2-ylcarbamate

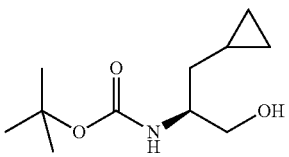

NaBH$_4$ (1.5 g, 39 mmol) was added in portions to a solution of (S)-methyl 2-(tert-butoxycarbonylamino)-3-cyclopropyl-propanoate (Example 135 a, 3.15 g, 13 mmol) in MeOH (30 mL) at room temperature. The mixture was stirred at room temperature for 2 h. H$_2$O (50 mL) was added and a white precipitate formed. The precipitate was collected by filtration and dried to give the title product (1.84 g, 66%) as white solid which was used in the next step without further purification; MS (EI): m/e=238.1 [M+Na]$^+$.

b) (S)-tert-Butyl 1-cyclopropyl-3-(2-methoxyethoxy) propan-2-ylcarbamate

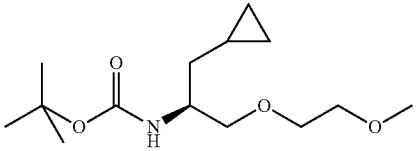 [SMILES: COCCOC[C@H](CC1CC1)NC(=O)OC(C)(C)C]

NaH (70%, 0.504 g, 15 mmol) was added in portions to a solution of (S)-tert-butyl 1-cyclopropyl-3-hydroxypropan-2-ylcarbamate (1.6 g, 7.5 mmol) in THF (30 mL) at room temperature. The mixture was stirred at room temperature for 20 min. 1-Bromo-2-methoxyethane (2.07 g, 15 mmol) was added and stirring was continued for 2 h. The reaction was quenched by careful addition of H$_2$O (5 mL). After evaporation of solvent the residue was diluted with ethyl acetate (20 mL) and H$_2$O (20 mL). The organic layer was washed with brine (20 mL), dried over Na$_2$SO$_4$, and concentrated to give the title product as yellow oil (1.01 g, 50%); MS (EI): m/e=296.2 [M+Na]$^+$.

c) (S)-1-Cyclopropyl-3-(2-methoxyethoxy)propan-2-amine

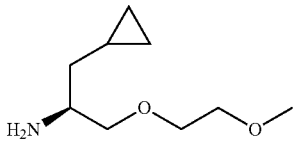

(S)-tert-Butyl 1-cyclopropyl-3-(2-methoxyethoxy)propan-2-ylcarbamate (1.01 g, 4 mmol) was dissolved in HCl/ethyl acetate (10 mL) and stirred at room temperature for 30 min. Then the reaction mixture was concentrated to give a residue, which was dissolved in H$_2$O (10 mL) and then washed with ethyl acetate (2×10 mL). The pH of the aqueous layer was adjusted to 9~10 with 5 N NaOH solution. After extraction with ethyl acetate (3×20 mL) the combined organic layers were washed with brine (50 mL), dried over Na$_2$SO$_4$ and concentrated to give the title product (0.072 g, 11%) as yellow oil; MS (EI): m/e=174.2 [M+Na]$^+$.

d) 6-Cyclopropylmethoxy-5-(3,3-difluoro-azetidin-1-yl)-pyridine-2-carboxylic acid [(S)-2-cyclopropyl-1-(2-methoxy-ethoxymethyl)-ethyl]-amide

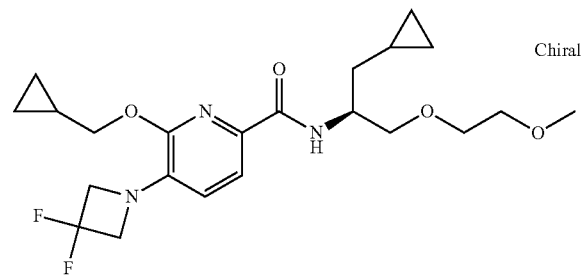 [SMILES: COCCOC[C@H](CC1CC1)NC(=O)c1ccc(N2CC(F)(F)C2)c(OCC2CC2)n1]

The title compound was synthesized in analogy to Example 1, using 6-cyclopropylmethoxy-5-(3,3-difluoro-azetidin-1-yl)-pyridine-2-carboxylic acid (Example 69 b) and (S)-2-cyclopropyl-1-(2-methoxy-ethoxymethyl)-ethylamine as starting materials, MS (EI): m/e=440.1 [M+H]$^+$.

Example 158

5-(3,3-Difluoro-azetidin-1-yl)-6-(2-methoxy-ethoxy)-pyridine-2-carboxylic acid ((S)-1-carbamoyl-3-methyl-butyl)-amide a) 5-(3,3-Difluoroazetidin-1-yl)-6-(2-methoxy-ethoxy)-pyridine-2-carboxylic acid methyl ester

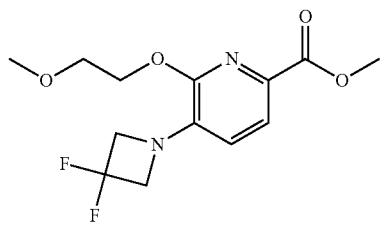

Under a nitrogen atmosphere a mixture of 5-bromo-6-(2-methoxyethoxy)-pyridine-2-carboxylic acid methyl ester (Example 142 b, 0.42 g, 1.45 mmol), 3,3-difluoroazetidine hydrochloride (0.22 g, 1.74 mmol), tris(dibenzylideneacetone)dipalladium (CAN 51364-51-3, 27 mg, 0.03 mmol), (R)-(+)-2,2'-bis(diphenylphosphino)-1,1'-binaphthyl (CAN 76189-55-4, 36 mg, 0.06 mmol) and cesium carbonate (1.4 g, 4.35 mmol) in toluene (50 mL) was stirred at 110° C. overnight. After evaporation of solvents the residue was partitioned between water (30 mL) and ethyl acetate (30 mL) and the aqueous phase was extracted with ethyl acetate (2×30 mL). The combined organic phase was washed with brine (30 mL), dried over anhydrous sodium sulfate, filtered and concentrated to give a residue which was purified by column chromatography (silica gel, 8 g, 15% ethyl acetate in petroleum ether) to give the title compound (0.3 g, 68%) as white solid; MS (EI): m/e=303.1 [M+H]$^+$.

b) 5-(3,3-Difluoro-azetidin-1-yl)-6-(2-methoxy-ethoxy)-pyridine-2-carboxylic acid

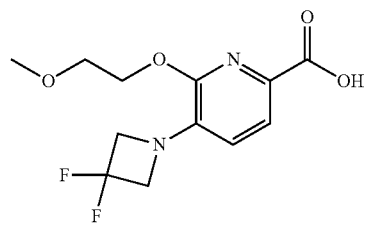 [SMILES: COCCOc1nc(C(=O)O)ccc1N1CC(F)(F)C1]

A solution of 5-(3,3-difluoroazetidin-1-yl)-6-(2-methoxy-ethoxy)-pyridine-2-carboxylic acid methyl ester (0.3 g, 1 mmol) and lithium hydroxide monohydrate (0.25 g, 6 mmol) in THF/H$_2$O (30 mL) was stirred at room temperature for 3 h. After removal of the organic solvent, the aqueous phase was extracted with ethyl acetate (20 mL) and then acidified with 6 N hydrochloric acid to pH 2 to form a precipitate which was collected by filtration and dried under reduced pressure to give the target compound (0.24 g, 84%) as off-white solid which was used directly in the next step without further purification; MS (EI): m/e=289.1 [M+H]$^+$.

c) 5-(3,3-Difluoro-azetidin-1-yl)-6-(2-methoxy-ethoxy)-pyridine-2-carboxylic acid ((S)-1-carbamoyl-3-methyl-butyl)-amide

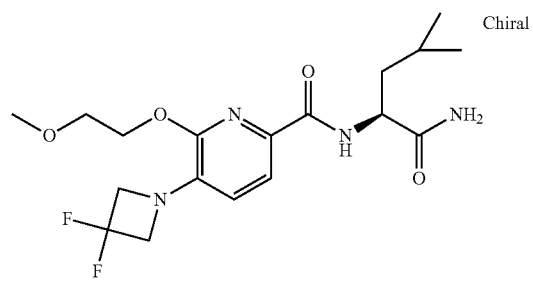 [SMILES: COCCOc1nc(C(=O)N[C@@H](CC(C)C)C(N)=O)ccc1N1CC(F)(F)C1]

The title compound was synthesized in analogy to Example 1, using 5-(3,3-difluoro-azetidin-1-yl)-6-(2-methoxy-ethoxy)-pyridine-2-carboxylic acid and (2S)-2-amino-4-methyl-pentanamide (CAN 687-51-4) as starting materials, MS (EI): m/e=401.1 [M+H]$^+$.

Example 159

5-Cyclopropylamino-6-cyclopropylmethoxy-pyridine-2-carboxylic acid (2-hydroxy-1,1-dimethyl-ethyl)-amide

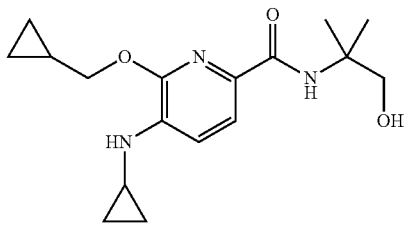 [SMILES: CC(C)(CO)NC(=O)c1ccc(NC2CC2)c(OCC2CC2)n1]

The title compound was synthesized in analogy to Example 1, using 5-cyclopropylamino-6-cyclopropylmethoxy-pyridine-2-carboxylic acid (Example 133 b) and 2-amino-2-methyl-1-propanol (CAN 124-68-5) as starting materials, MS (EI): m/e=401.1 [M+H]$^+$.

Example 160

6-Cyclopropylmethoxy-5-(1-hydroxy-cyclobutyl)-pyridine-2-carboxylic acid [1-methyl-1-(5-methyl-[1,2,4]oxadiazol-3-yl)-ethyl]-amide a) 6-Cyclopropylmethoxy-5-(1-hydroxy-cyclobutyl)-pyridine-2-carboxylic acid

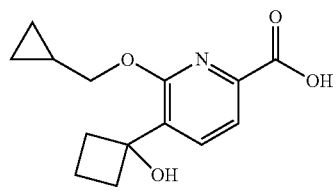 [SMILES: O=C(O)c1ccc(C2(O)CCC2)c(OCC2CC2)n1]

Under nitrogen atmosphere, BuLi (0.58 mL, 0.89 mmol) was added dropwise to a solution of 5-bromo-6-cyclopropylmethoxy-pyridine-2-carboxylic acid (Example 9 d, 0.2 g, 0.74 mmol) in THF (20 mL) at −78° C. The reaction mixture was stirred for 1 h at −78° C. then cyclobutanone (CAN 1191-95-3, 1.11 mL, 1.47 mmol) in THF (3 mL) was added to the above solution at −78° C. The reaction mixture was allowed to warm to ambient temperature and stirred for 1 h. The reaction mixture was then quenched with NH$_4$Cl and the pH was adjusted to 2 by addition of 1 N HCl. The mixture was extracted with ethyl acetate (3×10 mL); the organic layers were combined, washed with brine (2×10 mL) and dried over Na$_2$SO$_4$. The solvent was removed under reduced pressure and the crude product was used for the next step without further purification; MS (EI): m/e=264.1 [M+H]$^+$.

b) 6-Cyclopropylmethoxy-5-(1-hydroxy-cyclobutyl)-pyridine-2-carboxylic acid [1-methyl-1-(5-methyl-[1,2,4]oxadiazol-3-yl)-ethyl]-amide

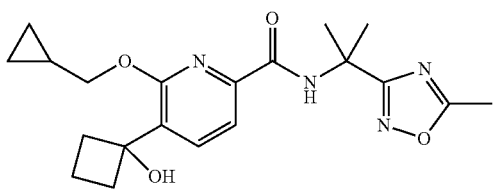 [SMILES: Cc1nc(C(C)(C)NC(=O)c2ccc(C3(O)CCC3)c(OCC3CC3)n2)no1]

The title compound was synthesized in analogy to Example 1, using 6-cyclopropylmethoxy-5-(1-hydroxy-cyclobutyl)-pyridine-2-carboxylic acid and α,α,5-trimethyl-1,2,4-oxadiazole-3-methanamine (CAN 1153831-97-0) as starting materials, MS (EI): m/e=387.2 [M+H]$^+$.

Example 161

5-Cyclopropyl-6-(2-methoxy-ethoxy)-pyridine-2-carboxylic acid ((S)-1-carbamoyl-2-cyclopropyl-ethyl)-amide

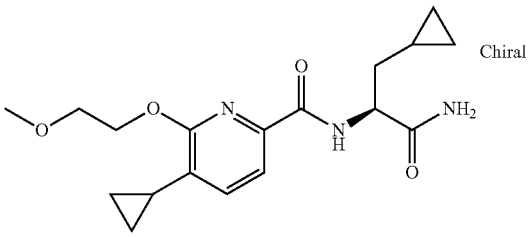 [SMILES: COCCOc1nc(C(=O)N[C@@H](CC2CC2)C(N)=O)ccc1C1CC1]

The title compound was synthesized in analogy to Example 1, using 5-cyclopropyl-6-(2-methoxyethoxy)-pyridine-2-carboxylic acid (Example 142 d) and (S)-2-amino-3-cyclopropyl-propionamide (CAN 156077-93-9) as starting materials, MS (EI): m/e=348.1 [M+H]$^+$.

Example 162

5-[Bis-(2,2,2-trifluoro-ethyl)-amino]-6-cyclopropylmethoxy-pyridine-2-carboxylic acid ((S)-1-carbamoyl-2-cyclopropyl-ethyl)-amide a) 5-(Bis(2,2,2-trifluoroethyl)amino)-6-(cyclopropylmethoxy)-pyridine-2-carboxylic acid methyl ester

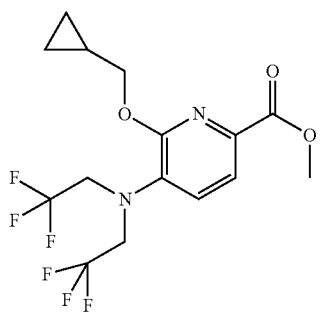

Under a nitrogen atmosphere, a solution of 5-bromo-6-(cyclopropylmethoxy)-pyridine-2-carboxylic acid methyl ester (Example 114 a, 1 g, 3.5 mmol), bis(2,2,2-trifluoroethyl)amine (1.90 g, 10 mmol), (±)-2,2'-bis(diphenylphosphino)-1,1'-binaphthalene (CAN 98327-87-8, 0.435 g, 1 mmol), tris(dibenzylideneacetone) dipalladium (CAN 51364-51-3, 0.32 g, 0.35 mmol) and cesium carbonate (CAN 534-17-8, 3.4 g, 10 mmol) in toluene (50 mL) was reacted overnight at 110° C. The reaction mixture was concentrated under reduced pressure, dissolved in water, extracted with ethyl acetate (50 mL), the aqueous layer was adjusted to pH 2 with conc. HCl, then extracted with ethyl acetate (3×50 mL), washed with brine (2×50 mL), dried over Na$_2$SO$_4$ and concentrated under reduced pressure. The residue was purified by column chromatography (silica gel, 10 g, 20% ethyl acetate in petroleum ether) to yield the title compound (0.5 g, 29.7%) as a yellow oil; MS: m/e=387.1 [M+H]$^+$.

b) 5-[Bis-(2,2,2-trifluoro-ethyl)-amino]-6-cyclopropylmethoxy-pyridine-2-carboxylic acid

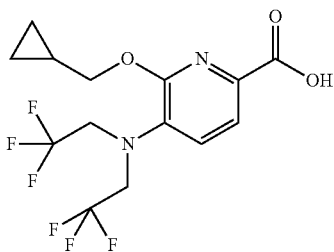 [SMILES: O=C(O)c1ccc(N(CC(F)(F)F)CC(F)(F)F)c(OCC2CC2)n1]

A solution of 5-(bis(2,2,2-trifluoroethyl)amino)-6-(cyclopropylmethoxy)-pyridine-2-carboxylic acid methyl ester (60 mg, 0.16 mmol) and sodium hydroxide (9 mg, 0.23 mmol) in ethanol (20 mL) was reacted for 2 h at 90° C. The reaction mixture was concentrated under reduced pressure, dissolved in water and extracted with ethyl acetate (10 mL). The pH of the aqueous layer was adjusted to 2 by addition of 1 N hydrochloric acid; the aqueous layer was extracted with ethyl acetate (3×10 mL), washed with brine (2×10 mL), dried over Na$_2$SO$_4$ and evaporated to dryness (0.03 g, crude). The crude product was used for next step without further purification; MS: m/e=373.1 [M+H]$^+$.

c) 5-[Bis-(2,2,2-trifluoro-ethyl)-amino]-6-cyclopropylmethoxy-pyridine-2-carboxylic acid ((S)-1-carbamoyl-2-cyclopropyl-ethyl)-amide

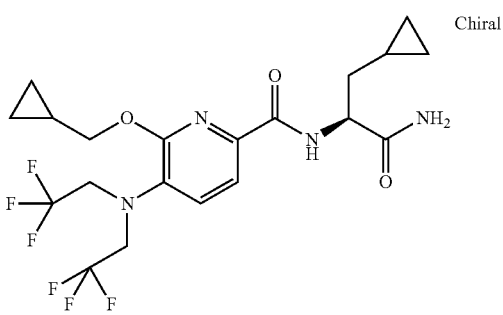 [SMILES: NC(=O)[C@H](CC1CC1)NC(=O)c1ccc(N(CC(F)(F)F)CC(F)(F)F)c(OCC2CC2)n1]

The title compound was synthesized in analogy to Example 1, using 5-[bis-(2,2,2-trifluoro-ethyl)-amino]-6-cyclopropylmethoxy-pyridine-2-carboxylic acid and (S)-2-amino-3-cyclopropyl-propionamide (CAN 156077-93-9) as starting materials, MS (EI): m/e=483.1 [M+H]$^+$.

Example 163

5-Cyclopropyl-6-cyclopropylmethoxy-pyridine-2-carboxylic acid [(S)-2-cyclopropyl-1-(5-methyl-[1,2,4]oxadiazol-3-yl)-ethyl]-amide

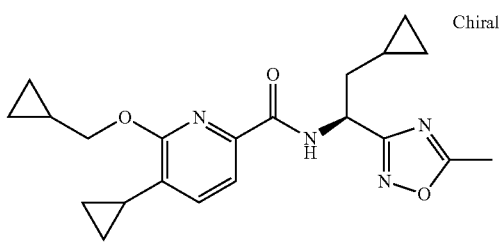 [SMILES: Cc1nc([C@H](CC2CC2)NC(=O)c2ccc(C3CC3)c(OCC3CC3)n2)no1]

The title compound was synthesized in analogy to Example 1, using 5-cyclopropyl-6-cyclopropylmethoxy-pyridine-2-carboxylic acid (Example 42 a) and (S)-2-cyclopropyl-1-(5-methyl-[1,2,4]oxadiazol-3-yl)-ethylamine (Example 38 e) as starting materials, MS (EI): m/e=383.2 [M+H]$^+$.

Example 164

6-(3-Chloro-phenyl)-5-(3,3-difluoro-azetidin-1-yl)-pyridine-2-carboxylic acid [(S)-2-cyclopropyl-1-(5-methyl-[1,2,4]oxadiazol-3-yl)-ethyl]-amide

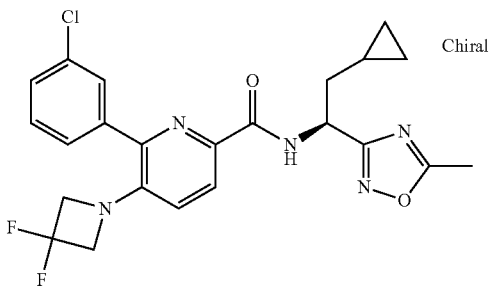 [SMILES: Cc1nc([C@H](CC2CC2)NC(=O)c2ccc(N3CC(F)(F)C3)c(-c3cccc(Cl)c3)n2)no1]

The title compound was synthesized in analogy to Example 1, using 6-(3-chloro-phenyl)-5-(3,3-difluoro-azetidin-1-yl)-pyridine-2-carboxylic acid (Example 140 a) and (S)-2-cyclopropyl-1-(5-methyl-[1,2,4]oxadiazol-3-yl)-ethylamine (Example 38 e) as starting materials, MS (EI): m/e=474.1 [M+H]$^+$.

Example 165

5-[Bis-(2,2,2-trifluoro-ethyl)-amino]-6-cyclopropylmethoxy-pyridine-2-carboxylic acid (1-ethyl-1-methylcarbamoyl-propyl)-amide

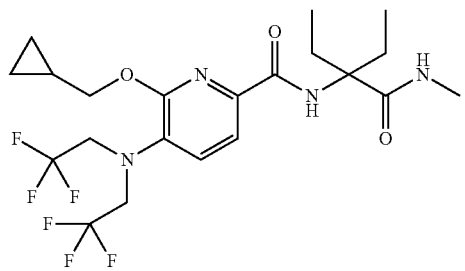 [SMILES: CCC(CC)(NC(=O)c1ccc(N(CC(F)(F)F)CC(F)(F)F)c(OCC2CC2)n1)C(=O)NC]

The title compound was synthesized in analogy to Example 1, using 5-[bis-(2,2,2-trifluoro-ethyl)-amino]-6-cyclopropylmethoxy-pyridine-2-carboxylic acid (Example 162 b) and 2-amino-2-ethyl-N-methyl-butyramide (Example 70 b) as starting materials, MS (EI): m/e=499.2 [M+H]$^+$.

Example 166

5-Cyclopropyl-6-(tetrahydro-furan-2-ylmethoxy)-pyridine-2-carboxylic acid [1-methyl-1-(5-methyl-[1,2,4]oxadiazol-3-yl)-ethyl]-amide

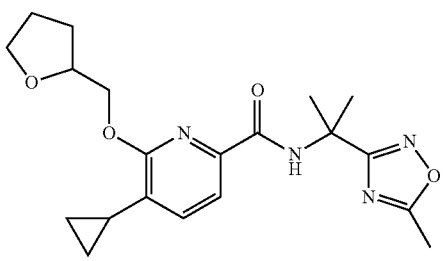 [SMILES: Cc1nc(C(C)(C)NC(=O)c2ccc(C3CC3)c(OCC3CCCO3)n2)no1]

a) 5-Bromo-6-(tetrahydro-furan-2-ylmethoxy)-pyridine-2-carboxylic acid

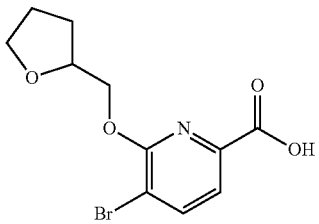 [SMILES: O=C(O)c1ccc(Br)c(OCC2CCCO2)n1]

5-Bromo-6-chloropicolinic acid (200 mg, 846 µmol; CAN 959958-25-9) and powdered potassium hydroxide (190 mg, 3.38 mmol) were combined with DMSO (1.93 mL) to give a colorless solution which was stirred for 15 min at ambient temperature before tetrahydro-2-furanmethanol (130 mg, 123 µl, 1.27 mmol, CAN 97-99-4) was added, and stirring continued for 1 day at ambient temperature. The reaction mixture was poured into a mixture of ice-water and 1 M NaOH, and extracted with t-butylmethyl ether (2×25 mL) and washed with ice-water/brine. The water phases were combined acidified with ice/1 N HCl and extracted with isopropyl acetate (2×30 mL). The organic layers were washed with ice-water/brine (2×30 mL), dried with $Na_2SO_4$ and concentrated in vacuo to give the title compound (254 mg, 99%) as light brown oil; MS (ESI): 301.8 $[M-H]^-$.

b) 5-Cyclopropyl-6-(tetrahydro-furan-2-ylmethoxy)-pyridine-2-carboxylic acid

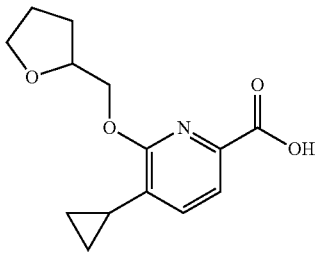 [SMILES: O=C(O)c1ccc(C2CC2)c(OCC2CCCO2)n1]

Palladium(II)acetate (1.19 mg, 5.3 µmol), butylbis(tricyclo[3.3.1.1³,⁷]dec-1-yl)-phosphine (2.85 mg, 7.94 µmol, CAN 321921-71-5), potassium cyclopropyltrifluoroborate (39.6 mg, 267 µmol) and cesium carbonate (259 mg, 794 µmol) were combined to give a white solid. To this solid a degassed solution of 5-bromo-6-(tetrahydro-furan-2-ylmethoxy)-pyridine-2-carboxylic acid (80 mg, 265 µmol) in toluene (2.02 mL)/water (224 µL) was added through a septum cap. The reaction mixture was heated to 120° C. and stirred for 20 h. After cooling to ambient temperature the reaction mixture was diluted with water (2 mL), poured onto 20 mL ice water/brine/1 N HCl, extracted with isopropyl acetate (2×40 mL), and washed with 20 mL ice water/brine. The organic layers were dried with $Na_2SO_4$ and concentrated in vacuo to give a light brown oily residue which was purified by preparative TLC (silica gel, 2.0 mm, DCM/MeOH, 49:1). The title compound (25 mg, 36%) was isolated as light yellow liquid; MS (ESI): 262.0 $[M-H]^-$.

b) 5-Cyclopropyl-6-(tetrahydro-furan-2-ylmethoxy)-pyridine-2-carboxylic acid [1-methyl-1-(5-methyl-[1,2,4]oxadiazol-3-yl)-ethyl]-amide The title compound was synthesized in analogy to Example 1, using 5-cyclopropyl-6-(tetrahydro-furan-2-ylmethoxy)-pyridine-2-carboxylic acid (Example 166 b) and α,α,5-trimethyl-1,2,4-oxadiazole-3-methanamine (CAN 1153831-97-0) as starting materials, MS (EI): m/e=387.0 $[M+H]^+$.

Example 167

N-(2-Cyanopropan-2-yl)-5-cyclopropyl-6-(cyclopropylmethoxy)picolinamide

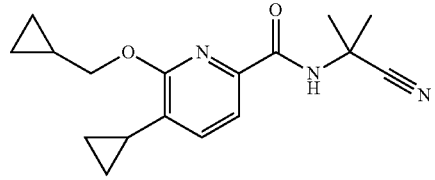 [SMILES: CC(C)(C#N)NC(=O)c1ccc(C2CC2)c(OCC2CC2)n1]

The title compound was synthesized in analogy to Example 1, using 5-cyclopropyl-6-cyclopropylmethoxy-pyridine-2-carboxylic acid (Example 42 a) and 2-amino-2-methyl-propanenitrile, (CAN 19355-69-2) as starting materials, LC-MS (UV peak area/ESI) 89%, 300.1702 $(M+H)^+$.

Example 168

(S)-5-Cyclopropyl-6-(cyclopropylmethoxy)-N-(3,3-dimethyl-1-(methylamino)-1-oxobutan-2-yl)picolinamide Chiral

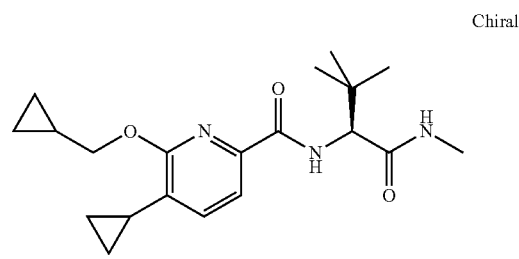 [SMILES: CNC(=O)[C@@H](NC(=O)c1ccc(C2CC2)c(OCC2CC2)n1)C(C)(C)C]

The title compound was synthesized in analogy to Example 1, using 5-cyclopropyl-6-cyclopropylmethoxy-pyridine-2-carboxylic acid (Example 42 a) and (2S)-2-amino- N,3,3-trimethyl-butanamide, (CAN 89226-12-0) as starting materials, LC-MS (UV peak area/ESI) 96%, 360.2272 (M+H)+.

Example 169

N-(1-Amino-2,3-dimethyl-1-oxobutan-2-yl)-5-cyclopropyl-6-(cyclopropylmethoxy)picolinamide

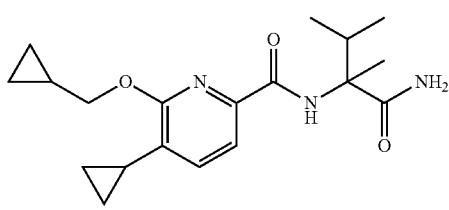 [SMILES: CC(C)C(C)(NC(=O)c1ccc(C2CC2)c(OCC2CC2)n1)C(N)=O]

The title compound was synthesized in analogy to Example 1, using 5-cyclopropyl-6-cyclopropylmethoxy-pyridine-2-carboxylic acid (Example 42 a) and 2-amino-2,3-dimethyl-butanamide (CAN 40963-14-2) as starting materials, LC-MS (UV peak area/ESI) 96%, 346.2136 (M+H)+.

Example 170

N-(1-Amino-2-methyl-1-oxobutan-2-yl)-5-cyclopropyl-6-(cyclopropylmethoxy)picolinamide

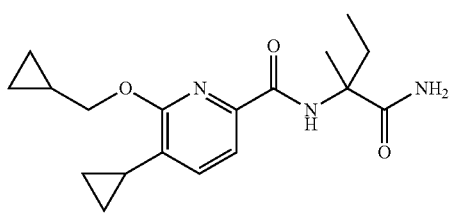 [SMILES: CCC(C)(NC(=O)c1ccc(C2CC2)c(OCC2CC2)n1)C(N)=O]

The title compound was synthesized in analogy to Example 1, using 5-cyclopropyl-6-cyclopropylmethoxy-pyridine-2-carboxylic acid (Example 42 a) and 2-amino-2-methyl-butanamide (CAN 59209-90-4) as starting materials, LC-MS (UV peak area/ESI) 96%, 332.1982 (M+H)+.

Example 171

5-Cyclopropyl-6-(cyclopropylmethoxy)-N-(1-(5-methyl-1,2,4-oxadiazol-3-yl)cyclobutyl)picolinamide

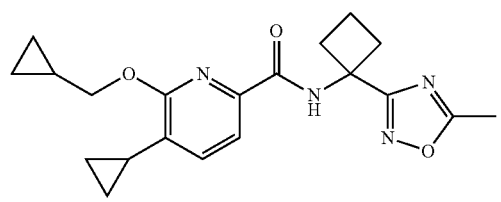 [SMILES: Cc1nc(C2(NC(=O)c3ccc(C4CC4)c(OCC4CC4)n3)CCC2)no1]

The title compound was synthesized in analogy to Example 1, using 5-cyclopropyl-6-cyclopropylmethoxy-pyridine-2-carboxylic acid (Example 42 a) and 1-(5-methyl-1,2,4-oxadiazol-3-yl)-cyclobutanamine hydrochloride (1:1) (CAN 1170897-28-5) as starting materials, LC-MS (UV peak area/ESI) 97.8%, 369.1914 (M+H)+.

Example 172

(S)-N-(2-Amino-2-oxo-1-phenylethyl)-5-cyclopropyl-6-(cyclopropylmethoxy)picolinamide

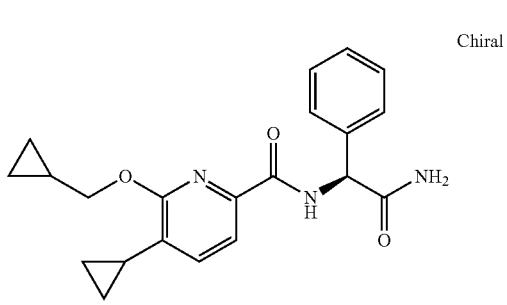 [SMILES: NC(=O)[C@@H](NC(=O)c1ccc(C2CC2)c(OCC2CC2)n1)c1ccccc1]

The title compound was synthesized in analogy to Example 1, using 5-cyclopropyl-6-cyclopropylmethoxy-pyridine-2-carboxylic acid (Example 42 a) and (αS)-α-aminobenzeneacetamide hydrochloride (1:1) (CAN 60079-51-8) as starting materials, LC-MS (UV peak area/ESI) 98%, 366.1814 (M+H)+.

Example 173

(R)-N-(2-Amino-2-oxo-1-phenylethyl)-5-cyclopropyl-6-(cyclopropylmethoxy)picolinamide

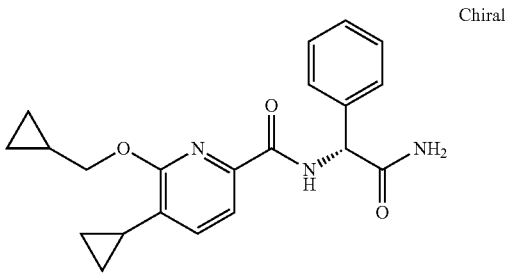 [SMILES: NC(=O)[C@H](NC(=O)c1ccc(C2CC2)c(OCC2CC2)n1)c1ccccc1]

The title compound was synthesized in analogy to Example 1, using 5-cyclopropyl-6-cyclopropylmethoxy-pyridine-2-carboxylic acid (Example 42 a) and (αR)-α-aminobenzeneacetamide hydrochloride (1:1) (CAN 63291-39-4) as starting materials, LC-MS (UV peak area/ESI) 100%, 366.1808 (M+H)+.

Example 174

(R)-5-Cyclopropyl-6-(cyclopropylmethoxy)-N-(1-hydroxy-4-methylpentan-2-yl)picolinamide

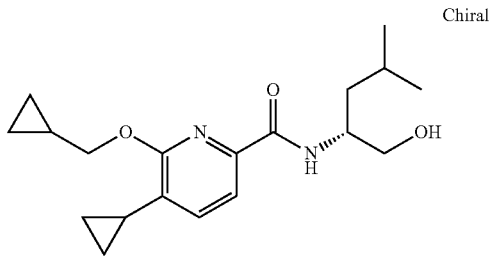 [SMILES: CC(C)C[C@H](CO)NC(=O)c1ccc(C2CC2)c(OCC2CC2)n1]
Chiral

The title compound was synthesized in analogy to Example 1, using 5-cyclopropyl-6-cyclopropylmethoxy-pyridine-2-carboxylic acid (Example 42 a) and (2R)-2-amino-4-methyl-1-pentanol (CAN 53448-09-2) as starting materials, LC-MS (UV peak area/ESI) 100%, 333.2165 (M+H)$^+$.

Example 175

5-Cyclopropyl-6-(cyclopropylmethoxy)-N-(1-(hydroxymethyl)cyclopentyl)picolinamide

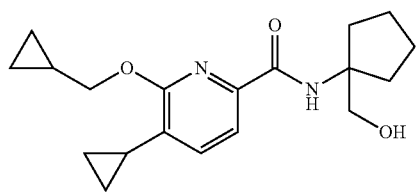 [SMILES: O=C(NC1(CO)CCCC1)c1ccc(C2CC2)c(OCC2CC2)n1]

The title compound was synthesized in analogy to Example 1, using 5-cyclopropyl-6-cyclopropylmethoxy-pyridine-2-carboxylic acid (Example 42 a) and 1-amino-cyclopentanemethanol (CAN 10316-79-7) as starting materials, LC-MS (UV peak area/ESI) 100%, 331.2014 (M+H)$^+$.

Example 176

5-Cyclopropyl-6-(cyclopropylmethoxy)-N-(2-(3-methyl-1,2,4-oxadiazol-5-yl)propan-2-yl)picolinamideinamide

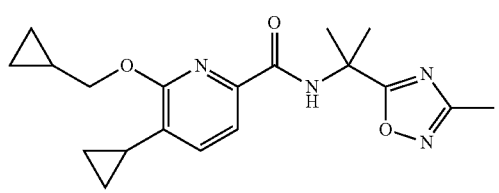 [SMILES: Cc1noc(C(C)(C)NC(=O)c2ccc(C3CC3)c(OCC3CC3)n2)n1]

The title compound was synthesized in analogy to Example 1, using 5-cyclopropyl-6-cyclopropylmethoxy-pyridine-2-carboxylic acid (Example 42 a) and α,α3-trimethyl-1,2,4-oxadiazole-5-methanamine (CAN 1248289-21-5) as starting materials, LC-MS (UV peak area/ESI) 100%, 357.1921 (M+H)$^+$.

Example 177

5-Bromo-6-(4-fluoro-phenoxy)-pyridine-2-carboxylic acid ((S)-1-carbamoyl-3-methyl-butyl)-amide

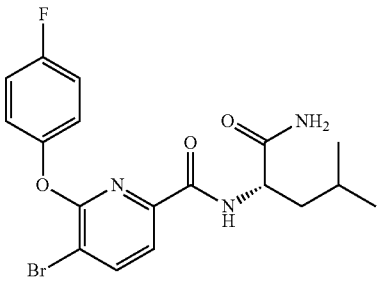 [SMILES: CC(C)C[C@H](NC(=O)c1ccc(Br)c(Oc2ccc(F)cc2)n1)C(N)=O]

a) 5-Bromo-6-chloro-pyridine-2-carboxylic acid ((S)-1-carbamoyl-3-methyl-butyl)-amide

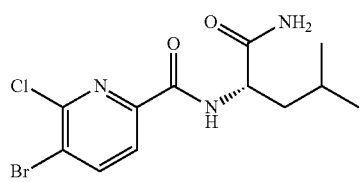 [SMILES: CC(C)C[C@H](NC(=O)c1ccc(Br)c(Cl)n1)C(N)=O]

The title compound was synthesized in analogy to Example 1, using 5-bromo-6-chloropicolinic acid (CAN 959958-25-9) and (2S)-2-amino-4-methyl-pentanamide (CAN 687-51-4) as starting materials, MS (EI): m/e=350.0 [M+H]$^+$.

b) 5-Bromo-6-(4-fluoro-phenoxy)-pyridine-2-carboxylic acid ((S)-1-carbamoyl-3-methyl-butyl)-amide 5-Bromo-6-chloro-pyridine-2-carboxylic acid ((S)-1-carbamoyl-3-methyl-butyl)-amide (50 mg, 143 μmol) was dissolved in DMF (0.5 mL) to give a colorless solution. 4-Fluorophenol (19.3 mg, 172 μmol) and sodium carbonate (45.6 mg, 430 μmol) were added successively to give a yellow solution. The reaction mixture was stirred at 120° C. over the weekend, cooled to ambient temperature and poured into 40 mL water. The mixture was extracted with isopropyl acetate (2×40 mL), organic phases were combined, dried with Na$_2$SO$_4$ and concentrated in vacuo. The residue was purified by preparative TLC (silica gel, 2.0 mm, isopropyl acetate) to give the title compound (23 mg, 38%) as colorless oil, MS (ESI): m/e=421.9 [M−H]$^-$.

Example 178

N-(1-Amino-2,4-dimethyl-1-oxopentan-2-yl)-5-cyclopropyl-6-(cyclopropylmethoxy)picolinamide

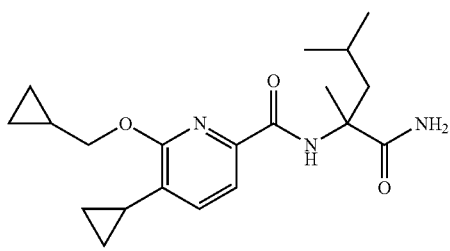 [SMILES: CC(C)CC(C)(NC(=O)c1ccc(C2CC2)c(OCC2CC2)n1)C(N)=O]

The title compound was synthesized in analogy to Example 1, using 5-cyclopropyl-6-cyclopropylmethoxy-pyridine-2-carboxylic acid (Example 42 a) and 2-amino-2,4-dimethyl-pentanamide (CAN 113509-60-7) as starting materials, LC-MS (UV peak area/ESI) 100%, 360.2287 (M+H)$^+$.

Example 179

N-(1-Amino-3,3-dimethyl-1-oxobutan-2-yl)-5-cyclopropyl-6-(cyclopropylmethoxy)picolinamide

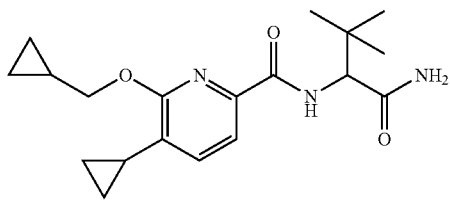 [SMILES: CC(C)(C)C(NC(=O)c1ccc(C2CC2)c(OCC2CC2)n1)C(N)=O]

The title compound was synthesized in analogy to Example 1, using 5-cyclopropyl-6-cyclopropylmethoxy-pyridine-2-carboxylic acid (Example 42 a) and 2-amino-3,3-dimethyl-butanamide hydrochloride (1:1) (CAN 359844-68-1) as starting materials, LC-MS (UV peak area/ESI) 100%, 346.2113 (M+H)$^+$.

Example 180

5-Cyclopropyl-6-cyclopropylmethoxy-pyridine-2-carboxylic acid (4-carbamoyl-tetrahydro-pyran-4-yl)-amide

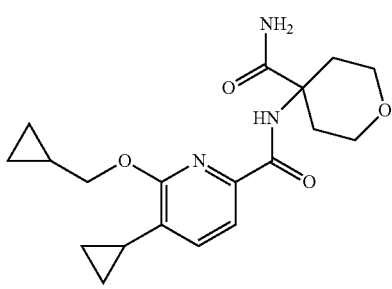 [SMILES: NC(=O)C1(NC(=O)c2ccc(C3CC3)c(OCC3CC3)n2)CCOCC1]

The title compound was synthesized in analogy to Example 1, using 5-cyclopropyl-6-cyclopropylmethoxy-pyridine-2-carboxylic acid (Example 42 a) and 4-aminotetrahydro-2H-pyran-4-carboxamide (CAN 1183378-09-7) as starting materials, MS (EI): m/e=360.1 [M+H]$^+$.

Example 181

(S)-5-cyclopropyl-6-(cyclopropylmethoxy)-N-(4-methyl-1-(methylamino)-1-oxopentan-2-yl)picolinamide

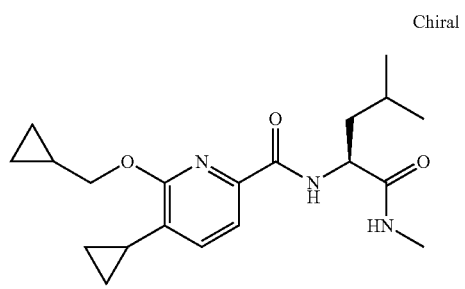 [SMILES: CNC(=O)[C@H](CC(C)C)NC(=O)c1ccc(C2CC2)c(OCC2CC2)n1]

The title compound was synthesized in analogy to Example 1, using 5-cyclopropyl-6-cyclopropylmethoxy-pyridine-2-carboxylic acid (Example 42 a) and (2S)-2-amino-N,4-dimethyl-pentanamide monohydrochloride (CAN 99145-71-8) as starting materials, MS (D): m/e=360.1 [M+H]$^+$.

Example 182

(S)-5-Cyclopropyl-6-(cyclopropylmethoxy)-N-(4,4-dimethyl-1-(methylamino)-1-oxopentan-2-yl)picolinamide

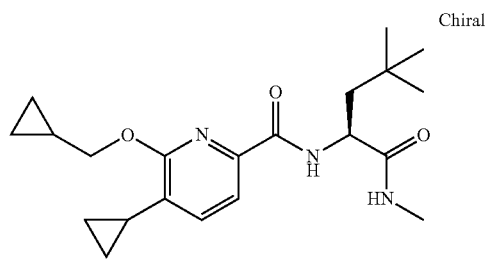 [SMILES: CNC(=O)[C@H](CC(C)(C)C)NC(=O)c1ccc(C2CC2)c(OCC2CC2)n1]

The title compound was synthesized in analogy to Example 1, using 5-cyclopropyl-6-cyclopropylmethoxy-pyridine-2-carboxylic acid (Example 42 a) and (2S)-2-amino-N,4,4-trimethyl-pentanamide (CAN 1160161-70-5) as starting materials, MS (EI): m/e=374.1 [M+H]$^+$.

Example 183

5-Cyclopropyl-N-((S)-3,3-dimethyl-1-(methylamino)-1-oxobutan-2-yl)-6-((tetrahydrofuran-2-yl)methoxy)picolinamide

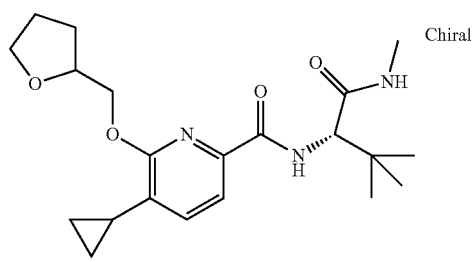 [SMILES: CNC(=O)[C@@H](NC(=O)c1ccc(C2CC2)c(OCC2CCCO2)n1)C(C)(C)C]

The title compound was synthesized in analogy to Example 1, using 5-cyclopropyl-6-(tetrahydro-furan-2-yl-methoxy)-pyridine-2-carboxylic acid (Example 166 b) and (2S)-2-amino-N,3,3-trimethyl-butanamide, (CAN 89226-12-0) as starting materials, MS (EI): m/e=390.4 [M+H]$^+$.

Example 184

5-Cyclopropyl-N-((S)-4-methyl-1-(methylamino)-1-oxopentan-2-yl)-6-((tetrahydrofuran-2-yl)methoxy)picolinamide

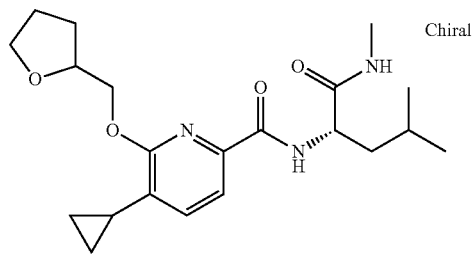 [SMILES: CNC(=O)[C@H](CC(C)C)NC(=O)c1ccc(C2CC2)c(OCC2CCCO2)n1]

The title compound was synthesized in analogy to Example 1, using 5-cyclopropyl-6-(tetrahydro-furan-2-yl-methoxy)-pyridine-2-carboxylic acid (Example 166 b) and (2S)-2-amino-N,4-dimethyl-pentanamide monohydrochloride (CAN 99145-71-8) as starting materials, MS (EI): m/e=390.0 [M+H]$^+$.

Example 185

5-Cyclopropyl-N-((S)-4,4-dimethyl-1-(methylamino)-1-oxopentan-2-yl)-6-((tetrahydrofuran-2-yl)methoxy)picolinamide

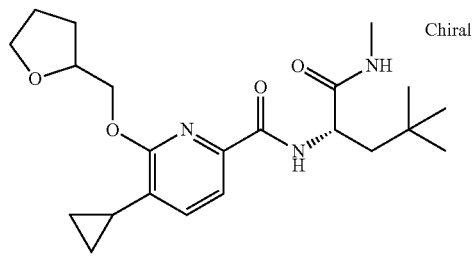 [SMILES: CNC(=O)[C@H](CC(C)(C)C)NC(=O)c1ccc(C2CC2)c(OCC2CCCO2)n1]

The title compound was synthesized in analogy to Example 1, using 5-cyclopropyl-6-(tetrahydro-furan-2-yl-methoxy)-pyridine-2-carboxylic acid (Example 166 b) and (2S)-2-amino-N,4,4-trimethyl-pentanamide (CAN 1160161-70-5) as starting materials, MS (EI): m/e=404.1 [M+H]$^+$.

Example 186

N-((S)-1-Amino-4-methyl-1-oxopentan-2-yl)-5-cyclopropyl-6-((tetrahydrofuran-2-yl)methoxy)picolinamide

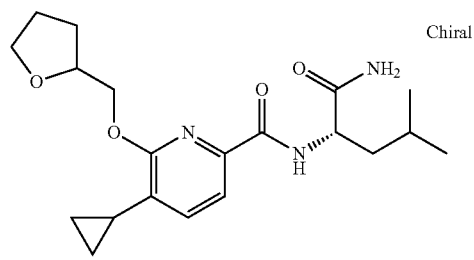 [SMILES: CC(C)C[C@H](NC(=O)c1ccc(C2CC2)c(OCC2CCCO2)n1)C(N)=O]

a) 5-Bromo-6-(tetrahydro-furan-2-ylmethoxy)-pyridine-2-carboxylic acid ((S)-1-carbamoyl-3-methyl-butyl)-amide

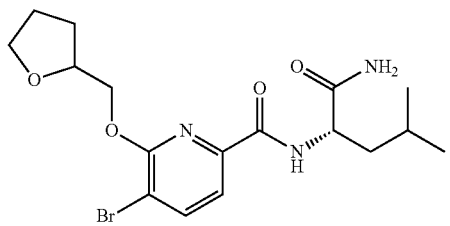 [SMILES: CC(C)C[C@H](NC(=O)c1ccc(Br)c(OCC2CCCO2)n1)C(N)=O]

The title compound was synthesized in analogy to Example 1, using 5-bromo-6-(tetrahydro-furan-2-yl-methoxy)-pyridine-2-carboxylic acid (Example 166 a) and (2S)-2-amino-4-methyl-pentanamide (CAN 687-51-4) as starting materials, MS (EI): m/e=416.0 [M+H]$^+$.

b) N-((S)-1-amino-4-methyl-1-oxopentan-2-yl)-5-cyclopropyl-6-((tetrahydrofuran-2-yl)methoxy)picolinamide The title compound was synthesized in analogy to Example 166 b, using 5-bromo-6-(tetrahydro-furan-2-yl-methoxy)-pyridine-2-carboxylic acid ((S)-1-carbamoyl-3-methyl-butyl)-amide (Example 186 a) and potassium cyclopropyltrifluoroborate as starting materials, MS (EI): m/e=376.2 [M+H]$^+$.

Example 187

5-Cyclopropyl-6-(4-fluoro-phenoxy)-pyridine-2-carboxylic acid ((S)-1-carbamoyl-3-methyl-butyl)-amide

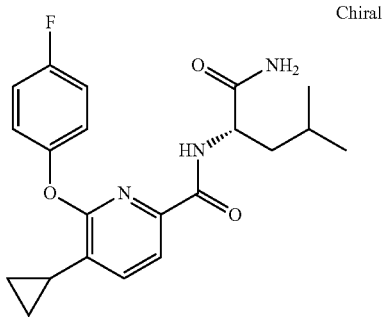 [SMILES: CC(C)C[C@H](NC(=O)c1ccc(C2CC2)c(Oc2ccc(F)cc2)n1)C(N)=O]

The title compound was synthesized in analogy to Example 166 b, using 5-bromo-6-(4-fluoro-phenoxy)-pyridine-2-carboxylic acid ((S)-1-carbamoyl-3-methyl-butyl)-amide (Example 177 b) and potassium cyclopropyltrifluoroborate as starting materials, MS (EI): m/e=386.0 [M+H]$^+$.

Example 188

5-Bromo-6-(tetrahydro-furan-2-ylmethoxy)-pyridine-2-carboxylic acid ((S)-2,2-dimethyl-1-methyl-carbamoyl-propyl)-amide

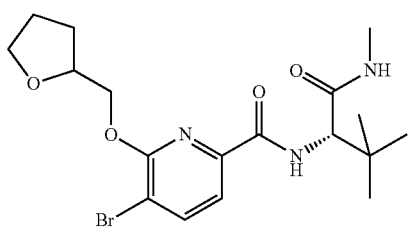 [SMILES: CNC(=O)[C@@H](NC(=O)c1ccc(Br)c(OCC2CCCO2)n1)C(C)(C)C]

The title compound was synthesized in analogy to Example 1, using 5-bromo-6-(tetrahydro-furan-2-ylmethoxy)-pyridine-2-carboxylic acid (Example 166 a) and (2S)-2-amino-N,3,3-trimethyl-butanamide, (CAN 89226-12-0) as starting materials, MS (EI): m/e=428.0 [M+H]$^+$.

Example 189

5-Cyclopropyl-N-(1-(5-methyl-1,2,4-oxadiazol-3-yl)cyclobutyl)-6-(pyridin-2-ylmethoxy)picolinamide a) 5-Bromo-6-(pyridin-2-ylmethoxy)-pyridine-2-carboxylic acid

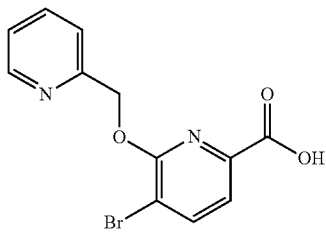 [SMILES: O=C(O)c1ccc(Br)c(OCc2ccccn2)n1]

The title compound was synthesized in analogy to Example 9 d, using 5-bromo-6-chloro-pyridine-2-carboxylic acid and 2-pyridinemethanol (CAN 586-98-1) as starting materials, LC-MS (UV peak area/ESI) 100%, 308.9876 (M+H)$^+$.

b) 5-Cyclopropyl-6-(pyridin-2-ylmethoxy)-pyridine-2-carboxylic acid

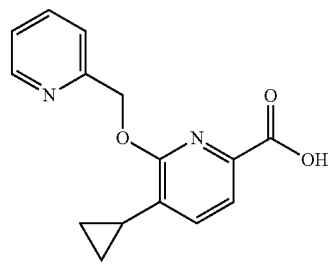 [SMILES: O=C(O)c1ccc(C2CC2)c(OCc2ccccn2)n1]

The title compound was synthesized in analogy to Example 42 a, using 5-bromo-6-(pyridin-2-ylmethoxy)-pyridine-2-carboxylic acid and cyclopropylboronic acid (CAN 411235-57-9) as starting materials, LC-MS (UV peak area/ESI) 100%, 271.1081 (M+H)$^+$.

c) 5-Cyclopropyl-N-(1-(5-methyl-1,2,4-oxadiazol-3-yl)cyclobutyl)-6-(pyridin-2-ylmethoxy)picolinamide

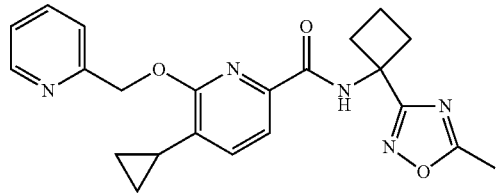 [SMILES: Cc1nc(C2(NC(=O)c3ccc(C4CC4)c(OCc4ccccn4)n3)CCC2)no1]

The title compound was synthesized in analogy to Example 1, using 5-cyclopropyl-6-(pyridin-2-ylmethoxy)-pyridine-2-carboxylic acid and 1-(5-methyl-1,2,4-oxadiazol-3-yl)-cyclobutanamine hydrochloride (1:1) (CAN 1170897-28-5) as starting materials, MS (EI): m/e=406.2 [M+H]$^+$.

Example 190

5-Cyclopropyl-N-(cyclopropyl(5-methyl-1,2,4-oxadiazol-3-yl)methyl)-6-(cyclopropylmethoxy)picolinamide

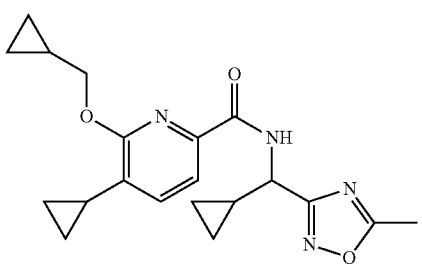 [SMILES: Cc1nc(C(NC(=O)c2ccc(C3CC3)c(OCC3CC3)n2)C2CC2)no1]

The title compound was synthesized in analogy to Example 1, using 5-cyclopropyl-6-cyclopropylmethoxy-pyridine-2-carboxylic acid (Example 42 a) and cyclopropyl-(5- methyl-[1,2,4]oxadiazol-3-yl)-methylamine (which can e.g. be prepared in a similar manner than (S)-2-cyclopropyl-1-(5-methyl-[1,2,4]oxadiazol-3-yl)-ethylamine (Example 38 e)) as starting materials, MS (EI): m/e=369.2 [M+H]$^+$.

Example 191

5-Cyclopropyl-6-cyclopropylmethoxy-pyridine-2-carboxylic acid ((R)-1-hydroxymethyl-1,2-dimethyl-propyl)-amide

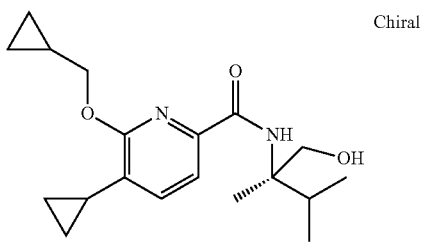 [SMILES: CC(C)[C@](C)(CO)NC(=O)c1ccc(C2CC2)c(OCC2CC2)n1]

The title compound was synthesized in analogy to Example 1, using 5-cyclopropyl-6-cyclopropylmethoxy-pyridine-2-carboxylic acid (Example 42 a) and (R)-2-amino-2,3-dimethyl-butan-1-ol [CAN 155158-75-1] as starting materials, MS (EI): m/e=333.2 [M+H]$^+$.

Example 192

(S)-6-(3-Chlorophenyl)-N-(3,3-dimethyl-1-(methylamino)-1-oxobutan-2-yl)picolinamide

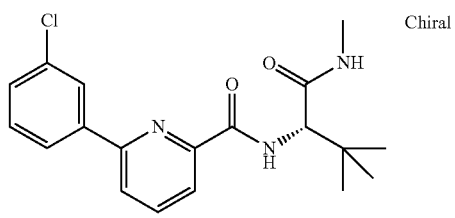 [SMILES: CNC(=O)[C@@H](NC(=O)c1cccc(-c2cccc(Cl)c2)n1)C(C)(C)C]

The title compound was synthesized in analogy to Example 1, using 6-(3-chlorophenyl)-2-pyridinecarboxylic acid (CAN 863704-38-5) and (2S)-2-amino-N,3,3-trimethyl-butanamide (CAN 89226-12-0) as starting materials, MS (EI): m/e=360.0 [M+H]$^+$.

Example 193

(S)-6-(3-Chlorophenyl)-N-(4,4-dimethyl-1-(methylamino)-1-oxopentan-2-yl)picolinamide

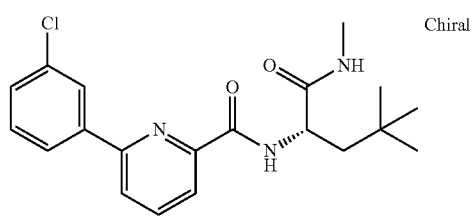 [SMILES: CNC(=O)[C@H](CC(C)(C)C)NC(=O)c1cccc(-c2cccc(Cl)c2)n1]

The title compound was synthesized in analogy to Example 1, using 6-(3-chlorophenyl)-2-pyridinecarboxylic acid (CAN 863704-38-5) and (2S)-2-amino-N,4,4-trimethyl-pentanamide (CAN 1160161-70-5) as starting materials, MS (EI): m/e=374.1 [M+H]$^+$.

Example 194

5-Cyclopropyl-6-(cyclopropylmethoxy)-N-(4-hydroxy-2-methylbutan-2-yl)picolinamide

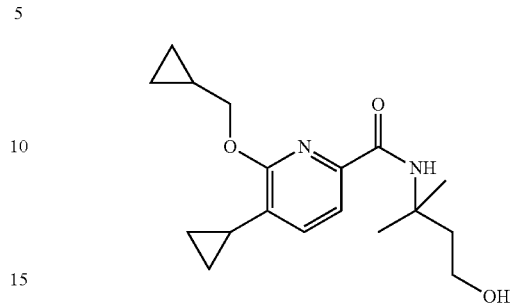

The title compound was synthesized in analogy to Example 1, using 5-cyclopropyl-6-cyclopropylmethoxy-pyridine-2-carboxylic acid (Example 42 a) and 3-amino-3-methyl-butan-1-ol (CAN 42514-50-1) as starting materials, LC-MS (UV peak area/ESI) 100%, 319.1 (M+H)$^+$.

Example 195

(S)-5-Cyclopropyl-N-(3,3-dimethyl-1-(methylamino)-1-oxobutan-2-yl)-6-((tetrahydro-2H-pyran-4-yl)methoxy)picolinamide

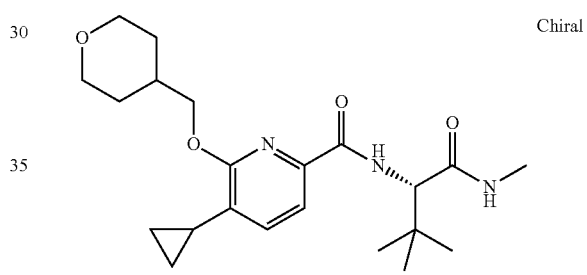

The title compound was synthesized in analogy to Example 1, using 5-cyclopropyl-6-(tetrahydro-pyran-4-ylmethoxy)-pyridine-2-carboxylic acid (which can e.g. be prepared in a similar manner than 5-cyclopropyl-6-(tetrahydro-furan-2-ylmethoxy)-pyridine-2-carboxylic acid (Example 166 b)) and (2S)-2-amino-N,3,3-trimethyl-butanamide (CAN 89226-12-0) as starting materials, MS (EI): m/e=404.3 [M+H]$^+$.

Example 196

(S)-5-Cyclopropyl-N-(4,4-dimethyl-1-(methylamino)-1-oxopentan-2-yl)-6-((tetrahydro-2H-pyran-4-yl)methoxy)picolinamide

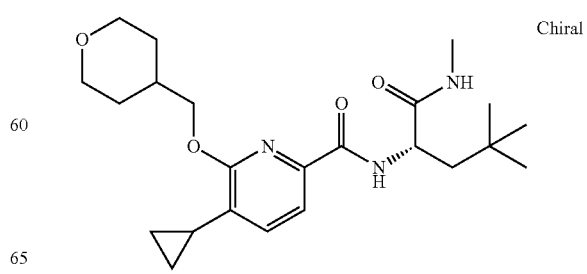

The title compound was synthesized in analogy to Example 1, using 5-cyclopropyl-6-(tetrahydro-pyran-4-yl-methoxy)-pyridine-2-carboxylic acid (which can e.g. be prepared in a similar manner than 5-cyclopropyl-6-(tetrahydro-furan-2-ylmethoxy)-pyridine-2-carboxylic acid (Example 166 b)) and (2S)-2-amino-N,4,4-trimethyl-pentanamide (CAN 1160161-70-5) as starting materials, MS (EI): m/e=418.3 [M+H]⁺.

Example 197

(−)-5-Cyclopropyl-6-cyclopropylmethoxy-pyridine-2-carboxylic acid [cyclopropyl-(5-methyl-[1,2,4] oxadiazol-3-yl)-methyl]-amide

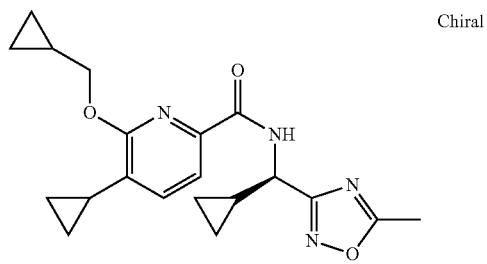 [SMILES: Cc1nc([C@H](NC(=O)c2ccc(C3CC3)c(OCC3CC3)n2)C2CC2)no1]

The title compound can be obtained by chiral chromatography from 5-cyclopropyl-N-(cyclopropyl(5-methyl-1,2,4-oxadiazol-3-yl)methyl)-6-(cyclopropylmethoxy)picolinamide (Example 190), MS (EI): m/e=369.2 [M+H]⁺.

Example 198

(+)-5-Cyclopropyl-6-cyclopropylmethoxy-pyridine-2-carboxylic acid [cyclopropyl-(5-methyl-[1,2,4] oxadiazol-3-yl)-methyl]-amide

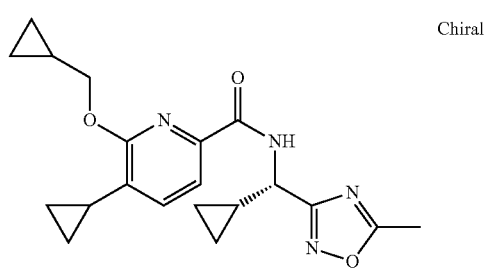 [SMILES: Cc1nc([C@@H](NC(=O)c2ccc(C3CC3)c(OCC3CC3)n2)C2CC2)no1]

The title compound can be obtained by chiral chromatography from 5-cyclopropyl-N-(cyclopropyl(5-methyl-1,2,4-oxadiazol-3-yl)methyl)-6-(cyclopropylmethoxy)picolinamide (Example 190), MS (EI): m/e=369.2 [M+H]⁺.

Example 199

5-Cyclopropyl-N-(2-(5-methyl-1,2,4-oxadiazol-3-yl) propan-2-yl)-6-(pyridin-2-ylmethoxy)picolinamide

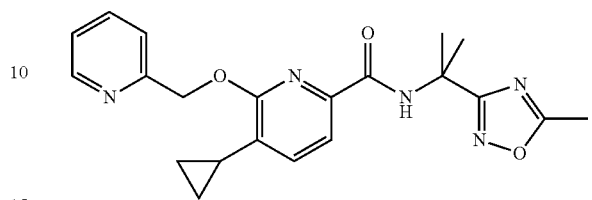

The title compound was synthesized in analogy to Example 1, using 5-cyclopropyl-6-(pyridin-2-ylmethoxy)-pyridine-2-carboxylic acid (Example 189 b) and α,α,5-trimethyl-1,2,4-oxadiazole-3-methanamine (CAN 1153831-97-0) as starting materials, MS (EI): m/e=394.2 [M+H]⁺.

Example 200

(S)-N-(1-Amino-4-methyl-1-oxopentan-2-yl)-5-cyclopropyl-6-(pyridin-2-ylmethoxy)picolinamide

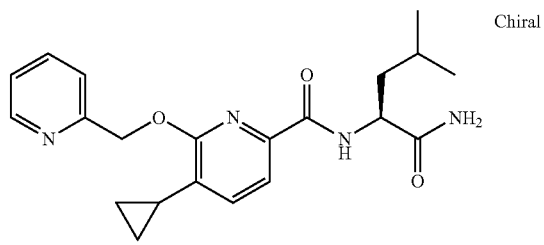 [SMILES: CC(C)C[C@H](NC(=O)c1ccc(C2CC2)c(OCc2ccccn2)n1)C(N)=O]

The title compound was synthesized in analogy to Example 1, using 5-cyclopropyl-6-(pyridin-2-ylmethoxy)-pyridine-2-carboxylic acid (Example 189 b) and (2S)-2-amino-4-methyl-pentanamide (CAN 687-51-4) as starting materials, MS (EI): m/e=383.2 [M+H]⁺.

Example 201

(S)-5-Cyclopropyl-N-(3,3-dimethyl-1-(methylamino)-1-oxobutan-2-yl)-6-(pyridin-2-ylmethoxy) picolinamide

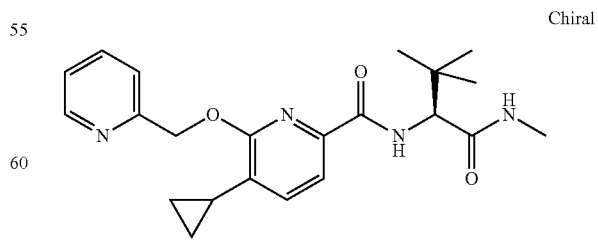

The title compound was synthesized in analogy to Example 1, using 5-cyclopropyl-6-(pyridin-2-ylmethoxy)-pyridine-2-carboxylic acid (Example 189 b) and (2S)-2- amino-N,3,3-trimethyl-butanamide (CAN 89226-12-0) as starting materials, MS (EI): m/e=397.2 [M+H]+.

Example 202

5-Cyclopropyl-N-(2-(5-methyl-1,2,4-oxadiazol-3-yl) propan-2-yl)-6-((tetrahydro-2H-pyran-4-yl)methoxy) picolinamide

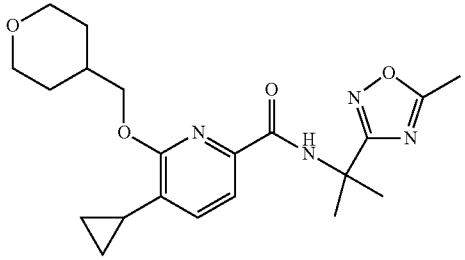 [SMILES: Cc1nc(C(C)(C)NC(=O)c2ccc(C3CC3)c(OCC3CCOCC3)n2)no1]

The title compound was synthesized in analogy to Example 1, using 5-cyclopropyl-6-(tetrahydro-pyran-4-yl-methoxy)-pyridine-2-carboxylic acid (which can e.g. be prepared in a similar manner than 5-cyclopropyl-6-(tetrahydro-furan-2-ylmethoxy)-pyridine-2-carboxylic acid (Example 166 b)) and α,α,5-trimethyl-1,2,4-oxadiazole-3-methanamine (CAN 1153831-97-0) as starting materials, MS (EI): m/e=401.2 [M+H]+.

Example 203

(S)-5-Cyclopropyl-N-(4-methyl-1-(methylamino)-1-oxopentan-2-yl)-6-((tetrahydro-2H-pyran-4-yl)methoxy)picolinamide

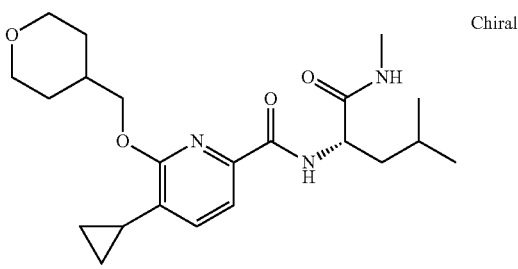 [SMILES: CNC(=O)[C@H](CC(C)C)NC(=O)c1ccc(C2CC2)c(OCC2CCOCC2)n1]

The title compound was synthesized in analogy to Example 1, using 5-cyclopropyl-6-(tetrahydro-pyran-4-yl-methoxy)-pyridine-2-carboxylic acid (which can e.g. be prepared in a similar manner than 5-cyclopropyl-6-(tetrahydro-furan-2-ylmethoxy)-pyridine-2-carboxylic acid (Example 166 b)) and (2S)-2-amino-4-methyl-pentanamide (CAN 687-51-4) as starting materials, MS (EI): m/e=404.2 [M+H]+.

Example 204

(S)-N-(3,3-Dimethyl-1-(methylamino)-1-oxobutan-2-yl)-6-phenylpicolinamide

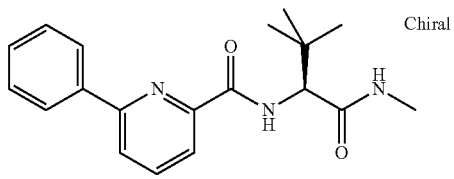 [SMILES: CNC(=O)[C@@H](NC(=O)c1cccc(-c2ccccc2)n1)C(C)(C)C]

The title compound can be prepared in analogy to Example 1, using 6-phenyl-pyridine-2-carboxylic acid (CAN 39774-28-2) and (2S)-2-amino-N,3,3-trimethyl-butanamide (CAN 89226-12-0) as starting materials, MS (EI): m/e=326.2 [M+H]+.

Example 205

(S)-N-(4-Methyl-1-(methylamino)-1-oxopentan-2-yl)-6-phenylpicolinamide

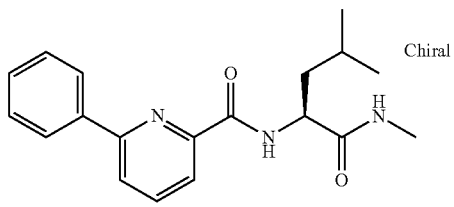 [SMILES: CNC(=O)[C@H](CC(C)C)NC(=O)c1cccc(-c2ccccc2)n1]

The title compound can be prepared in analogy to Example 1, using 6-phenyl-pyridine-2-carboxylic acid (CAN 39774-28-2) and (2S)-2-amino-4-methyl-pentanamide (CAN 687-51-4) as starting materials, MS (EI): m/e=326.2 [M+H]+.

Example 206

5-(3,3-Difluoroazetidin-1-yl)-N-((S)-3,3-dimethyl-1-(methylamino)-1-oxobutan-2-yl)-6-((tetrahydrofuran-2-yl)methoxy)picolinamide

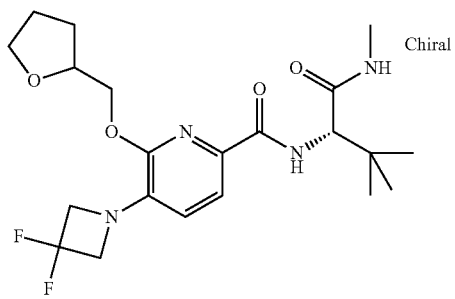 [SMILES: CNC(=O)[C@@H](NC(=O)c1ccc(N2CC(F)(F)C2)c(OCC2CCCO2)n1)C(C)(C)C]

The title compound was synthesized by addition of 3,3-difluoroazetidine hydrochloride (CAN 288315-03-7) to 5-bromo-6-(tetrahydro-furan-2-ylmethoxy)-pyridine-2-carboxylic acid ((S)-2,2-dimethyl-1-methylcarbamoyl-propyl)-amide (Example 188) in analogy to the procedure described in Example 69 a, MS (EI): m/e=441.0 [M+H]$^+$.

Example 207

2-(6-(Cyclopropylmethoxy)-5-(3,3-difluoroazetidin-1-yl)picolinamido)-2-ethylbutanoic acid

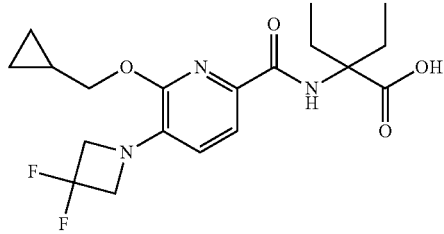 [SMILES: CCC(CC)(NC(=O)c1ccc(N2CC(F)(F)C2)c(OCC2CC2)n1)C(=O)O]

The title compound can e.g. be synthesized by: i) coupling of 6-cyclopropylmethoxy-5-(3,3-difluoro-azetidin-1-yl)-pyridine-2-carboxylic acid (Example 69 b) with 2-amino-2-ethyl-butyric acid methyl ester (CAN 70974-26-4) in analogy to Example 1; and ii) saponification of the ester group in analogy to the conditions described in Example 48 e), MS (EI): m/e=396.1 [M−H]$^-$.

Example 208

(S)-6-(Cyclopropylmethoxy)-5-(3,3-difluoroazetidin-1-yl)-N-(3,3-dimethyl-1-(methylamino)-1-oxobutan-2-yl)picolinamide

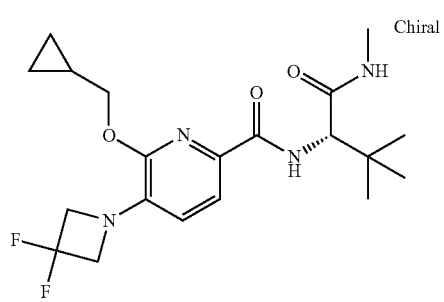 [SMILES: CNC(=O)[C@@H](NC(=O)c1ccc(N2CC(F)(F)C2)c(OCC2CC2)n1)C(C)(C)C]

The title compound was synthesized in analogy to Example 1, using 6-cyclopropylmethoxy-5-(3,3-difluoroazetidin-1-yl)-pyridine-2-carboxylic acid (Example 69 b) and (2S)-2-amino-N,3,3-trimethyl-butanamide (CAN 89226-12-0) as starting materials, MS (D): m/e=411.4 [M+H]$^+$.

Example 209

(S)-6-(Cyclopropylmethoxy)-5-(3,3-difluoroazetidin-1-yl)-N-(4,4-dimethyl-1-(methylamino)-1-oxopentan-2-yl)picolinamide

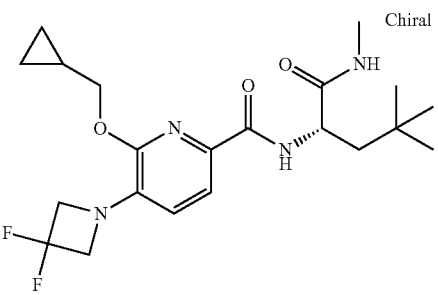 [SMILES: CNC(=O)[C@H](CC(C)(C)C)NC(=O)c1ccc(N2CC(F)(F)C2)c(OCC2CC2)n1]

The title compound was synthesized in analogy to Example 1, using 6-cyclopropylmethoxy-5-(3,3-difluoroazetidin-1-yl)-pyridine-2-carboxylic acid (Example 69 b) and (2S)-2-amino-N,4,4-trimethyl-pentanamide (CAN 1160161-70-5) as starting materials, MS (EI): m/e=425.0 [M+H]$^+$.

Example 210

(S)-6-(3-Fluorophenyl)-N-(4-methyl-1-(methylamino)-1-oxopentan-2-yl)picolinamide

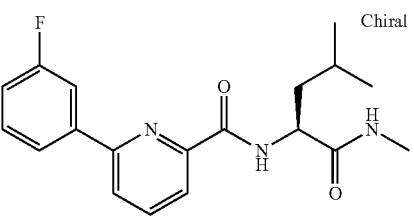 [SMILES: CNC(=O)[C@H](CC(C)C)NC(=O)c1cccc(-c2cccc(F)c2)n1]

The title compound can be prepared in analogy to Example 1, using 6-(3-fluoro-phenyl)-pyridine-2-carboxylic acid (CAN 887982-40-3) and (2S)-2-amino-4-methyl-pentanamide (CAN 687-51-4) as starting materials, LC-MS (UV peak area/ESI) 100%, 344.1768 (M+H)$^+$.

Example 211

(S)-N-(4-Methyl-1-(methylamino)-1-oxopentan-2-yl)-6-(3-(trifluoromethyl)phenyl)picolinamide

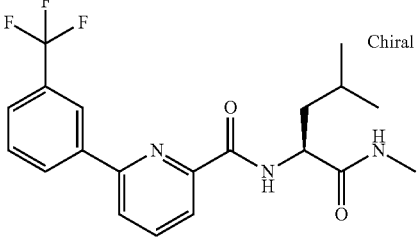

The title compound can be prepared in analogy to Example 1, using 6-(3-trifluoromethyl-phenyl)-pyridine-2-carboxylic acid (CAN 887982-06-1) and (2S)-2-amino-4-methyl-pentanamide (CAN 687-51-4) as starting materials, LC-MS (UV peak area/ESI) 99.5%, 394.1734 (M+H)+.

Example 212

(S)-6-(3-Chloro-4-fluorophenyl)-N-(4-methyl-1-(methylamino)-1-oxopentan-2-yl)picolinamide

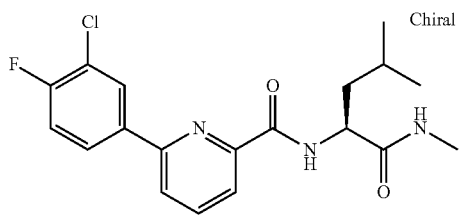 [SMILES: CNC(=O)[C@H](CC(C)C)NC(=O)c1cccc(-c2ccc(F)c(Cl)c2)n1]

The title compound can be prepared in analogy to Example 1, using 6-(3-chloro-4-fluoro-phenyl)-pyridine-2-carboxylic acid (CAN 1261922-29-5) and (2S)-2-amino-4-methyl-pentanamide (CAN 687-51-4) as starting materials, LC-MS (UV peak area/ESI) 97.8%, 378.1376 (M+H)+.

Example 213

(S)-N-(3,3-Dimethyl-1-(methylamino)-1-oxobutan-2-yl)-6-(3-fluorophenyl)picolinamide

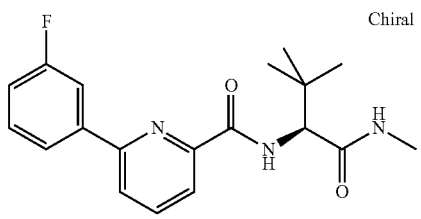 [SMILES: CNC(=O)[C@@H](NC(=O)c1cccc(-c2cccc(F)c2)n1)C(C)(C)C]

The title compound can be prepared in analogy to Example 1, using 6-(3-fluoro-phenyl)-pyridine-2-carboxylic acid (CAN 887982-40-3) and (2S)-2-amino-N,3,3-trimethyl-butanamide (CAN 89226-12-0) as starting materials, LC-MS (UV peak area/ESI) 99.1%, 344.1774 (M+H)+.

Example 214

(S)-N-(3,3-Dimethyl-1-(methylamino)-1-oxobutan-2-yl)-6-(3-(trifluoromethyl)phenyl)-picolinamide

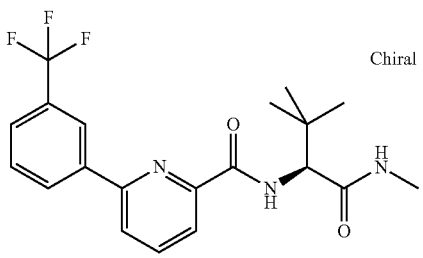 [SMILES: CNC(=O)[C@@H](NC(=O)c1cccc(-c2cccc(C(F)(F)F)c2)n1)C(C)(C)C]

The title compound can be prepared in analogy to Example 1, using 6-(3-trifluoromethyl-phenyl)-pyridine-2-carboxylic acid (CAN 887982-06-1) and (2S)-2-amino-N,3,3-trimethyl-butanamide (CAN 89226-12-0) as starting materials, LC-MS (UV peak area/ESI) 99.0%, 394.1735 (M+H)+.

Example 215

(S)-N-(3,3-Dimethyl-1-(methylamino)-1-oxobutan-2-yl)-6-(3-methoxyphenyl) picolinamide

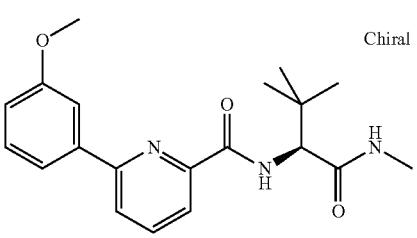 [SMILES: CNC(=O)[C@@H](NC(=O)c1cccc(-c2cccc(OC)c2)n1)C(C)(C)C]

The title compound can be prepared in analogy to Example 1, using 6-(3-methoxy-phenyl)-pyridine-2-carboxylic acid (CAN 887982-11-8) and (2S)-2-amino-N,3,3-trimethyl-butanamide (CAN 89226-12-0) as starting materials, LC-MS (UV peak area/ESI) 99.1%, 356.1961 (M+H)+.

Example 216

(S)-6-(3-Chloro-4-fluorophenyl)-N-(3,3-dimethyl-1-(methylamino)-1-oxobutan-2-yl)picolinamide

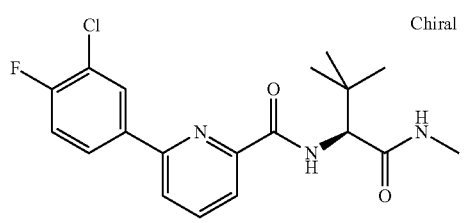 [SMILES: CNC(=O)[C@@H](NC(=O)c1cccc(-c2ccc(F)c(Cl)c2)n1)C(C)(C)C]

The title compound can be prepared in analogy to Example 1, using 6-(3-chloro-4-fluoro-phenyl)-pyridine-2-carboxylic acid (CAN 1261922-29-5) and (2S)-2-amino-N,3,3-trimethyl-butanamide (CAN 89226-12-0) as starting materials, LC-MS (UV peak area/ESI) 98.4%, 378.1372 (M+H)+.

Example 217

(S)-5-Cyclopropyl-6-(cyclopropylmethoxy)-N-(2,2,2-trifluoro-1-(pyridin-3-yl)ethyl)-picolinamide

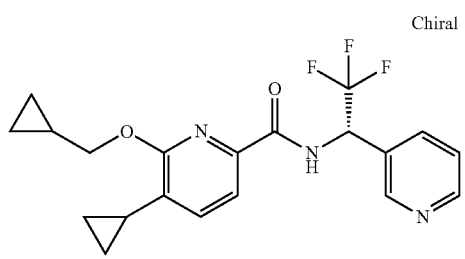 [SMILES: O=C(N[C@@H](c1cccnc1)C(F)(F)F)c1ccc(C2CC2)c(OCC2CC2)n1]

The title compound was synthesized in analogy to Example 1, using 5-cyclopropyl-6-cyclopropylmethoxy-pyridine-2-carboxylic acid (Example 42 a) and (S)-2,2,2-trifluoro-1-pyridin-3-yl-ethylamine (CAN 336105-46-5) as starting materials, MS (EI): m/e=392.2 [M+H]⁺.

Example 218

(R)-5-Cyclopropyl-6-(cyclopropylmethoxy)-N-(2,2,2-trifluoro-1-(pyridin-3-yl)ethyl)-picolinamide

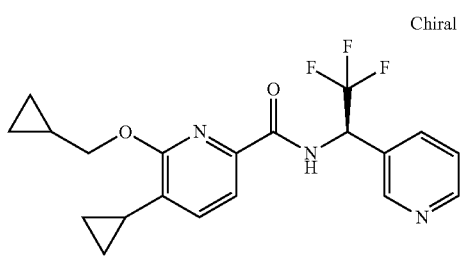 [SMILES: O=C(N[C@H](c1cccnc1)C(F)(F)F)c1ccc(C2CC2)c(OCC2CC2)n1]

The title compound was synthesized in analogy to Example 1, using 5-cyclopropyl-6-cyclopropylmethoxy-pyridine-2-carboxylic acid (Example 42 a) and (R)-2,2,2-trifluoro-1-pyridin-3-yl-ethylamine (CAN 1212813-98-3) as starting materials, MS (EI): m/e=392.2 [M+H]⁺.

Example 219

5-Cyclopropyl-6-(tetrahydro-pyran-4-ylmethoxy)-pyridine-2-carboxylic acid [cyclopropyl-(5-methyl-[1,2,4]oxadiazol-3-yl)-methyl]-amide

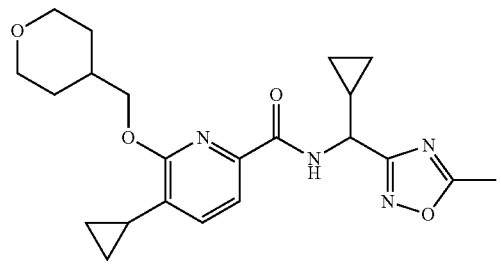 [SMILES: Cc1nc(C(NC(=O)c2ccc(C3CC3)c(OCC3CCOCC3)n2)C2CC2)no1]

The title compound was synthesized in analogy to Example 1, using 5-cyclopropyl-6-(tetrahydro-pyran-4-ylmethoxy)-pyridine-2-carboxylic acid (which can e.g. be prepared in a similar manner than 5-cyclopropyl-6-(tetrahydrofuran-2-ylmethoxy)-pyridine-2-carboxylic acid (Example 166 b)) and cyclopropyl-(5-methyl-[1,2,4]oxadiazol-3-yl)-methylamine (which can e.g. be prepared in a similar manner than (S)-2-cyclopropyl-1-(5-methyl-[1,2,4]oxadiazol-3-yl)-ethylamine (Example 38 e)) as starting materials, MS (EI): m/e=413.1 [M+H]⁺.

Example 220

2-({5-[Bis-(2,2,2-trifluoro-ethyl)-amino]-6-cyclopropylmethoxy-pyridine-2-carbonyl}-amino)-2-ethyl-butyric acid methyl ester

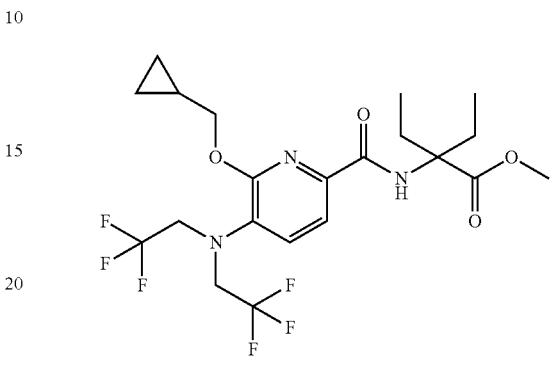

The title compound was synthesized in analogy to Example 1, using 5-[bis-(2,2,2-trifluoro-ethyl)-amino]-6-cyclopropylmethoxy-pyridine-2-carboxylic acid (Example 162 b) and methyl 2-amino-2-ethylbutanoate hydrochloride (CAN 92398-54-4) as starting materials, MS (EI): m/e=500.1 [M+H]⁺.

Example 221

6-Cyclopropylmethoxy-5-(3,3-difluoro-azetidin-1-yl)-pyridine-2-carboxylic acid [cyclopropyl-(5-methyl-[1,2,4]oxadiazol-3-yl)-methyl]-amide

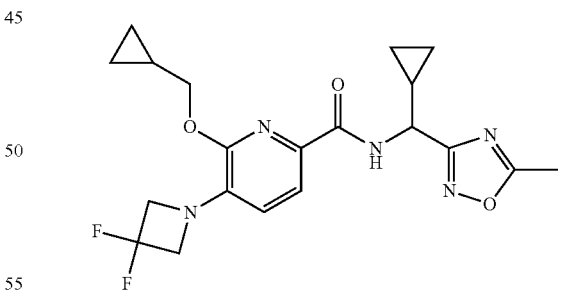

The title compound was synthesized in analogy to Example 1, using 6-cyclopropylmethoxy-5-(3,3-difluoro-azetidin-1-yl)-pyridine-2-carboxylic acid (Example 69 b) and cyclopropyl-(5-methyl-[1,2,4]oxadiazol-3-yl)-methylamine (which can e.g. be prepared in a similar manner than (S)-2-cyclopropyl-1-(5-methyl-[1,2,4]oxadiazol-3-yl)-ethylamine (Example 38 e)) as starting materials, MS (EI): m/e=420.0 [M+H]⁺.

Example 222

5-Cyclopropyl-6-cyclopropylmethoxy-pyridine-2-carboxylic acid ((S)-2-cyclopropyl-1-dimethylcarbamoyl-ethyl)-amide

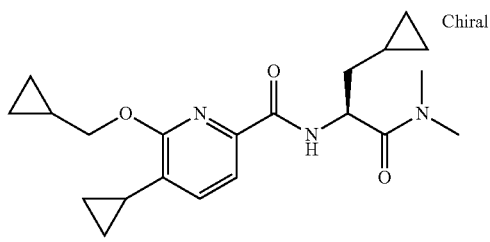 [SMILES: CN(C)C(=O)[C@H](CC1CC1)NC(=O)c1ccc(C2CC2)c(OCC2CC2)n1]

a) (S)-tert-Butyl 3-cyclopropyl-1-(dimethylamino)-1-oxopropan-2-ylcarbamate

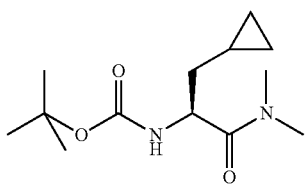 [SMILES: CN(C)C(=O)[C@H](CC1CC1)NC(=O)OC(C)(C)C]

The title compound was synthesized in analogy to Example 1, using (S)-2-(tert-butoxycarbonylamino)-3-cyclopropylpropanoic acid (CAN 89483-06-7) and dimethylamine hydrochloride as starting materials. MS (EI): m/e=256.3 [M]$^+$.

b) (S)-2-Amino-3-cyclopropyl-N,N-dimethylpropanamide hydrochloride

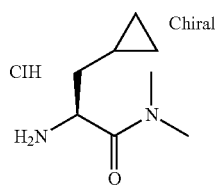

A 4M solution of HCl in dioxane (4.68 mL, 18.7 mmol) was added to a solution of (S)-tert-butyl 3-cyclopropyl-1-(dimethylamino)-1-oxopropan-2-ylcarbamate (1.2 g, 4.68 mmol) in ethanol (10 mL). After 16 h stirring at ambient temperature the solvent was removed under reduced pressure. The remaining solid was digerated with diethyl ether (10 mL), filtered off, washed with diethyl ether (3×5 mL) and dried for 3 h in vacuo at 40° C. to give the title compound as off-white solid (820 mg, 91%). MS (EI): m/e=157.1 [M+H]$^+$.

c) 5-Cyclopropyl-6-cyclopropylmethoxy-pyridine-2-carboxylic acid ((S)-2-cyclopropyl-1-dimethylcarbamoyl-ethyl)-amide The title compound was synthesized in analogy to Example 1, using 5-cyclopropyl-6-cyclopropylmethyloxy-pyridine-2-carboxylic acid (Example 42 a) and (S)-2-amino-3-cyclopropyl-N,N-dimethylpropanamide hydrochloride as starting materials, LC-MS (UV peak area/ESI) 100%, 372.2278 (M+H)$^+$.

Example 223

5-Cyclopropyl-6-(tetrahydro-pyran-4-ylmethoxy)-pyridine-2-carboxylic acid (2,2,2-trifluoro-1-pyridin-2-yl-ethyl)-amide

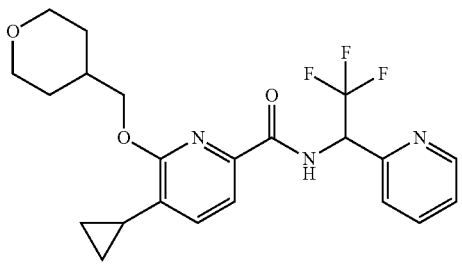 [SMILES: O=C(NC(c1ccccn1)C(F)(F)F)c1ccc(C2CC2)c(OCC2CCOCC2)n1]

The title compound was synthesized in analogy to Example 1, using 5-cyclopropyl-6-(tetrahydro-pyran-4-ylmethoxy)-pyridine-2-carboxylic acid (which can e.g. be prepared in a similar manner than 5-cyclopropyl-6-(tetrahydrofuran-2-ylmethoxy)-pyridine-2-carboxylic acid (Example 166 b)) and 2,2,2-trifluoro-1-(pyridin-2-yl)ethanamine (CAN 503173-14-6) as starting materials, MS (EI): m/e=436.1 [M+H]$^+$.

Example 224

6-Cyclopropylmethoxy-5-(3,3-difluoro-azetidin-1-yl)-pyridine-2-carboxylic acid (2,2,2-trifluoro-1-pyridin-2-yl-ethyl)-amide

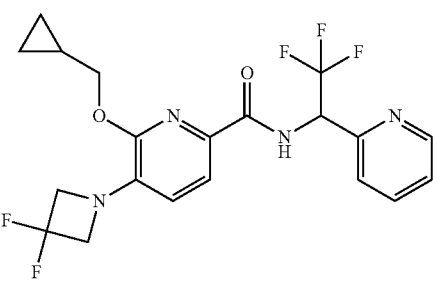 [SMILES: O=C(NC(c1ccccn1)C(F)(F)F)c1ccc(N2CC(F)(F)C2)c(OCC2CC2)n1]

The title compound was synthesized in analogy to Example 1, using 6-cyclopropylmethoxy-5-(3,3-difluoro-azetidin-1-yl)-pyridine-2-carboxylic acid (Example 69 b) and 2,2,2-trifluoro-1-(pyridin-2-yl)ethanamine (CAN 503173-14-6) as starting materials, MS (EI): m/e=443.1 [M+H]$^+$.

Example 225

5-Cyclopropyl-6-cyclopropylmethoxy-pyridine-2-carboxylic acid ((−)-methylcarbamoyl-phenyl-methyl)-amide

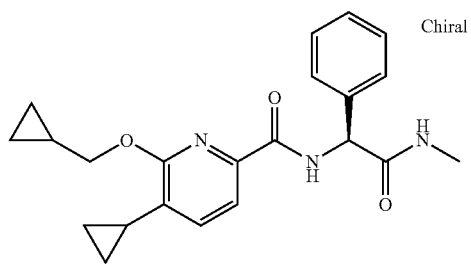 [SMILES: CNC(=O)[C@@H](NC(=O)c1ccc(C2CC2)c(OCC2CC2)n1)c1ccccc1]

The title compound was synthesized in analogy to Example 1, using 5-cyclopropyl-6-cyclopropylmethyloxy-pyridine-2-carboxylic acid (Example 42 a) and (αR)-α-amino-N-methyl-benzeneacetamide hydrochloride (1:1) (CAN 97549-10-5) as starting materials. Racemization occurred during the synthesis and the product was isolated by chiral chromatography on Chiralpak AD using heptane/20% ethanol as eluent. The (−)-enantiomer was isolated. LC-MS (UV peak area/ESI) 100%, 380.1968 (M+H)$^+$, $\alpha_D^{20}$ (MeOH)= −6.0°.

Example 226

5-Cyclopropyl-6-cyclopropylmethoxy-pyridine-2-carboxylic acid ((+)-dimethylcarbamoyl-phenyl-methyl)-amide

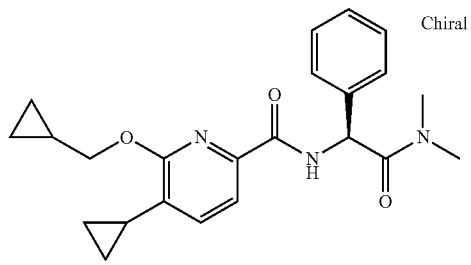 [SMILES: CN(C)C(=O)[C@@H](NC(=O)c1ccc(C2CC2)c(OCC2CC2)n1)c1ccccc1]

The title compound was synthesized in analogy to Example 1, using 5-cyclopropyl-6-cyclopropylmethyloxy-pyridine-2-carboxylic acid (Example 42 a) and (αR)-α-amino-N,N-dimethyl-benzeneacetamide hydrochloride (1:1) (CAN 129157-29-5) as starting materials. Racemization occurred during the synthesis and the product was isolated by chiral chromatography on Reprosil Chiral NR using heptane/20% ethanol as eluent. The (+)-enantiomer was isolated. LC-MS (UV peak area/ESI) 100%, 394.2120 (M+H)$^+$, $\alpha_D^{20}$ (MeOH)=+44.4°.

Example 227

5-Cyclopropyl-6-cyclopropylmethoxy-pyridine-2-carboxylic acid ((−)-dimethylcarbamoyl-phenyl-methyl)-amide

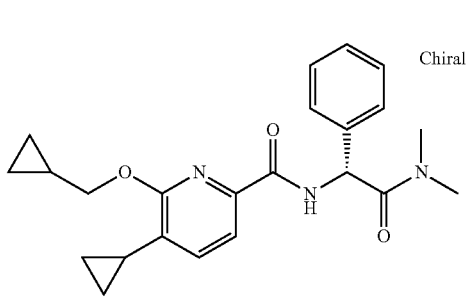 [SMILES: CN(C)C(=O)[C@H](NC(=O)c1ccc(C2CC2)c(OCC2CC2)n1)c1ccccc1]

The title compound was synthesized in analogy to Example 1, using 5-cyclopropyl-6-cyclopropylmethyloxy-pyridine-2-carboxylic acid (Example 42 a) and (αR)-α-amino-N,N-dimethyl-benzeneacetamide hydrochloride (1:1) (CAN 129157-29-5) as starting materials. Racemization occurred during the synthesis and the product was isolated by chiral chromatography on Reprosil Chiral NR using heptane/20% ethanol as eluent. The (−)-enantiomer was isolated. LC-MS (UV peak area/ESI) 100%, 394.2126 (M+H)$^+$, $\alpha_D^{20}$ (MeOH)=−44.9°.

Example 228

6-Cyclopropylmethoxy-5-trifluoromethyl-pyridine-2-carboxylic acid ((S)-3,3-dimethyl-1-methylcarbamoyl-butyl)-amide

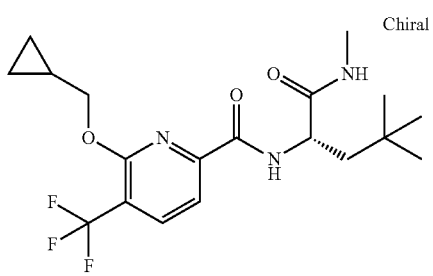 [SMILES: CNC(=O)[C@H](CC(C)(C)C)NC(=O)c1ccc(C(F)(F)F)c(OCC2CC2)n1]

The title compound was synthesized in analogy to Example 1, using 6-cyclopropylmethoxy-5-trifluoromethyl-pyridine-2-carboxylic acid (Example 113 d) and (2S)-2-amino-N,4,4-trimethyl-pentanamide (CAN 1160161-70-5) as starting materials, MS (EI): m/e=402.1 [M+H]$^+$.

Example 229

6-Cyclopropylmethoxy-5-trifluoromethyl-pyridine-2-carboxylic acid [cyclopropyl-(5-methyl-[1,2,4]oxadiazol-3-yl)-methyl]-amide

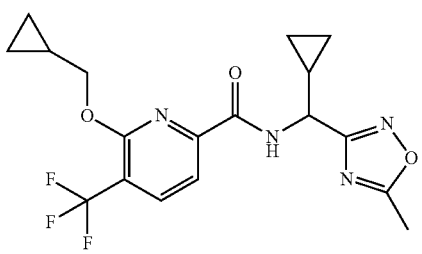 [SMILES: Cc1nc(C(NC(=O)c2ccc(C(F)(F)F)c(OCC3CC3)n2)C2CC2)no1]

The title compound was synthesized in analogy to Example 1, using 6-cyclopropylmethoxy-5-trifluoromethyl-pyridine-2-carboxylic acid (Example 113 d) and cyclopropyl-(5-methyl-[1,2,4]oxadiazol-3-yl)-methylamine (which can e.g. be prepared in a similar manner than (S)-2-cyclopropyl-1-(5-methyl-[1,2,4]oxadiazol-3-yl)-ethylamine (Example 38 e)) as starting materials, MS (EI): m/e=397.0 [M+H]+.

Example 230

6-(Tetrahydro-pyran-4-ylmethoxy)-5-trifluoromethyl-pyridine-2-carboxylic acid ((S)-3,3-dimethyl-1-methylcarbamoyl-butyl)-amide

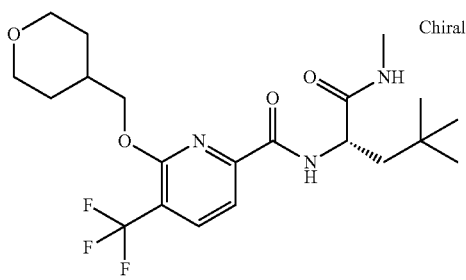 [SMILES: CNC(=O)[C@H](CC(C)(C)C)NC(=O)c1ccc(C(F)(F)F)c(OCC2CCOCC2)n1]

a) 6-Chloro-5-(trifluoromethyl)picolinic acid

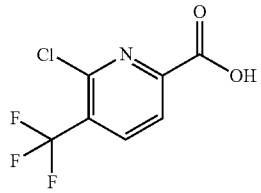 [SMILES: O=C(O)c1ccc(C(F)(F)F)c(Cl)n1]

The title compound was synthesized in analogy to the procedure described in Example 125 b), using methyl 6-chloro-5-(trifluoromethyl)picolinate (Example 113 c) as starting material. MS (EI): m/e=223.9 [M−H]−.

b) 6-((Tetrahydro-2H-pyran-4-yl)methoxy)-5-(trifluoromethyl)picolinic acid

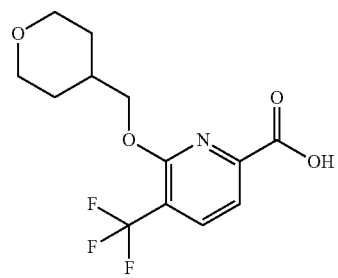 [SMILES: O=C(O)c1ccc(C(F)(F)F)c(OCC2CCOCC2)n1]

6-Chloro-5-(trifluoromethyl)picolinic acid (330 mg, 1.46 mmol) and powdered potassium hydroxide (328 mg, 5.85 mmol) were dissolved in DMSO (9 mL). The solution was stirred for 15 min. at ambient temperature. (Tetrahydro-2H-pyran-4-yl)methanol (170 mg, 170 µL, 1.46 mmol; CAN 14774-37-9) was added. The mixture was stirred for 1 d at ambient temp., poured onto ice water/brine/1N HCl (75 mL) and extracted with EtOAc (2×150 mL). The combined extracts were washed with ice water/brine (75 mL), dried over Na2SO4. The solvent was removed under reduced pressure to give the title compound as a grey solid (385 mg, 86%) which was used in the next step without further purification. MS: 304.0 [M−H]−.

c) 6-(Tetrahydro-pyran-4-ylmethoxy)-5-trifluoromethyl-pyridine-2-carboxylic acid ((S)-3,3-dimethyl-1-methylcarbamoyl-butyl)-amide The title compound was synthesized in analogy to Example 1, using 6-((tetrahydro-2H-pyran-4-yl)methoxy)-5-(trifluoromethyl)picolinic acid and (2S)-2-amino-N,4,4-trimethyl-pentanamide (CAN 1160161-70-5) as starting materials, MS (EI): m/e=446.4 [M+H]+.

Example 231

5-Cyclopropyl-6-cyclopropylmethoxy-pyridine-2-carboxylic acid ((S)-1-dimethylcarbamoyl-3-methyl-butyl)-amide

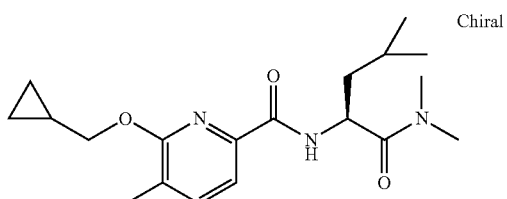

The title compound was synthesized in analogy to Example 1, using 5-cyclopropyl-6-cyclopropylmethyloxy-pyridine-2-carboxylic acid (Example 42 a) and (2S)-2-amino-N,N,4-trimethyl-pentanamide hydrochloride (1:1) (CAN 207595-81-1) as starting materials, LC-MS (UV peak area/ESI) 100%, 374.2240 (M+H)+.

Example 232

6-(3-Chloro-4-fluoro-phenyl)-pyridine-2-carboxylic acid [cyclopropyl-(5-methyl-[1,2,4]oxadiazol-3-yl)-methyl]-amide

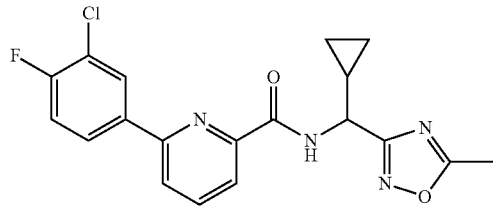 [SMILES: Cc1nc(C(NC(=O)c2cccc(-c3ccc(F)c(Cl)c3)n2)C2CC2)no1]

a) 6-Bromo-pyridine-2-carboxylic acid [cyclopropyl-(5-methyl-[1,2,4]oxadiazol-3-yl)-methyl]-amide

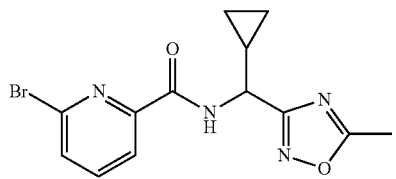 [SMILES: Cc1nc(C(NC(=O)c2cccc(Br)n2)C2CC2)no1]

The title compound can be prepared in analogy to Example 1, using 6-bromo-2-pyridinecarboxylic acid (CAN 21190-87-4) and cyclopropyl-(5-methyl-[1,2,4]oxadiazol-3-yl)-methylamine (which can e.g. be prepared in a similar manner than (S)-2-cyclopropyl-1-(5-methyl-[1,2,4]oxadiazol-3-yl)-ethylamine (Example 38 e) as starting materials, LC-MS (UV peak area/ESI) 97%, 337.0289 (M+H)⁺.

b) 6-(3-Chloro-4-fluoro-phenyl)-pyridine-2-carboxylic acid [cyclopropyl-(5-methyl-[1,2,4]oxadiazol-3-yl)-methyl]-amide The title compound can be prepared in analogy to Example 177 b, using 6-Bromo-pyridine-2-carboxylic acid [cyclopropyl-(5-methyl-[1,2,4]oxadiazol-3-yl)-methyl]-amide (Example 232 a) and B-(3-chloro-4-fluorophenyl)-boronic acid (CAN 144432-85-9) as starting materials, MS (EI): m/e=387.1 [M+H]⁺.

Example 233

2-{[5-Cyclopropyl-6-(tetrahydro-furan-2-yl-methoxy)-pyridine-2-carbonyl]-amino}-2-ethyl-butyric acid methyl ester

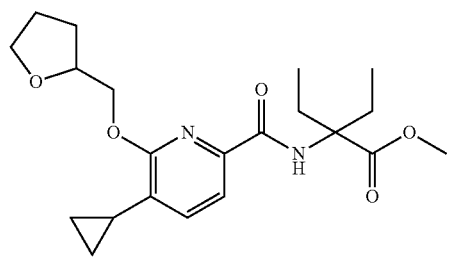 [SMILES: CCC(CC)(NC(=O)c1ccc(C2CC2)c(OCC2CCCO2)n1)C(=O)OC]

The title compound was synthesized in analogy to Example 1, using 5-cyclopropyl-6-(tetrahydro-furan-2-yl-methoxy)-pyridine-2-carboxylic acid (Example 166 b) and methyl 2-amino-2-ethylbutanoate hydrochloride (CAN 92398-54-4) as starting materials, MS (EI): m/e=391.3 [M+H]⁺.

Example 234

6-Cyclopropylmethoxy-5-(6-oxa-1-aza-spiro[3.3]hept-1-yl)-pyridine-2-carboxylic acid ((S)-3,3-dimethyl-1-methylcarbamoyl-butyl)-amide

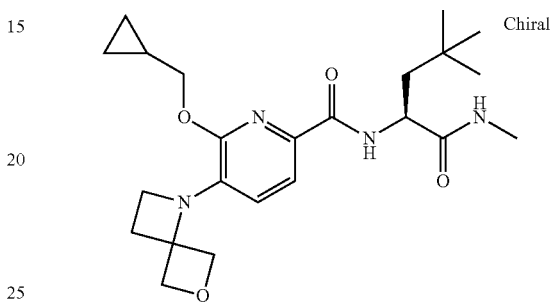

a) 6-Cyclopropylmethoxy-5-(6-oxa-1-aza-spiro[3.3]hept-1-yl)-pyridine-2-carboxylic acid methyl ester

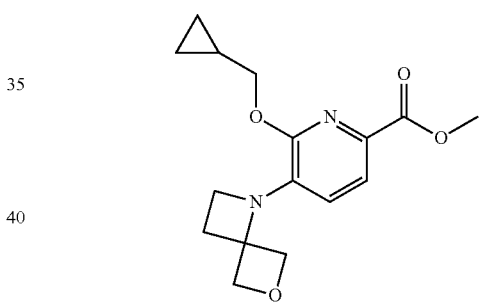

The title compound was synthesized in analogy to the procedure described in Example 32 a), using 5-bromo-6-(cyclopropylmethoxy)-pyridine-2-carboxylic acid methyl ester (Example 9 d) and 6-oxa-1-azaspiro[3.3]heptane, oxalate salt (CAN 1359655-43-8) as starting materials. MS (EI): m/e=305.0 [M+H]⁺.

b) 6-Cyclopropylmethoxy-5-(6-oxa-1-aza-spiro[3.3]hept-1-yl)-pyridine-2-carboxylic acid

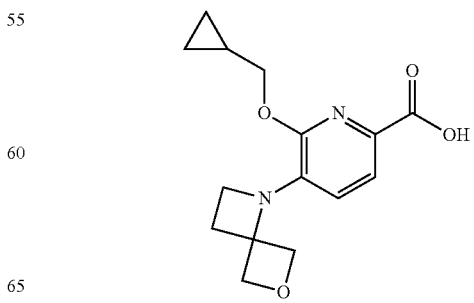

The title compound was synthesized in analogy to the procedure described in Example 125 b), using 6-cyclopropylmethoxy-5-(6-oxa-1-aza-spiro[3.3]hept-1-yl)-pyridine-2-carboxylic acid methyl ester as starting material. MS (EI): m/e=289.0 [M−H]⁻.

c) 6-Cyclopropylmethoxy-5-(6-oxa-1-aza-spiro[3.3]hept-1-yl)-pyridine-2-carboxylic acid ((S)-3,3-dimethyl-1-methylcarbamoyl-butyl)-amide The title compound was synthesized in analogy to Example 1, using 6-(cyclopropylmethoxy)-5-(6-oxa-1-aza-spiro[3.3]heptan-1-yl)picolinic acid and (2S)-2-amino-N,4,4-trimethyl-pentanamide (CAN 1160161-70-5) as starting materials. MS (EI): m/e=431.1 [M+H]⁺.

Example 235

6-Cyclopropylmethoxy-5-(6-oxa-1-aza-spiro[3.3]hept-1-yl)-pyridine-2-carboxylic acid [1-methyl-1-(5-methyl-[1,2,4]oxadiazol-3-yl)-ethyl]-amide

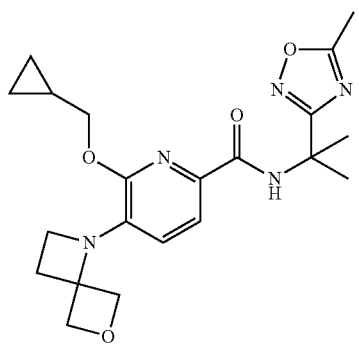 [SMILES: Cc1nc(C(C)(C)NC(=O)c2ccc(N3CCC34COC4)c(OCC3CC3)n2)no1]

The title compound was synthesized in analogy to Example 1, using 6-(cyclopropylmethoxy)-5-(6-oxa-1-aza-spiro[3.3]heptan-1-yl)picolinic acid (Example 234 b) and α,α,5-trimethyl-1,2,4-oxadiazole-3-methanamine (CAN 1153831-97-0) as starting materials. MS (EI): m/e=414.1 [M+H]⁺.

Example 236

6-Cyclopropylmethoxy-5-(6-oxa-1-aza-spiro[3.3]hept-1-yl)-pyridine-2-carboxylic acid [cyclopropyl-(5-methyl-[1,2,4]oxadiazol-3-yl)-methyl]-amide

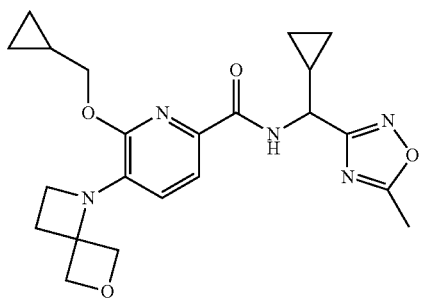 [SMILES: Cc1nc(C(NC(=O)c2ccc(N3CCC34COC4)c(OCC3CC3)n2)C2CC2)no1]

The title compound was synthesized in analogy to Example 1, using 6-(cyclopropylmethoxy)-5-(6-oxa-1-aza-spiro[3.3]heptan-1-yl)picolinic acid (Example 234 b) and cyclopropyl-(5-methyl-[1,2,4]oxadiazol-3-yl)-methylamine (which can e.g. be prepared in a similar manner than (S)-2-cyclopropyl-1-(5-methyl-[1,2,4]oxadiazol-3-yl)-ethylamine (Example 38 e) as starting materials. MS (EI): m/e=426.0 [M+H]⁺.

Example 237

6-Cyclopropylmethoxy-5-(3,3-difluoro-azetidin-1-yl)-pyridine-2-carboxylic acid ((R)-2,2,2-trifluoro-1-pyridin-3-yl-ethyl)-amide

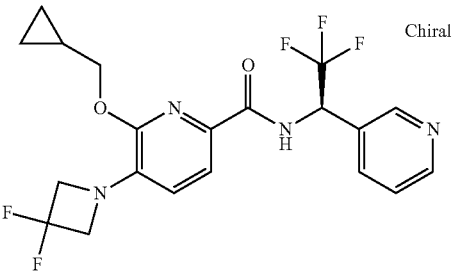 [SMILES: O=C(N[C@H](c1cccnc1)C(F)(F)F)c1ccc(N2CC(F)(F)C2)c(OCC2CC2)n1]

The title compound was synthesized in analogy to Example 1, using 6-cyclopropylmethoxy-5-(3,3-difluoro-azetidin-1-yl)-pyridine-2-carboxylic acid (Example 69 b) and (R)-2,2,2-trifluoro-1-pyridin-3-yl-ethylamine (CAN 1212813-98-3) as starting materials. MS (EI): m/e=443.1 [M+H]⁺.

Example 238

2-Ethyl-2-{[6-(tetrahydro-pyran-4-ylmethoxy)-5-trifluoromethyl-pyridine-2-carbonyl]-amino}-butyric acid methyl ester

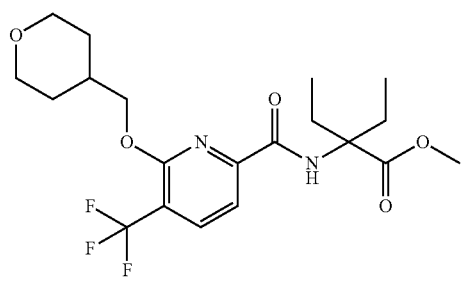 [SMILES: CCC(CC)(NC(=O)c1ccc(C(F)(F)F)c(OCC2CCOCC2)n1)C(=O)OC]

The title compound was synthesized in analogy to Example 1, using 6-((tetrahydro-2H-pyran-4-yl)methoxy)-5-(trifluoromethyl)picolinic acid (Example 230 b) and methyl 2-amino-2-ethylbutanoate hydrochloride (CAN 92398-54-4) as starting materials, MS (EI): m/e=433.5 [M+H]⁺.

Example 239

(S)-2-[(5-Cyclopropyl-6-cyclopropylmethoxy-pyridine-2-carbonyl)-amino]-3,3-dimethyl-butyric acid methyl ester

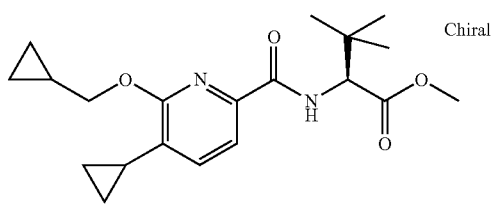 [SMILES: COC(=O)[C@@H](NC(=O)c1ccc(C2CC2)c(OCC2CC2)n1)C(C)(C)C]

The title compound was synthesized in analogy to Example 1, using 5-cyclopropyl-6-cyclopropylmethyloxy-pyridine-2-carboxylic acid (Example 42a) and 3-methyl-L-valine methyl ester hydrochloride (1:1) (CAN 63038-27-7) as starting materials, MS (ESI) 361.3 (M+H)$^+$.

Example 240

5-Cyclopropyl-6-cyclopropylmethoxy-pyridine-2-carboxylic acid ((−)-2,2,2-trifluoro-1-pyridin-2-yl-ethyl)-amide

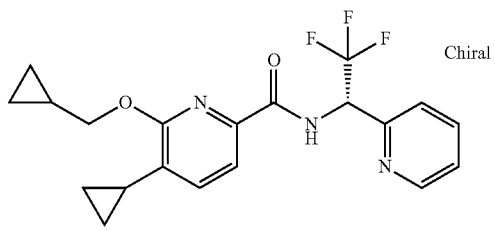 [SMILES: O=C(N[C@@H](c1ccccn1)C(F)(F)F)c1ccc(C2CC2)c(OCC2CC2)n1]

The title compound was synthesized in analogy to Example 1, using 5-cyclopropyl-6-cyclopropylmethyloxy-pyridine-2-carboxylic acid (Example 42a) and α-(trifluoromethyl)-2-pyridinemethanamine (CAN 503173-14-6) as starting materials. The product was isolated by chiral chromatography on Reprosil Chiral NR using heptane/20% ethanol as eluent. The (S)-(−)-enantiomer was isolated. LC-MS (UV peak area/ESI) 100%, 392.1950 (M+H)$^+$; $\alpha_D^{20}$ (MeOH)=−91.1°.

Example 241

5-Cyclopropyl-6-cyclopropylmethoxy-pyridine-2-carboxylic acid [(−)-1-(5-methyl-[1,2,4]oxadiazol-3-yl)-ethyl]-amide

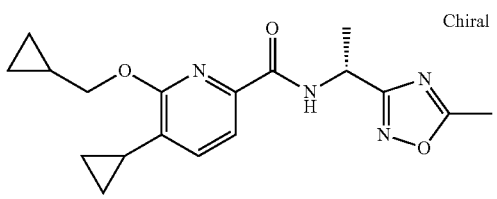 [SMILES: Cc1nc([C@@H](C)NC(=O)c2ccc(C3CC3)c(OCC3CC3)n2)no1]

The title compound was synthesized in analogy to Example 1, using 5-cyclopropyl-6-cyclopropylmethyloxy-pyridine-2-carboxylic acid (Example 42a) and α,5-dimethyl-1,2,4-oxadiazole-3-methanamine (CAN 1153834-40-2) as starting materials. The product was isolated by chiral chromatography on Chiralpak AD using heptane/20% ethanol as eluent. The (−)-enantiomer was isolated. LC-MS (UV peak area/ESI) 98.1%, 343.1767 (M+H)$^+$, $\alpha_D^{20}$ (MeOH)=−28.2°.

Example 242

5-Cyclopropyl-6-cyclopropylmethoxy-pyridine-2-carboxylic acid [(+)-3-methyl-1-(5-methyl-[1,2,4]oxadiazol-3-yl)-butyl]-amide

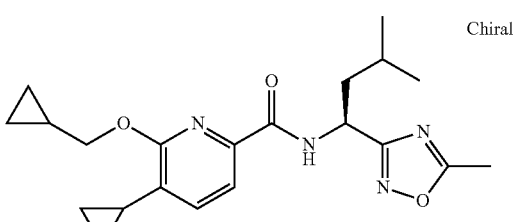

The title compound was synthesized in analogy to Example 1, using 5-cyclopropyl-6-cyclopropylmethyloxy-pyridine-2-carboxylic acid (Example 42a) and 5-methyl-α-(2-methylpropyl)-1,2,4-oxadiazole-3-methanamine (CAN 1155538-06-9) as starting materials. The product was isolated by chiral chromatography on Chiralpak AD using heptane/8% ethanol as eluent. The (+)-enantiomer was isolated. LC-MS (UV peak area/ESI) 100%, 385.2234 (M+H)$^+$, $\alpha_D^{20}$ (MeOH)=+22.5°.

Example 243

5-Cyclopropyl-6-cyclopropylmethoxy-pyridine-2-carboxylic acid [(−)-3-methyl-1-(5-methyl-[1,2,4]oxadiazol-3-yl)-butyl]-amide

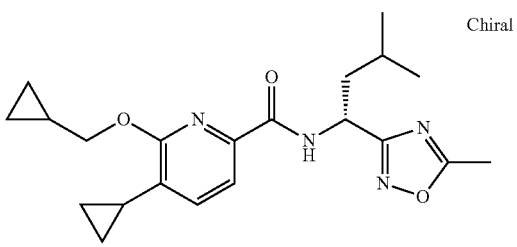 [SMILES: Cc1nc([C@@H](CC(C)C)NC(=O)c2ccc(C3CC3)c(OCC3CC3)n2)no1]

The title compound was synthesized in analogy to Example 1, using 5-cyclopropyl-6-cyclopropylmethyloxy-pyridine-2-carboxylic acid (Example 42a) and 5-methyl-α-(2-methylpropyl)-1,2,4-oxadiazole-3-methanamine (CAN 1155538-06-9) as starting materials. The product was isolated by chiral chromatography on Chiralpak AD using heptane/8% ethanol as eluent. The (−)-enantiomer was isolated. LC-MS (UV peak area/ESI) 100%, 385.2234 (M+H)⁺, $\alpha_D^{20}$ (MeOH)=−24.8°.

Example 244

5-Cyclopropyl-6-cyclopropylmethoxy-pyridine-2-carboxylic acid [(+)-1-(5-methyl-[1,2,4]oxadiazol-3-yl)-propyl]-amide

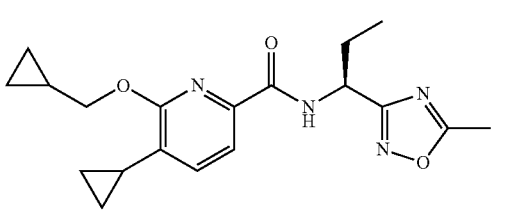

The title compound was synthesized in analogy to Example 1, using 5-cyclopropyl-6-cyclopropylmethyloxy-pyridine-2-carboxylic acid (Example 42a) and α-ethyl-5-methyl-1,2,4-oxadiazole-3-methanamine hydrochloride (1:1) (CAN 111997-68-3) as starting materials. The product was isolated by chiral chromatography on Chiralpak AD using heptane/8% ethanol as eluent. The (+)-enantiomer was isolated. LC-MS (UV peak area/ESI) 98.5%, 357.1925 (M+H)⁺, $\alpha_D^{20}$ (MeOH)=+36.7°.

Example 245

5-Cyclopropyl-6-cyclopropylmethoxy-pyridine-2-carboxylic acid [(−)-1-(5-methyl-[1,2,4]oxadiazol-3-yl)-propyl]-amide

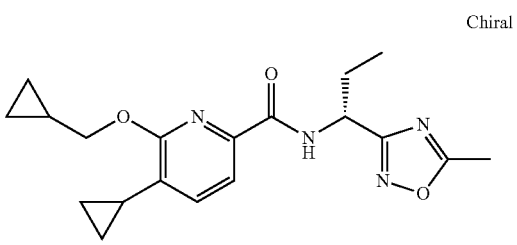 [SMILES: CC[C@@H](NC(=O)c1ccc(C2CC2)c(OCC2CC2)n1)c1noc(C)n1]

The title compound was synthesized in analogy to Example 1, using 5-cyclopropyl-6-cyclopropylmethyloxy-pyridine-2-carboxylic acid (Example 42a) and α-ethyl-5-methyl-1,2,4-oxadiazole-3-methanamine hydrochloride (1:1) (CAN 111997-68-3) as starting materials. The product was isolated by chiral chromatography on Chiralpak AD using heptane/8% ethanol as eluent. The (−)-enantiomer was isolated. LC-MS (UV peak area/ESI) 100%, 357.1913 (M+H)⁺, $\alpha_D^{20}$ (MeOH)=−35.1°.

Example 246

5-Cyclopropyl-6-cyclopropylmethoxy-pyridine-2-carboxylic acid ((−)-cyano-methyl-methyl)-amide

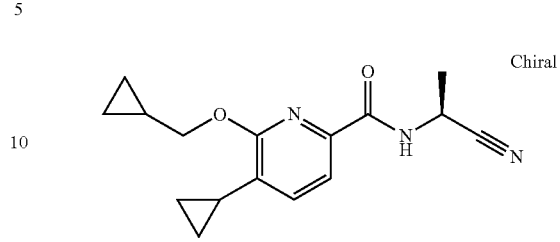

The title compound was synthesized in analogy to Example 1, using 5-cyclopropyl-6-cyclopropylmethyloxy-pyridine-2-carboxylic acid (Example 42a) and 2-amino-propanenitrile monohydrochloride (CAN 2134-48-7) as starting materials. The product was isolated by chiral chromatography on Reprosil Chiral NR using heptane/15% ethanol as eluent. The (−)-enantiomer was isolated. LC-MS (UV peak area/ESI) 100%, 286.1552 (M+H)⁺, $\alpha_D^{20}$ (MeOH)=−9.6°.

Example 247

5-Cyclopropyl-6-cyclopropylmethoxy-pyridine-2-carboxylic acid ((−)-1-cyano-3-methyl-butyl)-amide

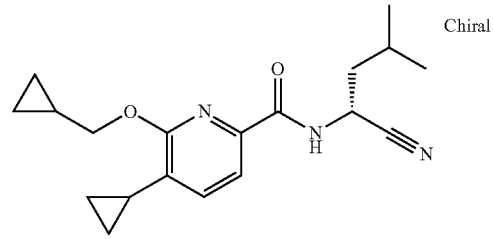 [SMILES: CC(C)C[C@H](C#N)NC(=O)c1ccc(C2CC2)c(OCC2CC2)n1]

The title compound was synthesized in analogy to Example 1, using 5-cyclopropyl-6-cyclopropylmethyloxy-pyridine-2-carboxylic acid (Example 42a) and 2-amino-4-methyl-pentanenitrile (CAN 65451-12-9) as starting materials. The product was isolated by chiral chromatography on Reprosil Chiral NR using heptane/15% ethanol as eluent. The (−)-enantiomer was isolated. LC-MS (UV peak area/ESI) 100%, 328.2026 (M+H)⁺, $\alpha_D^{20}$ (MeOH)=−8.0°.

Example 248

5-Cyclopropyl-6-cyclopropylmethoxy-pyridine-2-carboxylic acid ((+)-cyano-cyclopropyl-methyl)-amide

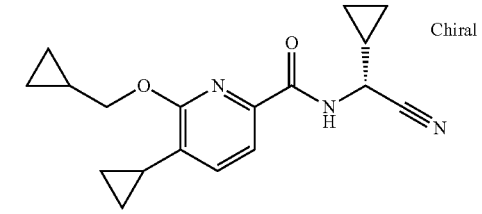 [SMILES: N#C[C@H](NC(=O)c1ccc(C2CC2)c(OCC2CC2)n1)C1CC1]

The title compound was synthesized in analogy to Example 1, using 5-cyclopropyl-6-cyclopropylmethyloxypyridine-2-carboxylic acid (Example 42 a) and α-amino-cyclopropaneacetonitrile (CAN 149357-92-6) as starting materials. The product was isolated by chiral chromatography on Reprosil Chiral NR using heptane/20% ethanol as eluent. The (+)-enantiomer was isolated. LC-MS (UV peak area/ESI) 100%, 312.1706 (M+H)$^+$, $\alpha_D^{20}$ (MeOH)=+9.0°.

Example 249

2-[(6-Cyclopropylmethoxy-5-trifluoromethyl-pyridine-2-carbonyl)-amino]-2-ethyl-butyric acid methyl ester

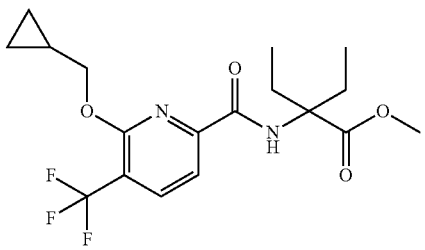 [SMILES: CCC(CC)(NC(=O)c1ccc(C(F)(F)F)c(OCC2CC2)n1)C(=O)OC]

The title compound was synthesized in analogy to Example 1, using 6-cyclopropylmethoxy-5-trifluoromethyl-pyridine-2-carboxylic acid (Example 113 d) and methyl 2-amino-2-ethylbutanoate hydrochloride (CAN 92398-54-4) as starting materials. MS (EI): m/e=389.0 [M+H]$^+$.

Example 250

5-Cyclopropyl-6-(tetrahydro-furan-2-ylmethoxy)-pyridine-2-carboxylic acid (1-ethyl-1-methylcarbamoyl-propyl)-amide

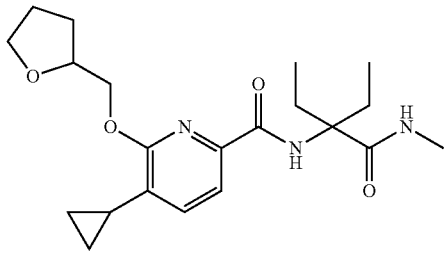 [SMILES: CCC(CC)(NC(=O)c1ccc(C2CC2)c(OCC2CCCO2)n1)C(=O)NC]

a) 2-(5-Cyclopropyl-6-((tetrahydrofuran-2-yl)methoxy)picolinamido)-2-ethylbutanoic acid

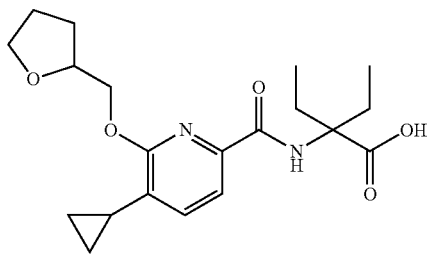 [SMILES: CCC(CC)(NC(=O)c1ccc(C2CC2)c(OCC2CCCO2)n1)C(=O)O]

Methyl 2-(5-cyclopropyl-6-((tetrahydrofuran-2-yl)methoxy)picolinamido)-2-ethylbutanoate (60 mg, 154 μmol, Example 233) and lithium hydroxide hydrate (7.74 mg, 184 μmol) were dissolved in a mixture of THF (600 μL) and water (150 μL). The reaction mixture was stirred for 48 h at ambient temp. Additional sodium hydroxide (24.6 mg, 614 μmol) was added and stirring was continued at 70° C. for additional 3 d. The mixture was poured onto ice water/brine/1N HCl (25 mL) and extracted with EtOAc (2×30 mL). The combined extracts were washed with ice water/brine (25 mL) and dried over Na$_2$SO$_4$. Concentration in vacuo afforded the title compound (49 mg, 85%) as a light yellow waxy solid. MS: 375.3 [M−H]$^-$.

b) 5-Cyclopropyl-6-(tetrahydro-furan-2-ylmethoxy)-pyridine-2-carboxylic acid (1-ethyl-1-methylcarbamoyl-propyl)-amide The title compound was synthesized in analogy to Example 1, using 2-(5-cyclopropyl-6-((tetrahydrofuran-2-yl)methoxy)picolinamido)-2-ethylbutanoic acid and methanamine hydrochloride as starting materials, MS (EI): m/e=390.3 [M+H]$^+$.

Example 251

2-[(5-Cyclopropyl-6-cyclopropylmethoxy-pyridine-2-carbonyl)-amino]-2-ethyl-butyric acid methyl ester

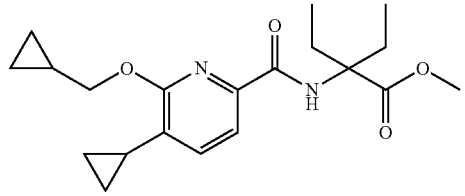 [SMILES: CCC(CC)(NC(=O)c1ccc(C2CC2)c(OCC2CC2)n1)C(=O)OC]

The title compound was synthesized in analogy to Example 1, using 5-cyclopropyl-6-cyclopropylmethyloxy-pyridine-2-carboxylic acid (Example 42a) and 2-amino-2-ethyl-butanoic acid ethyl ester hydrochloride (1:1) (CAN 70974-26-4) as starting materials, LC-MS (UV peak area/ESI) 100%, 361.2120 (M+H)$^+$.

Example 252

2-[(6-Cyclopropylmethoxy-5-trifluoromethyl-pyridine-2-carbonyl)-amino]-2-ethyl-butyric acid

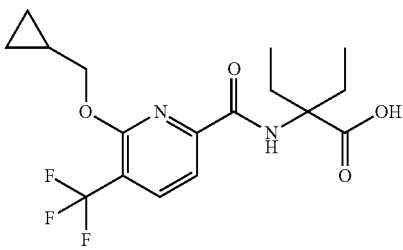 [SMILES: CCC(CC)(NC(=O)c1ccc(C(F)(F)F)c(OCC2CC2)n1)C(=O)O]

213 a) Ethyl 2-(6-(cyclopropylmethoxy)-5-(trifluoromethyl)picolinamido)-2-ethylbutanoate

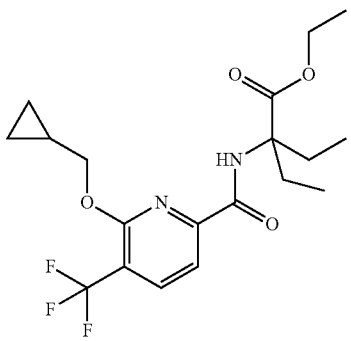 [SMILES: CCOC(=O)C(CC)(CC)NC(=O)c1ccc(C(F)(F)F)c(OCC2CC2)n1]

The title compound was synthesized in analogy to Example 1, using 6-cyclopropylmethoxy-5-trifluoromethyl-pyridine-2-carboxylic acid (Example 113 d) and ethyl 2-amino-2-ethylbutanoate hydrochloride (CAN 1135219-29-2) as starting materials, MS (EI): m/e=403.4 [M+H]$^+$.

b) 2-[(6-Cyclopropylmethoxy-5-trifluoromethyl-pyridine-2-carbonyl)-amino]-2-ethyl-butyric acid Ethyl 2-(6-(cyclopropylmethoxy)-5-(trifluoromethyl)picolinamido)-2-ethylbutanoate (62 mg, 154 μmol) was dissolved in a mixture of 1 M aqueous sodium hydroxide solution (616 μL, 616 μmol), THF (600 μL) and MeOH (600 μL). The mixture was stirred at 60° C. for 3 d, poured onto ice water/brine/1N HCl (20 mL) and extracted with EtOAc (2×30 mL). The combined extracts were washed with ice water/brine (20 mL) and dried over Na$_2$SO$_4$. The solvent was removed in vacuo to give the title compound (58 mg, quant.) as a light yellow solid. MS: 373.1 [M−H]$^-$.

Example 253

6-(Tetrahydro-pyran-4-ylmethoxy)-5-trifluoromethyl-pyridine-2-carboxylic acid (1-ethyl-1-methyl-carbamoyl-propyl)-amide

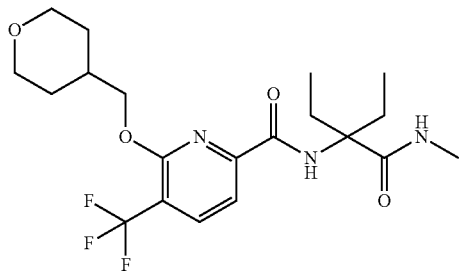 [SMILES: CCC(CC)(NC(=O)c1ccc(C(F)(F)F)c(OCC2CCOCC2)n1)C(=O)NC]

214 a) 2-Ethyl-2-(6-((tetrahydro-2H-pyran-4-yl)methoxy)-5-(trifluoromethyl)picolinamido)butanoic acid

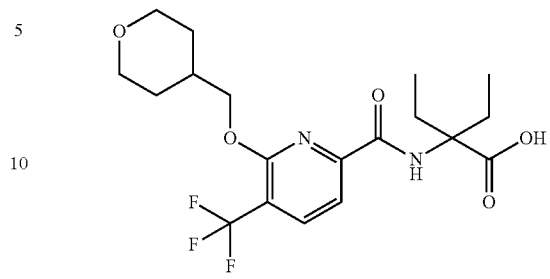

The title compound was synthesized in analogy to the procedure described in Example 252 b), using methyl 2-ethyl-2-(6-((tetrahydro-2H-pyran-4-yl)methoxy)-5-(trifluoromethyl)picolinamido)butanoate (Example 238) as starting material. MS (EI): m/e=417.0 [M−H]$^-$.

b) 6-(Tetrahydro-pyran-4-ylmethoxy)-5-trifluoromethyl-pyridine-2-carboxylic acid (1-ethyl-1-methyl-carbamoyl-propyl)-amide The title compound was synthesized in analogy to Example 1, using 2-ethyl-2-(6-((tetrahydro-2H-pyran-4-yl)methoxy)-5-(trifluoromethyl)picolinamido)butanoic acid and methanamine hydrochloride as starting materials. MS (EI): m/e=432.3 [M+H]$^+$.

Example 254

2-Ethyl-2-{[6-(tetrahydro-furan-2-ylmethoxy)-5-trifluoromethyl-pyridine-2-carbonyl]-amino}-butyric acid ethyl ester

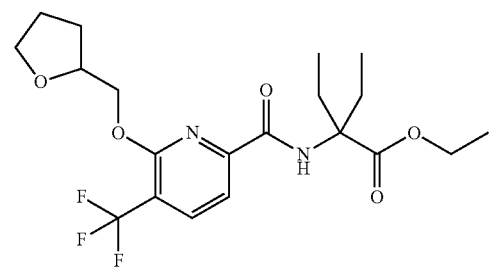 [SMILES: CCOC(=O)C(CC)(CC)NC(=O)c1ccc(C(F)(F)F)c(OCC2CCCO2)n1]

a) 6-((Tetrahydrofuran-2-yl)methoxy)-5-(trifluoromethyl)picolinic acid

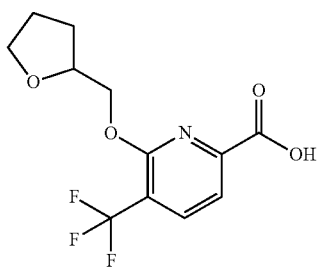 [SMILES: O=C(O)c1ccc(C(F)(F)F)c(OCC2CCCO2)n1]

The title compound was prepared in analogy to the procedure described in Example 230 b), using 6-chloro-5-(trifluoromethyl)picolinic acid and (tetrahydrofuran-2-yl)methanol (CAN 97-99-4) as starting materials. MS: 290.0 [M−H]$^-$.

b) 2-Ethyl-2-{[6-(tetrahydro-furan-2-ylmethoxy)-5-trifluoromethyl-pyridine-2-carbonyl]-amino}-butyric acid ethyl ester The title compound was synthesized in analogy to Example 1, using 6-((tetrahydrofuran-2-yl)methoxy)-5-(trifluoromethyl)picolinic acid and ethyl 2-amino-2-ethylbutanoate hydrochloride (CAN 1135219-29-2) as starting materials. MS (EI): m/e=433.4 [M+H]⁺.

Example 255

6-Cyclopropylmethoxy-5-(3,3-difluoro-azetidin-1-yl)-pyridine-2-carboxylic acid (dimethylcarbamoyl-phenyl-methyl)-amide

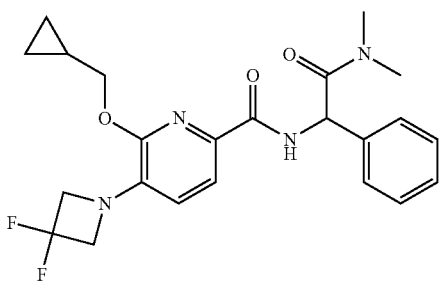 [SMILES: CN(C)C(=O)C(NC(=O)c1ccc(N2CC(F)(F)C2)c(OCC2CC2)n1)c1ccccc1]

The title compound was synthesized in analogy to Example 1, using 6-cyclopropylmethoxy-5-(3,3-difluoro-azetidin-1-yl)-pyridine-2-carboxylic acid (Example 69 b) and 2-amino-N,N-dimethyl-2-phenylacetamide hydrochloride (CAN 1214036-19-7) as starting materials. MS (EI): m/e=445.1 [M+H]⁺.

Example 256

6-Cyclopropylmethoxy-5-(3,3-difluoro-azetidin-1-yl)-pyridine-2-carboxylic acid ((S)-2-cyclopropyl-1-dimethylcarbamoyl-ethyl)-amide

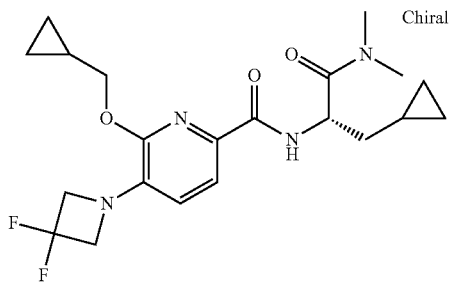 [SMILES: CN(C)C(=O)[C@H](CC1CC1)NC(=O)c1ccc(N2CC(F)(F)C2)c(OCC2CC2)n1]

The title compound was synthesized in analogy to Example 1, using 6-cyclopropylmethoxy-5-(3,3-difluoro-azetidin-1-yl)-pyridine-2-carboxylic acid (Example 69 b) and (S)-2-amino-3-cyclopropyl-N,N-dimethylpropanamide hydrochloride (Example 222 b) as starting materials. MS (EI): m/e=423.0 [M+H]⁺.

Example 257

2-[(5-Cyclopropyl-6-cyclopropylmethoxy-pyridine-2-carbonyl)-amino]-2-ethyl-butyric acid ethyl ester

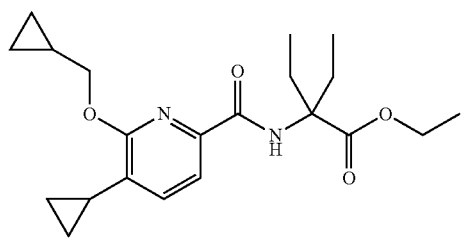 [SMILES: CCOC(=O)C(CC)(CC)NC(=O)c1ccc(C2CC2)c(OCC2CC2)n1]

The title compound was synthesized in analogy to Example 1, using 5-cyclopropyl-6-cyclopropylmethyloxy-pyridine-2-carboxylic acid (Example 42 a) and ethyl 2-amino-2-ethylbutanoate hydrochloride (CAN 1135219-29-2) as starting materials. MS (EI): m/e=375.0 [M+H]⁺.

Example 258

(S)-3-Cyclopropyl-2-[(5-cyclopropyl-6-cyclopropyl-methoxy-pyridine-2-carbonyl)-amino]-propionic acid methyl ester

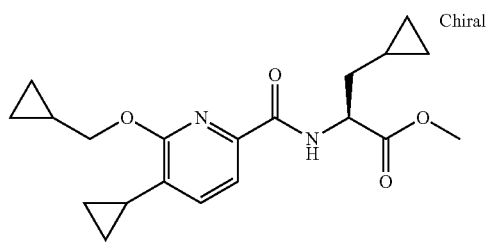 [SMILES: COC(=O)[C@H](CC1CC1)NC(=O)c1ccc(C2CC2)c(OCC2CC2)n1]

The title compound was synthesized in analogy to Example 1, using 5-cyclopropyl-6-cyclopropylmethyloxy-pyridine-2-carboxylic acid (Example 42a) and (αS)-α-amino-cyclopropanepropanoic acid methyl ester hydrochloride (1:1) (CAN 206438-31-5) as starting materials, LC-MS (UV peak area/ESI) 100%, 359.153 (M+H)⁺.

Example 259

6-Cyclopropylmethoxy-5-trifluoromethyl-pyridine-2-carboxylic acid (1-ethyl-1-methylcarbamoyl-propyl)-amide

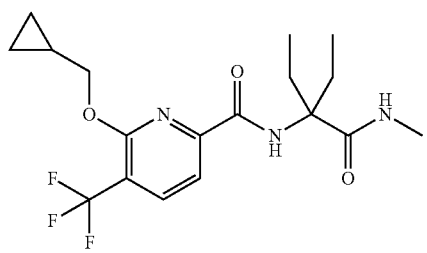 [SMILES: CCC(CC)(NC(=O)c1ccc(C(F)(F)F)c(OCC2CC2)n1)C(=O)NC]

a) 2-(6-(Cyclopropylmethoxy)-5-(trifluoromethyl) picolinamido)-2-ethylbutanoic acid

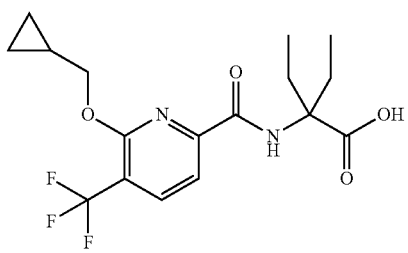 [SMILES: CCC(CC)(NC(=O)c1ccc(C(F)(F)F)c(OCC2CC2)n1)C(=O)O]

The title compound was synthesized in analogy to the procedure described in Example 252 b), using methyl 2-(6-(cyclopropylmethoxy)-5-(trifluoromethyl)picolinamido)-2-ethylbutanoate (Example 249) as starting material. MS (EI): m/e=373.1 [M−H]−.

b) 6-Cyclopropylmethoxy-5-trifluoromethyl-pyridine-2-carboxylic acid (1-ethyl-1-methylcarbamoyl-propyl)-amide The title compound was synthesized in analogy to Example 1, using 2-(6-(cyclopropylmethoxy)-5-(trifluoromethyl)picolinamido)-2-ethylbutanoic acid and methanamine hydrochloride as starting materials. MS (EI): m/e=388.0 [M+H]+.

Example 260

6-(3-Chloro-4-fluoro-phenyl)-pyridine-2-carboxylic acid [(−)-cyclopropyl-(5-methyl-[1,2,4]oxadiazol-3-yl)-methyl]-amide

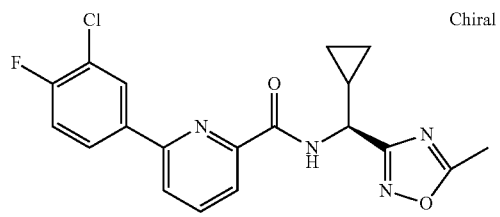 [SMILES: Cc1nc([C@@H](NC(=O)c2cccc(-c3ccc(F)c(Cl)c3)n2)C2CC2)no1]

The title compound was isolated by chiral chromatography of the racemate (Example 232) on Reprosil Chiral NR using heptane/30% 2-propanol as eluent. The (−)-enantiomer was isolated; MS (EI) 387.4 (M+H)+.

Example 261

6-(3-Chloro-4-fluoro-phenyl)-pyridine-2-carboxylic acid [(+)-cyclopropyl-(5-methyl-[1,2,4]oxadiazol-3-yl)-methyl]-amide

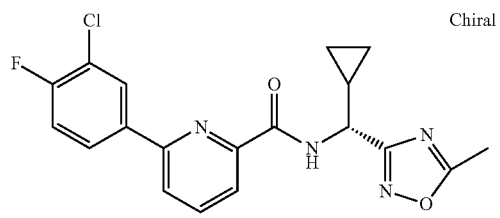 [SMILES: Cc1nc([C@H](NC(=O)c2cccc(-c3ccc(F)c(Cl)c3)n2)C2CC2)no1]

The title compound was isolated by chiral chromatography of the racemate (Example 232) on Reprosil Chiral NR using heptane/30% 2-propanol as eluent. The (−)-enantiomer was isolated; MS (EI) 387.3 (M+H)+.

Example 262

6-(Tetrahydro-pyran-4-ylmethoxy)-5-trifluoromethyl-pyridine-2-carboxylic acid (1-dimethylcarbamoyl-1-ethyl-propyl)-amide

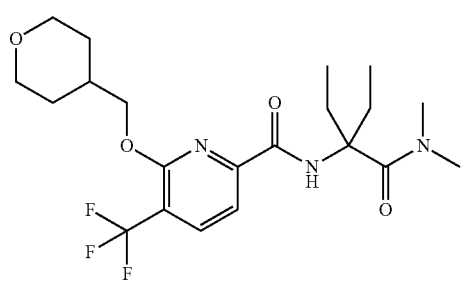 [SMILES: CCC(CC)(NC(=O)c1ccc(C(F)(F)F)c(OCC2CCOCC2)n1)C(=O)N(C)C]

The title compound was synthesized in analogy to Example 1, using 2-ethyl-2-(6-(((tetrahydro-2H-pyran-4-yl) methoxy)-5-(trifluoromethyl)picolinamido)butanoic acid (Example 253 a) and dimethylamine hydrochloride as starting materials. MS (EI): m/e=463.4 [M+NH4]+.

Example 263

2-{[6-Cyclopropylmethoxy-5-(6-oxa-1-aza-spiro [3.3]hept-1-yl)-pyridine-2-carbonyl]-amino}-2-ethyl-butyric acid ethyl ester

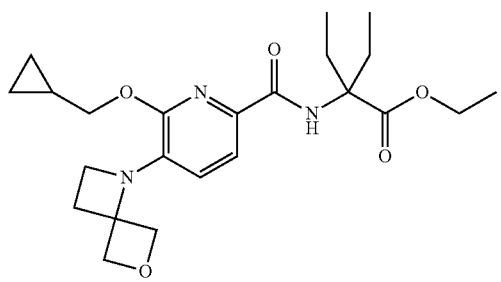 [SMILES: CCOC(=O)C(CC)(CC)NC(=O)c1ccc(N2CCC23COC3)c(OCC2CC2)n1]

The title compound was synthesized in analogy to Example 1, using 6-cyclopropylmethoxy-5-(6-oxa-1-aza-spiro[3.3]hept-1-yl)-pyridine-2-carboxylic acid (Example 234 b) and ethyl 2-amino-2-ethylbutanoate hydrochloride (CAN 1135219-29-2) as starting materials. MS (EI): m/e=432.3 [M+H]+.

Example 264

6-(Tetrahydro-furan-2-ylmethoxy)-5-trifluoromethyl-pyridine-2-carboxylic acid (1-dimethylcarbamoyl-1-ethyl-propyl)-amide

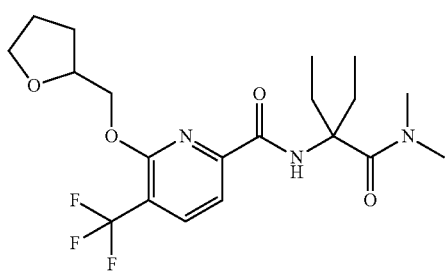 [SMILES: CCC(CC)(NC(=O)c1ccc(C(F)(F)F)c(OCC2CCCO2)n1)C(=O)N(C)C]

The title compound was synthesized in analogy to Example 1, using 2-ethyl-2-(6-((tetrahydro-2H-pyran-4-yl)methoxy)-5-(trifluoromethyl)picolinamido)butanoic acid (Example 253 a) and dimethylamine hydrochloride as starting materials. MS (EI): m/e=432.1 [M+H]$^+$.

Example 265

2-[(5-Bromo-6-cyclopropylmethoxy-pyridine-2-carbonyl)-amino]-2-ethyl-butyric acid ethyl ester

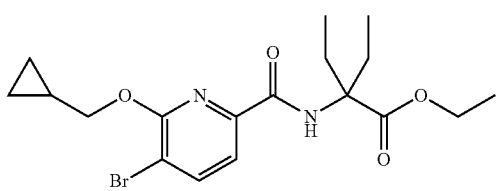 [SMILES: CCOC(=O)C(CC)(CC)NC(=O)c1ccc(Br)c(OCC2CC2)n1]

The title compound was synthesized in analogy to Example 1, using 5-bromo-6-(cyclopropylmethoxy)-pyridine-2-carboxylic acid (Example 9 d) and ethyl 2-amino-2-ethylbutanoate hydrochloride (CAN 1135219-29-2) as starting materials. MS (EI): m/e=415.0 [M+H]$^+$.

Example 266

2-{[6-Cyclopropylmethoxy-5-(3,3-difluoro-azetidin-1-yl)-pyridine-2-carbonyl]-amino}-2-ethyl-butyric acid ethyl ester

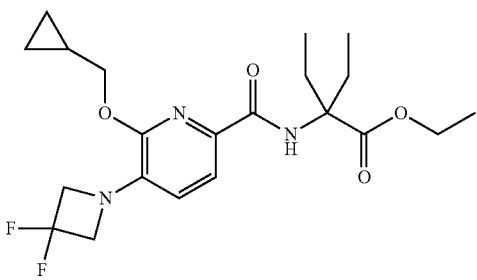 [SMILES: CCOC(=O)C(CC)(CC)NC(=O)c1ccc(N2CC(F)(F)C2)c(OCC2CC2)n1]

The title compound was synthesized in analogy to the procedure described in Example 69 a, using ethyl 2-(5-bromo-6-(cyclopropylmethoxy)picolinamido)-2-ethylbutanoate (Example 265) and 3,3-difluoroazetidine hydrochloride (CAN 288315-03-7) as starting materials. MS (EI): m/e=426.0 [M+H]$^+$.

Example 267

6-(4-Chloro-3-fluoro-phenyl)-pyridine-2-carboxylic acid [1-methyl-1-(5-methyl-[1,2,4]oxadiazol-3-yl)-ethyl]-amide

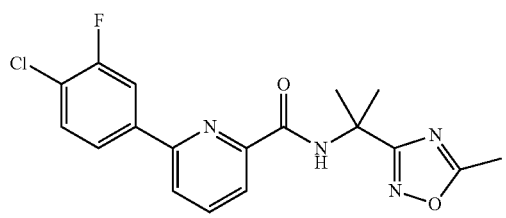 [SMILES: Cc1nc(C(C)(C)NC(=O)c2cccc(-c3ccc(Cl)c(F)c3)n2)no1]

a) 6-Bromo-pyridine-2-carboxylic acid [1-methyl-1-(5-methyl-[1,2,4]oxadiazol-3-yl)-ethyl]-amide

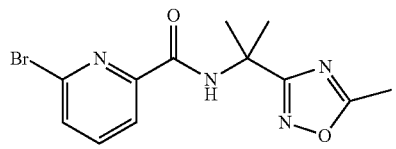 [SMILES: Cc1nc(C(C)(C)NC(=O)c2cccc(Br)n2)no1]

The title compound can be prepared in analogy to Example 1, using 6-bromo-2-pyridinecarboxylic acid (CAN 21190-87-4) and α,α,5-trimethyl-1,2,4-oxadiazole-3-methanamine hydrochloride (1:1) (CAN 1240526-27-5) as starting materials, LC-MS (UV peak area/ESI) 85%, 325.0293 (M+H)$^+$.

b) 6-(4-Chloro-3-fluoro-phenyl)-pyridine-2-carboxylic acid [1-methyl-1-(5-methyl-[1,2,4]oxadiazol-3-yl)-ethyl]-amide The title compound can be prepared in analogy to Example 177 b, using 6-bromo-pyridine-2-carboxylic acid [1-methyl-1-(5-methyl-[1,2,4]oxadiazol-3-yl)-ethyl]amide (Example 267a) and B-(4-chloro-3-fluorophenyl)-boronic acid (CAN 137504-86-0) as starting materials, LC-MS (UV peak area/ESI) 100%, 375.1017 (M+H)$^+$.

Example 268

6-(3-Chloro-4-fluoro-phenyl)-pyridine-2-carboxylic acid [1-methyl-1-(5-methyl-[1,2,4]oxadiazol-3-yl)-ethyl]-amide

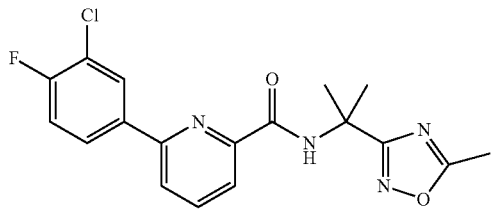 [SMILES: Cc1nc(C(C)(C)NC(=O)c2cccc(-c3ccc(F)c(Cl)c3)n2)no1]

The title compound was synthesized in analogy to Example 267 b, 6-bromo-pyridine-2-carboxylic acid [1-methyl-1-(5-methyl-[1,2,4]oxadiazol-3-yl)-ethyl]-amide (Example 267a) and B-(3-chloro-4-fluorophenyl)-boronic acid (CAN 144432-85-9) as starting materials, LC-MS (UV peak area/ESI) 91%, 375.1018 (M+H)⁺.

Example 269

2-{[6-Cyclopropylmethoxy-5-(3,3-difluoro-2-oxo-azetidin-1-yl)-pyridine-2-carbonyl]-amino}-2-ethyl-butyric acid methyl ester

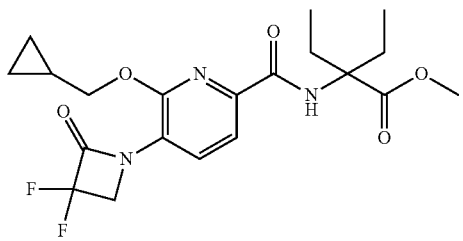 [SMILES: CCC(CC)(NC(=O)c1ccc(N2CC(F)(F)C2=O)c(OCC2CC2)n1)C(=O)OC]

The title compound was isolated in less than 1% yield in a reaction combining 6-cyclopropylmethoxy-5-(3,3-difluoro-azetidin-1-yl)-pyridine-2-carboxylic acid (Example 69 b) and methyl 2-amino-2-ethylbutanoate hydrochloride (CAN 92398-54-4) as starting materials in analogy to the procedure described in Example 1. We believe 6-cyclopropylmethoxy-5-(3,3-difluoro-azetidin-1-yl)-pyridine-2-carboxylic acid was contaminated with a small amount of 6-cyclopropyl-methoxy-5-(3,3-difluoro-2-oxo-azetidin-1-yl)-pyridine-2-carboxylic acid; MS (EI): m/e=426.0 [M+H]⁺.

Example 270

(S)-2-[(5-Cyclopropyl-6-cyclopropylmethoxy-pyridine-2-carbonyl)-amino]-4-methyl-pentanoic acid methyl ester

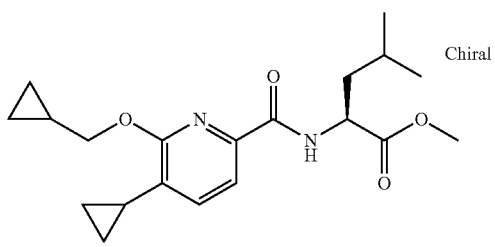 [SMILES: COC(=O)[C@H](CC(C)C)NC(=O)c1ccc(C2CC2)c(OCC2CC2)n1]

The title compound was synthesized in analogy to Example 1, using 5-cyclopropyl-6-cyclopropylmethyloxy-pyridine-2-carboxylic acid (Example 42a) and L-leucine methyl ester hydrochloride (1:1) (CAN 7517-19-3) as starting materials, LC-MS (UV peak area/ESI) 100%, 361.2120 (M+H)⁺.

Example 271

6-Cyclopropylmethoxy-5-(3,3-difluoro-azetidin-1-yl)-pyridine-2-carboxylic acid (1-cyano-3-methyl-butyl)-amide

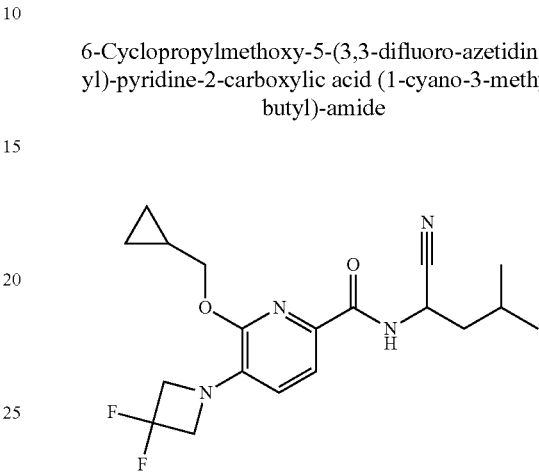

The title compound was synthesized in analogy to Example 1, using 6-cyclopropylmethoxy-5-(3,3-difluoro-azetidin-1-yl)-pyridine-2-carboxylic acid (Example 69 b) and 2-amino-4-methylpentanenitrile hydrochloride (CAN 72177-82-3) as starting materials. MS (EI): m/e=379.1 [M+H]⁺.

Example 272

6-Cyclopropylmethoxy-5-(3,3-difluoro-azetidin-1-yl)-pyridine-2-carboxylic acid [3-methyl-1-(5-methyl-[1,2,4]oxadiazol-3-yl)-butyl]-amide

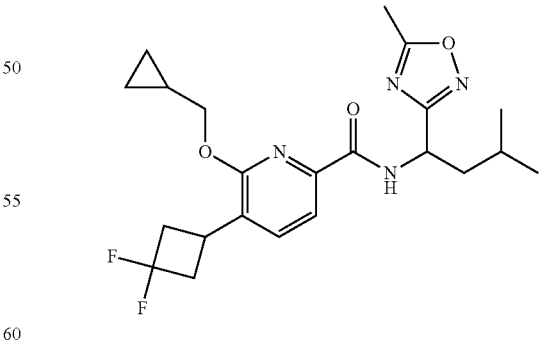

The title compound was synthesized in analogy to Example 1, using 6-cyclopropylmethoxy-5-(3,3-difluoro-azetidin-1-yl)-pyridine-2-carboxylic acid (Example 69 b) and 5-methyl-α-(2-methylpropyl)-1,2,4-oxadiazole-3-methanamine (CAN 1155538-06-9) as starting materials. MS (EI): m/e=436.0 [M+H]⁺.

Example 273

6-Cyclopropylmethoxy-5-(3,3-difluoro-azetidin-1-yl)-pyridine-2-carboxylic acid (1-hydroxymethyl-1,3-dimethyl-butyl)-amide

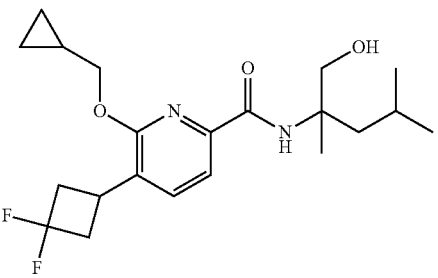 [SMILES: CC(C)CC(C)(CO)NC(=O)c1ccc(C2CC(F)(F)C2)c(OCC2CC2)n1]

The title compound was synthesized in analogy to Example 1, using 6-cyclopropylmethoxy-5-(3,3-difluoro-azetidin-1-yl)-pyridine-2-carboxylic acid (Example 69 b) and 2-amino-2,4-dimethylpentan-1-ol (CAN 13893-55-5) as starting materials. MS (EI): m/e=398.1 [M+H]$^+$.

Example 274

5-Cyclopropyl-6-cyclopropylmethoxy-pyridine-2-carboxylic acid [1-(azetidine-1-carbonyl)-1-ethyl-propyl]-amide

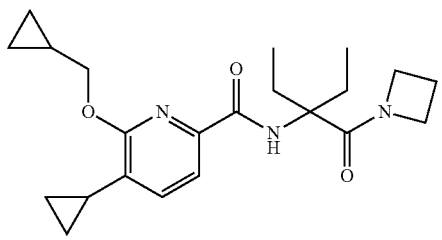 [SMILES: CCC(CC)(NC(=O)c1ccc(C2CC2)c(OCC2CC2)n1)C(=O)N1CCC1]

a) 2-(5-Cyclopropyl-6-(cyclopropylmethoxy)picolinamido)-2-ethylbutanoic acid

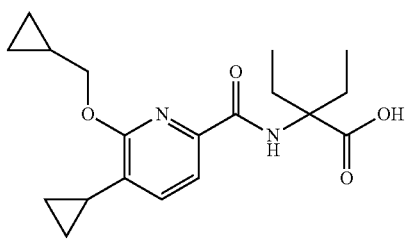 [SMILES: CCC(CC)(NC(=O)c1ccc(C2CC2)c(OCC2CC2)n1)C(=O)O]

The title compound was synthesized in analogy to the procedure described in Example 252 b), using ethyl 2-(5-cyclopropyl-6-(cyclopropylmethoxy)picolinamido)-2-ethylbutanoate (example 257) as the starting material. MS (EI): m/e=347.1 [M+H]$^+$.

b) 5-Cyclopropyl-6-cyclopropylmethoxy-pyridine-2-carboxylic acid [1-(azetidine-1-carbonyl)-1-ethyl-propyl]-amide The title compound was synthesized in analogy to Example 1, using 2-(5-cyclopropyl-6-(cyclopropylmethoxy)picolinamido)-2-ethylbutanoic acid and azetidine (CAN 503-29-7) as starting materials. MS (EI): m/e=386.0 [M+H]$^+$.

Example 275

5-Cyclopropyl-6-cyclopropylmethoxy-pyridine-2-carboxylic acid [1-ethyl-1-(2-methoxy-ethylcarbamoyl)-propyl]-amide

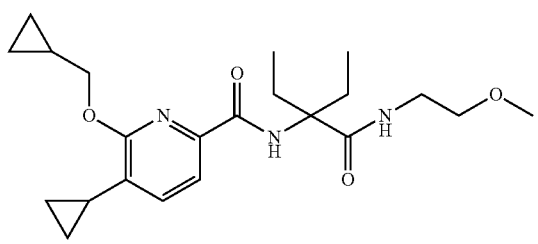 [SMILES: CCC(CC)(NC(=O)c1ccc(C2CC2)c(OCC2CC2)n1)C(=O)NCCOC]

The title compound was synthesized in analogy to Example 1, using 2-(5-cyclopropyl-6-(cyclopropylmethoxy)picolinamido)-2-ethylbutanoic acid (Example 274 a) and 2-methoxyethanamine (CAN 109-85-3) as starting materials. MS (EI): m/e=404.4 [M+H]$^+$.

Example 276

5-Cyclopropyl-6-cyclopropylmethoxy-pyridine-2-carboxylic acid [1-ethyl-1-(ethyl-methyl-carbamoyl)-propyl]-amide

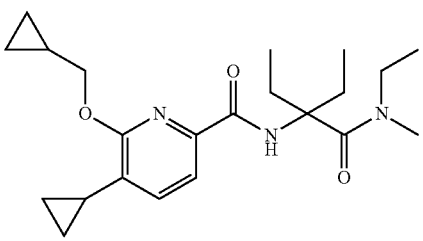 [SMILES: CCN(C)C(=O)C(CC)(CC)NC(=O)c1ccc(C2CC2)c(OCC2CC2)n1]

The title compound was synthesized in analogy to Example 1, using 2-(5-cyclopropyl-6-(cyclopropylmethoxy)picolinamido)-2-ethylbutanoic acid (Example 274 a) and N-methylethanamine (CAN 624-78-2) as starting materials. MS (EI): m/e=388.0 [M+H]$^+$.

Example 277

6-(4-Fluoro-benzyl)-pyridine-2-carboxylic acid ((S)-1-carbamoyl-3-methyl-butyl)-amide

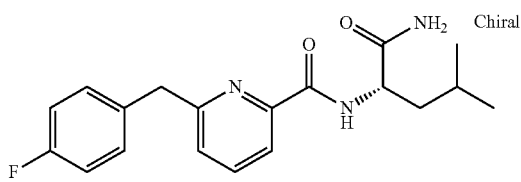 [SMILES: CC(C)C[C@H](NC(=O)c1cccc(Cc2ccc(F)cc2)n1)C(N)=O]

a) 6-(4-Fluorobenzyl)picolinic acid

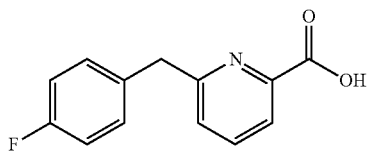 [SMILES: O=C(O)c1cccc(Cc2ccc(F)cc2)n1]

6-(4-Fluorobenzyl)picolinonitrile (24 mg, 113 μmol; CAN 1237431-32-1) and powdered sodium hydroxide (18.1 mg, 452 μmol) were dissolved in water (3 mL). The reaction mixture was heated to 90° C. for 2.5 h. Additional powdered sodium hydroxide (18.1 mg, 452 μmol) was added and heating was continued for another 2.5 h. The reaction mixture was poured onto 25 mL ice/0.1N HCl and extracted with EtOAc (2×20 mL). The combined organic layers were washed with ice water/brine (25 mL), dried over $Na_2SO_4$ and concentrated in vacuo to give the title compound (21 mg, 80%) as light yellow oil which was used in the next step without further purification. MS (EI): m/e=230.1 [M−H]⁻.

b) 6-(4-Fluoro-benzyl)-pyridine-2-carboxylic acid ((S)-1-carbamoyl-3-methyl-butyl)-amide The title compound was synthesized in analogy to Example 1, using 6-(4-fluorobenzyl)picolinic acid and (2S)-2-amino-4-methyl-pentanamide (CAN 687-51-4) as starting materials. MS (EI): m/e=344.0 [M+H]⁺.

Example 278

6-(4-Fluoro-benzyl)-pyridine-2-carboxylic acid ((R)-2,2,2-trifluoro-1-pyridin-2-yl-ethyl)-amide

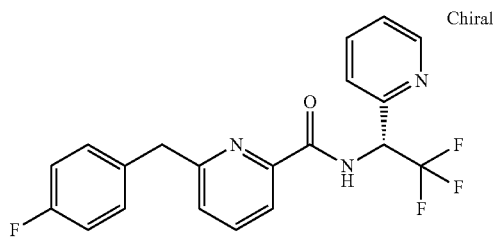 [SMILES: O=C(N[C@H](c1ccccn1)C(F)(F)F)c1cccc(Cc2ccc(F)cc2)n1]

The title compound was synthesized in analogy to Example 1, using 6-(4-fluorobenzyl)picolinic acid (Example 277 a) and (R)-2,2,2-trifluoro-1-(pyridin-2-yl)ethanamine hydrochloride (CAN 1228565-87-4) as starting materials. MS (EI): m/e=390.1 [M+H]⁺.

Example 279

5-Cyclopropyl-6-cyclopropylmethoxy-pyridine-2-carboxylic acid ((S)-1-hydroxymethyl-1,2-dimethyl-propyl)-amide

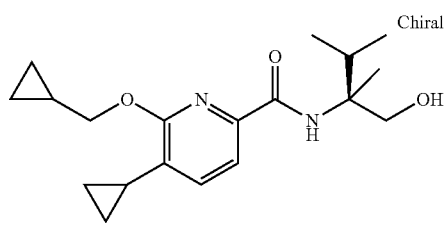 [SMILES: CC(C)[C@@](C)(CO)NC(=O)c1ccc(C2CC2)c(OCC2CC2)n1]

The title compound was synthesized in analogy to Example 1, using 5-cyclopropyl-6-cyclopropylmethyloxy-pyridine-2-carboxylic acid (Example 42a) and (2S)-2-amino-2,3-dimethyl-1-butanol (CAN 956102-64-0) as starting materials, LC-MS (UV peak area/ESI) 100%, 333.2175 (M+H)⁺.

Example 280

5-Bromo-6-(3-methyl-oxetan-3-ylmethoxy)-pyridine-2-carboxylic acid (1-methyl-1-thiazol-2-yl-ethyl)-amide

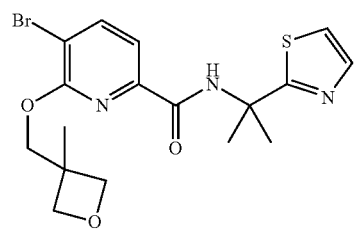 [SMILES: CC1(COc2nc(C(=O)NC(C)(C)c3nccs3)ccc2Br)COC1]

a) 5-Bromo-6-chloropicolinic acid

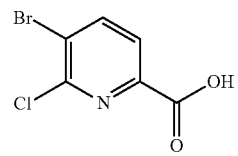 [SMILES: O=C(O)c1ccc(Br)c(Cl)n1]

In a 500 ml two-necked-round-bottom flask, 3-bromo-2-chloro-6-methylpyridine (CAN 185017-72-5) (4.0 g, 19.4 mmol) was suspended in $H_2O$ (160 ml) to give a colorless suspension. Under stirring, sodium dodecyl sulfate (64 mg, 222 μmol) and KMnO4 (9.19 g, 58.1 mmol) were added. The reaction mixture was stirred at 100° C. for 18 h. The reaction was then cooled to RT and 100 ml $NaHSO_3$-solution (40%) was added dropwise under ice bath-cooling (decolorization).

A white precipitate formed and the mixture was stirred a further 30 min. The reaction mixture was acidified with 120 ml 2N-HCl followed by extraction with ethyl acetate (2×200 ml). The combined organic layer was dried over Na₂SO₄, filtered off and concentrated in vacuo to give a white solid containing a mixture of starting material and the product. The solid was dissolved in 50 ml TBME/THF 9:1 and under stirring was added 15 ml 2N—NaOH which formed a suspension. The suspension was then extracted with 100 ml water. The water-layer was washed with 50 ml TBME. The water-layer was acidified with 20 ml 2N-HCl which was then extracted with a mixture TBME/THF 9:1 (2×50 ml). The combined organic layers were dried over Na₂SO₄, filtered off and concentrated in vacuo to dryness to give the title compound (1.8 g, 39%) as a white solid; MS (LC/MS): 235.9[M–H]⁻.

b) 5-Bromo-6-(3-methyl-oxetan-3-ylmethoxy)-pyridine-2-carboxylic acid

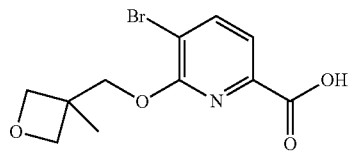 [SMILES: CC1(COc2nc(C(=O)O)ccc2Br)COC1]

To a solution of 5-bromo-6-chloropicolinic acid (Example 280a) (0.75 g, 3.17 mmol) in dry DMF (18 ml) under argon was added (3-methyloxetan-3-yl)-methanol (389 mg, 3.81 mmol) and NaH (279 mg, 6.98 mmol) was added by portions. The reaction mixture was stirred at room temperature for 20 min until gas release ceased. The reaction mixture was then stirred at 110° C. for 16 h. The reaction mixture was diluted with ethyl acetate, and the solution was poured into a separatory funnel with 10 ml aq. solution 1.0M HCl. After extraction, the organic phase was collected and the aqueous phase was back extracted with ethylacetate. The organic phases were combined, dried over Na₂SO₄ and evaporated down in vacuo. The residue was purified by preparative HPLC to give the title compound (260 mg, 27%), MS (EI): m/e=302.0 [M+H]⁺.

c) 5-Bromo-6-(3-methyl-oxetan-3-ylmethoxy)-pyridine-2-carboxylic acid (1-methyl-1-thiazol-2-yl-ethyl)-amide To a solution of 5-bromo-6-(3-methyl-oxetan-3-yl-methoxy)-pyridine-2-carboxylic acid (Example 280b) (30 mg, 100 μmol) in dry DMF (1 ml) was added 4-(4,6-dimethoxy-1,3,5-triazin-2-yl)-4-methylmorpholinium chloride (29.1 mg, 105 μmol) and Hunig's base (52.4 uL, 300 umol). The reaction was stirred at r.t for 30 min, followed by addition of α,α-Dimethyl-2-thiazolemethanamine (Example 12c) (14.2 mg, 100 μmol). The reactions was stirred at room temperature overnight and monitored by LC-MS. When the reaction was complete, purification was directly done by preparative HPLC without any work-up procedure to give the title compound (9.8 mg, 23%). MS (EI): m/e=425.9 [M+H]⁺.

Example 281

5-Bromo-6-(3-methyl-oxetan-3-ylmethoxy)-pyridine-2-carboxylic acid (3-thiazol-2-yl-oxetan-3-yl)-amide

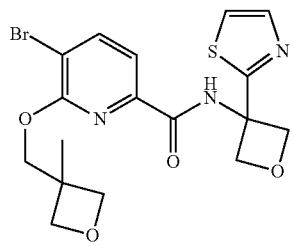 [SMILES: CC1(COc2nc(C(=O)NC3(c4nccs4)COC3)ccc2Br)COC1]

a) 2-Methyl-propane-2-sulfinic acid (3-thiazol-2-yl-oxetan-3-yl)-amide

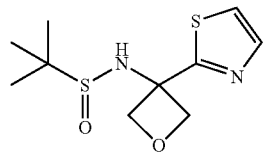 [SMILES: CC(C)(C)S(=O)NC1(c2nccs2)COC1]

A solution of n-butyllithium in hexanes (1.6 M, 2.5 mL, 3.99 mmol) was added dropwise to a solution of thiazole (364 mg, 4.23 mmol) in tetrahydrofuran (30 mL) at −78° C. The resulting mixture was stirred for 30 min at −78° C. before a solution of 2-methyl-n-(oxetan-3-ylidene)propane-2-sulfinamide (CAN 1158098-73-7) (500 mg, 2.85 mmol) in tetrahydrofuran (3.5 mL) was added dropwise at −78° C. The reaction solution was stirred for an additional 30 min at −78° C. before being warmed to 22° C., and then was quenched with saturated aqueous ammonium chloride solution. The crude reaction mixture was then partitioned between water and ethyl acetate. The aqueous layer was further extracted with ethyl acetate and the organic layers were combined. The combined layers were washed with saturated aqueous sodium chloride solution, and the washed solution was dried with anhydrous sodium sulfate and evaporated down to dryness. The crude product was purified by flash-column chromatography (40% ethyl acetate-hexanes, grading to 100% ethyl acetate, then flushing with 10% methanol-dichloromethane) to give the title compound (495 mg, 67%). MS (EI): m/e=261.0 [M+H]⁺.

b) 3-(Thiazol-2-yl)oxetan-3-amine hydrochloride

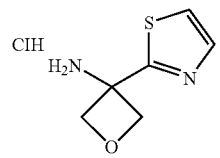

A 4.0 M solution of hydrochloric acid (117 μL, 467 μmol) in dioxane was added to a solution of 2-methyl-propane-2-sulfinic acid (3-thiazol-2-yl-oxetan-3-yl)-amide (Example 281a) (81 mg, 311 μmol) in methanol (0.5 mL) at 0° C. The mixture was stirred at 0° C. for 5 min before the solvents were removed under reduced pressure. The resulting white solid was triturated with diethyl ether and filtered off. The solid was further washed with diethyl ether and dried under high vacuum to yield the title compound (42 mg, 70%) as a white solid. MS (EI): m/e=157.1 [M+H]⁺.

c) 5-Bromo-6-(3-methyl-oxetan-3-ylmethoxy)-pyridine-2-carboxylic acid (3-thiazol-2-yl-oxetan-3-yl)-amide The title compound was synthesized in analogy to Example 280c, using 5-bromo-6-(3-methyl-oxetan-3-ylmethoxy)-pyridine-2-carboxylic acid (Example 280b) and 3-(thiazol-2-yl)oxetan-3-amine hydrochloride (Example 281b) as starting materials, MS (EI): m/e=440.4 [M+H]⁺.

Example 282

5-Bromo-6-(2,2,2-trifluoro-ethoxy)-pyridine-2-carboxylic acid (3-thiazol-2-yl-oxetan-3-yl)-amide

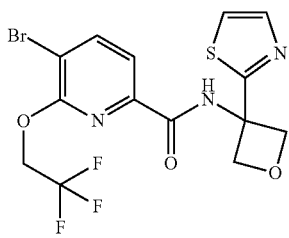 [SMILES: O=C(NC1(c2nccs2)COC1)c1ccc(Br)c(OCC(F)(F)F)n1]

a) 5-Bromo-6-(2,2,2-trifluoro-ethoxy)-pyridine-2-carboxylic acid

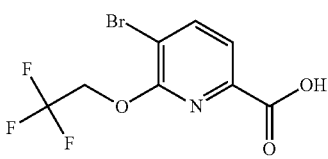 [SMILES: O=C(O)c1ccc(Br)c(OCC(F)(F)F)n1]

In a 25 mL round-bottomed flask, 5-bromo-6-chloropicolinic acid (433 mg, 1.83 mmol) and powdered potassium hydroxide (411 mg, 7.32 mmol) were combined with DMSO (1.9 ml) to give a colorless solution which was stirred at room temperature for 15 min. 2,2,2-trifluoroethanol (275 mg, 198 µl, 2.75 mmol, Eq: 1.5) was added. The reaction mixture was stirred for 24 h at ambient temperature. Since the reaction was complete, 0.75 extra equivalents of 2,2,2-trifluoroethanol was added and the reaction was stirred 48 h at ambient temperature. The reaction mixture was poured onto 1 M HCl/ice water (1×20 mL), extracted with iPrOAc (2×25 mL). The organic layers were dried over Na₂SO₄ and filtered, removed under reduced pressure to give the title compound as a white solid after recrystallization from CH₂Cl₂ and heptane (409 mg, 1.36 mmol, 74.4% yield), MS (EI): m/e=299.9 [M+H]⁺.

b) 5-Bromo-6-(2,2,2-trifluoro-ethoxy)-pyridine-2-carboxylic acid (3-thiazol-2-yl-oxetan-3-yl)-amide The title compound was synthesized in analogy to Example 280c, using 5-bromo-6-(2,2,2-trifluoro-ethoxy)-pyridine-2-carboxylic acid (Example 282a) and 3-(thiazol-2-yl)oxetan-3-amine hydrochloride (Example 281b) as starting materials, MS (EI): m/e=438.0 [M+H]⁺.

Example 283

5-Bromo-6-(3-methyl-oxetan-3-ylmethoxy)-pyridine-2-carboxylic acid (2,2,2-trifluoro-1-pyridin-2-yl-ethyl)-amide

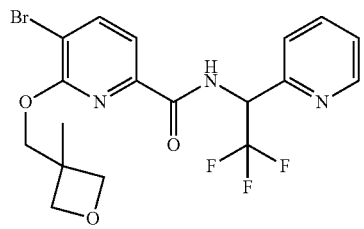 [SMILES: CC1(COc2nc(C(=O)NC(c3ccccn3)C(F)(F)F)ccc2Br)COC1]

The title compound was synthesized in analogy to Example 280c, using 5-bromo-6-(2,2,2-trifluoro-ethoxy)-pyridine-2-carboxylic acid (Example 282a) and 2,2,2-trifluoro-1-(pyridin-2-yl)ethanamine (CAN 35272-15-2) as starting materials, MS (EI): m/e=460.4 [M+H]⁺.

Example 284

5-Cyclopropyl-6-cyclopropylmethoxy-pyridine-2-carboxylic acid [1-(cyclopropylmethyl-carbamoyl)-1-ethyl-propyl]-amide

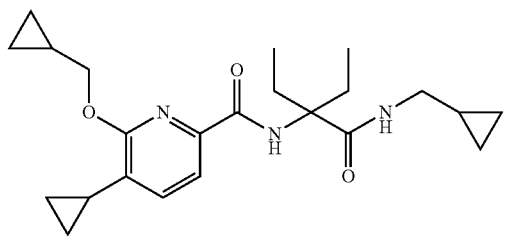 [SMILES: CCC(CC)(NC(=O)c1ccc(C2CC2)c(OCC2CC2)n1)C(=O)NCC1CC1]

The title compound was synthesized in analogy to Example 1, using 2-(5-cyclopropyl-6-(cyclopropylmethoxy)picolinamido)-2-ethylbutanoic acid (Example 274 a) and cyclopropylmethanamine (CAN 2516-47-4) as starting materials. MS (EI): m/e=400.1 [M+H]⁺.

Example 285

5-Cyclopropyl-6-cyclopropylmethoxy-pyridine-2-carboxylic acid (1-methyl-1-pyridin-2-yl-ethyl)-amide

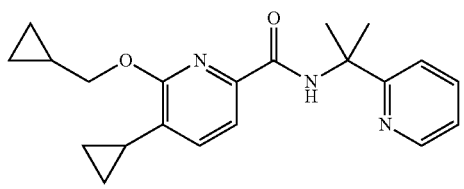 [SMILES: CC(C)(NC(=O)c1ccc(C2CC2)c(OCC2CC2)n1)c1ccccn1]

The title compound was synthesized in analogy to Example 1, using 5-cyclopropyl-6-cyclopropylmethyloxy-pyridine-2-carboxylic acid (Example 42a) and α,α-dimethyl-2-pyridinemethanamine (CAN 52568-28-2) as starting materials, LC-MS (UV peak area/ESI) 100%, 352.2021 (M+H)⁺.

Example 286

6-(4-Fluoro-benzyl)-pyridine-2-carboxylic acid ((S)-3,3-dimethyl-1-methylcarbamoyl-butyl)-amide

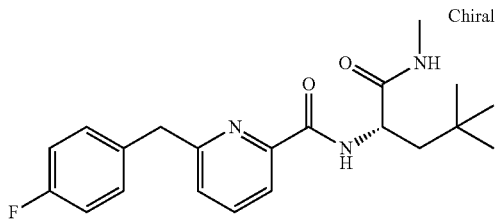 [SMILES: CNC(=O)[C@H](CC(C)(C)C)NC(=O)c1cccc(Cc2ccc(F)cc2)n1]

The title compound was synthesized in analogy to Example 1, using 6-(4-fluorobenzyl)picolinic acid (Example 277 a) and (2S)-2-amino-N,4,4-trimethyl-pentanamide (CAN 1160161-70-5) as starting materials. MS (EI): m/e=372.0 [M+H]⁺.

Example 287

5-Cyclopropyl-6-cyclopropylmethoxy-pyridine-2-carboxylic acid [1-(3,3-difluoro-azetidine-1-carbonyl)-1-ethyl-propyl]-amide

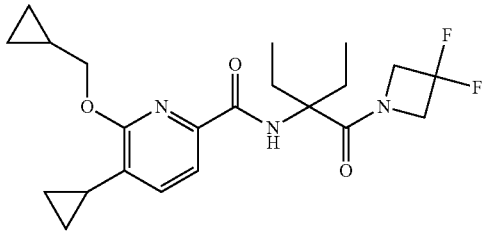 [SMILES: CCC(CC)(NC(=O)c1ccc(C2CC2)c(OCC2CC2)n1)C(=O)N1CC(F)(F)C1]

The title compound was synthesized in analogy to Example 1, using 2-(5-cyclopropyl-6-(cyclopropylmethoxy)picolinamido)-2-ethylbutanoic acid (Example 274 a) and 3,3-difluoroazetidine hydrochloride (CAN 288315-03-7) as starting materials. MS (EI): m/e=422.0 [M+H]⁺.

Example 288

5-(3,3-Difluoro-azetidin-1-yl)-6-(2,2,2-trifluoro-ethoxy)-pyridine-2-carboxylic acid (1-methyl-4-thiazol-2-yl-ethyl)-amide

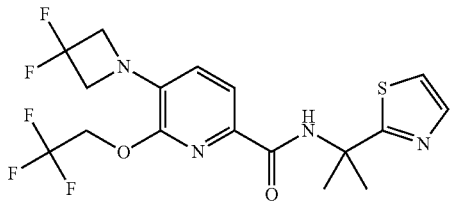 [SMILES: CC(C)(NC(=O)c1ccc(N2CC(F)(F)C2)c(OCC(F)(F)F)n1)c1nccs1]

a) 5-Bromo-6-(2,2,2-trifluoro-ethoxy)-pyridine-2-carboxylic acid (1-methyl-1-thiazol-2-yl-ethyl)-amide

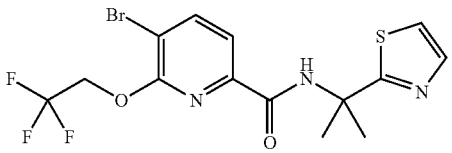 [SMILES: CC(C)(NC(=O)c1ccc(Br)c(OCC(F)(F)F)n1)c1nccs1]

The title compound was synthesized in analogy to Example 280c, using 5-bromo-6-(2,2,2-trifluoro-ethoxy)-pyridine-2-carboxylic acid (Example 282a) and α,α-dimethyl-2-thiazolemethanamine (Example 12c) as starting materials, MS (EI): m/e=424.3 [M+H]⁺.

b) 5-(3,3-Difluoro-azetidin-1-yl)-6-(2,2,2-trifluoro-ethoxy)-pyridine-2-carboxylic acid (1-methyl-1-thiazol-2-yl-ethyl)-amide To a solution of 5-bromo-6-(2,2,2-trifluoro-ethoxy)-pyridine-2-carboxylic acid (1-methyl-1-thiazol-2-yl-ethyl)-amide (Example 288a) (63.6 mg, 150 μmol) in dry toluene (1 ml) was added 3,3-difluoroazetidine hydrochloride (21.4 mg, 165 μmol), BINAP (9.34 mg, 15.0 μmol), Pd(OAc)₂ (3.37 mg, 15.0 μmol) and Cs₂CO₃ (122 mg, 375 μmol). The reaction was stirred at 120° C. overnight and controlled by LC-MS. Evaporation of the volatiles, residue was redissolved in DMF and directly purified by preparative HPLC to give the title compound (21 mg, 48 umol, 32%), MS (EI): m/e=437.4 [M+H]⁺.

Example 289

2-[(6-Cyclopropylmethoxy-5-pyrrolidin-1-yl-pyridine-2-carbonyl)-amino]-2-ethyl-butyric acid ethyl ester

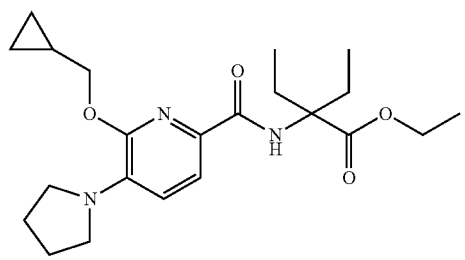 [SMILES: CCOC(=O)C(CC)(CC)NC(=O)c1ccc(N2CCCC2)c(OCC2CC2)n1]

The title compound was synthesized in analogy to the procedure described in Example 32 a, using 2-[(5-bromo-6-cyclopropylmethoxy-pyridine-2-carbonyl)-amino]-2-ethyl-butyric acid ethyl ester (Example 265) and pyrrolidine (CAN 123-75-1) as starting materials. MS (EI): m/e=404.4 [M+H]⁺.

Example 290

6-Cyclopropylmethoxy-5-(3,3-difluoro-azetidin-1-yl)-pyridine-2-carboxylic acid (1-methyl-5-oxo-pyrrolidin-3-yl)-amide

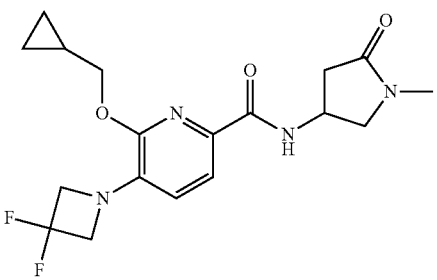 [SMILES: CN1CC(NC(=O)c2ccc(N3CC(F)(F)C3)c(OCC3CC3)n2)CC1=O]

The title compound was synthesized in analogy to Example 1, using 6-cyclopropylmethoxy-5-(3,3-difluoro-azetidin-1-yl)-pyridine-2-carboxylic acid (Example 69 b) and 4-amino-1-methylpyrrolidin-2-one hydrochloride (CAN 1228838-07-0) as starting materials. MS (EI): m/e=381.3 [M+H]$^+$.

Example 291

2-[(6-Cyclopropylmethoxy-5-pyrrolidin-1-yl-pyridine-2-carbonyl)-amino]-2-ethyl-butyric acid

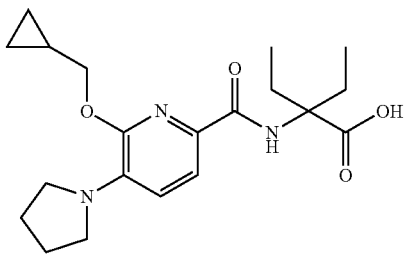 [SMILES: CCC(CC)(NC(=O)c1ccc(N2CCCC2)c(OCC2CC2)n1)C(=O)O]

In analogy to the procedure described in Example 252 b, 2-[(6-cyclopropylmethoxy-5-pyrrolidin-1-yl-pyridine-2-carbonyl)-amino]-2-ethyl-butyric acid ethyl ester (Example 289) was treated with sodium hydroxide to give the title compound as colorless oil. MS: 376.3 [M+H]$^+$.

Example 292

6-Cyclopropylmethoxy-5-(3,3-difluoro-azetidin-1-yl)-pyridine-2-carboxylic acid (1,1-dioxo-tetrahydro-1$\lambda^6$-thiophen-3-yl)-amide

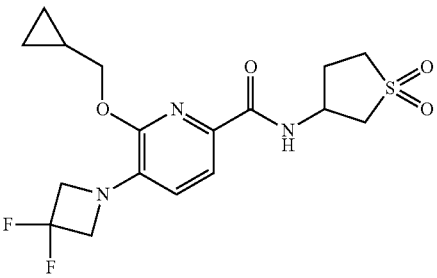 [SMILES: O=C(NC1CCS(=O)(=O)C1)c1ccc(N2CC(F)(F)C2)c(OCC2CC2)n1]

The title compound was synthesized in analogy to Example 1, using 6-cyclopropylmethoxy-5-(3,3-difluoro-azetidin-1-yl)-pyridine-2-carboxylic acid (Example 69 b) and 1,1-dioxidotetrahydrothien-3-ylamine (CAN 6338-70-1) as starting materials. MS (EI): m/e=402.1 [M+H]$^+$.

Example 293

6-Cyclopropylmethoxy-5-(3,3-difluoro-azetidin-1-yl)-pyridine-2-carboxylic acid N'-(1,1-dioxo-tetrahydro-1$\lambda^6$-thiophen-3-yl)-hydrazide

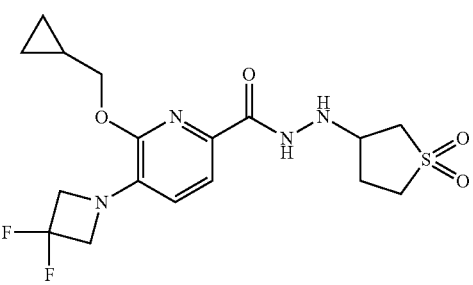 [SMILES: O=C(NNC1CCS(=O)(=O)C1)c1ccc(N2CC(F)(F)C2)c(OCC2CC2)n1]

6-(Cyclopropylmethoxy)-5-(3,3-difluoroazetidin-1-yl)picolinic acid (10 mg, 35.2 μmol, Example 69 b), 3-sulfanyl hydrazine hydrochloride (6.34 mg, 42.2 μmol; CAN 1004-15-5), 1-hydroxybenzotriazole hydrate (10.8 mg, 70.4 μmol), 1-(3-dimethylaminopropyl)-3-ethylcarbodiimide hydrochloride (12.1 mg, 70.4 μmol) and N-ethyl-N-isopropylpropan-2-amine (18.2 mg, 24.6 μL, 141 μmol) were dissolved in DMF (100 μL). The reaction mixture was stirred for 1 d at ambient temperature, poured onto 1 M HCl/icewater (20 mL) and extracted with EtOAc (2×25 mL). The combined extracts were washed with icewater (2×25 mL), dried over Na$_2$SO$_4$ and the solvent was removed under reduced pressure to give 23 mg of crude product which was purified by preparative TLC (silica gel, 1.0 mm, heptane/EtOAc 2:1, elution with EtOAc) to give the title compound (5 mg, 34%) as colorless oil. MS (EI): m/e=417.3 [M+H]$^+$.

Example 294

5-Cyclopropyl-6-cyclopropylmethoxy-pyridine-2-carboxylic acid [1-methyl-1-(4-methyl-thiazol-2-yl)-ethyl]-amide

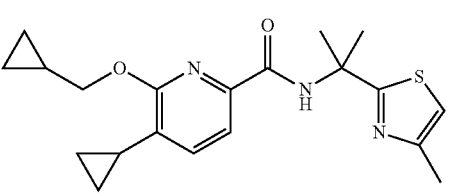 [SMILES: Cc1csc(C(C)(C)NC(=O)c2ccc(C3CC3)c(OCC3CC3)n2)n1]

The title compound was synthesized in analogy to Example 1, using 5-cyclopropyl-6-cyclopropylmethyloxy-pyridine-2-carboxylic acid (Example 42a) and α,α,5-trimethyl-2-thiazolemethanamine (CAN 1155530-59-8) as starting materials, LC-MS (UV peak area/ESI) 97%, 372.1742 (M+H)⁺.

Example 295

5-(3,3-Difluoro-azetidin-1-yl)-6-(3-methyl-oxetan-3-ylmethoxy)-pyridine-2-carboxylic acid (1-methyl-1-thiazol-2-yl-ethyl)-amide

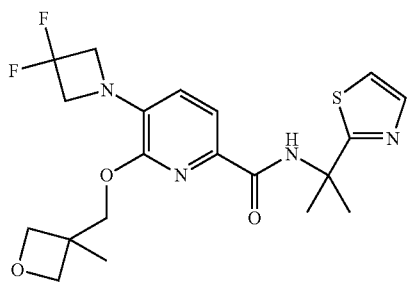 [SMILES: CC1(COc2nc(C(=O)NC(C)(C)c3nccs3)ccc2N2CC(F)(F)C2)COC1]

The title compound was synthesized in analogy to Example 288b, using 5-bromo-6-(3-methyl-oxetan-3-yl-methoxy)-pyridine-2-carboxylic acid (1-methyl-1-thiazol-2-yl-ethyl)-amide (Example 281c) and 3,3-difluoroazetidine hydrochloride as starting materials, MS (EI): m/e=439.3 [M+H]⁺.

Example 296

5-Cyclopropyl-6-cyclopropylmethoxy-pyridine-2-carboxylic acid [1-(5-amino-[1,2,4]oxadiazol-3-yl)-1-methyl-ethyl]-amide

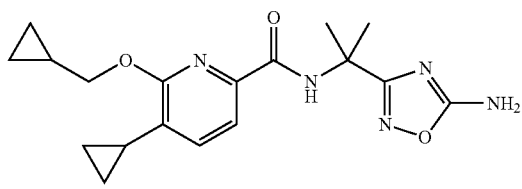 [SMILES: CC(C)(NC(=O)c1ccc(C2CC2)c(OCC2CC2)n1)c1noc(N)n1]

a) [1-(5-Amino-[1,2,4]oxadiazol-3-yl)-1-methyl-ethyl]-carbamic acid tert-butyl ester

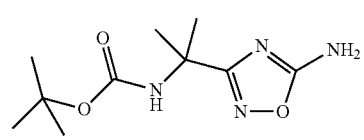 [SMILES: CC(C)(C)OC(=O)NC(C)(C)c1noc(N)n1]

To a colorless solution of [1-(N-hydroxycarbamidoyl)-1-methyl-ethyl]carbamic acid tert-butyl ester (CAN 1251430-04-2, 5.9 g, 27.2 mmol) in DMF (11.8 mL) and in an inert gas atmosphere was added 1-piperidinecarbonitrile (CAN 1530-87-6) with stirring (3.29 g, 3.46 mL, 29.9 mmol). The reaction mixture was heated and stirred for 2.5 hours at 130° C. After cooling to room temperature ice-water (400 mL) was added and the mixture was extracted with ethyl acetate (3×200 mL), organic phases were washed with ice water (200 mL), combined, dried with Na₂SO₄ and concentrated in vacuo. The residue was purified by chromatography on silica gel with mixtures of ethyl acetate/n-heptane as eluent to give the title compound as white solid (5.0 g, 76%); LC-MS (UV peak area/ESI) 83%, 243.1453 (M+H)⁺.

b) 3-(1-Amino-1-methyl-ethyl)-[1,2,4]oxadiazol-5-ylamine hydrochloride (1:1)

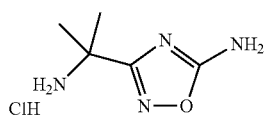

To a solution of [1-(5-amino-[1,2,4]oxadiazol-3-yl)-1-methyl-ethyl]carbamic acid tert-butyl ester (1.6 g, 6.6 mmol) in ethanol (30 mL) was added HCl in dioxane (4 M, 6.6 ml, 26.4 mmol) and the reaction mixture was stirred 16 hours at room temperature. The reaction mixture was concentrated in vacuo and dried by applying high vacuum at 40° C. for 4 hours to give the title compound as off-white solid (1.2 g, quant.); LC-MS (UV peak area/ESI) 99.9%, 143.0927 (M+H)⁺.

c) 5-Cyclopropyl-6-cyclopropylmethoxy-pyridine-2-carboxylic acid [1-(5-amino-[1,2,4]oxadiazol-3-yl)-1-methyl-ethyl]-amide The title compound was synthesized in analogy to Example 1, using 5-cyclopropyl-6-cyclopropylmethyloxy-pyridine-2-carboxylic acid (Example 42a) and 3-(1-amino-1-methyl-ethyl)-[1,2,4]oxadiazol-5-ylamine hydrochloride (1:1) (Example 296b) as starting materials, LC-MS (UV peak area/ESI) 98%, 358.1879 (M+H)⁺.

Example 297

6-(2,2,3,3,3-Pentafluoro-propoxy)-pyridine-2-carboxylic acid (1-ethyl-1-methylcarbamoyl-propyl)-amide

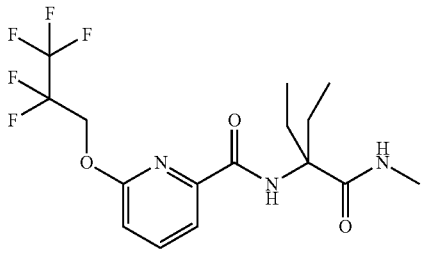 [SMILES: CCC(CC)(NC(=O)c1cccc(OCC(F)(F)C(F)(F)F)n1)C(=O)NC]

a) 5-Bromo-6-(2,2,3,3,3-pentafluoro-propoxy)-pyridine-2-carboxylic acid

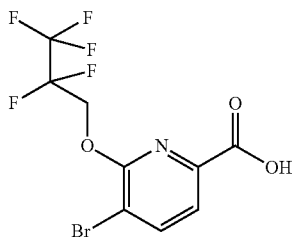 [SMILES: O=C(O)c1ccc(Br)c(OCC(F)(F)C(F)(F)F)n1]

5-Bromo-6-chloro-2-pyridinecarboxylic acid (CAN 959958-25-9; 0.6 g, 2.54 mmol) and potassium tert-butoxide (712 mg, 6.34 mmol) were combined with DMF (30 mL) and THF (10 mL) to give a yellow suspension. To this suspension was added 2,2,3,3,3-pentafluoro-1-propanol (CAN 422-05-9; 3.01 g, 2 ml, 20.1 mmol) and the mixture was heated to 140° C. for 20 hours. After cooling the mixture was poured was poured into ethyl acetate (75 mL) and the combined mixture was washed with cold 1 M HCl (1×10 mL). The aqueous layer was extracted with ethyl acetate (50 mL). The organic layers were combined, dried with Na₂SO₄ and concentrated in vacuo. The residue was purified by chromatography (silica gel, 20 g, 0% to 100% ethyl acetate in heptane) and further purified by preparative HPLC to give the title compound (0.176 g 20%) as off white solid; MS (EI) 350.1 (M+H)⁺.

b) 6-(2,2,3,3,3-Pentafluoro-propoxy)-pyridine-2-carboxylic acid and 5-cyclopropyl-6-(2,2,3,3,3-pentafluoro-propoxy)-pyridine-2-carboxylic acid

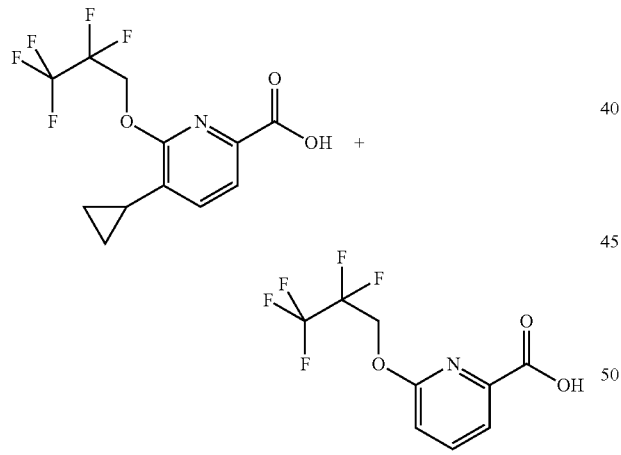

Palladium(II)acetate (2.44 mg, 10.9 µmol), butylbis(tricyclo[3.3.1.1³,⁷]dec-1-yl)-phosphine, (5.8 mg, 16.3 µmol), (T-4)-cyclopropyltrifluoro-borate(1-) potassium (1:1) (80 mg, 543 µmol) and cesium carbonate (531 mg, 1.63 mmol) were combined to give a white solid. To this solid a solution of 5-bromo-6-(2,2,3,3,3-pentafluoro-propoxy)-pyridine-2-carboxylic acid (190 mg, 543 µmol) in toluene (4.8 mL) and water (532 µl) (evacuated and flushed with argon) was added through a septum cap. The reaction mixture was heated to 120° C. and stirred for 20 hours. After cooling to ambient temperature the reaction mixture was diluted with water (20 mL), poured onto a mixture of ice-water/brine/1 N HCl (200 mL) and extracted with ethyl acetate (2×200 mL). The organic phases were washed with 200 mL icewater/brine, combined, dried with Na₂SO₄ and concentrated in vacuo to give a yellow oil. The crude material was purified by flash chromatography (silica gel, 20 g, ethyl acetate) to get 195 mg of a mixture 1/1 of both products as yellow solid which was used without further purification.

c) 6-(2,2,3,3,3-Pentafluoro-propoxy)-pyridine-2-carboxylic acid (1-ethyl-1-methylcarbamoyl-propyl)-amide The title compound was synthesized in analogy to Example 1, using the mixture of 6-(2,2,3,3,3-pentafluoro-propoxy)-pyridine-2-carboxylic acid and 5-cyclopropyl-6-(2,2,3,3,3-pentafluoro-propoxy)-pyridine-2-carboxylic acid (Example 297b) and 2-amino-2-ethyl-N-methyl-butyramide (Example 70b) as starting materials, the product was isolated by preparative HPLC; LC-MS (UV peak area/ESI) 100%, 398.1488 (M+H)⁺.

Example 298

5-Cyclopropyl-6-(2,2,3,3,3-pentafluoro-propoxy)-pyridine-2-carboxylic acid (1-ethyl-1-methylcarbamoyl-propyl)-amide

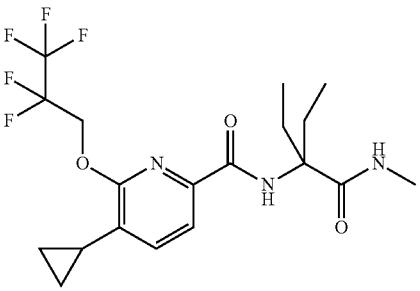 [SMILES: CCC(CC)(NC(=O)c1ccc(C2CC2)c(OCC(F)(F)C(F)(F)F)n1)C(=O)NC]

The title compound was synthesized in analogy to Example 1, using the mixture of 6-(2,2,3,3,3-pentafluoro-propoxy)-pyridine-2-carboxylic acid and 5-cyclopropyl-6-(2,2,3,3,3-pentafluoro-propoxy)-pyridine-2-carboxylic acid (Example 297b) and 2-amino-2-ethyl-N-methyl-butyramide (Example 70b) as starting materials, the product was isolated by preparative HPLC; LC-MS (UV peak area/ESI) 97%, 438.1810 (M+H)⁺.

Example 299

5-Cyclopropyl-6-(2,2,3,3,3-pentafluoro-propoxy)-pyridine-2-carboxylic acid ((S)-3,3-dimethyl-1-methylcarbamoyl-butyl)-amide Chiral

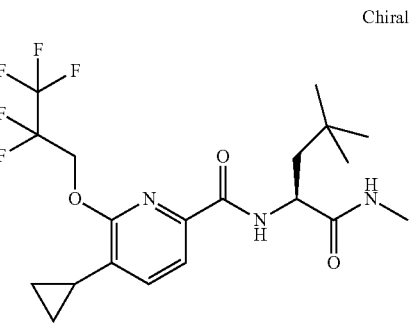

The title compound was synthesized in analogy to Example 1, using the mixture of 6-(2,2,3,3,3-pentafluoro-propoxy)-pyridine-2-carboxylic acid and 5-cyclopropyl-6-(2,2,3,3,3-pentafluoro-propoxy)-pyridine-2-carboxylic acid (Example 297b) and (2S)-2-amino-N,4,4-trimethyl-pentanamide (CAN 1160161-70-5) as starting materials, the product was isolated by preparative HPLC; LC-MS (UV peak area/ESI) 100%, 452.1962 (M+H)+.

Example 300

5-Cyclopropyl-6-(2,2,3,3,3-pentafluoro-propoxy)-pyridine-2-carboxylic acid [(S)-2-cyclopropyl-1-(5-methyl-[1,2,4]oxadiazol-3-yl)-ethyl]-amide

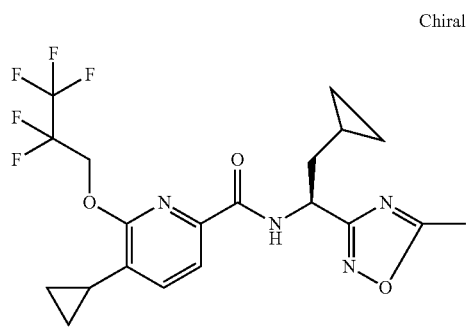 [SMILES: Cc1nc([C@H](CC2CC2)NC(=O)c2ccc(C3CC3)c(OCC(F)(F)C(F)(F)F)n2)no1]

Chiral

The title compound was synthesized in analogy to Example 1, using the mixture of 6-(2,2,3,3,3-pentafluoro-propoxy)-pyridine-2-carboxylic acid and 5-cyclopropyl-6-(2,2,3,3,3-pentafluoro-propoxy)-pyridine-2-carboxylic acid (Example 297b) and (S)-2-cyclopropyl-1-5-methyl-[1,2,4]oxadiazol-3-yl)-ethylamine (Example 38e) as starting materials, the product was isolated by preparative HPLC; LC-MS (UV peak area/ESI) 100%, 461.1607 (M+H)+.

Example 301

5-Cyclopropyl-6-(2,2,2-trifluoro-ethoxy)-pyridine-2-carboxylic acid ((S)-carbamoyl-phenyl-methyl)-amide

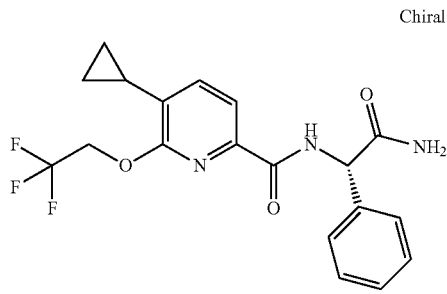 [SMILES: NC(=O)[C@@H](NC(=O)c1ccc(C2CC2)c(OCC(F)(F)F)n1)c1ccccc1]

Chiral a) 5-Cyclopropyl-6-(2,2,2-trifluoro-ethoxy)-pyridine-2-carboxylic acid

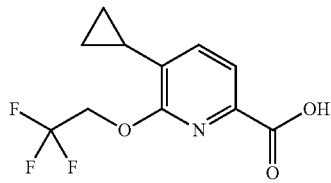 [SMILES: O=C(O)c1ccc(C2CC2)c(OCC(F)(F)F)n1]

In a 150 ml round-bottom-flask, Pd(OAc)2 (15.7 mg, 70.0 μmol), butyl-1-adamantylphosphin (37.6 mg, 105 μmol), potassium cyclopropyltrifluoroborate (523 mg, 3.53 mmol), cesium carbonate (3.42 g, 10.5 mmol) and 5-bromo-6-(2,2,2-trifluoroethoxy)picolinic acid (Example 282a) (1.05 g, 3.5 mmol) were combined. The flask was evacuated in vacuo and flushed with argon three times, followed by addition of a mixture toluene (25 ml)/H2O (3 ml) through a septum cap. The reaction mixture was heated to 120° C., stirred for 20 h and then cooled to ambient temperature. Evaporation of volatiles in vacuo and the residue was redissolved in ethyl acetate and extracted with 1M HCl (12.5 ml). The aqueous phase was back-extracted with ethyl acetate. The combined organic layers were dried over Na2SO4 and concentrated in vacuo The crude material was purified by flash chromatography (silica gel, 50 g, 0% to 5% MeOH in DCM) to give the title compound (530 mg, 58%). MS (EI): m/e=262.2[M+H]+.

b) 5-Cyclopropyl-6-(2,2,2-trifluoro-ethoxy)-pyridine-2-carboxylic acid ((5)-carbamoyl-phenyl-methyl)-amide The title compound was synthesized in analogy to Example 280c, using 5-cyclopropyl-6-(2,2,2-trifluoroethoxy)-pyridine-2-carboxylic acid (Example 301a) and (S)-2-amino-2-phenyl-acetamide hydrochloride (CAN 60079-51-8) as starting materials, MS (EI): m/e=394.1 [M+H]+.

Example 302

5-Cyclopropyl-6-(2,2,2-trifluoro-ethoxy)-pyridine-2-carboxylic acid (2,2,2-trifluoro-1-pyridin-2-yl-ethyl)-amide

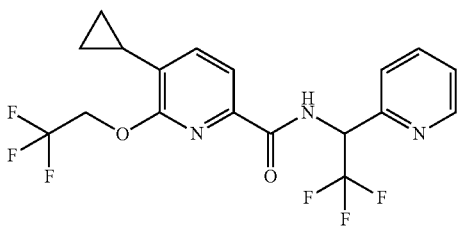 [SMILES: O=C(NC(c1ccccn1)C(F)(F)F)c1ccc(C2CC2)c(OCC(F)(F)F)n1]

The title compound was synthesized in analogy to Example 280c, using 5-cyclopropyl-6-(2,2,2-trifluoroethoxy)-pyridine-2-carboxylic acid (Example 301a) and 2,2,2-trifluoro-1-(pyridin-2-yl)ethanamine (CAN 35272-15-2) as starting materials, MS (EI): m/e=420.1 [M+H]+.

Example 303

5-Cyclopropyl-6-(2,2,2-trifluoro-ethoxy)-pyridine-2-carboxylic acid ((S)-1-hydroxymethyl-3-methyl-butyl)-amide Chiral

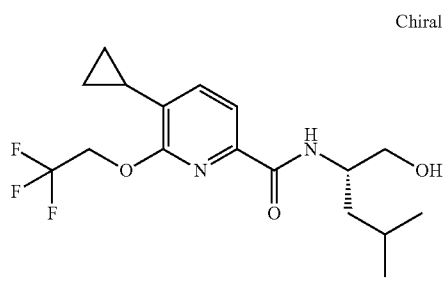 [SMILES: CC(C)C[C@@H](CO)NC(=O)c1ccc(C2CC2)c(OCC(F)(F)F)n1]

The title compound was synthesized in analogy to Example 280c, using 5-cyclopropyl-6-(2,2,2-trifluoro-ethoxy)-pyridine-2-carboxylic acid (Example 301a) and L-leucinol (CAN 17016-87-4) as starting materials, MS (EI): m/e=361.3 [M+H]$^+$.

Example 304

5-Cyclopropyl-6-(2,2,2-trifluoro-ethoxy)-pyridine-2-carboxylic acid (3-thiazol-2-yl-oxetan-3-yl)-amide

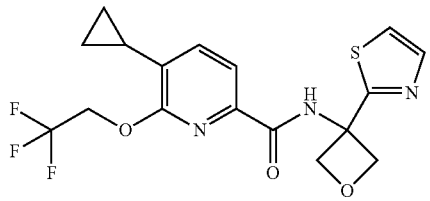 [SMILES: O=C(NC1(c2nccs2)COC1)c1ccc(C2CC2)c(OCC(F)(F)F)n1]

The title compound was synthesized in analogy to Example 280c, using 5-cyclopropyl-6-(2,2,2-trifluoro-ethoxy)-pyridine-2-carboxylic acid (Example 301a) and 3-(thiazol-2-yl)oxetan-3-amine hydrochloride (Example 281b) as starting materials, MS (EI): m/e=400.1 [M+H]$^+$.

Example 305

5-Cyclopropyl-6-(2,2,2-trifluoro-ethoxy)-pyridine-2-carboxylic acid (1-methyl-1-thiazol-2-yl-ethyl)-amide

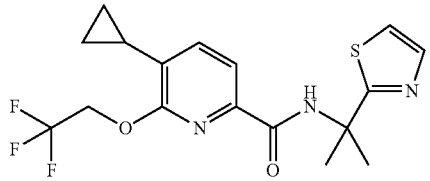 [SMILES: CC(C)(NC(=O)c1ccc(C2CC2)c(OCC(F)(F)F)n1)c1nccs1]

The title compound was synthesized in analogy to Example 280c, using 5-cyclopropyl-6-(2,2,2-trifluoro-ethoxy)-pyridine-2-carboxylic acid (Example 301a) and α,α-dimethyl-2-thiazolemethanamine (Example 12c) as starting materials, MS (EI): m/e=386.3 [M+H]$^+$.

Example 306

5-Cyclopropyl-6-(2,2,2-trifluoro-ethoxy)-pyridine-2-carboxylic acid (2,2-dimethyl-1-thiazol-2-yl-propyl)-amide

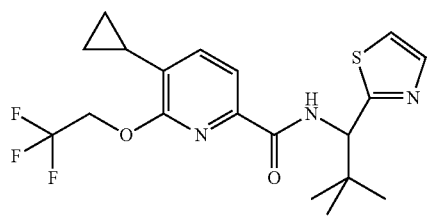 [SMILES: CC(C)(C)C(NC(=O)c1ccc(C2CC2)c(OCC(F)(F)F)n1)c1nccs1]

a) (E)-N-(2,2-Dimethylpropylidene)-2-methylpropane-2-sulfinamide

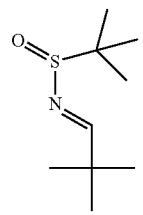

To a solution of pivalaldehyde (2 g, 2.56 ml, 23.2 mmol) in dry dichloromethane (150 mL) under argon atmosphere was added 2-methylpropane-2-sulfinamide (3.38 g, 27.9 mmol) and titanium (IV) ethoxide (6.36 g, 5.84 ml, 27.9 mmol) to give a colorless solution. The reaction mixture was stirred at r.t overnight and quenched by slow addition of water while the reaction still stirring until a precipitate formed. The reaction mixture was then filtered through a pad of celite. The filtrate was extracted with water, the organic phase was collected, dried over Na$_2$SO$_4$ and evaporated down in vacuo to give the title compound (3.6 gr, 82%) as crude oil. The crude was used without any further purification for the next step, MS (EI): m/e=190.3 [M+H]$^+$.

b) N-(2,2-Dimethyl-1-(thiazol-2-yl)propyl)-2-methylpropane-2-sulfinamide

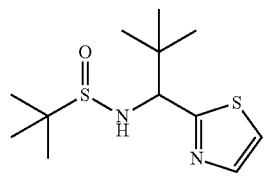 [SMILES: CC(C)(C)C(NS(=O)C(C)(C)C)c1nccs1]

To a solution of thiazole (247 mg, 206 µl, 2.91 mmol) in 10 mL dry THF under argon at −73° C. was slowly added a 1.6M solution of BuLi in hexane (1.82 ml, 2.91 mmol). The resulting reaction mixture was stirred at −75° C. for 30 min and a solution of (E)-N-(2,2-dimethylpropylidene)-2-methylpropane-2-sulfinamide (Example 306a) (500 mg, 2.64 mmol) in 5 mL dry THF was added. The reaction mixture was stirred at −75° C. for 30 min, then cooling bath was removed and reaction stirred at r.t for 1 h. The reaction was quenched by the addition of few drops of water, the reaction mixture poured into ethyl acetate, and the solution was then extracted with aqueous NaHCO₃ 1M. The organic phase was collected, dried over Na₂SO₄ and evaporated down to dryness to give the title compound (666 mg, 92%) as crude dark orange oil. The crude was used without any further purification, MS (EI): m/e=275.2 [M+H]⁺.

c) 5-Cyclopropyl-6-(2,2,2-trifluoro-ethoxy)-pyridine-2-carboxylic acid (2,2-dimethyl-1-thiazol-2-yl-propyl)-amide To a solution of N-(2,2-dimethyl-1-(thiazol-2-yl)propyl)-2-methylpropane-2-sulfinamide (Example 306c) (666 mg, 2.43 mmol) in methanol (15 ml) was added a solution 4.0M HCl in dioxane (3.03 ml, 12.1 mmol) to give a light red solution. The reaction mixture was stirred at r.t for 1 h and reaction was then evaporated down to dryness. The crude solid was triturated in diethyl ether, filtered off and dried under high vacuum to give the title compound (346 mg, 69%) as an off-white solid which was used to synthesize the title compound in analogy to Example 280c, using 5-cyclopropyl-6-(2,2,2-trifluoro-ethoxy)-pyridine-2-carboxylic acid (Example 301a) as starting material, MS (EI): m/e=414.3 [M+H]⁺.

Example 307

6-Cyclopropylmethoxy-5-(3,3-difluoro-azetidin-1-yl)-pyridine-2-carboxylic acid [1-(3,3-difluoro-azetidine-1-carbonyl)-1-ethyl-propyl]-amide

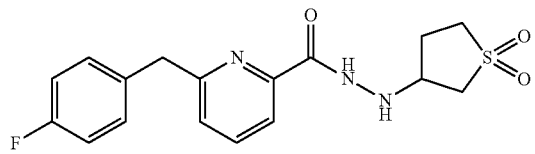

a) 2-(6-(Cyclopropylmethoxy)-5-(3,3-difluoroazetidin-1-yl)picolinamido)-2-ethylbutanoic acid

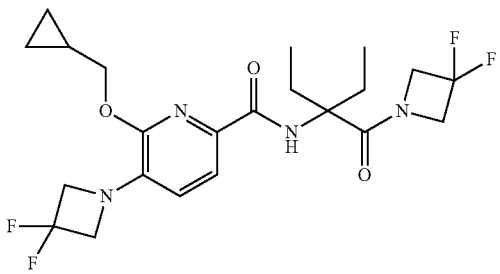 [SMILES: CCC(CC)(NC(=O)c1ccc(N2CC(F)(F)C2)c(OCC2CC2)n1)C(=O)N1CC(F)(F)C1]

In analogy to the procedure described in Example 252 b), 2-{[6-cyclopropylmethoxy-5-(3,3-difluoro-azetidin-1-yl)-pyridine-2-carbonyl]-amino}-2-ethyl-butyric acid ethyl ester (Example 266) was treated with sodium hydroxide to give the title compound as colorless oil. MS: 396.2 [M−H]⁻.

b) 6-Cyclopropylmethoxy-5-(3,3-difluoro-azetidin-1-yl)-pyridine-2-carboxylic acid [1-(3,3-difluoro-azetidine-1-carbonyl)-1-ethyl-propyl]-amide In analogy to the procedure described in Example 293, 2-(6-(cyclopropylmethoxy)-5-(3,3-difluoroazetidin-1-yl)picolinamido)-2-ethylbutanoic acid and 3,3-difluoroazetidine (CAN 679431-52-8) were condensed to the title product. MS (EI): m/e=471.4 [M−H]⁻.

Example 308

6-(4-Fluoro-benzyl)-pyridine-2-carboxylic acid N'-(1,1-dioxo-tetrahydro-1λ⁶-thiophen-3-yl)-hydrazide

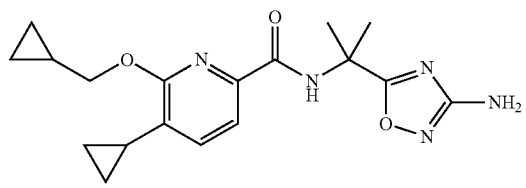

In analogy to the procedure described in Example 293, 6-(4-fluorobenzyl)picolinic acid (Example 277 a) and 3-sulfanyl hydrazine hydrochloride (CAN 1004-15-5) were condensed to the title product. MS (EI): m/e=364.1 [M+H]⁺.

Example 309

5-Cyclopropyl-6-cyclopropylmethoxy-pyridine-2-carboxylic acid [1-(3-amino-[1,2,4]oxadiazol-5-yl)-1-methyl-ethyl]-amide

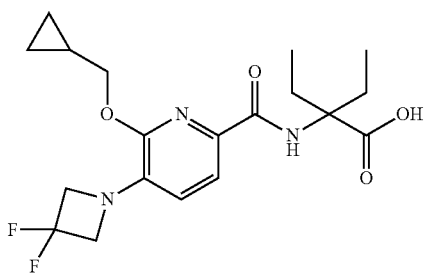 [SMILES: CCC(CC)(NC(=O)c1ccc(N2CC(F)(F)C2)c(OCC2CC2)n1)C(=O)O]

a) [1-(3-Amino-[1,2,4]oxadiazol-5-yl)-1-methyl-ethyl]-carbamic acid tert-butyl ester

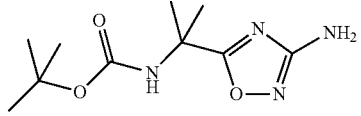 [SMILES: CC(C)(C)OC(=O)NC(C)(C)c1nc(N)no1]

To a colorless solution of N-[(1,1-dimethylethoxy)carbonyl]-2-methyl-alanine (CAN 30992-29-1; 1.0 g, 4.92 mmol) in DMF (24 mL) was added (benzotriazol-1-yloxy)tripyrrolidinophosphonium hexafluorophosphate (3.07 g, 5.9 mmol) and DIEA (1.72 mL, 4.9 mmol), and the resulting pale yellow solution was stirred under argon for 30 minutes at room temperature. This mixture was added dropwise over 40 minutes to a suspension of hydroxyguanidine sulfate monohydrate (3.93 g, 14.8 mmol), DIEA (2.6 mL, 7.4 mmol), and molecular sieves (4 Å, 2 g) in DMF (35 mL) under argon, the temperature not exceeding 25° C. Once addition was complete another 2 g of molecular sieves was added and the reaction mixture (pale yellow suspension) was stirred for 1.5 hours under argon at room temperature then stirred at 130° C. for 20 hours. After cooling to room temperature the mixture was filtered through Celite®. The filtrate was concentrated in vacuo (HV pump) and the residue was stirred vigorously with 2-methoxy-2-methylpropane (40 mL) and 1N NaOH (40 mL) for 20 h. Phases were separated; the aqueous phase was washed with 2-methoxy-2-methylpropane (2×10 mL). Combined organic extracts were washed with water, then dried with Na$_2$SO$_4$, filtered and concentrated in vacuo. The residue was purified by chromatography (silica gel, 50 g, 0% to 100% EtOAc in hexanes) to give the title compound (106 mg, 8.9%), which was used without further purification.

b) 5-(1-Amino-1-methyl-ethyl)-[1,2,4]oxadiazol-3-ylamine hydrochloride (1:1)

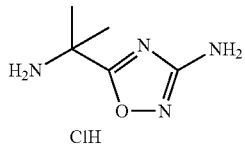

To a solution of [1-(3-amino-[1,2,4]oxadiazol-5-yl)-1-methyl-ethyl]carbamic acid tert-butyl ester (100 mg, 0.41 mmol) in ethanol (2 mL) was added HCl in dioxane (4 M, 0.41 ml, 1.65 mmol) and the reaction mixture was stirred 16 hours at room temperature. The reaction mixture was concentrated in vacuo and dried by applying high vacuum at 40° C. for 4 hours to give the title compound as white solid (75 mg, quant.); LC-MS (UV peak area/ESI) nd, 143.0928 (M+H)$^+$.

c) 5-Cyclopropyl-6-cyclopropylmethoxy-pyridine-2-carboxylic acid [1-(3-amino-[1,2,4]oxadiazol-5-yl)-1-methyl-ethyl]-amide The title compound was synthesized in analogy to Example 1, using 5-cyclopropyl-6-cyclopropylmethyloxy-pyridine-2-carboxylic acid (Example 42a) and 5-(1-amino-1-methyl-ethyl)-[1,2,4]oxadiazol-3-ylamine hydrochloride (1:1) (Example 309 b) as starting materials, LC-MS (UV peak area/ESI) 100%, 358.1872 (M+H)$^+$.

Example 310

6-Cyclopropylmethoxy-5-(3,3-difluoro-azetidin-1-yl)-pyridine-2-carboxylic acid [(S)-1-(3,3-difluoro-azetidine-1-carbonyl)-2,2-dimethyl-propyl]-amide

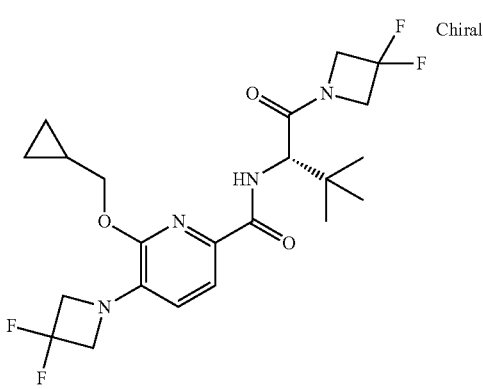 [SMILES: CC(C)(C)[C@H](NC(=O)c1ccc(N2CC(F)(F)C2)c(OCC2CC2)n1)C(=O)N1CC(F)(F)C1]

a) (S)-Methyl 2-(6-(cyclopropylmethoxy)-5-(3,3-difluoroazetidin-1-yl)picolinamido)-3,3-dimethylbutanoate

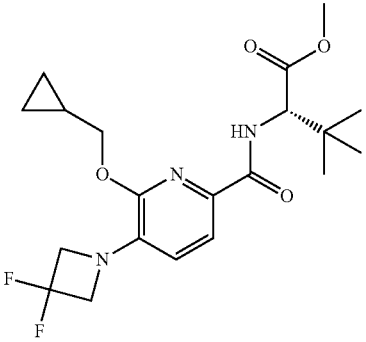 [SMILES: COC(=O)[C@@H](NC(=O)c1ccc(N2CC(F)(F)C2)c(OCC2CC2)n1)C(C)(C)C]

The title compound was synthesized in analogy to Example 1, using 6-(cyclopropylmethoxy)-5-(3,3-difluoro-azetidin-1-yl)picolinic acid (Example 69 b) and (S)-methyl 2-amino-3,3-dimethylbutanoate hydrochloride (CAN 63038-27-7) as starting materials. MS (EI): m/e=412.3 [M+H]$^+$.

b) (S)-2-(6-(Cyclopropylmethoxy)-5-(3,3-difluoroazetidin-1-yl)picolinamido)-3,3-dimethylbutanoic acid

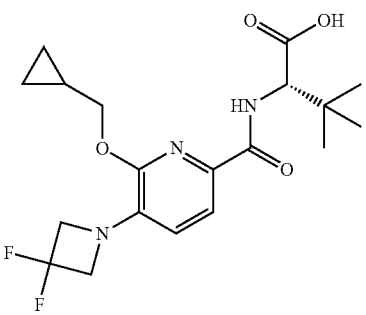 [SMILES: CC(C)(C)[C@H](NC(=O)c1ccc(N2CC(F)(F)C2)c(OCC2CC2)n1)C(=O)O]

In analogy to the procedure described in Example 5 c), (S)-methyl 2-(6-(cyclopropylmethoxy)-5-(3,3-difluoroazetidin-1-yl)picolinamido)-3,3-dimethylbutanoate was saponified with lithium hydroxide to obtain the title compound. MS (EI): m/e=396.1 [M−H]$^−$.

c) 6-Cyclopropylmethoxy-5-(3,3-difluoro-azetidin-1-yl)-pyridine-2-carboxylic acid [(S)-1-(3,3-difluoro-azetidine-1-carbonyl)-2,2-dimethyl-propyl]-amide The title compound was synthesized in analogy to Example 1, using (S)-2-(6-(cyclopropylmethoxy)-5-(3,3-difluoroazetidin-1-yl)picolinamido)-3,3-dimethylbutanoic acid and 3,3-difluoroazetidine hydrochloride (CAN 288315-03-7)) as starting materials. MS (EI): m/e=473.0 [M+H]$^+$.

Example 311

6-Cyclopropylmethoxy-5-(3,3-difluoro-azetidin-1-yl)-pyridine-2-carboxylic acid [(S)-1-(3,3-difluoro-azetidine-1-carbonyl)-3-methyl-butyl]-amide

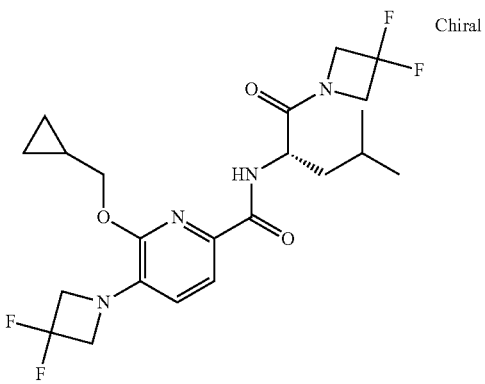 [SMILES: CC(C)C[C@H](NC(=O)c1ccc(N2CC(F)(F)C2)c(OCC2CC2)n1)C(=O)N1CC(F)(F)C1]

a) (S)-Ethyl 2-(6-(cyclopropylmethoxy)-5-(3,3-difluoroazetidin-1-yl)picolinamido)-4-methylpentanoate

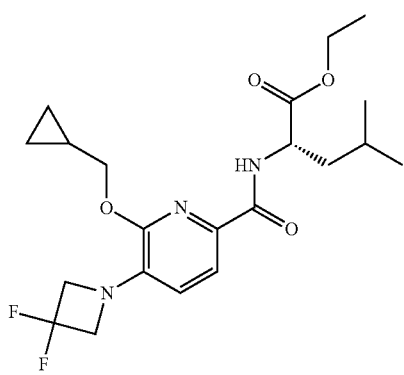 [SMILES: CCOC(=O)[C@H](CC(C)C)NC(=O)c1ccc(N2CC(F)(F)C2)c(OCC2CC2)n1]

The title compound was synthesized in analogy to Example 1, using 6-(cyclopropylmethoxy)-5-(3,3-difluoroazetidin-1-yl)picolinic acid (Example 69 b) and (S)-ethyl 2-amino-4-methylpentanoate hydrochloride (CAN 2743-40-0) as starting materials. MS (EI): m/e=426.3 [M+H]+.

b) (S)-2-(6-(Cyclopropylmethoxy)-5-(3,3-difluoro-azetidin-1-yl)picolinamido)-4-methylpentanoic acid

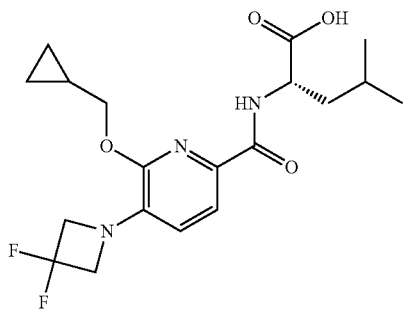 [SMILES: CC(C)C[C@H](NC(=O)c1ccc(N2CC(F)(F)C2)c(OCC2CC2)n1)C(=O)O]

In analogy to the procedure described in Example 5 c), (S)-ethyl 2-(6-(cyclopropylmethoxy)-5-(3,3-difluoroazetidin-1-yl)picolinamido)-4-methylpentanoate was saponified with lithium hydroxide to obtain the title compound. MS (EI): m/e=396.3 [M−H]−.

c) 6-Cyclopropylmethoxy-5-(3,3-difluoro-azetidin-1-yl)-pyridine-2-carboxylic acid [(S)-1-(3,3-difluoro-azetidine-1-carbonyl)-2,2-dimethyl-propyl]-amide The title compound was synthesized in analogy to Example 1, using (S)-2-(6-(cyclopropylmethoxy)-5-(3,3-difluoroazetidin-1-yl)picolinamido)-4-methylpentanoic acid and 3,3-difluoroazetidine hydrochloride (CAN 288315-03-7) as starting materials. MS (EI): m/e=473.3 [M+H]+.

Example 312

2-[(6-Cyclopropylmethoxy-5-trifluoromethyl-pyridine-2-carbonyl)-amino]-2-ethyl-butyric acid ethyl ester

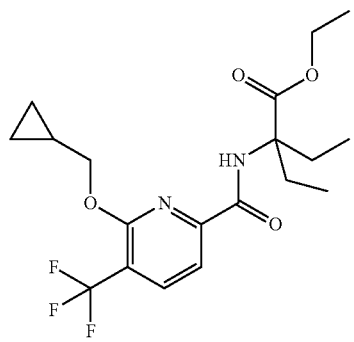 [SMILES: CCOC(=O)C(CC)(CC)NC(=O)c1ccc(C(F)(F)F)c(OCC2CC2)n1]

In analogy to the procedure described in Example 293, 6-cyclopropylmethoxy-5-trifluoromethyl-pyridine-2-carboxylic acid (Example 113 d) and ethyl 2-amino-2-ethylbutanoate hydrochloride (CAN 1135219-29-2) were condensed to the title product. MS (EI): m/e=403.4 [M+H]+.

Example 313

5-Cyclopropyl-6-((R)-3-hydroxy-1-trifluoromethyl-propoxy)-pyridine-2-carboxylic acid (1-ethyl-1-methylcarbamoyl-propyl)-amide

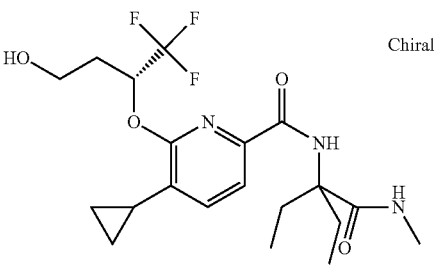 [SMILES: CCC(CC)(NC(=O)c1ccc(C2CC2)c(O[C@H](CCO)C(F)(F)F)n1)C(=O)NC]

249 a) 5-Cyclopropyl-6-((R)-3-hydroxy-1-trifluoromethyl-propoxy)-pyridine-2-carboxylic acid

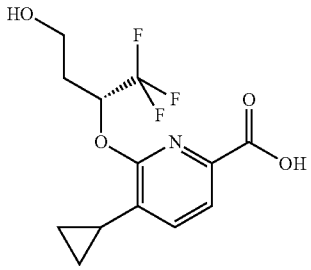 [SMILES: O=C(O)c1ccc(C2CC2)c(O[C@H](CCO)C(F)(F)F)n1]

6-Chloro-5-cyclopropyl-2-pyridinecarboxylic acid (CAN 1211530-95-8; 100 mg, 506 µmol), (R)-4,4,4-trifluorobutane-1,3-diol (219 mg, 1.52 mmol) and potassium tert-butoxide (114 mg, 1.01 mmol) were combined with DMF (2 mL) to give a white suspension. The reaction mixture was heated to 140° C. and stirred for 20 h. After cooling the mixture was poured into cold 1 M HCl (15 mL) and extracted with ethyl acetate (2×75 mL). The phases were combined, dried with $Na_2SO_4$ and concentrated in vacuo. The residue was purified by preparative HPLC to give the title compound (12 mg, 7.8%) and its regioisomer; MS (EI) 304.2 $(M+H)^+$.

b) 5-Cyclopropyl-6-((R)-3-hydroxy-1-trifluoromethyl-propoxy)-pyridine-2-carboxylic acid (1-ethyl-1-methylcarbamoyl-propyl)-amide The title compound was synthesized in analogy to Example 1, using 5-cyclopropyl-6-((R)-3-hydroxy-1-trifluoromethyl-propoxy)-pyridine-2-carboxylic acid (Example 313a) and 2-amino-2-ethyl-N-methyl-butyramide (Example 70b) as starting materials; MS (EI) 432.4 $(M+H)^+$.

Example 314

5-Cyclopropyl-6-((R)-4,4,4-trifluoro-3-hydroxy-butoxy)-pyridine-2-carboxylic acid (1-ethyl-1-methylcarbamoyl-propyl)-amide

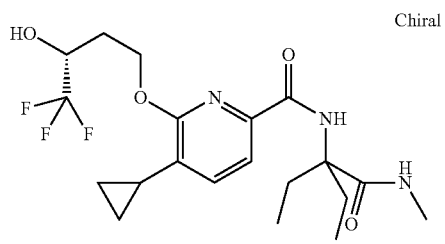 [SMILES: CCC(CC)(NC(=O)c1ccc(C2CC2)c(OCC[C@@H](O)C(F)(F)F)n1)C(=O)NC]

Chiral

250 a) 5-Cyclopropyl-6-((R)-3-hydroxy-1-trifluoromethyl-propoxy)-pyridine-2-carboxylic acid

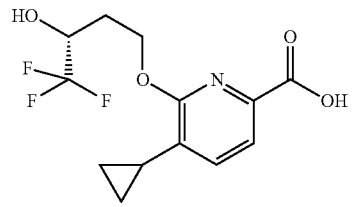 [SMILES: O=C(O)c1ccc(C2CC2)c(OCC[C@@H](O)C(F)(F)F)n1]

6-Chloro-5-cyclopropyl-2-pyridinecarboxylic acid (CAN 1211530-95-8; 100 mg, 506 µmol), (R)-4,4,4-trifluorobutane-1,3-diol (219 mg, 1.52 mmol) and potassium tert-butoxide (114 mg, 1.01 mmol) were combined with DMF (2 mL) to give a white suspension. The reaction mixture was heated to 140° C. and stirred for 20 h. After cooling the mixture was poured into cold 1 M HCl (15 mL) and extracted with ethyl acetate (2×75 mL). The phases were combined, dried with $Na_2SO_4$ and concentrated in vacuo. The residue was purified by preparative HPLC to give the title compound (8 mg, 5.2%) and its regioisomer; MS (EI) 304.2 $(M+H)^+$.

b) 5-Cyclopropyl-6-((R)-4,4,4-trifluoro-3-hydroxy-butoxy)-pyridine-2-carboxylic acid (1-ethyl-1-methylcarbamoyl-propyl)-amide The title compound was synthesized in analogy to Example 1, using 5-cyclopropyl-6-((R)-3-hydroxy-1-trifluoromethyl-propoxy)-pyridine-2-carboxylic acid (Example 314a) and 2-amino-2-ethyl-N-methyl-butyramide (Example 70b) as starting materials; MS (EI) 432.4 $(M+H)^+$.

Example 315

6-Cyclopropylmethoxy-5-(3,3-difluoro-azetidin-1-yl)-pyridine-2-carboxylic acid (3-methyl-1-pyridin-2-yl-butyl)-amide

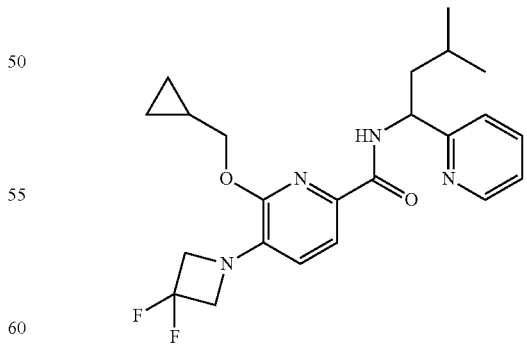

In analogy to the procedure described in Example 293, 6-(cyclopropylmethoxy)-5-(3,3-difluoroazetidin-1-yl)picolinic acid (Example 69 b) and 3-methyl-1-(pyridin-2-yl)butan-1-amine (CAN 825647-69-6) were condensed to the title product. MS (EI): m/e=431.4 $[M+H]^+$.

Example 316

6-Cyclopropylmethoxy-5-trifluoromethyl-pyridine-2-carboxylic acid [1-(3,3-difluoro-azetidine-1-carbonyl)-1-ethyl-propyl]-amide

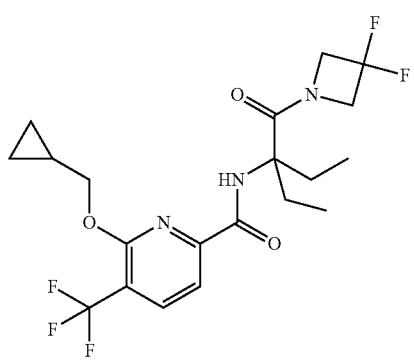 [SMILES: CCC(CC)(NC(=O)c1ccc(C(F)(F)F)c(OCC2CC2)n1)C(=O)N1CC(F)(F)C1]

In analogy to the procedure described in Example 293, 2-[(6-cyclopropylmethoxy-5-trifluoromethyl-pyridine-2-carbonyl)-amino]-2-ethyl-butyric acid (Example 252 b) and 3,3-difluoroazetidine hydrochloride (CAN 288315-03-7) were condensed to the title product. MS (EI): m/e=450.0 [M+H]$^+$.

Example 317

6-[(4-Fluoro-phenyl)-hydroxy-methyl]-pyridine-2-carboxylic acid ((S)-1-carbamoyl-3-methyl-butyl)-amide

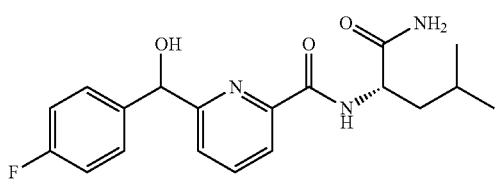 [SMILES: CC(C)C[C@H](NC(=O)c1cccc(C(O)c2ccc(F)cc2)n1)C(N)=O]

a) Methyl 6-((4-fluorophenyl)(hydroxy)methyl)picolinate

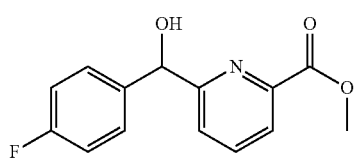 [SMILES: COC(=O)c1cccc(C(O)c2ccc(F)cc2)n1]

A suspension of (6-bromopyridin-2-yl)(4-fluorophenyl)methanol (1 g, 3.54 mmol; CAN 875562-77-9), 1,1'-bis(diphenylphosphino)ferrocene-palladium(II)dichloride dichloromethane complex (174 mg, 0.06 eq.; CAN 95464-05-4) and triethylamine (464 mg, 639 μL, 4.6 mmol) in methanol (10 mL) was shaken in an autoclave under 70 bar carbon monoxide pressure at 110° C. for 18 h. The reaction mixture was filtered and concentrated in vacuo. The crude material was purified by flash chromatography (silica gel, 70 g, 20% to 60% EtOAc in heptane) to give the title compound (853 mg, 92%) as pale yellow oil. MS (EI): m/e=262.0 [M+H]$^+$.

b) 6-((4-Fluorophenyl)(hydroxy)methyl)picolinic acid

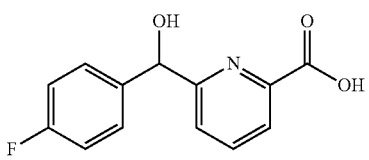 [SMILES: O=C(O)c1cccc(C(O)c2ccc(F)cc2)n1]

In analogy to the procedure described in Example 5 c), methyl 6-((4-fluorophenyl)(hydroxy)methyl)picolinate was saponified with lithium hydroxide to obtain the title compound. MS (EI): m/e=246.1 [M–H]$^-$.

c) 6-[(4-Fluoro-phenyl)-hydroxy-methyl]-pyridine-2-carboxylic acid ((S)-1-carbamoyl-3-methyl-butyl)-amide The title compound was synthesized in analogy to Example 1, using 6-((4-fluorophenyl)(hydroxy)methyl)picolinic acid and (2S)-2-amino-4-methyl-pentanamide (CAN 687-51-4) as starting materials. MS (EI): m/e=360.1 [M+H]$^+$.

Example 318

6-[(4-Fluoro-phenyl)-hydroxy-methyl]-pyridine-2-carboxylic acid [(S)-3-methyl-1-(5-methyl-[1,2,4]oxadiazol-3-yl)-butyl]-amide

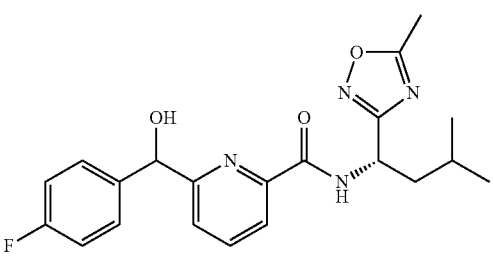 [SMILES: Cc1nc([C@H](CC(C)C)NC(=O)c2cccc(C(O)c3ccc(F)cc3)n2)no1]

The title compound was synthesized in analogy to Example 1, using 6-((4-fluorophenyl)(hydroxy)methyl)picolinic acid and (S)-5-methyl-α-(2-methylpropyl)-1,2,4-oxadiazole-3-methanamine hydrochloride (which was prepared from (2S)-2-[(tert-butoxycarbonyl)amino]-4-methylpentanoic acid (CAN 13139-15-6) in analogy to the procedures described in Example 38 a to e) as starting materials. MS (EI): m/e=399.2 [M+H]+.

Example 319

5-Cyclopropyl-6-((S)-3-hydroxy-1-trifluoromethyl-propoxy)-pyridine-2-carboxylic acid (1-ethyl-1-methylcarbamoyl-propyl)-amide

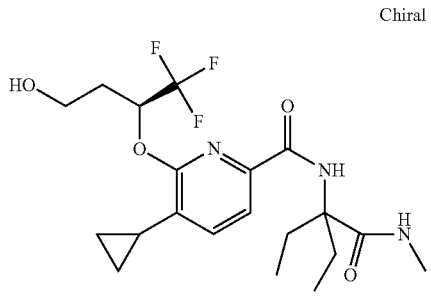 [SMILES: CCC(CC)(NC(=O)c1ccc(C2CC2)c(O[C@@H](CCO)C(F)(F)F)n1)C(=O)NC]

a) 5-Cyclopropyl-6-((S)-3-hydroxy-1-trifluoromethyl-propoxy)-pyridine-2-carboxylic acid

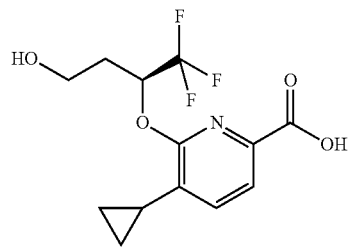 [SMILES: O=C(O)c1ccc(C2CC2)c(O[C@@H](CCO)C(F)(F)F)n1]

6-Chloro-5-cyclopropyl-2-pyridinecarboxylic acid (CAN 1211530-95-8; 180 mg, 901 µmol), (S)-4,4,4-trifluorobutane-1,3-diol (394 mg, 2.73 mmol) and potassium tert-butoxide (307 mg, 2.73 mmol) were combined with DMF (3 mL) to give a white suspension. The reaction mixture was heated to 140° C. and stirred for 48 h. After cooling the mixture was poured into cold 1 M HCl (15 mL) and extracted with ethyl acetate (2×75 mL). The phases were combined, dried with Na$_2$SO$_4$ and concentrated in vacuo. The residue was purified by preparative HPLC to give the title compound (15 mg, 5.4%) and its regioisomer; MS (EI) 304.2 (M+H)+.

b) 5-Cyclopropyl-6-((S)-3-hydroxy-1-trifluoromethyl-propoxy)-pyridine-2-carboxylic acid (1-ethyl-1-methylcarbamoyl-propyl)-amide The title compound was synthesized in analogy to Example 1, using 5-cyclopropyl-6-((S)-3-hydroxy-1-trifluoromethyl-propoxy)-pyridine-2-carboxylic acid (Example 319a) and 2-amino-2-ethyl-N-methyl-butyramide (Example 70b) as starting materials; MS (EI) 432.4 (M+H)+.

Example 320

5-Cyclopropyl-6-((S)-4,4,4-trifluoro-3-hydroxy-butoxy)-pyridine-2-carboxylic acid (1-ethyl-1-methylcarbamoyl-propyl)-amide

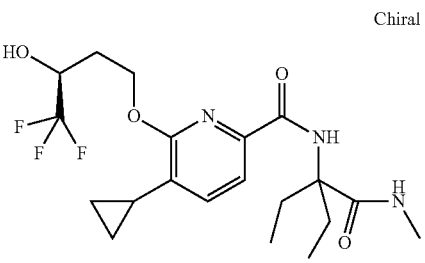 [SMILES: CCC(CC)(NC(=O)c1ccc(C2CC2)c(OCC[C@H](O)C(F)(F)F)n1)C(=O)NC]

a) 5-Cyclopropyl-6-((S)-3-hydroxy-1-trifluoromethyl-propoxy)-pyridine-2-carboxylic acid

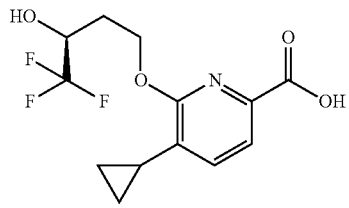 [SMILES: O=C(O)c1ccc(C2CC2)c(OCC[C@H](O)C(F)(F)F)n1]

6-Chloro-5-cyclopropyl-2-pyridinecarboxylic acid (CAN 1211530-95-8; 180 mg, 901 µmol), (S)-4,4,4-trifluorobutane-1,3-diol (394 mg, 2.73 mmol) and potassium tert-butoxide (307 mg, 2.73 mmol) were combined with DMF (3 mL) to give a white suspension. The reaction mixture was heated to 140° C. and stirred for 48 h. After cooling the mixture was poured into cold 1 M HCl (15 mL) and extracted with ethyl acetate (2×75 mL). The phases were combined, dried with Na$_2$SO$_4$ and concentrated in vacuo. The residue was purified by preparative HPLC to give the title compound (23 mg, 8.3%) and its regioisomer; MS (EI) 304.2 (M+H)+.

b) 5-Cyclopropyl-6-((S)-4,4,4-trifluoro-3-hydroxy-butoxy)-pyridine-2-carboxylic acid (1-ethyl-1-methylcarbamoyl-propyl)-amide The title compound was synthesized in analogy to Example 1, using 5-cyclopropyl-6-((S)-3-hydroxy-1-trifluoromethyl-propoxy)-pyridine-2-carboxylic acid (Example 320a) and 2-amino-2-ethyl-N-methyl-butyramide (Example 70b) as starting materials; MS (EI) 432.4 (M+H)+.

Example 321

6-Cyclopropylmethoxy-5-(3,3-difluoro-azetidin-1-yl)-pyridine-2-carboxylic acid (3-methyl-1-pyridazin-3-yl-butyl)-amide

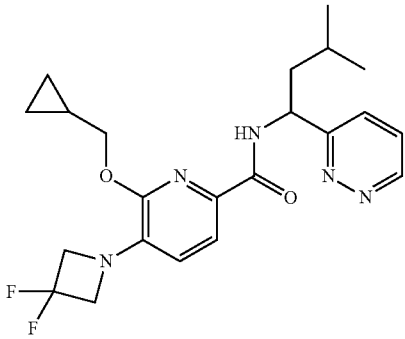 [SMILES: CC(C)CC(NC(=O)c1ccc(N2CC(F)(F)C2)c(OCC2CC2)n1)c1cccnn1]

a) 3-Methyl-1-(pyridazin-3-yl)butan-1-amine

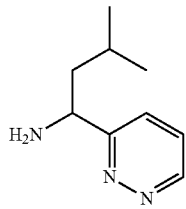

A suspension of 3-methyl-1-(pyridazin-3-yl)butan-1-one (0.85 g, 5.2 mmol; CAN 138835-88-8), sodium cyanoborohydride (1.2 g, 19.2 mmol) and ammonium acetate (1.28 g, 16.6 mmol) in methanol (11.1 mL) was heated at 70° C. for 12 h. The solvent was removed under reduced pressure and the residual oil was partitioned between EtOAc and 1 M aqueous HCl solution. The aqueous layer was basified with 10% aqueous NaOH solution and extracted with EtOAc. The combined extracts were washed with brine and dried over Na₂SO₄. Filtration and evaporation provided the title compound (233 mg, 27%) as brown oil which was sufficiently pure to be used in the next reaction step. MS (EI): m/e=166.2 [M+H]+.

b) 6-Cyclopropylmethoxy-5-(3,3-difluoro-azetidin-1-yl)-pyridine-2-carboxylic acid (3-methyl-1-pyridazin-3-yl-butyl)-amide In analogy to the procedure described in Example 293, 6-(cyclopropylmethoxy)-5-(3,3-difluoroazetidin-1-yl)picolinic acid (Example 69 b) and 3-methyl-1-(pyridazin-3-yl)butan-1-amine were condensed to the title product. MS (EI): m/e=432.4 [M+H]+.

Example 322

6-Cyclopropylmethoxy-5-(3-oxo-azetidin-1-yl)-pyridine-2-carboxylic acid [1-methyl-1-(5-methyl-[1,2,4]oxadiazol-3-yl)-ethyl]-amide

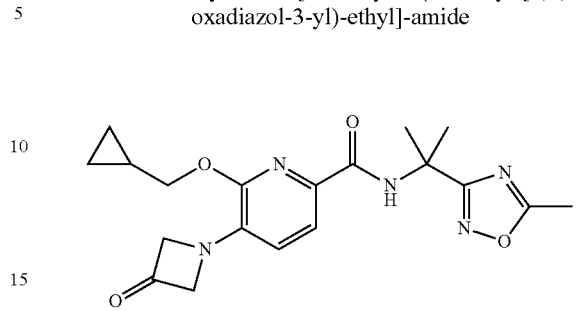

a) 5-Bromo-6-cyclopropylmethoxy-pyridine-2-carboxylic acid [1-methyl-1-(5-methyl-[1,2,4]oxadiazol-3-yl)-ethyl]-amide

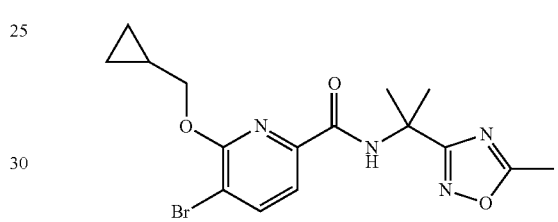

The title compound was synthesized in analogy to Example 1, using 5-bromo-6-cyclopropylmethoxy-pyridine-2-carboxylic acid (Example 9d) and α,α,5-trimethyl-1,2,4-oxadiazole-3-methanamine (Example 33d) as starting materials; MS (EI) 455.1 (M+H)+.

b) 6-Cyclopropylmethoxy-5-(3-hydroxy-azetidin-1-yl)-pyridine-2-carboxylic acid [1-methyl-1-(5-methyl-[1,2,4]oxadiazol-3-yl)-ethyl]-amide

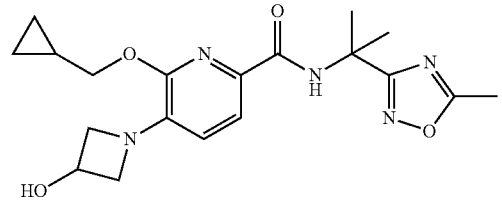 [SMILES: Cc1nc(C(C)(C)NC(=O)c2ccc(N3CC(O)C3)c(OCC3CC3)n2)no1]

5-Bromo-6-cyclopropylmethoxy-pyridine-2-carboxylic acid [1-methyl-1-(5-methyl-[1,2,4]oxadiazol-3-yl)-ethyl]-amide (150 mg, 380 µmol) was dissolved in toluene (6.0 mL) to give a colorless solution. This solution was degassed under an Argon stream for 5 minutes. Cesium carbonate (371 mg, 1.14 mmol), Pd₂(dba)₃CHCl₃ (39.3 mg, 38.0 µmol), [rac]-BINAP (47.3 mg, 75.9 µmol) and 3-azetidinol hydrochloride (1:1) (CAN 18621-18-6; 49.9 mg, 455 µmol) were added and the mixture was heated for 18 hours in a microwave oven to 100° C. After cooling to room temperature the mixture was diluted with ethyl acetate (5 mL) and water (3 mL), filtered through Celite® and the filter pad was washed with water (10 mL) and ethyl acetate (30 mL). Phases were separated and the aqueous phase was extracted with ethyl acetate (20 mL). Organic phases were combined, dried with Na₂SO₄, and concentrated in vacuo. The residue was purified by flash chromatography (silica gel. 20 g, 0% to 100% ethyl acetate in heptane) to give the title compound (80 mg, 54%) as yellow solid; NMR complies.

c) 6-Cyclopropylmethoxy-5-(3-oxo-azetidin-1-yl)-pyridine-2-carboxylic acid [1-methyl-1-(S-methyl-[1,2,4]oxadiazol-3-yl)-ethyl]-amide To a solution of oxalyl chloride (14.4 mg, 9.94 µl, 114 µmol) in dichloromethane (1 mL) was added with stirring DMSO (17.7 mg, 16.1 µl, 227 µmol) in dichloromethane (0.5 mL) at −60° C. The mixture was stirred for 15 minutes at −60° C. to −50° C. A solution of 6-cyclopropylmethoxy-5-(3-hydroxy-azetidin-1-yl)-pyridine-2-carboxylic acid [1-methyl-1-(5-methyl-[1,2,4]oxadiazol-3-yl)-ethyl]-amide (40 mg, 103 µmol) in dichloromethane (1 mL) was added at −50° C. over a period of 2 minutes. Stirring continued for 1 hour at −60° C. to −50° C. Afterwards triethylamine (52.2 mg, 72.0 µl, 516 µmol) was added and the reaction mixture was allowed to warm up slowly to room temperature and stirred for another 16 hours at room temperature. Water (10 mL) was added and the mixture was extracted with dichloromethane (3×10 mL). The organic phases were combined, dried with Na₂SO₄, and concentrated in vacuo. The residue was purified by flash chromatography (silica gel, 5 g, 0% to 100% ethyl acetate in heptane) to give the title compound (34 mg, 85%) as off-white solid; LC-MS (UV peak area/ESI) 92%, 386.1820 (M+H)⁺.

Example 323

5-Cyclopropyl-6-cyclopropylmethoxy-pyridine-2-carboxylic acid [(+)-1-cyclopropyl-1-(5-methyl-[1,2,4]oxadiazol-3-yl)-ethyl]-amide

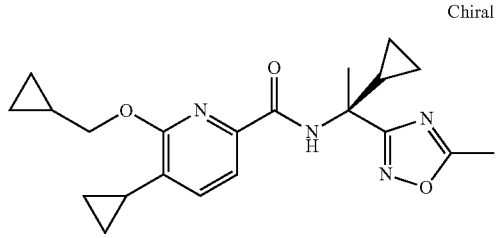 [SMILES: Cc1nc([C@@](C)(NC(=O)c2ccc(C3CC3)c(OCC3CC3)n2)C2CC2)no1]

The title compound was synthesized in analogy to Example 1, using 5-cyclopropyl-6-cyclopropylmethyloxy-pyridine-2-carboxylic acid (Example 42a) and α-cyclopropyl-α,5-dimethyl-1,2,4-oxadiazole-3-methanamine (CAN 1155536-64-3) as starting materials. The product was isolated by chiral chromatography on Lux 5u Amylose-2 using heptane/15% 2-propanol as eluent. The (+)-enantiomer was isolated. LC-MS (UV peak area/ESI) 100%, 383.2090 (M+H)⁺, $\alpha_D^{20}$ (MeOH)=+49.30

Example 324

5-Cyclopropyl-6-cyclopropylmethoxy-pyridine-2-carboxylic acid [(+1-cyclopropyl-1-(5-methyl-[1,2,4]oxadiazol-3-yl)-ethyl]-amide

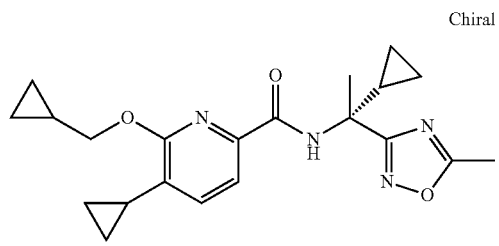 [SMILES: Cc1nc([C@](C)(NC(=O)c2ccc(C3CC3)c(OCC3CC3)n2)C2CC2)no1]

The title compound was synthesized in analogy to Example 1, using 5-cyclopropyl-6-cyclopropylmethyloxy-pyridine-2-carboxylic acid (Example 42a) and α-cyclopropyl-α,5-dimethyl-1,2,4-oxadiazole-3-methanamine (CAN 1155536-64-3) as starting materials. The product was isolated by chiral chromatography on Lux 5u Amylose-2 using heptane/15% 2-propanol as eluent. The (−)-enantiomer was isolated. LC-MS (UV peak area/ESI) 100%, 383.2082 (M+H)⁺, $\alpha_D^{20}$ (MeOH)=−44.7°

Example 325

6-Cyclopropylmethoxy-5-(3,3-difluoro-azetidin-1-yl)-pyridine-2-carboxylic acid (3-methyl-1-pyridin-3-yl-butyl)-amide

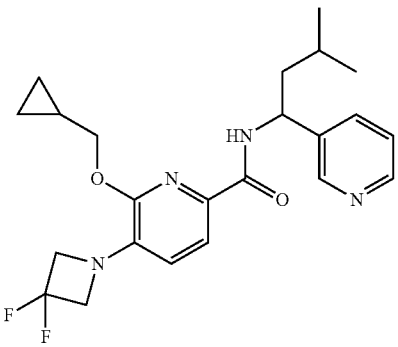 [SMILES: CC(C)CC(NC(=O)c1ccc(N2CC(F)(F)C2)c(OCC2CC2)n1)c1cccnc1]

In analogy to the procedure described in Example 293, 6-(cyclopropylmethoxy)-5-(3,3-difluoroazetidin-1-yl)picolinic acid (Example 69 b) and 3-methyl-1-(pyridin-3-yl)butan-1-amine (CAN 938459-12-2) were condensed to the title product. MS (EI): m/e=431.5 [M+H]⁺.

Example 326

5-Cyclopropyl-6-(4-fluoro-benzyl)-pyridine-2-carboxylic acid ((S)-1-carbamoyl-2-cyclopropyl-ethyl)-amide

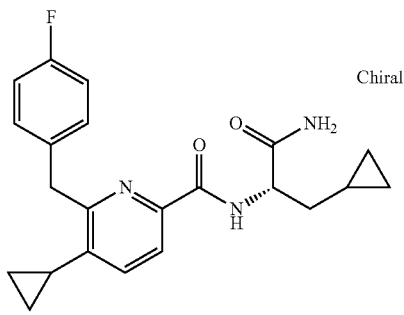 [SMILES: NC(=O)[C@H](CC1CC1)NC(=O)c1ccc(C2CC2)c(Cc2ccc(F)cc2)n1]

The title compound was synthesized in analogy to Example 1, using 5-cyclopropyl-6-(4-fluoro-benzyl)-pyridine-2-carboxylic acid (Example 155 g) and (S)-2-amino-3-cyclopropylpropanamide hydrochloride (Example 97 a) as starting materials. MS (EI): m/e=382.1 [M+H]+.

Example 327

5-Cyclopropyl-6-(4-fluoro-benzyl)-pyridine-2-carboxylic acid [(S)-2-cyclopropyl-1-(5-methyl-[1,2,4]oxadiazol-3-yl)-ethyl]-amide

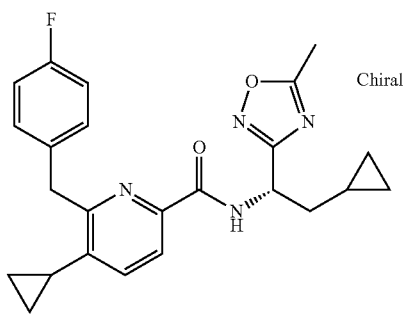 [SMILES: Cc1nc([C@H](CC2CC2)NC(=O)c2ccc(C3CC3)c(Cc3ccc(F)cc3)n2)no1]

The title compound was synthesized in analogy to Example 1, using 5-cyclopropyl-6-(4-fluoro-benzyl)-pyridine-2-carboxylic acid (Example 155 g) and (S)-2-cyclopropyl-1-5-methyl-[1,2,4]oxadiazol-3-yl)-ethylamine (Example 38e) as starting materials. MS (EI): m/e=421.1 [M+H]+.

Example 328

5-Cyclopropyl-6-cyclopropylmethoxy-pyridine-2-carboxylic acid [(S)-carbamoyl-(4-fluoro-phenyl)-methyl]-amide

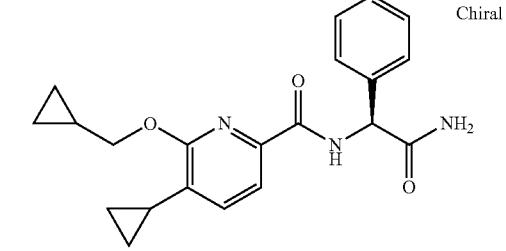

The title compound was synthesized in analogy to Example 1, using 5-cyclopropyl-6-cyclopropylmethyloxy-pyridine-2-carboxylic acid (Example 42a) and (αS)-α-amino-4-fluoro-benzeneacetamide (CAN 785041-04-5) as starting materials; LC-MS (UV peak area/ESI) 100%, 384.1716 (M+H)+.

Example 329

5-Cyclopropyl-6-cyclopropylmethoxy-pyridine-2-carboxylic acid [(S)-carbamoyl-(4-chloro-phenyl)-methyl]-amide

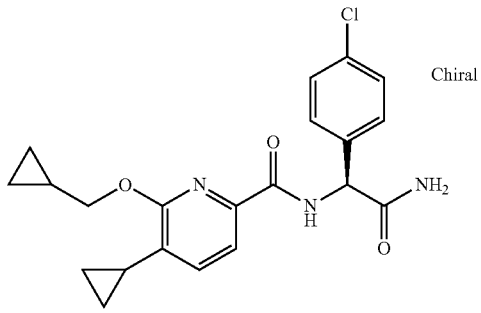 [SMILES: NC(=O)[C@@H](NC(=O)c1ccc(C2CC2)c(OCC2CC2)n1)c1ccc(Cl)cc1]

The title compound was synthesized in analogy to Example 1, using 5-cyclopropyl-6-cyclopropylmethyloxy-pyridine-2-carboxylic acid (Example 42a) and (αS)-α- amino-4-chloro-benzeneacetamide (CAN 488836-04-0) as starting materials; LC-MS (UV peak area/ESI) 95%, 400.1434 (M+H)+.

Example 330

6-(2-Methyl-propane-1-sulfonyl)-pyridine-2-carboxylic acid ((S)-1-carbamoyl-3-methyl-butyl)-amide

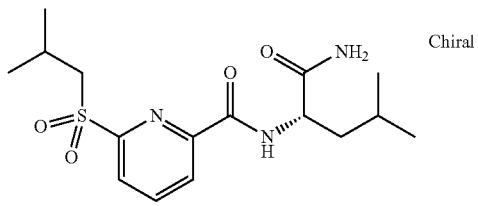 [SMILES: CC(C)C[C@H](NC(=O)c1cccc(S(=O)(=O)CC(C)C)n1)C(N)=O]

a) 6-(Isobutylsulfonyl)picolinonitrile

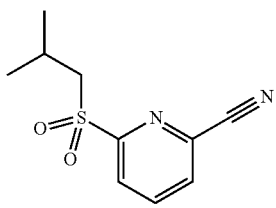

A mixture of 6-(isobutylthio)picolinonitrile (109 mg, 567 µmol; CAN 1342094-07-8) and 3-chlorobenzoperoxoic acid (293 mg, 1.7 mmol) in dichloromethane (3 mL) was stirred at ambient temperature for 24 h, quenched with aqueous $Na_2S_2O_3$ solution and diluted with dichloromethane. The organic layer was washed with sat. aqueous $NaHCO_3$ solution, dried over $Na_2SO_4$ and concentrated in vacuo to give the title compound (126 mg, 99%) as white solid which was sufficiently pure to be used in the next step. MS (EI): m/e=225.1 [M+H]+.

b) 6-(Isobutylsulfonyl)picolinic acid

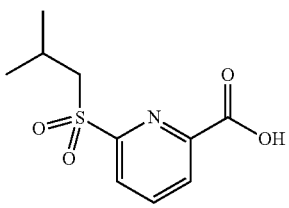 [SMILES: CC(C)CS(=O)(=O)c1cccc(C(=O)O)n1]

A suspension of 6-(isobutylsulfonyl)picolinonitrile (126 mg, 562 µmol) and powdered sodium hydroxide (89.9 mg, 2.25 mmol) in water (15 mL) was heated to 90° C. for 24 h, poured into ice water/0.1 N aqueous HCl solution (1:1) and extracted 3 times with EtOAc. The organic layers were washed with ice water/brine (1:1), dried over $Na_2SO_4$ and concentrated in vacuo to give the title compound (116 mg, 85%) as white solid which was sufficiently pure to be used in the next reaction step. MS (EI): m/e=241.9 [M−H]−.

c) 6-(2-Methyl-propane-1-sulfonyl)-pyridine-2-carboxylic acid ((S)-1-carbamoyl-3-methyl-butyl)-amide The title compound was synthesized in analogy to Example 1, using 6-(isobutylsulfonyl)picolinic acid and (2S)-2-amino-4-methyl-pentanamide (CAN 687-51-4) as starting materials. MS (EI): m/e=356.2 [M+H]+.

Example 331

6-Isobutylsulfanyl-pyridine-2-carboxylic acid ((S)-1-carbamoyl-3-methyl-butyl)-amide

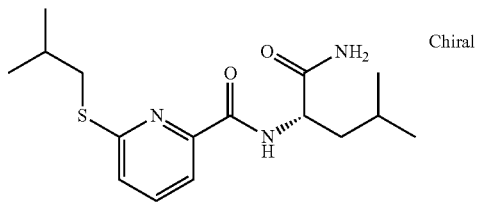 [SMILES: CC(C)CSc1cccc(C(=O)N[C@@H](CC(C)C)C(N)=O)n1]

The title compound was synthesized in analogy to Example 1, using 6-(isobutylthio)picolinic acid (CAN 1247607-03-9) and (2S)-2-amino-4-methyl-pentanamide (CAN 687-51-4) as starting materials. MS (EI): m/e=324.2 [M+H]+.

Example 332

5-Cyclopropyl-6-(4-fluoro-benzyl)-pyridine-2-carboxylic acid ((S)-2,2,2-trifluoro-1-pyridin-2-yl-ethyl)-amide

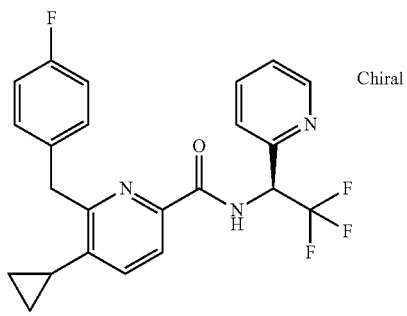 [SMILES: O=C(N[C@@H](c1ccccn1)C(F)(F)F)c1ccc(C2CC2)c(Cc2ccc(F)cc2)n1]

The title compound was synthesized in analogy to Example 1, using 5-cyclopropyl-6-(4-fluoro-benzyl)-pyridine-2-carboxylic acid (Example 155 g) and (S)-2,2,2-trifluoro-1-(pyridin-2-yl)ethanamine hydrochloride (CAN 336105-45-4) as starting materials. MS (EI): m/e=430.3 [M+H]⁺.

Example 333

2-{[5-Cyclopropyl-6-(4-fluoro-benzyl)-pyridine-2-carbonyl]-amino}-2-ethyl-butyric acid

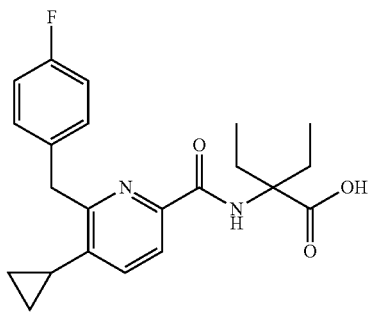 [SMILES: CCC(CC)(NC(=O)c1ccc(C2CC2)c(Cc2ccc(F)cc2)n1)C(=O)O]

a) Ethyl 2-(5-cyclopropyl-6-(4-fluorobenzyl)picolinamido)-2-ethylbutanoate

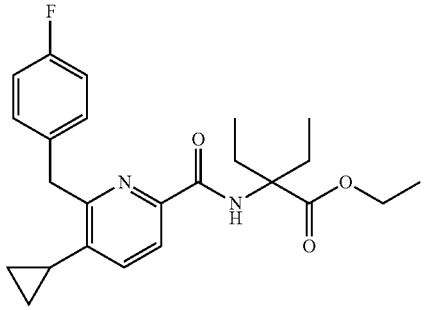 [SMILES: CCOC(=O)C(CC)(CC)NC(=O)c1ccc(C2CC2)c(Cc2ccc(F)cc2)n1]

The title compound was synthesized in analogy to Example 1, using 5-cyclopropyl-6-(4-fluoro-benzyl)-pyridine-2-carboxylic acid (Example 155 g) and ethyl 2-amino-2-ethylbutanoate hydrochloride (CAN 1135219-29-2) as starting materials. MS (EI): m/e=413.1 [M+H]⁺.

b) 2-{[5-Cyclopropyl-6-(4-fluoro-benzyl)-pyridine-2-carbonyl]-amino}-2-ethyl-butyric acid In analogy to the procedure described in Example 252 b), ethyl 2-(5-cyclopropyl-6-(4-fluorobenzyl)picolinamido)-2-ethylbutanoate was treated with sodium hydroxide to give the title compound as white solid. MS: 383.3 [M−H]⁻.

Example 334

6-Cyclopropylmethoxy-5-(3-oxo-pyrrolidin-1-yl)-pyridine-2-carboxylic acid [1-methyl-1-(5-methyl-[1,2,4]oxadiazol-3-yl)-ethyl]-amide

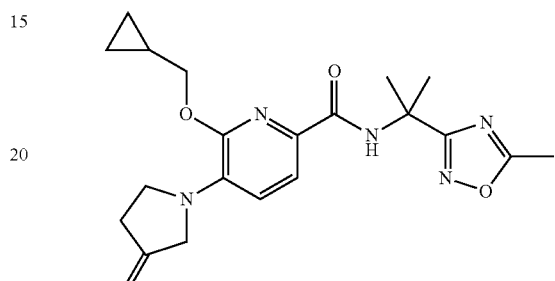

a) 6-Cyclopropylmethoxy-5-((S)-3-hydroxy-pyrrolidin-1-yl)-pyridine-2-carboxylic acid [1-methyl-1-(5-methyl-[1,2,4]oxadiazol-3-yl)-ethyl]-amide

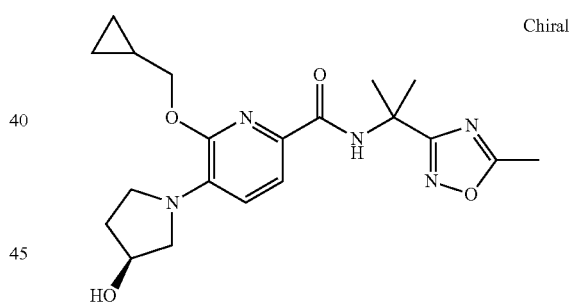

The title compound was synthesized in analogy to Example 322b, using 5-bromo-6-cyclopropylmethoxy-pyridine-2-carboxylic acid [1-methyl-1-(5-methyl-[1,2,4]oxadiazol-3-yl)-ethyl]-amide (Example 322a) and (3S)-3-[[(1,1-dimethylethyl)dimethylsilyl]oxy]-pyrrolidine (CAN 207113-36-8) as starting materials. The protecting group was removed with tetrabutylammonium fluoride in THF; LC-MS (UV peak area/ESI) 100%, 402.2134 (M+H)⁺.

c) 6-Cyclopropylmethoxy-5-(3-oxo-pyrrolidin-1-yl)-pyridine-2-carboxylic acid [1-methyl-1-(5-methyl-[1,2,4]oxadiazol-3-yl)-ethyl]-amide The title compound was synthesized in analogy to Example 322c, using 6-cyclopropylmethoxy-5-((S)-3-hydroxy-pyrrolidin-1-yl)-pyridine-2-carboxylic acid [1-methyl-1-(5-methyl-[1,2,4]oxadiazol-3-yl)-ethyl]-amide (Example 334a) as starting material; LC-MS (UV peak area/ESI) 100%, 400.1987 (M+H)+.

Example 335

6-(2-Methyl-propane-1-sulfonyl)-pyridine-2-carboxylic acid [(S)-3-methyl-1-(5-methyl-[1,2,4]oxadiazol-3-yl)-butyl]-amide

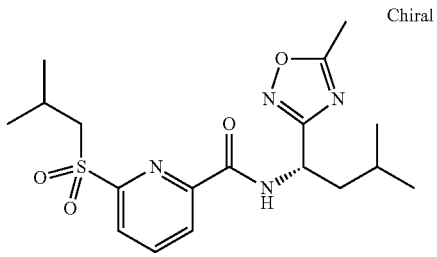 [SMILES: Cc1nc([C@H](CC(C)C)NC(=O)c2cccc(S(=O)(=O)CC(C)C)n2)no1]

The title compound was synthesized in analogy to Example 1, using 6-(isobutylsulfonyl)picolinic acid (Example 330 b) and (S)-5-methyl-α-(2-methylpropyl)-1,2,4-oxadiazole-3-methanamine hydrochloride (which was prepared from (2S)-2-[(tert-butoxycarbonyl)amino]-4-methylpentanoic acid (CAN 13139-15-6) in analogy to the procedures described in Example 38 a to e) as starting materials. MS (EI): m/e=395.2 [M+H]+.

Example 336

(S)-2-{[5-Cyclopropyl-6-(4-fluoro-benzyl)-pyridine-2-carbonyl]-amino}-4-methyl-pentanoic acid

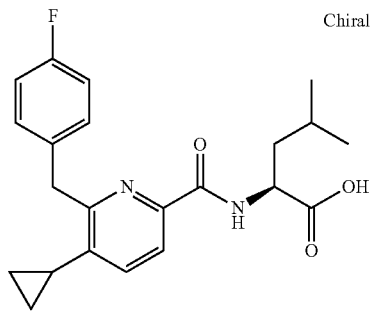 [SMILES: CC(C)C[C@H](NC(=O)c1ccc(C2CC2)c(Cc2ccc(F)cc2)n1)C(=O)O]

a) (S)-Ethyl 2-(5-cyclopropyl-6-(4-fluorobenzyl) picolinamido)-4-methylpentanoate The title compound was synthesized in analogy to Example 1, using 5-cyclopropyl-6-(4-fluoro-benzyl)-pyridine-2-carboxylic acid (Example 155 g) and (S)-ethyl 2-amino-4-methylpentanoate hydrochloride (CAN 2743-40-0) as starting materials. MS (EI): m/e=413.2 [M+H]+.

b) (S)-2-{[5-Cyclopropyl-6-(4-fluoro-benzyl)-pyridine-2-carbonyl]-amino}-4-methyl-pentanoic acid In analogy to the procedure described in Example 5 c), (S)-ethyl 2-(5-cyclopropyl-6-(4-fluorobenzyl)picolinamido)-4-methylpentanoate was saponified with lithium hydroxide to obtain the title compound. MS (EI): m/e=385.2 [M+H]+.

Example 337

2-{[5-Cyclopropyl-6-(tetrahydro-pyran-4-ylmethoxy)-pyridine-2-carbonyl]-amino}-2-ethyl-butyric acid

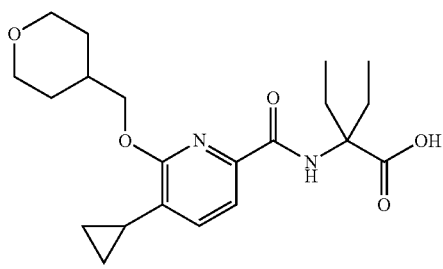 [SMILES: CCC(CC)(NC(=O)c1ccc(C2CC2)c(OCC2CCOCC2)n1)C(=O)O]

a) Ethyl 2-(5-cyclopropyl-6-((tetrahydro-2H-pyran-4-yl)methoxy)picolinamido)-2-ethylbutanoate

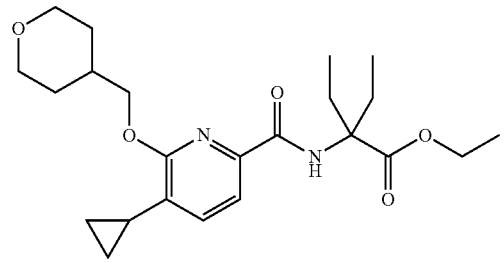 [SMILES: CCOC(=O)C(CC)(CC)NC(=O)c1ccc(C2CC2)c(OCC2CCOCC2)n1]

The title compound was synthesized in analogy to Example 1, using 5-cyclopropyl-6-(tetrahydro-pyran-4-ylmethoxy)-pyridine-2-carboxylic acid (which can e.g. be prepared in a similar manner than 5-cyclopropyl-6-(tetrahydrofuran-2-ylmethoxy)-pyridine-2-carboxylic acid (Example 166 b)) and ethyl 2-amino-2-ethylbutanoate hydrochloride (CAN 1135219-29-2) as starting materials. MS (EI): m/e=419.3 [M+H]+.

b) 2-{[5-Cyclopropyl-6-(tetrahydro-pyran-4-ylmethoxy)-pyridine-2-carbonyl]-amino}-2-ethyl-butyric acid In analogy to the procedure described in Example 252 b), ethyl 2-(5-cyclopropyl-6-((tetrahydro-2H-pyran-4-yl)methoxy)picolinamido)-2-ethylbutanoate was treated with sodium hydroxide to give the title compound as white solid. MS: 389.3 [M−H]−.

Example 338

5-Cyclopropyl-6-cyclopropylmethoxy-pyridine-2-carboxylic acid [1-methyl-1-(4-methyl-5-oxo-4,5-dihydro-[1,2,4]oxadiazol-3-yl)-ethyl]-amide

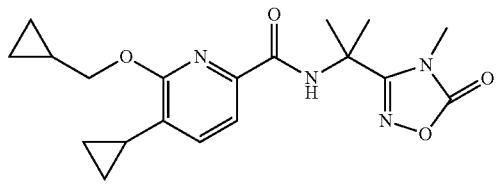 [SMILES: Cn1c(C(C)(C)NC(=O)c2ccc(C3CC3)c(OCC3CC3)n2)noc1=O]

a) [1-Methyl-1-(5-oxo-4,5-dihydro-[1,2,4]oxadiazol-3-yl)-ethyl]-carbamic acid tert-butyl ester

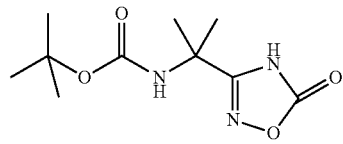 [SMILES: CC(C)(C)OC(=O)NC(C)(C)c1noc(=O)[nH]1]

To a colorless solution of [1-(N-hydroxycarbamidoyl)-1-methyl-ethyl]carbamic acid tert-butyl ester (CAN 1251430-04-2, 1.0 g, 4.6 mmol) in DMF (7.5 mL) was added pyridine (455 mg, 465 µl, 5.75 mmol). The mixture was cooled to 0° C. and methyl chloroformate (478 mg, 392 µl, 5.06 mmol) was added in one portion. The mixture was allowed to warm up and stirred at room temperature for another 90 minutes. Solvents were removed in vacuo and the residue was partitioned between ethyl acetate (30 mL) and water (15 mL). The aqueous phase was extracted with ethyl acetate (30 mL), organic phases were combined, dried with MgSO$_4$ and concentrated in vacuo. The residue (1.2 g white solid) was combined with pyridine (5 mL) and stirred for 3 hours at reflux temperature. The pyridine was removed in vacuo to give the title compound (1.0 g, 89%) as off-white solid; LC-MS (ESI) 242.1151 (M−H)$^−$.

b) [1-Methyl-1-(4-methyl-5-oxo-4,5-dihydro-[1,2,4]oxadiazol-3-yl)-ethyl]-carbamic acid tert-butyl ester

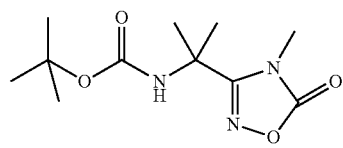 [SMILES: Cn1c(C(C)(C)NC(=O)OC(C)(C)C)noc1=O]

To a colorless solution of [1-methyl-1-(5-oxo-4,5-dihydro-[1,2,4]oxadiazol-3-yl)-ethyl]-carbamic acid tert-butyl ester (1.5 g, 6.17 mmol) in THF (30.0 mL) was added methanol (296 mg, 374 µl, 9.25 mmol) and triphenylphosphine (1.94 g, 7.4 mmol). The mixture was cooled to 0-5° C. and diisopropyl azodicarboxylate (1.5 g, 1.46 ml, 7.4 mmol) was added slowly over a period of 20 minutes at max: 5° C. The mixture was stirred for another 30 minutes at 0-5° C. and for 16 hours at room temperature. Solvents were removed in vacuo and the residue was purified by flash chromatography (silica gel, 70 g, 0% to 100% ethyl acetate in heptane) to give the title compound (1.4 g, 89%) as white solid; GC-MS (EI) 98%, 257.0 (M)$^+$.

c) 3-(1-Amino-1-methyl-ethyl)-4-methyl-4H-[1,2,4]oxadiazol-5-one hydrochloride (1:1)

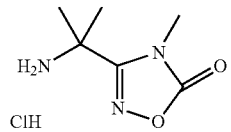

To a solution of [1-methyl-1-(4-methyl-5-oxo-4,5-dihydro-[1,2,4]oxadiazol-3-yl)-ethyl]-carbamic acid tert-butyl ester (1.45 g, 5.64 mmol) in ethanol (15 mL) was added 4M-HCl in dioxane (5.64 mL, 22.5 mmol) and the reaction mixture was stirred at room temperature for 16 hours. The solution was concentrated in vacuo to a volume of 5 mL. With stirring diethyl ether (15 mL) was added drop by drop over a period of 30 minutes and stirring was continued for another 30 minutes. The precipitate was isolated by filtration, washed with diethyl ether (3×1 mL) and dried in vacuo, to give the title compound (1.0 g, 95%) as white solid; GC-MS (EI) 157.0 (M)$^+$.

d) 5-Cyclopropyl-6-cyclopropylmethoxy-pyridine-2-carboxylic acid [1-methyl-1-(4-methyl-5-oxo-4,5-dihydro-[1,2,4]oxadiazol-3-yl)-ethyl]-amide The title compound was synthesized in analogy to Example 1, using 5-cyclopropyl-6-cyclopropylmethyloxy-pyridine-2-carboxylic acid (Example 42a) and 3-(1-amino-1-methyl-ethyl)-4-methyl-4H-[1,2,4]oxadiazol-5-one hydrochloride (1:1) (Example 338c) as starting materials; LC-MS (UV peak area/ESI) 99%, 373.1870 (M+H)$^+$.

Example 339

6-Cyclopropylmethoxy-5-(3,3-difluoro-azetidin-1-yl)-pyridine-2-carboxylic acid (3-methyl-1-pyrimidin-2-yl-butyl)-amide

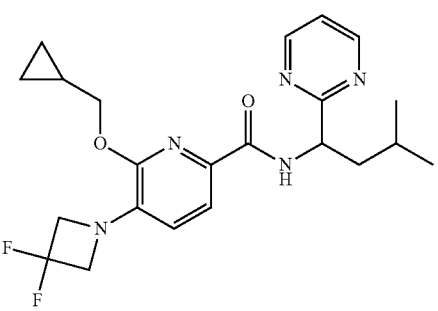 [SMILES: CC(C)CC(NC(=O)c1ccc(N2CC(F)(F)C2)c(OCC2CC2)n1)c1ncccn1]

The title compound was synthesized in analogy to Example 1, using 6-cyclopropylmethoxy-5-(3,3-difluoro-azetidin-1-yl)-pyridine-2-carboxylic acid (Example 69 b)

Example 340

6-Cyclopropylmethoxy-5-(3,3-difluoro-azetidin-1-yl)-pyridine-2-carboxylic acid [1-cyclopropyl-1-(5-methyl-[1,2,4]oxadiazol-3-yl)-ethyl]-amide

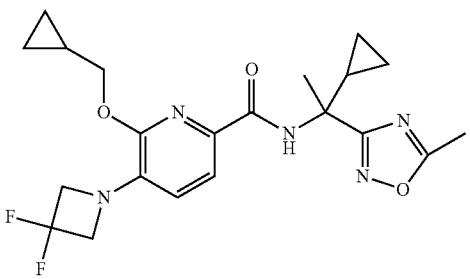 [SMILES: Cc1nc(C(C)(NC(=O)c2ccc(N3CC(F)(F)C3)c(OCC3CC3)n2)C2CC2)no1]

The title compound was synthesized in analogy to Example 1, using 6-cyclopropylmethoxy-5-(3,3-difluoro-azetidin-1-yl)-pyridine-2-carboxylic acid (Example 69 b) and α-cyclopropyl-α,5-dimethyl-1,2,4-oxadiazole-3-methanamine (CAN 1155536-64-3) as starting materials. MS (EI): m/e=434.5 [M+H]+.

Example 341

6-Cyclopropylmethoxy-5-(3,3-difluoro-azetidin-1-yl)-pyridine-2-carboxylic acid [2-cyclopropyl-1-methyl-1-(5-methyl-[1,2,4]oxadiazol-3-yl)-ethyl]-amide

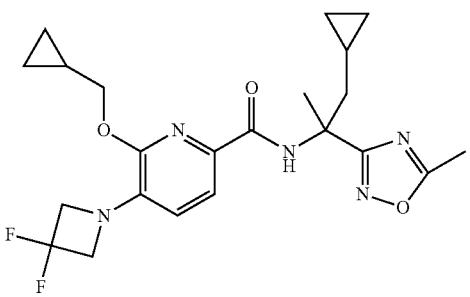 [SMILES: Cc1nc(C(C)(CC2CC2)NC(=O)c2ccc(N3CC(F)(F)C3)c(OCC3CC3)n2)no1]

a) 2-Amino-3-cyclopropyl-2-methyl-propionitrile

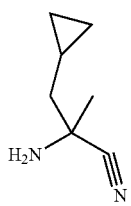

To a solution of 1-cyclopropyl-propan-2-one (1.0 g, 10.2 mmol; CAN 4160-75-2) and aqueous ammonia (25% in water, 15 mL) in EtOH (10 mL) was added ammonium chloride (1.63 g, 30.61 mmol). The reaction mixture was stirred at ambient temperature for 1 hour. To this was added potassium cyanide (900 mg, 15.3 mmol) portion wise and the reaction mixture was stirred at ambient temperature for 12 h. Ice water (50 mL) was added and the mixture was extracted with ethyl acetate (3×50 mL). The organic phases were washed with ice water, combined, dried with $Na_2SO_4$ and concentrated in vacuo to give the title compound (0.8 g, 63%) as yellow oil. $^1$H-NMR (DMSO, 400 MHz): 0.14-0.16 (d, 6.4 Hz, 2H); 0.45-0.49 (d, 6.4 Hz, 2H); 0.78-0.85 (m, 1H); 1.39 (s, 3H); 1.46-1.51 (m, 1H), 1.53-1.63 (m, 1H); 2.52 (br s, 2H).

b) (Cyano-cyclopropylmethyl-methyl-methyl)-carbamic acid tert-butyl ester

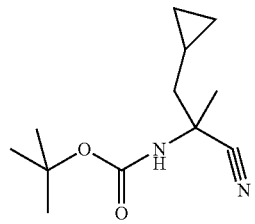 [SMILES: CC(C#N)(CC1CC1)NC(=O)OC(C)(C)C]

To a solution of 2-amino-3-cyclopropyl-2-methyl-propionitrile (0.8 g, 6.45 mmol) and diisopropyl ethyl amine (3.36 mL, 19.8 mmol) in dichloromethane (20 mL) was added di-tert-butyl dicarbonate (2.38 mL, 9.76 mmol). The reaction mixture was stirred at ambient temperature for 12 hours. The organic phase was washed with ice water, brine, dried with $Na_2SO_4$ and concentrated in vacuo. The residue was purified by chromatography (silica gel, 100 g, 1:9 ethyl acetate/n-hexane) to give the title compound (0.8 g, 66%) as light yellow liquid. $^1$H-NMR (DMSO, 400 MHz): 0.12-0.21 (m, 2H); 0.46-0.48 (m, 2H); 0.72-0.77 (m, 1H); 1.44 (s, 9H); 1.55 (s, 3H); 1.66-1.68 (dd, 13.8 Hz & 7.2 Hz, 1H); 1.82-1.87 (dd, 13.8 Hz & 7.2 Hz, 1H); 7.47 (br s, 1H).

c) [2-Cyclopropyl-1-(N-hydroxycarbamimidoyl)-1-methyl-ethyl]-carbamic acid tert-butyl ester

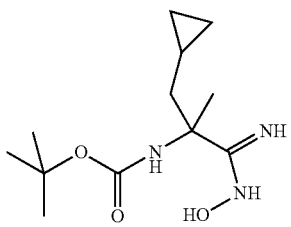 [SMILES: CC(C)(C)OC(=O)NC(C)(CC1CC1)C(=N)NO]

Sodium bi carbonate (0.204 g, 2.9 mmol) was dissolved in EtOH (10 mL) and water (10 mL). Hydroxylamine hydrochloride (0.204 g, 2.9 mmol) was added at 25° C. A solution of (cyano-cyclopropylmethyl-methyl-methyl)-carbamic acid tert-butyl ester (3) (0.7 g, 2.67 mmol) in ethanol (5 mL) was added thereto and the resulting reaction mixture was heated at 80° C. for 12 hours. After evaporation of solvents, the residue was dissolved in ethyl acetate (30 mL) and then filtered. The filtrate was concentrated in vacuo. The residue was purified by chromatography (Combi-Flash, 40 g, 5:95 ethyl acetate/ n-hexane) to give the title compound (0.45 g, 65%) as white solid; LC-MS (ELSD peak area, ESI) 100%, 258.2 [M+H]⁺.

d) [2-Cyclopropyl-1-methyl-1-(5-methyl-[1,2,4]oxadiazol-3-yl)-ethyl]-carbamic acid tert-butyl ester

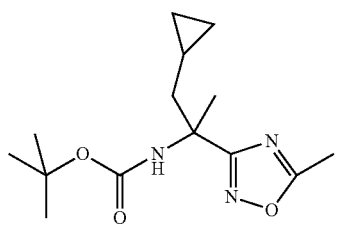 [SMILES: Cc1nc(C(C)(CC2CC2)NC(=O)OC(C)(C)C)no1]

To a solution of [2-cyclopropyl-1-(N-hydroxycarbamimidoyl)-1-methyl-ethyl]-carbamic acid tert-butyl ester (300 mg, 1.16 mmol) in acetic anhydride (10 mL) was heated to 100° C. and stirred for 5 hours. After evaporation of solvents, the residue was dissolved in H₂O (20 mL) and basified by aqueous NaHCO₃ solution (pH~7-8). The aqueous layer was extracted with ethyl acetate (3×50 mL). The combined organic layers were washed with water (20 mL), brine (20 mL), dried over Na₂SO₄ and concentrated in vacuo. The crude product was purified by column chromatography (silica gel, 100-200 mesh, 20 g, eluting with 20% ethyl acetate in petroleum ether) to give the title compound (0.15 g; 46%) as colorless sticky solid. ¹H-NMR (DMSO, 400 MHz): 0.012-0.014 (m, 2H); 0.31-0.38 (m, 2H); 0.56-0.58 (m, 1H); 1.32 (s, 9H); 1.55 (s, 3H); 1.69-1.98 (brs, 2H); 2.56 (s, 3H), 7.19 (br s, 1H).

e) 2-Cyclopropyl-1-methyl-1-(5-methyl-[1,2,4]oxadiazol-3-yl)-ethylamine hydrochloride

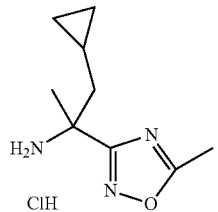

To a solution of [2-cyclopropyl-1-methyl-1-(5-methyl-[1,2,4]oxadiazol-3-yl)-ethyl]-carbamic acid tert-butyl ester (0.4 g, 1.43 mmol) in methanol (10 mL) was added hydrochloric acid (4N in dioxane, 3.5 mL, 14.8 mmol) and the reaction mixture was stirred at ambient temperature for 4 hours. The organic layer was washed with brine (20 mL), dried over anhydrous Na₂SO₄ and concentrated to give the title product (0.25 g, 81%) as a light yellow solid. ¹H-NMR (DMSO, 400 MHz): 0.010-0.02 (m, 2H); 0.38-0.42 (m, 2H); 0.61-0.63 (m, 1H); 1.67 (s, 3H); 1.78-1.91 (m, 2H); 2.66 (s, 3H); 8.89 (br s, 3H).

f) 6-Cyclopropylmethoxy-5-(3,3-difluoro-azetidin-1-yl)-pyridine-2-carboxylic acid [2-cyclopropyl-1-methyl-1-(5-methyl-[1,2,4]oxadiazol-3-yl)-ethyl]-amide The title compound was synthesized in analogy to Example 1, using 6-cyclopropylmethoxy-5-(3,3-difluoro-azetidin-1-yl)-pyridine-2-carboxylic acid (Example 69 b) and 2-cyclopropyl-1-methyl-1-(5-methyl-[1,2,4]oxadiazol-3-yl)-ethylamine hydrochloride as starting materials. MS (D): m/e=448.5 [M+H]⁺.

Example 342

6-Cyclopropylmethoxy-5-(3,3-difluoro-azetidin-1-yl)-pyridine-2-carboxylic acid ((S)-1-carbamoyl-3-methylsulfanyl-propyl)-amide

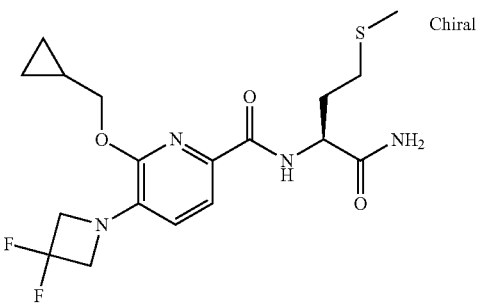 [SMILES: CSCC[C@H](NC(=O)c1ccc(N2CC(F)(F)C2)c(OCC2CC2)n1)C(N)=O]

The title compound was synthesized in analogy to Example 1, using 6-cyclopropylmethoxy-5-(3,3-difluoro-azetidin-1-yl)-pyridine-2-carboxylic acid (Example 69 b) and (2S)-2-amino-4-(methylthio)-butanamide, monohydrochloride (CAN 14510-08-1) as starting materials. MS (EI): m/e=415.16 [M+H]⁺.

Example 343

6-(3-Chloro-4-fluoro-phenyl)-pyridine-2-carboxylic acid [(S)-2-cyclopropyl-1-(5-methyl-[1,2,4]oxadiazol-3-yl)-ethyl]-amide

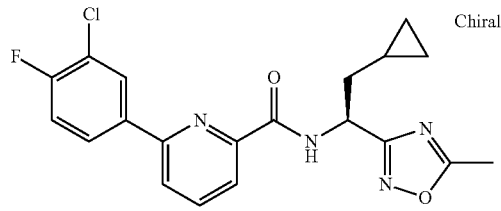 [SMILES: Cc1nc([C@H](CC2CC2)NC(=O)c2cccc(-c3ccc(F)c(Cl)c3)n2)no1]

a) 6-Bromo-pyridine-2-carboxylic acid [(S)-2-cyclopropyl-1-(5-methyl-[1,2,4]oxadiazol-3-yl)-ethyl]-amide

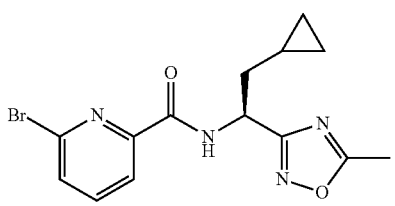 [SMILES: Cc1nc([C@H](CC2CC2)NC(=O)c2cccc(Br)n2)no1]

The title compound can be prepared in analogy to Example 1, using 6-bromo-2-pyridinecarboxylic acid (CAN 21190-

87-4) and (S)-2-cyclopropyl-1-(5-methyl-[1,2,4]oxadiazol-3-yl)-ethylamine (Example 38e) as starting materials, MS (EI) 353.0 (M+H)+.

b) 6-(3-Chloro-4-fluoro-phenyl)-pyridine-2-carboxylic acid [(S)-2-cyclopropyl-1-(5-methyl-[1,2,4]oxadiazol-3-yl)-ethyl]-amide The title compound can be prepared in analogy to Example 177b, using 6-bromo-pyridine-2-carboxylic acid [(S)-2-cyclopropyl-1-(5-methyl-[1,2,4]oxadiazol-3-yl)-ethyl]-amide (Example 343a) and B-(3-chloro-4-fluorophenyl)-boronic acid (CAN 144432-85-9) as starting materials, LC-MS (UV peak area/ESI) 100%, 401.1179 (M+H)+.

Example 344

6-Cyclopropylmethoxy-5-pyrrolidin-1-yl-pyridine-2-carboxylic acid {(S)-3-methyl-1-[(7-nitro-benzo[1,2,5]oxadiazol-4-ylamino)-methyl]-butyl}-amide

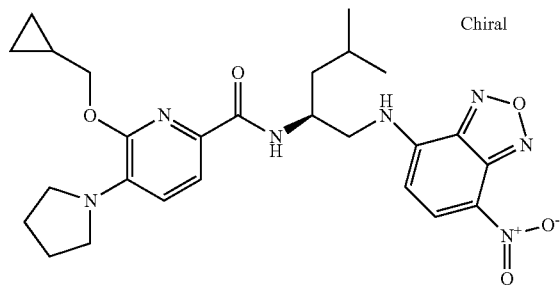 [SMILES: CC(C)C[C@@H](CNc1ccc([N+](=O)[O-])c2nonc12)NC(=O)c1ccc(N2CCCC2)c(OCC2CC2)n1]

a) 6-Cyclopropylmethoxy-5-pyrrolidin-1-yl-pyridine-2-carboxylic acid ((S)-1-azidomethyl-3-methyl-butyl)-amide

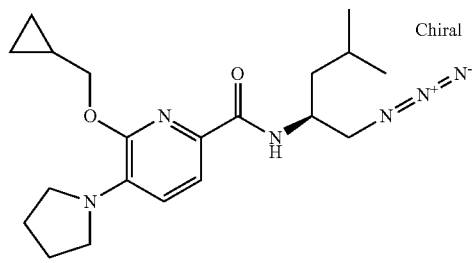 [SMILES: CC(C)C[C@@H](CN=[N+]=[N-])NC(=O)c1ccc(N2CCCC2)c(OCC2CC2)n1]

To a colorless solution of 6-cyclopropylmethoxy-5-pyrrolidin-1-yl-pyridine-2-carboxylic acid ((S)-1-hydroxymethyl-3-methyl-butyl)-amide (Example 14b; 231 mg, 639 µmol) in DMF (25.6 mL) and CCl4 (6.4 mL) was added sodium azide (49.9 mg, 767 µmol) and triphenylphosphine (352 mg, 1.34 mmol). The resulting reaction mixture was stirred at 90° C. for 4 hours. After cooling to room temperature the solvent was removed in vacuo. The residue was partitioned between water and ethyl acetate; the organic phases were washed with brine, combined, dried with Na2SO4, filtered and concentrated in vacuo. The residue, a brown waxy solid, was purified by flash chromatography (silica gel, 50 g, 0% to 60% ethyl acetate in heptane) to give the title compound (110 mg, 45%) as white solid; MS (ESI) 387.3 (M+H)+.

b) 6-Cyclopropylmethoxy-5-pyrrolidin-1-yl-pyridine-2-carboxylic acid ((S)-1-aminomethyl-3-methyl-butyl)-amide

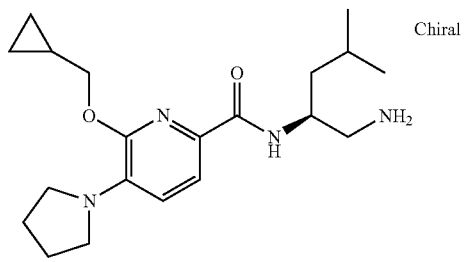 [SMILES: CC(C)C[C@@H](CN)NC(=O)c1ccc(N2CCCC2)c(OCC2CC2)n1]

6-Cyclopropylmethoxy-5-pyrrolidin-1-yl-pyridine-2-carboxylic acid ((S)-1-azidomethyl-3-methyl-butyl)-amide (107 mg, 277 µmol) was combined with 2-propanol (725 µl) to give an off-white suspension. To this suspension was added triethylamine (56.0 mg, 77.2 µl, 554 µmol), 1,3-propanedithiol (3.00 mg, 2.8 µl, 27.7 µmol) and sodium borohydride (15.7 mg, 415 µmol). The resulting reaction mixture was stirred at room temperature for 20 hours. Volatiles were removed in vacuo and the residue was stirred with 10% citric acid solution (5 mL) and a mixture of ethyl acetate/heptane (5 mL, 1:1). The aqueous layer was brought with 2N NaOH to pH=12 and extracted twice with ethyl acetate. The organic phases were combined, dried with Na2SO4, and concentrated in vacuo to give the title compound (32 mg, 32%) as colorless, viscous oil that was used without further purification in the next step; MS (ESI) 361.3 (M+H)+.

c) 6-Cyclopropylmethoxy-5-pyrrolidin-1-yl-pyridine-2-carboxylic acid {(S)-3-methyl-1-[(7-nitro-benzo[1,2,5]oxadiazol-4-ylamino)-methyl]-butyl}-amide To a colorless solution of 6-cyclopropylmethoxy-5-pyrrolidin-1-yl-pyridine-2-carboxylic acid ((S)-1-aminomethyl-3-methyl-butyl)-amide (30 mg, 83.2 µmol) in THF (555 µl) was added 7-nitro-2,1,3-benzoxadiazol-4-amine (CAN 10199-91-4, 19.9 mg, 100 µmol). The reaction mixture was stirred at room temperature for 30 minutes, followed by stirring at reflux temperature for 2 hours. After cooling to room temperature the mixture was poured into water (20 mL) and extracted with ethyl acetate (20 mL). The organic phase was washed with brine; and the aqueous phases were extracted with ethyl acetate. The organic phases were combined, dried with Na2SO4, and concentrated in vacuo. The black, solid residue was purified by flash chromatography (basic silica gel, 10 g, 0% to 100% ethyl acetate in a 1:1 mixture of dichloromethane and heptane) to give the title compound (25 mg, 57%) as brown solid; LC-MS (UV peak area/ESI) 100%, 524.2609 (M+H)+.

Example 345

6-Cyclopropylmethoxy-5-(3,3-difluoro-azetidin-1-yl)-pyridine-2-carboxylic acid ((S)-1-carbamoyl-3-methanesulfonyl-propyl)-amide

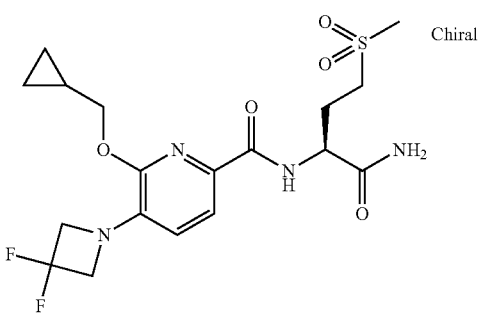 [SMILES: CS(=O)(=O)CC[C@H](NC(=O)c1ccc(N2CC(F)(F)C2)c(OCC2CC2)n1)C(N)=O]

(S)-N-(1-amino-4-(methylthio)-1-oxobutan-2-yl)-6-(cyclopropylmethoxy)-5-(3,3-difluoroazetidin-1-yl)picolinamide (10 mg, 24.1 µmol; Example 342) was dissolved in dichloromethane (200 µL). The yellow solution was cooled to 0° C. 3-Chlorobenzene-carboperoxoic acid (8.33 mg, 48.3 µmol) was added. The reaction mixture was stirred for 1 d at ambient temp. poured onto icewater/sat. NaHCO₃-solution (20 mL), and extracted with dichloromethane (30 mL). The extract was washed with icewater/brine (20 mL). The aqueous layer was back extracted with dichloromethane (30 mL). The organic layers were combined, dried over Na₂SO₄ and concentrated in vacuo to give a yellow solid which was purified by preparative tlc (silica gel, EtOAc, elution with dichloromethane/EtOAc 1:1) to give the title compound (11 mg, 37%) as a white oil. MS (EI): m/e=447.4 [M+H]+.

Example 346

5-Cyclopropyl-6-isobutylsulfanyl-pyridine-2-carboxylic acid ((S)-1-carbamoyl-3-methyl-butyl)-amide

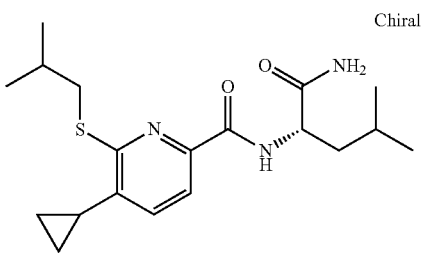 [SMILES: CC(C)CSc1nc(C(=O)N[C@@H](CC(C)C)C(N)=O)ccc1C1CC1]

a) 5-Bromo-6-(isobutylthio)picolinic acid

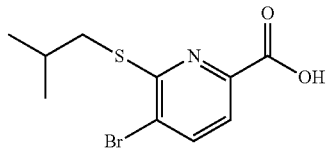

5-Bromo-6-chloropicolinic acid (2 g, 8.46 mmol; CAN 959958-25-9), 2-methylpropane-1-thiol (915 mg, 1.1 mL, 10.2 mmol) and cesium carbonate (6.89 g, 21.1 mmol) were suspended in DMSO (100 mL). The reaction mixture was heated to 150° C. and stirred for 1 d and was poured onto icewater/1N HCl (100 mL). The aqueous layer was extracted with EtOAc (2×250 mL). The combined extracts were washed with icewater/brine (100 mL), dried over Na₂SO₄ and concentrated in vacuo to give the title compound (2.49 g, 51%) as an orange solid which was used in the next step without further purification. MS (EI): m/e=288.4 [M−H]−.

b) Methyl 5-bromo-6-(isobutylthio)picolinate

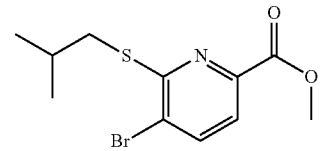 [SMILES: COC(=O)c1ccc(Br)c(SCC(C)C)n1]

5-Bromo-6-(isobutylthio)picolinic acid (500 mg, 1.72 mmol) was dissolved in methanol (5 mL) to give a yellow solution. Sulfuric acid (169 mg, 92.3 µL, 1.72 mmol) was added. The reaction mixture was heated to 80° C. and stirred for 1 d. The reaction mixture was cooled to 0° C. and poured onto icewater/brine (25 mL). The aqueous layer was extracted with EtOAc (2×40 mL) and washed with icewater/brine (20 mL). The organic layers were combined, dried over Na₂SO₄ and concentrated in vacuo to give crude title compound as a yellow oil. The oil was purified by flash chromatography (silica gel, 5 g, 0% to 15% EtOAc in heptane) to give the title product (205 mg, 39%) as a colorless oil. MS (EI): m/e=306.3 [M+H]+.

c) 5-Cyclopropyl-6-(isobutylthio)picolinic acid

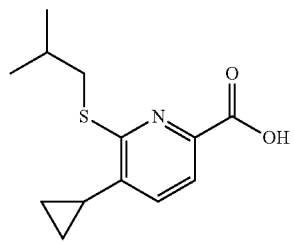 [SMILES: CC(C)CSc1nc(C(=O)O)ccc1C1CC1]

The title compound was prepared in analogy to the procedure described in Example 5 a), using methyl 5-bromo-6-(isobutylthio)picolinate as starting material. MS (EI): m/e=252.4 [M+H]+.

d) 5-Cyclopropyl-6-isobutylsulfanyl-pyridine-2-carboxylic acid ((S)-1-carbamoyl-3-methyl-butyl)-amide The title compound was synthesized in analogy to Example 1, using 5-cyclopropyl-6-(isobutylthio)picolinic acid and (2S)-2-amino-4-methyl-pentanamide (CAN 687-51-4) as starting materials. MS (EI): m/e=364.5 [M+H]$^+$.

Example 347

6-(3-Fluoro-phenyl)-pyridine-2-carboxylic acid [(S)-2-cyclopropyl-1-(5-methyl-[1,2,4]oxadiazol-3-yl)-ethyl]-amide

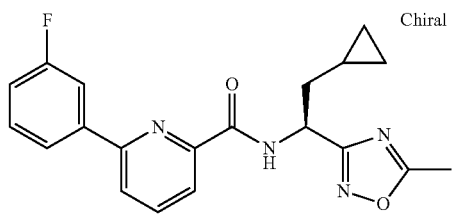 [SMILES: Cc1nc([C@H](CC2CC2)NC(=O)c2cccc(-c3cccc(F)c3)n2)no1]

The title compound can be prepared in analogy to Example 177b, using 6-bromo-pyridine-2-carboxylic acid [(S)-2-cyclopropyl-1-(5-methyl-[1,2,4]oxadiazol-3-yl)-ethyl]-amide (Example 343a) and B-(3-fluorophenyl)-boronic acid (CAN 768-35-4) as starting materials, LC-MS (UV peak area/ESI) 99%, 367.1571 (M+H)$^+$.

Example 348

6-(4-Fluoro-3-trifluoromethyl-phenyl)-pyridine-2-carboxylic acid [(S)-2-cyclopropyl-1-(5-methyl-[1,2,4]oxadiazol-3-yl)-ethyl]-amide

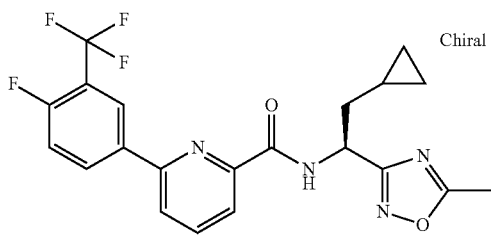 [SMILES: Cc1nc([C@H](CC2CC2)NC(=O)c2cccc(-c3ccc(F)c(C(F)(F)F)c3)n2)no1]

The title compound can be prepared in analogy to Example 177b, using 6-bromo-pyridine-2-carboxylic acid [(S)-2-cyclopropyl-1-(5-methyl-[1,2,4]oxadiazol-3-yl)-ethyl]-amide (Example 343a) and B-(4-fluoro-3-(trifluoromethyl)-phenyl)-boronic acid (CAN 182344-23-6) as starting materials, LC-MS (UV peak area/ESI) 100%, 435.1442 (M+H)$^+$.

Example 349

5-Cyclopropyl-6-cyclopropylmethoxy-pyridine-2-carboxylic acid (3-methanesulfonyl-1,1-dimethyl-propyl)-amide

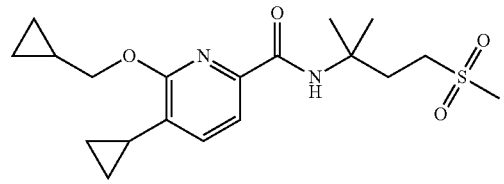 [SMILES: CC(C)(CCS(C)(=O)=O)NC(=O)c1ccc(C2CC2)c(OCC2CC2)n1]

The title compound was synthesized in analogy to Example 1, using 5-cyclopropyl-6-cyclopropylmethyloxy-pyridine-2-carboxylic acid (Example 42a) and 2-methyl-4-(methylsulfonyl)-2-butanamine (CAN 1250515-16-2) as starting materials; LC-MS (UV peak area/ESI) 95%, 381.1843 (M+H)$^+$.

Example 350

5-Cyclopropyl-6-cyclopropylmethoxy-pyridine-2-carboxylic acid [1-methyl-1-(5-methyl-thiazol-2-yl)-ethyl]-amide

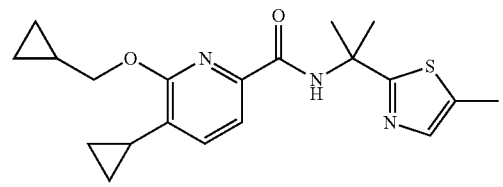 [SMILES: Cc1cnc(C(C)(C)NC(=O)c2ccc(C3CC3)c(OCC3CC3)n2)s1]

The title compound was synthesized in analogy to Example 1, using 5-cyclopropyl-6-cyclopropylmethyloxy-pyridine-2-carboxylic acid (Example 42a) and α,α,5-trimethyl-2-thiazolemethanamine (CAN 1155530-59-8) as starting materials; LC-MS (UV peak area/ESI) 94%, 372.1743 (M+H)$^+$.

Example 351

5-Cyclopropyl-6-(2-methyl-propane-1-sulfonyl)-pyridine-2-carboxylic acid ((S)-1-carbamoyl-3-methyl-butyl)-amide

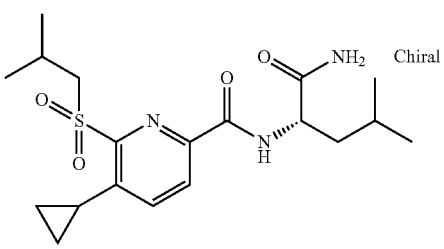 [SMILES: CC(C)C[C@H](NC(=O)c1ccc(C2CC2)c(S(=O)(=O)CC(C)C)n1)C(N)=O]

a) Methyl 5-bromo-6-(isobutylsulfonyl)picolinate

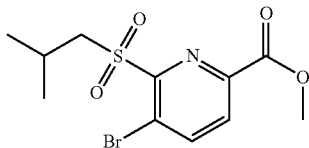 [SMILES: COC(=O)c1ccc(Br)c(S(=O)(=O)CC(C)C)n1]

Methyl 5-bromo-6-(isobutylthio)picolinate (30 mg, 98.6 µmol, Example 346 b) was dissolved in dichloromethane (1 mL). The solution was cooled to 0° C. 3-Chlorobenzo-peroxoic acid (34.0 mg, 197 µmol) was added. The reaction mixture was stirred for 1 d at ambient temp., poured onto icewater (20 mL) and extracted with dichloromethane (2×30 mL). The extract was washed with a 10% aqueous $Na_2O_3S_2$-solution (15 mL). The aqueous layer was back-extracted with dichloromethane (30 mL). The combined organic layers were washed with an aqueous 10% sodium hydrogen carbonate solution, dried over $Na_2SO_4$ and concentrated in vacuo to give the crude product as a white solid. Filtration through silica gel (3 g, heptane/EtOAc 1:1) provided the title compound (19 mg, 70%) as a white oil. MS (EI): m/e=338.3 [M+H]+.

b) 5-Cyclopropyl-6-(isobutylsulfonyl)picolinic acid

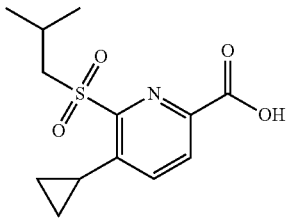 [SMILES: CC(C)CS(=O)(=O)c1nc(C(=O)O)ccc1C1CC1]

The title compound was prepared in analogy to the procedure described in Example 5 a), using methyl 5-bromo-6-(isobutylsulfonyl)picolinate as starting material. MS (EI): m/e=284.3 [M+H]+.

c) 5-Cyclopropyl-6-(2-methyl-propane-1-sulfonyl)-pyridine-2-carboxylic acid ((S)-1-carbamoyl-3-methyl-butyl)-amide The title compound was synthesized in analogy to Example 1, using 5-cyclopropyl-6-(isobutylsulfonyl)picolinic acid and (S)-2-amino-4-methylpentanamide hydrochloride (CAN 687-51-4) as starting materials. MS (EI): m/e=395.5 [M+H]+.

Example 352

5-Cyclopropyl-6-(2-methyl-propane-1-sulfonyl)-pyridine-2-carboxylic acid [(S)-2-cyclopropyl-1-(5-methyl-[1,2,4]oxadiazol-3-yl)-ethyl]-amide

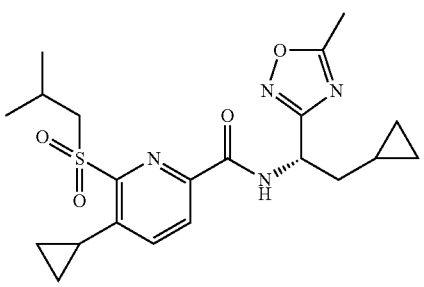 [SMILES: Cc1nc([C@H](CC2CC2)NC(=O)c2ccc(C3CC3)c(S(=O)(=O)CC(C)C)n2)no1]

The title compound was synthesized in analogy to Example 1, using 5-cyclopropyl-6-(2-methyl-propane-1-sulfonyl)-pyridine-2-carboxylic acid (Example 351 b) and (S)-2-cyclopropyl-1-5-methyl-[1,2,4]oxadiazol-3-yl)-ethylamine (Example 38e) as starting materials. MS (EI): m/e=433.2 [M+H]+.

Example 353

6-Cyclopropylmethoxy-5-(3,3-difluoro-azetidin-1-yl)-pyridine-2-carboxylic acid [1-methyl-1-(5-methyl-thiazol-2-yl)-ethyl]-amide

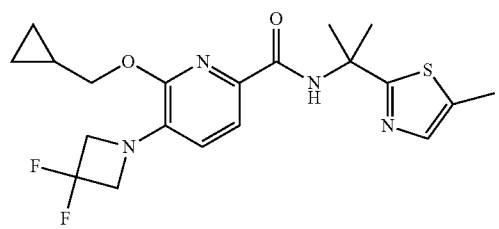 [SMILES: Cc1cnc(C(C)(C)NC(=O)c2ccc(N3CC(F)(F)C3)c(OCC3CC3)n2)s1]

The title compound was synthesized in analogy to Example 1, using 6-cyclopropylmethyloxy-5-(3,3-difluoro-azetidin-1-yl)-pyridine-2-carboxylic acid (Example 69b) and α,α,5-trimethyl-2-thiazolemethanamine (CAN 1155530-59-8) as starting materials; LC-MS (UV peak area/ESI) 100%, 422.4588 (M+H)+.

Example 354

6-Cyclopropylmethoxy-5-(3,3-difluoro-azetidin-1-yl)-pyridine-2-carboxylic acid ((R)-3-methyl-1-pyridazin-3-yl-butyl)-amide

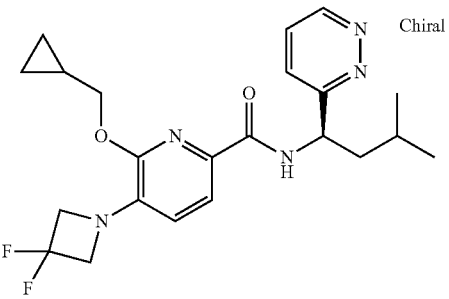 [SMILES: CC(C)C[C@@H](NC(=O)c1ccc(N2CC(F)(F)C2)c(OCC2CC2)n1)c1cccnn1]

The title compound was synthesized in analogy to Example 1, using 6-cyclopropylmethoxy-5-(3,3-difluoro-azetidin-1-yl)-pyridine-2-carboxylic acid (Example 69 b) and 3-methyl-1-(pyridazin-3-yl)butan-1-amine (Example 321 a) as starting materials. The product was isolated by chiral chromatography on Reprosil Chiral NR using a mixture of heptane, ethanol and 2-propanol as eluent. The (+)-enantiomer was isolated. MS (EI): m/e=432.5 [M+H]+.

Example 355

6-Cyclopropylmethoxy-5-(3,3-difluoro-azetidin-1-yl)-pyridine-2-carboxylic acid ((S)-3-methyl-1-pyridazin-3-yl-butyl)-amide

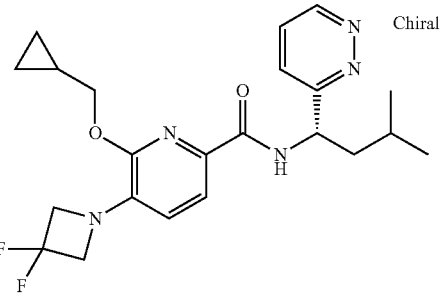

The title compound was synthesized in analogy to Example 1, using 6-cyclopropylmethoxy-5-(3,3-difluoro-azetidin-1-yl)-pyridine-2-carboxylic acid (Example 69 b) and 3-methyl-1-(pyridazin-3-yl)butan-1-amine (Example 321 a) as starting materials. The product was isolated by chiral chromatography on Reprosil Chiral NR using a mixture of heptane, ethanol and 2-propanol as eluent. The (−)-enantiomer was isolated. MS (EI): m/e=432.5 [M+H]$^+$.

Example 356

5-Cyclopropyl-6-cyclopropylmethoxy-pyridine-2-carboxylic acid [1-ethyl-1-(2-hydroxy-ethylcarbamoyl)-propyl]-amide

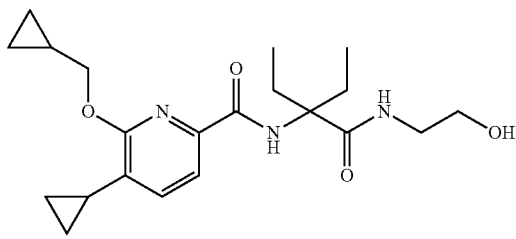 [SMILES: CCC(CC)(NC(=O)c1ccc(C2CC2)c(OCC2CC2)n1)C(=O)NCCO]

The title compound was synthesized in analogy to Example 1, using 2-(5-cyclopropyl-6-(cyclopropylmethoxy) picolinamido)-2-ethylbutanoic acid (Example 274 a) and 2-(trimethylsilyloxy)ethanamine (CAN 5804-92-2)-as starting materials. MS (EI): m/e=390.5 [M+H]$^+$.

Example 357

5-Cyclopropyl-6-cyclopropylmethoxy-pyridine-2-carboxylic acid [(+)-2-cyclopropyl-1-methyl-1-(5-methyl-[1,2,4]oxadiazol-3-yl)-ethyl]-amide

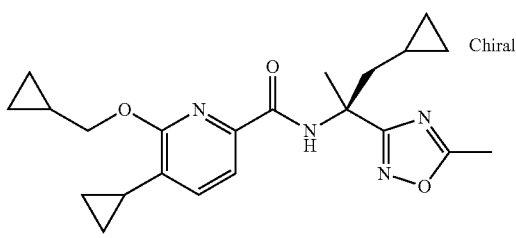 [SMILES: Cc1nc([C@](C)(CC2CC2)NC(=O)c2ccc(C3CC3)c(OCC3CC3)n2)no1]

a) 2-Amino-3-cyclopropyl-2-methyl-propionitrile

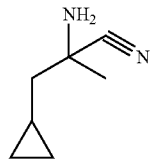

To a solution of 1-cyclopropyl-propan-2-one (CAN 4160-75-2; 1.0 g, 10.2 mmol) and aqueous ammonia (25% in water, 10 mL) in ethanol (10 mL) was added ammonium chloride (1.63 g, 30.6 mmol). The reaction mixture was stirred at ambient temperature for 1 hour. To this was added potassium cyanide (1 g, 15.30 mmol) portion wise, and the reaction mixture was stirred at ambient temperature for 12 h. Ice water (50 mL) was added and extracted with ethyl acetate (3×50 mL). The organic phases were washed with ice-water, combined, dried with Na$_2$SO$_4$ and concentrated in vacuo to give the title compound (0.8 g, 62.99%) as yellow oil; NMR (400 MHz, DMSO) δ=2.52 (bds, 2H); 1.6-1.5 (m, 1H); 1.49-1.4 (m, 1H); 1.39 (S, 3H); 0.85-0.75 (m, 1H); 0.49-0.44 (m, 2H); 0.16-0.14 (m, 2H).

b) (1-Cyano-2-cyclopropyl-1-methyl-ethyl)-carbamic acid tert-butyl ester

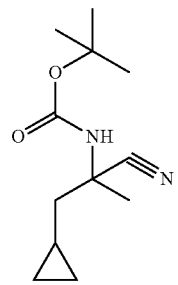 [SMILES: CC(C#N)(CC1CC1)NC(=O)OC(C)(C)C]

To a solution of 2-amino-3-cyclopropyl-2-methyl-propionitrile (1.0 g, 6.4 mmol) and triethyl amine (3.36 mL, 19.8 mmol) in dichloromethane (20 mL) was added di-tert-butyl dicarbonate (CAN 24424-99-5, 2.38 mL, 9.47 mmol). The reaction mixture was stirred at ambient temperature for 12 hours. The organic phase was washed with ice water, brine, dried with Na$_2$SO$_4$ and concentrated in vacuo. The residue was purified by chromatography (silica gel, 50 g, 1:9 ethyl acetate/n-hexane) to give the title compound (1.2 g, 66%) as light yellow liquid; LC-MS (UV peak area, ESI) 83%, 225.14 (M+H).

c) [2-Cyclopropyl-1-(N-hydroxycarbamimidoyl)-1-methyl-ethyl]-carbamic acid tert-butyl ester

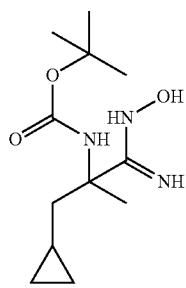 [SMILES: CC(C)(C)OC(=O)NC(C)(CC1CC1)C(=N)NO]

Sodium bicarbonate (247.52 mg, 2.94 mmol) was dissolved in water (2 mL) and hydroxylamine hydrochloride (204.747 mg, 2.94 mmol) was added. A solution of (1-cyano-2-cyclopropyl-1-methyl-ethyl)-carbamic acid tert-butyl ester (600 mg, 2.69 mmol) in ethanol (10 mL) was added thereto and the resulting reaction mixture was heated at 80° C. for 12 hours. After evaporation of solvents, the residue was dissolved with ethyl acetate (20 mL) and then filtered. The filtrate was concentrated in vacuo. The residue was purified by chromatography (silica gel, 25 g, 3:7 ethyl acetate/n-hexane) to give the title compound (450 mg, 66%) as white solid; LC-MS (UV peak area, ESI) 100%, 258.4 (M+H).

d) 2-Cyclopropyl-1-methyl-1-(5-methyl-[1,2,4]oxadiazol-3-yl)-ethyl]-carbamic acid tert-butyl ester

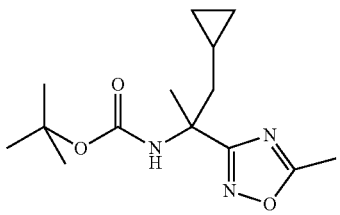 [SMILES: Cc1nc(C(C)(CC2CC2)NC(=O)OC(C)(C)C)no1]

A solution of [2-cyclopropyl-1-(N-hydroxycarbamimidoyl)-1-methyl-ethyl]-carbamic acid tert-butyl ester (300 mg, 1.16 mmol) in acetic anhydride (10 mL) was heated to 120° C. and stirred for 4 hours. After evaporation of solvents, the residue was purified by column chromatography (silica gel, 20 g, eluting with 20% ethyl acetate in petroleum ether) to give the title compound (0.2 g; 61%) as colorless sticky liquid; LC-MS (UV peak area, ESI) 90%, 282.2 (M+H).

e) 2-Cyclopropyl-1-methyl-1-(5-methyl-[1,2,4]oxadiazol-3-yl)-ethylamine

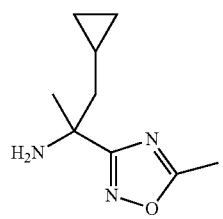

To a solution of 2-cyclopropyl-1-methyl-1-(5-methyl-[1,2,4]oxadiazol-3-yl)-ethyl]-carbamic acid tert-butyl ester (0.2 g, 0.7 mmol) in methanol (5 mL) was added hydrochloric acid (4N in dioxane, 0.87 mL, 3.5 mmol) and the reaction mixture was stirred at ambient temperature for 4 hours. Then water (20 mL) was added. The water phase was washed with ethyl acetate (2×20 mL) and adjusted with 2 M sodium hydroxide solution to pH=9~10. It was then extracted with ethyl acetate (2×20 mL). The organic layer was washed with brine (20 mL), dried over anhydrous $Na_2SO_4$ and concentrated to give crude product as a white solid (0.1 g, 78%); LC-MS (UV peak area, ESI) 80%, 182.0 (M+H).

f) 5-Cyclopropyl-6-cyclopropylmethoxy-pyridine-2-carboxylic acid [(+)-2-cyclopropyl-1-methyl-1-(5-methyl-[1,2,4]oxadiazol-3-yl)-ethyl]-amide The title compound was synthesized in analogy to Example 1, using 5-cyclopropyl-6-cyclopropylmethyloxy-pyridine-2-carboxylic acid (Example 42a) and 2-cyclopropyl-1-methyl-1-(5-methyl-[1,2,4]oxadiazol-3-yl)-ethylamine (Example 357e) as starting materials. The product was isolated by chiral chromatography on Reprosil Chiral NR using heptane/10% 2-propanol as eluent. The (+)-enantiomer was isolated. LC-MS (UV peak area/ESI) 100%, 397.2230 $(M+H)^+$, $\alpha_D^{20}$ (MeOH)=+25.7°.

Example 358

5-Cyclopropyl-6-cyclopropylmethoxy-pyridine-2-carboxylic acid [(−)-2-cyclopropyl-1-methyl-1-(5-methyl-[1,2,4]oxadiazol-3-yl)-ethyl]-amide

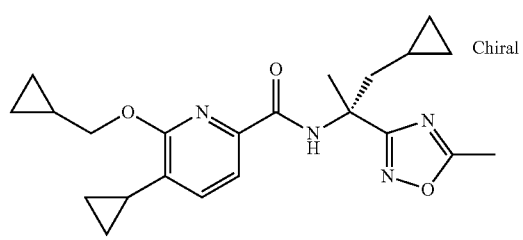 [SMILES: Cc1nc([C@@](C)(CC2CC2)NC(=O)c2ccc(C3CC3)c(OCC3CC3)n2)no1]

The title compound was synthesized in analogy to Example 1, using 5-cyclopropyl-6-cyclopropylmethyloxy-pyridine-2-carboxylic acid (Example 42a) and 2-cyclopropyl-1-methyl-1-(5-methyl-[1,2,4]oxadiazol-3-yl)-ethylamine (Example 357e) as starting materials. The product was isolated by chiral chromatography on Reprosil Chiral NR using heptane/10% 2-propanol as eluent. The (−)-enantiomer was isolated. LC-MS (UV peak area/ESI) 100%, 397.2244 $(M+H)^+$, $\alpha_D^{20}$ (MeOH)=−22.3°.

Example 359

6-Cyclopropylmethoxy-5-(3,3-difluoro-azetidin-1-yl)-pyridine-2-carboxylic acid tert-butylamide

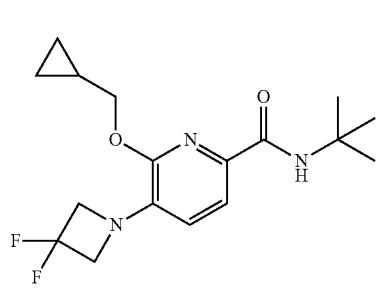 [SMILES: CC(C)(C)NC(=O)c1ccc(N2CC(F)(F)C2)c(OCC2CC2)n1]

The title compound was synthesized in analogy to Example 1, using 6-cyclopropylmethoxy-5-(3,3-difluoro-azetidin-1-yl)-pyridine-2-carboxylic acid (Example 69 b) and tert-butylamine (CAN 75-64-9) as starting materials. MS (EI): m/e=340.5 [M+H]⁺.

Example 360

2-{[5-Cyclopropyl-6-(2-methyl-propane-1-sulfonyl)-pyridine-2-carbonyl]-amino}-2-ethyl-butyric acid ethyl ester

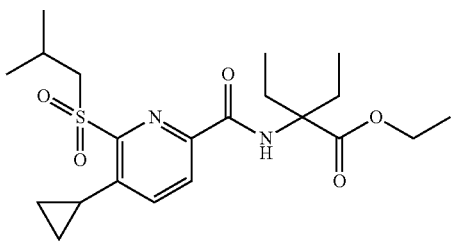 [SMILES: CCOC(=O)C(CC)(CC)NC(=O)c1ccc(C2CC2)c(S(=O)(=O)CC(C)C)n1]

The title compound was synthesized in analogy to Example 1, using 5-cyclopropyl-6-(isobutylsulfonyl)picolinic acid (Example 351 b) and 2-amino-2-ethyl-butanoic acid ethyl ester (CAN 189631-96-7) as starting materials. MS (EI): m/e=425.4 [M+H]⁺.

Example 361

5-Cyclopropyl-6-(2-methyl-propane-1-sulfonyl)-pyridine-2-carboxylic acid ((S)-3,3-dimethyl-1-methylcarbamoyl-butyl)-amide

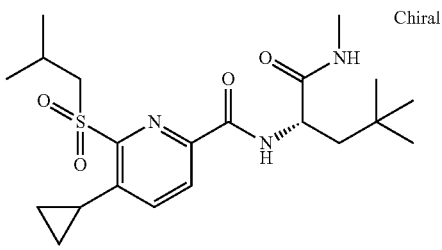 [SMILES: CNC(=O)[C@H](CC(C)(C)C)NC(=O)c1ccc(C2CC2)c(S(=O)(=O)CC(C)C)n1]

The title compound was synthesized in analogy to Example 1, using 5-cyclopropyl-6-(isobutylsulfonyl)picolinic acid (Example 351 b) and (2S)-2-amino-N,4,4-trimethyl-pentanamide (CAN 1160161-70-5) as starting materials. MS (EI): m/e=424.6 [M+H]⁺.

Example 362

5-Cyclopropyl-6-cyclopropylmethoxy-pyridine-2-carboxylic acid ((S)-2-oxo-tetrahydro-furan-3-yl)-amide

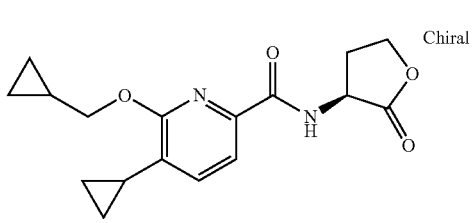 [SMILES: O=C(N[C@H]1CCOC1=O)c1ccc(C2CC2)c(OCC2CC2)n1]

The title compound was synthesized in analogy to Example 1, using 5-cyclopropyl-6-cyclopropylmethyloxy-pyridine-2-carboxylic acid (Example 42a) and (3S)-3-aminodihydro-2(3H)-furanone (CAN 2185-02-6) as starting materials; LC-MS (UV peak area/ESI) 100%, 317.1500 (M+H)⁺.

Example 363

N'-(5-Cyclopropyl-6-cyclopropylmethoxy-pyridine-2-carbonyl)-N-cyclopropylmethyl-hydrazinecarboxylic acid tert-butyl ester

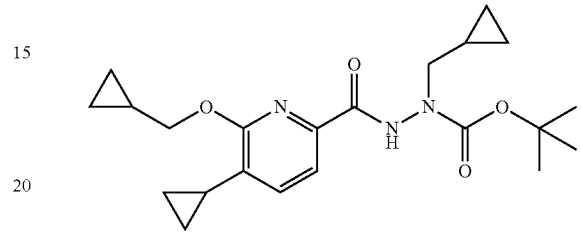

The title compound was synthesized in analogy to Example 1, using 5-cyclopropyl-6-cyclopropylmethyloxy-pyridine-2-carboxylic acid (Example 42a) and 1-(cyclopropylmethyl)-hydrazinecarboxylic acid 1,1-dimethylethyl ester (CAN 1314973-05-1) as starting materials; LC-MS (UV peak area/ESI) 100%, 402.2375 (M+H)⁺.

Example 364

5-Cyclopropyl-6-(2-methyl-propane-1-sulfonyl)-pyridine-2-carboxylic acid ((S)-2,2-dimethyl-1-methylcarbamoyl-propyl)-amide

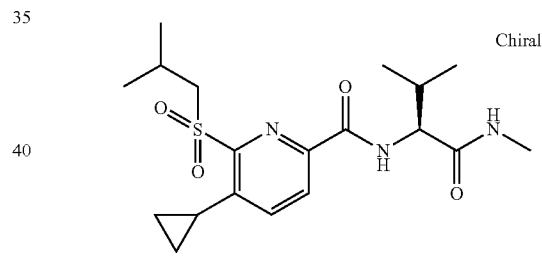

The title compound was synthesized in analogy to Example 1, using 5-cyclopropyl-6-(isobutylsulfonyl)picolinic acid (Example 351 b) and (2S)-2-amino-N,3,3-trimethyl-butanamide (CAN 89226-12-0) as starting materials. MS (EI): m/e=410.6 [M+H]⁺.

Example 365

5-Cyclopropyl-6-(2-methyl-propane-1-sulfonyl)-pyridine-2-carboxylic acid ((S)-2,2,2-trifluoro-1-pyridin-3-yl-ethyl)-amide

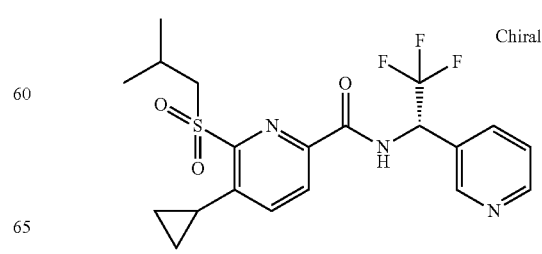

The title compound was synthesized in analogy to Example 1, using 5-cyclopropyl-6-(isobutylsulfonyl)picolinic acid (Example 351 b) and (S)-2,2,2-trifluoro-1-(pyridin-3-yl)ethanamine hydrochloride (CAN 336105-46-5) as starting materials. MS (EI): m/e=442.4 [M+H]⁺.

Example 366

(S)-2-[(5-Cyclopropyl-6-cyclopropylmethoxy-pyridine-2-carbonyl)-amino]-4-methyl-pentanoic acid tert-butyl ester

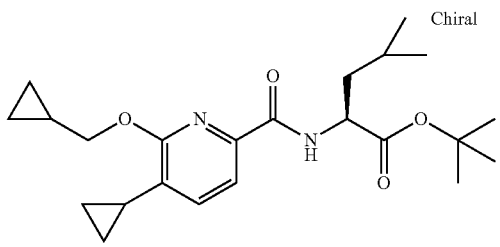 [SMILES: CC(C)C[C@H](NC(=O)c1ccc(C2CC2)c(OCC2CC2)n1)C(=O)OC(C)(C)C]

The title compound was synthesized in analogy to Example 1, using 5-cyclopropyl-6-cyclopropylmethyloxy-pyridine-2-carboxylic acid (Example 42a) and L-leucine 1,1-dimethylethyl ester hydrochloride (1:1) (CAN 2748-02-9) as starting materials; LC-MS (UV peak area/ESI) 98.7%, 403.2599 (M+H)⁺.

Example 367

5-Cyclopropyl-6-(2-methyl-propane-1-sulfonyl)-pyridine-2-carboxylic acid (1-ethyl-1-methylcarbamoyl-propyl)-amide

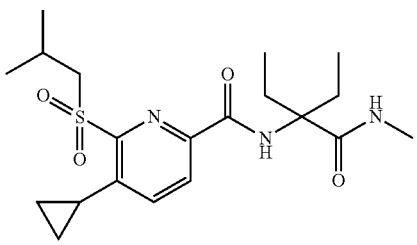 [SMILES: CCC(CC)(NC(=O)c1ccc(C2CC2)c(S(=O)(=O)CC(C)C)n1)C(=O)NC]

The title compound was synthesized in analogy to Example 1, using 5-cyclopropyl-6-(isobutylsulfonyl)picolinic acid (Example 351 b) and 2-amino-2-ethyl-N-methyl-butyramide (Example 70 b) as starting materials. MS (EI): m/e=410.21 [M+H]⁺.

Example 368

5-Cyclopropyl-6-cyclopropylmethoxy-pyridine-2-carboxylic acid tert-butylamide

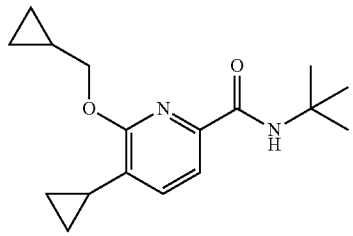 [SMILES: CC(C)(C)NC(=O)c1ccc(C2CC2)c(OCC2CC2)n1]

The title compound was synthesized in analogy to Example 1, using 5-cyclopropyl-6-cyclopropylmethyloxy-pyridine-2-carboxylic acid (Example 42 a) and tert-butylamine (CAN 75-64-9) as starting materials. MS (EI): m/e=289.4 [M+H]⁺.

Example 369

5-Cyclopropyl-6-(tetrahydro-furan-2-ylmethoxy)-pyridine-2-carboxylic acid tert-butylamide

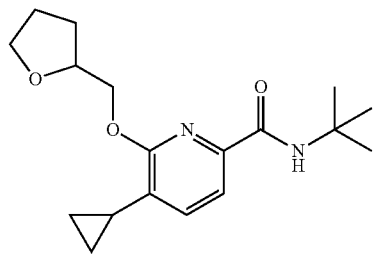 [SMILES: CC(C)(C)NC(=O)c1ccc(C2CC2)c(OCC2CCCO2)n1]

The title compound was synthesized in analogy to Example 1, using 2-(5-cyclopropyl-6-((tetrahydrofuran-2-yl)methoxy)picolinamido)-2-ethylbutanoic acid (Example 166 b) and tert-butylamine (CAN 75-64-9) as starting materials. MS (EI): m/e=319.4 [M+H]⁺.

Example 370

6-Cyclopropylmethoxy-5-(3,3-difluoro-azetidin-1-yl)-pyridine-2-carboxylic acid (3-methyl-oxetan-3-yl)-amide

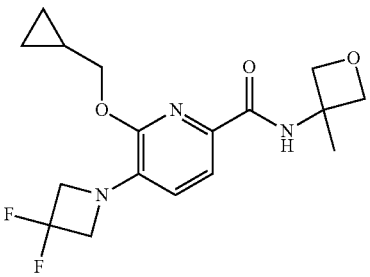 [SMILES: CC1(NC(=O)c2ccc(N3CC(F)(F)C3)c(OCC3CC3)n2)COC1]

The title compound was synthesized in analogy to Example 1, using 6-cyclopropylmethoxy-5-(3,3-difluoro-azetidin-1-yl)-pyridine-2-carboxylic acid (Example 69 b) and (3-methyloxetan-3-yl)-amine (CAN 874473-14-0) as starting materials.

Example 371

5-Cyclopropyl-6-cyclopropylmethoxy-pyridine-2-carboxylic acid (2-oxo-[1,3]oxazinan-3-yl)-amide

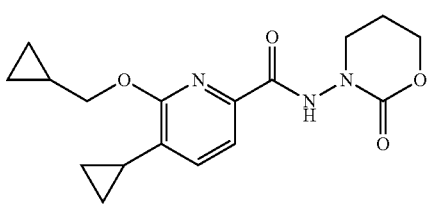 [SMILES: O=C(NN1CCCOC1=O)c1ccc(C2CC2)c(OCC2CC2)n1]

The title compound was synthesized in analogy to Example 1, using 5-cyclopropyl-6-cyclopropylmethyloxy-pyridine-2-carboxylic acid (Example 42a) and 3-aminotetrahydro-2H-1,3-oxazin-2-one (CAN 54924-47-9) as starting materials; LC-MS (UV peak area/ESI) 98.7%, 332.1612 (M+H)+.

Example 372

5-Cyclopropyl-6-(2,2,2-trifluoro-1-methyl-ethoxy)-pyridine-2-carboxylic acid ((S)-1-carbamoyl-3-methyl-butyl)-amide

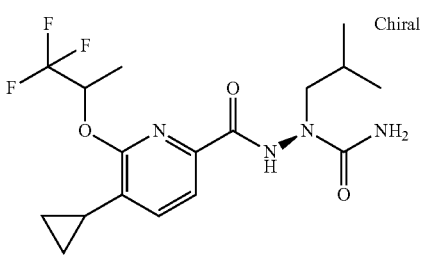

a) 5-Bromo-6-(1,1,1-trifluoropropan-2-yloxy)picolinic acid

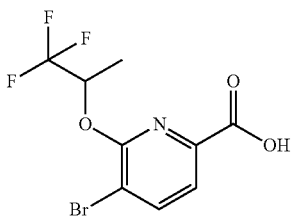 [SMILES: CC(Oc1nc(C(=O)O)ccc1Br)C(F)(F)F]

5-Bromo-6-chloropicolinic acid (5 g, 21.1 mmol; CAN 959958-25-9) was dissolved in DMSO (100 mL) to give a colorless solution. To this solution potassium hydroxide (4.75 g, 84.6 mmol) was added. The reaction mixture turned into a white suspension which was stirred for 15 min. Then 1,1,1-trifluoropropan-2-ol (2.41 g, 1.92 mL, 21.1 mmol) was added. The mixture was stirred for 1 d at ambient temp., poured onto icewater/1N HCl (200 mL) and extracted with EtOAc (2×400 mL). The organic layers were washed with icewater/brine (200 mL), combined and dried over Na$_2$SO$_4$ and concentrated in vacuo to give the title compound (6.9 g, quant.) as orange solid. MS (EI): m/e=312.3 [M−H]−.

b) 5-Cyclopropyl-6-(1,1,1-trifluoropropan-2-yloxy)picolinic acid

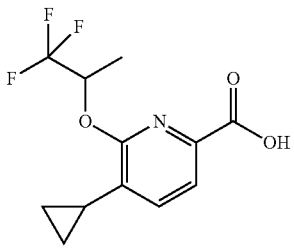 [SMILES: CC(Oc1nc(C(=O)O)ccc1C1CC1)C(F)(F)F]

5-Bromo-6-(1,1,1-trifluoropropan-2-yloxy)picolinic acid (2 g, 6.37 mmol), potassium cyclopropyltrifluoroborate (952 mg, 6.43 mmol), cesium carbonate (6.22 g, 19.1 mmol) and palladium(II)acetate (28.6 mg, 127 µmol) were suspended in toluene (55 mL) and water (6.11 mL) under an argon atmosphere. Butyl-1-adamantylphosphin (68.5 mg, 191 µmol) was added, the reaction mixture was heated to 120° C. for 1 d, poured onto icewater/1N HCl (150 mL) and extracted with EtOAc (2×300 mL). The combined organic layers were washed with icewater/brine (150 mL), dried over Na$_2$SO$_4$ and concentrated in vacuo to give the title compound (1.38 g, 79%) as a yellow solid. MS (EI): m/e=276.2 [M+H]+.

c) 5-Cyclopropyl-6-(2,2,2-trifluoro-1-methyl-ethoxy)-pyridine-2-carboxylic acid ((S)-1-carbamoyl-3-methyl-butyl)-amide The title compound was synthesized in analogy to Example 1, using 5-cyclopropyl-6-(1,1,1-trifluoropropan-2-yloxy)picolinic acid and (2S)-2-amino-4-methyl-pentanamide (CAN 687-51-4) as starting materials. MS (EI): m/e=388.4 [M+H]+.

Example 373

5-Cyclopropyl-6-(2,2,2-trifluoro-1-methyl-ethoxy)-pyridine-2-carboxylic acid [1-methyl-1-(5-methyl-[1,2,4]oxadiazol-3-yl)-ethyl]-amide

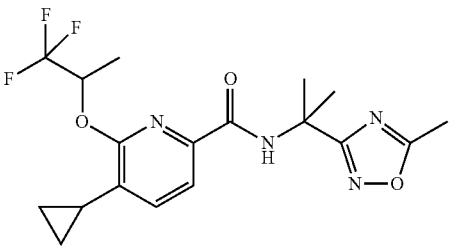 [SMILES: Cc1nc(C(C)(C)NC(=O)c2ccc(C3CC3)c(OC(C)C(F)(F)F)n2)no1]

The title compound was synthesized in analogy to Example 1, using 5-cyclopropyl-6-(1,1,1-trifluoropropan-2-yloxy)picolinic acid (Example 372 b) and α,α,5-trimethyl-1,2,4-oxadiazole-3-methanamine (CAN 1153831-97-0) as starting materials. MS (EI): m/e=399.5 [M+H]+.

Example 374

5-Cyclopropyl-6-cyclopropylmethoxy-pyridine-2-carboxylic acid ((+)-carbamoyl-cyclopropyl-methyl)-amide

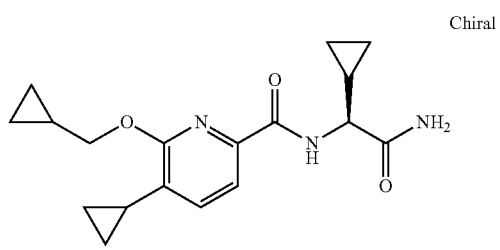 [SMILES: NC(=O)[C@@H](NC(=O)c1ccc(C2CC2)c(OCC2CC2)n1)C1CC1]

The title compound was synthesized in analogy to Example 1, using 5-cyclopropyl-6-cyclopropylmethyloxy-pyridine-2-carboxylic acid (Example 42a) and α-amino-cyclopropaneacetamide (CAN 1100749-41-4) as starting materials. The product was isolated by chiral chromatography on Chiralpak AD using heptane/20% 2-propanol as eluent. The (+)-enantiomer was isolated. LC-MS (UV peak area/ESI) 97.7%, 330.1804 (M+H)$^+$, $\alpha_D^{20}$ (MeOH)=+43.3°.

Example 375

5-Cyclopropyl-6-cyclopropylmethoxy-pyridine-2-carboxylic acid ((−)-carbamoyl-cyclopropyl-methyl)-amide

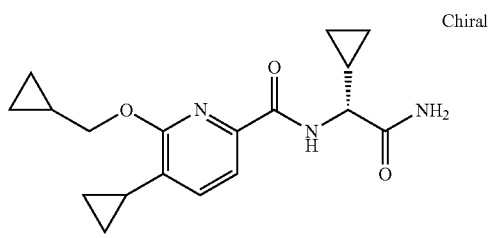 [SMILES: NC(=O)[C@H](NC(=O)c1ccc(C2CC2)c(OCC2CC2)n1)C1CC1]

The title compound was synthesized in analogy to Example 1, using 5-cyclopropyl-6-cyclopropylmethyloxy-pyridine-2-carboxylic acid (Example 42a) and α-amino-cyclopropaneacetamide (CAN 1100749-41-4) as starting materials. The product was isolated by chiral chromatography on Chiralpak AD using heptane/20% 2-propanol as eluent. The (−)-enantiomer was isolated. LC-MS (UV peak area/ESI) 100%, 330.1806 (M+H)$^+$; $\alpha_D^{20}$ (MeOH)=−40.1°.

Example 376

6-Cyclopropylmethoxy-5-(3,3-difluoro-azetidin-1-yl)-pyridine-2-carboxylic acid ((+)-carbamoyl-cyclopropyl-methyl)-amide

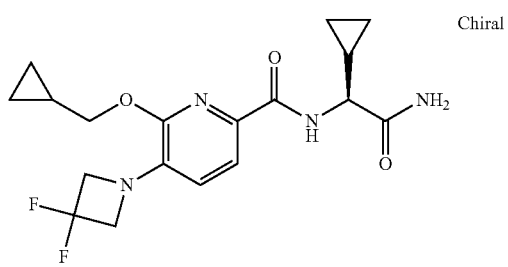 [SMILES: NC(=O)[C@@H](NC(=O)c1ccc(N2CC(F)(F)C2)c(OCC2CC2)n1)C1CC1]

The title compound was synthesized in analogy to Example 1, using 6-cyclopropylmethyloxy-5-(3,3-difluoro-azetidin-1-yl)-pyridine-2-carboxylic acid (Example 69b) and α-amino-cyclopropaneacetamide (CAN 1100749-41-4) as starting materials. The product was isolated by chiral chromatography on Chiralpak AD using heptane/40% ethanol as eluent. The (+)-enantiomer was isolated. LC-MS (UV peak area/ESI) 100%, 381.1739 (M+H)$^+$, $\alpha_D^{20}$ (MeOH)=+35.0°.

Example 377

6-Cyclopropylmethoxy-5-(3,3-difluoro-azetidin-1-yl)-pyridine-2-carboxylic acid ((−)-carbamoyl-cyclopropyl-methyl)-amide

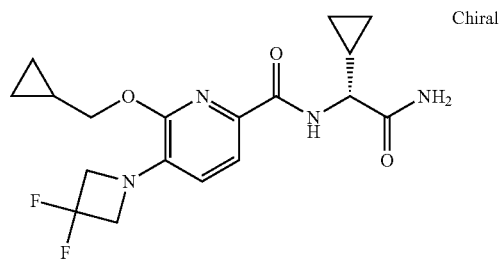 [SMILES: NC(=O)[C@H](NC(=O)c1ccc(N2CC(F)(F)C2)c(OCC2CC2)n1)C1CC1]

The title compound was synthesized in analogy to Example 1, using 6-cyclopropylmethyloxy-5-(3,3-difluoro-azetidin-1-yl)-pyridine-2-carboxylic acid (Example 69 b) and α-amino-cyclopropaneacetamide (CAN 1100749-41-4) as starting materials. The product was isolated by chiral chromatography on Chiralpak AD using heptane/40% ethanol as eluent. The (−)-enantiomer was isolated. LC-MS (UV peak area/ESI) 100%, 381.1734 (M+H)$^+$, $\alpha_D^{20}$ (MeOH)=−23.5°.

Example 378

6-Cyclopropylmethoxy-5-(3,3-difluoro-azetidin-1-yl)-pyridine-2-carboxylic acid (1-trifluoromethyl-cyclopropyl)-amide

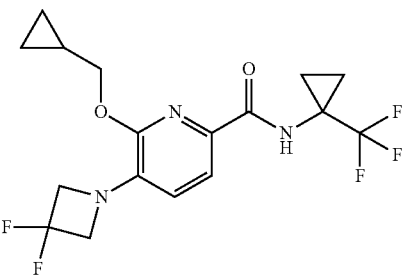 [SMILES: O=C(NC1(C(F)(F)F)CC1)c1ccc(N2CC(F)(F)C2)c(OCC2CC2)n1]

The title compound was synthesized in analogy to Example 1, using 6-cyclopropylmethoxy-5-(3,3-difluoro-azetidin-1-yl)-pyridine-2-carboxylic acid (Example 69 b) and 1-(trifluoromethyl)cyclopropanamine (CAN 112738-68-8) as starting materials. MS (EI): m/e=392.4 [M+H]$^+$.

Example 379

(+)-5-Cyclopropyl-6-cyclopropylmethoxy-pyridine-2-carboxylic acid [(S)-2-cyclopropyl-1-(3-hydroxy-pyrrolidin-1-ylcarbamoyl)-ethyl]-amide

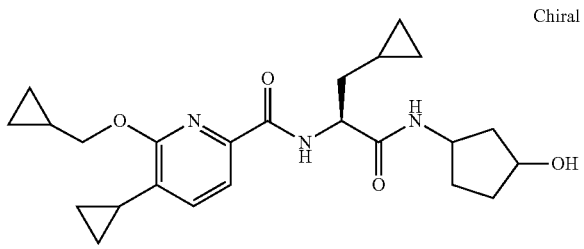 [SMILES: O=C(N[C@@H](CC1CC1)C(=O)NC1CCC(O)C1)c1ccc(C2CC2)c(OCC2CC2)n1]

a) (S)-3-Cyclopropyl-2-[(5-cyclopropyl-6-cyclopropylmethoxy-pyridine-2-carbonyl)-amino]-propionic acid

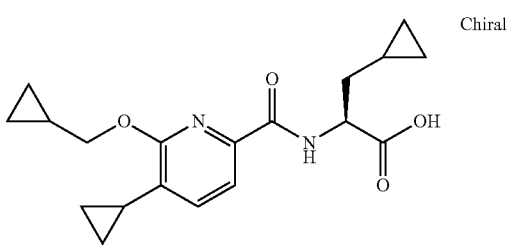 [SMILES: O=C(N[C@@H](CC1CC1)C(=O)O)c1ccc(C2CC2)c(OCC2CC2)n1]

(S)-3-Cyclopropyl-2-[(5-cyclopropyl-6-cyclopropyl-methoxy-pyridine-2-carbonyl)-amino]-propionic acid methyl ester (Example 258, 42 mg, 117 µmol) was dissolved in THF (2 mL). After addition of water (0.66 mL) and lithium hydroxide monohydrate (14.8 mg, 352 µmol) the mixture was heated and stirred for 3 hours at reflux temperature. The mixture was cooled to room temperature, water (7 mL) was added and the mixture was acidified with 1 N HCl. The mixture was then extracted with ethyl acetate (14 and 7 mL), organic layers were washed with brine (10 mL), combined, dried over anhydrous $Na_2SO_4$ and concentrated in vacuo to give the title compound (36 mg, quant) as white solid; LC-MS (UV peak area/ESI) 100%, 345.1814 (M+H)$^+$.

b) 5-Cyclopropyl-6-cyclopropylmethoxy-pyridine-2-carboxylic acid [(S)-2-cyclopropyl-1-((RS)-3-hydroxy-pyrrolidin-1-ylcarbamoyl)-ethyl]-amide

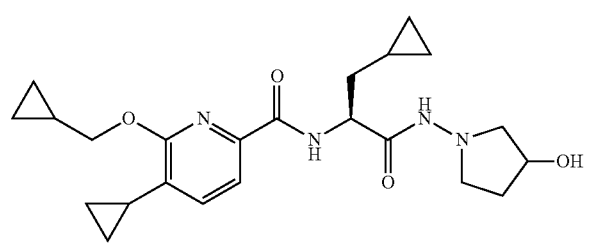 [SMILES: O=C(N[C@@H](CC1CC1)C(=O)NN1CCC(O)C1)c1ccc(C2CC2)c(OCC2CC2)n1]

To a solution of (S)-3-cyclopropyl-2-[(5-cyclopropyl-6-cyclopropylmethoxy-pyridine-2-carbonyl)-amino]-propionic acid (100 mg, 0.29 mmol) in DMF (3 mL), was added TBTU (103 mg, 0.319 mmol), DIEA (249 µL, 1.45 mmol) and finally 1-amino-3-pyrrolidinol (CAN 887591-10-8, 30 mg, 0.29 mmol). The reaction mixture was stirred for 16 h at room temperature, concentrated in vacuo and purified by flash chromatography (silica gel, 10 g, 0% to 20% methanol in dichloromethane) to give the title compound, an epimeric mixture of products, (90 mg, 72%) as white foam; LC-MS (UV peak area/ESI) 96%, 429.2493 (M+H)$^+$.

c) (+)-5-Cyclopropyl-6-cyclopropylmethoxy-pyridine-2-carboxylic acid [(S)-2-cyclopropyl-1-(3-hydroxy-pyrrolidin-1-ylcarbamoyl)-ethyl]-amide The title compound was isolated by chiral chromatography of Example 379 b on Chiralpak AD using heptane/20% ethanol as eluent. The (+)-enantiomer was isolated.

LC-MS (UV peak area/ESI) 100%, 429.2495 (M+H)$^+$, $\alpha_D^{20}$ (MeOH)=+54.4°.

Example 380

(−)-5-Cyclopropyl-6-cyclopropylmethoxy-pyridine-2-carboxylic acid [(S)-2-cyclopropyl-1-(3-hydroxy-pyrrolidin-1-ylcarbamoyl)-ethyl]-amide

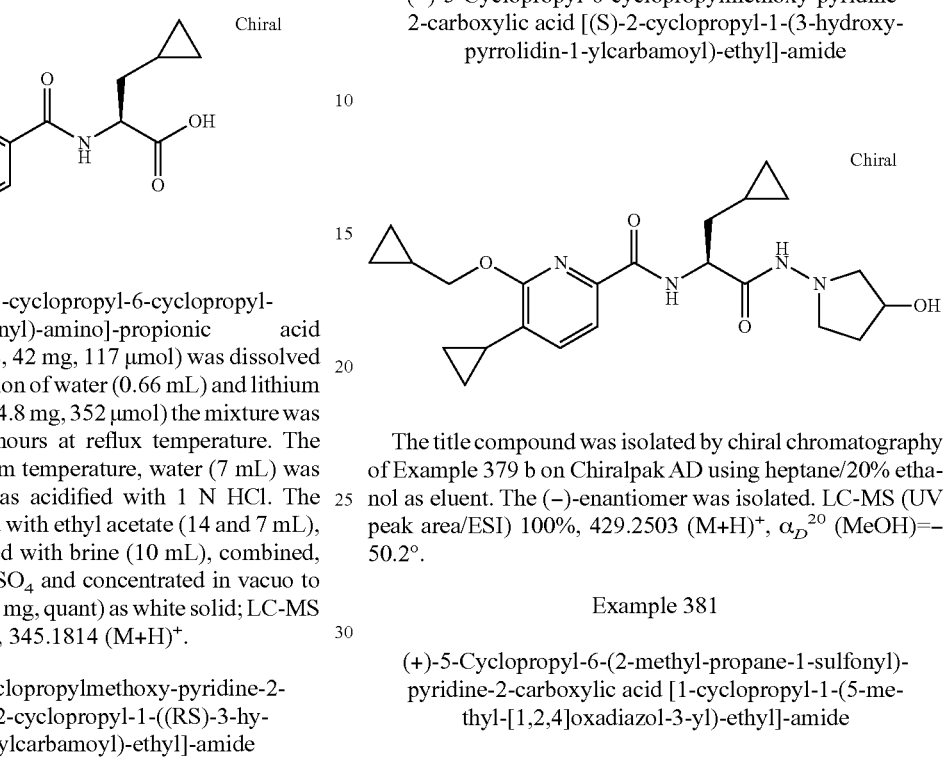

The title compound was isolated by chiral chromatography of Example 379 b on Chiralpak AD using heptane/20% ethanol as eluent. The (−)-enantiomer was isolated. LC-MS (UV peak area/ESI) 100%, 429.2503 (M+H)$^+$, $\alpha_D^{20}$ (MeOH)=−50.2°.

Example 381

(+)-5-Cyclopropyl-6-(2-methyl-propane-1-sulfonyl)-pyridine-2-carboxylic acid [1-cyclopropyl-1-(5-methyl-[1,2,4]oxadiazol-3-yl)-ethyl]-amide

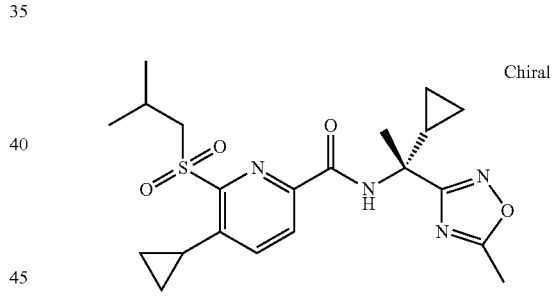

a) 5-Cyclopropyl-6-(2-methyl-propane-1-sulfonyl)-pyridine-2-carboxylic acid [(R,S)-1-cyclopropyl-1-(5-methyl-[1,2,4]oxadiazol-3-yl)-ethyl]-amide

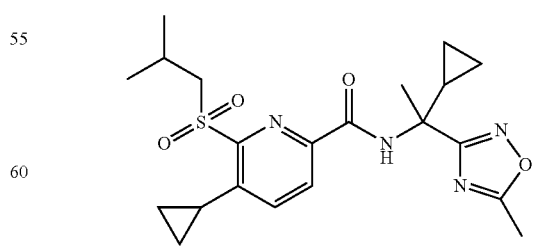

The title compound was synthesized in analogy to Example 1, using 5-cyclopropyl-6-(isobutylsulfonyl)picolinic acid (Example 351 b) and α-cyclopropyl-α,5-dimethyl-1,2,4-oxadiazole-3-methanamine (CAN 1155536-64-3) as starting materials. MS (EI): m/e=433.4 [M+H]+.

b) (+)-5-Cyclopropyl-6-(2-methyl-propane-1-sulfonyl)-pyridine-2-carboxylic acid [1-cyclopropyl-1-(5-methyl-[1,2,4]oxadiazol-3-yl)-ethyl]-amide The title compound was isolated by chiral chromatography of Example 381 a). The (+)-enantiomer was isolated. MS (EI): m/e=433.4 [M+H]+.

Example 382

(−)-5-Cyclopropyl-6-(2-methyl-propane-1-sulfonyl)-pyridine-2-carboxylic acid [1-cyclopropyl-1-(5-methyl-[1,2,4]oxadiazol-3-yl)-ethyl]-amide

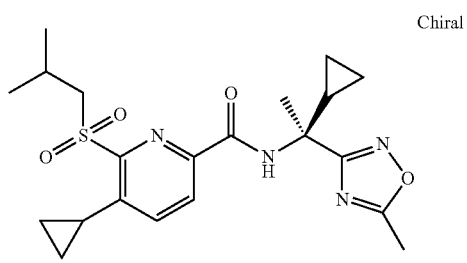 [SMILES: Cc1nc([C@@](C)(NC(=O)c2ccc(C3CC3)c(S(=O)(=O)CC(C)C)n2)C2CC2)no1]

Chiral

The title compound was isolated by chiral chromatography of Example 381 a). The (−)-enantiomer was isolated. MS (EI): m/e=433.4 [M+H]+.

Example 383

Pharmacological Tests

The following tests were carried out in order to determine the activity of the compounds of formula I:

Radioligand Binding Assay

The affinity of the compounds of the invention for cannabinoid CB1 receptors was determined using recommended amounts of membrane preparations (PerkinElmer) of human embryonic kidney (HEK) cells expressing the human CNR1 or CNR2 receptors in conjunction with 1.5 or 2.6 nM [3H]-CP-55,940 (Perkin Elmer) as radioligand, respectively. Binding was performed in binding buffer (50 mM Tris, 5 mM MgCl2, 2.5 mM EDTA, and 0.5% (wt/vol) fatty acid free BSA, pH 7.4 for CB1 receptor and 50 mM Tris, 5 mM MgCl2, 2.5 mM EGTA, and 0.1% (wt/vol) fatty acid free BSA, pH 7.4 for CB2 receptor) in a total volume of 0.2 ml for 1 h at 30° C. shaking. The reaction was terminated by rapid filtration through microfiltration plates coated with 0.5% polyethylenimine (UniFilter GF/B filter plate; Packard). Bound radioactivity was analyzed for Ki using nonlinear regression analysis (Activity Base, ID Business Solution, Limited), with the Kd values for [3H]CP55,940 determined from saturation experiments. The compounds of formula (I) show an excellent affinity for the CB2 receptor.

The compounds according to formula (I) have an activity in the above assay (Ki) between 0.5 nM and 10 μM. Particular compounds of formula (I) have an activity in the above assay (Ki) between 0.5 nM and 3 μM. Other particular compounds of formula (I) have an activity in the above assay (Ki) between 0.5 nM and 100 nM.

cAMP Assay

CHO cells expressing human CB1 or CB2 receptors are seeded 17-24 hours prior to the experiment 50.000 cells per well in a black 96 well plate with flat clear bottom (Corning Costar #3904) in DMEM (Invitrogen No. 31331), 1×HT supplement, with 10% fetal calf serum and incubated at 5% $CO_2$ and 37° C. in a humidified incubator. The growth medium was exchanged with Krebs Ringer Bicarbonate buffer with 1 mM IBMX and incubated at 30° C. for 30 min Compounds were added to a final assay volume of 100 μl and incubated for 30 min at 30° C. Using the cAMP-Nano-TRF detection kit the assay (Roche Diagnostics) was stopped by the addition of 50 μl lysis reagent (Tris, NaCl, 1.5% Triton X100, 2.5% NP40, 10% $NaN_3$) and 50 μl detection solutions (20 μM mAb Alexa700-cAMP 1:1, and 48 μM Ruthenium-2-AHA-cAMP) and shaken for 2 h at room temperature. The time-resolved energy transfer is measured by a TRF reader (Evotec Technologies GmbH), equipped with a ND:YAG laser as excitation source. The plate is measured twice with the excitation at 355 nm and at the emission with a delay of 100 ns and a gate of 100 ns, total exposure time 10 s at 730 (bandwidth 30 nm) or 645 nm (bandwidth 75 nm), respectively. The FRET signal is calculated as follows: FRET=T730-Alexa730-P(T645-B645) with P=Ru730-B730/Ru645-B645, where T730 is the test well measured at 730 nM, T645 is the test well measured at 645 nm, B730 and B645 are the buffer controls at 730 nm and 645 nm, respectively. cAMP content is determined from the function of a standard curve spanning from 10 μM to 0.13 nM cAMP.

$EC_{50}$ values were determined using Activity Base analysis (ID Business Solution, Limited). The $EC_{50}$ values for a wide range of cannabinoid agonists generated from this assay for reference compounds were in agreement with the values published in the scientific literature.

In the foregoing assay, the compounds according to the invention have a human CB2 $EC_{50}$ which is between 0.5 nM and 10 μM. Particular compounds according to the invention have a human CB2 $EC_{50}$ between 0.5 nM and 1 μM. Further particular compounds according to the invention have a human CB2 $EC_{50}$ between 0.5 nM and 100 nM. They exhibit at least 10 fold selectivity against the human CB 1 receptor in, either both of the radioligand and cAMP assay, or in one of these two assays.

Results obtained for representative compounds of the invention are given in the following table.

| Example | human CB2 $EC_{50}$ [μM] | human CB1 $EC_{50}$ [μM] |
|---|---|---|
| 1 | 0.0685 | — |
| 2 | 0.0577 | — |
| 3 | 0.3408 | >10 |
| 4 | 0.0772 | — |
| 5 | 0.4345 | — |
| 6 | 0.376 | — |
| 7 | 0.0321 | — |
| 8 | 0.0996 | >10 |
| 9 | 0.0558 | >10 |
| 10 | 0.0883 | >10 |
| 11 | 0.0636 | >10 |
| 12 | 0.1051 | >10 |
| 13 | 0.4265 | >10 |
| 14 | 0.003 | >10 |
| 15 | 0.0959 | >10 |
| 16 | 0.0166 | >10 |
| 17 | 0.5662 | >10 |
| 18 | 0.097 | >10 |
| 19 | 0.4146 | >10 |
| 20 | 0.2616 | >10 |
| 21 | 0.2202 | >10 |
| 22 | 0.6349 | >10 |

| Example | human CB2 EC$_{50}$ [μM] | human CB1 EC$_{50}$ [μM] |
|---|---|---|
| 23 | 0.0482 | >10 |
| 24 | 0.0156 | >10 |
| 25 | 0.2913 | >10 |
| 26 | 0.6908 | >10 |
| 27 | 0.0046 | >10 |
| 28 | 0.5637 | >10 |
| 29 | 0.3239 | >10 |
| 30 | 0.6577 | >10 |
| 31 | 0.4232 | >10 |
| 32 | 0.00155 | 1.3911 |
| 33 | 0.0231 | >10 |
| 34 | 0.0537 | >10 |
| 35 | 0.0071 | >10 |
| 36 | 0.9735 | >10 |
| 37 | 0.6249 | >10 |
| 38 | 0.0997 | >10 |
| 39 | 0.3033 | >10 |
| 40 | 0.0308 | >10 |
| 41 | 0.0999 | >10 |
| 42 | 1.4776 | >10 |
| 43 | 0.2749 | >10 |
| 44 | 0.0135 | 1.6148 |
| 45 | 0.0871 | 1.0649 |
| 46 | 0.2904 | >10 |
| 47 | 0.1384 | >10 |
| 48 | 0.4768 | >10 |
| 49 | 0.3078 | >10 |
| 50 | 0.1329 | 1.4886 |
| 51 | 0.1273 | >10 |
| 52 | 0.3215 | >10 |
| 53 | 0.0457 | >10 |
| 54 | 0.0114 | 2.1582 |
| 55 | 0.0317 | 1.3873 |
| 56 | 0.1733 | >10 |
| 57 | 0.3192 | >10 |
| 58 | 0.1038 | 1.1053 |
| 59 | 0.0325 | >10 |
| 60 | 0.0622 | >10 |
| 61 | 1.4785 | >10 |
| 62 | 0.0115 | 0.5608 |
| 63 | 0.1123 | >10 |
| 64 | 0.0189 | 1.4641 |
| 65 | 0.0338 | >10 |
| 66 | 0.2158 | >10 |
| 67 | 0.7971 | >10 |
| 68 | 0.4287 | >10 |
| 69 | 0.006 | 0.3797 |
| 70 | 0.0574 | >10 |
| 71 | 0.0612 | >10 |
| 72 | 0.0328 | >10 |
| 73 | 0.0407 | 1.3184 |
| 74 | 0.0089 | >10 |
| 75 | 0.0152 | >10 |
| 76 | 0.1847 | >10 |
| 77 | 1.4028 | >10 |
| 78 | 0.0046 | >10 |
| 79 | 2.0386 | >10 |
| 80 | 0.1338 | 0.0058 |
| 81 | 0.4167 | >10 |
| 82 | 0.1403 | 2.2935 |
| 83 | 0.347 | >10 |
| 84 | 0.2918 | >10 |
| 85 | 0.1862 | >10 |
| 86 | 0.0331 | >10 |
| 87 | 0.4763 | >10 |
| 88 | 0.3558 | >10 |
| 89 | 0.1187 | 1.362 |
| 90 | 0.2173 | >10 |
| 91 | 0.632 | >10 |
| 92 | 0.3203 | >10 |
| 93 | 0.1201 | >10 |
| 94 | 0.1294 | >10 |
| 95 | 0.0839 | >10 |
| 96 | 0.0958 | 1.441 |
| 97 | 0.5079 | >10 |
| 98 | 0.0276 | >10 |
| 99 | 0.0597 | >10 |
| 100 | 0.0012 | 0.8013 |
| 101 | 0.1023 | >10 |
| 102 | 0.0627 | >10 |
| 103 | 0.007 | >10 |
| 104 | 0.5166 | >10 |
| 105 | 0.2079 | >10 |
| 106 | 0.215 | >10 |
| 107 | 0.0107 | 1.4572 |
| 108 | 0.1903 | >10 |
| 109 | 0.178 | >10 |
| 110 | 0.2243 | >10 |
| 111 | 0.0069 | >10 |
| 112 | 0.0154 | >10 |
| 113 | 0.1995 | >10 |
| 114 | 0.0057 | 0.7032 |
| 115 | 0.0066 | 0.9529 |
| 116 | 0.0859 | 1.4461 |
| 117 | 0.3501 | >10 |
| 118 | 0.0134 | 1.5526 |
| 119 | 0.2271 | >10 |
| 120 | 0.2594 | >10 |
| 121 | 0.111 | 1.3529 |
| 122 | 0.1576 | >10 |
| 123 | 0.02 | >10 |
| 124 | 0.0792 | >10 |
| 125 | 0.2088 | >10 |
| 126 | 0.2396 | >10 |
| 127 | 0.2237 | >10 |
| 128 | 0.2401 | >10 |
| 129 | 0.1841 | >10 |
| 130 | 0.05 | >10 |
| 131 | 0.0784 | >10 |
| 132 | 0.0008 | 1.1323 |
| 133 | 0.0377 | >10 |
| 134 | 0.0051 | 0.1507 |
| 135 | 0.0382 | >10 |
| 136 | 0.0654 | >10 |
| 137 | 0.211 | >10 |
| 138 | 0.0267 | >10 |
| 139 | 0.1131 | >10 |
| 140 | 0.3046 | >10 |
| 141 | 0.4591 | >10 |
| 142 | 0.0144 | >10 |
| 143 | 0.41 | >10 |
| 144 | 0.0228 | 0.7392 |
| 145 | 0.2894 | >10 |
| 146 | 0.0366 | >10 |
| 147 | 0.9219 | >10 |
| 148 | 0.0841 | >10 |
| 149 | 0.1745 | >10 |
| 150 | 0.1568 | >10 |
| 151 | 0.3509 | >10 |
| 152 | 0.442 | >10 |
| 153 | 0.2929 | >10 |
| 154 | 0.1498 | >10 |
| 155 | 0.0007 | 0.1226 |
| 156 | 0.334 | >10 |
| 157 | 0.0274 | >10 |
| 158 | 0.0229 | >10 |
| 159 | 0.7805 | >10 |
| 160 | 0.1238 | >10 |
| 161 | 0.1241 | >10 |
| 162 | 0.0544 | 0.6741 |
| 163 | 0.0145 | >10 |
| 164 | 0.2488 | >10 |
| 165 | 0.0072 | 1.2015 |
| 166 | 0.0305 | >10 |
| 167 | 0.2055 | >10 |
| 168 | 0.0006 | 0.3126 |
| 169 | 0.1825 | >10 |
| 170 | 0.1939 | >10 |
| 171 | 0.0468 | >10 |
| 172 | 0.0101 | >10 |
| 173 | 0.0231 | >10 |
| 174 | 0.032 | >10 |

| Example | human CB2 EC$_{50}$ [μM] | human CB1 EC$_{50}$ [μM] |
| --- | --- | --- |
| 175 | 0.0478 | >10 |
| 176 | 0.1142 | >10 |
| 177 | 0.1958 | >10 |
| 178 | 0.0422 | >10 |
| 179 | 0.0038 | 0.5142 |
| 180 | 0.4226 | >10 |
| 181 | 0.0013 | 0.2306 |
| 182 | 0.0017 | >10 |
| 183 | 0.004 | 0.1021 |
| 184 | 0.0039 | >10 |
| 185 | 0.0075 | >10 |
| 186 | 0.0011 | 1.488 |
| 187 | 0.0522 | >10 |
| 188 | 0.005 | 0.3752 |
| 189 | 0.3807 | >10 |
| 190 | 0.0204 | >10 |
| 191 | 0.0577 | >10 |
| 192 | 0.0642 | 1.5353 |
| 193 | 0.0994 | >10 |
| 194 | 0.0991 | >10 |
| 195 | 0.0014 | 0.2059 |
| 196 | 0.0103 | >10 |
| 197 | 0.0332 | >10 |
| 198 | 0.0068 | >10 |
| 199 | 0.151 | >10 |
| 200 | 0.0233 | >10 |
| 201 | 0.0267 | >10 |
| 202 | 0.0236 | 0.6151 |
| 203 | 0.0027 | 0.0749 |
| 204 | 0.0132 | 0.7372 |
| 205 | 0.0578 | >10 |
| 206 | 0.025 | >10 |
| 207 | 0.0144 | >10 |
| 208 | 0.0089 | >10 |
| 209 | 0.0025 | >10 |
| 210 | 0.062 | >10 |
| 211 | 0.0571 | >10 |
| 212 | 0.0134 | >10 |
| 213 | 0.0128 | 0.3611 |
| 214 | 0.0537 | 1.6276 |
| 215 | 0.1254 | >10 |
| 216 | 0.0027 | 0.1156 |
| 217 | 0.0411 | >10 |
| 218 | 0.0241 | >10 |
| 219 | 0.0108 | 2.1419 |
| 220 | 0.0016 | 0.1287 |
| 221 | 0.0128 | 10 |
| 222 | 0.0032 | >10 |
| 223 | 0.0109 | 0.655 |
| 224 | 0.0222 | 0.6475 |
| 225 | 0.0484 | >10 |
| 226 | 0.0199 | >10 |
| 227 | 0.0408 | >10 |
| 228 | 0.0168 | >10 |
| 229 | 0.0524 | >10 |
| 230 | 0.0294 | 1.5912 |
| 231 | 0.0014 | 0.6781 |
| 232 | 0.015 | 1.6326 |
| 233 | 0.0001 | 0.071 |
| 234 | 0.0083 | >10 |
| 235 | 0.0413 | >10 |
| 236 | 0.0365 | >10 |
| 237 | 0.0975 | >10 |
| 238 | 0.0004 | 0.1462 |
| 239 | 0.0011 | 0.0919 |
| 240 | 0.0661 | >10 |
| 241 | 0.0491 | >10 |
| 242 | 0.0012 | >10 |
| 243 | 0.0221 | 0.8302 |
| 244 | 0.0141 | >10 |
| 245 | 0.0205 | >10 |
| 246 | 0.215 | 2.4723 |
| 247 | 0.0056 | >10 |
| 248 | 0.051 | >10 |
| 249 | 0.0022 | >10 |
| 250 | 0.0095 | >10 |
| 251 | 0.0014 | 0.0906 |
| 252 | 0.5521 | >10 |
| 253 | 0.0143 | >10 |
| 254 | 0.0023 | 0.5184 |
| 255 | 0.0613 | >10 |
| 256 | 0.0093 | >10 |
| 257 | 0.0023 | 0.3469 |
| 258 | 0.0071 | >10 |
| 259 | 0.0051 | >10 |
| 260 | 0.0249 | >10 |
| 261 | 0.0101 | 0.26 |
| 262 | 0.0748 | >10 |
| 263 | 0.0045 | >10 |
| 264 | 0.0027 | 0.6019 |
| 265 | 0.0028 | >10 |
| 266 | 0.002 | 1.2977 |
| 267 | 0.0264 | >10 |
| 268 | 0.0087 | 0.3369 |
| 269 | 0.0473 | >10 |
| 270 | 0.0013 | 0.0914 |
| 271 | 0.0079 | >10 |
| 272 | 0.0043 | >10 |
| 273 | 0.0054 | 1.2462 |
| 274 | 0.0016 | 0.3514 |
| 275 | 0.0518 | >10 |
| 276 | 0.0246 | >10 |
| 277 | 0.0166 | 1.6984 |
| 278 | 0.0202 | 0.3571 |
| 279 | 0.023 | >10 |
| 280 | 0.1178 | 1.4926 |
| 281 | 0.4473 | >10 |
| 282 | 0.3679 | >10 |
| 283 | 0.1086 | >10 |
| 284 | 0.027 | >10 |
| 285 | 0.0316 | 0.7034 |
| 286 | 0.0082 | 1.8658 |
| 287 | 0.0036 | >10 |
| 288 | 0.1633 | >10 |
| 289 | 0.0014 | 0.2343 |
| 290 | 0.846 | >10 |
| 291 | 0.4134 | >10 |
| 292 | 0.8739 | >10 |
| 293 | 0.7905 | >10 |
| 294 | 0.1121 | >10 |
| 295 | 0.2593 | >10 |
| 296 | 0.0608 | >10 |
| 297 | 0.9624 | >10 |
| 298 | 0.0142 | >10 |
| 299 | 0.0276 | 0.6032 |
| 300 | 0.0318 | >10 |
| 301 | 0.1297 | >10 |
| 302 | 0.5874 | >10 |
| 303 | 0.038 | >10 |
| 304 | 0.1354 | >10 |
| 305 | 0.0503 | >10 |
| 306 | 0.1383 | >10 |
| 307 | 0.0047 | >10 |
| 308 | 0.5798 | >10 |
| 309 | 0.1764 | >10 |
| 310 | 0.0147 | >10 |
| 311 | 0.0084 | >10 |
| 312 | 0.0024 | >10 |
| 313 | 0.9812 | >10 |
| 314 | 0.0161 | 1.2573 |
| 315 | 0.1906 | 2.3204 |
| 316 | 0.0031 | >10 |
| 317 | 0.0242 | >10 |
| 318 | 0.0251 | >10 |
| 319 | 0.3444 | >10 |
| 320 | 0.0044 | 0.3227 |
| 321 | 0.0189 | >10 |
| 322 | 0.4242 | >10 |
| 323 | 0.0009 | 0.181 |
| 324 | 0.0041 | >10 |
| 325 | 0.0175 | >10 |
| 326 | 0.0002 | 0.059 |

-continued

| Example | human CB2 EC$_{50}$ [μM] | human CB1 EC$_{50}$ [μM] |
|---------|--------------------------|--------------------------|
| 327 | 0.0011 | 0.0136 |
| 328 | 0.0039 | >10 |
| 329 | 0.0211 | >10 |
| 330 | 0.8692 | >10 |
| 331 | 0.0166 | >10 |
| 332 | 0.0045 | 0.091 |
| 333 | 0.008 | 0.081 |
| 334 | 0.1082 | >10 |
| 335 | 0.9622 | >10 |
| 336 | 0.239 | >10 |
| 337 | 0.0345 | 0.475 |
| 338 | 0.5343 | >10 |
| 339 | 0.0649 | >10 |
| 340 | 0.0057 | >10 |
| 341 | 0.0084 | >10 |
| 342 | 0.0028 | >10 |
| 343 | 0.0035 | >10 |
| 344 | 0.0256 | >10 |
| 345 | 0.2952 | >10 |
| 346 | 0.011 | >10 |
| 347 | 0.05 | >10 |
| 348 | 0.0246 | >10 |
| 349 | 0.4766 | >10 |
| 350 | 0.0036 | >10 |
| 351 | 0.0399 | >10 |
| 352 | 0.1891 | >10 |
| 353 | 0.0049 | >10 |
| 354 | 0.0149 | >10 |
| 355 | 0.0801 | >10 |
| 356 | 0.0052 | >10 |
| 357 | 0.0015 | 0.1994 |
| 358 | 0.0049 | 0.4889 |
| 359 | 0.0069 | >10 |
| 360 | 0.0024 | 0.0885 |
| 361 | 0.0425 | >10 |
| 362 | 0.4412 | >10 |
| 363 | 0.038 | >10 |
| 364 | 0.0129 | >10 |
| 365 | 0.0139 | >10 |
| 366 | 0.0264 | >10 |
| 367 | 0.1954 | >10 |
| 368 | 0.0263 | >10 |
| 369 | 0.012 | >10 |
| 370 | 0.0964 | >10 |
| 371 | 0.4362 | >10 |
| 372 | 0.0534 | >10 |
| 373 | 0.1267 | >10 |
| 374 | 0.0281 | >10 |
| 375 | 0.3577 | >10 |
| 376 | 0.0595 | >10 |
| 377 | 0.1777 | >10 |
| 378 | 0.0064 | >10 |
| 379 | 0.0264 | >10 |
| 380 | 0.5841 | >10 |
| 381 | 0.0114 | 0.2403 |
| 382 | 0.0508 | >10 |

β-Arrestin Translocation Assay—PathHunter™ (DiscoveRx)

PathHunter™ β-arrestin CHO-K1 CNR1 cell line (catalog number #93-0200C2) and the β-arrestin CHO-K1 CNR2 cell line (catalog number #93-0706C2) were purchased from DiscoveRx Corporation. The cell line was engineered to express the β-galactosidase EA fragment fused to β-arrestin and the ProLink complementary peptide fused to the target receptor. The PathHunter™ protein complementation assay (DiscoveRx Corporation #93-0001) was performed according to the manufacturer's protocol. Assay plates were seeded containing 7500 (CNR1) and 10000 (CNR2) cells in 384 well plates (Corning Costar #3707, white, clear bottom) in 20 μL cell plating reagent 2 (Discoverx #93-0563R$^2$A). After incubation at 37° C. (5% CO$_2$, 95% relative humidity) overnight, 5 μl of test compound was added (1% final DMSO concentration) and the incubation continued at 30° C. for 90 min. Detection reagent (12 μl) was then added and the incubation continued at room temperature for 60 min. Plates were then analyzed for a chemiluminescent signal using a Victor $^3$V reader (Perkin Elmer).

Example A

Film coated tablets containing the following ingredients can be manufactured in a conventional manner:

| Ingredients | Per tablet | |
|-------------|------------|--|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is then mixed with sodium starch glycolate and magnesium stearate and compressed to yield kernels of 120 or 350 mg respectively. The kernels are lacquered with an aq. solution/suspension of the above mentioned film coat.

Example B

Capsules containing the following ingredients can be manufactured in a conventional manner:

| Ingredients | Per capsule |
|-------------|-------------|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene glycol 400 and water for injection (part). The pH is adjusted to 5.0 by addition of acetic acid. The volume is adjusted to 1.0 ml by addition of the residual amount of water. The solution is filtered, filled into vials using an appropriate overage and sterilized.

The invention claimed is:
1. A compound selected from the group consisting of:
Methyl 2-methyl-2-(5-methyl-6-(2,2,2-trifluoroethoxy)picolinamido)propanoate;
2-[(6-Cyclohexyl-pyridine-2-carbonyl)-amino]-2-methyl-propionic acid methyl ester;
2-{[6-Cyclopropylmethoxy-5-(tetrahydro-pyran-4-yl)-pyridine-2-carbonyl]amino}-2-methyl-propionic acid methyl ester;
6-Cyclopropylmethoxy-5-(tetrahydro-pyran-4-yl)-pyridine-2-carboxylic acid [1-methyl-1(5-methyl-[1,2,4]oxadiazol-3-yl)-ethyl]-amide;6-(3-Chloro-phenyl)-pyridine-2-carboxylic acid piperidin-1-ylamide;
2-{[6-Cyclopropylmethoxy-5-(1H-pyrazol-3-yl)-pyridine-2-carbonyl]-amino}-2-methyl-propionic acid methyl ester;
6-Cyclopropylmethoxy-5-pyrrolidin-1-yl-pyridine-2-carboxylic acid ((S)-1-hydroxymethyl-3-methyl-butyl)-amide;
2-[(6-Cyclopropylmethoxy-5-pyrrolidin-1-yl-pyridine-2-carbonyl)-amino]-2-methyl-propionic acid methyl ester;
6-Cyclopropylmethoxy-5-(2-methyl-pyrrolidin-1-yl)-pyridine-2-carboxylic acid ((S)-1-carbamoyl-3-methyl-butyl)-amide;
6-Cyclopropylmethoxy-5-pyrrolidin-1-yl-pyridine-2-carboxylic acid [1-methyl-1-(5-methyl-[1,2,4]oxadiazol-3-yl)-ethyl]-amide;
6-Cyclopropylmethoxy-5-(tetrahydro-pyran-4-yl)-pyridine-2-carboxylic acid (1-methyl-1-thiazol-2-yl-ethyl)-amide;
6-Cyclopropylmethoxy-5-pyrrolidin-1-yl-pyridine-2-carboxylic acid (1,1-dimethyl-3-moipholin-4-yl-propyl)-amide;
6-Cyclopropylmethoxy-5-methyl-pyridine-2-carboxylic acid (1-methyl-1-methylcarbamoyl-ethyl)-amide;
6-(Tetrahydro-pyran-4-yl)-pyridine-2-carboxylic acid piperidin-1-ylamide;
5-Cyclopentyl-6-cyclopropylmethoxy-pyridine-2-carboxylic acid (1-methyl-1-methylcarbamoyl-ethyl)-amide;
6-(3-Chloro-phenyl)-pyridine-2-carboxylic acid [1-methyl-1-(5-methyl-[1,2,4]oxadiazol-3-yl)-ethyl]-amide;
5-Cyclopropyl-6-cyclopropylmethoxy-pyridine-2-carboxylic acid piperidin-1-ylamide;
5-Cyclopropyl-6-cyclopropylmethoxy-pyridine-2-carboxylic acid (1-methyl-1-methylcarbamoyl-ethyl)-amide;
5-Cyclopropyl-6-cyclopropylmethoxy-pyridine-2-carboxylic acid (1-methyl-1-thiazol-2-yl-ethyl)-amide;
5-Cyclopropyl-6-cyclopropylmethoxy-pyridine-2-carboxylic acid [1-methyl-1-(5-methyl-[1,2,4]oxadiazol-3-yl)-ethyl]-amide;
6-Cyclopropylmethoxy-5-methyl-pyridine-2-carboxylic acid piperidin-1-ylamide;
5-Cyclopentyl-6-cyclopropylmethoxy-pyridine-2-carboxylic acid [(S)-2-cyclopropyl-1-(5-methyl-[1,2,4]oxadiazol-3-yl)-ethyl]-amide;
5-Cyclopentyl-6-cyclopropylmethoxy-pyridine-2-carboxylic acid [1-methyl-1-(5-methyl-[1,2,4]oxadiazol-3-yl)-ethyl]-amide;
5-Cyclopentyl-6-cyclopropylmethoxy-pyridine-2-carboxylic acid (1-methyl-1-thiazol-2-yl-ethyl)-amide;
6-Cyclopropylmethoxy-5-methyl-pyridine-2-carboxylic acid [(S)-2-cyclopropyl-1-(5-methyl-[1,2,4]oxadiazol-3-yl)-ethyl]-amide;
6-Cyclopropylmethoxy-5-(tetrahydro-pyran-4-yl)-pyridine-2-carboxylic acid ((S)-2-cyclopropyl-1-thiazol-2-yl-ethyl)-amide;
6-Cyclopropylmethoxy-5-(2-oxo-pyrrolidin-1-yl)-pyridine-2-carboxylic acid (1-methyl-1-oxazol-2-yl-ethyl)-amide;
6-Cyclopropylmethoxy-5-methyl-pyridine-2-carboxylic acid (1-methyl-1-thiazol-2-yl-ethyl)-amide;
6-Cyclopropylmethoxy-5-pyrrolidin-1-yl-pyridine-2-carboxylic acid [1-(4,5-dihydro-oxazol-2-yl)-1-methyl-ethyl]-amide;
6-Cyclopropylmethoxy-5-methyl-pyridine-2-carboxylic acid ((S)-3-methyl-1-thiazol-2-yl-butyl)-amide;
6-Cyclopropylmethoxy-5-methyl-pyridine-2-carboxylic acid ((S)-2-cyclopropyl-1-thiazol-2-yl-ethyl-amide;
6-Cyclopropylmethoxy-pyridine-2-carboxylic acid piperidin-1-ylamide;
6-Cyclopropylmethoxy-5-(3,3-difluoro-azetidin-1-yl)-pyridine-2-carboxylic acid (1-methyl-1-thiazol-2-yl-ethyl)-amide;
5-Cyclopropyl-6-cyclopropylmethoxy-pyridine-2-carboxylic acid (1-methyl-1-[1,2,4]oxadiazol-3-yl-ethyl)-amide;
5-Cyclopropyl-6-cyclopropylmethoxy-pyridine-2-carboxylic acid (1-ethyl-1-methylcarbamoyl-propyl)-amide;
6-Cyclopropylmetboxy-5-(3-hydroxy-azetidin-1-yl)-pyridine-2-carboxylic acid (1-methyl-1-thiazol-2-yl-ethyl)-amide;
6-(4-Chloro-phenyl)-pyridine-2-carboxylic acid (1-ethyl-1-methylcarbamoyl-propyl)-amide;
6-(Cyclopropylmethoxy)-5-(1,1-dioxido-1,2-isothiazolidin-2-yl)-N-[2-(1,3-thiazol-2-yl) propan-2-yl]pyridine-2-carboxamide;
6-Cyclopropylmethoxy-5-(3,3-difluoro-pyrrolidin-1-yl)-pyridine-2-carboxylic acid (1-ethyl-1-methylcarbamoyl-propyl)-amide;
6-Cyclopropylmethoxy-5-(3,3-difluoro-pyrrolidin-1-yl)-pyridine-2-carboxylic acid (1-methyl-1-methylcarbamoybethyl)-amide;
6-(3-Chloro-phenyl)-5-methoxy-pyridine-2-carboxylic acid (1-methyl-1-thiazol-2-yl-ethyl)-amide;
5-Chloro-6-cyclopropylmethoxy-pyridine-2-carboxylic acid (1-methyl-1-[1,2,4]oxadiazol-3-yl-ethyl)-amide;
6-Cyclohexyl-pyridine-2-carboxylic acid (2-hydroxy-cyclohexyl)-amide;
6-Cyclopropylmethoxy-5-(tetrahydro-pyran-4-yl)-pyridine-2-carboxylic acid (1-ethyl-1-methylcarbamoyl-propyl)-amide;
6-Cyclopropylmethoxy-5-(3,3-difluoro-azetidin-1-yl)-pyridine-2-carboxylic acid (1-ethyl-1-methylcarbamoyl-propyl)-amide;
6-Cyclopropylmethoxy-5-(3,3-difluoro-azetidin-1-yl)-pyridine-2-carboxylic acid (1-methyl-1-methylcarbamoyl-ethyl)-amide;
2-[(6-Cyclohexyl-pyridine-2-carbonyl)-amino]-cyclohexanecarboxylic acid methyl ester;
6-Cyclopropylmethoxy-5-(tetrahydro-pyran-4-yl)-pyridine-2-carboxylic acid (1-methyl-1-oxazol-2-yl-ethyl)-amide;
6-Cyclopentyl-pyridine-2-carboxylic acid piperidin-1-ylamide;
5-Cyclopropyl-6-cyclopropylmethoxy-pyridine-2-carboxylic acid ((S)-1-carbamoyl-2-cyclopropyl-ethyl)-amide;

5-Cyclopropyl-6-cyclopropylmethoxy-pyridine-2-carboxylic acid ((S)-2-cyclopropyl-1-thiazol-2-yl-ethyl)-amide;
5-Cyclopropyl-6-cyclopropylmethoxy-pyridine-2-carboxylic acid ((S)-1-carbamoyl-3-methyl-butyl)-amide;
6-Cyclopropylmethoxy-5-(3,3-difluoro-azetidin-1-yl)-pyridine-2-carboxylic acid [1-methyl-1-(5-methyl-[1,2,4]oxadiazol-3-yl)-ethyl]-amide;
6-Cyclopropylmethoxy-5-(3,3-difluoro-azetidin-1-yl)-pyridine-2-carboxylic acid ((S)-1-carbamoyl-2-cyclopropyl-ethyl)-amide;
5-Cyclopentyl-6-cyclopropylmethoxy-pyridine-2-carboxylic acid ((S)-1-carbamoyl-2-cyclopropyl-ethyl)-amide;
5-Chloro-6-cyclopropylmethoxy-pyridine-2-carboxylic acid [1-methyl-1-(5-methyl-[1,2,4]oxadiazol-3-yl)-ethyl]-amide;
5-Chloro-6-cyclopropylmethoxy-pyridine-2-carboxylic acid (1-ethyl-1-methylcarbamoyl-propyl)-amide;
5-Bromo-6-cyclopropylmethoxy-pyridine-2-carboxylic acid ((S)-1-carbamoyl-2-cyclopropyl-ethyl)-amide;
5-Cyclopentyl-6-cyclopropylmethoxy-pyridine-2-carboxylic acid (1-ethyl-1-methylcarbamoyl-propyl)-amide;
6-Cyclopropylmethoxy-5-(3,3-difluoro-pyrrolidin-1-yl)-pyridine-2-carboxylic acid ((S)-1-carbamoyl-2-cyclopropyl-ethyl)-amide;
6-Cyclopropylmethoxy-5-trifluoromethyl-pyridine-2-carboxylic acid ((S)-1-carbamoyl-2-cyclopropyl-ethyl)-amide;
6-Cyclopropylmethoxy-5-(tetrahydro-furan-3-yl)-pyridine-2-carboxylic acid ((S)-1-carbamoyl-3-methyl-butyl)-amide;
6-Cyclopropylmethoxy-5-(tetrahydro-furan-2-yl)-pyridine-2-carboxylic acid ((S)-1-carbamoyl-3-methyl-butyl)-amide;
5-Cyclopropyl-6-cyclopropylmethoxy-pyridine-2-carboxylic acid [2-(2-methoxy-ethoxy)-1,1-dimethyl-ethyl]-amide;
6-Cyclopropylmethoxy-5-trifluoromethyl-pyridine-2-carboxylic acid ((S)-1-carbamoyl-3-methyl-butyl)-amide;
6-Cyclopropylmethoxy-5-trifluoromethyl-pyridine-2-carboxylic acid (1-methyl-1-[1,2,4]oxadiazol-3-yl-ethyl)-amide;
6-Cyclopropylmethoxy-5-trifluoromethyl-pyridine-2-carboxylic acid [1-methyl-1-(5-methyl-[1,2,4]oxadiazol-3-yl)-ethyl]-amide;
6-Cyclopropylmethoxy-5-trifluoromethyl-pyridine-2-carboxylic acid (1-methyl-1-thiazol-2-yl-ethyl)-amide;
6-Cyclohexyl-pyridine-2-carboxylic acid (2-hydroxymethyl-cyclohexyl)-amide;
6-Cyclopropylmethoxy-5-(tetrahydro-furan-2-yl)-pyridine-2-carboxylic acid [1-methyl-1-(5-methyl-[1,2,4]oxadiazol-3-yl)-ethyl]-amide;
6-Cyclopropylmethoxy-5-(tetrahydro-furan-3-yl)-pyridine-2-carboxylic acid [1-methyl-1-(5-methyl-[1,2,4]oxadiazol-3-yl)-ethyl]-amide;
6-Cyclopropylmethoxy-5-trifluoromethyl-pyridine-2-carboxylic acid (1-methyl-1-oxazol-2-yl-ethyl)-amide;
6-Cyclopropylmethoxy-5-methyl-pyridine-2-carboxylic acid ((S)-1-carbamoyl-2-cyclopropyl-ethyl)-amide;
6-Cyclopropylmethoxy-5-(3-hydroxy-azetidin-1-yl)-pyridine-2-carboxylic acid ((S)-1-carbamoyl-3-methyl-butyl)-amide;
6-Cyclopropylmethoxy-5-(3,3-difluoro-azetidin-1-yl)-pyridine-2-carboxylic acid ((S)-1-carbamoyl-3-methyl-butyl)-amide;
5-Cyclopropylamino-6-cyclopropylmethoxy-pyridine-2-carboxylic acid ((S)-1-carbamoyl-2-cyclopropyl-ethyl)-amide;
5-Cyclopropylamino-6-cyclopropylmethoxy-pyridine-2-carboxylic acid ((S)-1-carbamoyl-3-methyl-butyl)-amide;
6-Cyclopropylmethoxy-5-(3,3-difluoro-azetidin-1-yl)-pyridine-2-carboxylic acid ((S)-1-cyclopropylmethyl-2-hydroxy-2-methyl-propyl)-amide;
6-Cyclopropylmethoxy-5-(tetrahydro-furan-3-yl)-pyridine-2-carboxylic acid ((S)-1-carbamoyl-2-cyclopropyl-ethyl-amide;
6-Cyclopropylmethoxy-5-(3,3-difluoro-azetidin-1-yl)-pyridine-2-carboxylic acid (2-hydroxy-cyclohexyl)-amide;
6-Cyclopropylmethoxy-5-(3,3-difluoro-azetidin-1-yl)-pyridine-2-carboxylic acid [(S)-2-cyclopropyl-1-(5-methyl-[1,2,4]oxadiazol-3-yl)-ethyl]-amide;
5-Cyclopropyl-6-cyclopropylmethoxy-pyridine-2-carboxylic acid ((S)-1-cyclopropylmethyl-2-hydroxy-2-methyl-propyl)-amide;
6-Cyclopropylmethoxy-5-(tetrahydro-furan-3-yl)-pyridine-2-carboxylic acid (2-hydroxy-1,1-dimethyl-ethyl)-amide;
5-Cyclopropyl-6-(2-methoxy-ethoxy)-pyridine-2-carboxylic acid ((S)-1-carbamoyl-3-methyl-butyl)-amide;
6-Cyclopropylmethoxy-5-(3,3-difluoro-azetidin-1-yl)-pyridine-2-carboxylic acid ((S)-2-cyclopropyl-1-thiazol-2-yl-ethyl)-amide;
6-Cyclopropylmethoxy-5-(3,3-difluoro-azetidin-1-yl)-pyridine-2-carboxylic acid (pyridin-2-ylmethyl)-amide;
[6-Cyclopropylmethoxy-5-(3,3-difluoro-azetidin-1-yl)-pyridin-2-yl]-((S)-2-hydroxymethyl-pyrrolidin-1-yl)-methanone;
6-Cyclopropylmethoxy-5-(3-hydroxy-oxetan-3-yl)-pyridine-2-carboxylic acid ((S)-1-carbamoyl-3-methyl-butyl)-amide;
5-Cyclopropyl-6-(2-methoxy-ethoxy)-pyridine-2-carboxylic acid [1-methyl-1-(5-methyl-[1,2,4]oxadiazol-3-yl)-ethyl]amide;
5-Cyclopropyl-6-cyclopropylmethoxy-pyridine-2-carboxylic acid (1,1-dimethyl-3-morpholin-4-yl-propyl)-amide;
5-Cyclopropyl-6-(4-fluoro-benzyl)-pyridine-2-carboxylic acid ((S)-1-carbamoyl-3-methyl-butyl)-amide;
6-Cyclopropylmethoxy-5-(3,3-difluoro-azetidin-1-yl)-pyridine-2-carboxylic acid [(S)-2-cyclopropyl-1-(2-methoxy-ethoxymethyl)-ethyl]-amide;
5-Cyclopropylamino-6-cyclopropylmethoxy-pyridine-2-carboxylic acid (2-hydroxy-1,1-dimethyl-ethyl)-amide;
6-Cyclopropylmethoxy-5-(1-hydroxy-cyclobutyl)-pyridine-2-carboxylic acid [1-methyl-1-(5-methyl-[1,2,4]oxadiazol-3-yl)-ethyl]-amide;
5-Cyclopropyl-6-(2-methoxy-ethoxy)-pyridine-2-carboxylic acid ((S)-1-carbamoyl-2-cyclopropyl-ethyl)-amide;
5-[Bis-(2,2,2-trifluoro-ethyl)-amino]-6-cyclopropylmethoxy-pyridine-2-carboxylic acid ((S)-1-carbamoyl-2-cyclopropyl-ethyl)-amide;
5-Cyclopropyl-6-cyclopropylmethoxy-pyridine-2-carboxylic acid [(S)-2-cyclopropyl-1-(5-methyl-[1,2,4]oxadiazol-3-yl)-ethyl]-amide;
5-[Bis-(2,2,2-trifluoro-ethyl)-amino]-6-cyclopropylmethoxy-pyridine-2-carboxylic acid (1-ethyl-1-methylcarbamoyl-propyl)-amide;

5-Cyclopropyl-6-(tetrahydro-furan-2-ylmethoxy)-pyridine-2-carboxylic acid [1-methyl-1-(5-methyl-[1,2,4]oxadiazol-3-yl)-ethyl]-amide;

N-(2-Cyanopropan-2-yl)-5-cyclopropyl-6-(cyclopropylmethoxy)picolinamide;

(S)-5-Cyclopropyl-6-(cyclopropylmethoxy)-N-(3,3-dimethyl-1-(methylamino)-1-oxobutan-2-yl)picolinamide;

N-(1-Amino-2,3-dimethyl-1-oxobutan-2-yl)-5-cyclopropyl-6-(cyclopropylmethoxy)picolinamide;

N-(1-Amino-2-methyl-1-oxobutan-2-yl)-5-cyclopropyl-6-(cyclopropylmethoxy)picolinamide;

5-Cyclopropyl-6-(cyclopropylmethoxy)-N-(1-(5-methyl-1,2,4-oxadiazol-3-yl)cyclobutyl)picolinamide;

(S)-N-(2-Amino-2-oxo-1-phenylethyl)-5-cyclopropyl-6-(cyclopropylmethoxy)picolinamide;

(R)-N-(2-Amino-2-oxo-1-phenylethyl)-5-cyclopropyl-6-(cyclopropylmethoxy)picolinamide;

(R)-5-Cyclopropyl-6-(cyclopropylmethoxy)-N-(1-hydroxy-4-methylpentan-2-yl)picolinamide;

5-Cyclopropyl-6-(cyclopropylmethoxy)-N-(1-(hydroxymethyl)cyclopentyl)picolinamide;

5-Cyclopropyl-6-(cyclopropylmethoxy)-N-(2-(3-methyl-1,2,4-oxadiazol-5-yl)propan-2-yl)picolinamide;

5-Bromo-6-(4-fluoro-phenoxy)-pyridine-2-carboxylic acid ((S)-1-carbamoyl-3-methyl-butyl)-amide;

N-(1-Amino-2,4-dimethyl-1-oxopentan-2-yl)-5-cyclopropyl-6-(cyclopropylmethoxy)picolinamide;

N-(1-Amino-3,3-dimethyl-1-oxobutan-2-yl)-5-cyclopropyl-6-(cyclopropylmethoxy)picolinamide;

5-Cyclopropyl-6-cyclopropylmethoxy-pyridine-2-carboxylic acid (4-carbamoyl-tetrahydro-pyran-4-yl)-amide;

(S)-5-Cyclopropyl-6-(cyclopropylmethoxy)-N-(4-methyl-1-(methylamino)-1-oxopentan-2-yl)picolinamide;

(S)-5-Cyclopropyl-6-(cyclopropylmethoxy)-N-(4,4-dimethyl-1-(methylamino)-1-oxopentan-2-yl)picolinamide;

5-Cyclopropyl-N-((S)-3,3-dimethyl-1-(methylamino)-1-oxobutan-2-yl)-6-((tetrahydrofuran-2-yl)methoxy)picolinamide;

5-Cyclopropyl-N-((S)-4-methyl-1-(methylamino)-1-oxopentan-2-yl)-6-((tetrahydrofuran-2-yl)methoxy)picolinamide;

5-Cyclopropyl-N-((S)-4,4-dimethyl-1-(methylamino)-1-oxopentan-2-yl)-6-((tetrahydrofuran-2-yl)methoxy)picolinamide;

N-((S)-1-Amino-4-methyl-1-oxopentan-2-yl)-5-cyclopropyl-6-((tetrahydrofuran-2-yl)methoxy)picolinamide;

5-Cyclopropyl-6-(4-fluoro-phenoxy)-pyridine-2-carboxylic acid ((S)-1-carbamoyl-3-methyl-butyl)-amide;

5-Bromo-6-(tetrahydro-furan-2-ylmethoxy)-pyridine-2-carboxylic acid ((S)-2,2-dimethyl-1-methylcarbamoyl-propyl)-amide;

5-Cyclopropyl-N-(1-(5-methyl-1,2,4-oxadiazol-3-yl)cyclobutyl)-6-(pyridin-2-ylmethoxy)picolinamide;

5-Cyclopropyl-N-(cyclopropyl(5-methyl-1,2,4-oxadiazol-3-yl)methyl)-6-(cyclopropylmethoxy)picolinamide;

5-Cyclopropyl-6-cyclopropylmethoxy-pyridine-2-carboxylic acid ((R)-1-hydroxymethyl-1,2-dimethyl-propyl)-amide;

5-Cyclopropyl-6-(cyclopropylmethoxy)-N-(4-hydroxy-2-methylbutan-2-yl)picolinamide;

(S)-5-Cyclopropyl-N-(3,3-dimethyl-1-(methylamino)-1-oxobutan-2-yl)-6-((tetrahydro-2H-pyran-4-yl)methoxy)picolinamide;

(S)-5-Cyclopropyl-N-(4,4-dimethyl-1-(methylamino)-1-oxopentan-2-yl)-6-((tetrahydro-2H-pyran-4-yl)methoxy)picolinamide;

(−)-5-Cyclopropyl-6-cyclopropylmethoxy-pyridine-2-carboxylic acid [cyclopropyl-(5-methyl-[1,2,4]oxadiazol-3-yl)-methyl]-amide;

(+)-5-Cyclopropyl-6-cyclopropylmethoxy-pyridine-2-carboxylic acid [cyclopropyl-(5-methyl-[1,2,4]oxadiazol-3-yl)-methyl]-amide;

5-Cyclopropyl-N-(2-(5-methyl-1,2,4-oxadiazol-3-yl)propan-2-yl)-6-(pyridin-2-ylmethoxy)picolinamide;

(S)-N-(1-Amino-4-methyl-1-oxopentan-2-yl)-5-cyclopropyl-6-(pyridin-2-ylmethoxy)picolinamide;

(S)-5-Cyclopropyl-N-(3,3-dimethyl-1-(methylamino)-1-oxobutan-2-yl)-6-(pyridin-2-ylmethoxy)picolinamide;

5-Cyclopropyl-N-(2-(5-methyl-1,2,4-oxadiazol-3-yl)propan-2-yl)-6-((tetrahydro-2H-pyran-4-yl)methoxy)picolinamide;

(S)-5-Cyclopropyl-N-(4-methyl-1-(methylamino)-1-oxopentan-2-yl)-6-((tetrahydro-2H-pyran-4-yl)methoxy)picolinamide;

2-(6-(Cyclopropylmethoxy)-5-(3,3-difluoroazetidin-1-yl)picolinamido)-2-ethylbutanoic acid;

(S)-6-(Cyclopropylmethoxy)-5-(3,3-difluoroazetidin-1-yl)-N-(3,3-dimethyl-1-(methylamino)-1-oxobutan-2-yl)picolinamide;

(S)-6-(Cyclopropylmethoxy)-5-(3,3-difluoroazetidin-1-yl)-N-(4,4-dimethyl-1-(methylamino)-1-oxopentan-2-yl)picolinamide;

(S)-N-(4-Methyl-1-(methylamino)-1-oxopentan-2-yl)-6-(3-(trifluoromethyl)phenyl)picolinamide;

(S)-N-(3,3-Dimethyl-1-(methylamino)-1-oxobutan-2-yl)-6-(3-(trifluoromethyl)phenyl)picolinamide;

(S)-5-Cyclopropyl-6-(cyclopropylmethoxy)-N-(2,2,2-trifluoro-1-(pyridin-3-yl)ethyl)picolinamide;

(R)-5-Cyclopropyl-6-(cyclopropylmethoxy)-N-(2,2,2-trifluoro-1-(pyridin-3-yl)ethyl)picolinamide;

5-Cyclopropyl-6-(tetrahydro-pyran-4-ylmethoxy)-pyridine-2-carboxylic acid [cyclopropyl-(5-methyl-[1,2,4]oxadiazol-3-yl)-methy]-amide;

2-({5-[Bis-(2,2,2-trifluoro-ethyl)-amino]-6-cyclopropylmethoxy-pyridine-2-carbonyl}-amino)-2-ethyl-butyric acid methyl ester;

6-Cyclopropylmethoxy-5-(3,3-difluoro-azetidin-1-yl)-pyridine-2-carboxylic acid [cyclopropyl-(5-methyl-[1,2,4]oxadiazol-3-yl)-methyl]-amide;

5-Cyclopropyl-6-cyclopropylmethoxy-pyridine-2-carboxylic acid ((S)-2-cyclopropyl-1-dimethylcarbamoyl-ethyl)-amide;

5-Cyclopropyl-6-(tetrahydro-pyran-4-ylmethoxy)-pyridine-2-carboxylic acid (2,2,2-trifluoro-1-pyridin-2-yl-ethyl)-amide;

6-Cyclopropylmethoxy-5-(3,3-difluoro-azetidin-1-yl)-pyridine-2-carboxylic acid (2,2,2-trifluoro-1-pyridin-2-yl-ethyl)-amide;

5-Cyclopropyl-6-cyclopropylmethoxy-pyridine-2-carboxylic acid ((−)-methylcarbamoyl-phenyl-methyl)-amide;

5-Cyclopropyl-6-cyclopropylmethoxy-pyridine-2-carboxylic acid ((+)-dimethylcarbamoyl-phenyl-methyl)-amide;

5-Cyclopropyl-6-cyclopropylmethoxy-pyridine-2-carboxylic acid ((−)-dimethylcarbamoyl-phenyl-methyl)-amide;

6-Cyclopropylmethoxy-5-trifluoromethyl-pyridine-2-carboxylic acid ((S)-3,3-dimethyl-1-methylcarbamoyl-butyl)-amide;

6-Cyclopropylmethoxy-5-trifluoromethyl-pyridine-2-carboxylic acid [cyclopropyl-(5-methyl-[1,2,4]oxadiazol-3-yl)-methyl]-amide;
6-(Tetrahydro-pyran-4-ylmethoxy)-5-trifluoromethyl-pyridine-2-carboxylic acid ((S)-3,3-dimethyl-1-methylcarbamoyl-butyl)-amide;
5-Cyclopropyl-6-cyclopropylmethoxy-pyridine-2-carboxylic acid ((S)-1-dimethylcarbamoyl-3-methyl-butyl)-amide;
2-{[5-Cyclopropyl-6-(tetrahydro-furan-2-ylmethoxy)-pyridine-2-carbonyl]-amino}-2-ethyl-butyric acid methyl ester;
6-Cyclopropylmethoxy-5-(6-oxa-1-aza-spiro[3.3]hept-1-yl)-pyridine-2-carboxylic acid ((S)-3,3-dimethyl-1-methylcarbamoyl-butyl)-amide;
6-Cyclopropylmethoxy-5-(6-oxa-1-aza-spiro[3.3]hept-1-yl)-pyridine-2-carboxylic acid [1-methyl-1-(5-methyl-[1,2,4]oxadiazol-3-yl)-ethyl]-amide;
6-Cyclopropylmethoxy-5-(6-oxa-1-aza-spiro[3.3]hept-1-yl)-pyridine-2-carboxylic acid [cyclopropyl-(5-methyl-[1,2,4]oxadiazol-3-yl)-methyl]-amide;
6-Cyclopropylmethoxy-5-(3,3-difluoro-azetidin-1-yl)-pyridine-2-carboxlic acid ((R)-2,2,2-trifluoro-1-pyridin-3-yl-ethyl)-amide;
2-Ethyl-2-{[6-(tetrahydro-pyran-4-ylmethoxy)-5-trifluoromethyl-pyridine-2-carbonyl]-amino}-butyric acid methyl ester;
(S)-2-[(5-Cyclopropyl-6-cyclopropylmethoxy-pyridine-2-carbonyl)-amino]-3,3-dimethyl-butyric acid methyl ester;
5-Cyclopropyl-6-cyclopropylmethoxy-pyridine-2-carboxylic acid ((S)-2,2,2-trifluoro-1-pyridin-2-yl-ethyl)-amide;
5-Cyclopropyl-6-cyclopropylmethoxy-pyridine-2-carboxylic acid [(−)-1-(5-methyl-[1,2,4]oxadiazol-3-yl)-ethyl]-amide;
5-Cyclopropyl-6-cyclopropylmethoxy-pyridine-2-carboxylic acid [(+)-3-methyl-1-(5-methyl-[1,2,4]oxadiazol-3-yl)-butyl]-amide;
5-Cyclopropyl-6-cyclopropylmethoxy-pyridine-2-carboxylic acid [(+)-3-methyl-1-(5-methyl-[1,2,4]oxadiazol-3-yl)-butyl]-amide;
5-Cyclopropyl-6-cyclopropylmethoxy-pyridine-2-carboxylic acid [(+)-1-(5-methyl-[1,2,4]oxadiazol-3-yl)-propyl]-amide;
5-Cyclopropyl-6-cyclopropylmethoxy-pyridine-2-carboxylic acid [(−)-1-(5-methyl-[1,2,4]oxadiazol-3-yl)-propyl]-amide;
5-Cyclopropyl-6-cyclopropylmethoxy-pyridine-2-carboxylic acid ((−)-cyano-methyl-methyl)-amide;
5-Cyclopropyl-6-cyclopropylmethoxy-pyridine-2-carboxylic acid ((−)-1-cyano-3-methyl-butyl)-amide;
5-Cyclopropyl-6-cyclopropylmethoxy-pyridine-2-carboxylic acid ((+)-cyano-cyclopropyl-methyl)-amide;
2-[(6-Cyclopropylmethoxy-5-trifluoromethyl-pyridine-2-carbonyl)-amino]-2-ethyl-butyric acid methyl ester;
5-Cyclopropyl-6-(tetrahydro-furan-2-ylmethoxy)-pyridine-2-carboxylic acid (1-ethyl-1-methylcarbamoyl-propyl)-amide;
2-[(5-Cyclopropyl-6-cyclopropylmethoxy-pyridine-2-carbonyl)-amino]-2-ethyl-butyric acid methyl ester;
2-[(6-Cyclopropylmethoxy-5-trifluoromethyl-pyridine-2-carbonyl)-amino]-2-ethyl-butyric acid;
6-(Tetrahydro-pyran-4-ylmethoxy)-5-trifluoromethyl-pyridine-2-carboxylic acid (1-ethyl-1-methylcarbamoyl-propyl)-amide;
2-Ethyl-2-{[6-(tetrahydro-furan-2-ylmethoxy)-5-trifluoromethyl-pyridine-2-carbonyl]-amino}-butyric acid ethyl ester;
6-Cyclopropylmethoxy-5-(3,3-difluoro-azetidin-1-yl)-pyridine-2-carboxylic acid (dimethylcarbamoyl-phenyl-methyl)-amide;
6-Cyclopropylmethoxy-5-(3,3-difluoro-azetidin-1-yl)-pyridine-2-carboxylic acid ((S)-2-cyclopropyl-1-dimethylcarbamoyl-ethyl)-amide;
2-[(5-Cyclopropyl-6-cyclopropylmethoxy-pyridine-2-carbonyl)-amino]-2-ethyl-butyric acid ethyl ester;
(S)-3-Cyclopropyl-2-[(5-cyclopropyl-6-cyclopropylmethoxy-pyridine-2-carbonyl)-amino]-propionic acid methyl ester;
6-Cyclopropylmethoxy-5-trifluoromethyl-pyridine-2-carboxylic acid (1-ethyl-1-methylcarbamoyl-propyl)-amide;
6-(Tetrahydro-pyran-4-ylmethoxy)-5-trifluoromethyl-pyridine-2-carboxylic acid (1-dimethylcarbamoyl-1-ethyl-propyl)-amide;
2-{[6-Cyclopropylmethoxy-5-(6-oxa-1-aza-spiro[3.3]hept-1-yl)-pyridine-2-carbonyl]amino}-2-ethyl-butyric acid ethyl ester;
6-(Tetrahydro-furan-2-ylmethoxy)-5-trifluoromethyl-pyridine-2-carboxylic acid (1-dimethylcarbamoyl-1-ethyl-propyl)-amide;
2-[(5-Bromo-6-cyclopropylmethoxy-pyridine-2-carbonyl)-amino]-2-ethyl-butyric acid ethyl ester;
2-{[6-Cyclopropylmethoxy-5-(3,3-difluoro-azetidin-1-yl)-pyridine-2-carbonyl]-amino}-2-ethyl-butyric acid ethyl ester;
2-{[6-Cyclopropylmethoxy-5-(3,3-difluoro-2-oxo-azetidin-1-yl)-pyridine-2-carbonyl]-amino}-2-ethyl-butyric acid methyl ester;
(S)-2-[(5-Cyclopropyl-6-cyclopropylmethoxy-pyridine-2-carbonyl)-amino]-4-methyl-pentanoic acid methyl ester;
6-Cyclopropylmethoxy-5-(3,3-difluoro-azetidin-1-yl)-pyridine-2-carboxylic acid (1-cyano-3-methyl-butyl)-amide;
6-Cyclopropylmethoxy-5-(3,3-difluoro-azetidin-1-yl)-pyridine-2-carboxylic acid [3-methyl-1-(5-methyl-[1,2,4]oxadiazol-3-yl)-butyl]-amide;
6-Cyclopropylmethoxy-5-(3,3-difluoro-azetidin-1-yl)-pyridine-2-carboxylic acid (1-hydroxymethyl-1,3-dimethyl-butyl)-amide;
5-Cyclopropyl-6-cyclopropylmethoxy-pyridine-2-carboxylic acid [1-(azetidine-1-carbonyl)-1-ethyl-propyl]-amide;
5-Cyclopropyl-6-cyclopropylmethoxy-pyridine-2-carboxylic acid [1-ethyl-1-(2-methoxy-ethylcarbamoyl)-propyl]-amide;
5-Cyclopropyl-6-cyclopropylmethoxy-pyridine-2-carboxylic acid [1-ethyl-1-(ethyl-methyl-carbamoyl)-propyl]-amide;
6-(4-Fluoro-benzyl)-pyridine-2-carboxylic acid ((S)-1-carbamoyl-3-methyl-butyl)-amide;
6-(4-Fluoro-benzyl)-pyridine-2-carboxylic acid ((R)-2,2,2-trifluoro-1-pyridin-2-yl-ethyl)-amide;
5-Cyclopropyl-6-cyclopropylmethoxy-pyridine-2-carboxylic acid ((S)-1-hydroxymethyl-1,2-dimethyl-propyl)-amide;
5-Bromo-6-(3-methyl-oxetan-3-ylmethoxy)-pyridine-2-carboxylic acid (1-methyl-1-thiazol-2-yl-ethyl)-amide;
5-Bromo-6-(3-methyl-oxetan-3-ylmethoxy)-pyridine-2-carboxylic acid (3-thiazol-2-yl-oxetan-3-yl)-amide;

5-Bromo-6-(2,2,2-trifluoro-ethoxy)-pyridine-2-carboxylic acid (3-thiazol-2-yl-oxetan-3-yl)-amide;
5-Bromo-6-(3-methyl-oxetan-3-ylmethoxy)-pyridine-2-carboxylic acid (2,2,2-trifluoro-1-pyridin-2-yl-ethyl)-amide;
5-Cyclopropyl-6-cyclopropylmethoxy-pyridine-2-carboxylic acid [1-(cyclopropylmethyl-carbamoyl)-1-ethyl-propyl]-amide;
5-Cyclopropyl-6-cyclopropylmethoxy-pyridine-2-carboxylic acid (1-methyl-1-pyridin-2-yl-ethyl)-amide;
6-(4-Fluoro-benzyl)-pyridine-2-carboxylic acid ((S)-3,3-dimethyl-1-methylcarbamoyl-butyl)-amide;
5-Cyclopropyl-6-cyclopropylmethoxy-pyridine-2-carboxylic acid [1-(3,3-difluoro-azetidine-1-carbonyl)-1-ethyl-propyl]-amide;
2-[(6-Cyclopropylmethoxy-5-pyrrolidin-1-yl-pyridine-2-carbonyl)-amino]-2-ethyl-butyric acid ethyl ester;
6-Cyclopropylmethoxy-5-(3,3-difluoro-azetidin-1-yl)-pyridine-2-carboxylic acid (1-methyl-5-oxo-pyrrolidin-3-yl)-amide;
2[(6-Cyclopropylmethoxy-5-pyrrolidin-1-yl-pyridine-2-carbonyl)-amino]-2-ethyl-butyric acid;
6-Cyclopropylmethoxy-5-(3,3-difluoro-azetidin-1-yl)-pyridine-2-carboxylic acid (1,1-dioxo-tetrahydro-1$\lambda^6$-thiophen-3-yl)-amide;
6-Cyclopropylmethoxy-5-(3,3-difluoro-azetidin-1-yl)-pyridine-2-carboxylic acid N'-(1,1-dioxo-tetrahydro-1$\lambda^6$-thiophen-3-yl)-hydrazide;
5-Cyclopropyl-6-cyclopropylmethoxy-pyridine-2-carboxylic acid [1-methyl-1-(4-methyl-thiazol-2-yl)-ethyl]-amide;
5-Cyclopropyl-6-cyclopropylmethoxy-pyridine-2-carboxylic acid [1-(5-amino-[1,2,4]oxadiazol-3-yl)-1-methyl-ethyl]-amide;
6-(2,2,3,3,3-Pentafluoro-propoxy)-pyridine-2-carboxylic acid (1-ethyl-1-methylcarbamoyl-propyl)-amide;
5-Cyclopropyl-6-(2,2,3,3,3-pentafluoro-propoxy)-pyridine-2-carboxylic acid (1-ethyl-1-methylcarbamoyl-propyl)-amide;
5-Cyclopropyl-6-(2,2,3,3,3-pentafluoro-propoxy)-pyridine-2-carboxylic acid ((S)-3,3-dimethyl-1-methylcarbamoyl-butyl)-amide;
5-Cyclopropyl-6-(2,2,3,3,3-pentafluoro-propoxy)-pyridine-2-carboxylic acid [(S)-2-cyclopropyl-1-(5-methyl-[1,2,4]oxadiazol-3-yl)-ethyl]-amide;
5-Cyclopropyl-6-(2,2,2-trifluoro-ethoxy)-pyridine-2-carboxylic acid ((S)-carbamoyl-phenyl-methyl)-amide;
5-Cyclopropyl-6-(2,2,2-trifluoro-ethoxy)-pyridine-2-carboxylic acid (2,2,2-trifluoro-1-pyridin-2-yl-ethyl)-amide;
5-Cyclopropyl-6-(2,2,2-trifluoro-ethoxy)-pyridine-2-carboxylic acid ((S)-1-hydroxymethyl-3-methyl-butyl)-amide;
5-Cyclopropyl-6-(2,2,2-trifluoro-ethoxy)-pyridine-2-carboxylic acid (3-thiazol-2-yl-oxetan-3-yl)-amide;
5-Cyclopropyl-6-(2,2,2-trifluoro-ethoxy)-pyridine-2-carboxylic acid (1-methyl-1-thiazol-2-yl-ethyl)-amide;
5-Cyclopropyl-6-(2,2,2-trifluoro-ethoxy)-pyridine-2-carboxylic acid (2,2-dimethyl-1-thiazol-2-yl-propyl)-amide;
6-Cyclopropylmethoxy-5-(3,3-difluoro-azetidin-1-yl)-pyridine-2-carboxylic acid [1-(3,3-difluoro-azetidine-1-carbonyl)-1-ethyl-propyl]-amide;
6-(4-Fluoro-benzyl)-pyridine-2-carboxylic acid N'-(1,1-dioxo-tetrahydro-1$\lambda^6$-thiophen-3-yl)-hydrazide;
5-Cyclopropyl-6-cyclopropylmethoxy-pyridine-2-carboxylic acid [1-(3-amino-[1,2,4]oxadiazol-5-yl)-1-methyl-ethyl]-amide;
6-Cyclopropylmethoxy-5-(3,3-difluoro-azetidin-1-yl)-pyridine-2-carboxylic acid [(S)-1-(3,3-difluoro-azetidine-1-carbonyl)-2,2-dimethyl-propyl]-amide;
6-Cyclopropylmethoxy-5-(3,3-difluoro-azetidin-1-yl)-pyridine-2-carboxylic acid [(S)-1-(3,3-difluoro-azetidine-1-carbonyl)-3-methyl-butyl]-amide;
2-[(6-Cyclopropylmethoxy-5-trifluoromethyl-pyridine-2-carbonyl)-amino]-2-ethyl-butyric acid ethyl ester;
5-Cyclopropyl-6-((R)-3-hydroxy-1-trifluoromethyl-propoxy)-pyridine-2-carboxylic acid (1-ethyl-1-methylcarbamoyl-propyl)-amide;
5-Cyclopropyl-6-((R)-4,4,4-trifluoro-3-hydroxy-butoxy)-pyridine-2-carboxylic acid (1-ethyl-1-methylcarbamoyl-propyl)-amide;
6-Cyclopropylmethoxy-5-(3,3-difluoro-azetidin-1-yl)-pyridine-2-carboxylic acid (3-methyl-1-pyridin-2-yl-butyl)-amide;
6-Cyclopropylmethoxy-5-trifluoromethyl-pyridine-2-carboxylic acid [1-(3,3-difluoro-azetidine-1-carbonyl)-1-ethyl-propyl]-amide;
6-[(4-Fluoro-phenyl)-hydroxy-methyl]-pyridine-2-carboxylic acid ((S)-1-carbamoyl-3-methyl-butyl)-amide;
6-[(4-Fluoro-phenyl)-hydroxy-methyl]-pyridine-2-carboxylic acid [(S)-3-methyl-1-(5-methyl-[1,2,4]oxadiazol-3-yl)-butyl]-amide;
5-Cyclopropyl-6-((S)-3-hydroxy-1-trifluoromethyl-propoxy)-pyridine-2-carboxylic acid (1-ethyl-1-methylcarbamoyl-propyl)-amide;
5-Cyclopropyl-6-((S)-4,4,4-trifluoro-3-hydroxy-butoxy)-pyridine-2-carboxylic acid (1-ethyl-1-methylcarbamoyl-propyl)-amide;
6-Cyclopropylmethoxy-5-(3,3-difluoro-azetidin-1-yl)-pyridine-2-carboxylic acid (3-methyl-1-pyridazin-3-yl-butyl)-amide;
6-Cyclopropylmethoxy-5-(3-oxo-azetidin-1-yl)-pyridine-2-carboxylic acid [1-methyl-1-(5-methyl-[1,2,4]oxadiazol-3-yl)-ethyl]amide;
5-Cyclopropyl-6-cyclopropylmethoxy-pyridine-2-carboxylic acid [(+)-1-cyclopropyl-1-(5-methyl-[1,2,4]oxadiazol-3-yl)-ethyl]-amide;
5-Cyclopropyl-6-cyclopropylmethoxy-pyridine-2-carboxylic acid [(−)-1-cyclopropyl-1-(5-methyl-[1,2,4]oxadiazol-3-yl)-ethyl]amide;
6-Cyclopropylmethoxy-5-(3,3-difluoro-azetidin-1-yl)-pyridine-2-carboxylic acid (3-methyl-1-pyridin-3-yl-butyl)-amide;
5-Cyclopropyl-6-(4-fluoro-benzyl)-pyridine-2-carboxylic acid ((S)-1-carbamoyl-2-cyclopropyl-ethyl)-amide;
5-Cyclopropyl-6-(4-fluoro-benzyl)-pyridine-2-carboxylic acid [(S)-2-cyclopropyl-1-(5-methyl-[1,2,4]oxadiazol-3-yl)-ethyl]-amide;
5-Cyclopropyl-6-cyclopropylmethoxy-pyridine-2-carboxylic acid [(S)-carbamoyl-(4-fluoro-phenyl)-methyl]-amide;
5-Cyclopropyl-6-cyclopropylmethoxy-pyridine-2-carboxylic acid [(S)-carbamoyl-(4-chloro-phenyl)-methyl]-amide;
6-(2-Methyl-propane-1-sulfonyl)-pyridine-2-carboxylic acid ((S)-1-carbamoyl-3-methyl-butyl)-amide;
6-Isobutylsulfanyl-pyridine-2-carboxylic acid ((S)-1-carbamoyl-3-methyl-butyl)-amide;
5-Cyclopropyl-6-(4-fluoro-benzyl)-pyridine-2-carboxylic acid ((S)-2,2,2-trifluoro-1-pyridin-2-yl-ethyl)-amide;

2-{[5-Cyclopropyl-6-(4-fluoro-benzyl)-pyridine-2-carbonyl]-amino}-2-ethyl-butyric acid;

6-Cyclopropylmethoxy-5-(3-oxo-pyrrolidin-1-yl)-pyridine-2-carboxylic acid [1-methyl-1-(5-methyl-[1,2,4]oxadiazol-3-yl)-ethyl]-amide, 6-(2-Methyl-propane-1-sulfonyl)-pyridine-2-carboxylic acid [(S)-3-methyl-1-(5-methyl-[1,2,4]oxadiazol-3-yl)-butyl]-amide;

(S)-2-{[5-Cyclopropyl-6-(4-fluoro-benzyl)-pyridine-2-carbonyl]-amino}-4-methyl-pentanoic acid;

2-{[5-Cyclopropyl-6-(tetrahydro-pyran-4-ylmethoxy)-pyridine-2-carbonyl]-amino}-2-ethyl-butyric acid;

5-Cyclopropyl-6-cyclopropylmethoxy-pyridine-2-carboxylic acid [1-methyl-1-(4-methyl-5-oxo-4,5-dihydro-[1,2,4]oxadiazol-3-yl)-ethyl]-amide;

6-Cyclopropylmethoxy-5-(3,3-difluoro-azetidin-1-yl)-pyridine-2-carboxylic acid (3-methyl-1-pyrimidin-2-yl-butyl)-amide;

6-Cyclopropylmethoxy-5-(3,3-difluoro-azetidin-1-yl)-pyridine-2-carboxylic acid [1-cyclopropyl-1-(5-methyl-[1,2,4]oxadiazol-3-yl)-ethyl]-amide;

6-Cyclopropylmethoxy-5-(3,3-difluoro-azetidin-1-yl)-pyridine-2-carboxylic acid [2-cyclopropyl-1-methyl-1-(5-methyl-[1,2,4]oxadiazol-3-yl)-ethyl]-amide;

6-Cyclopropylmethoxy-5-(3,3-difluoro-azetidin-1-yl)-pyridine-2-carboxylic acid ((S)-1-carbamoyl-3-methylsulfanyl-propyl)-amide;

6-Cyclopropylmethoxy-5-pyrrolidin-1-yl-pyridine-2-carboxylic acid {(S)-3-methyl-1-[(7-nitro-benzo[1,2,5]oxadiazol-4-ylamino)-methyl]-butyl}-amide;

6-Cyclopropylmethoxy-5-(3,3-difluoro-azetidin-1-yl)-pyridine-2-carboxylic acid ((S)-1-carbamoyl-3-methanesulfonyl-propyl)-amide;

5-Cyclopropyl-6-isobutylsulfanyl-pyridine-2-carboxylic acid ((S)-1-carbamoyl-3-methyl-butyl)-amide;

6-(4-Fluoro-3-trifluoromethyl-phenyl)-pyridine-2-carboxylic acid [(S)-2-cyclopropyl-1-(5-methyl-[1,2,4]oxadiazol-3-yl)-ethyl]-amide;

5-Cyclopropyl-6-cyclopropylmethoxy-pyridine-2-carboxylic acid (3-methanesulfonyl-1,1-dimethyl-propyl)-amide;

5-Cyclopropyl-6-cyclopropylmethoxy-pyridine-2-carboxylic acid [1-methyl-1-(5-methyl-thiazol-2-yl)-ethyl]-amide;

5-Cyclopropyl-6-(2-methyl-propane-1-sulfonyl)-pyridine-2-carboxylic acid ((S)-1-carbamoyl-3-methyl-butyl)-amide;

5-Cyclopropyl-6-(2-methyl-propane-1-sulfonyl)-pyridine-2-carboxylic acid [(S)-2-cyclopropyl-1-(5-methyl-[1,2,4]oxadiazol-3-yl)-ethyl]-amide;

6-Cyclopropylmethoxy-5-(3,3-difluoro-azetidin-1-yl)-pyridine-2-carboxylic acid [1-methyl-1-(5-methyl-thiazol-2-yl)-ethyl]-amide;

6-Cyclopropylmethoxy-5-(3,3-difluoro-azetidin-1-yl)-pyridine-2-carboxylic acid ((R)-3-methyl-1-pyridazin-3-yl-butyl)-amide;

6-Cyclopropylmethoxy-5-(3,3-difluoro-azetidin-1-yl)-pyridine-2-carboxylic acid ((S)-3-methyl-1-pyridazin-3-yl-butyl)-amide;

5-Cyclopropyl-6-cyclopropylmethoxy-pyridine-2-carboxylic acid [1-ethyl-1-(2-hydroxy-ethylcarbamoyl)-propyl]-amide;

5-Cyclopropyl-6-cyclopropylmethoxy-pyridine-2-carboxylic acid [(+)-cyclopropyl-1-methyl-1-(5-methyl-[1,2,4]oxadiazol-3-yl)-ethyl]-amide;

5-Cyclopropyl-6-cyclopropylmethoxy-pyridine-2-carboxylic acid [(−)-2-cyclopropyl-1-methyl-1-(5-methyl-[1,2,4]oxadiazol-3-yl)-ethyl]-amide;

6-Cyclopropylmethoxy-5-(3,3-difluoro-azetidin-1-yl)-pyridine-2-carboxylic acid tert-butylamide;

2-{[5-Cyclopropyl-6-(2-methyl-propane-1-sulfonyl)-pyridine-2-carbonyl]-amino}-2-ethyl-butyric acid ethyl ester;

5-Cyclopropyl-6-(2-methyl-propane-1-sulfonyl)-pyridine-2-carboxylic acid ((S)-3,3-dimethyl-1-methylcarbamoyl-butyl)-amide;

5-Cyclopropyl-6-cyclopropylmethoxy-pyridine-2-carboxylic acid ((S)-2-oxo-tetrahydro-furan-3-yl)-amide;

N'-(5-Cyclopropyl-6-cyclopropylmethoxy-pyridine-2-carbonyl)-N-cyclopropylmethyl-hydrazinecarboxylic acid tert-butyl ester;

5-Cyclopropyl-6-(2-methyl-propane-1-sulfonyl)-pyridine-2-carboxylic acid ((S)-2,2-dimethyl-1-methylcarbamoyl-propyl)-amide;

5-Cyclopropyl-6-(2-methyl-propane-1-sulfonyl)-pyridine-2-carboxylic acid ((S)-2,2,2-trifluoro-1-pyridin-3-yl-ethyl)-amide;

(S)-2-[(5-Cyclopropyl-6-cyclopropylmethoxy-pyridine-2-carbonyl)-amino]-4-methyl-pentanoic acid tert-butyl ester;

5-Cyclopropyl-6-(2-methyl-propane-1-sulfonyl)-pyridine-2-carboxylic acid (1-ethyl-1-methylcarbamoyl-propyl)-amide;

5-Cyclopropyl-6-cyclopropylmethoxy-pyridine-2-carboxylic acid tert-butylamide;

5-Cyclopropyl-6-(tetrahydro-furan-2-ylmethoxy)-pyridine-2-carboxylic acid tert-butylamide;

6-Cyclopropylmethoxy-5-(3,3-difluoro-azetidin-1-yl)-pyridine-2-carboxylic acid (3-methyl-oxetan-3-yl)-amide;

5-Cyclopropyl-6-cyclopropylmethoxy-pyridine-2-carboxylic acid (2-oxo[1,3]oxazinan-3-yl)-amide;

5-Cyclopropyl-6-(2,2,2-trifluoro-1-methyl-ethoxy)-pyridine-2-carboxylic acid ((S)-1-carbamoyl-3methyl-butyl)-amide;

5-Cyclopropyl-6-(2,2,2-trifluoro-1-methyl-ethoxy)-pyridine-2-carboxylic acid [1-methyl-1(5-methyl-[1,2,4]oxadiazol-3-yl)-ethyl]-amide;

5-Cyclopropyl-6-cyclopropylmethoxy-pyridine-2-carboxylic acid ((+)-carbamoyl-cyclopropyl-methyl)-amide;

5-Cyclopropyl-6-cyclopropylmethoxy-pyridine-2-carboxylic acid ((−)-carbamoyl-cyclopropyl-methyl)-amide;

6-Cyclopropylmethoxy-5-(3,3-difluoro-azetidin-1-yl)-pyridine-2-carboxylic acid ((+)-carbamoyl-cyclopropyl-methyl)-amide;

6-Cyclopropylmethoxy-5-(3,3-difluoro-azetidin-1-yl)-pyridine-2-carboxylic acid ((−)-carbamoyl-cyclopropyl-methyl)-amide;

6-Cyclopropylmethoxy-5-(3,3-difluoro-azetidin-1-yl)-pyridine-2-carboxylic acid (1-trifluoromethyl-cyclopropyl)-amide;

(+)-5-Cyclopropyl-6-cyclopropylmethoxy-pyridine-2-carboxylic acid [(S)-2-cyclopropyl-1-(3-hydroxy-pyrrolidin-1-ylcarbamoyl)-ethyl]-amide;

(−)-5-Cyclopropyl-6-cyclopropylmethoxy-pyridine-2-carboxylic acid [(S)-2-cyclopropyl-1-(3-hydroxy-pyrrolidin-1-ylcarbamoyl)-ethyl]-amide;

(+)-5-Cyclopropyl-6-(2-methyl-propane-1-sulfonyl)-pyridine-2-carboxylic acid [1-cyclopropyl-1-(5-methyl-[1,2,4]oxadiazol-3-yl)-ethyl]-amide; and (−)-5-Cyclopropyl-6-(2-methyl-propane-1-sulfonyl)-pyridine-2-carboxylic acid [1-cyclopropyl-1-(5-methyl-[1,2,4]oxadiazol-3-yl)-ethyl]-amide.

2. A compound selected from the group consisting of:
6-Cyclopropylrnethoxy-5-(tetrahydro-pyran-4-yl)-pyridine-2-carboxylic acid [1-methyl-1-(5-methyl-[1,2,4]oxadiazol-3-yl)-ethyl]-amide;
6-Cyclopropylmethoxy-5-pyrrolidin-1-yl-pyridine-2-carboxylic acid ((S)-1-hydroxymethyl-3-methyl-butyl)-amide;
6-Cyclopropylmethoxy-5-(2-methyl-pyrrolidin-1-yl)-pyridine-2-carboxylic acid ((S)-1-carbamoyl-3-methyl-butyl)-amide;
6-Cyclopropylmethoxy-5-pyrrolidin-1-yl-pyridine-2-carboxylic acid (1,1-dimethyl-3-morpholin-4-yl-propyl)-amide;
5-Cyclopentyl-6-cyclopropylmethoxy-pyridine-2-carboxylic acid (1-methyl-1-methylcarbamoyl-ethyl)-amide;
5-Cyclopropyl-6-cyclopropylmethoxy-pyridine-2-carboxylic acid (1-methyl-1-thiazol-2-yl-ethyl)-amide;
5-Cyclopentyl-6-cyclopropylmethoxy-pyridine-2-carboxylic acid [(S)-2-cyclopropyl-1-(5-methyl-[1,2,4]oxadiazol-3-yl)-ethyl]-amide;
6-Cyclopropylmethoxy-5-methyl-pyridine-2-carboxylic acid ((S)-3-methyl-1-thiazol-2-yl-butyl)-amide;
6-Cyclopropylmethoxy-5-(3,3-difluoro-azetidin-1-yl)-pyridine-2-carboxylic acid (1-methyl-1-thiazol-2-yl-ethyl)-amide;
6-Cyclopropylmethoxy-5-(3,3-difluoro-pyrrolidin-1-yl)-pyridine-2-carboxylic acid (1-ethyl-1-methylcarbamoyl-propyl)-amide;
6-Cyclopropylmethoxy-5-(3,3-difluoro-azetidin-1-yl)-pyridine-2-carboxylic acid (1-ethyl-1-methylcarbamoyl-propyl)-amide;
5-Cyclopropyl-6-cyclopropylmethoxy-pyridine-2-carboxylic acid ((S)-1-carbamoyl-2-cyclopropyl-ethyl)-amide;
5-Cyclopropyl-6-cyclopropylmethoxy-pyridine-2-carboxylic acid ((S)-1-carbamoyl-3-methyl-butyl)-amide;
6-Cyclopropylmethoxy-5-(3,3-difluoro-azetidin-1-yl)-pyridine-2-carboxylic acid ((S)-1-carbamoyl-2-cyclopropyl-ethyl)-amide;
6-Cyclopropylmethoxy-5-(3,3-difluoro-pyrrolidin-1-yl)-pyridine-2-carboxylic acid ((S)-1-carbamoyl-2-cyclopropyl-ethyl)-amide;
6-Cyclopropylmethoxy-5-(tetrahydro-furan-3-yl)-pyridine-2-carboxylic acid ((S)-1-carbamoyl-3-methyl-butyl)-amide;
6-Cyclopropylmethoxy-5-(tetrahydro-furan-2-yl)-pyridine-2-carboxylic acid ((S)-1-carbamoyl-3-methyl-butyl)-amide;
6-Cyclopropylmethoxy-5-trifluoromethyl-pyridine-2-carboxylic acid ((S)-1-carbamoyl-3-methyl-butyl)-amide;
6-Cyclopropylmethoxy-5-(tetrahydro-furan-2-yl)-pyridine-2-carboxylic acid [1-methyl-1-(5-methyl-[1,2,4]oxadiazol-3-yl)-ethyl]-amide;
6-Cyclopropylmethoxy-5-(3,3-difluoro-azetidin-1-yl)-pyridine-2-carboxylic acid ((S)-1-carbamoyl-3-methyl-butyl)-amide;
5-Cyclopropylamino-6-cyclopropylmethoxy-pyridine-2-carboxylic acid ((S)-1-carbamoyl-3-methyl-butyl)-amide;
6-Cyclopropylmethoxy-5-(3,3-difluoro-azetidin-1-yl)-pyridine-2-carboxylic acid ((S)-1-cyclopropyl-2-hydroxy-2-methyl-propyl)-amide;
6-Cyclopropylmethoxy-5-(3,3-difluoro-azetidin-1-yl)-pyridine-2-carboxylic acid ((S)-2-cyclopropyl-1-thiazol-2-yl-ethyl)-amide;
5-Cyclopropyl-6-(4-fluoro-benzyl)-pyridine-2-carboxylic acid ((S)-1-carbamoyl-3-methyl-butyl)-amide;
6-Cyclopropylmethoxy-5-(3,3-difluoro-azetidin-1-yl)-pyridine-2-carboxylic acid [(S)-2-cyclopropyl-1-(2-methoxy-ethoxymethyl)-ethyl]amide;
5-Cyclopropyl-6-cyclopropylmethoxy-pyridine-2-carboxylic acid [(S)-2-cyclopropyl-1-(5-methyl-[1,2,4]oxadiazol-3-yl)-ethyl]amide;
5-[Bis-(2,2,2-trifluoro-ethyl)-amino]-6-cyclopropylmethoxy-pyridine-2-carboxylic acid (1-ethyl-1-methylcarbamoyl-propyl)-amide;
(S)-5-Cyclopropyl-6-(cyclopropylmethoxy)-N-(3,3-dimethyl-1-(methylamino)-1-oxobutan-2-yl)picolinamide;
(S)-N-(2-amino-2-oxo-1-phenylethyl)-5-cyclopropyl-6-(cyclopropylmethoxy)picolinamide;
N-((S)-1-amino-4-methyl-1-oxopentan-2-yl)-5-cyclopropyl-6-((tetrahydrofuran-2-yl)methoxy)picolinamide;
5-Cyclopropyl-6-cyclopropylmethoxy-pyridine-2-carboxylic acid ((R)-1-hydroxymethyl-1,2-dimethyl-propyl)-amide;
(S)-5-Cyclopropyl-N-(4,4-dimethyl-1-(methylamino)-1-oxopentan-2-yl)-6-((tetrahydro-2H-pyran-4-yl)methoxy)picolinamide;
(+)-5-Cyclopropyl-6-cyclopropylmethoxy-pyridine-2-carboxylic acid [(SR)-cyclopropyl-(5-methyl-[1,2,4]oxadiazol-3-yl)-methyl]-amide;
2-(6-(Cyclopropylmethoxy)-5-(3,3-difluoroazetidin-1-yl)picolinamido)-2-ethylbutanoic acid;
5-Cyclopropyl-6-(tetrahydro-pyran-4-ylmethoxy)-pyridine-2-carboxylic acid [cyclopropyl-(5-methyl-[1,2,4]oxadiazol-3-yl)-methyl]-amide;
5-Cyclopropyl-6-cyclopropylmethoxy-pyridine-2-carboxylic acid ((S)-2-cyclopropyl-1-dimethylcarbamoyl-ethyl)-amide;
5-Cyclopropyl-6-cyclopropylmethoxy-pyridine-2-carboxylic acid ((+)-dimethylcarbamoyl-phenyl-methyl)-amide;
6-Cyclopropylmethoxy-5-trifluoromethyl-pyridine-2-carboxylic acid ((S)-3,3-dimethyl-1-methylcarbamoyl-butyl)-amide;
2-{[5-Cyclopropyl-6-(tetrahydro-furan-2-ylmethoxy)-pyridine-2-carbonyl]-amino}-2-ethyl-butyric acid methyl ester;
6-Cyclopropylmethoxy-5-(6-oxa-1-aza-spiro[3.3]hept-1-yl)-pyridine-2-carboxylic acid ((S)-3,3-dimethyl-1-methylcarbamoyl-butyl)-amide;
2-Ethyl-2-{[6-(tetrahydro-pyran-4-ylmethoxy)-5-trifluoromethyl-pyridine-2-carbonyl]-amino}-butyric acid methyl ester;
(S)-2-[(5-Cyclopropyl-6-cyclopropylmethoxy-pyridine-2-carbonyl)-amino]-3,3-dimethyl-butyric acid methyl ester;
5-Cyclopropyl-6-cyclopropylmethoxy-pyridine-2-carboxylic acid [(+)-1-(5-methyl-[1,2,4]oxadiazol-3-yl)-butyl]amide;
5-Cyclopropyl-6-cyclopropylmethoxy-pyridine-2-carboxylic acid ((−)-1-cyano-3-methyl-butyl)-amide;
+(S)-3-Cyclopropyl-2-[(5-cyclopropyl-6-cyclopropylmethoxy-pyridine-2-carbonyl)-amino]-propionic acid methyl ester;
6-Cyclopropylmethoxy-5-trifluoromethyl-pyridine-2-carboxylic acid (1-ethyl-1-methylcarbamoyl-propyl)-amide;

6-Cyclopropylmethoxy-5-(3,3-difluoro-azetidin-1-yl)-pyridine-2-carboxylic acid (1-hydroxymethyl-1,3-dimethyl-butyl)-amide;

5-Cyclopropyl-6-cyclopropylmethoxy-pyridine-2-carboxylic acid [1-ethyl-1-(ethyl-methyl-carbamoyl)-propyl]-amide;

6-(4-Fluoro-benzyl)-pyridine-2-carboxylic acid ((R)-2,2,2-trifluoro-1-pyridin-2-yl-ethyl)-amide;

5-Cyclopropyl-6-cyclopropylmethoxy-pyridine-2-carboxylic acid ((S)-1-hydroxymethyl-1,2-dimethyl-propyl)-amide;

5-Cyclopropyl-6-cyclopropylmethoxy-pyridine-2-carboxylic acid [1-(3,3-difluoro-azetidine-1-carbonyl)-1-ethyl-propyl]-amide;

5-Cyclopropyl-6-(2,2,3,3,3-pentafluoro-propoxy)-pyridine-2-carboxylic acid (1-ethyl-1-methylcarbamoyl-propyl)-amide;

5-Cyclopropyl-6-(2,2,3,3,3-pentafluoro-propoxy)-pyridine-2-carboxylic acid ((S)-3,3-dimethyl-1-methylcarbamoyl-butyl)-amide;

6-Cyclopropylmethoxy-5-(3,3-difluoro-azetidin-1-yl)-pyridine-2-carboxylic acid [1-(3,3-difluoro-azetidine-1-carbonyl)-1-ethyl-propyl]-amide;

5-Cyclopropyl-6-((R)-4,4,4-trifluoro-3-hydroxy-butoxy)-pyridine-2-carboxylic acid (1-ethyl-1-methylcarbamoyl-propyl)-amide;

6-Cyclopropylmethoxy-5-trifluoromethyl-pyridine-2-carboxylic acid [1-(3,3-difluoro-azetidine-1-carbonyl)-1-ethyl-propyl]-amide;

6-[(4-Fluoro-phenyl)-hydroxy-methyl]-pyridine-2-carboxylic acid ((S)-1-carbamoyl-3-methyl-butyl)-amide;

5-Cyclopropyl-6-((S)-4,4,4-trifluoro-3-hydroxy-butoxy)-pyridine-2-carboxylic acid (1-ethyl-1-methylcarbamoyl-propyl)-amide;

5-Cyclopropyl-6-cyclopropylmethoxy-pyridine-2-carboxylic acid [(+)-1-cyclopropyl-1-(5-methyl-[1,2,4]oxadiazol-3-yl)-ethyl]amide;

6-Cyclopropylmethoxy-5-(3,3-difluoro-azetidin-1-yl)-pyridine-2-carboxylic acid (3-methyl-1-pyridin-3-yl-butyl)-amide;

5-Cyclopropyl-6-(4-fluoro-benzyl)-pyridine-2-carboxylic acid ((S)-1-carbamoyl-2-cyclopropyl-ethyl)-amide;

5-Cyclopropyl-6-cyclopropylmethoxy-pyridine-2-carboxylic acid [(S)-carbamoyl-(4-fluoro-phenyl)-methyl]-amide;

5-Cyclopropyl-6-(4-fluoro-benzyl)-pyridine-2-carboxylic acid ((S)-2,2,2-trifluoro-1-pyridin-2-yl-ethyl)-amide;

6-Cyclopropylmethoxy-5-(3,3-difluoro-azetidin-1-yl)-pyridine-2-carboxylic acid [1-cyclopropyl-1-(5-methyl-[1,2,4]oxadiazol-3-yl)-ethyl]-amide;

6-Cyclopropylmethoxy-5-(3,3-difluoro-azetidin-1-yl)-pyridine-2-carboxylic acid [2-cyclopropyl-1-methyl-1-(5-methyl-[1,2,4]oxadiazol-3-yl)-ethyl]amide;

6-(3-Chloro-4-fluoro-phenyl)-pyridine-2-carboxylic acid [(S)-2-cyclopropyl-1-(5-methyl-[1,2,4]oxadiazol-3-yl)-ethyl]-amide;

6-Cyclopropylmethoxy-5-pyrrolidin-1-yl-pyridine-2-carboxylic acid {(S)-3-methyl-1-[(7-nitro-benzo[1,2,5]oxadiazol-4-ylamino)-methyl]-butyl}-amide;

5-Cyclopropyl-6-isobutylsulfanyl-pyridine-2-carboxylic acid ((S)-1-carbamoyl-3-methyl-butyl)-amide;

5-Cyclopropyl-6-(2-methyl-propane-1-sulfonyl)-pyridine-2-carboxylic acid ((S)-1-carbamoyl-3-methyl-butyl)-amide;

6-Cyclopropylmethoxy-5-(3,3-difluoro-azetidin-1-yl)-pyridine-2-carboxylic acid [1-methyl-1-(5-methyl-thiazol-2-yl)-ethyl]-amide;

6-Cyclopropylmethoxy-5-(3,3-difluoro-azetidin-1-yl)-pyridine-2-carboxylic acid ((R)-3-methyl-1-pyridazin-3-yl-butyl)-amide;

5-Cyclopropyl-6-cyclopropylmethoxy-pyridine-2-carboxylic acid [(+)-2-cyclopropyl-1-methyl-1-(5-methyl-[1,2,4]oxadiazol-3-yl)-ethyl]-amide;

5-Cyclopropyl-6-cyclopropylmethoxy-pyridine-2-carboxylic acid [(−)-2-cyclopropyl-1-methyl-1-(5-methyl-[1,2,4]oxadiazol-3-yl)-ethyl]amide;

6-Cyclopropylmethoxy-5-(3,3-difluoro-azetidin-1-yl)-pyridine-2-carboxylic acid tert-butylamide;

5-Cyclopropyl-6-(2-methyl-propane-1-sulfonyl)-pyridine-2-carboxylic acid ((S)-2,2,2-trifluoro-1-pyridine-3-yl-ethyl)-amide;

5-Cyclopropyl-6-cyclopropylmethoxy-pyridine-2-carboxylic acid ((+)-carbamoyl-cyclopropyl-methyl)-amide;

6-Cyclopropylmethoxy-5-(3,3-difluoro-azetidin-1-yl)-pyridine-2-carboxylic acid (1-trifluoromethyl-cyclopropyl)-amide; and (+)-5-Cyclopropyl-6-(2-methyl-propane-1-sulfonyl)-pyridine-2-carboxylic acid [1-cyclopropyl-1-(5-methyl-[1,2,4]oxadiazol-3-yl)-ethyl]-amide.

3. A compound selected from the group consisting of:

2-[(6-Cyclohexyl-pyridine-2-carbonyl)-amino]-2-methyl-propionic acid methyl ester;

2-{[6-Cyclopropylmethoxy-5-(tetrahydro-pyran-4-yl)-pyridine-2-carbonyl]-amino}-2-methyl-propionic acid methyl ester;

6-Cyclopropylmethoxy-5-(tetrahydro-pyran-4-yl)-pyridine-2-carboxylic acid [1-methyl-1-(5-methyl-[1,2,4]oxadiazol-3-yl)-ethyl]amide;

6-(3-Chloro-phenyl)-pyridine-2-carboxylic acid piperidin-1-ylamide;

2-{[6-Cyclopropylmethoxy-5-(1H-pyrazol-3-yl)-pyridine-2-carbonyl]-amino}-2-methyl-propionic acid methyl ester;

6-Cyclopropylmethoxy-5-pyrrolidin-1-yl-pyridine-2-carboxylic acid ((S)-1-hydroxymethyl-3-methyl-butyl)-amide;

2-[(6-Cyclopropylmethoxy-5-pyrrolidin-1-yl-pyridine-2-carbonyl)-amino]-2-methyl-propionic acid methyl ester;

6-Cyclopropylmethoxy-5-(2-methyl-pyrrolidin-1-yl)-pyridine-2-carboxylic acid ((S)-1-carbamoyl-3-methyl-butyl)-amide;

6-Cyclopropylmethoxy-5-pyrrolidin-1-yl-pyridine-2-carboxylic acid [1-methyl-1-(5-methyl-[1,2,4]oxadiazol-3-yl)-ethyl]-amide;

6-Cyclopropylmethoxy-5-(tetrahydro-pyran-4-yl)-pyridine-2-carboxylic acid (1-methyl-1-thiazol-2-yl-ethyl)-amide;

6-Cyclopropylmethoxy-5-pyrrolidin-1-yl-pyridine-2-carboxylic acid (1,1-dimethyl-3-morpholin-4-yl-propyl)-amide;

6-Cyclopropylmethoxy-5-methyl-pyridine-2-carboxylic acid (1-methyl-1-methylcarbamoyl-ethyl)-amide;

5-Cyclopentyl-6-cyclopropylmethoxy-pyridine-2-carboxylic acid (1-methyl-1-methylcarbamoyl-ethyl)-amide;

5-Cyclopropyl-6-cyclopropylmethoxy-pyridine-2-carboxylic acid piperidin-1-ylamide;

5-Cyclopropyl-6-cyclopropylmethoxy-pyridine-2-carboxylic acid (1-methyl-1-methylcarbamoyl-ethyl)-amide;

5-Cyclopropyl-6-cyclopropylmethoxy-pyridine-2-carboxylic acid (1-methyl-1-thiazol-2-yl-ethyl)-amide;

5-Cyclopropyl-6-cyclopropylmethoxy-pyridine-2-carboxylic acid [1-methyl-1-(5-methyl-[1,2,4]oxadiazol-3-yl)-ethyl]-amide;
6-Cyclopropylmethoxy-5-methyl-pyridine-2-carboxylic acid piperidin-1-ylamide;
5-Cyclopentyl-6-cyclopropylmethoxy-pyridine-2-carboxylic acid [(S)-2-cyclopropyl-1-(5-methyl-[1,2,4]oxadiazol-3-yl)-ethyl]-amide;
5-Cyclopentyl-6-cyclopropylmethoxy-pyridine-2-carboxylic acid [1-methyl-1-(5-methyl-[1,2,4]oxadiazol-3-yl)-ethyl]-amide;
5-Cyclopentyl-6-cyclopropylmethoxy-pyridine-2-carboxylic acid (1-methyl-1-thiazol-2-yl-ethyl)-amide;
6-Cyclopropylmethoxy-5-methyl-pyridine-2-carboxylic acid [(S)-2-cyclopropyl-1-(5-methyl-[1,2,4]oxadiazol-3-yl)-ethyl]-amide;
6-Cyclopropylmethoxy-5-(tetrahydro-pyran-4-yl)-pyridine-2-carboxylic acid ((S)-2-cyclopropyl-1-thiazol-2-yl-ethyl)-amide;
6-Cyclopropylmethoxy-5-(2-oxo-pyrrolidin-1-yl)-pyridine-2-carboxylic acid (1-methyl-1-oxazol-2-yl-ethyl)-amide;
6-Cyclopropylmethoxy-5-methyl-pyridine-2-carboxylic acid (1-methyl-1-thiazol-2-yl-ethyl)-amide;
6-Cyclopropylmethoxy-5-pyrrolidin-1-yl-pyridine-2-carboxylic acid [1-(4,5-dihydro-oxazol-2-yl)-1-methyl-ethyl]-amide;
6-Cyclopropylmethoxy-5-methyl-pyridine-2-carboxylic acid ((S)-3-methyl-1-thiazol-2-yl-butyl)-amide;
6-Cyclopropylmethoxy-5-methyl-pyridine-2-carboxylic acid ((S)-2-cyclopropyl-1-thiazol-2-yl-ethyl)-amide;
6-Cyclopropylmethoxy-pyridine-2-carboxylic acid piperidin-1-ylamide;
6-Cyclopropylmethoxy-5-(3,3-difluoro-azetidin-1-yl)-pyridine-2-carboxylic acid (1-methyl-1-thiazol-2-yl-ethyl)-amide;
5-Cyclopropyl-6-cyclopropylmethoxy-pyridine-2-carboxylic acid (1-methyl-1-[1,2,4]oxadiazol-3-yl-ethyl)-amide;
5-Cyclopropyl-6-cyclopropylmethoxy-pyridine-2-carboxylic acid (1-ethyl-1-methylcarbamoyl-propyl)-amide;
6-Cyclopropylmethoxy-5-(3-hydroxy-azetidin-1-yl)-pyridine-2-carboxylic acid (1-methyl-1-thiazol-2-yl-ethyl)-amide;
6-(Cyclopropylmethoxy)-5-(1,1-dioxido-1,2-isothiazolidin-2-yl)-N-[2-(1,3-thiazol-2-yl)propan-2-yl]pyridine-2-carboxamide;
6-Cyclopropylmethoxy-5-(3,3-difluoro-pyrrolidin-1-yl)-pyridine-2-carboxylic acid (1-ethyl-1-methylcarbamoyl-propyl)-amide;
6-Cyclopropylmethoxy-5-(3,3-difluoro-pyrrolidin-1-yl)-pyridine-2-carboxylic acid (1-methyl-1-methylcarbamoyl-ethyl)-amide;
5-Chloro-6-cyclopropylmethoxy-pyridine-2-carboxylic acid (1-methyl-1-[1,2,4]oxadiazol-3-yl-ethyl)-amide;
6-Cyclohexyl-pyridine-2-carboxylic acid (2-hydroxy-cyclohexyl)-amide;
6-Cyclopropylmethoxy-5-(tetrahydro-pyran-4-yl)-pyridine-2-carboxylic acid (1-ethyl-1-methylcarbamoyl-propyl)-amide;
6-Cyclopropylmethoxy-5-(3,3-difluoro-azetidin-1-yl)-pyridine-2-carboxylic acid (1-ethyl-1-methylcarbamoyl-propyl)-amide;
6-Cyclopropylmethoxy-5-(3,3-difluoro-azetidin-1-yl)-pyridine-2-carboxylic acid (1-methyl-1-methylcarbamoyl-ethyl)-amide;
2-[(6-Cyclohexyl-pyridine-2-carbonyl)-amino]-cyclohexanecarboxylic acid methyl ester;
6-Cyclopropylmethoxy-5-(tetrahydro-pyran-4-yl)-pyridine-2-carboxylic acid (1-methyl-1-oxazol-2-yl-ethyl)-amide;
6-Cyclopentyl-pyridine-2-carboxylic acid piperidin-1-ylamide;
5-Cyclopropyl-6-cyclopropylmethoxy-pyridine-2-carboxylic acid ((S)-1-carbamoyl-2-cyclopropyl-ethyl)-amide;
5-Cyclopropyl-6-cyclopropylmethoxy-pyridine-2-carboxylic acid ((S)-2-cyclopropyl-1-thiazol-2-yl-ethyl)-amide;
5-Cyclopropyl-6-cyclopropylmethoxy-pyridine-2-carboxylic acid ((S)-1-carbamoyl-3-methyl-butyl)-amide;
6-Cyclopropylmethoxy-5-(3,3-difluoro-azetidin-1-yl)-pyridine-2-carboxylic acid [1-methyl-1-(5-methyl-[1,2,4]oxadiazol-3-yl)-ethyl]-amide;
6-Cyclopropylmethoxy-5-(3,3-difluoro-azetidin-1-yl)-pyridine-2-carboxylic acid ((S)-1-carbamoyl-2-cyclopropyl-ethyl)-amide;
5-Cyclopentyl-6-cyclopropylmethoxy-pyridine-2-carboxylic acid ((S)-1-carbamoyl-2-cyclopropyl-ethyl)-amide;
5-Chloro-6-cyclopropylmethoxy-pyridine-2-carboxylic acid [1-methyl-1-(5-methyl-[1,2,4]oxadiazol-3-yl)-ethyl]amide;
5-Chloro-6-cyclopropylmethoxy-pyridine-2-carboxylic acid (1-ethyl-1-methylcarbamoyl-propyl)-amide;
5-Bromo-6-cyclopropylmethoxy-pyridine-2-carboxylic acid ((S)-1-carbamoyl-2-cyclopropyl-ethyl)-amide;
5-Cyclopentyl-6-cyclopropylmethoxy-pyridine-2-carboxylic acid (1-ethyl-1-methylcarbamoyl-propyl)-amide;
6-Cyclopropylmethoxy-5-(3,3-difluoro-pyrrolidin-1-yl)-pyridine-2-carboxylic acid ((S)-1-carbamoyl-2-cyclopropyl-ethyl)-amide;
6-Cyclopropylmethoxy-5-trifluoromethyl-pyridine-2-carboxylic acid ((S)-1-carbamoyl-2-cyclopropyl-ethyl)-amide;
6-Cyclopropylmethoxy-5-(tetrahydro-furan-3-yl)-pyridine-2-carboxylic acid ((S)-1-carbamoyl-3-methyl-butyl)-amide;
6-Cyclopropylmethoxy-5-(tetrahydro-furan-2-yl)-pyridine-2-carboxylic acid ((S)-1-carbamoyl-3-methyl-butyl)-amide;
5-Cyclopropyl-6-cyclopropylmethoxy-pyridine-2-carboxylic acid [2-(2-methoxy-ethoxy)-1,1-dimethyl-ethyl]-amide;
6-Cyclopropylmethoxy-5-trifluoromethyl-pyridine-2-carboxylic acid ((S)-1-carbamoyl-3-methyl-butyl)-amide;
6-Cyclopropylmethoxy-5-trifluoromethyl-pyridine-2-carboxylic acid (1-methyl-1-[1,2,4]oxadiazol-3-yl-ethyl)-amide;
6-Cyclopropylmethoxy-5-trifluoromethyl-pyridine-2-carboxylic acid [1-methyl-1-(5-methyl-[1,2,4]oxadiazol-3-yl)-ethyl]-amide;
6-Cyclopropylmethoxy-5-trifluoromethyl-pyridine-2-carboxylic acid (1-methyl-1-thiazol-2-yl-ethyl)-amide;
6-Cyclohexyl-pyridine-2-carboxylic acid (2-hydroxymethyl-cyclohexyl)-amide;
6-Cyclopropylmethoxy-5-(tetrahydro-furan-2-yl)-pyridine-2-carboxylic acid [1-methyl-1-(5-methyl-[1,2,4]oxadiazol-3-yl)-ethyl]amide;
6-Cyclopropylmethoxy-5-(tetrahydro-furan-3-yl)-pyridine-2-carboxylic acid [1-methyl-1-(5-methyl-[1,2,4]oxadiazol-3-yl)-ethyl]amide;

6-Cyclopropylmethoxy-5-trifluoromethyl-pyridine-2-carboxylic acid (1-methyl-1-oxazol-2-yl-ethyl)-amide;
6-Cyclopropylmethoxy-5-methyl-pyridine-2-carboxylic acid ((S)-1-carbamoyl-2-cyclopropyl-ethyl)-amide;
6-Cyclopropylmethoxy-5-(3-hydroxy-azetidin-1-yl)-pyridine-2-carboxylic acid ((S)-1-carbamoyl-3-methyl-butyl)-amide;
6-Cyclopropylmethoxy-5-(3,3-difluoro-azetidin-1-yl)-pyridine-2-carboxylic acid ((S)-1-carbamoyl-3-methyl-butyl)-amide;
5-Cyclopropylamino-6-cyclopropylmethoxy-pyridine-2-carboxylic acid ((S)-1-carbamoyl-2-cyclopropyl-ethyl)-amide;
5-Cyclopropylamino-6-cyclopropylmethoxy-pyridine-2-carboxylic acid ((S)-1-carbamoyl-3-methyl-butyl)-amide;
6-Cyclopropylmethoxy-5-(3,3-difluoro-azetidin-1-yl)-pyridine-2-carboxylic acid ((S)-1-cyclopropylmethyl-2-hydroxy-2-methyl-propyl)-amide;
6-Cyclopropylmethoxy-5-(tetrahydro-furan-3-yl)-pyridine-2-carboxylic acid ((S)-1-carbamoyl-2-cyclopropyl-ethyl)-amide;
6-Cyclopropylmethoxy-5-(3,3-difluoro-azetidin-1-yl)-pyridine-2-carboxylic acid (2-hydroxy-cyclohexyl)-amide;
6-Cyclopropylmethoxy-5-(3,3-difluoro-azetidin-1-yl)-pyridine-2-carboxylic acid [(S)-2-cyclopropyl-1-(5-methyl[1,2,4]oxadiazol-3-yl)-ethyl]-amide;
5-Cyclopropyl-6-cyclopropylmethoxy-pyridine-2-carboxylic acid ((S)-1-cyclopropylmethyl-2-hydroxy-2-methyl-propyl)-amide;
6-Cyclopropylmethoxy-5-(tetrahydro-furan-3-yl)-pyridine-2-carboxylic acid (2-hydroxy-1,1-dimethyl-ethyl)-amide;
5-Cyclopropyl-6-(2-methoxy-ethoxy)-pyridine-2-carboxylic acid ((S)-1-carbamoyl-3-methyl-butyl)-amide;
6-Cyclopropylmethoxy-5-(3,3-difluoro-azetidin-1-yl)-pyridine-2-carboxylic acid ((S)-2-cyclopropyl-1-thiazol-2-yl-ethyl)-amide;
6-Cyclopropylmethoxy-5-(3,3-difluoro-azetidin-1-yl)-pyridine-2-carboxylic acid (pyridin-2-ylmethyl)-amide;
[6-Cyclopropylmethoxy-5-(3,3-difluoro-azetidin-1-yl)-pyridin-2-yl]-((S)-2-hydroxymethyl-pyrrolidin-1-yl)-methanone;
6-Cyclopropylmethoxy-5-(3-hydroxy-oxetan-3-yl)-pyridine-2-carboxylic acid ((S)-1-carbamoyl-3 methyl-butyl)-amide;
5-Cyclopropyl-6-(2-methoxy-ethoxy)-pyridine-2-carboxylic acid [1-methyl-1-(5-methyl-[1,2,4]oxadiazol-3-yl)-ethyl]-amide;
5-Cyclopropyl-6-cyclopropylmethoxy-pyridine-2-carboxylic acid (1,1-dimethyl-3-morpholin-4-yl-propyl)-amide;
5-Cyclopropyl-6-(4-fluoro-benzyl)-pyridine-2-carboxylic acid ((S)-1-carbamoyl-3-methyl-butyl)-amide;
6-Cyclopropylmethoxy-5-(3,3-difluoro-azetidin-1-yl)-pyridine-2-carboxylic acid [(S)-2-cyclopropyl-1-(2-methoxy-ethoxymethyl)-ethyl]-amide;
5-Cyclopropylamino-6-cyclopropylmethoxy-pyridine-2-carboxylic acid (2-hydroxy-1,1-dimethyl-ethyl)-amide;
6-Cyclopropylmethoxy-5-(1-hydroxy-cyclobutyl)-pyridine-2-carboxylic acid [1-methyl-1-(5-methyl-[1,2,4]oxadiazol-3-yl)-ethyl]amide;
5-Cyclopropyl-6-(2-methoxy-ethoxy)-pyridine-2-carboxylic acid ((S)-1-carbamoyl-2-cyclopropyl-ethyl)-amide;
5-[Bis-(2,2,2-trifluoro-ethyl)-amino]-6-cyclopropylmethoxy-pyridine-2-carboxylic acid ((S)-1-carbamoyl-2-cyclopropyl-ethyl)-amide;
5-Cyclopropyl-6-cyclopropylmethoxy-pyridine-2-carboxylic acid [(S)-2-cyclopropyl-1-(5-methyl-[1,2,4]oxadiazol-3-yl)-ethyl]amide;
5-[Bis-(2,2,2-trifluoro-ethyl)-amino]-6-cyclopropylmethoxy-pyridine-2-carboxylic acid (1-ethyl-1-methylcarbamoyl-propyl)-amide;
5-Cyclopropyl-6-(tetrahydro-furan-2-ylmethoxy)-pyridine-2-carboxylic acid [1-methyl-1-(5-methyl-[1,2,4]oxadiazol-3-yl)-ethyl]-amide;
N-(2-Cyanopropan-2-yl)-5-cyclopropyl-6-(cyclopropylmethoxy)picolinamide;
(S)-5-Cyclopropyl-6-(cyclopropylmethoxy)-N-(3,3-dimethyl-1-(methylamino)-1-oxobutan-2-yl)picolinamide;
N-(1-Amino-2,3-dimethyl-1-oxobutan-2-yl)-5-cyclopropyl-6-(cyclopropylmethoxy)picolinamide;
N-(1-Amino-2-methyl-1-oxobutan-2-yl)-5-cyclopropyl-6-(cyclopropylmethoxy) picolinamide;
5-Cyclopropyl-6-(cyclopropylmethoxy)-N-(1-(5-methyl-1,2,4-oxadiazol-3-yl)cyclobutyl)picolinarnide;
(S)-N-(2-Amino-2-oxo-1-phenylethyl)-5-cyclopropyl-6-(cyclopropylmethoxy)picolinamide;
(R)-N-(2-Amino-2-oxo-1-phenylethyl)-5-cyclopropyl-6-(cyclopropylmethoxy)picolinamide;
(R)-5-Cyclopropyl-6-(cyclopropylmethoxy)-N-(1-hydroxy-4-methylpentan-2-yl)picolinamide;
5-Cyclopropyl-6-(cyclopropylmethoxy)-N-(1-(hydroxymethypcyclopentyl)picolinamide;
5-Cyclopropyl-6-(cyclopropylmethoxy)-N-(2-(3-methyl-1,2,4-oxadiazol-5-yl)propart-2-yl)picolinamide;
N-(1-Amino-2,4-dimethyl-1-oxopentan-2-yl)-5-cyclopropyl-6-(cyclopropylmethoxy)picolinamide;
N-(1-Amino-3,3-dimethyl-1-oxobutan-2-yl)-5-cyclopropyl-6-(cyclopropylmethoxy)picolinamide;
5-Cyclopropyl-6-cyclopropylmethoxy-pyridine-2-carboxylic acid (4-carbamoyl-tetrahydro-pyran-4-yl)-amide;
(S)-5-Cyclopropyl-6-(cyclopropylmethoxy)-N-(4-methyl-1-(methylamino)- -oxopentan-2-yl)picolinamide;
(S)-5-Cyclopropyl-6-(cyclopropylmethoxy)-N-(4,4-dimethyl-1-(methylamino)-1-oxopentan-2-yl)picolinamide;
5-Cyclopropyl-N-((S)-3,3-dimethyl-1-(methylamino)-1-oxobutan-2-yl)-6-((tetrahydrofuran-2-yl)methoxy)picolinamide;
5-Cyclopropyl-N-((S)-4-methyl-1-(methylamino)-1-oxopentan-2-yl)-6-((tetrahydrofuran-2-yl)methoxy)picolinamide;
5-Cyclopropyl-N-((S)-4,4-dimethyl-1-(methylamino)-1-oxopentan-2-yl)-6-((tetrahydrofuran-2-y1)methoxy)picolinamide;
N-((S)-1-Amino-4-methyl-1-oxopentan-2-yl)-5-cyclopropyl-6-((tetrahydrofuran-2-yl)methoxy)picolinamide;
5-Cyclopropyl-6-(4-fluoro-phenoxy)-pyridine-2-carboxylic acid ((S)-1-carbamoyl-3-methyl-butyl)-amide;
5-Cyclopropyl-N-(1-(5-methyl-1,2,4-oxadiazol-3-yl)cyclobutyl)-6-(pyridin-2-ylmethoxy)picolinamide;
5-Cyclopropyl-N-(cyclopropyl(5-methyl-1,2,4-oxadiazol-3-yl)methyl)-6-(cyclopropylmethoxy)picolinamide;
5-Cyclopropyl-6-cyclopropylmethoxy-pyridine-2-carboxylic acid ((R)-1-hydroxymethyl-1,2-dimethyl-propyl)-amide;

5-Cyclopropyl-6-(cyclopropylmethoxy)-N-(4-hydroxy-2-methylbutan-2-yl)picolinamide;
(S)-5-Cyclopropyl-N-(3,3-dimethyl-1-(methylamino)-1-oxobutan-2-yl)-6-((tetrahydro-2H-pyran-4-yl)methoxy)picolinamide;
(S)-5-Cyclopropyl-N-(4,4-dimethyl-1-(methylamino)-1-oxopentan-2-yl)-6-((tetrahydro-2H-pyran-4-yl)methoxy)picolinamide;
(−)-5-Cyclopropyl-6-cyclopropylmethoxy-pyridine-2-carboxylic acid [cyclopropyl-(5-methyl-[1,2,4]oxadiazol-3-yl)-methyl]-amide;
(+)-5-Cyclopropyl-6-cyclopropylmethoxy-pyridine-2-carboxylic acid [cyclopropyl-(5-methyl-[1,2,4]oxadiazol-3-yl)-methyl]amide;
5-Cyclopropyl-N-(2-(5-methyl-1,2,4-oxadiazol-3-yl)propan-2-yl)-6-(pyridin-2-ylmethoxy)picolinamide;
(S)-N-(1-Amino-4-methyl-1-oxopentan-2-yl)-5-cyclopropyl-6-(pyridin-2-ylmethoxy)picolinamide;
(S)-5-Cyclopropyl-N-(3,3-dimethyl-1-(methylamino)-1-oxobutan-2-yl)-6-(pyridin-2-ylmethoxy)picolinamide;
5-Cyclopropyl-N-(2-(5-methyl-1,2,4-oxadiazol-3-yl)propan-2-yl)-6-((tetrahydro-2H-pyran-4-yl)methoxy)picolinamide;
(S)-5-Cyclopropyl-N-(4-methyl-1-(methylamino)-1-oxopentan-2-yl)-6-((tetrahydro-2H-pyran-4-yl)methoxy)picolinamide;
2-(6-(Cyclopropylmethoxy)-5-(3,3-difluoroazetidin-1-yl)picolinamido)-2-ethylbutanoic acid;
(S)-6-(Cyclopropylmethoxy)-5-(3,3-difluoroazetidin-1-yl)-N-(3,3-dimethyl-1-(methylamino)-1-oxobutan-2-yl)picolinamide;
(S)-6-(Cyclopropylmethoxy)-5-(3,3-difluoroazetidin-1-yl)-N-(4,4-dimethyl-1-(methylamino)-1-oxopentan-2-yl)picolinamide;
(S)-5-Cyclopropyl-6-(cyclopropylmethoxy)-N-(2,2,2-trifluoro-1-(pyridin-3-yl)ethyl)picolinamide;
(R)-5-Cyclopropyl-6-(cyclopropylmethoxy)-N-(2,2,2-trifluoro-1-(pyridin-3-yl)ethyl)picolinamide;
5-Cyclopropyl-6-(tetrahydro-pyran-4-ylmethoxy)-pyridine-2-carboxylic acid [cyclopropyl-(5-methyl-[1,2,4]oxadiazol-3-yl)-methyl]-amide;
6-Cyclopropylmethoxy-5-(3,3-difluoro-azetidin-1-yl)-pyridine-2-carboxylic acid [cyclopropyl-(5-methyl-[1,2,4]oxadiazol-3-yl)-methyl]amide;
5-Cyclopropyl-6-cyclopropylmethoxy-pyridine-2-carboxylic acid ((S)-2-cyclopropyl-1-dimethylcarbamoyl-ethyl)-amide;
5-Cyclopropyl-6-(tetrahydro-pyran-4-ylmethoxy)-pyridine-2-carboxylic acid (2,2,2-trifluoro-1-pyridin-2-yl-ethyl)-amide;
6-Cyclopropylmethoxy-5-(3,3-difluoro-azetidin-1-yl)-pyridine-2-carboxylic acid (2,2,2-trifluoro-1-pyridin-2-yl-ethyl)-amide;
5-Cyclopropyl-6-cyclopropylmethoxy-pyridine-2-carboxylic acid ((−)-methylcarbamoyl-phenyl-methyl)-amide;
5-Cyclopropyl-6-cyclopropylmethoxy-pyridine-2-carboxylic acid ((+)-dimethylcarbamoyl-phenyl-methyl)-amide;
5-Cyclopropyl-6-cyclopropylmethoxy-pyridine-2-carboxylic acid ((−)-dimethylcarbamoyl-phenyl-methyl)-amide;
6-Cyclopropylmethoxy-5-trifluoromethyl-pyridine-2-carboxylic acid ((S)-3,3-dimethyl-1-methylcarbamoyl-butyl)-amide;
6-Cyclopropylmethoxy-5-trifluoromethyl-pyridine-2-carboxylic acid [cyclopropyl-(5-methyl-[1,2,4]oxadiazol-3-yl)-methyl]-amide;
5-Cyclopropyl-6-cyclopropylmethoxy-pyridine-2-carboxylic acid ((S)-1-dimethylcarbamoyl-3-methyl-butyl)-amide;
2-{[5-Cyclopropyl-6-(tetrahydro-furan-2-ylmethoxy)-pyridine-2-carbonyl]-amino}-2-ethyl-butyric acid methyl ester;
6-Cyclopropylmethoxy-5-(6-oxa-1-aza-spiro[3.3]hept-1-yl)-pyridine-2-carboxylic acid ((S)-3,3-dimethyl-1-methylcarbarnoyl-butyl)-amide;
6-Cyclopropylmethoxy-5-(6-oxa-1-aza-spiro[3.3]hept-1-yl)-pyridine-2-carboxylic acid [1-methyl-1-(5-methyl-[1,2,4]oxadiazol-3-yl)-ethyl]amide;
6-Cyclopropylmethoxy-5-(6-oxa-1-aza-spiro[3.3]hept-1-yl)-pyridine-2-carboxylic acid [cyclopropyl-(5-methyl-[1,2,4]oxadiazol-3-yl)-methyl]amide;
6-Cyclopropylmethoxy-5-(3,3-difluoro-azetidin-1-yl)-pyridine-2-carboxylic acid ((R)-2,2,2-trifluoro-1-pyridin-3-yl-ethyl)-amide;
(S)-2-[(5-Cyclopropyl-6-cyclopropylmethoxy-pyridine-2-carbonyl)-amino]-3,3-dimethyl-butyric acid methyl ester;
5-Cyclopropyl-6-cyclopropylmethoxy-pyridine-2-carboxylic acid ((S)-2,2,2-trifluoro-1-pyridin-2-yl-ethyl)-amide;
5-Cyclopropyl-6-cyclopropylmethoxy-pyridine-2-carboxylic acid [(−)-1-(5-methyl-[1,2,4]oxadiazol-3-yl)-ethyl]-amide;
5-Cyclopropyl-6-cyclopropylmethoxy-pyridine-2-carboxylic acid [(+)-3-methyl-1-(5-methyl-[1,2,4]oxadiazol-3-yl)-butyl]-amide;
5-Cyclopropyl-6-cyclopropylmethoxy-pyridine-2-carboxylic acid [(−)-3-methyl-1-(5-methyl-[1,2,4]oxadiazol-3-yl)-butyl]-amide;
5-Cyclopropyl-6-cyclopropylmethoxy-pyridine-2-carboxylic acid [(+)-1-(5-methyl-[1,2,4]oxadiazol-3-yl)-propyl]amide;
5-Cyclopropyl-6-cyclopropylmethoxy-pyridine-2-carboxylic acid [(−)-1-(5-methyl-[1,2,4]oxadiazol-3-yl)-propyl]amide;
5-Cyclopropyl-6-cyclopropylmethoxy-pyridine-2-carboxylic acid ((−)-cyano-methyl-methyl)-amide;
5-Cyclopropyl-6-cyclopropylmethoxy-pyridine-2-carboxylic acid ((−)-1-cyano-3-methyl-butyl)-amide;
5-Cyclopropyl-6-cyclopropylmethoxy-pyridine-2-carboxylic acid ((+)-cyano-cyclopropyl-methyl)-amide;
2-[(6-Cyclopropylmethoxy-5-trifluoromethyl-pyridine-2-carbonyl)-amino]-2-ethyl-butyric acid methyl ester;
5-Cyclopropyl-6-(tetrahydro-furan-2-ylmethoxy)-pyridine-2-carboxylic acid (1-ethyl-1-methylcarbamoyl-propyl)-amide;
2-[(5-Cyclopropyl-6-cyclopropylmethoxy-pyridine-2-carbonyl)-amino]-2-ethyl-butyric acid methyl ester;
2-[(6-Cyclopropylmethoxy-5-trifluoromethyl-pyridine-2-carbonyl)-amino]-2-ethyl-butyric acid;
6-Cyclopropylmethoxy-5-(3,3-difluoro-azetidin-1-yl)-pyridine-2-carboxylic acid (dimethylcarbamoyl-phenyl-methyl)-amide;
6-Cyclopropylmethoxy-5-(3,3-difluoro-azetidin-1-yl)-pyridine-2-carboxylic acid ((S)-2-cyclopropyl-1-dimethylcarbamoyl-ethyl)-amide;
2-[(5-Cyclopropyl-6-cyclopropylmethoxy-pyridine-2-carbonyl)-amino]-2-ethyl-butyric acid ethyl ester;

(S)-3-Cyclopropyl-2-[(5-cyclopropyl-6-cyclopropyl-methoxy-pyridine-2-carbonyl)-amino]-propionic acid methyl ester;

6-Cyclopropylmethoxy-5-trifluoromethyl-pyridine-2-carboxylic acid (1-ethyl-1-methylcarbamoyl-propyl)-amide;

2-{[6-Cyclopropylmethoxy-5-(6-oxa-1-aza-spiro[3.3]hept-1-yl)-pyridine-2-carbonyl]-amino}-2-ethyl-butyric acid ethyl ester;

2-[(5-Bromo-6-cyclopropylmethoxy-pyridine-2-carbonyl)-amino]-2-ethyl-butyric acid ethyl ester;

2-{[6-Cyclopropylmethoxy-5-(3,3-difluoro-azetidin-1-yl)-pyridine-2-carbonyl]-amino}-2-ethyl-butyric acid ethyl ester;

2-{[6-Cyclopropylmethoxy-5-(3,3-difluoro-2-oxo-azetidin-1-yl)-pyridine-2-carbonyl]-amino-}2-ethyl-butyric acid methyl ester;

(S)-2-[(5-Cyclopropyl-6-cyclopropylmethoxy-pyridine-2-carbonyl)-amino]-4-methyl-pentanoic acid methyl ester;

6-Cyclopropylmethoxy-5-(3,3-difluoro-azetidin-1-yl)-pyridine-2-carboxylic acid (1-cyano-3-methyl-butyl)-amide;

6-Cyclopropylmethoxy-5-(3,3-difluoro-azetidin-1-yl)-pyridine-2-carboxylic acid [3-methyl-1-(5-methyl-[1,2,4]oxadiazol-3-yl)-butyl]-amide;

6-Cyclopropylmethoxy-5-(3,3-difluoro-azetidin-1-yl)-pyridine-2-carboxylic acid (1-hydroxymethyl-1,3-dimethyl-butyl)-amide;

5-Cyclopropyl-6-cyclopropylmethoxy-pyridine-2-carboxylic acid [1-(azetidine-1-carbonyl)-1-ethyl-propyl]-amide;

5-Cyclopropyl-6-cyclopropylmethoxy-pyridine-2-carboxylic acid [1-ethyl-1-(2-methoxy-ethylcarbamoyl)-propyl]-amide;

5-Cyclopropyl-6-cyclopropylmethoxy-pyridine-2-carboxylic acid [1-ethyl-1-(ethyl-methyl-carbamoyl)-propyl]-amide;

5-Cyclopropyl-6-cyclopropylmethoxy-pyridine-2-carboxylic acid ((S)-1-hydroxymethyl-1,2-dimethyl-propyl)-amide;

5-Cyclopropyl-6-cyclopropylmethoxy-pyridine-2-carboxylic acid [1-(cyclopropylmethyl-carbamoyl)-1-ethyl-propyl]-amide;

5-Cyclopropyl-6-cyclopropylmethoxy-pyridine-2-carboxylic acid (1-methyl-1-pyridin-2-yl-ethyl)-amide;

5-Cyclopropyl-6-cyclopropylmethoxy-pyridine-2-carboxylic acid [1-(3,3-difluoro-azetidine-1-carbonyl)-1-ethyl-propyl]amide;

2-[(6-Cyclopropylmethoxy-5-pyrrolidin-1-yl-pyridine-2-carbonyl)-amino]-2-ethyl-butyric acid ethyl ester;

6-Cyclopropylmethoxy-5-(3,3-difluoro-azetidin-1-yl)-pyridine-2-carboxylic acid (1-methyl-5-oxo-pyrrolidin-3-yl)-amide;

2-[(6-Cyclopropylmethoxy-5-pyrrolidin-1-yl-pyridine-2-carbonyl)-amino]-2-ethyl-butyric acid;

6-Cyclopropylmethoxy-5-(3,3-difluoro-azetidin-1-yl)-pyridine-2-carboxylic acid (1,1-dioxo-tetrahydro-1λ$^6$-thiophen-3-yl)-amide;

6-Cyclopropylmethoxy-5-(3,3-difluoro-azetidin-1yl)-pyridine-2-carboxylic acid N'-(1,1-dioxo-tetrahydro-1λ$^6$-thiophen-3-yl)-hydrazide;

5-Cyclopropyl-6-cyclopropylmethoxy-pyridine-2-carboxylic acid [1-methyl-1-(4-methyl-thiazol-2-yl)-ethyl]-amide;

5-Cyclopropyl-6-cyclopropylmethoxy-pyridine-2-carboxylic acid [1-(5-amino-[1,2,4]oxadiazol-3-yl)-1-methyl-ethyl]-amide;

5-Cyclopropyl-6-(2,2,3,3,3-pentafluoro-propoxy)-pyridine-2-carboxylic acid (1-ethyl-1-methylcarbamoyl-propyl)-amide;

5-Cyclopropyl-6-(2,2,3,3,3-pentafluoro-propoxy)-pyridine-2-carboxylic acid ((S)-3,3-dimethyl-1-methylcarbamoyl-butyl)-amide;

5-Cyclopropyl-6-(2,2,3,3,3-pentafluoro-propoxy)-pyridine-2-carboxylic acid [(S)-2-cyclopropyl-1-(5-methyl-[1,2,4]oxadiazol-3-yl)-ethyl]-amide;

5-Cyclopropyl-6-(2,2,2-trifluoro-ethoxy)-pyridine-2-carboxylic acid ((S)-carbamoyl-phenyl-methyl)-amide;

5-Cyclopropyl-6-(2,2,2-trifluoro-ethoxy)-pyridine-2-carboxylic acid (2,2,2-trifluoro-1-pyridin-2-yl-ethyl)-amide;

5-Cyclopropyl-6-(2,2,2-trifluoro-ethoxy)-pyridine-2-carboxylic acid ((S)-1-hydroxymethyl-3-methyl-butyl)-amide;

5-Cyclopropyl-6-(2,2,2-trifluoro-ethoxy)-pyridine-2-carboxylic acid (3-thiazol-2-yl-oxetan-3-yl)-amide;

5-Cyclopropyl-6-(2,2,2-trifluoro-ethoxy)-pyridine-2-carboxylic acid (1-methyl-1-thiazol-2-yl-ethyl)-amide;

5-Cyclopropyl-6-(2,2,2-trifluoro-ethoxy)-pyridine-2-carboxylic acid (2,2-dimethyl-1-thiazol-2-yl-propyl)-amide;

6-Cyclopropylmethoxy-5-(3,3-difluoro-azetidin-1-yl)-pyridine-2-carboxylic acid [1-(3,3-difluoro-azetidine-1-carbonyl)-1-ethyl-propyl]-amide;

5-Cyclopropyl-6-cyclopropylmethoxy-pyridine-2-carboxylic acid [1-(3-amino-[1,2,4]oxadiazol-5-yl)-1-methyl-ethyl]-amide;

6-Cyclopropylmethoxy-5-(3,3-difluoro-azetidin-1-yl)-pyridine-2-carboxylic acid [(S)-1-(3,3-difluoro-azetidine-1-carbonyl)-2,2-dimethyl-propyl]-amide;

6-Cyclopropylmethoxy-5-(3,3-difluoro-azetidin-1-yl)-pyridine-2-carboxylic acid [(S)-1-(3,3-difluoro-azetidine-1-carbonyl)-3-methyl-butyl]amide;

2-[(6-Cyclopropylmethoxy-5-trifluoromethyl-pyridine-2-carbonyl)-amino]-2-ethyl-butyric acid ethyl ester;

5-Cyclopropyl-6-((R)-3-hydroxy-1-trifluoromethyl-propoxy)-pyridine-2-carboxylic acid (1-ethyl-1-methylcarbamoyl-propyl)-amide;

5-Cyclopropyl-6-((R)-4,4,4-trifluoro-3-hydroxy-butoxy)-pyridine-2-carboxylic acid (1-ethyl-1-methylcarbamoyl-propyl)-amide;

6-Cyclopropylmethoxy-5-(3,3-difluoro-azetidin-1-yl)-pyridine-2-carboxylic acid (3-methyl-1-pyridin-2-yl-butyl)-amide;

6-Cyclopropylmethoxy-5-trifluoromethyl-pyridine-2-carboxylic acid [1-(3,3-difluoro-azetidine-1-carbonyl)-1-ethyl-propyl]-amide;

5-Cyclopropyl-6-((S)-3-hydroxy-1-trifluoromethyl-propoxy)-pyridine-2-carboxylic acid (1-ethyl-1-methylcarbamoyl-propyl)-amide;

5-Cyclopropyl-6-((S)-4,4,4-trifluoro-3-hydroxy-butoxy)-pyridine-2-carboxylic acid (1-ethyl-1-methylcarbamoyl-propyl)-amide;

6-Cyclopropylmethoxy-5-(3,3-difluoro-azetidin-1-yl)-pyridine-2-carboxylic acid (3-methyl-1-pyridazin-3-yl-butyl)-amide;

6-Cyclopropylmethoxy-5-(3-oxo-azetidin-1-yl)-pyridine-2-carboxylic acid [1-methyl-1-(5-methyl-[1,2,4]oxadiazol-3-yl)-ethyl]-amide;

5-Cyclopropyl-6-cyclopropylmethoxy-pyridine-2-carboxylic acid [(+)-1-cyclopropyl-1-(5-methyl-[1,2,4]oxadiazol-3-yl)-ethyl]-amide;
5-Cyclopropyl-6-cyclopropylmethoxy-pyridine-2-carboxylic acid [(−)-1-cyclopropyl-1-(5-methyl-[1,2,4]oxadiazol-3-yl)-ethyl]-amide;
6-Cyclopropylmethoxy-5-(3,3-difluoro-azetidin-1-yl)-pyridine-2-carboxylic acid (3-methyl-1-pyridin-3-yl-butyl)-amide;
5-Cyclopropyl-6-(4-fluoro-benzyl)-pyridine-2-carboxylic acid ((S)-1-carbamoyl-2-cyclopropyl-ethyl)-amide;
5-Cyclopropyl-6-(4-fluoro-benzyl)-pyridine-2-carboxylic acid [(S)-2-cyclopropyl-1-(5-methyl-[1,2,4]oxadiazol-3-yl)-ethyl]amide;
5-Cyclopropyl-6-cyclopropylmethoxy-pyridine-2-carboxylic acid [(S)-carbamoyl-(4-fluoro-phenyl)-methyl]-amide;
5-Cyclopropyl-6-cyclopropylmethoxy-pyridine-2-carboxylic acid [(S)-carbamoyl-(4-chloro-phenyl)-methyl]-amide;
5-Cyclopropyl-6-(4-fluoro-benzyl)-pyridine-2-carboxylic acid ((S)-2,2,2-trifluoro-1-pyridin-2-yl-ethyl)-amide;
2-{[5-Cyclopropyl-6-(4-fluoro-benzyl)-pyridine-2-carbonyl]-amino}-2-ethyl-butyric acid;
6-Cyclopropylmethoxy-5-(3-oxo-pyrrolidin-1-yl)-pyridine-2-carboxylic acid [1-methyl-1-(5-methyl-[1,2,4]oxadiazol-3-yl)-ethyl]-amide,
(S)-2-{[5-Cyclopropyl-6-(4-fluoro-benzyl)-pyridine-2-carbonyl]-amino}-4-methyl-pentanoic acid;
2-{[5-Cyclopropyl-6-(tetrahydro-pyran-4-ylmethoxy)-pyridine-2-carbonyl]-amino}-2-ethyl-butyric acid;
6-Cyclopropylmethoxy-5-(3,3-difluoro-azetidin-1-yl)-pyridine-2-carboxylic acid (3-methyl-1-pyrimidin-2-yl-butyl)-amide;
6-Cyclopropylmethoxy-5-(3,3-difluoro-azetidin-1-yl)-pyridine-2-carboxylic acid [1-cyclopropyl-1-(5-methyl-[1,2,4]oxadiazol-3-yl)-ethyl]-amide;
6-Cyclopropylmethoxy-5-(3,3-difluoro-azetidin-1-yl)-pyridine-2-carboxylic acid [2-cyclopropyl-1-methyl-1-(5-methyl-[1,2,4]oxadiazol-3-yl)-ethyl]-amide;
6-Cyclopropylmethoxy-5-(3,3-difluoro-azetidin-1-yl)-pyridine-2-carboxylic acid ((S)-1-carbamoyl-3-methylsulfanyl-propyl)-amide;
6-Cyclopropylmethoxy-5-pyrrolidin-1-yl-pyridine-2-carboxylic acid {(S)-3-methyl-1-[(7-nitro-benzo[1,2,5]oxadiazol-4-ylamino)-methyl]-butyl}-amide;
6-Cyclopropylmethoxy-5-(3,3-difluoro-azetidin-1-yl)-pyridine-2-carboxylic acid ((S)-1-carbamoyl-3-methanesulfonyl-propyl)-amide;
5-Cyclopropyl-6-isobutylsulfanyl-pyridine-2-carboxylic acid ((S)-1-carbamoyl-3-methyl-butyl)-amide;
5-Cyclopropyl-6-cyclopropylmethoxy-pyridine-2-carboxylic acid (3-methanesulfonyl-1,1-dimethyl-propyl)-amide;
5-Cyclopropyl-6-cyclopropylmethoxy-pyridine-2-carboxylic acid [1-methyl-1-(5-methyl-thiazol-2-yl)-ethyl]-amide;
5-Cyclopropyl-6-(2-methyl-propane-1-sulfonyl)-pyridine-2-carboxylic acid ((S)-1-carbamoyl-3-methyl-butyl)-amide;
5-Cyclopropyl-6-(2-methyl-propane-1-sulfonyl)-pyridine-2-carboxylic acid [(S)-2-cyclopropyl-1-(5-methyl-[1,2,4]oxadiazol-3-yl)-ethyl]-amide;
6-Cyclopropylmethoxy-5-(3,3-difluoro-azetidin-1-yl)-pyridine-2-carboxylic acid [1-methyl-1-(5-methyl-thiazol-2-yl)-ethyl]-amide;
6-Cyclopropylmethoxy-5-(3,3-difluoro-azetidin-1-yl)-pyridine-2-carboxylic acid ((R)-3-methyl-1-pyridazin-3-yl-butyl)-amide;
6-Cyclopropylrnethoxy-5-(3,3-difluoro-azetidin-1-yl)-pyridine-2-carboxylic acid ((S)-3-methyl-1-pyridazin-3-yl-butyl)-amide;
5-Cyclopropyl-6-cyclopropylmethoxy-pyridine-2-carboxylic acid [1-ethyl-1-(2-hydroxy-ethylcarbamoyl)-propyl]-amide;
5-Cyclopropyl-6-cyclopropylmethoxy-pyridine-2-carboxylic acid [(+)-2-cyclopropyl-1-methyl-1-(5-methyl-[1,2,4]oxadiazol-3-yl)-ethyl]-amide;
5-Cyclopropyl-6-cyclopropylmethoxy-pyridine-2-carboxylic acid [(+2-cyclopropyl-1-methyl-1-(5-methyl-[1,2,4]oxadiazol-3-yl)-ethyl]-amide;
6-Cyclopropylmethoxy-5-(3,3-difluoro-azetidin-1-yl)-pyridine-2-carboxylic acid tert-butylamide;
2-{[5-Cyclopropyl-6-(2-methyl-propane-1-sulfonyl)-pyridine-2-carbonyl]-amino-}-2-ethyl-butyric acid ethyl ester;
5-Cyclopropyl-6-(2-methyl-propane-1-sulfonyl)-pyridine-2-carboxylic acid ((S)-3,3-dimethyl-1-methylcarbamoyl-butyl)-amide;
5-Cyclopropyl-6-cyclopropylmethoxy-pyridine-2-carboxylic acid ((S)-2-oxo-tetrahydro-furan-3-yl)-amide;
N'-(5-Cyclopropyl-6-cyclopropylmethoxy-pyridine-2-carbonyl)-N-cyclopropylmethyl-hydrazinecarboxylic acid tert-butyl ester;
5-Cyclopropyl-6-(2-methyl-propane-1-sulfonyl)-pyridine-2-carboxylic acid ((S)-2,2-dimethyl-1-methylcarbamoyl-propyl)-amide;
5-Cyclopropyl-6-(2-methyl-propane-1-sulfonyl)-pyridine-2-carboxylic acid ((S)-2,2,2-trifluoro-1-pyridin-3-yl-ethyl)-amide;
(S)-2-[(5-Cyclopropyl-6-cyclopropylmethoxy-pyridine-2-carbonyl)-amino]-4-methyl-pentanoic acid tert-butyl ester:
5-Cyclopropyl-6-(2-methyl-propane-1-sulfonyl)-pyridine-2-carboxylic acid (1-ethyl-1-methylcarbamoyl-propyl)-amide;
5-Cyclopropyl-6-cyclopropylmethoxy-pyridine-2-carboxylic acid tert-butylamide;
5-Cyclopropyl-6-(tetrahydro-furan-2-ylmethoxy)-pyridine-2-carboxylic acid tert-butylamide;
6-Cyclopropylmethoxy-5-(3,3-difluoro-azetidin-1-yl)-pyridine-2-carboxylic acid (3-methyl-oxetan-3-yl)-amide;
5-Cyclopropyl-6-cyclopropylmethoxy-pyridine-2-carboxylic acid (2-oxo-[1,3]oxazinan-3-yl)-amide;
5-Cyclopropyl-6-(2,2,2-trifluoro-1-methyl-ethoxy)-pyridine-2-carboxylic acid ((S)-1-carbamoyl-3-methyl-butyl)-amide;
5-Cyclopropyl-6-(2,2,2-trifluoro-1-methyl-ethoxy)-pyridine-2-carboxylic acid [1-methyl-1-(5-methyl-[1,2,4]oxadiazol-3-yl)-ethyl]-amide;
5-Cyclopropyl-6-cyclopropylmethoxy-pyridine-2-carboxylic acid ((+)-carbamoyl-cyclopropyl-methyl)-amide;
5-Cyclopropyl-6-cyclopropylmethoxy-pyridine-2-carboxylic acid ((−)-carbamoyl-cyclopropyl-methyl)-amide;
6-Cyclopropylmethoxy-5-(3,3-difluoro-azetidin-1-yl)-pyridine-2-carboxylic acid ((+)-carbamoyl-cyclopropyl-methyl)-amide;
6-Cyclopropylmethoxy-5-(3,3-difluoro-azetidin-1-yl)-pyridine-2-carboxylic acid ((−)-carbamoyl-cyclopropyl-methyl)-amide;

6-Cyclopropylmethoxy-5-(3,3-difluoro-azetidin-1-yl)-pyridine-2-carboxylic acid (1-trifluoromethyl-cyclopropyl)-amide;
(+)-5-Cyclopropyl-6-cyclopropylmethoxy-pyridine-2-carboxylic acid [(S)-2-cyclopropyl-1-(3-hydroxy-pyrrolidin-1-ylcarbamoyl)-ethyl]-amide;
(−)-5-Cyclopropyl-6-cyclopropylmethoxy-pyridine-2-carboxylic acid [(S)-2-cyclopropyl-1-(3-hydroxy-pyrrolidin-1-ylcarbarnoyl)-ethyl]amide;
(+)-5-Cyclopropyl-6-(2-methyl-propane-1-sulfonyl)-pyridine-2-carboxylic acid [1-cyclopropyl-1-(5-methyl-[1,2,4]oxadiazol-3-yl)-ethyl]amide; and
(−)-5-Cyclopropyl-6-(2-methyl-propane-1-sulfonyl)-pyridine-2-carboxylic acid [1-cyclopropyl-1-(5-methyl-[1,2,4]oxadiazol-3-yl)-ethyl]-amide.

4. A compound selected from the group consisting of:
6-Cyclopropylmethoxy-5-(tetrahydro-pyran-4-yl)-pyridine-2-carboxylic acid [1-methyl-1-(5-methyl-[1,2,4]oxadiazol-3-yl)-ethyl]-amide;
6-Cyclopropylmethoxy-5-pyrrolidin-1-yl-pyridine-2-carboxylic acid ((S)-1-hydroxymethyl-3-methyl-butyl)-amide;
6-Cyclopropylmethoxy-5-(2-methyl-pyrrolidin-1-yl)-pyridine-2-carboxylic acid ((S)-1-carbamoyl-3-methyl-butyl)-amide;
6-Cyclopropylmethoxy-5-pyrrolidin-1-yl-pyridine-2-carboxylic acid (1,1-dimethyl-3-morpholin-4-yl-propyl)-amide;
5-Cyclopentyl-6-cyclopropylmethoxy-pyridine-2-carboxylic acid (1-methyl-1-methylcarbamoyl-ethyl)-amide;
5-Cyclopropyl-6-cyclopropylmethoxy-pyridine-2-carboxylic acid (1-methyl-1-thiazol-2-yl-ethyl)-amide;
5-Cyclopentyl-6-cyclopropylmethoxy-pyridine-2-carboxylic acid [(S)-2-cyclopropyl-1-(5-methyl-[1,2,4]oxadiazol-3-yl)-ethyl]-amide;
6-Cyclopropylmethoxy-5-methyl-pyridine-2-carboxylic acid ((S)-3-methyl-1-thiazol-2-yl-butyl)-amide;
6-Cyclopropylmethoxy-5-(3,3-difluoro-azetidin-1-yl)-pyridine-2-carboxylic acid (1-methyl-1-thiazol-2-yl-ethyl)-amide;
6-Cyclopropylmethoxy-5-(3,3-difluoro-pyrrolidin-1-yl)-pyridine-2-carboxylic acid (1-ethyl-1-methylcarbamoyl-propyl)-amide;
6-Cyclopropylmethoxy-5-(3,3-difluoro-azetidin-1-yl)-pyridine-2-carboxylic acid (1-ethyl-1-methylcarbamoyl-propyl)-amide;
5-Cyclopropyl-6-cyclopropylmethoxy-pyridine-2-carboxylic acid ((S)-1-carbamoyl-2-cyclopropyl-ethyl)-amide;
5-Cyclopropyl-6-cyclopropylmethoxy-pyridine-2-carboxylic acid ((S)-1-carbamoyl-3-methyl-butyl)-amide;
6-Cyclopropylmethoxy-5-(3,3-difluoro-azetidin-1-yl)-pyridine-2-carboxylic acid ((S)-1-carbamoyl-2-cyclopropyl-ethyl)-amide;
6-Cyclopropylmethoxy-5-(3,3-difluoro-pyrrolidin-1-yl)-pyridine-2-carboxylic acid ((S)-1-carbamoyl-2-cyclopropyl-ethyl)-amide;
6-Cyclopropylmethoxy-5-(tetrahydro-furan-3-yl)-pyridine-2-carboxylic acid ((S)-1-carbamoyl-3-methyl-butyl)-amide;
6-Cyclopropylmethoxy-5-(tetrahydro-furan-2-yl)-pyridine-2-carboxylic acid ((S)-1-carbamoyl-3-methyl-butyl)-amide;
6-Cyclopropylmethoxy-5-trifluoromethyl-pyridine-2-carboxylic acid ((S)-1-carbamoyl-3-methyl-butyl)-amide;
6-Cyclopropylmethoxy-5-(tetrahydro-furan-2-yl)-pyridine-2-carboxylic acid [1-methyl-1-(5-methyl-[1,2,4]oxadiazol-3-yl)-ethyl]-amide;
6-Cyclopropylmethoxy-5-(3,3-difluoro-azetidin-1-yl)-pyridine-2-carboxylic acid ((S)-1-carbamoyl-3-methyl-butyl)-amide;
5-Cyclopropylamino-6-cyclopropylmethoxy-pyridine-2-carboxylic acid ((S)-1-carbamoyl-3-methyl-butyl)-amide;
6-Cyclopropylmethoxy-5-(3,3-difluoro-azetidin-1-yl)-pyridine-2-carboxylic acid ((S)-1-cyclopropylmethyl-2-hydroxy-2-methyl-propyl)-amide;
6-Cyclopropylmethoxy-5-(3,3-difluoro-azetidin-1-yl)-pyridine-2-carboxylic acid ((S)-2-cyclopropyl-1-thiazol-2-yl-ethyl)-amide;
5-Cyclopropyl-6-(4-fluoro-benzyl)-pyridine-2-carboxylic acid ((S)-1-carbamoyl-3-methyl-butyl)-amide;
6-Cyclopropylmethoxy-5-(3,3-difluoro-azetidin-1-yl)-pyridine-2-carboxylic acid [(S)-2-cyclopropyl-1-(2-methoxy-ethoxymethyl)-ethyl]-amide;
5-Cyclopropyl-6-cyclopropylmethoxy-pyridine-2-carboxylic acid [(S)-2-cyclopropyl-1-(5-methyl-[1,2,4]oxadiazol-3-yl)-ethyl]-amide;
5-[Bis-(2,2,2-trifluoro-ethyl)-amino]-6-cyclopropylmethoxy-pyridine-2-carboxylic acid (1-ethyl-1-methylcarbamoyl-propyl)-amide;
(S)-5-Cyclopropyl-6-(cyclopropylmethoxy)-N-(3,3-dimethyl-1-(methylamino)-1-oxobutan-2-yl)picolinamide;
(S)-N-(2-amino-2-oxo-1-phenylethyl)-5-cyclopropyl-6-(cyclopropylmethoxy)picolinamide;
N-((S)-1-amino-4-methyl-1-oxopentan-2-yl)-5-cyclopropyl-6-((tetrahydrofuran-2-yl)methoxy)picolinamide;
5-Cyclopropyl-6-cyclopropylmethoxy-pyridine-2-carboxylic acid ((R)-1-hydroxymethyl-1,2-dimethyl-propyl)-amide;
(S)-5-Cyclopropyl-N-(4,4-dimethyl-1-(methylamino)-1-oxopentan-2-yl)-6-((tetrahydro-2H-pyran-4-yl)methoxy)picolinamide;
(+)-5-Cyclopropyl-6-cyclopropylmethoxy-pyridine-2-carboxylic acid [(SR)-cyclopropyl-(5-methyl-[1,2,4]oxadiazol-3-yl)-methyl]amide;
2-(6-(Cyclopropylmethoxy)-5-(3,3-difluoroazetidin-1-yl)picolinamido)-2-ethylbutanoic acid;
5-Cyclopropyl-6-(tetrahydro-pyran-4-ylmethoxy)-pyridine-2-carboxylic acid [cyclopropyl-(5-methyl-[1,2,4]oxadiazol-3-yl)-methyl]-amide;
5-Cyclopropyl-6-cyclopropylmethoxy-pyridine-2-carboxylic acid ((S)-2-cyclopropyl-1-dimethylcarbamoyl-ethyl)-amide;
5-Cyclopropyl-6-cyclopropylmethoxy-pyridine-2-carboxylic acid ((+)-dimethylcarbamoyl-phenyl-methyl)-amide;
6-Cyclopropylmethoxy-5-trifluoromethyl-pyridine-2-carboxylic acid ((S)-3,3-dimethyl-1-methylcarbamoyl-butyl)-amide;
2-{[5-Cyclopropyl-6-(tetrahydro-furan-2-ylmethoxy)-pyridine-2-carbonyl]-amino}-2-ethyl-butyric acid methyl ester;
6-Cyclopropylmethoxy-5-(6-oxa-1-aza-spiro[3.3]hept-1-yl)-pyridine-2-carboxylic acid ((S)-3,3-dimethyl-1-methylcarbamoyl-butyl)-amide;
(S)-2-[(5-Cyclopropyl-6-cyclopropylmethoxy-pyridine-2-carbonyl)-amino]-3,3-dimethyl-butyric acid methyl ester;
5-Cyclopropyl-6-cyclopropylmethoxy-pyridine-2-carboxylic acid [(+)-1-(5-methyl-[1,2,4]oxadiazol-3-yl)-butyl]-amide;

5-Cyclopropyl-6-cyclopropylmethoxy-pyridine-2-carboxylic acid ((−)-1-cyano-3-methyl-butyl)-amide;
+(S)-3-Cyclopropyl-2-[(5-cyclopropyl-6-cyclopropylmethoxy-pyridine-2-carbonyl)-amino]-propionic acid methyl ester;
6-Cyclopropylmethoxy-5-trifluoromethyl-pyridine-2-carboxylic acid (1-ethyl-1-methylcarbamoyl-propyl)-amide;
6-Cyclopropylmethoxy-5-(3,3-difluoro-azetidin-1-yl)-pyridine-2-carboxylic acid (1-hydroxymethyl-1,3-dimethyl-butyl)-amide;
5-Cyclopropyl-6-cyclopropylmethoxy-pyridine-2-carboxylic acid [1-ethyl-1-(ethyl-methyl-carbamoyl)-propyl]-amide;
5-Cyclopropyl-6-cyclopropylmethoxy-pyridine-2-carboxylic acid ((S)-1-hydroxymethyl-1,2-dimethyl-propyl)-amide;
5-Cyclopropyl-6-cyclopropylmethoxy-pyridine-2-carboxylic acid [1-(3,3-difluoro-azetidine-1-carbonyl)-1-ethyl-propyl]-amide;
5-Cyclopropyl-6-(2,2,3,3,3-pentafluoro-propoxy)-pyridine-2-carboxylic acid (1-ethyl-1-methylcarbamoyl-propyl)-amide;
5-Cyclopropyl-6-(2,2,3,3,3-pentafluoro-propoxy)-pyridine-2-carboxylic acid ((S)-3,3-dimethyl-1-methylcarbamoyl-butyl)-amide;
6-Cyclopropylmethoxy-5-(3,3-difluoro-azetidin-1-yl)-pyridine-2-carboxylic acid [1-(3,3-difluoro-azetidine-1-carbonyl)-1-ethyl-propyl]-amide;
5-Cyclopropyl-6-((R)-4,4,4-trifluoro-3-hydroxy-butoxy)-pyridine-2-carboxylic acid (1-ethyl-1-methylcarbamoyl-propyl)-amide;
6-Cyclopropylmethoxy-5-trifluoromethyl-pyridine-2-carboxylic acid [1-(3,3-difluoro-azetidine-1-carbonyl)-1-ethyl-propyl]-amide;
5-Cyclopropyl-6-((S)-4,4,4-trifluoro-3-hydroxy-butoxy)-pyridine-2-carboxylic acid (1-ethyl-1-methylcarbamoyl-propyl)-amide;
5-Cyclopropyl-6-cyclopropylmethoxy-pyridine-2-carboxylic acid [(+)-1-cyclopropyl-1-(5-methyl-[1,2,4]oxadiazol-3-yl)-ethyl]-amide;
6-Cyclopropylmethoxy-5-(3,3-difluoro-azetidin-1-yl)-pyridine-2-carboxylic acid (3-methyl-1-pyridin-3-yl-butyl)-amide;
5-Cyclopropyl-6-(4-fluoro-benzyl)-pyridine-2-carboxylic acid ((S)-1-carbamoyl-2-cyclopropyl-ethyl)-amide;
5-Cyclopropyl-6-cyclopropylmethoxy-pyridine-2-carboxylic acid [(S)-carbamoyl-(4-fluoro-phenyl)-methyl]-amide;
5-Cyclopropyl-6-(4-fluoro-benzyl)-pyridine-2-carboxylic acid ((S)-2,2,2-trifluoro-1-pyridin-2-yl-ethyl)-amide;
6-Cyclopropylmethoxy-5-(3,3-difluoro-azetidin-1-yl)-pyridine-2-carboxylic acid [1-cyclopropyl-1-(5-methyl-[1,2,4]oxadiazol-3-yl)-ethyl]-amide;
6-Cyclopropylmethoxy-5-(3,3-difluoro-azetidin-1-yl)-pyridine-2-carboxylic acid [2-cyclopropyl-1-methyl-1-(5-methyl-[1,2,4]oxadiazol-3-yl)-ethyl]-amide;
6-(3-Chloro-4-fluoro-phenyl)-pyridine-2-carboxylic acid [(S)-2-cyclopropyl-1-(5-methyl-[1,2,4]oxadiazol-3-yl)-ethyl]-amide;
6-Cyclopropylmethoxy-5-pyrrolidin-1-yl-pyridine-2-carboxylic acid {(S)-3-methyl-1-[(7-nitro-benzo[1,2,5]oxadiazol-4-ylamino)-methyl]-butyl}-amide;
5-Cyclopropyl-6-isobutylsulfanyl-pyridine-2-carboxylic acid ((S)-1-carbamoyl-3-methyl-butyl)-amide;
5-Cyclopropyl-5-(2-methyl-propane-1-sulfonyl)-pyridine-2-carboxylic acid ((S)-1-carbamoyl-3-methyl-butyl)-amide;
6-Cyclopropylmethoxy-5-(3,3-difluoro-azetidin-1-yl)-pyridine-2-carboxylic acid [1-methyl-1-(5-methyl-thiazol-2-yl)-ethyl]-amide;
6-Cyclopropylmethoxy-5-(3,3-difluoro-azetidin-1-yl)-pyridine-2-carboxylic acid ((R)-3-methyl-1-pyridazin-3-yl-butyl)-amide;
5-Cyclopropyl-6-cyclopropylmethoxy-pyridine-2-carboxylic acid [(+)-2-cyclopropyl-1-methyl-1-(5-methyl-[1,2,4]oxadiazol-3-yl)-ethyl]-amide;
5-Cyclopropyl-6-cyclopropylmethoxy-pyridine-2-carboxylic acid [(−)-2-cyclopropyl-1-methyl-1-(5-methyl-[1,2,4]oxadiazol-3-yl)-ethyl]-amide;
6-Cyclopropylmethoxy-5-(3,3-difluoro-azetidin-1-yl)-pyridine-2-carboxylic acid tert-butylamide;
5-Cyclopropyl-6-(2-methyl-propane-1-sulfonyl)-pyridine-2-carboxylic acid ((S)-2,2,2-trifluoro-1-pyridin-3-yl-ethyl)-amide;
5-Cyclopropyl-6-cyclopropylmethoxy-pyridine-2-carboxylic acid ((+)-carbamoyl-cyclopropyl-methyl)-amide;
6- Cyclopropylmethoxy-5-(3,3-difluoro-azetidin-1-yl)-pyridine-2-carboxylic acid (1-trifluoromethyl-cyclopropyl)-amide; and
(+)-5-Cyclopropyl-6-(2-methyl-propane-1-sulfonyl)-pyridine-2-carboxylic acid [1-cyclopropyl-1-(5-methyl-[1,2,4]oxadiazol-3-yl)-ethyl]-amide.

* * * * *